(12) United States Patent
Fremont et al.

(10) Patent No.: US 7,498,419 B2
(45) Date of Patent: Mar. 3, 2009

(54) CRYSTALS AND STRUCTURE OF DOMAIN III OF WEST NILE VIRUS ENVELOPE PROTEIN IN ASSOCIATION WITH A FAB FRAGMENT OF A NEUTRALIZING ANTIBODY

(75) Inventors: Daved H. Fremont, St. Louis, MO (US); Grant Nybakken, St. Louis, MO (US); Michael Diamond, St. Louis, MO (US)

(73) Assignee: Washington University, St. Louis, MO (US)

( * ) Notice: Subject to any disclaimer, the term of this patent is extended or adjusted under 35 U.S.C. 154(b) by 49 days.

(21) Appl. No.: 11/251,227

(22) Filed: Oct. 14, 2005

(65) Prior Publication Data

US 2006/0115837 A1 Jun. 1, 2006

Related U.S. Application Data

(60) Provisional application No. 60/619,273, filed on Oct. 14, 2004, provisional application No. 60/702,803, filed on Jul. 26, 2005.

(51) Int. Cl.
*C07K 16/00* (2006.01)
*G01N 31/00* (2006.01)
*A61K 39/00* (2006.01)

(52) U.S. Cl. ............... 530/387.9; 436/4; 424/139.1
(58) Field of Classification Search ............... None
See application file for complete search history.

(56) References Cited

U.S. PATENT DOCUMENTS

2006/0067940 A1 * 3/2006 Diamond et al. ......... 424/159.1

OTHER PUBLICATIONS

Appendix A: List of Space Group Symbols and Crystal System. No date.*
McPherson, A. Current Approaches to Macromolecular Crystallization. European Journal of Biochemistry. 1990. vol. 189, pp. 1-23.*
Kundrot, C.E. Which Strategy for a Protein Crystallization Project? Cellular Molecular Life Science. 2004. vol. 61, pp. 525-536.*
Cudney R. Protein Crystallization and Dumb Luck. The Rigaku Journal. 1999. vol. 16, No. 1, pp. 1-7.*
Drenth, "Principles of Protein X-Ray Crystallography", 2nd Edition, 1999 Springer-Verlag New York Inc., Chapter 1, p. 1-21.*
Giege et al. Crystallogenesis of Biological Macromolecules: Facts and Perspectives, Acta Cryst. D., 1994, D50:339-350.*
Nybakken et al. Structural Basis of West Nile Virus Neutralization by a Therapeutic Antibody. Nature. Sep. 2005. vol. 437, pp. 764-768.*
Oliphant et al. Development of a Humanized Monoclonal Antibody with Therapeutic Potential Against West Nile Virus. Nature Medicine. 2005. vol. 11, pp. 522-530.*
Benevenuti et al., Crystallization of Soluble Proteins in Vapor Diffusion for X-ray Crystallography, Nature Protocols, published on-line Jun. 28, 2007, 2(7):1633-1651.*
Nybakken et al., "Crystal Structure of the West Nile Virus Envelope Glycoprotein," *J. Virol.* 80: 11467-11474 (Dec. 2006), American Society for Microbiology, Washington, DC.
Tickle et al., "High-throughput protein crystallography and drug discovery," *Chem. Soc. Rev.* 33: 558-565 (2004), The Royal Society of Chemistry, London, England.
Yazaki et al., "Humanization of the anti-CEA T84.66 antibody based on crystal structure data," *Protein Engineering, Design & Selection* 17(5): 481-489 (2004), Oxford University Press, Oxford, England.

* cited by examiner

*Primary Examiner*—Suzanne M. Noakes
(74) *Attorney, Agent, or Firm*—Drinker Biddle & Reath LLP

(57) ABSTRACT

The present invention provides crystalline forms of domain III of the West Nile Virus ("WNV") envelope protein in complex with a Fab fragment of a neutralizing antibody, methods of obtaining such crystals and high-resolution structures and atomic structure coordinates. The crystals of the invention and the atomic structural information are useful for solving crystal and solution structures of related and unrelated proteins, and for screening for, identifying or designing compounds or antibodies that bind to, modulate a biological activity of, or neutralize infection mediated by flaviviral envelope proteins.

1 Claim, 27 Drawing Sheets

Figure 1

Figure 4:
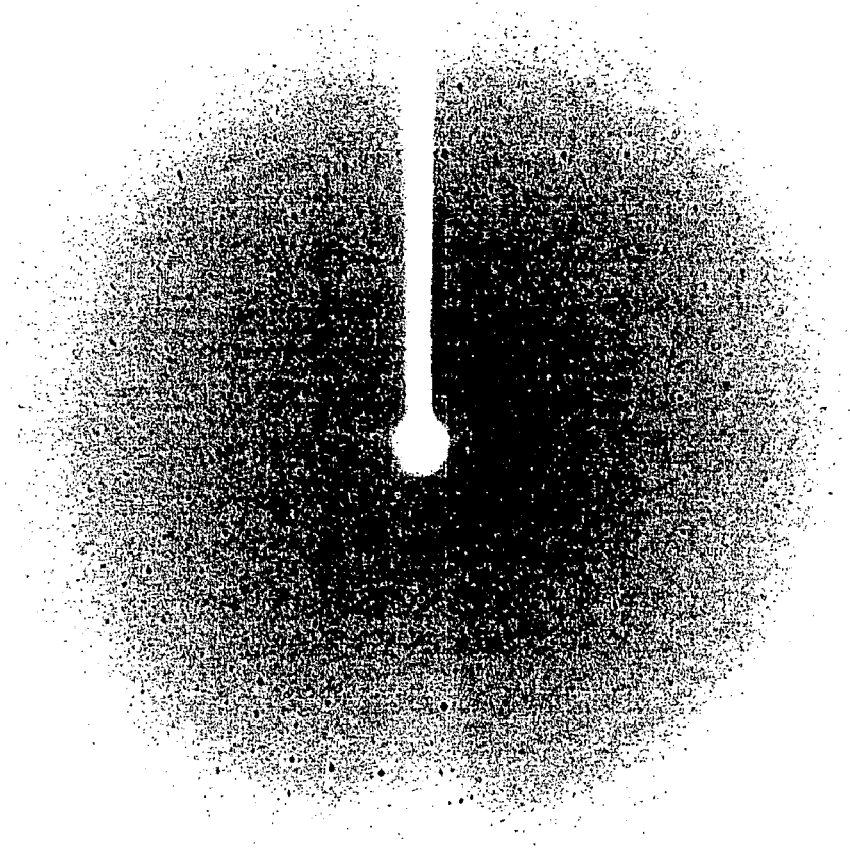

```
 1          10         20         30         40         50
QLKGTTYGVC  SKAFKFLGTP  ADTGHGTVVL  ELQYTGTDGP  CKVPISSVAS  ..

60         70         80         90        100
LNDLTPVGRL  VTVNPFVSVA  TANAKVLIEL  EPPFGDSYIV  VGRGEQQINH  ..

110        120
HWHKSGSSIG  KAFTTTLKGA  ..
```

Figure 2

```
       1          10          20          30          40          50
  . .  QVQLQQSGSE  LMKPGASVQI  SCKATGYTFS  DYWIEWVKQR  PGHGLEWIGI 60          70          80          90         100
  . . LCGTGRTRYN  EKLKAMATFT  ADTSSNTAFM  QLSSLTSEDS  AVYYCARSAS 110         118
  . . YGDYADYWGH  GTTLTVSS
```

Figure 3

```
          1         10         20         30         40         50
        . DIVMTQSHKF MSTSVGDRVS ITCKASQDVS TAVAWYQQKP GQSPKLLISW 60         70         80         90        100
        . ASTRHTGVPD RFTGSGSGTD YTLTISSVQA EDLALYYCQQ HYTTPLTFGA

107
        . GTKLELK
```

E16/DIII interface

| Van der Waals contacts[c] | | E16/DIII direct hydrogen bonds[b] | | | E16/DIII water mediated hydrogen bonds[b] | |
|---|---|---|---|---|---|---|
| DIII | E16 | DIII | E16 | Distance (Å) | DIII | E16 |
| Tyr$^{E302}$ | Arg$^{H56}$ (10) | Glu$^{E390}$ (Oε2) | Thr$^{H28}$ (N) | 2.61 | Ser$^{E306}$ (O) | Asp$^{H31}$ (O) |
| Ser$^{E306}$ | Trp$^{H33}$ (5), Leu$^{H52}$ (1) | Glu$^{E390}$ (Oε2) | Thr$^{H28}$ (Oγ1) | 2.59 | Ser$^{E306}$ (O) | Trp$^{H33}$ (N) |
| Lys$^{E307}$ | Trp$^{H33}$ (2), Ser$^{H95}$ (5), Ala$^{H96}$ (4), Ser$^{H97}$ (4), Gly$^{H99}$ (4) | Glu$^{E390}$ (N) | Asp$^{H31}$ (Oδ2) | 3.01 | Ser$^{E306}$ (O) | Ser$^{H95}$ (O) |
| Ala$^{E308}$ | Ser$^{H97}$ (4), Tyr$^{H98}$ (2) | Gln$^{E391}$ (Nε2) | Asp$^{H31}$ (O) | 3.05 | Lys$^{E307}$ (Nζ) | Asp$^{H31}$ (O) |
| Phe$^{E309}$ | Tyr$^{H98}$ (1) | Glu$^{E390}$ (Oε1) | Tyr$^{H32}$ (OH) | 2.48 | Lys$^{E307}$ (Nζ) | Trp$^{H33}$ (N) |
| Thr$^{E330}$ | Trp$^{L50}$ (4), Ser$^{H97}$ (1), Tyr$^{H98}$ (6), Gly$^{H99}$ (2) | Ser$^{E306}$ (Oγ) | Trp$^{H33}$ (Nε1) | 2.62 | Lys$^{E307}$ (Nζ) | Ser$^{H95}$ (O) |
| Gly$^{E331}$ | Asp$^{H100}$ (2) | Asp$^{E333}$ (O) | Arg$^{H56}$ (NH1) | 2.91 | Phe$^{E309}$ (O) | Tyr$^{H98}$ (OH) |
| Thr$^{E332}$ | His$^{L91}$ (2), Tyr$^{L92}$ (2), Thr$^{L93}$ (3), Thr$^{L94}$ (1), Arg$^{H58}$ (6), Asp$^{H100}$ (7) | Thr$^{E332}$ (Oγ1) | Arg$^{H58}$ (NH1) | 2.78 | Thr$^{E330}$ (O) | His$^{L91}$ (Nδ1) |
| Asp$^{E333}$ | Arg$^{H56}$ (6), Arg$^{H58}$ (2) | Lys$^{E307}$ (Nζ) | Ser$^{H95}$ (Oγ) | 2.50 | Thr$^{E330}$ (O) | His$^{L91}$ (O) |
| Ala$^{E365}$ | Tyr$^{L92}$ (1), Thr$^{L93}$ (4) | Lys$^{E307}$ (Nζ) | Ala$^{H96}$ (O) | 2.87 | Thr$^{E330}$ (O) | Asp$^{H100}$ (N) |
| Thr$^{E366}$ | Tyr$^{L92}$ (11) | Gln$^{E391}$ (Oε1) | Ser$^{H97}$ (Oγ) | 2.80 | Thr$^{E332}$ (O) | Thr$^{L93}$ (Oγ1) |
| Ala$^{E367}$ | Trp$^{L50}$ (1), His$^{L91}$ (1), Tyr$^{L92}$ (7) | Ala$^{E308}$ (N) | Ser$^{H97}$ (O) | 2.79 | Thr$^{E332}$ (O) | Thr$^{L94}$ (N) |
| Asn$^{E368}$ | Ser$^{L30}$ (8), Trp$^{L50}$ (7) | Thr$^{E332}$ (N) | Asp$^{H100}$ (Oδ1) | 3.27 | Thr$^{E332}$ (O) | Thr$^{L94}$ (Oγ1) |
| Gly$^{E389}$ | Asp$^{H31}$ (3) | Asn$^{E368}$ (Oδ1) | Ser$^{L30}$ (Oγ) | 2.59 | Ala$^{E365}$ (O) | Thr$^{L93}$ (Oγ1) |
| Glu$^{E390}$ | Tyr$^{H27}$ (3), Thr$^{H28}$ (8), Asp$^{H31}$ (3), Tyr$^{H32}$ (11) | Ala$^{E367}$ (N) | Tyr$^{L92}$ (O) | 2.82 | Ala$^{E365}$ (O) | Thr$^{L94}$ (N) |
| Gln$^{E391}$ | Asp$^{H31}$ (8), Tyr$^{H32}$ (2), Ser$^{H97}$ (5) | Ala$^{E365}$ (O) | Thr$^{L93}$ (Oγ1) | 2.98 | Ala$^{E365}$ (O) | Thr$^{L94}$ (Oγ1) |

[c] Van der Waals contacts have interatomic distance ≤ 4.0 Å
[b] Putative H-bonds defined by HBPlus (McDonald, IK)

SEQUENCE LISTING

<160> NUMBER OF SEQ ID NOS: 4

<210> SEQ ID NO 1
<211> LENGTH: 120
<212> TYPE: PRT
<213> ORGANISM: West Nile Virus

<400> SEQUENCE: 1

```
Gln Leu Lys Gly Thr Thr Tyr Gly Val Cys Ser Lys Ala Phe Lys Phe
 1               5                  10                  15

Leu Gly Thr Pro Ala Asp Thr Gly His Gly Thr Val Val Leu Glu Leu
            20                  25                  30

Gln Tyr Thr Gly Thr Asp Gly Pro Cys Lys Val Pro Ile Ser Ser Val
        35                  40                  45

Ala Ser Leu Asn Asp Leu Thr Pro Val Gly Arg Leu Val Thr Val Asn
50                  55                  60

Pro Phe Val Ser Val Ala Thr Ala Asn Ala Lys Val Leu Ile Glu Leu
65                  70                  75                  80

Glu Pro Pro Phe Gly Asp Ser Tyr Ile Val Val Gly Arg Gly Glu Gln
                85                  90                  95

Gln Ile Asn His His Trp His Lys Ser Gly Ser Ser Ile Gly Lys Ala
            100                 105                 110

Phe Thr Thr Thr Leu Lys Gly Ala
        115                 120
```

<210> SEQ ID NO 2
<211> LENGTH: 118
<212> TYPE: PRT
<213> ORGANISM: West Nile Virus

<400> SEQUENCE: 2

```
Gln Val Gln Leu Gln Gln Ser Gly Ser Glu Leu Met Lys Pro Gly Ala
 1               5                  10                  15

Ser Val Gln Ile Ser Cys Lys Ala Thr Gly Tyr Thr Phe Ser Asp Tyr
            20                  25                  30

Trp Ile Glu Trp Val Lys Gln Arg Pro Gly His Gly Leu Glu Trp Ile
        35                  40                  45

Gly Ile Leu Cys Gly Thr Gly Arg Thr Arg Tyr Asn Glu Lys Leu Lys
    50                  55                  60

Ala Met Ala Thr Phe Thr Ala Asp Thr Ser Ser Asn Thr Ala Phe Met
65                  70                  75                  80

Gln Leu Ser Ser Leu Thr Ser Glu Asp Ser Ala Val Tyr Tyr Cys Ala
                85                  90                  95

Arg Ser Ala Ser Tyr Gly Asp Tyr Ala Asp Tyr Trp Gly His Gly Thr
            100                 105                 110
```

```
Thr Leu Thr Val Ser Ser
        115

<210> SEQ ID NO 3
<211> LENGTH: 107
<212> TYPE: PRT
<213> ORGANISM: West Nile Virus

<400> SEQUENCE: 3

Asp Ile Val Met Thr Gln Ser His Lys Phe Met Ser Thr Ser Val Gly
 1               5                  10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Ser Trp Ala Ser Thr Arg His Thr Gly Val Pro Asp Arg Phe Thr Gly
50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Tyr Thr Thr Pro Leu
                85                  90                  95

Thr Phe Gly Ala Gly Thr Lys Leu Glu Leu Lys
            100                 105

<210> SEQ ID NO 4
<211> LENGTH: 501
<212> TYPE: PRT
<213> ORGANISM: West Nile Virus

<400> SEQUENCE: 4

Phe Asn Cys Leu Gly Met Ser Asn Arg Asp Phe Leu Glu Gly Val Ser
 1               5                  10                  15

Gly Ala Thr Trp Val Asp Leu Val Leu Glu Gly Asp Ser Cys Val Thr
            20                  25                  30

Ile Met Ser Lys Asp Lys Pro Thr Ile Asp Val Lys Met Met Asn Met
        35                  40                  45

Glu Ala Ala Asn Leu Ala Glu Val Arg Ser Tyr Cys Tyr Leu Ala Thr
50                  55                  60

Val Ser Asp Leu Ser Thr Lys Ala Ala Cys Pro Thr Met Gly Glu Ala
65                  70                  75                  80

His Asn Asp Lys Arg Ala Asp Pro Ala Phe Val Cys Arg Gln Gly Val
                85                  90                  95

Val Asp Arg Gly Trp Gly Asn Gly Cys Gly Leu Phe Gly Lys Gly Ser
            100                 105                 110

Ile Asp Thr Cys Ala Lys Phe Ala Cys Ser Thr Lys Ala Ile Gly Arg
        115                 120                 125

Thr Ile Leu Lys Glu Asn Ile Lys Tyr Glu Val Ala Ile Phe Val His
130                 135                 140

Gly Pro Thr Thr Val Glu Ser His Gly Asn Tyr Ser Thr Gln Val Gly
145                 150                 155                 160

Ala Thr Gln Ala Gly Arg Phe Ser Ile Thr Pro Ala Ala Pro Ser Tyr
                165                 170                 175

Thr Leu Lys Leu Gly Glu Tyr Gly Glu Val Thr Val Asp Cys Glu Pro
            180                 185                 190

Arg Ser Gly Ile Asp Thr Asn Ala Tyr Tyr Val Met Thr Val Gly Thr
        195                 200                 205
```

-continued

```
Lys Thr Phe Leu Val His Arg Glu Trp Phe Met Asp Leu Asn Leu Pro
    210             215             220

Trp Ser Ser Ala Gly Ser Thr Val Trp Arg Asn Arg Glu Thr Leu Met
225             230             235             240

Glu Phe Glu Glu Pro His Ala Thr Lys Gln Ser Val Ile Ala Leu Gly
            245             250             255

Ser Gln Glu Gly Ala Leu His Gln Ala Leu Ala Gly Ala Ile Pro Val
            260             265             270

Glu Phe Ser Ser Asn Thr Val Lys Leu Thr Ser Gly His Leu Lys Cys
        275             280             285

Arg Val Lys Met Glu Lys Leu Gln Leu Lys Gly Thr Thr Tyr Gly Val
        290             295             300

Cys Ser Lys Ala Phe Lys Phe Leu Gly Thr Pro Ala Asp Thr Gly His
305             310             315             320

Gly Thr Val Val Leu Glu Leu Gln Tyr Thr Gly Thr Asp Gly Pro Cys
            325             330             335

Lys Val Pro Ile Ser Ser Val Ala Ser Leu Asn Asp Leu Thr Pro Val
            340             345             350

Gly Arg Leu Val Thr Val Asn Pro Phe Val Ser Val Ala Thr Ala Asn
        355             360             365

Ala Lys Val Leu Ile Glu Leu Glu Pro Pro Phe Gly Asp Ser Tyr Ile
    370             375             380

Val Val Gly Arg Gly Glu Gln Gln Ile Asn His His Trp His Lys Ser
385             390             395             400

Gly Ser Ser Ile Gly Lys Ala Phe Thr Thr Thr Leu Lys Gly Ala Gln
            405             410             415

Arg Leu Ala Ala Leu Gly Asp Thr Ala Trp Asp Phe Gly Ser Val Gly
            420             425             430

Gly Val Phe Thr Ser Val Gly Lys Ala Val His Gln Val Phe Gly Gly
        435             440             445

Ala Phe Arg Ser Leu Phe Gly Gly Met Ser Trp Ile Thr Gln Gly Leu
    450             455             460

Leu Gly Ala Leu Leu Leu Trp Met Gly Ile Asn Ala Arg Asp Arg Ser
465             470             475             480

Ile Ala Leu Thr Phe Leu Ala Val Gly Gly Val Leu Leu Phe Leu Ser
            485             490             495

Val Asn Val His Ala
            500
```

CRYSTALS AND STRUCTURE OF DOMAIN III OF WEST NILE VIRUS ENVELOPE PROTEIN IN ASSOCIATION WITH A FAB FRAGMENT OF A NEUTRALIZING ANTIBODY

This application is entitled to and claims benefit of U.S. Provisional Application No. 60/619,273, filed Oct. 14, 2004, and of U.S. Provisional Application No. 60/702,803, filed Jul. 26, 2005, each of which is hereby incorporated by reference in its entirety.

The present invention was made, in part, with support from a grant from the United States Government, NIH grant number A161373. The government of the United States may have certain rights in this invention.

1. FIELD OF THE INVENTION

The present invention provides crystalline forms of domain III of the West Nile Virus ("WNV") envelope protein in complex with a Fab fragment of a neutralizing antibody, methods of obtaining such crystals and high-resolution structures and atomic structure coordinates. The crystals of the invention and the atomic structural information are useful for solving crystal and solution structures of related and unrelated proteins, and for screening for, identifying or designing compounds or antibodies that bind to, modulate a biological activity of, or neutralize infection mediated by flaviviral envelope proteins.

2. BACKGROUND OF THE INVENTION

A member of the flavivirus genus of the Flaviviridae family, WNV is a neurotropic enveloped virus with a single-stranded, positive-polarity 11-kilobase RNA genome and is closely related to viruses that cause dengue fever, yellow fever, and the Japanese, Saint Louis, and Murray Valley encephalitides. WNV cycles between mosquitoes and birds but also infects humans, horses, and other vertebrate species. It is endemic in parts of Africa, Europe, the Middle East, and Asia, and outbreaks throughout the United States during the past five years indicate that it has established its presence in the Western Hemisphere. Infected humans develop a febrile illness that can progress rapidly to a meningitis or fatal encephalitis syndrome. See Granwehr et al., 2004, *Lancet Infect Dis* 4:547-56; Hubalek et al., 1999, *Emerg Inf Dis* 5:643-650; and Petersen et al., 2003, JAMA 290:524-8. At present, treatment is supportive and no vaccine exists for human use.

The molecular and structural basis of antibody-mediated protection against WNV and other flaviviruses remains speculative. Based on the sequencing of in vitro neutralization escape variants and the site-specific substitution of specific charged or polar residues, most neutralizing antibodies against flaviviruses appear to localize to domain III. See Beasley and Aaskov, 2001, *Virology* 279:447-58; Beasley et al., 2002, *J. Virol.* 76:13097-13100; Cecilia and Gould, 1991, *Virology* 181:70-7; Crill and Roehrig, 2001, *J. Virol.* 75:7769-73; Lin et al., 1994, *Virology* 202:885-90; Roehrig et al., 1983, *Virology* 128:118-26; Schlesinger et al., 1996, *J. Gen. Virol.* 77:1277-85; Seif et al., 1995, *Vaccine* 13:1515-21; Volk et al., 2004, *J. Biol. Chem.* 279:38755-38761; and Wu et al., 1997, *Virus. Res.* 51:173-81. However, putative contact residues for individual mAbs that have been identified by neutralization escape may be flawed because mutations may cause local unfolding that abolish multiple antibody epitopes. Moreover, many of these studies did not confirm that the mapped neutralizing mAbs also abolished infection *in vivo* in animals. As an alternative strategy, one group recently used NMR to map a neutralizing mAb against Japanese encephalitis virus (JEV). See Wu et al., 2003, *J. Biol. Chem.* 278: 46007-46013. Chemical shifts in domain III of JEV were detected after mAb binding at residues E302-312, E322-329, E360-372, and E385-392, corresponding to the top portion of an exposed β-barrel. Although additional information was obtained, NMR and its solution structure do not provide any insight as to the structural basis for antibody recognition of the neutralizing epitope.

Recently, prophylactic and therapeutic efficacy of pooled, immune human γ-globulin has been demonstrated in mice infected with WNV. See Agrawal and Petersen, 2003, *J. Infect. Dis.* 188:1-4; Ben-Nathan et al., 2003, *J. Infect. Dis.* 188:5-12; and Engle et al., 2003, *J. Virol.* 77:12941-12949. Because human γ-globulin is made from human blood plasma, it has an inherent risk of transmitting known and unknown infectious agents. More recently, a monoclonal antibody (mAb) therapeutic against WNV E protein has been developed that is ~1,000-fold more potent that pooled human γ-globulin in its ability to neutralize virus infection *in vitro* and *in vivo*. This antibody (E16), which recognizes domain III, was cloned, humanized, expressed and confirmed as therapeutically effective in an established mouse model of WNV infection.

Nonetheless, additional antibodies that can bind and neutralize WNV more strongly may be needed for effective treatment and/or prevention of WNV infection. Such antibodies could be designed and constructed by identifying amino acids of the antibodies that mediate the antigen-antibody interaction. These amino acids can be selectively altered to generate antibody variants that could be screened for enhanced WNV binding and/or neutralization.

Further, small molecule therapeutics that can mimic antibodies that bind and/or neutralize WNV infection would also be of use, as such small molecules may be easier and less expensive to manufacture and easier to administer orally. Such small molecule therapeutics could be designed based on the three-dimensional structure coordinates of an antibody that binds domain III of WNV E protein in complex with the domain III.

In addition, a small molecule therapeutic such as an antigen that mimics the domain III epitope recognized by E16 could be administered to generate an immune response against WNV. A composition comprising an antigen that mimics WNV would provide a safer method of preventing WNV infection. An effective antigen mimic of WNV could be administered, to persons with a functioning immune system, as an immunoprophylactic to raise an immune response against the virus with minimal or no danger of infection caused by the immunoprophylactic itself.

Still further, a small molecule therapeutic that can interact with antibody-WNV complexes to stimulate antibody-mediated neutralization of WNV infection would also be of significant utility in treatment and/or prevention of WNV infection. In addition, a greater understanding of the interaction between neutralizing antibodies and domain III of WNV E protein is needed to inform strategies for designing vaccines that will elicit strong and broadly neutralizing immune responses. The present invention provides a substantial advancement towards these and other unrealized needs.

3. SUMMARY OF THE INVENTION

In one aspect, the invention provides crystalline forms of polypeptide complexes corresponding to a Fab fragment of a neutralizing antibody in complex with domain III of the WNV E protein. The crystals of the invention comprise crystallized polypeptide complexes corresponding to the wild-type or mutated domain III of WNV E protein in complex with a Fab fragment of a neutralizing antibody, e.g., a Fab fragment prepared from monoclonal antibody E16 (WNV DIII-E16 Fab complex). The crystals of the invention include native crystals, in which the crystallized WNV DIII-E16 Fab complex is substantially pure; heavy-atom atom derivative crystals, in which the crystallized WNV DIII-E16 Fab complex is in association with one or more heavy-metal atoms; and poly-crystals, in which the crystallized WNV DIII-E16 Fab complex is in association with one or more additional compounds, including but not limited to, cofactors, ligands, substrates, substrate analogs, inhibitors, allosteric effectors, etc. to form a crystalline poly-complex. Preferably, such compounds bind a catalytic or active site. The poly-crystals may be native poly-crystals, in which the poly-complex is substantially pure, or they may be heavy-atom derivative poly-crystals, in which the poly-complex is in association with one or more heavy-metal atoms.

In certain embodiments, the crystals of the invention are generally characterized by a unit cell of a=52.4+/−0.2 Å, b=83.3+/−0.2 Å, c=110.6+/−0.2 Å, and are preferably of diffraction quality. A typical diffraction pattern is illustrated in FIG. 4. In more preferred embodiments, the crystals of the invention are of sufficient quality to permit the determination of the three-dimensional X-ray diffraction structure of the crystalline polypeptide(s) to high resolution, preferably to a resolution of greater than about 3 Å, typically in the range of about 2 Å to about 3 Å.

The invention also provides methods of making the crystals of the invention. Generally, crystals of the invention are grown by dissolving substantially pure polypeptide complexes in an aqueous buffer that includes a precipitant at a concentration just below that necessary to precipitate the polypeptide complexes. Water is then removed by controlled evaporation to produce precipitating conditions, which are maintained until crystal growth ceases.

Poly-crystals of the invention are prepared by soaking a native crystal prepared according to the above method in a liquor comprising the compound to be added to the poly-crystal of the desired complex. Alternatively, the poly-crystals may be prepared by co-crystallizing the polypeptide complexes in the presence of the compound according to the method discussed above.

Heavy-atom derivative crystals of the invention may be prepared by soaking native crystals or poly-crystals prepared according to the above method in a liquor comprising a salt of a heavy atom or an organometallic compound. Alternatively, heavy-atom derivative crystals may be prepared by crystallizing a polypeptide complex comprising selenomethionine and/or selenocysteine residues according to the methods described previously for preparing native crystals.

In another aspect, the invention provides machine-computer-readable media embedded with the three-dimensional structural information obtained from the crystals of the invention, or portions or substrates thereof. Such three-dimensional structural information will typically include the atomic structure coordinates of the crystallized polypeptide complex or poly-complex, or the atomic structure coordinates of a portion thereof such as, for example, an active or binding site, but may include other structural information, such as vector representations of the atomic structures coordinates, etc. The types of machine- or computer-readable media into which the structural information is embedded typically include magnetic tape, floppy discs, hard disc storage media, optical discs, CD-ROM, DVD, electrical storage media such as RAM or ROM, and hybrids of any of these storage media. Such media further include paper on which is recorded the structural information that can be read by a scanning device and converted into a three-dimensional structure with an OCR. The machine-readable media of the invention may further comprise additional information that is useful for representing the three-dimensional structure, including, but not limited to, thermal parameters, chain identifiers, and connectivity information.

The invention is illustrated by way of working examples demonstrating the crystallization and characterization of crystals, the collection of diffraction data, and the determination and analysis of the three-dimensional structure of WNV DIII-E16 Fab complex.

The atomic structure coordinates and machine-readable media of the invention have a variety of uses. For example, the coordinates are useful for solving the three-dimensional X-ray diffraction and/or solution structures of other proteins, including mutant WNV E proteins, both alone or in complex with E16 Fab, or a portion thereof, complexes comprising WNV E protein and E16 Fab in combination with one or more additional compounds, and unrelated proteins, to high resolution. Structural information may also be used in a variety of molecular modeling and computer-based screening applications to, for example, intelligently design mutants of the WNV E protein and/or a neutralizing antibody, or fragments thereof, that have altered biological activity, to identify additional neutralizing antibodies, or fragments thereof, that bind WNV DIII, to identify antibodies that bind neutralizing epitopes of WNV DIII in preference to enhancing epitopes of WNV DIII, to intelligently design antibodies, or fragments thereof, that bind WNV III with high affinity, or to design vaccines capable of inducing immune responses that inhibit WNV E protein binding.

Thus, in other aspects, the invention provides methods that comprise mutating an amino acid of the antibody which when mutated is predicted to increase the affinity with which the antibody binds the domain III of WNV E protein.

In still other aspects, the invention provides a method for identifying a neutralizing epitope of a domain III of a flaviviral envelope protein, comprising comparing an amino acid sequence of the domain III of the flaviviral envelope protein to an amino acid sequence of a domain III of a WNV E protein, and identifying the amino acids of the domain III of the flaviviral envelope protein corresponding to a neutralizing epitope of the domain III of the WNV E protein, thereby identifying the neutralizing epitope of the flaviviral envelope protein.

In yet other aspects, the invention provides a purified antibody that specifically binds a neutralizing epitope of domain III of WNV E protein, with the proviso that the antibody is not 5H10, 3A3, 5C5, 7H2, 11C, 17C8, 10C5, 8B10, E1, E16, E24, E27, E33, E34, E40, E43, E47, E49, and/or E58. These monoclonal antibodies are described in Beasley & Barrett, 2002, *J. Virol* 76:13097-13100; Oliphant et al., 2005, *Nature Medicine* 11:522-530; and Sanchez et al., 2005, *Virology* 336:70-82, each of which is hereby incorporated by reference in its entirety.

In still other aspects, the invention provides a pharmaceutical composition comprising an antibody of the invention and a pharmaceutically acceptable excipient, diluent, vehicle, or carrier.

In yet other aspects, the invention provides a kit comprising a pharmaceutical composition of the invention.

In still other aspects, the invention provides a method of treating WNV infection, comprising administering to a subject an effective amount of a purified antibody that binds a neutralizing epitope of domain III of WNV E protein, with the proviso that the antibody is not 5H10, 3A3, 5C5, 7H2, 11C, 17C8, 10C5, 8B10, E1, E16, E24, E27, E33, E34, E40, E43, E47, E49, and/or E58.

In yet other aspects, the invention provides a method of preventing WNV infection, comprising administering to a subject an effective amount of a purified antibody that binds a neutralizing epitope of domain III of WNV E protein with higher affinity than the antibody binds an enhancing epitope of domain III of WNV E protein at neutralizing concentrations, with the proviso that the antibody is not 5H10, 3A3, 5C5, 7H2, 11C, 17C8, 10C5, 8B10, E1, E16, E24, E27, E33, E34, E40, E43, E47, E49, and/or E58.

In still other aspects, the invention provides a WNV immunogen comprising a peptide corresponding to amino acids 300-309, 330-333, 365-368, or 389-391 of WNV E protein, using SEQ ID NO:4 for numbering. In certain embodiments, the peptide is arranged in the three dimensional conformation of amino acids 300-309, 330-333, 365-368, or 389-391, respectively, of WNV E protein according to the structural coordinates shown in Table 7. In certain embodiments, the immunogen does not comprise the entire amino acid sequence of domain III of WNV E protein.

In yet other aspects, the invention provides a pharmaceutical composition comprising a WNV immunogen of the invention and a pharmaceutically acceptable excipient, diluent, vehicle, or carrier.

In still other aspects, the invention provides a method of inducing in a subject an immune response against domain III of WNV E protein, comprising administering to a subject a WNV immunogen of the invention.

The atomic structure coordinates and machine-readable media may also be used to computationally design and to identify compounds that bind the polypeptide(s) or a portion or fragment of the polypeptide(s), such as the active site. Such compounds may be used as lead compounds in pharmaceutical efforts to identify compounds as a therapeutic or prophylactic approach toward the prevention or treatment of, e.g., WNV or other flaviviral infection.

The examples demonstrate that the crystal structure of WNV DIII-E16 Fab complex has been determined to 2.5 Å resolution.

3.1 Abbreviations

The amino acid notations used herein for the twenty genetically encoded L-amino acids are conventional and are as follows:

| Amino Acid | One-Letter Symbol | Three-Letter Symbol |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |

-continued

| Amino Acid | One-Letter Symbol | Three-Letter Symbol |
|---|---|---|
| Tryptophan | W | Trp |
| Tyrosine | Y | Tyr |
| Valine | V | Val |

As used herein, unless specifically delineated otherwise, the three-letter amino acid abbreviations designate amino acids in the L-configuration. Amino acids in the D-configuration are preceded with a "D-." For example, Arg designates L-arginine and D-Arg designates D-arginine. Likewise, the capital one-letter abbreviations refer to amino acids in the L-configuration. Lower-case one-letter abbreviations designate amino acids in the D-configuration. For example, "R" designates L-arginine and "r" designates D-arginine.

Unless noted otherwise, when polypeptide sequences are presented as a series of one-letter and/or three-letter abbreviations, the sequences are presented in the N→C direction, in accordance with common practice.

The abbreviation "WNV" is used herein to refer to "West Nile Virus."

The abbreviation "E protein" is used herein to refer to "envelope protein."

The abbreviation "DIII" is used herein to refer to "domain III of envelope protein."

3.2 DEFINITIONS

As used herein, the following terms shall have the following meanings:

"Genetically Encoded Amino Acid" refers to L-isomers of the twenty amino acids that are defined by genetic codons. The genetically encoded amino acids are the L-isomers of glycine, alanine, valine, leucine, isoleucine, serine, methionine, threonine, phenylalanine, tyrosine, tryptophan, cysteine, proline, histidine, aspartic acid, asparagine, glutamic acid, glutamine, arginine and lysine.

"Genetically Non-Encoded Amino Acid" refers to amino acids that are not defined by genetic codons. Genetically non-encoded amino acids include derivatives or analogs of the genetically-encoded amino acids that are capable of being enzymatically incorporated into nascent polypeptides using conventional expression systems, such as selenomethionine (SeMet) and selenocysteine (SeCys); isomers of the genetically-encoded amino acids that are not capable of being enzymatically incorporated into nascent polypeptides using conventional expression systems, such as D-isomers of the genetically-encoded amino acids; L- and D-isomers of naturally occurring a-amino acids that are not defined by genetic codons, such as α-aminoisobutyric acid (Aib); L- and D-isomers of synthetic α-amino acids that are not defined by genetic codons, such as _____; and other amino acids such as β-amino acids, γ-amino acids, etc. In addition to the D-isomers of the genetically-encoded amino acids, common genetically non-encoded amino acids include, but are not limited to norleucine (Nle), penicillamine (Pen), N-methylvaline (MeVal), homocysteine (hCys), homoserine (hSer), 2,3-diaminobutyric acid (Dab) and ornithine (Orn). Additional exemplary genetically non-encoded amino acids are found, for example, in *Practical Handbook of Biochemistry and Molecular Biology,* 1989, Fasman, Ed., CRC Press, Inc., Boca Raton, Fla., pp. 3-76 and the various references cited therein.

"Hydrophilic Amino Acid" refers to an amino acid having a side chain exhibiting a hydrophobicity of less than zero according to the normalized consensus hydrophobicity scale of Eisenberg et al., 1984, *J. Mol. Biol.* 179:125-142. Genetically encoded hydrophilic amino acids include Thr (T), Ser (S), His (H), Glu (E), Asn (N), Gln (Q), Asp (D), Lys (K) and Arg (R). Genetically non-encoded hydrophilic amino acids include the D-isomers of the above-listed genetically-encoded amino acids, ornithine (Orn), 2,3-diaminobutyric acid (Dab) and homoserine (hSer).

"Acidic Amino Acid" refers to a hydrophilic amino acid having a side chain pK value of less than 7 under physiological conditions. Acidic amino acids typically have negatively charged side chains at physiological pH due to loss of a hydrogen ion. Genetically encoded acidic amino acids include Glu (E) and Asp (D). Genetically non-encoded acidic amino acids include D-Glu (e) and D-Asp (d).

"Basic Amino Acid" refers to a hydrophilic amino acid having a side chain pK value of greater than 7 under physiological conditions. Basic amino acids typically have positively charged side chains at physiological pH due to association with hydronium ion. Genetically encoded basic amino acids include His (H), Arg (R) and Lys (K). Genetically non-encoded basic amino acids include the D-isomers of the above-listed genetically-encoded amino acids, ornithine (Orn) and 2,3-diaminobutyric acid (Dab).

"Polar Amino Acid" refers to a hydrophilic amino acid having a side chain that is uncharged at physiological pH, but which comprises at least one covalent bond in which the pair of electrons shared in common by two atoms is held more closely by one of the atoms. Genetically encoded polar amino acids include Asn (N), Gln (Q), Ser (S), and Thr (T). Genetically non-encoded polar amino acids include the D-isomers of the above-listed genetically-encoded amino acids and homoserine (hSer).

"Hydrophobic Amino Acid" refers to an amino acid having a side chain exhibiting a hydrophobicity of greater than zero according to the normalized consensus hydrophobicity scale of Eisenberg et al., 1984, *J. Mol. Biol.* 179:125-142. Genetically encoded hydrophobic amino acids include Pro (P), Ile (I), Phe (F), Val (V), Leu (L), Trp (W), Met (M), Ala (A), Gly (G) and Tyr (Y). Genetically non-encoded hydrophobic amino acids include the D-isomers of the above-listed genetically-encoded amino acids, norleucine (Nle) and N-methyl valine (MeVal).

"Aromatic Amino Acid" refers to a hydrophobic amino acid having a side chain comprising at least one aromatic or heteroaromatic ring. The aromatic or heteroaromatic ring may contain one or more substituents such as —OH, —SH, —CN, —F, —Cl, —Br, —I, —NO$_2$, —NO, —NH$_2$, —NHR, —NRR, —C(O)R, —C(O)OH, —C(O)OR, —C(O)NH$_2$, —C(O)NHR, —C(O)NRR and the like where each R is independently (C$_1$-C$_6$) alkyl, (C$_1$-C$_6$) alkenyl, or (C$_1$-C$_6$) alkynyl. Genetically encoded aromatic amino acids include Phe (F), Tyr (Y), Trp (W) and His (H). Genetically non-encoded aromatic amino acids include the D-isomers of the above-listed genetically-encoded amino acids.

"Apolar Amino Acid" refers to a hydrophobic amino acid having a side chain that is uncharged at physiological pH and which has bonds in which the pair of electrons shared in common by two atoms is generally held equally by each of the two atoms (i.e., the side chain is not polar). Genetically encoded apolar amino acids include Leu (L), Val (V), Ile (I), Met (M), Gly (G) and Ala (A). Genetically non-encoded apolar amino acids include the D-isomers of the above-listed genetically-encoded amino acids, norleucine (Nle) and N-methyl valine (MeVal).

"Aliphatic Amino Acid" refers to a hydrophobic amino acid having an aliphatic hydrocarbon side chain. Genetically encoded aliphatic amino acids include Ala (A), Val (V), Leu (L) and Ile (I). Genetically non-encoded aliphatic amino acids include the D-isomers of the above-listed genetically-encoded amino acids, norleucine (Nle) and N-methyl valine (MeVal).

"Helix-Breaking Amino Acid" refers to those amino acids that have a propensity to disrupt the structure of α-helices when contained at internal positions within the helix. Amino acid residues exhibiting helix-breaking properties are well-known in the art (see, e.g., Chou & Fasman, 1978, *Ann. Rev. Biochem.* 47:251-276) and include Pro (P), D-Pro (p), Gly (G) and potentially all D-amino acids (when contained in an L-polypeptide; conversely, L-amino acids disrupt helical structure when contained in a D-polypeptide).

"Cysteine-like Amino Acid" refers to an amino acid having a side chain capable of participating in a disulfide linkage. Thus, cysteine-like amino acids generally have a side chain containing at least one thiol (—SH) group. Cysteine-like amino acids are unusual in that they can form disulfide bridges with other cysteine-like amino acids. The ability of Cys (C) residues and other cysteine-like amino acids to exist in a polypeptide in either the reduced free —SH or oxidized disulfide-bridged form affects whether they contribute net hydrophobic or hydrophilic character to a polypeptide. Thus, while Cys (C) exhibits a hydrophobicity of 0.29 according to the consensus scale of Eisenberg (Eisenberg, 1984, supra), it is to be understood that for purposes of the present invention Cys (C) is categorized as a polar hydrophilic amino acid, notwithstanding the general classifications defined above. Other cysteine-like amino acids are similarly categorized as polar hydrophilic amino acids. Typical cysteine-like residues include, for example, penicillamine (Pen), homocysteine (hCys), etc.

As will be appreciated by those of skill in the art, the above-defined classes or categories are not mutually exclusive. Thus, amino acids having side chains exhibiting two or more physico-chemical properties can be included in multiple categories. For example, amino acid side chains having aromatic groups that are further substituted with polar substituents, such as Tyr (Y), may exhibit both aromatic hydrophobic properties and polar or hydrophilic properties, and could therefore be included in both the aromatic and polar categories. Typically, amino acids will be categorized in the class or classes that most closely define their net physico-chemical properties. The appropriate categorization of any amino acid will be apparent to those of skill in the art.

The classifications of the genetically encoded and common non-encoded amino acids according to the categories defined above are summarized in Table I, below. It is to be understood that Table I is for illustrative purposes only and does not purport to be an exhaustive list of the amino acid residues belonging to each class. Other amino acid residues not specifically mentioned herein can be readily categorized based on their observed physical and chemical properties in light of the definitions provided herein.

TABLE I

CLASSIFICATIONS OF COMMONLY ENCOUNTERED AMINO ACIDS

| Classification | Genetically Encoded | Genetically Non-Encoded |
|---|---|---|
| Hydrophobic | | |
| Aromatic | F, Y, W, H | f, y, w, h |
| Apolar | L, V, I, M, G, A, P | l, v, i, m, a, p, Nle, MeVal |
| Aliphatic | A, V, L, I | a, v, l, I, Nle, MeVal |

TABLE I-continued

CLASSIFICATIONS OF COMMONLY
ENCOUNTERED AMINO ACIDS

| Classification | Genetically Encoded | Genetically Non-Encoded |
|---|---|---|
| Hydrophilic | | |
| Acidic | D, E | d, e |
| Basic | H, K, R | h, k, r, Orn, Dab |
| Polar | C, Q, N, S, T | c, q, n, s, t, hSer |
| Helix-Breaking | P, G | P |

"Wild-type domain III of West Nile Virus E protein Domain III" or "wild-type domain III of WNV E protein" refers to a polypeptide having an amino acid sequence that corresponds identically to the amino acid sequence of a naturally-occurring domain III of WNV E protein.

A "neutralizing antibody" refers to a monoclonal antibody that can bind to an envelope protein of a flavivirus and reduce or prevent infection by a flavivirus of a permissive cell.

An "antibody" or "antibodies" refers to monoclonal antibodies, multispecific antibodies, human antibodies, humanized antibodies, synthetic antibodies, chimeric antibodies, camelized antibodies, single-chain Fvs (scFv), single chain antibodies, Fab fragments, F(ab') fragments, disulfide-linked Fvs (sdFv), intrabodies, and anti-idiotypic (anti-Id) antibodies (including, e.g., anti-Id and anti-anti-Id antibodies), bispecific, and epitope-binding fragments of any of the above. In particular, antibodies include immunoglobulin molecules and immunologically active fragments of immunoglobulin molecules, i.e., molecules that contain an antigen binding site. Immunoglobulin molecules can be of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass.

A "Fab" or a "Fab fragment" refers to a portion of a monoclonal antibody that corresponds to the constant and variable regions of an immunoglobulin light chain in association with the first constant region ($C_H1$ domain), variable region, and a portion of the hinge region of an immunoglobulin heavy chain.

"Domain III of West Nile Virus E protein comiplexed with E16 Fab," "Domain III of WNV E protein complexed with E16 Fab," or "WNV DIII-E16 Fab complex," or "WNV DIII-Fab complex" refers to E16 Fab in association with domain III of WNV E protein, as each of those terms is defined herein.

"Crystallized domain III of West Nile Virus E Protein complexed with a Fab fragment of a neutralizing antibody," "crystallized domain III of WNV E protein complexed with a Fab fragment of a neutralizing antibody," "crystallized WNV DIII-Fab complex," or "crystallized WNV DIII-E16 Fab complex" refers to a complex comprising a polypeptide having an amino acid sequence which corresponds identically to SEQ ID NO:1, a polypeptide having an amino acid sequence which corresponds exactly to SEQ ID NO:2, and a polypeptide having an amino acid sequence which corresponds exactly to SEQ ID NO:3, and which complex is in crystalline form. Thus, "crystallized domain III of West Nile Virus E Protein complexed with a Fab fragment of a neutralizing antibody," "crystallized domain III of WNV E protein complexed with a Fab fragment of a neutralizing antibody," or "crystallized WNV DIII-Fab complex" each refers to a complex of polypeptides comprising domain III of WNV E protein complexed with a Fab fragment of the neutralizing antibody E16.

"Association" refers to a condition of proximity between a chemical entity or compound, or portions or fragments thereof, and a polypeptide, or portions or fragments thereof. The association may be non-covalent, i.e., where the juxtaposition is energetically favored by, e.g., hydrogen-bonding, van der Waals, electrostatic or hydrophobic interactions, or it may be covalent.

"Poly-Complex," as used herein, refers to a polypeptide complex in association with one or more additional compounds beyond those present in the polypeptide complex. Such compounds include, by way of example and not limitation, cofactors, ligands, substrates, substrate analogues, inhibitors, allosteric effectors, etc.

"Domain III" of WNV E protein or "WNV DIII" refers to amino acids 296 to 415 of WNV E protein.

"Mutant" refers to a polypeptide or combination of polypeptides characterized by an amino acid sequence that differs from the wild-type sequence(s) by the substitution of at least one amino acid residue of the wild-type sequence(s) with a different amino acid residue and/or by the addition and/or deletion of one or more amino acid residues to or from the wild-type sequence(s). The additions and/or deletions can be from an internal region of the wild-type sequence and/or at either or both of the N- or C-termini. A mutant may have, but need not have, receptor binding, in the case of mutant WNV E proteins, or neutralization, in the case of mutant antibodies or antibody fragments, activity. Preferably, a mutant displays biological activity that is substantially similar to that of the wild-type WNV E protein or antibody or antibody fragment.

"Conservative Mutant" refers to a mutant in which at least one amino acid residue from the wild-type sequence(s) is substituted with a different amino acid residue that has similar physical and chemical properties, i.e., an amino acid residue that is a member of the same class or category, as defined above. For example, a conservative mutant may be a polypeptide or combination of polypeptides that differs in amino acid sequence from the wild-type sequence(s) by the substitution of a specific aromatic Phe (F) residue with an aromatic Tyr (Y) or Trp (W) residue.

"Non-Conservative Mutant" refers to a mutant in which at least one amino acid residue from the wild-type sequence(s) is substituted with a different amino acid residue that has dissimilar physical and/or chemical properties, i.e., an amino acid residue that is a member of a different class or category, as defined above. For example, a non-conservative mutant may be a polypeptide or combination of polypeptides that differs in amino acid sequence from the wild-type sequence by the substitution of an acidic Glu (E) residue with a basic Arg (R), Lys (K) or Orn residue.

"Deletion Mutant" refers to a mutant having an amino acid sequence or sequences that differs from the wild-type sequence(s) by the deletion of one or more amino acid residues from the wild-type sequence(s). The residues may be deleted from internal regions of the wild-type sequence(s) and/or from one or both termini.

"Truncated Mutant" refers to a deletion mutant in which the deleted residues are from the N- and/or C-terminus of the wild-type sequence(s).

"Extended Mutant" refers to a mutant in which additional residues are added to the N- and/or C-terminus of the wild-type sequence(s).

"Methionine mutant" refers to (1) a mutant in which at least one methionine residue of the wild-type sequence(s) is replaced with another residue, preferably with an aliphatic residue, most preferably with a Leu (L) or Ile (I) residue; or (2) a mutant in which a non-methionine residue, preferably an aliphatic residue, most preferably a Leu (L) or Ile (I) residue, of the wild-type sequence(s) is replaced with a methionine residue.

"Selenomethionine mutant" refers to (1) a mutant which includes at least one selenomethionine (SeMet) residue, typically by substitution of a Met residue of the wild-type sequence(s) with a SeMet residue, or by addition of one or more SeMet residues at one or both termini, or (2) a methionine mutant in which at least one Met residue is substituted with a SeMet residue. Preferred SeMet mutants are those in which each Met residue is substituted with a SeMet residue.

"Cysteine mutant" refers to (1) a mutant in which at least one cysteine residue of the wild-type sequence(s) is replaced with another residue, preferably with a Ser (S) residue; or (2) a mutant in which a non-cysteine residue, preferably a Ser (S) residue, of the wild-type sequence(s) is replaced with a cysteine residue.

"Selenocysteine mutant" refers to (1) a mutant which includes at least one selenocysteine (SeCys) residue, typically by substitution of a Cys residue of the wild-type sequence(s) with a SeCys residue, or by addition of one or more SeCys residues at one or both termini, or (2) a cysteine mutant in which at least one Cys residue is substituted with a SeCys residue. Preferred SeCys mutants are those in which each Cys residue is substituted with a SeCys residue.

"Homologue" refers to a polypeptide having at least 80% amino acid sequence identity or having a BLAST score of $1 \times 10^{-6}$ over at least 100 amino acids (Altschul et al., 1997, *Nucleic Acids Res.* 25:3389-402) with WNV E protein or any functional domain, e.g., domain III, of WNV E protein, as defined by Mukhopadhyay et al., 2003, *Science* 302:248.

"Polypeptide complex" refers to an association of two or more, usually three polypeptides. For example, a polypeptide complex as used herein includes domain III of WNV E protein in association with a Fab fragment of a neutralizing antibody, as each of these terms is defined herein.

"Crystal" refers to a composition comprising a polypeptide complex in crystalline form. The term "crystal" includes native crystals, heavy-atom derivative crystals and poly-crystals, as defined herein.

"Native Crystal" refers to a crystal wherein the polypeptide complex is substantially pure. As used herein, native crystals do not include crystals of polypeptide complexes comprising amino acids that are modified with heavy atoms, such as crystals of selenomethionine mutants, selenocysteine mutants, etc.

"Heavy-atom Derivative Crystal" refers to a crystal wherein the polypeptide complex is in association with one or more heavy-metal atoms. As used herein, heavy-atom derivative crystals include native crystals into which a heavy metal atom is soaked, as well as crystals of selenomethionine mutants and selenocysteine mutants.

"Poly-Crystal" refers to a composition comprising a polycomplex, as defined above, in crystalline form. Poly-crystals include native poly-crystals and heavy-atom derivative poly-crystals.

"X-ray Diffraction" refers to a type of wave interference created when high energy X-ray radiation interacts with any obstruction in its traveling path. The obstruction is often in the form of a crystal of protein, nucleic acid, or inorganic compound. The electrons that surround the atoms in the crystal, rather than the atomic nuclei, are the entities which physically interact with the incoming X-ray photons. When X-ray radiation hits the atoms in a crystal, they make the electronic clouds of the atoms move as does any electromagnetic wave. The re-emitted X-ray radiation gives rise to constructive or destructive interferences. This phenomenon is called X-ray diffraction. In X-ray crystallography, the X-ray diffraction patterns of closely spaced lattices of atoms in the crystal are recorded and then analyzed to reveal the structural nature of the crystal. For example, the spacing between the crystal lattices can be determined using Bragg's law. X-ray diffraction is widely used in chemistry and biochemistry to determine the structures of an immense variety of molecules, including inorganic compounds, DNA and proteins. X-ray diffraction is commonly carried out using single crystals of a material, but if these are not available, microcrystalline powdered samples may also be used, although this requires different equipment. A detailed discussion on X-ray diffraction may be found in Chapter 4 in "Principles of Protein X-ray Crystallography" by Drenth, second edition 1999, Springer-Verlag Inc.

"Bragg's Law" refers to the principle that defines the diffraction conditions that give rise to constructive interferences. When the phase shift of the incident radiation is proportional to $2\pi$, the condition can be expressed as: $n\lambda=2d \sin(\theta)$, where n is an integer; $\lambda$ is the wavelength of the X-ray radiation, or radiations caused by moving electrons, protons and neutrons; d is the spacing between the planes in the atomic lattice, and $\theta$ is the angle between the incident ray and the scattering planes.

"Laue Diffraction" refers to the diffraction pattern obtained from a stationary crystal exposed to a continuous range of wavelengths of X-rays (e.g. polychromatic or "white" radiation). The application of monochromatic X-ray radiation limited the use of Laue diffraction until the availability of synchrotrons that provide fully polychromatic beams with smooth spectral profiles. Synchrotron radiations have high intensity, very small divergence, which renders them ideal sources for Laue diffraction of protein crystals. There are at least two practical variants of the Laue method, the back-reflection and the transmission Laue diffraction. In the back-reflection method, the reflection recorder is placed between the X-ray source and the crystal. The beams that are diffracted in a backward direction are recorded. One side of the cone of Laue reflections is defined by the transmitted beam. The recorder intersects the cone, with the diffraction spots generally lying on a hyperbola. In the transmission Laue diffraction, the reflection recorder is placed behind the crystal to record beams which are transmitted through the crystal. One side of the cone of Laue reflections is defined by the transmitted beam. The recorder intersects the cone, with the diffraction spots generally lying on an ellipse. Under Laue diffraction, protein diffraction pattern at high intensity synchrotron X-ray sources can be taken in times as short as 150 picoseconds (Srajer et al., 1996, *Science* 274:1726-1729). The greatest advantage of Laue diffraction is its time efficiency under synchrotron radiations. Laue diffraction is extensively discussed in "Time resolved macromolecular crystallography," by Cruickshank et al., 1992, Oxford University Press.

"Neutron Diffraction" refers to a crystallography technique that uses neutrons to determine the atomic structure of a material. Neutrons are particles found in the atomic nucleus. In a nuclear reactor, neutrons can be set free when nuclei decay (fission, radioactivity). All quantum particles can exhibit wave phenomena we typically associate with light or sound. Diffraction is one of these phenomena; it occurs when waves encounter obstacles whose size is comparable with the wavelength. If the wavelength of a quantum particle is short enough, atoms or their nuclei can serve as diffraction obstacles. When neutrons from a reactor are slowed down and selected properly, their wavelength lies near one angstrom (0.1 nanometer), the typical separation between atoms in a solid material. A neutron diffraction measurement typically uses a neutron source (e.g. a nuclear reactor or spallation source), a target (the material to be studied), and a detector. Other components may be needed to select the desired neutron wavelength. Some parts of the setup may also be movable. Since neutrons are not charged, they do not interact with the electron cloud surrounding the atom (unlike X-ray or electron diffraction). The neutrons will only interact with the nucleus of the atom. Thus, neutron diffraction reveals the atomic structure but not the charge distribution around the atom, although the two are usually very similar. Neutron diffraction reveals structural details of the target material, which are measured by recording the way in which neutrons are deflected. Neutrons can also change their speed during the scattering experiment; this can be used to study the types of vibrations that can occur in a solid. An important difference between neutron and X-ray diffraction is that neutrons are sensitive to magnetic forces in the material. The application of neutron diffraction in protein structure determination, in particular in determining the hydration level of protein crystals, is discussed in detail in articles by Cheng and Schoenborn, 1990, *Acta Cryst. B*46: 195-208; Langan et al., 2004, *J. Appl. Cryst.* 37:24-31; and Steinbach and Brooks, 1993, *Proc. Natl. Acad. Sci. USA* 90:9135-9139.

"Electron Diffraction" refers to the diffractions where the incident radiation is created by fast-moving electrons. The electrons are deflected not as particles but as waves, as in classical diffraction. The technique is typically used on crystal samples that have a regularly spaced atomic lattice. Most electron diffraction is performed with high energy electrons whose wavelengths are orders of magnitude smaller than the interplanar spacing in most crystals. For example, for 100 keV electrons, their wavelength $\lambda$ will be shorter than $3.7 \times 10^{-12}$ m. Typical lattice parameters for crystals are around 0.3 nanometers. The electrons are scattered by interaction with the positively charged atomic nuclei. Electrons are charged particles that interact very strongly with solids, so their penetration of crystals is very limited. Low-energy Electron Diffraction (LEED) and Reflection High-Energy Electron Diffraction (RHEED) are therefore considered to be surface science techniques, while transmission electron diffraction is limited to specimens less than 1 mm thick. In recent studies, however, electron diffraction has been applied to detect structural changes in the photo cycle of bacteriorhodopsin (Subramaniam et al., 1993, *EMBO J.* 12:1-8).

"Crystallization" in the context of protein X-ray crystallography refers to the processes during which soluble proteins are transformed into their crystalline forms. Crystals of a protein can be grown out of its solution state under experimental conditions that allow controlled phase transition. Such experimental conditions include a mixture of multiple solutions that often contain an aqueous solution of the target protein, a solution of one or a mixture of precipitants, and one or more compounds that contribute to the overall pH or ionic strength of the final mixture.

"Mother liquor" refers to the impure or complex residual solution that remains after the crystallization process. Once crystals are formed, they can be preserved in mother liquor when other experimental conditions remain unchanged. Solutions resembling the composition of a mother liquor are often used as carrier solutions for incorporating additional reagents into the already formed crystals, such as introducing heavy atoms or cryoprotectants.

"Diffraction Quality Crystal" refers to a crystal that is well-ordered and of a sufficient size, i.e., at least 10 μm, preferably at least 50 μm, and most preferably at least 100 μm in its smallest dimension such that it produces measurable diffraction to at least 3 Å resolution, preferably to at least 2 Å resolution, and most preferably to at least 1.5 Å resolution or lower. Diffraction quality crystals include native crystals, heavy-atom derivative crystals, and poly-crystals.

"Unit Cell" refers to the smallest and simplest volume element (i.e., parallelpiped-shaped block) of a crystal that is completely representative of the unit or pattern of the crystal, such that the entire crystal can be generated by translation of the unit cell. The dimensions of the unit cell are defined by six numbers: dimensions a, b and c and angles $\alpha$, $\beta$ and $\gamma$ (Blundel et al., 1976, Protein Crystallography, Academic Press). A crystal is an efficiently packed array of many unit cells.

"Triclinic Unit Cell" refers to a unit cell in which a $\neq$ b $\neq$ c and $\alpha \neq \beta \neq \gamma$.

"Monoclinic Unit Cell" refers to a unit cell in which a$\neq$b$\neq$c; $\alpha=\gamma=90°$; and $\beta \neq 90°$, defined to be $\geqq 90°$.

"Orthorhombic Unit Cell" refers to a unit cell in which a$\neq$b$\neq$c; and $\alpha=\beta=\gamma 90°$.

"Tetragonal Unit Cell" refers to a unit cell in which a$\neq$b$\neq$c; and $\alpha=\beta=\gamma 90°$.

"Trigonal/Rhombohedral Unit Cell" refers to a unit cell in which a$\neq$b$\neq$c; and $\alpha=\beta=\gamma \neq 90°$.

"Trigonal/Hexagonal Unit Cell" refers to a unit cell in which a=b=c; $\alpha=\beta=90°$; and $\gamma=120°$.

"Cubic Unit Cell" refers to a unit cell in which a=b=c; and $\alpha=\beta=\gamma 90°$.

"Crystal Lattice" refers to the array of points defined by the vertices of packed unit cells.

"Space Group" refers to the set of symmetry operations of a unit cell. In a space group designation (e.g., C2) the capital letter indicates the lattice type and the other symbols represent symmetry operations that can be carried out on the unit cell without changing its appearance.

"Asymmetric Unit" refers to the largest aggregate of molecules in the unit cell that possesses no symmetry elements that are part of the space group symmetry, but that can be juxtaposed on other identical entities by symmetry operations.

"Crystallogralhically-Related Dimer" refers to a dimer of two molecules wherein the symmetry axes or planes that relate the two molecules comprising the dimer coincide with the symmetry axes or planes of the crystal lattice.

"Non-Crystallogralphically-Related Dimer" refers to a dimer of two molecules wherein the symmetry axes or planes that relate the two molecules comprising the dimer do not coincide with the symmetry axes or planes of the crystal lattice.

"Isomorphous Replacement" refers to the method of using heavy-atom derivative crystals to obtain the phase information necessary to elucidate the three-dimensional structure of a crystallized polypeptide (Blundel et al., 1976, Protein Crystallography, Academic Press).

"Multi-Wavelength Anomalous Dispersion or MAD" refers to a crystallographic technique in which X-ray diffraction data are collected at several different wavelengths from a single heavy-atom derivative crystal, wherein the heavy atom has absorption edges near the energy of incoming X-ray radiation. The resonance between X-rays and electron orbitals leads to differences in X-ray scattering from absorption of the X-rays (known as anomalous scattering) and permits the locations of the heavy atoms to be identified, which in turn provides phase information for a crystal of a polypeptide. A detailed discussion of MAD analysis can be found in Hendrickson, 1985, *Trans. Am. Crystallogr. Assoc.* 21:11; Hendrickson et al., 1990, *EMBO J.* 9:1665; and Hendrickson, 1991, *Science* 4:91.

"Single Wavelength Anomalous Dispersion or SAD" refers to a crystallographic technique in which X-ray diffraction data are collected at a single wavelength from a single native or heavy-atom derivative crystal, and phase information is extracted using anomalous scattering information from atoms such as sulfur or chlorine in the native crystal or from the heavy atoms in the heavy-atom derivative crystal. The wavelength of X-rays used to collect data for this phasing technique need not be close to the absorption edge of the anomalous scatterer. A detailed discussion of SAD analysis can be found in Brodersen et al., 2000, *Acta Cryst., D*56:431-441.

"Single Isomorphous Replacement With Anomalous Scattering or SIRAS" refers to a crystallographic technique that combines isomorphous replacement and anomalous scattering techniques to provide phase information for a crystal of a polypeptide. X-ray diffraction data are collected at a single wavelength, usually from a single heavy-atom derivative crystal. Phase information obtained only from the location of the heavy atoms in a single heavy-atom derivative crystal leads to an ambiguity in the phase angle, which is resolved using anomalous scattering from the heavy atoms. Phase information is therefore extracted from both the location of the heavy atoms and from anomalous scattering of the heavy atoms. A detailed discussion of SIRAS analysis can be found in North, 1965, *Acta Cryst.* 18:212-216; Matthews, 1966, *Acta Cryst.* 20:82-86.

"Molecular Replacement" refers to the method of calculating initial phases for a new crystal of a polypeptide whose structure coordinates are unknown by orienting and positioning a polypeptide whose structure coordinates are known within the unit cell of the new crystal so as to best account for the observed diffraction pattern of the new crystal. Phases are then calculated from the oriented and positioned polypeptide and combined with observed amplitudes to provide an approximate Fourier synthesis of the structure of the polypeptides comprising the new crystal (Jones et al., 1991, *Acta Crystallogr.* 47:753-70; Brunger et al., 1998, *Acta Crystallogr. D. Biol. Crystallogr.* 54:905-21).

"Having substantially the same three-dimensional structure" refers to a polypeptide that is characterized by a set of atomic structure coordinates that have a root mean square deviation (r.m.s.d.) of less than or equal to about 2 Å when superimposed onto the atomic structure coordinates of Table 7 when at least about 50% to 100% of the Cα atoms of the coordinates are included in the superposition.

"Cα" As used herein, "Cα" refers to the alpha carbon of an amino acid residue.

A "neutralizing epitope" refers to an epitope of a flaviviral envelope protein that is specifically bound by an antibody that prevents effective infection by the flavivirus of a cell that would ordinarily be susceptible to infection by the flavivirus, when the antibody is present at neutralizing concentrations. One example of a neutralizing concentration of an antibody as determined by the plaque reduction neutralization test (PRNT$_{50}$) is at least about 10 ng/ml. For example, a WNV neutralizing epitope is defined by the region, or a portion thereof, contacted by the monoclonal antibody E16.

An "enhancing epitope" refers to an epitope of a flaviviral envelope protein that is specifically bound by an antibody that enhances infection by a flavivirus of cells expressing an Fc receptor, e.g., the Fcγ receptor, when the antibody is present at all concentrations in which antibody binding to virus occurs. It should be noted that neutralizing antibodies also can enhance infection, but only when their occupancy on the virion falls below a certain level."

"Purified," when used in relation to an antibody, refers to a composition of antibodies that each have substantially similar specificities; e.g., the antibodies in the composition each bind essentially the same epitope. One method to obtain a purified antibody is to affinity purify the antibody from a polyclonal antibody preparation using a molecule that comprises the epitope of interest but not undesirable epitope(s). For example, a molecule comprising a neutralizing epitope but not an enhancing epitope can be used to obtain a purified antibody that binds the neutralizing epitope that is substantially free (e.g., antibodies of other specificity constitute less than about 0.1% of the total preparation) of antibodies that specifically bind the enhancing epitope.

An "immune response" refers to one or more biological activities mediated by cells of the immune system in a subject. Such biological activities include, but are not limited to, production of antibodies; activation and proliferation of immune cells, such as, e.g., B cells, T cells, macrophages, leukocytes, lymphocytes, etc.; release of messenger molecules, such as cytokines, chemokines, interleukins, tumor necrosis factors, growth factors, etc.; and the like. An immune response is typically mounted when a cell of the immune system encounters non-self antigen that is recognized by a receptor present on the surface of the immune cell. The immune response preferably protects the subject to some degree against infection by a pathogen that bears the antigen against which the immune response is mounted.

An immune response may be "elicited," "induced," or "induced against" a particular antigen. Each of these terms is intended to be synonymous as used herein and refers to the ability of an immunogen to generate an immune response upon administration to a subject.

An "immunogen" is a molecule or combination of molecules that can induce an immune response in a subject when the immunogen is administered to the subject.

"Immunizing" refers to administering an immunogen to a subject.

An "effective amount" of an immunogen is an amount of the immunogen effective to elicit an immune response in a subject.

An "effective amount" of an antibody is an amount of the antibody that, when administered to a subject, is effective to treat, to prevent, or to ameliorate one or more symptoms of, infection by a pathogen expressing an epitope that the antibody specifically binds.

"Specific binding," or other grammatical forms of this phrase, refers to the ability of a molecule to non-covalently interact with another molecule with some affinity. For example, an antibody, "specifically binds" a WNV E protein, when it binds that E protein with higher affinity than any other WNV protein. As another example, an antibody, "specifically binds" an epitope of a WNV E protein, when it binds that epitope with higher affinity than any other epitope of the WNV E protein.

A "linker" refers to a molecule that joins two other molecules, either covalently or non-covalently, e.g., through ionic, van der Waals or hydrogen bonds, such as, for example, a nucleic acid molecule that hybridizes to one complementary sequence at the 5' end and to another complementary sequence at the 3' end, thus joining two non-complementary sequences.

A "pharmaceutical composition" refers to a composition suitable for pharmaceutical use in a mammal. A pharmaceutical composition comprises a pharmacologically effective amount of an active agent and a pharmaceutically acceptable carrier. "Pharmacologically effective amount" refers to that amount of an agent effective to produce the intended pharmacological result. "Pharmaceutically acceptable carrier" refers to any of the standard pharmaceutical carriers, vehicles, diluents, buffers, and excipients, such as a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in *Remington's Pharmaceutical Sciences,* 19th Ed. 1995, Mack Publishing Co., Easton. A "pharmaceutically acceptable salt" is a salt that can be formulated into a compound for pharmaceutical use including, e.g., metal salts (sodium, potassium, magnesium, calcium, etc.) and salts of ammonia or organic amines.

Preferred pharmaceutical carriers depend upon the intended mode of administration of the active agent. Typical modes of administration include enteral (e.g., oral, intranasal, rectal, or vaginal) or parenteral (e.g., subcutaneous, intramuscular, intravenous or intraperitoneal injection; or topical, transdermal, or transmucosal administration).

A "subject" of diagnosis, treatment, or administration is a human or non-human animal, including a mammal, such as a rodent (e.g., a mouse or rat), a lagomorph (e.g., a rabbit), or a primate. A subject of diagnosis, treatment, or administration is preferably a primate, and more preferably a human.

"Treatment" refers to therapeutic treatment. A "therapeutic" treatment is a treatment administered to a subject who exhibits signs of pathology for the purpose of diminishing, slowing the progression, eliminating, or halting those signs.

"Prevention" refers to prophylactic treatment. A "prophylactic" treatment is a treatment administered to a subject who does not exhibit signs of a disease or exhibits only early signs for the purpose of decreasing the risk of developing pathology.

"Hybridizing specifically to" or "specific hybridization" or "selectively hybridize to", refers to the binding, duplexing, or hybridizing of a nucleic acid molecule preferentially to a particular nucleotide sequence under stringent conditions when that sequence is present in a complex mixture (e.g., total cellular) DNA or RNA.

The term "stringent conditions" refers to conditions under which a nucleic acid will hybridize preferentially to a nucleic acid having a complementary sequence, and to a lesser extent to, or not at all to, other sequences. "Stringent hybridization" and "stringent hybridization wash conditions" in the context of nucleic acid hybridization experiments such as Southern and northern hybridizations are sequence dependent, and are different under different environmental parameters. An extensive guide to the hybridization of nucleic acids can be found in Tijssen, 1993, *Laboratory Techniques in Biochemistry and Molecular Biology—Hybridization with Nucleic Acid Probes,* part I, chapter 2, "Overview of principles of hybridization and the strategy of nucleic acid probe assays", Elsevier, N.Y.; Sambrook et al., 2001, *Molecular Cloning: A Laboratory Manual,* Cold Spring Harbor Laboratory, 3$^{rd}$ ed., NY; and Ausubel et al., eds., Current Edition, *Current Protocols in Molecular Biology,* Greene Publishing Associates and Wiley Interscience, N.Y.

Generally, highly stringent hybridization and wash conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Very stringent conditions are selected to be equal to the Tm for a particular probe.

One example of stringent hybridization conditions for hybridization of complementary nucleic acids which have more than about 100 complementary residues on a filter in a Southern or northern blot is 50% formalin with 1 mg of heparin at 42° C., with the hybridization being carried out overnight. An example of highly stringent wash conditions is 0.15 M NaCl at 72° C. for about 15 minutes. An example of stringent wash conditions is a 0.2× SSC wash at 65° C. for 15 minutes. See Sambrook et al. for a description of SSC buffer. A high stringency wash can be preceded by a low stringency wash to remove background probe signal. An exemplary medium stringency wash for a duplex of, e.g., more than about 100 nucleotides, is 1×SSC at 45° C. for 15 minutes. An exemplary low stringency wash for a duplex of, e.g., more than about 100 nucleotides, is 4-6×SSC at 40° C. for 15 minutes. In general, a signal to noise ratio of 2× (or higher) than that observed for an unrelated probe in the particular hybridization assay indicates detection of a specific hybridization.

4. BRIEF DESCRIPTION OF THE FIGURES

Figure 6:
Figure 7:
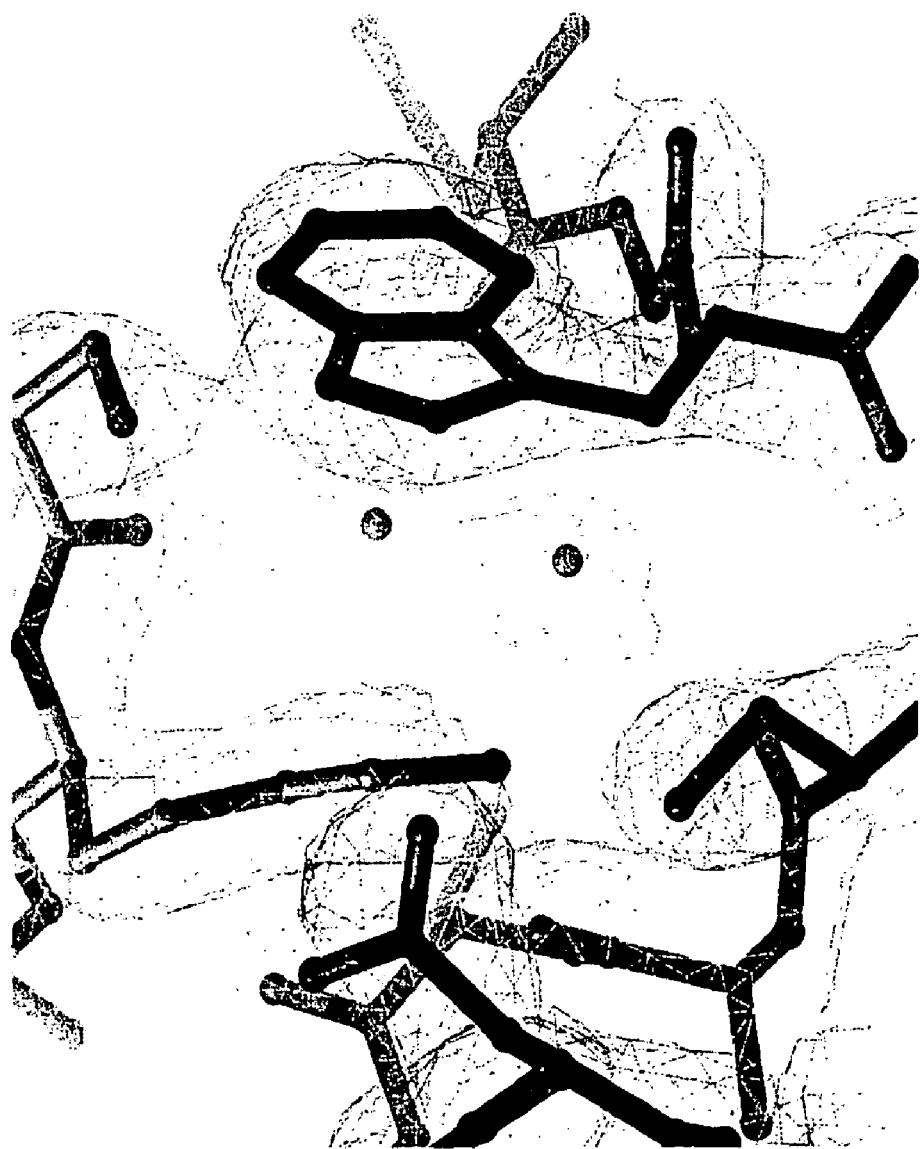
Figure 8:
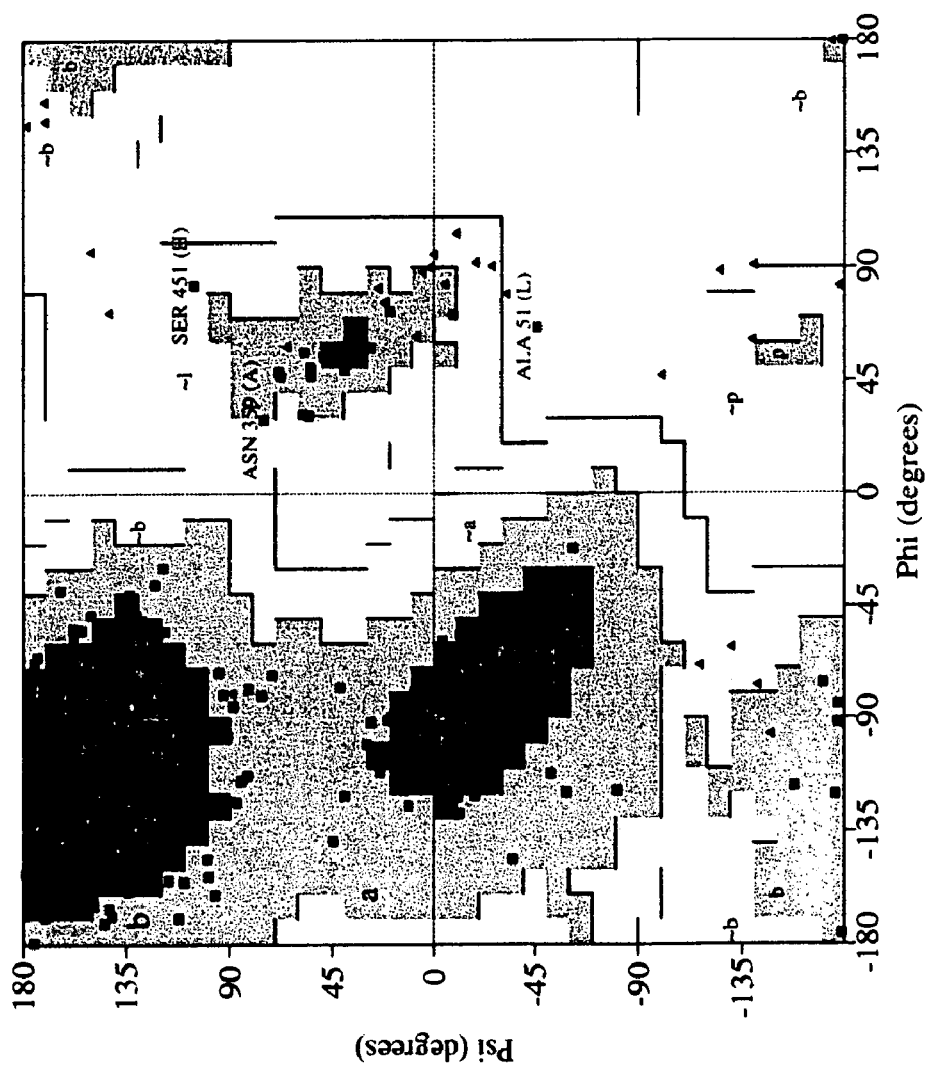
Figure 9:
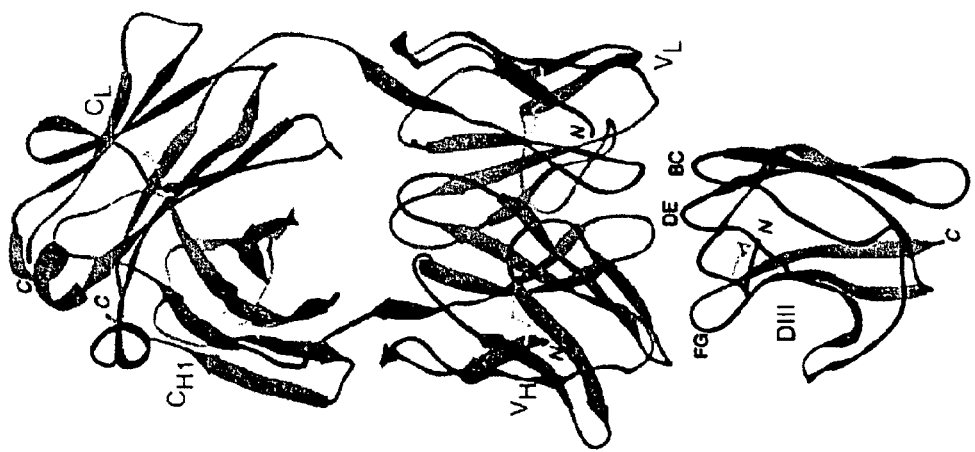
Figure 10:
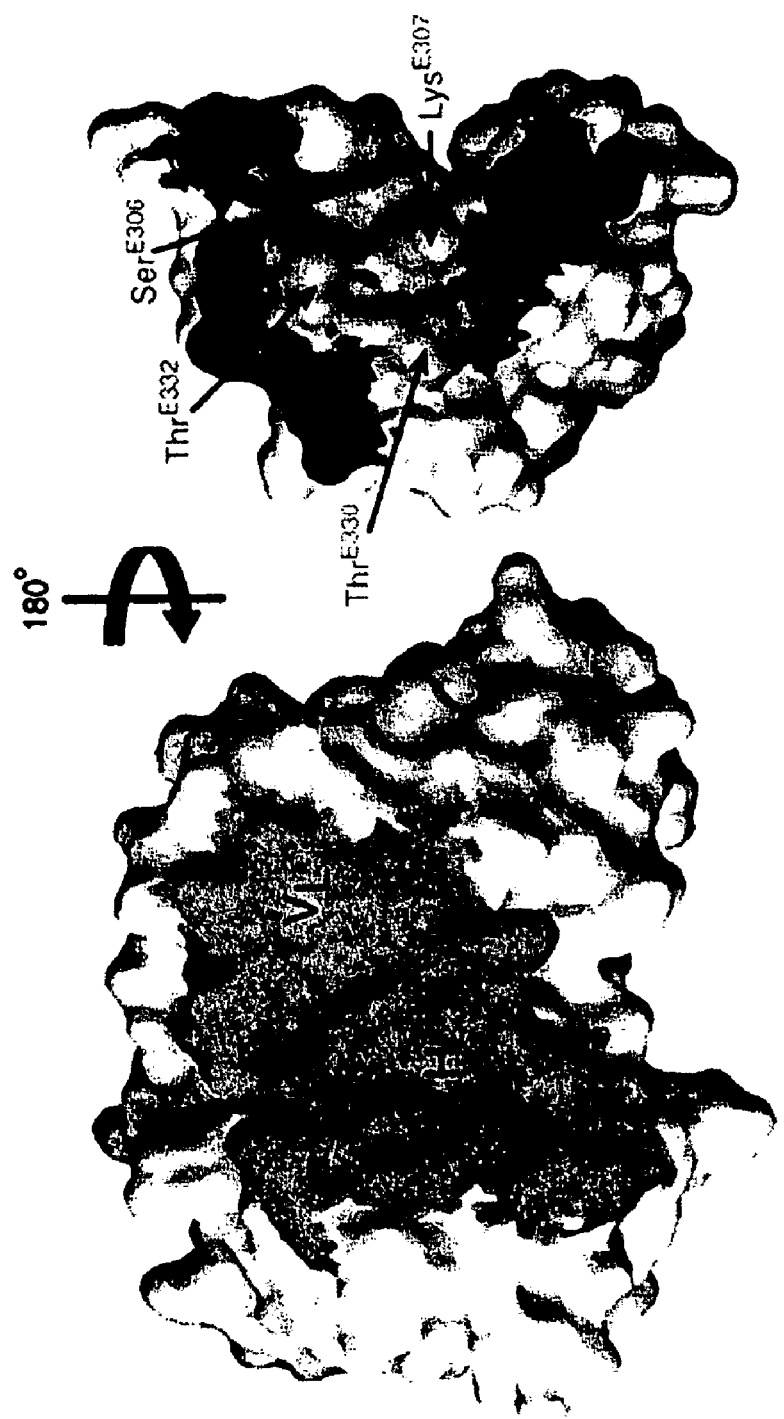
Figure 11:
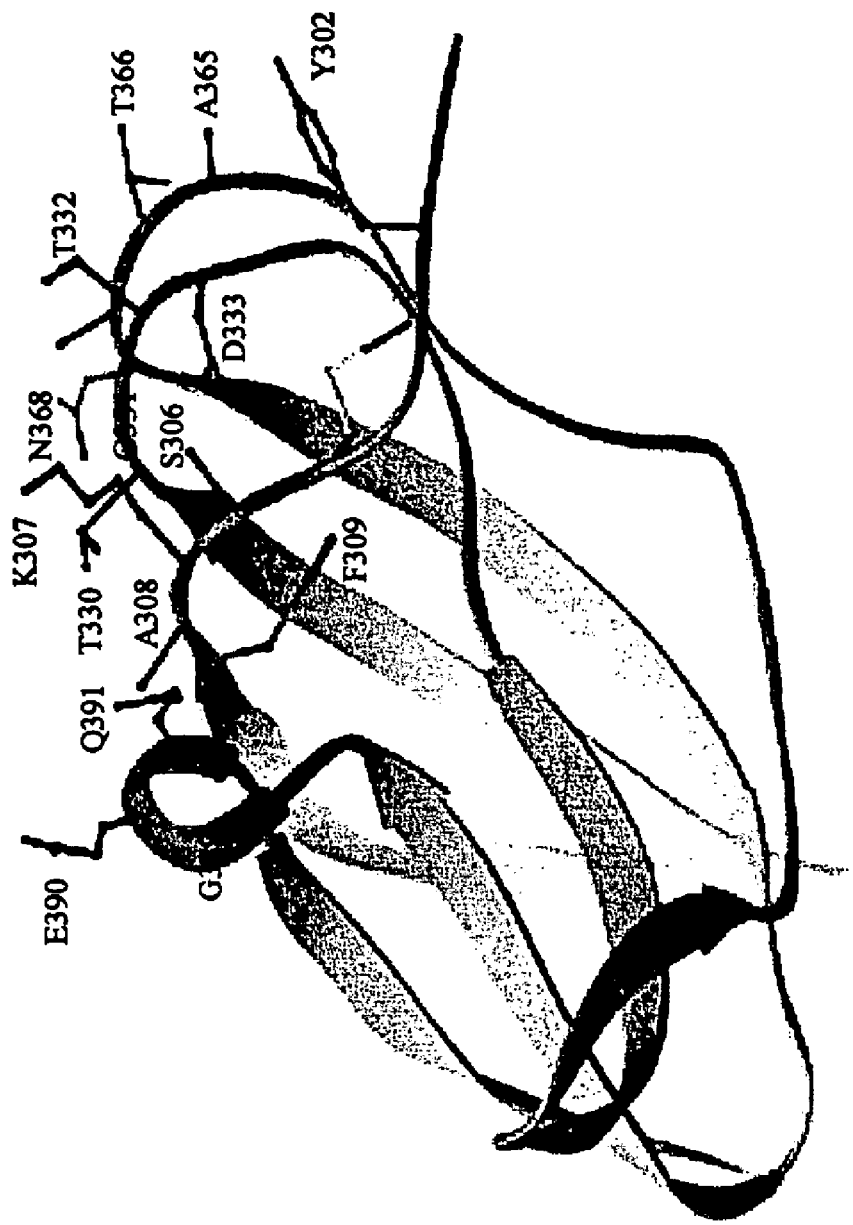
Figure 12:
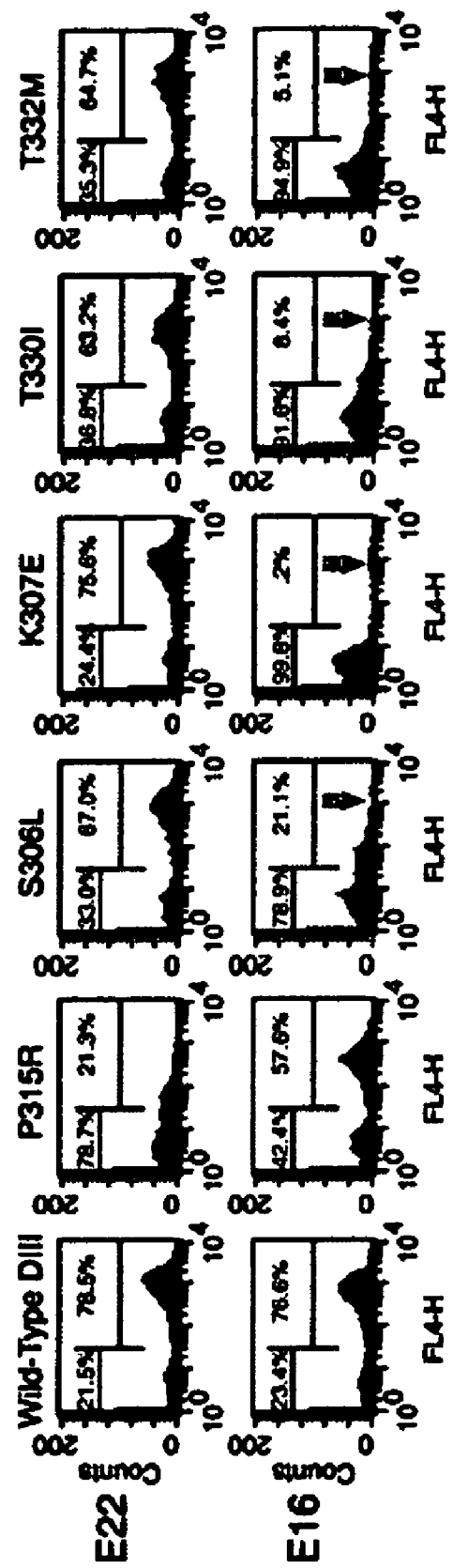
Figure 13:
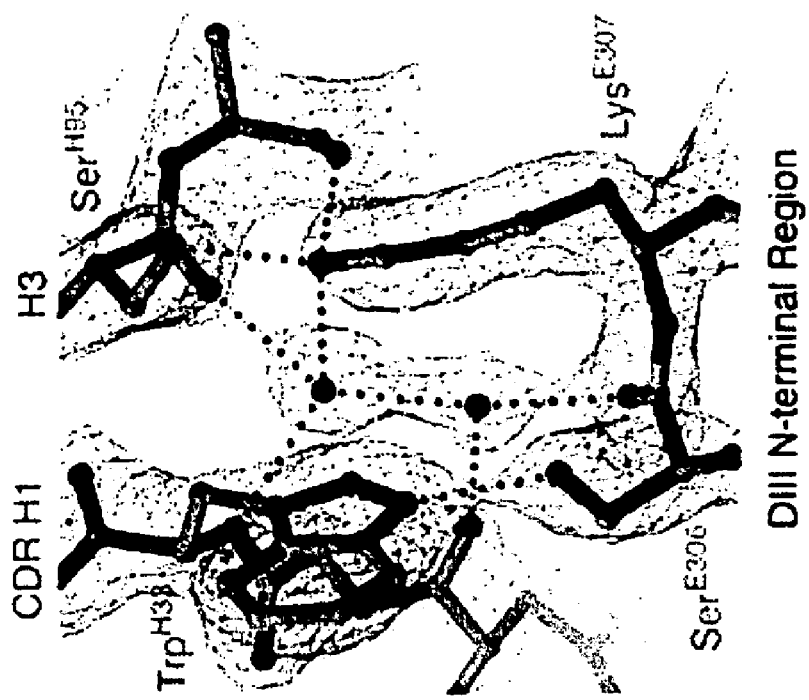
Figure 14:
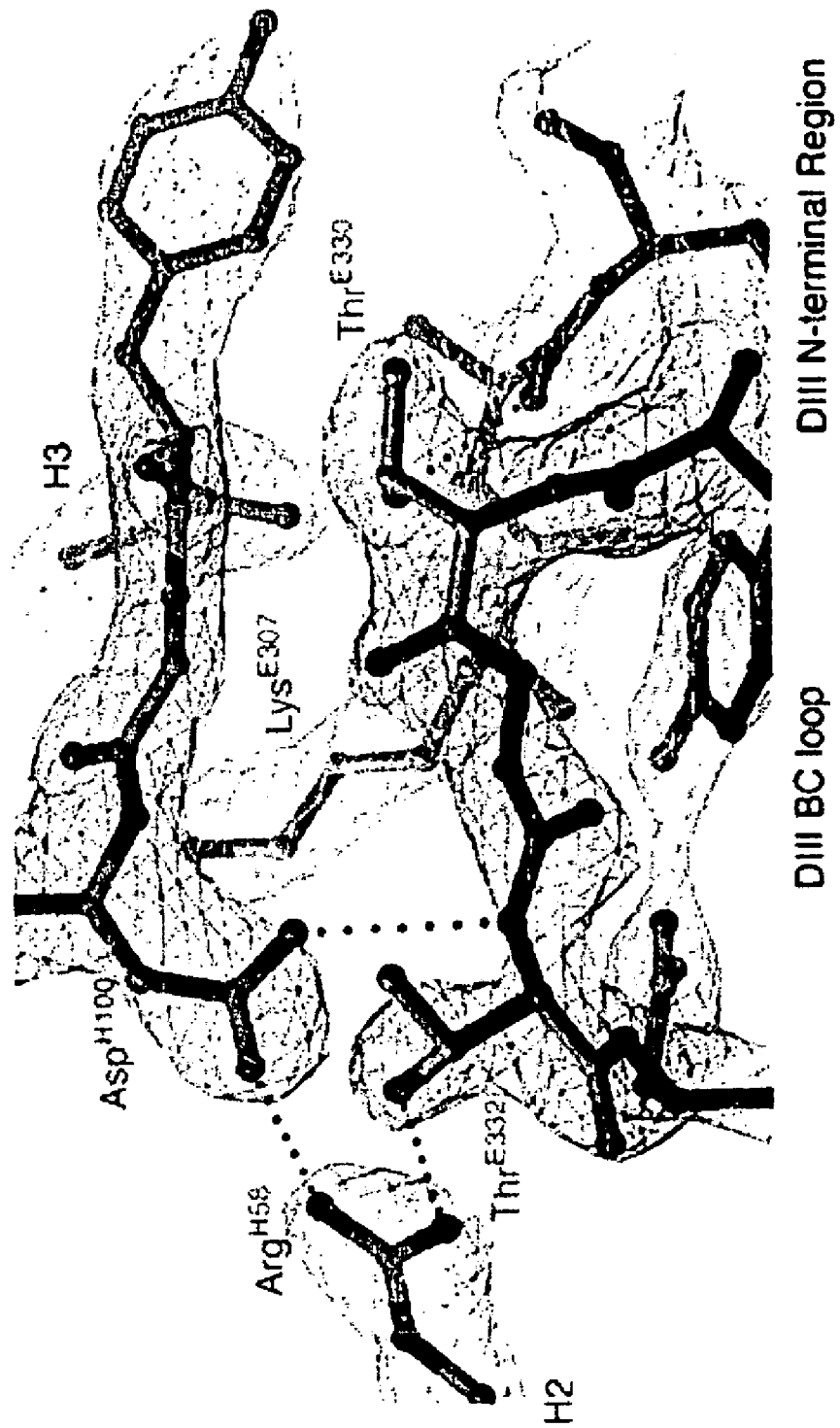
Figure 16:
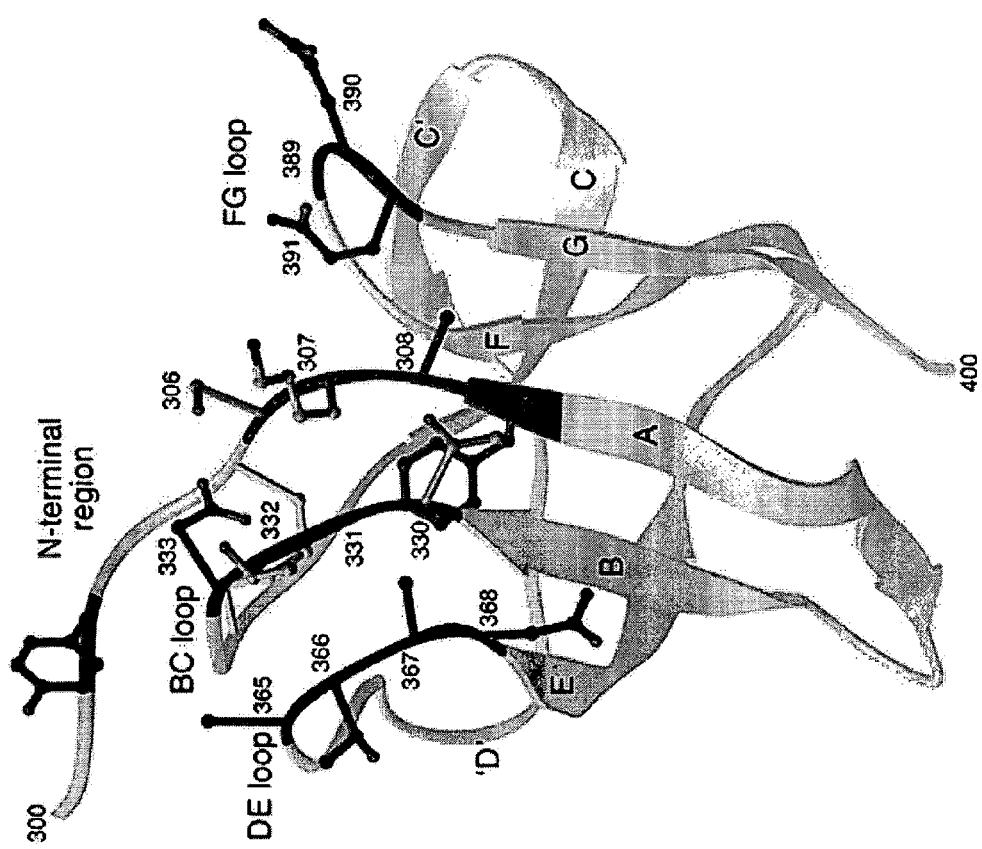
Figure 17:
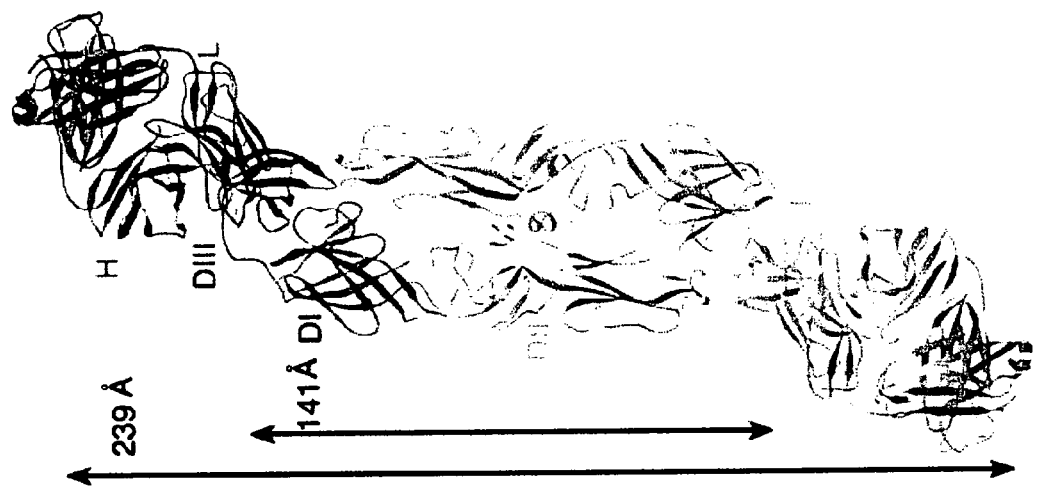
Figure 18:
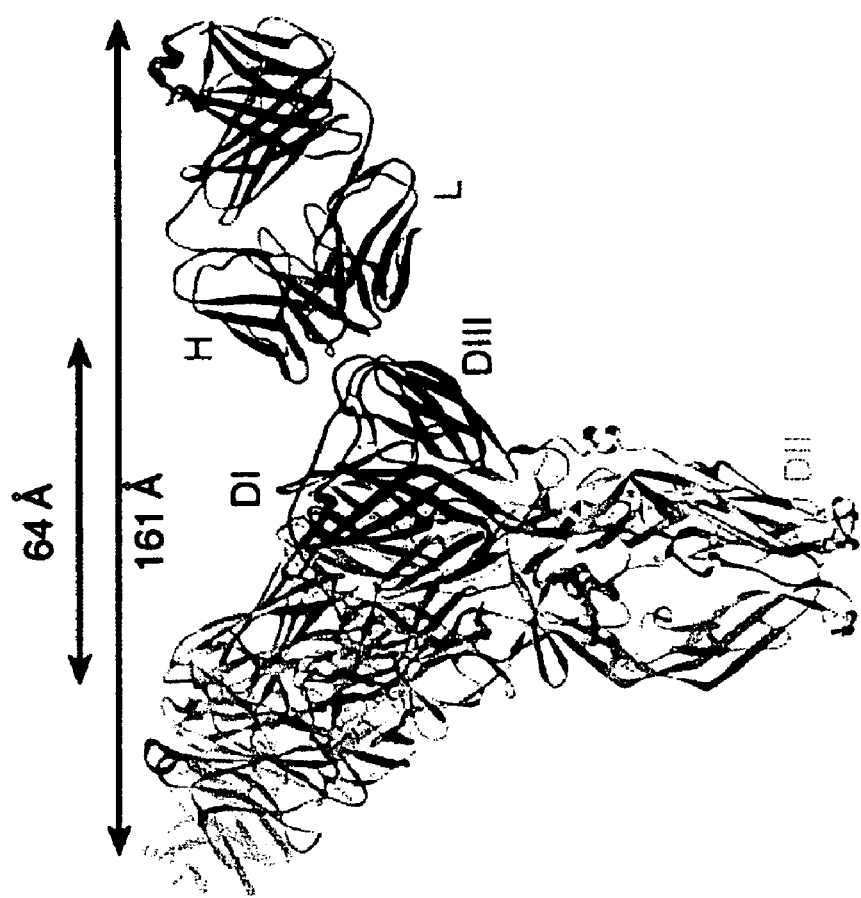
Figure 19:
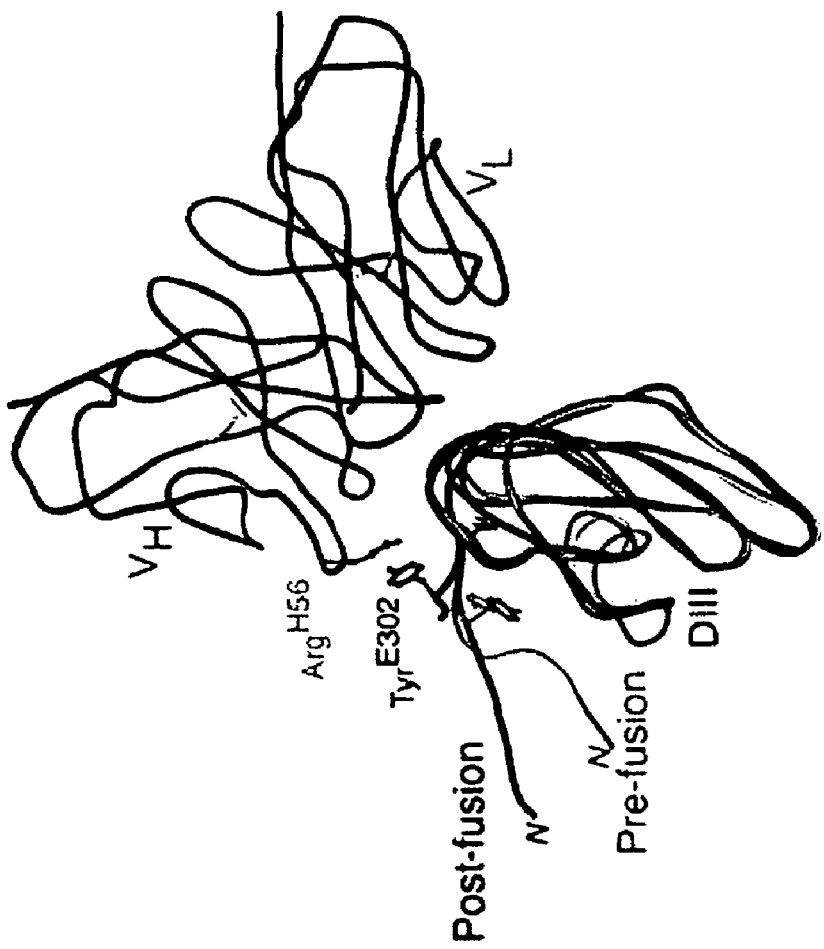
Figure 20:
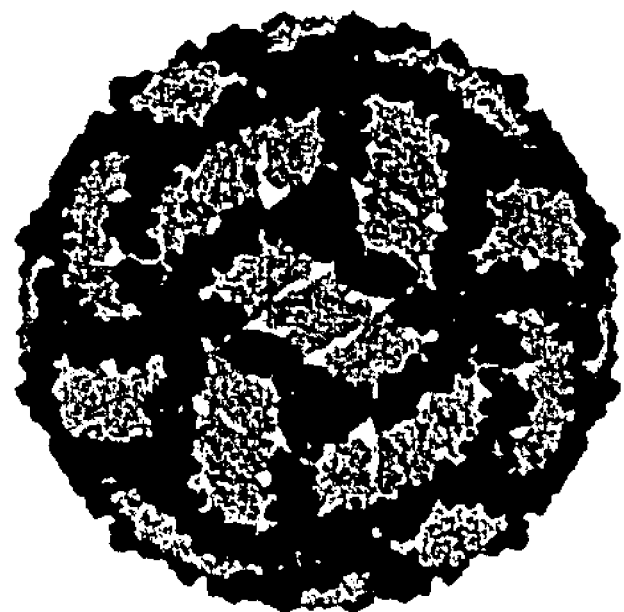
Figure 21B:
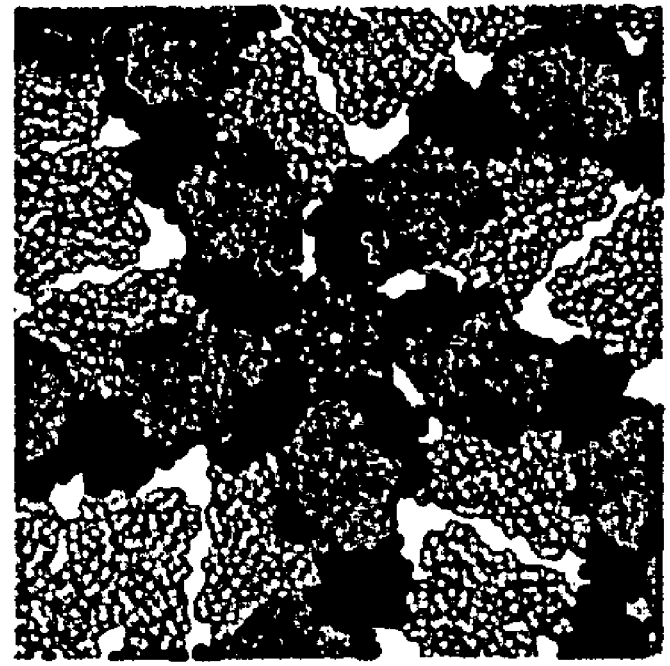
Figure 21A:
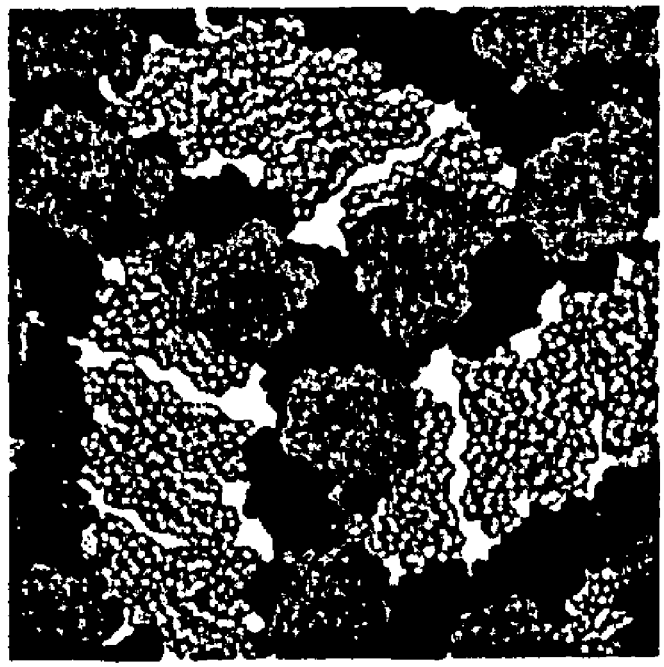
Figure 22:
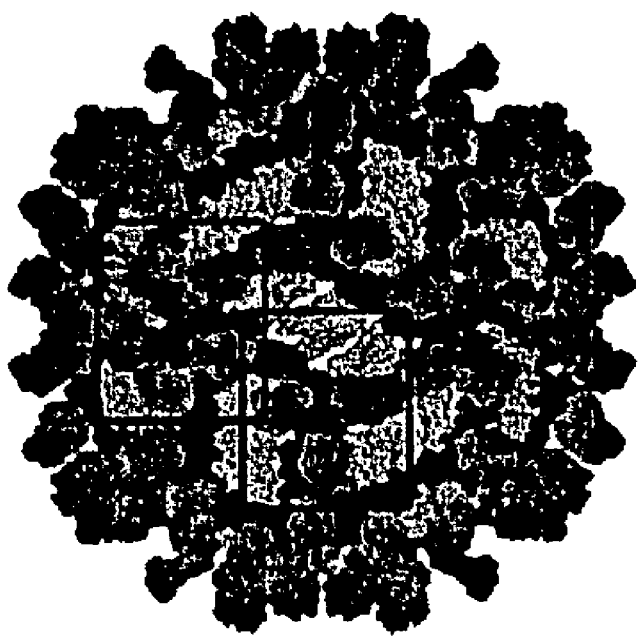
Figure 24:
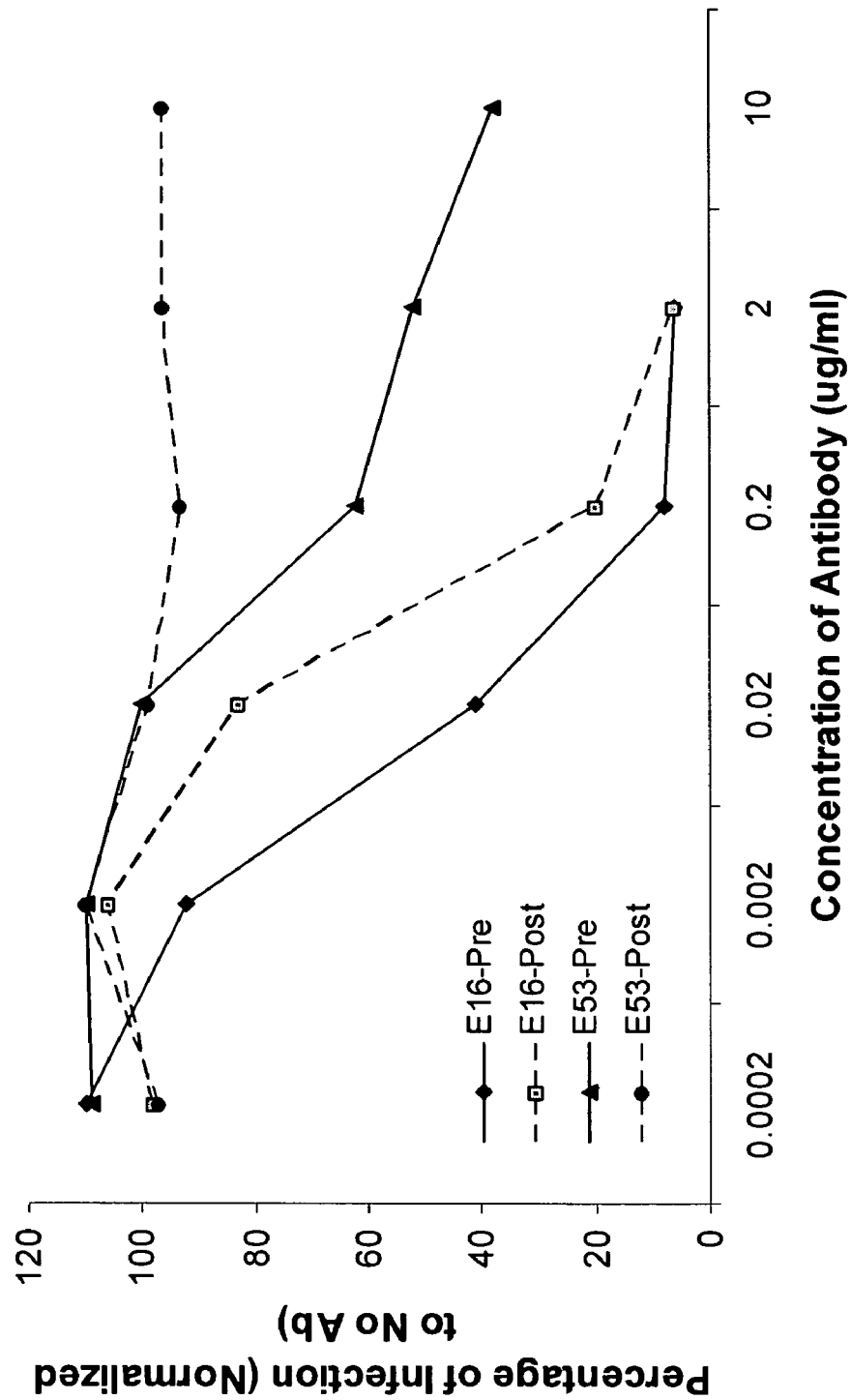
Figure 25:
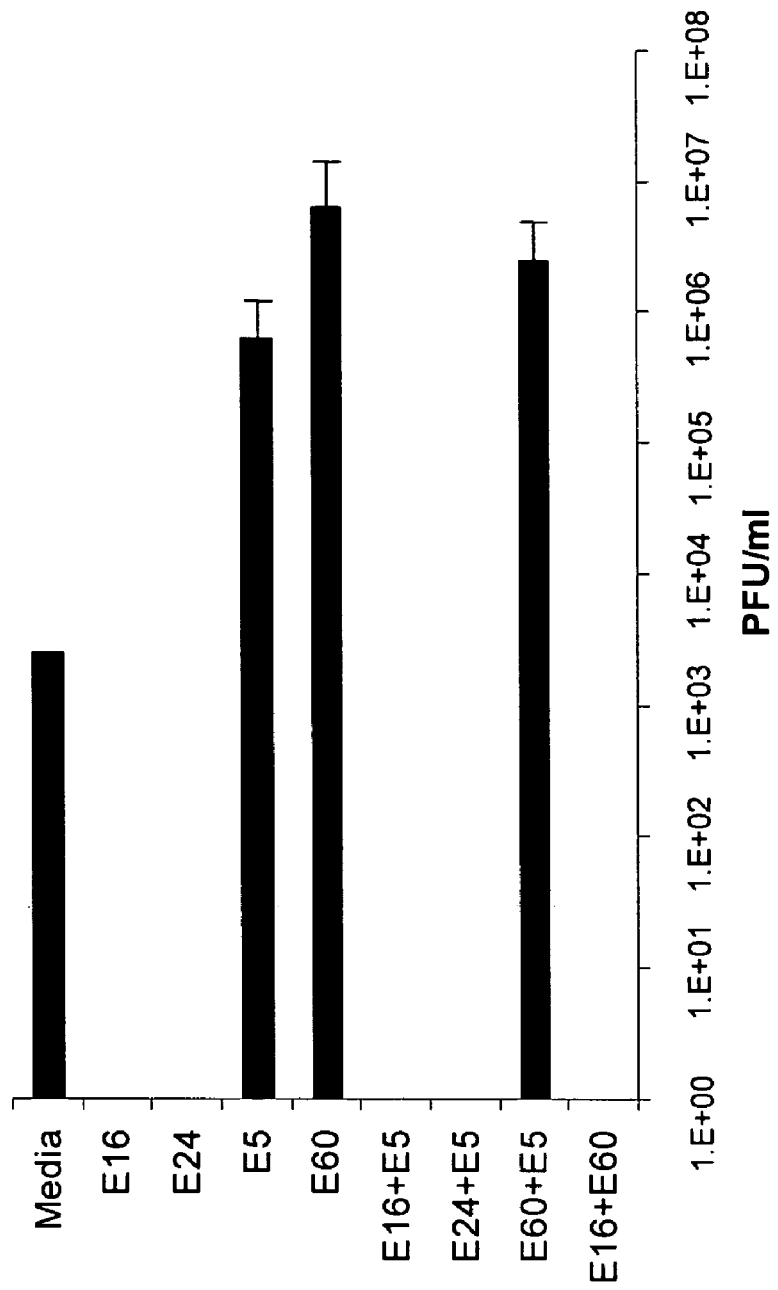
Figure 26:
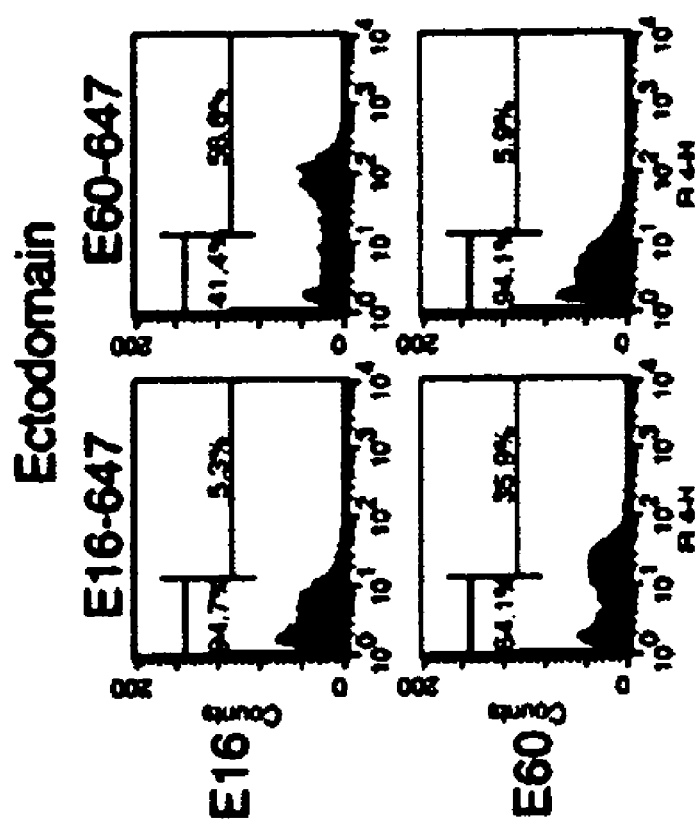

FIG. 1 provides the amino acid sequence of domain III of the WNV E protein identified with Genbank Accession No. AF196835, where amino acid 1 of FIG. 1 corresponds to amino acid 296 of WNV E protein (the amino acid sequence of domain III of WNV E protein is identified herein as SEQ ID NO:1; the amino acid sequence of WNV E protein is identified herein as SEQ ID NO:4);

FIG. 2 provides the amino acid sequence (SEQ ID NO:2)of the variable region of the light chain of monoclonal antibody E16, numbered according to the Kabat numbering system;

FIG. 3 provides the amino acid sequence (SEQ ID NO:3) of the variable region of the heavy chain of monoclonal antibody E16, numbered according to the Kabat numbering system;

FIG. 4 provides a diffraction pattern of the WNV DIII-E16 Fab complex, where the elution time of the WNV DIII-E16 Fab complex corresponds to a molecular weight of 60 kDa and the predicted molecular weight of the complex is 58 kDa;

Figure 5:
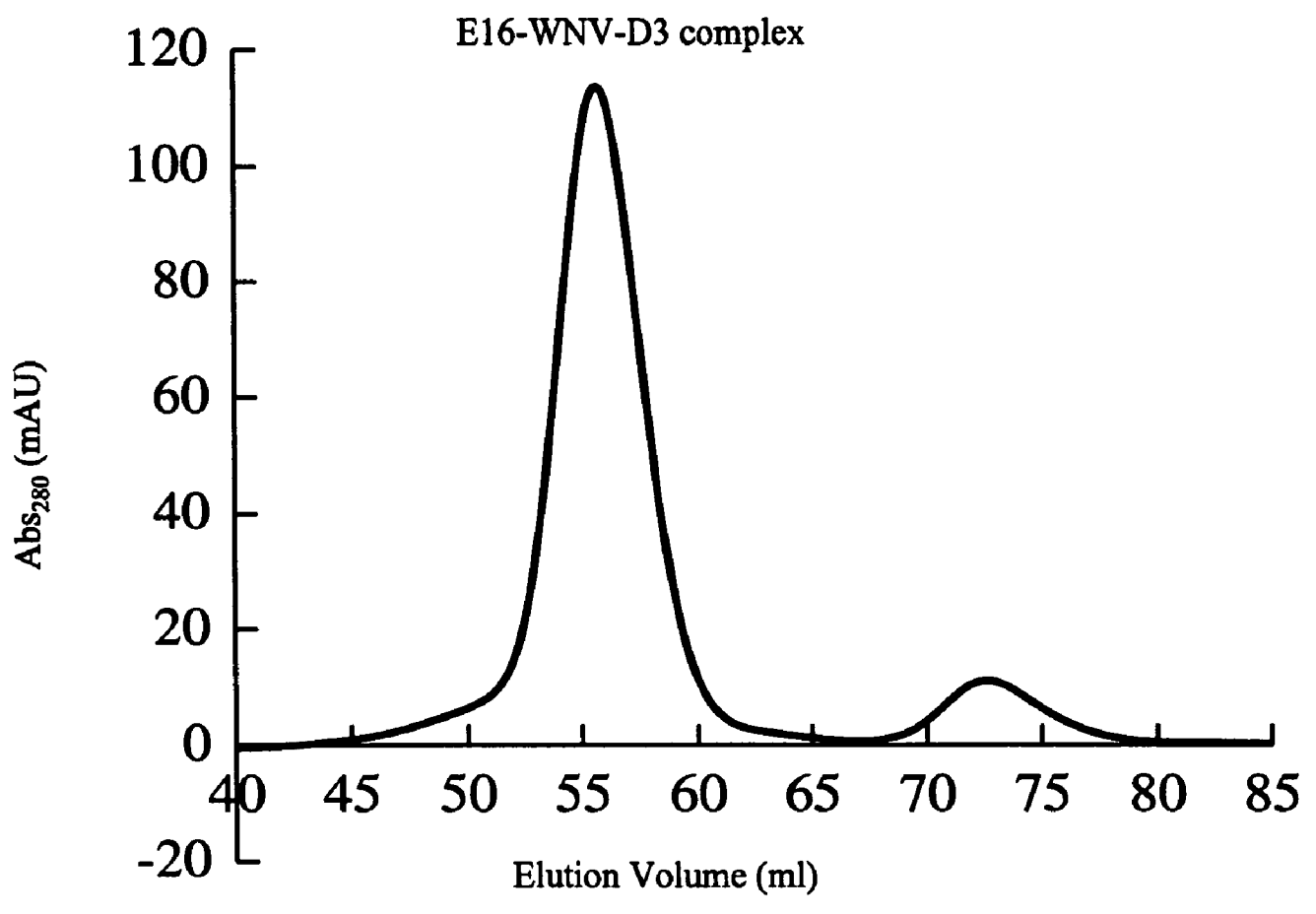

FIG. 5 provides a Superdex 75 chromatogram of the WNV DIII-E16 Fab complex purification;

FIG. 6 provides a representative WNV DIII-E16 Fab crystal;

FIG. 7 provides an electron density map of the WNV DIII-E16 Fab complex contoured at 1.3σ;

FIG. 8 provides a Ramachandran plot of the WNV DIII-E16 Fab complex;

FIG. 9 provides a ribbon diagram of the structure of the WNV DIII-E16 Fab complex;

FIG. 10 provides a grasp diagram of the interface between the E16 Fab fragment and WNV DIII (the WNV DIII is rotated 180° with respect to the vertical line in the figure);

FIG. 11 provides a ribbon diagram of WNV DIII;

FIG. 12 provides flow cytometry diagrams showing binding of E16 and E21 to yeast cells expressing wild-type or mutant versions of WNV DIII;

FIG. 13 provides diagrams showing detailed interactions of WNV DIII residues Ser$^{E306}$ and Lys$^{E307}$ with E16, with interfacial waters evident in the composite electron density omit map;

FIG. 14 provides a diagram showing interactions of Thr$^{E330}$ and Thr$^{E332}$ at the E16 interface;

Figure 15:
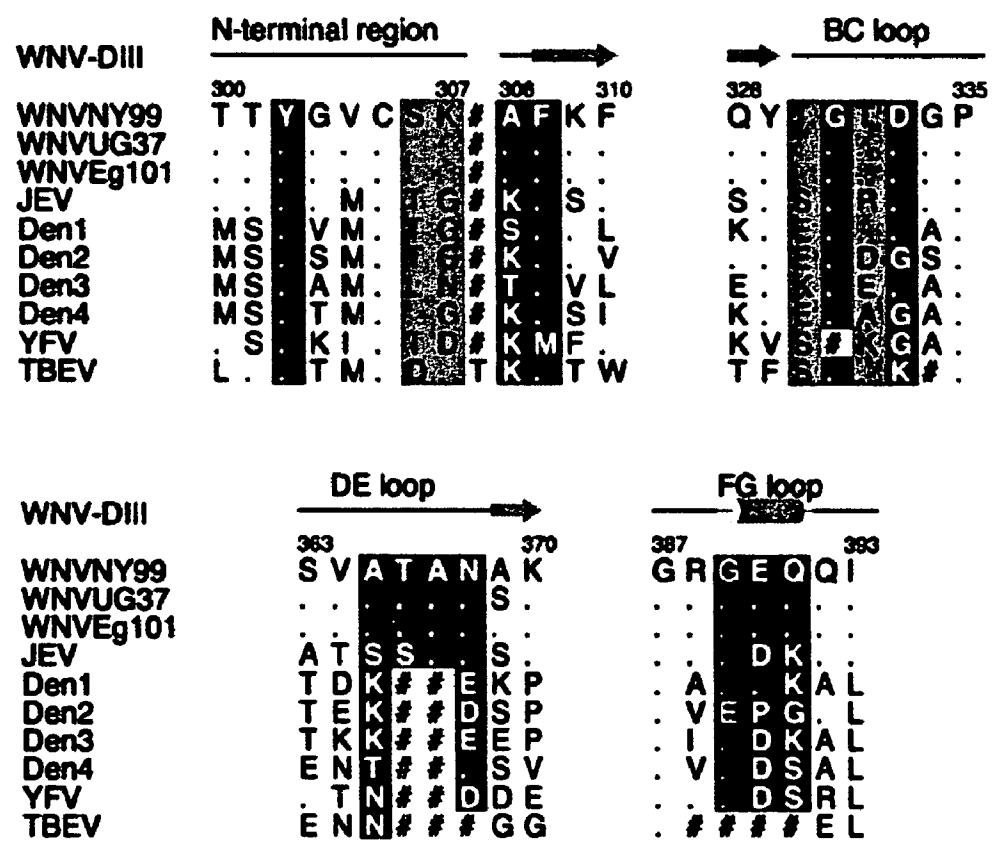

FIG. 15 provides a set of alignments showing the sequence of the four segments of WNV DIII contacted by E16 aligned with the analogous residues of other flaviviruses, where the WNV DIII residues contacted by E16 are highlighted in light and dark gray, and deletions are indicated with a (#) (SEQ ID NOS: 5-44 are disclosed respectively in order of appearance);

FIG. 16 provides a ribbon diagram showing the structure of the WNV DIII dominant neutralizing epitope as defined by the E16/DIII complex;

FIG. 17 provides a diagram showing E16 docked onto the DEN-2 E dimer where (1OAN) through WNV DIII ("DIII") super positioning indicates that binding likely occurs without WNV DI ("DI") or WNV DII (gray ribbon below DI) contacts;

FIG. 18 provides a diagram showing E16 docked onto the post-fusion DEN-2 E trimer (1OK8), indicating accessibility of the binding site;

FIG. 19 provides a diagram showing the conserved structure of WNV DIII from the E16 complex ("DIII"), the pre-fusion DEN-2 (IOKE, light gray), and post-fusion DEN-2 (1OK8, dark gray), where the interaction of E16 with the flavivirus conserved $Tyr^{E302}$ in the N-terminal region of WNV DIII is highlighted;

FIG. 20 provides a diagram showing the E16 structural epitope mapped onto the cryo-electron microscopic reconstruction of the WNV virion presented as 2.0 Å radius Cα atoms;

FIG. 21A provides a diagram showing E16/WNV DIII complexes docked around the icosahedral three-fold axis, while FIG. 21B provides a diagram showing that WNV DIII situated around the outer ring of the five-fold axis is permissive to E16 binding, but the inner ring appears to exclude E16 engagement;

FIG. 22 presents a diagram showing that saturation binding by E16 is predicted to entail the binding of 120 of 180 WNV epitopes with exclusion of binding to the inner-five fold WNV DIIIs;

Figure 23:
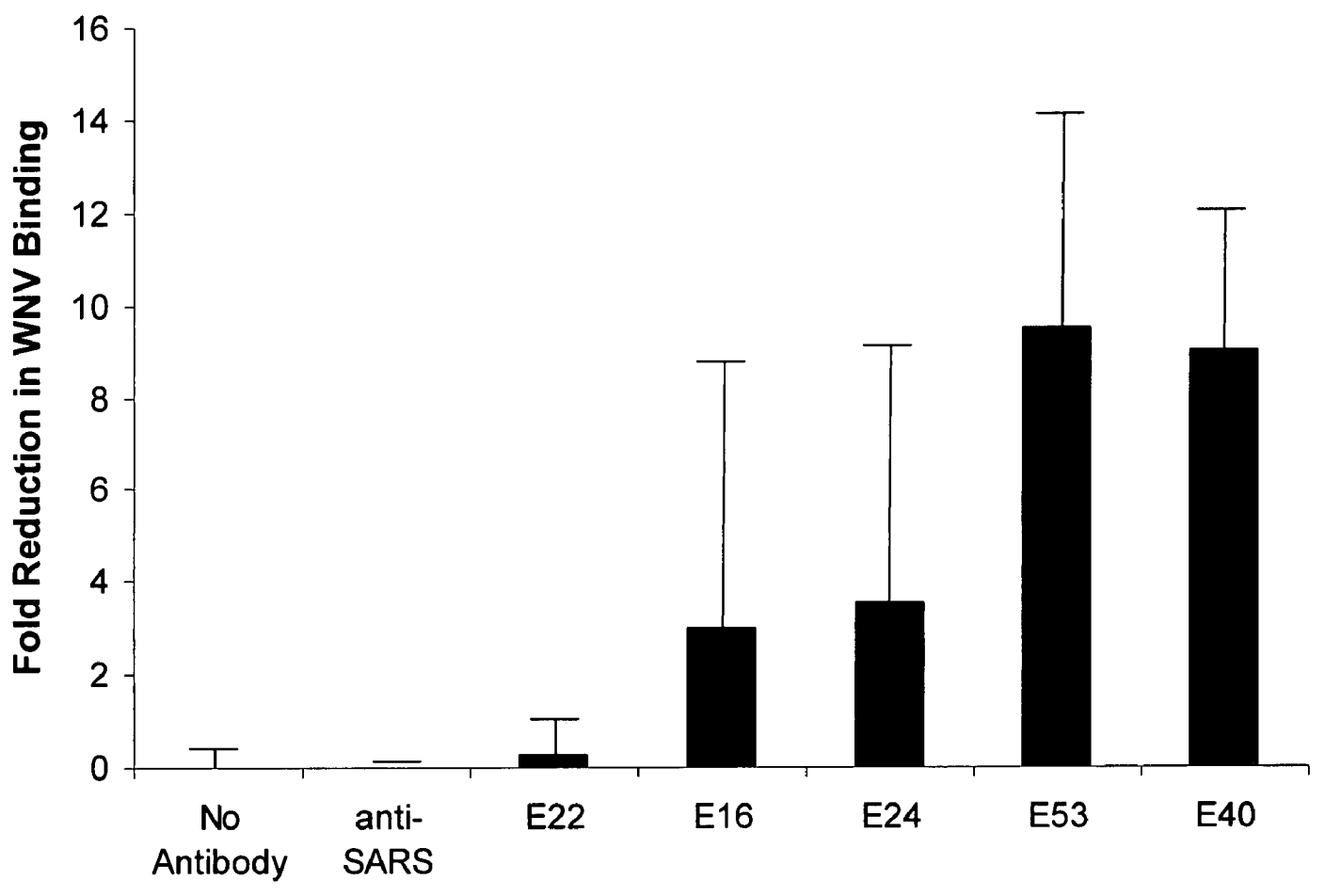

FIG. 23 presents graphs showing that two DI/DII specific neutralizing mAbs (E53 and E60) block cellular attachment significantly more than two DIII specific neutralizing antibodies (E16 and E24) or controls (no antibody, non-neutralizing mAb E22 or anti-SARS antibody ORF7a), reported as fold-reductions, with standard deviations, as the average of four to seven independent experiments performed in triplicate;

FIG. 24 presents graphs showing the dose-dependent blockade of WNV infection by E16 (black lines) and E53 (gray lines) in pre- and post-adsorption assays, reported as one of three representative experiments performed in duplicate;

FIG. 25 presents graphs showing that DIII specific mAbs effectively inhibit WNV infection of macrophages, while DI/DII specific E5 and E60 mAbs enhance infection. The data is one of three representative experiments performed in duplicate, with the dotted line representing the limit of sensitivity of the assay;

FIG. 26 presents graphs showing that pre-incubation with unlabeled mabs followed by addition of the APC-conjugates reveals that E16 and E60 both are self-competitive but not cross competitive for E binding; and FIG. 27 presents a table summarizing the interactions between WNV DIII amino acids and E16 Fab amino acids.

4.1 BRIEF DESCRIPTION OF THE TABLES

Table 1 provides contact residues of WNV DIII and E16 Fab;

Table 2 provides hydrophobic contacts between WNV DIII and E16 Fab; and

Table 3 provides hydrogen bond contacts between WNV DIII and E16 Fab.

Table 4 provides representative flaviviruses and citations to the amino acid sequences of flaviviral envelope proteins;

Table 5 summarizes the X-ray crystallography data sets of WNV DIII-E16 Fab complex crystals that were used to determine the structures of the crystalline WNV DIII-E16 Fab complexes of the invention;

Table 6 summarizes the X-ray crystallography refinement parameters of the structures of crystalline WNV DIII-E16 Fab complexes of the invention; and Table 7 provides the atomic structure coordinates of native WNV DIII-E16 Fab complex crystals of the invention as determined by X-ray crystallography. SEQ ID NOS: 45-53 are disclosed respectively in order of appearance.

5. DETAILED DESCRIPTION OF THE INVENTION

The present invention provides crystalline forms of polypeptide complexes corresponding to a Fab fragment of a neutralizing antibody in complex with domain III of the WNV E protein, an envelope protein obtained from a member of the viral family flaviviridae. Viruses from this family with related envelope proteins include, for example, WNV, Japanese encephalitis virus, Kunjin virus, Murray Valley encephalitis virus, Dengue virus, Montana myotis leukoencephalitis virus, Modoc virus, and Yellow Fever virus. In addition, the invention provides a three dimensional structure of such polypeptide complexes. Further, the invention provides methods of making high affinity antibodies that bind WNV DIII. Still further, the invention provides methods of identifying compounds that mimic WNV DIII and can be used to induce production of antibodies that recognize WNV DIII. In addition, the invention provides methods of identifying compounds that bind WNV DIII.

5.1 Crystalline WNV DIII-E16 Fab Complex

In one aspect, the invention provides crystals from which the atomic structure coordinates of the invention may be obtained, including native crystals and heavy-atom derivative crystals. Native crystals generally comprise substantially pure polypeptides corresponding to WNV DIII-E16 Fab complex in crystalline form.

It is to be understood that the crystalline WNV DIII-E16 Fab complex from which the atomic structure coordinates of the invention can be obtained is not limited to wild-type WNV DIII or wild-type E16 Fab. Indeed, the crystals may comprise mutants of wild-type WNV DIII or wild-type E16 Fab. Mutants of wild-type WNV DIII or wild-type E16 Fab are obtained by replacing at least one amino acid residue in the sequence of the wild-type WNV DIII or wild-type E16 Fab with a different amino acid residue, or by adding or deleting one or more amino acid residues within the wild-type sequence and/or at the N- and/or C-terminus of the wild-type WNV DIII or wild-type E16 Fab. Preferably, such mutants will crystallize under crystallization conditions that are substantially similar to those used to crystallize the wild-type WNV DIII-E16 Fab complex.

The types of mutants contemplated by this invention include conservative mutants, non-conservative mutants, deletion mutants, truncated mutants, extended mutants, methionine mutants, selenomethionine mutants, cysteine mutants and selenocysteine mutants. A mutant may have, but need not have, wild-type WNV DIII or wild-type E16 Fab binding activity. Preferably, a mutant displays biological activity that is substantially similar to that of the wild-type polypeptide. Methionine, selenomethionine, cysteine, and selenocysteine mutants are particularly useful for producing heavy-atom derivative crystals, as described in detail, below.

It will be recognized by one of skill in the art that the types of mutants contemplated herein are not mutually exclusive;

that is, for example, a polypeptide having a conservative mutation in one amino acid may in addition have a truncation of residues at the N-terminus, and several Leu or Ile→Met mutations.

In addition, conservative or non-conservative amino acid substitutions can be made to amino acids of WNV DIII or E16 Fab that are implicated in association of WNV DIII with E16 Fab. Such conservative or non-conservative substitutions can affect, e.g., the affinity with which E16 Fab binds WNV DIII. In certain embodiments, the conservative or non-conservative amino acid substitutions can increase the affinity with which E16 Fab binds WNV DIII. In other embodiments, the conservative or non-conservative amino acid substitutions can decrease the affinity with which E16 Fab binds WNV DIII.

Conservative amino acid substitutions are well-known in the art, and include substitutions made on the basis of a similarity in polarity, charge, solubility, hydrophobicity and/or the hydrophilicity of the amino acid residues involved. Typical conservative substitutions are those in which the amino acid is substituted with a different amino acid that is a member of the same class or category, as those classes are defined herein. Thus, typical conservative substitutions include aromatic to aromatic, apolar to apolar, aliphatic to aliphatic, acidic to acidic, basic to basic, polar to polar, etc. Other conservative amino acid substitutions are well known in the art. It will be recognized by those of skill in the art that generally, a total of about 20% or fewer, typically about 10% or fewer, most usually about 5% or fewer, of the amino acids in the wild-type polypeptide sequence can be conservatively substituted with other amino acids without deleteriously affecting the biological activity and/or three-dimensional structure of the molecule, provided that such substitutions do not involve residues that are critical for activity, as discussed above.

In some embodiments, it may be desirable to make mutations in the active site of a protein, e.g., to reduce or completely eliminate protein activity. Mutations that will reduce or completely eliminate the activity of a particular protein will be apparent to those of skill in the art. For example, the amino acids identified in Tables 1 or 2 could be mutated in order to reduce or eliminate the binding activity of E16 Fab.

The amino acid residue Cys (C) is unusual in that it can form disulfide bridges with other Cys (C) residues or other sulfhydryl-containing amino acids ("cysteine-like amino acids"). The ability of Cys (C) residues and other cysteine-like amino acids to exist in a polypeptide in either the reduced free —SH or oxidized disulfide-bridged form affects whether Cys (C) residues contribute net hydrophobic or hydrophilic character to a polypeptide. While Cys (C) exhibits a hydrophobicity of 0.29 according to the consensus scale of Eisenberg (Eisenberg, 1984, supra), it is to be understood that for purposes of the present invention Cys (C) is categorized as a polar hydrophilic amino acid, notwithstanding the general classifications defined above. Preferably, Cys residues that are known to participate in disulfide bridges, such as those linking the heavy chain to the light chain of an antibody, or a portion thereof, are not substituted or are conservatively substituted with other cysteine-like amino acids so that the residue can participate in a disulfide bridge. Typical cysteine-like residues include, for example, Pen, hCys, etc. Substitutions for Cys residues that interfere with crystallization are discussed infra.

While in most instances the amino acids of WNV DIII and/or E16 Fab will be substituted with genetically-encoded amino acids, in certain circumstances mutants may include genetically non-encoded amino acids. For example, non-encoded derivatives of certain encoded amino acids, such as SeMet and/or SeCys, may be incorporated into the polypeptide chain using biological expression systems (such SeMet and SeCys mutants are described in more detail, infra).

Alternatively, in instances where the mutant will be prepared in whole or in part by chemical synthesis, virtually any non-encoded amino acids may be used, ranging from D-isomers of the genetically encoded amino acids to non-encoded naturally-occurring natural and synthetic amino acids.

Conservative amino acid substitutions for many of the commonly known non-genetically encoded amino acids are well known in the art. Conservative substitutions for other non-encoded amino acids can be determined based on their physical properties as compared to the properties of the genetically encoded amino acids.

In some instances, it may be particularly advantageous or convenient to substitute, delete from and/or add amino acid residues to WNV DIII and/or E16 Fab in order to provide convenient cloning sites in cDNA encoding the polypeptide, to aid in purification of the polypeptide, etc. Such substitutions, deletions and/or additions that do not substantially alter the three dimensional structure of the native WNV DIII and/or E16 Fab will be apparent to those having skills in the art. These substitutions, deletions and/or additions include, but are not limited to, His tags, BirA tags, intein-containing self-cleaving tags, maltose binding protein fusions, glutathione S-transferase protein fusions, antibody fusions, green fluorescent protein fusions, signal peptide fusions, biotin accepting peptide fulsions, and the like. In certain embodiments, the WNV DIII comprises a His tag. In other embodiments, the WNV DIII comprises a BirA tag. In a preferred embodiment, the WNV DIII comprises a His tag and a BirA tag.

Mutations may also be introduced into a polypeptide sequence where there are residues, e.g., cysteine residues, that interfere with crystallization. Such cysteine residues can be substituted with an appropriate amino acid that does not readily form covalent bonds with other amino acid residues under crystallization conditions; e.g., by substituting the cysteine with Ala, Ser or Gly. Any cysteine located in a non-helical or non-β-stranded segment, based on secondary structure assignments, are good candidates for replacement.

It should be noted that the mutants contemplated herein need not exhibit WNV DIII or E16 Fab binding activity. Indeed, amino acid substitutions, additions or deletions that interfere with the binding activity of WNV DIII and/or E16 Fab are specifically contemplated by the invention. Such crystalline polypeptides, or the atomic structure coordinates obtained therefrom, can be used to provide phase information to aid the determination of the three-dimensional X-ray structures of other related or non-related crystalline polypeptides.

The heavy-atom derivative crystals from which the atomic structure coordinates of the invention are obtained generally comprise a crystalline WNV DIII-E16 Fab complex in association with one or more heavy metal atoms. The polypeptide may correspond to a complex comprising wild-type WNV DIII and wild-type E16 Fab or a complex comprising mutant WNV DIII and/or E16 Fab, which may optionally be in complex with one or more molecules, as previously described. There are two types of heavy-atom derivatives of polypeptides: heavy-atom derivatives resulting from exposure of the protein to a heavy metal in solution, wherein crystals are grown in medium comprising the heavy metal, or in crystalline form, wherein the heavy metal diffuses into the crystal, and heavy-atom derivatives wherein the polypeptide comprises heavy-atom containing amino acids, e.g., selenomethionine and/or selenocysteine mutants.

In practice, heavy-atom derivatives of the first type can be formed by soaking a native crystal in a solution comprising heavy metal atom salts, or organometallic compounds, e.g., lead chloride, gold thiomalate, ethylmercurithiosalicylic acid-sodium salt (thimerosal), uranyl acetate, platinum tetrachloride, osmium tetraoxide, zinc sulfate, and cobalt hexamine, which can diffuse through the crystal and bind to the crystalline polypeptide complex.

Heavy-atom derivatives of this type can also be formed by adding to a crystallization solution comprising the polypeptide complex to be crystallized an amount of a heavy metal atom salt, which may associate with the protein complex and be incorporated into the crystal. The location(s) of the bound heavy metal atom(s) can be determined by X-ray diffraction analysis of the crystal. This information, in turn, is used to generate the phase information needed to construct the three-dimensional structure of the protein.

Heavy-atom derivative crystals may also be prepared from polypeptides that include one or more SeMet and/or SeCys residues (SeMet and/or SeCys mutants). Such selenocysteine or selenomethionine mutants may be made from complexes comprising wild-type WNV DIII and E16 Fab or complexes comprising mutant WNV DIII and/or E16 Fab by expression of WNV DIII or E16-encoding cDNAs in auxotrophic $E.$ $coli$ strains. Hendrickson et al., 1990, $EMBO$ $J.$ 9:1665-1672. In this method, the wild-type or mutant WNV DIII or cDNAs encoding the heavy and/or light chains of E16 may be expressed in a host organism on a growth medium depleted of either natural cysteine or methionine (or both) but enriched in selenocysteine or selenomethionine (or both). Alternatively, selenocysteine or selenomethionine mutants may be made using nonauxotrophic $E.$ $coli$ strains, e.g., by inhibiting methionine biosynthesis in these strains with high concentrations of Ile, Lys, Phe, Leu, Val or Thr and then providing selenomethionine in the medium (Doublie, 1997, $Methods$ $in$ $Enzymology$ 276:523-530). Furthermore, selenocysteine can be selectively incorporated into polypeptides by exploiting the prokaryotic and eukaryotic mechanisms for selenocysteine incorporation into certain classes of proteins in vivo, as described in U.S. Pat. No. 5,700,660 to Leonard et al. (filed Jun. 7, 1995). One of skill in the art will recognize that selenocysteine is preferably not incorporated in place of cysteine residues that form disulfide bridges, as these may be important for maintaining the three-dimensional structure of the protein and are preferably not to be eliminated. One of skill in the art will further recognize that, in order to obtain accurate phase information, approximately one selenium atom should be incorporated for every 140 amino acid residues of the polypeptide chain. The number of selenium atoms incorporated into the polypeptide chain can be conveniently controlled by designing a Met or Cys mutant having an appropriate number of Met and/or Cys residues, as described more fully below.

In some instances, the polypeptide to be crystallized may not contain cysteine or methionine residues. For example, WNV DIII contains cysteine residues, but no methionine residues, while E16 Fab comprises methionine residues, but no cysteine residues that are not involved in intra- or intermolecular disulfide bonding. Therefore, if selenomethionine and/or selenocysteine mutants are to be used to obtain heavy-atom derivative crystals, methionine or cysteine residues may be introduced into the polypeptide chain of WNV DIII or E16 Fab, respectively.

Such mutations are preferably introduced into the polypeptide sequence at sites that will not disturb the overall protein fold. For example, a residue that is conserved among many members of the protein family or that is thought to be involved in maintaining its activity or structural integrity, as determined by, e.g., sequence alignments, should not be mutated to a Met or Cys. In addition, conservative mutations, such as Ser to Cys, or Leu or Ile to Met, are preferably introduced. One additional consideration is that, in order for a heavy-atom derivative crystal to provide phase information for structure determination, the location of the heavy atom(s) in the crystal unit cell should be determinable and provide phase information. Therefore, a mutation is preferably not introduced into a portion of the protein that is likely to be mobile, e.g., at, or within about 1-5 residues of, the N- and C-termini.

Conversely, if there are too many methionine and/or cysteine residues in a polypeptide sequence, over-incorporation of the selenium-containing side chains can lead to the inability of the polypeptide to fold and/or crystallize, and may potentially lead to complications in solving the crystal structure. In this case, methionine and/or cysteine mutants are prepared by substituting one or more of these Met and/or Cys residues with another residue. The considerations for these substitutions are the same as those discussed above for mutations that introduce methionine and/or cysteine residues into the polypeptide. Specifically, the Met and/or Cys residues are preferably conservatively substituted with Leu/Ile and Ser, respectively.

As DNA encoding cysteine and methionine mutants can be used in the methods described above for obtaining SeCys and SeMet heavy-atom derivative crystals, the preferred Cys or Met mutant will have one Cys or Met residue for every 140 amino acids.

5.2 Production of Polypeptides

The native and mutated WNV DIII and E16 polypeptides described herein may be chemically synthesized in whole or part using techniques that are well-known in the art (see, e.g., Creighton, 1983, Proteins: Structures and Molecular Principles, W.H. Freeman & Co., NY.). Alternatively, methods that are well known to those skilled in the art can be used to construct expression vectors containing the native or mutated WNV DIII and E16 polypeptide coding sequence and appropriate transcriptional/translational control signals. These methods include in vitro recombinant DNA techniques, synthetic techniques and $in$ $vivo$ recombination/genetic recombination. See, for example, the techniques described in the current editions of Sambrook et al., 2001, $Molecular$ $Cloning:$ $A$ $Laboratory$ $Manual,$ 3d Ed., Cold Spring Harbor Laboratory, NY and Ausubel et al., 2004, $Current$ $Protocols$ $in$ $Molecular$ $Biology,$ Greene Publishing Associates and Wiley Interscience, NY.

A variety of host-expression vector systems may be utilized to express the WNV DIII and E16 coding sequences. These include but are not limited to microorganisms such as bacteria transformed with recombinant bacteriophage DNA, plasmid DNA or cosmid DNA expression vectors containing the WNV DIII or E16 coding sequences; yeast transformed with recombinant yeast expression vectors containing the WNV DIII or E16 coding sequences; insect cell systems infected with recombinant virus expression vectors (e.g., baculovirus) containing the WNV DIII or E16 coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the WNV DIII or E16 coding sequences; or animal cell systems. The expression elements of these systems vary in their strength and specificities.

Specifically designed vectors allow the shuttling of DNA between hosts such as bacteria-yeast or bacteria-animal cells. An appropriately constructed expression vector may contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one that causes mRNAs to be initiated at high frequency.

Depending on the host/vector system utilized, any of a number of suitable transcription and translation elements, including constitutive and inducible promoters, may be used in the expression vector. For example, when cloning in bacterial systems, inducible promoters such as the T7 promoter, pL of bacteriophage λ, plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of the tyrosine kinase domain DNA, SV40-, BPV- and EBV-based vectors may be used with an appropriate selectable marker.

The expression vector may be introduced into host cells via any one of a number of techniques including but not limited to transformation, transfection, infection, protoplast fusion, and electroporation. The expression vector-containing cells are clonally propagated and individually analyzed to determine whether they produce WNV DIII or E16. Identification of WNV DIII- or E16-expressing host cell clones may be done by several means, including but not limited to immunological reactivity with anti-WNV DIII or anti-immunoglobulin antibodies, and the presence of host cell-associated WNV DIII or E16 biological activity.

Expression of WNV DIII or E16 cDNA may also be performed using in vitro produced synthetic mRNA. Synthetic mRNA can be efficiently translated in various cell-free systems, including but not limited to wheat germ extracts and reticulocyte extracts, as well as efficiently translated in cell based systems, including but not limited to microinjection into frog oocytes. Further, nucleic acids expressing WNV DIII or E16 cDNA can be constructed and expressed by gene synthesis using oligonucleotides. See Hoover & Lubkowski, 2002, *Nucleic Acids Res* 30:e43.

To determine the WNV DIII or E16 cDNA sequences that yields optimal levels of WNV DIII or E16 activity and/or WNV DIII or E16 protein, modified WNV DIII or E16 cDNA molecules are constructed. Host cells are transformed with the cDNA molecules and the levels of WNV DIII or E16 RNA and/or protein are measured.

Levels of WNV DIII or E16 protein in host cells are quantitated by a variety of methods such as immunoaffinity and/or ligand affinity techniques, WNV DIII- or E16-specific affinity beads or WNV DIII- or E16-specific antibodies are used to isolate [35]s-methionine labeled or unlabeled WNV DIII or E16 protein. Labeled or unlabeled WNV DIII or E16 protein is analyzed by SDS-PAGE. Unlabeled WNV DIII or E16 is detected by Western blotting, ELISA or RIA employing WNV DIII- or E16-specific antibodies.

Following expression of WNV DIII or E16 in a recombinant host cell, WNV DIII or E16 may be recovered to provide WNV DIII or E16 in active form. Several WNV DIII or E16 purification procedures are available and suitable for use. Recombinant WNV DIII or E16 may be purified from cell lysates or from conditioned culture media, by various combinations of, or individual application of, fractionation, or chromatography steps that are known in the art.

In addition, recombinant WNV DIII can be separated from other cellular proteins by use of an immuno-affinity column made with monoclonal or polyclonal antibodies specific for full length nascent WNV DIII or polypeptide fragments thereof. The E16 monoclonal antibody is well-suited for use in such protocols; however, any antibody specific for WNV DIII can be used to immuno-purify WNV DIII. Similarly, recombinant WNV DIII can be used in an immuno-affinity column to purify E16. Further, other reagents that bind to antibodies, such as, e.g., protein A can be use to affinity-purify the E16 monoclonal antibody.

Alternatively, WNV DIII or E16 may be recovered from a host cell in an unfolded, inactive form, e.g., from inclusion bodies of bacteria. Proteins recovered in this form may be solubilized using a denaturant, e.g., guanidinium hydrochloride, and then refolded into an active form using methods known to those skilled in the art, such as dialysis. See, for example, the techniques described in Sambrook et al., 2001, *Molecular Cloning: A Laboratory Manual*, 3d Ed., Cold Spring Harbor Laboratory, NY and Ausubel et al., 2004, *Current Protocols in Molecular Biology*, Greene Publishing Associates and Wiley Interscience, NY.

Further, E16 can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, (Cold Spring Harbor Laboratory Press, 2nd ed. 1988); Hammerling, et al., in: *Monoclonal Antibodies and T-Cell Hybridomas*, pp. 563-681 (Elsevier, N.Y., 1981) (both of which are incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Ascites fluid, which generally contains high levels of antibodies, can be generated by inoculating mice intraperitoneally with positive hybridoma clones.

Once a nucleic acid sequence encoding an antibody of the invention has been obtained according to standard techniques, the vector for the production of the antibody may be produced by recombinant DNA technology using techniques well known in the art. Methods which are well known to those skilled in the art can be used to construct expression vectors containing the antibody coding sequences and appropriate transcriptional and translational control signals. These methods include, for example, in vitro recombinant DNA techniques, synthetic techniques, and in vivo genetic recombination. (See, for example, the techniques described in Sambrook et al., 2001, *Molecular Cloning, A Laboratory Manual*, 3d Ed., Cold Spring Harbor Laboratory, Cold Spring Harbor, N.Y. and Ausubel et al. eds., 2004, *Current Protocols in Molecular Biology*, John Wiley & Sons, NY).

An expression vector comprising the nucleotide sequence of an antibody can be transferred to a host cell by conventional techniques (e.g., electroporation, liposomal transfection, and calcium phosphate precipitation) and the transfected cells are then cultured by conventional techniques to produce the antibody of the invention. In specific embodiments, the expression of the antibody is regulated by a constitutive, an inducible or a tissue, specific promoter.

The host cells used to express the recombinant antibodies of the invention may be either bacterial cells such as *Escherichia coli*, or, preferably, eukaryotic cells, especially for the expression of whole recombinant immunoglobulin molecule. In particular, mammalian cells such as Chinese hamster ovary cells (CHO), in conjunction with a vector such as the major intermediate early gene promoter element from human cytomegalovirus is an effective expression system for immunoglobulins (Foecking et al., 1998, *Gene* 45:101; Cockett et al., 1990, *Bio/Technology* 8:2).

A variety of host-expression vector systems may be utilized to express antibodies. Such host-expression systems represent vehicles by which the coding sequences of the antibodies may be produced and subsequently purified, but also represent cells which may, when transformed or transfected with the appropriate nucleotide coding sequences, express the antibodies of the invention in situ. These include, but are not limited to, microorganisms such as bacteria (e.g., *E. coli* and *B. subtilis*) transformed with recombinant bacteriophage DNA, plasmid DNA or cosmid DNA expression vectors containing immunoglobulin coding sequences; yeast (e.g., *Saccharomyces Pichia*) transformed with recombinant yeast expression vectors containing immunoglobulin coding sequences; insect cell systems infected with recombinant virus expression vectors (e.g., baculovirus) containing the immunoglobulin coding sequences; plant cell systems infected with recombinant virus expression vectors (e.g., cauliflower mosaic virus (CaMV) and tobacco mosaic virus (TMV)) or transformed with recombinant plasmid expression vectors (e.g., Ti plasmid) containing immunoglobulin coding sequences; or mammalian cell systems (e.g., COS, CHO, BHK, 293, 293T, 3T3 cells, lymphotic cells (see U.S. Pat. No. 5,807,715), Per C.6 cells (rat retinal cells developed by Crucell)) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the antibody being expressed. For example, when a large quantity of such a protein is to be produced, for the generation of pharmaceutical compositions of an antibody, vectors which direct the expression of high levels of fusion protein products that are readily purified may be desirable. Such vectors include, but are not limited to, the *E. coli* expression vector pUR278 (Ruther et al., 1983, *EMBO J.* 2:1791), in which the antibody coding sequence may be ligated individually into the vector in frame with the *lac Z* coding region so that a fusion protein is produced; pIN vectors (Inouye & Inouye, 1985, *Nucleic Acids Res.* 13:3101-3109; Van Heeke & Schuster, 1989, *J. Biol. Chem.* 24:5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (e.g., the polyhedrin gene) of the virus and placed under control of an AcNPV promoter (e.g., the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the immunoglobulin molecule in infected hosts (e.g., see Logan & Shenk, 1984, *Proc. Natl. Acad. Sci. USA* 81:355-359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, *Methods in Enzymol.* 153:51-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the finction of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 293T, 3T3, WI38, BT483, Hs578T, HTB2, BT20 and T47D, CRL7030 and Hs578Bst.

For long-term, high-yield production of recombinant proteins, stable expression is preferred. For example, cell lines which stably express an antibody of the invention may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibodies of the invention. Such engineered cell lines may be particularly useful in screening and evaluation of compounds that interact directly or indirectly with the antibodies of the invention.

A number of selection systems may be used, including but not limited to the herpes simplex virus thymidine kinase (Wigler et al., 1977, *Cell* 11:223), hypoxanthine-guanine phosphoribosyltransferase (Szybalska & Szybalski, 1992, Proc. Natl. Acad. Sci. USA 48:202), and adenine phosphoribosyltransferase (Lowy et al., 1980, Cell 22:817) genes can be employed in tk-, hgprt- or aprt- cells, respectively. Also, antimetabolite resistance can be used as the basis of selection for the following genes: dhfr, which confers resistance to methotrexate (Wigler et al., 1980, Proc. Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 Clinical Pharmacy 12:488-505; Wu and Wu, 1991, 3:87-95; Tolstoshev, 1993, Ann. Rev. Pharmacol. Toxicol. 32:573-596; Mulligan, 1993, Science 260:926-932; Morgan and Anderson, 1993, Ann. Rev. Biochem. 62:191-217; and May, 1993, TIB TECH 11:155-215); and hygro, which confers resistance to hygromycin (Santerre et al., 1984, Gene 30:147). Methods commonly known in the art of recombinant DNA technology which can be used are described in Ausubel et al. (eds.), 2004, Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al. (eds), 1994, Current Protocols in Human Genetics, John Wiley & Sons, NY.; and Colberre-Garapin et al., 1981, J Mol. Biol. 150:1.

The expression levels of an antibody can be increased by vector amplification (for a review, see Bebbington and Hentschel, The use of vectors based on gene amplification for the expression of cloned genes in mammalian cells in DNA cloning, Vol.3. (Academic Press, New York, 1987)). When a marker in the vector system expressing an antibody is amplifiable, increase in the level of inhibitor present in culture of host cell can increase the number of copies of the marker gene. Since the amplified region is associated with the nucleotide sequence of the antibody, production of the antibody can also increase. See Crouse et al., 1983, Mol. Cell. Biol. 3:257.

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain should be placed before the heavy chain to avoid an excess of toxic free heavy chain. See Proudfoot, 1986, Nature 322:52; and Kohler, 1980, Proc. Natl. Acad. Sci. USA 77:2197. The coding sequences for the heavy and light chains may comprise cDNA or genomic DNA.

Once the antibody of the invention has been recombinantly expressed, it may be purified by any method known in the art for purification of an antibody, for example, by chromatography (e.g., ion exchange, affinity, particularly by affinity for the specific antigen after Protein A, and sizing column chromatography), centrifugation, differential solubility, or by any other standard technique for the purification of proteins.

Still further, Fab fragments of E16 can be prepared from E16 according to any known method without limitation. Generally, Fab fragments of E16 are prepared by Papain digestion of E16; however, any technique that cleaves the E16 heavy chain at or near the hinge region can be used to prepare the Fab fragments. Repetitive protocols for making Fab fragments from antibodies, including monoclonal antibodies, are described in, e.g., Harlow et al., 1988, Antibodies: A Laboratory Manual, Cold Spring Harbor Laboratory Press, 2nd ed. These techniques can be used to prepare Fab fragments from E16 prepared according to any of the methods described herein.

5.3 Crystallization of Polypeptides and Characterization of Crystal

The native, heavy-atom derivative, and/or poly-crystals from which the atomic structure coordinates of the invention can be obtained by conventional means as are well-known in the art of protein crystallography, including batch, liquid bridge, dialysis, and vapor diffusion methods (see, e.g., McPherson, 1998, Crystallization of Biological Macromolecules, Cold Spring Harbor Press, New York; McPherson, 1990, Eur. J. Biochem. 189:1-23.; Weber, 1991, Adv. Protein Chem. 41:1-36).

Generally, native crystals are grown by dissolving substantially pure WNV DIII-E16 Fab complex in an aqueous buffer containing a precipitant at a concentration just below that necessary to precipitate the protein. Examples of precipitants include, but are not limited to, polyethylene glycol, ammonium sulfate, 2-methyl-2,4-pentanediol, sodium citrate, sodium chloride, glycerol, isopropanol, lithium sulfate, sodium acetate, sodium formate, potassium sodium tartrate, ethanol, hexanediol, ethylene glycol, dioxane, t-butanol and combinations thereof. Water is removed by controlled evaporation to produce precipitating conditions, which are maintained until crystal growth ceases.

In a preferred embodiment, native crystals are grown by vapor diffuision in sitting drops (McPherson, 1982, Preparation and Analysis of Protein Crystals, John Wiley, New York; McPherson, 1990, Eur. J. Biochem. 189:1-23). In this method, the polypeptide/precipitant solution is allowed to equilibrate in a closed container with a larger aqueous reservoir having a precipitant concentration optimal for producing crystals. Generally, less than about 25 µL of substantially pure polypeptide solution is mixed with an equal volume of reservoir solution, giving a precipitant concentration about half that required for crystallization. The sealed container is allowed to stand, usually for about 2-6 weeks, until crystals grow.

For native crystals from which the atomic structure coordinates of the invention are obtained, it has been found that hanging drops of about 1.5 µL containing about 0.5 µL of 10-15 mg/ml WNV DIII-E16 Fab complex in 20 mM HEPES (pH 7.5) and 0.01% $NaN_3$, about 0.5 µl of 0.1 M HEPES (pH 8.5), 19% PEG 4000, 0.1M glycine and 0.5 µl of deionized water over wells containing precipitant solution containing 100 mM HEPES (pH 8.5), 19% PEG 4000, and 100 mM glycine for about one week at 20° C. provide diffraction quality crystals.

In some embodiments in accordance with the present invention, a native crystal may be grown using a microbatch method. The microbatch crystallization method was originally developed to carry out protein crystallization by Douglas Instruments Ltd (Berkshire, United Kingdom) in collaboration with Imperial College, London. The method was developed to allow theoretical studies but can be used for routine large scale crystallization, since it is very rapid and uses only about as little as 0.1 to 1 µl of protein per trial. Like the original batch crystallization methods that were used in the early days of protein crystallization, the microbatch method involves the simple combination of protein with precipitants, buffers, etc., generally without any subsequent concentration step. The ingredients are simply mixed at their final concentrations. Because very small volumes are used, the droplets are generally covered, e.g., with paraffin oil, to prevent evaporation. Vapor Plates designed for batch crystallization available from Douglas Instruments can be used in such methods. These have 96 wells, each holding about 9 μl. Droplets with volumes from about 0.2 to about 2 μl are dispensed at the bottom of the wells. With a special microtip and highly accurate motorized syringes, very small droplets can be dispensed accurately. The dispensing error is generally around 20 nl.

Microbatch can be more effective than vapor diffusion for screening: for a given amount of time and material, more hits are usually found using the microbatch crystallization method (Baldock et al., 1996, *Journal of Crystal Growth* 168:170-174). Microbatch gives superior crystals for data collection in about 50% of proteins. In one example, a protein unstable to temperature changes, which couldn't be crystallized under vapor diffusion conditions, was crystallized using a microbatch method (Conti et al., 1996, *Acta Cryst. D52*: 876-878). Microbatch can be used for controlling nucleation by carefully varying the temperature (Blow et al., 1994, *Protein Science* 3:1638-43). A final advantage is that the thick skins that often form with vapor diffusion are eliminated (e.g. Pearl et al., 1994, *EMBO J.* 13:5810-5817). Microbatch complements, rather than replaces, vapor diffusion. The main disadvantage of microbatch is that it can be relatively difficult to change conditions using the same protein sample, but it is particularly useful for screening of crystallization conditions.

Of course, those having skill in the art will recognize that the above-described crystallization conditions can be varied. Such variations may be used alone or in combination, and include polypeptide solutions containing polypeptide concentrations between 0.01 mg/mL and 100 mg/mL, HEPES concentrations between 0.1 mM and 500 mM, glycine concentrations between 0.001 mM and 100 mM, pH ranges between 4.0 and 12.0; and reservoir solutions containing PEG 4000 concentrations between about 0.1% and 50% (w/v), polyethylene glycol of other molecular weights between 0.01% and 50.0% (v/v), $NaN_3$ concentrations between 0.001% and 10% (w/v), and temperature ranges between 5° C. and 40° C. Other buffer solutions may be used such as BIS-TRIS, MES, MOPS, MOPSO, PIPES, TRIS, and the like, so long as the desired pH range is maintained.

In some embodiments in accordance with the present invention, crystals are obtained by methods of high-throughput crystallization (HTC).

Heavy-atom derivative crystals can be obtained by soaking native crystals in mother liquor containing salts of heavy metal atoms.

Heavy-atom derivative crystals can also be obtained from SeMet and/or SeCys mutants, as described above for native crystals.

Mutant proteins may crystallize under slightly different crystallization conditions than wild-type protein, or under very different crystallization conditions, depending on the nature of the mutation, and its location in the protein. For example, a non-conservative mutation may result in alteration of the hydrophilicity of the mutant, which may in turn make the mutant protein either more soluble or less soluble than the wild-type protein. Typically, if a protein becomes more hydrophilic as a result of a mutation, it will be more soluble than the wild-type protein in an aqueous solution and a higher precipitant concentration will be needed to cause it to crystallize. Conversely, if a protein becomes less hydrophilic as a result of a mutation, it will be less soluble in an aqueous solution and a lower precipitant concentration will be needed to cause it to crystallize. If the mutation happens to be in a region of the protein involved in crystal lattice contacts, crystallization conditions may be affected in more unpredictable ways.

WNV DIII-E16 Fab complex crystals can be obtained by soaking a WNV DIII crystal in mother liquor containing E16 Fab, by soaking an E16 Fab crystal in mother liquor containing WNV DIII, or by co-crystallizing WNV DIII-E16 Fab complex.

5.4 Characterization of Crystals

The dimensions of a unit cell of a crystal are defined by six numbers, the lengths of three unique edges, a, b, and c, and three unique angles, α, β, and γ. The type of unit cell that comprises a crystal is dependent on the values of these variables, as discussed above in Section 3.2. While the following discussion relates to solving the structure of the compounds constituting the crystal by X-ray diffraction, one skilled in the art will recognize that other methods (e.g. Laue, electron or neutron diffraction) could also be used. Such methods are also intended to be within the scope of the present invention.

When a crystal is placed in an X-ray beam, the incident X-rays interact with the electron cloud of the molecules that make up the crystal, resulting in X-ray scatter. The combination of X-ray scatter with the lattice of the crystal gives rise to nonuniformity of the scatter; areas of high intensity are called diffracted X-rays. The angle at which diffracted beams emerge from the crystal can be computed by treating diffraction as if it were reflection from sets of equivalent, parallel planes of atoms in a crystal (Bragg's Law). The most obvious sets of planes in a crystal lattice are those that are parallel to the faces of the unit cell. These and other sets of planes can be drawn through the lattice points. Each set of planes is identified by three indices, hkl. The h index gives the number of parts into which the a edge of the unit cell is cut, the k index gives the number of parts into which the b edge of the unit cell is cut, and the l index gives the number of parts into which the c edge of the unit cell is cut by the set of hkl planes. Thus, for example, the 235 planes cut the a edge of each unit cell into halves, the b edge of each unit cell into thirds, and the c edge of each unit cell into fifths. Planes that are parallel to the bc face of the unit cell are the 100 planes; planes that are parallel to the ac face of the unit cell are the 010 planes; and planes that are parallel to the ab face of the unit cell are the 001 planes.

When a detector is placed in the path of the diffracted X-rays, in effect cutting into the sphere of diffraction, a series of spots, or reflections, are recorded to produce a "still" diffraction pattern. Each reflection is the result of X-rays reflecting off one set of parallel planes, and is characterized by an intensity, which is related to the distribution of molecules in the unit cell, and hkl indices, which correspond to the parallel planes from which the beam producing that spot was reflected. If the crystal is rotated about an axis perpendicular to the X-ray beam, a large number of reflections is recorded on the detector, resulting in a diffraction pattern as shown, for example, in FIG. 4.

The unit cell dimensions and space group of a crystal can be determined from its diffraction pattern. First, the spacing of reflections is inversely proportional to the lengths of the edges of the unit cell. Therefore, if a diffraction pattern is recorded when the X-ray beam is perpendicular to a face of the unit cell, two of the unit cell dimensions may be deduced from the spacing of the reflections in the x and y directions of the detector, the crystal-to-detector distance, and the wavelength of the X-rays. Those of skill in the art will appreciate that, in order to obtain all three unit cell dimensions, the crystal can be rotated such that the X-ray beam is perpendicular to another face of the unit cell. Second, the angles of a unit cell can be determined by the angles between lines of spots on the diffraction pattern. Third, the absence of certain reflections and the repetitive nature of the diffraction pattern, which may be evident by visual inspection, indicate the internal symmetry, or space group, of the crystal. Therefore, a crystal may be characterized by its unit cell and space group, as well as by its diffraction pattern.

Once the dimensions of the unit cell are determined, the likely number of polypeptides in the asymmetric unit can be deduced from the size of the polypeptide, the density of the average protein, and the typical solvent content of a protein crystal, which is usually in the range of 30-70% of the unit cell volume (Matthews, 1968, *J. Mol. Biol.* 33:491-497).

The WNV DIII-E16 Fab complex crystals of the present invention are generally characterized by a diffraction pattern, as shown in FIG. 4. The crystals are further characterized by unit cell dimensions and space group symmetry information obtained from the diffraction patterns, as described above. The crystals, which may be native crystals, heavy-atom derivative crystals or poly-crystals, have a orthorhombic unit cell (i.e., unit cells wherein $a \neq b \neq c$ and $\alpha=\beta=\gamma 90°$) and space group symmetry $P2_12_12_1$.

One form of crystalline WNV DIII-E16 Fab complex was obtained. In this form (designated "$P2_12_12_1$ form"), the unit cell has dimensions of a=52.4+/−0.2 Å, b=83.3 +/−0.2 Å, c=110.6+/ 0.2 Å. There are believed to be 3 molecules in the asymmetric unit: one molecule of WNV DIII, one light chain of E16, and one papain-cleaved heavy chain of E16.

5.5 Collection of Data and Determination of Structure Solutions

The diffraction pattern of a crystal is related to the three-dimensional shape of the molecules that constitute the crystal by a Fourier transform. It has been established that diffraction patterns of a crystal can result from X-ray diffraction as well as Laue, electron or neutron diffraction. X-ray diffraction has been the most widely used methods for determining macromolecular structures. It is therefore used in this section by way of illustration to discuss the processes of diffraction data collection and subsequent structure determination. The scope of the present invention is, however, by no means limited only to X-ray diffraction analyses of protein crystals. After enough diffraction data are collected for a crystal, the process of determining the solution is in essence a re-focusing of the diffracted X-rays to produce a three-dimensional image of the molecule in the crystal. Since lenses capable of focusing X-ray radiation do not yet exist, the structure determination can be done via mathematical operations that simulate the re-focusing process.

The sphere of diffraction has symmetry that depends on the internal symmetry of the crystal, which means that certain orientations of the crystal will produce the same set of reflections. Thus, a crystal with high symmetry has a more repetitive diffraction pattern, and there are fewer unique reflections that need to be recorded in order to have a complete representation of the diffraction. The goal of data collection, a dataset, is a set of consistently measured, indexed intensities for as many reflections as possible. A complete dataset is collected if at least 80%, preferably at least 90%, most preferably at least 95% of unique reflections are recorded. In one embodiment, a complete dataset is collected using one crystal. In another embodiment, a complete dataset is collected using more than one crystal of the same type.

Sources of X-rays include, but are not limited to, a rotating anode X-ray generator such as a Rigaku RU-200 or a beamline at a synchrotron light source, such as the Advanced Photon Source at Argonne National Laboratory, the Advanced Light Source at the Lawrence Berkeley Laboratory, and the Stanford Synchrotron Radiation Laboratory at the Stanford Linear Acceleration Center. Suitable detectors for recording diffraction patterns include, but are not limited to, X-ray sensitive film, multiwire area detectors, image plates coated with phosphorus, and CCD cameras. Typically, the detector and the X-ray beam remain stationary, so that, in order to record diffraction from different parts of the crystal's sphere of diffraction, the crystal itself is moved via an automated system of moveable circles called a goniostat.

One of the biggest problems in data collection, particularly from macromolecular crystals having a high solvent content, is the rapid degradation of the crystal in the X-ray beam. In order to slow the degradation, data is often collected from a crystal at liquid nitrogen temperatures. In order for a crystal to survive the initial exposure to liquid nitrogen, the formation of ice within the crystal can be prevented by the use of a cryoprotectant. Suitable cryoprotectants include, but are not limited to, low molecular weight polyethylene glycols, ethylene glycol, sucrose, glycerol, xylitol, and combinations thereof. Crystals may be soaked in a solution comprising the one or more cryoprotectants prior to exposure to liquid nitrogen, or the one or more cryoprotectants may be added to the crystallization solution. Data collection at liquid nitrogen temperatures may allow the collection of an entire dataset from one crystal.

Once a dataset is collected, the information is used to determine the three-dimensional structure of the molecule in the crystal. However, this cannot be done from a single measurement of reflection intensities because certain information, known as phase information, is lost between the three-dimensional shape of the molecule and its Fourier transform, the diffraction pattern. This phase information can be acquired by methods described below in order to perform a Fourier transform on the diffraction pattern to obtain the three-dimensional structure of the molecule in the crystal. It is the determination of phase information that in effect refocuses X-rays to produce the image of the molecule.

One method of obtaining phase information is by isomorphous replacement, in which heavy-atom derivative crystals are used. In this method, diffraction data for both heavy-atom derivative crystals and native crystals are collected. Differences in diffraction patterns between the native and derivative datasets can be used to determine the positions of heavy atoms bound to the molecules in the heavy-atom derivative crystal. This information can then be used to obtain the phase information necessary to elucidate the three-dimensional structure of the material that constitutes the native crystals (Blundel et al., 1976, Protein Crystallography, Academic Press). In more recent applications of the isomorphous replacement method, manual and automatic (as implemented by the program SHELX) search procedures have been applied to locate the position of the heavy atoms in the derivative crystals (Sheldrick et al., 1993, *Acta Cryst.* D49:18-23). In other recent applications of the isomorphous replacement method, the inert gas Xenon is introduced into a native crystal to form a heavy atom derivative crystal. Xenon atoms occupy holes in a protein molecule through pure Van der Waals interaction. Examples of isomorphous replacement by Xenon derivatized crystals can be found in Sauer et al., 1997, *J. Appl. Cryst.* 30:476-486 and Panjikar and Tucker, 2002, *Acta Cryst.* D58:1413-1420.

Another method of obtaining phase information is by molecular replacement, which is a method of calculating initial phases for a new crystal of a polypeptide whose structure coordinates are unknown by orienting and positioning a polypeptide whose structure coordinates are known within the unit cell of the new crystal so as to best account for the observed diffraction pattern of the new crystal. Phases are then calculated from the oriented and positioned polypeptide and combined with observed amplitudes to provide an approximate Fourier synthesis of the structure of the molecules comprising the new crystal. (Lattman, 1985, *Methods in Enzymology* 115:55-77; Rossmann, 1972, "The Molecular Replacement Method," *Int. Sci. Rev. Ser. No.* 13, Gordon & Breach, New York). The molecular replacement method can be used when a protein with unknown structure shares a certain degree of sequence homology with a protein whose structure is already known. Conventional molecular replacement methods comprise two search algorithms: a rotational search fnction and a translational search function. Molecular replacement methods can be found in many existing computer programs such as AMoRe (Navaza, 1994, *Acta, Cryst.* A50:157-163) CNS (Brunger et al., 1998, *Acta Cryst.* D54: 905-921), as well as many programs in the CCP4 package suites (Collaborative Computational Project, Number 4, 1994).

A third method of phase determination is multi-wavelength anomalous diffraction or MAD. In this method, X-ray diffraction data are collected at several different wavelengths from a single crystal containing at least one heavy atom with absorption edges near the energy of incoming X-ray radiation. The resonance between X-rays and electron orbitals leads to differences in X-ray scattering that permits the locations of the heavy atoms to be identified, which in turn provides phase information for a crystal of a polypeptide. MAD analysis uses a radiation source with capacity to adjust its output wavelength. Nearly all synchrotron source around the world are now equipped with the capacity. A detailed discussion of MAD analysis can be found in Hendrickson, 1985, *Trans. Am. Crystallogr. Assoc.* 21:11; Hendrickson et al., 1990, *EMBO J.* 9:1665-1672; and Hendrickson, 1991, *Science* 4:91. In the traditional approach, Se atoms (atomic number 34, in the same group at sulfur), usually in the form of Se-Met, are introduced into native protein prior to crystallization to add anomalous scattering property to the protein crystal (Hendrickson et al, 1990, *EMBO J.* 9:1665-1672; Leahy et al,. 1992, *Science,* 258:987-991). Incorporating Se-Met into protein is usually achieved by growing recombinant vectors in the presence of medium containing Se-Met supplement (Dyer et al., 2005, *Protein Sci.* 14:1508-1517).

A fourth method of determining phase information is single wavelength anomalous dispersion or SAD. In this technique, X-ray diffraction data are collected at a single wavelength from a single native or heavy-atom derivative crystal, and phase information is extracted using anomalous scattering information from atoms such as sulfur or chlorine in the native crystal or from the heavy atoms in the heavy-atom derivative crystal. The wavelength of X-rays used to collect data for this phasing technique need not be close to the absorption edge of the anomalous scatterer. A detailed discussion of SAD analysis can be found in Brodersen et al., 2000, *Acta Cryst.* D56:431-441. SAD eliminates the requirement for a radiation source with adjustable wavelengths. It is possible to utilize non-synchrotron radiation to determine protein structures by anomalous scattering. For example, the structure of human formylglycine-generating enzyme was determined by de novo calcium and sulfur SAD phasing at a non-synchrotron radiation source (Roeser et al., 2005, *Acta Cryst.* D61:1057-1066).

A fifth method of determining phase information is single isomorphous replacement with anomalous scattering or SIRAS. This technique combines isomorphous replacement and anomalous scattering techniques to provide phase information for a crystal of a polypeptide. X-ray diffraction data are collected at a single wavelength, usually from a single heavy-atom derivative crystal. Phase information obtained only from the location of the heavy atoms in a single heavy-atom derivative crystal leads to an ambiguity in the phase angle, which is resolved using anomalous scattering from the heavy atoms. Phase information is therefore extracted from both the location of the heavy atoms and from anomalous scattering of the heavy atoms. A detailed discussion of SIRAS analysis can be found in North, 1965, *Acta Cryst.* 18:212-216; Matthews, 1966, *Acta Cryst.* 20:82-86. It is possible to combine the techniques of MAD and SAD phasing with SIRAS and determine protein structure without synchrotron radiation. For example, the structure of *E. coli* argininosuccinate synthetase was determined using Cu-Kappa radiation in a non-synchrotron source with S-SAD, Se-SAD and S/Se-SIRAS phasing techniques (Lenike et al., 2002, *Acta Cryst.* D58:2096-2101).

Methods for phase determination have been discussed individually for the purpose of clear illustration. It is necessary to emphasize again that these methods are often combined in practice as previously stated. For example, the methods of MAD, SAD, and SIRAS were all explored when the structure of human mannose-6-phosphate/insulin-like growth factor II receptor was determined (Uson et al., 2002, *Acta Cryst.* D59:57-66). Also in this study, halide atoms, e.g. bromide and iodide as well as sulfur were used in extract the overall phase information of the molecule instead of the standard Se-Met MAD or SAD phasing techniques.

Once phase information is obtained, it is combined with the diffraction data to produce an electron density map, an image of the electron clouds that surround the molecules in the unit cell. The higher the resolution of the data, the more distinguishable are the features of the electron density map, e.g., amino acid side chains and the positions of carbonyl oxygen atoms in the peptide backbones, because atoms that are closer together are resolvable. A model of the macromolecule is then built into the electron density map with the aid of a computer, using as a guide all available information, such as the polypeptide sequence and the established rules of molecular structure and stereochemistry. Interpreting the electron density map is a process of finding the chemically reasonable conformation that fits the map precisely.

After a model is generated, a structure is refined. Refinement is the process of minimizing the function $\Phi$, which is the difference between observed and calculated intensity values (measured by an R-factor), and which is a function of the position, temperature factor, and occupancy of each non-hydrogen atom in the model. This usually involves alternate cycles of real space refinement, i.e., calculation of electron density maps and model building, and reciprocal space refinement, i.e., computational attempts to improve the agreement between the original intensity data and intensity data generated from each successive model. Refinement ends when the function $\Phi$ converges on a minimum wherein the model fits the electron density map and is stereochemically and conformationally reasonable. During refinement, ordered solvent molecules are added to the structure.

5.5.1 Structures of WNV DIII-E16 Fab Complex

The present invention provides, for the first time, the high-resolution three-dimensional structures and atomic structure coordinates of crystalline WNV DIII-E16 Fab complex as determined by X-ray crystallography. The specific methods used to obtain the structure coordinates are provided in the examples, *infra*. The atomic structure coordinates of crystalline WNV DIII-E16 Fab complex, obtained from the $P2_12_12_1$ form of the crystal to 2.5 Å resolution, are listed in Table 7.

Those having skill in the art will recognize that atomic structure coordinates as determined by X-ray crystallography are not without error. Thus, it is to be understood that any set of structure coordinates obtained for crystals of WNV DIII-E16 Fab complex, whether native crystals, heavy-atom derivative crystals or poly-crystals, that have a root mean square deviation ("r.m.s.d.") of less than or equal to about 2 Å when superimposed, using backbone atoms (N, Cα, C and O), on the structure coordinates listed in Table 7 are considered to be identical with the structure coordinates listed in the Table 5 when at least about 50% to 100% of the backbone atoms of the constituents of the WNV DIII-E16 Fab complex are included in the superposition.

Referring now to FIG. 9, the overall structure of the WNV DIII-E16 Fab complex shows that a convex pocket is formed by the variable regions of the heavy and light chains of E16 ($V_H$ and $V_L$, respectively) which encompasses a discontinuous conformational epitope on WNV DII. All references by number to amino acids of the heavy and light chains of E16 are according to the Kabat numbering system, while references by number to amino acids of WNV DII correspond to the sequence identified with Genbank Accession No. AF196835. The buried surface area of the interaction (1548 $Å^2$) is dominated by $V_H$, which accounts for approximately 67% of the buried surface area. All six CDR loops approach within 4.2 Å of WNV DIII although CDR1 and CDR2 of the light chain are only minimally involved. The surface complementarity of the interaction is 0.763 (light chain 0.793 and heavy chain 0.742), consistent with previously published antibody-antigen interactions.

The residues in the $V_L$ that approach within 4.2 Å of WNV DIII can be separated into three segments, corresponding to CDR1, CDR2 and CDR3 (See Table 1, which lists all residues on WNV-DII that have any atoms within 4.2 Å of E16). The second column demonstrates the contacted residue in WNV-E16 and the distance of the closest approach. There are additional main chain contacts in residues A309, A331, A365, A389, L91, H96 and H99). CDR1 and CDR2 provide a few amino acid contacts to WNV DIII, using Ser30L and Trp50L, respectively. The $V_L$ CDR3 interaction is more extensive, utilizing amino acid residues 91-94. In contrast, the heavy chain dominates the interaction with WNV DIII (See Table 1). CDR1 contracts DIII using residues Tyr27H, Thr28H, Asp31H, Tyr32H and Trp33H. CDR2 makes connects with residues Leu52H, Arg56H and Arg58H. Interestingly, CDR3 has significant interactions with WNV DIII accounting for ~33% of the buried interface, with contacts at residues 94 through 100. As is commonly observed in antibody interactions with antigen, many of the contacting residues have aromatic side chains. For example, of 21 residues that contact WNV DIII, 6 are aromatic (2 Trp and 4 Tyr).

TABLE 1

Contact residues of E16 Fab and WNV DIII

| WNV-DIII residue | E16 Residue | Chain | Distance |
|---|---|---|---|
| 302 | 56 | H | 3.54 |
| 306 | 33 | H | 2.61 |
| 306 | 52 | H | 3.57 |
| 307 | 33 | H | 3.80 |
| 307 | 100 | H | 4.02 |
| 307 | 95 | H | 2.49 |
| 307 | 96 | H | 2.87 |
| 308 | 98 | H | 3.84 |
| 309 | 98 | H | 3.84 |
| 330 | 50 | L | 3.61 |
| 330 | 98 | H | 4.03 |
| 330 | 99 | H | 3.42 |
| 331 | 100 | H | 3.95 |
| 332 | 94 | L | 3.76 |
| 332 | 58 | H | 2.77 |
| 332 | 100 | H | 2.89 |
| 332 | 91 | L | 3.26 |

TABLE 1-continued

Contact residues of E16 Fab and WNV DIII

| WNV-DIII residue | E16 Residue | Chain | Distance |
|---|---|---|---|
| 333 | 33 | H | 4.09 |
| 333 | 56 | H | 3.12 |
| 333 | 58 | H | 4.19 |
| 365 | 93 | L | 2.98 |
| 366 | 92 | L | 3.47 |
| 366 | 93 | L | 4.05 |
| 367 | 50 | L | 3.86 |
| 368 | 30 | L | 2.59 |
| 368 | 50 | L | 3.70 |
| 389 | 31 | H | 3.08 |
| 390 | 27 | H | 3.83 |
| 390 | 28 | H | 2.59 |
| 390 | 31 | H | 3.96 |
| 390 | 32 | H | 2.47 |
| 390 | 94 | H | 4.12 |
| 391 | 31 | H | 3.00 |
| 391 | 32 | H | 3.74 |
| 391 | 97 | H | 2.79 |

Further, crystallographic analysis revealed that WNV DIII forms a β barrel structure formed from seven anti-parallel β-strands in two beta sheets (See FIG. 9), consistent with previous X-ray and NMR studies of other flavivirus E proteins. See Modis et al., 2003, *Proc. Natl. Acad. Sci. USA* 100:6986-91; Rey et al., 1995, *Nature* 375:291-8; Volk et al., 2004, *J. Biol. Chem.* 279:38755-38761; and Yu et al., 2004, *Biochemistry* 43:9168-76. One anti-parallel beta sheet consists of beta strands β1 (F309-D317), β2 (V323-Y329), β4 (D348-P351) and β5 (A369-E376), arranged in that order. The second anti-parallel beta sheet is formed from strands β3 (I340-S345), β6 (G380-V386) and β7 (I393-K399) arranged with β6 as the center. Based on antibody epitope mapping studies, amino acids that appear to define antigenic differences between WNV and other flaviviruses are located near the N-terminus of WNV DIII, and occupy a large proportion of the binding interface (see FIG. 10).

Based on the co-crystal structure, WNV DIII provides a nonlinear epitope for binding of the neutralizing E16 Fab. Four different loops of WNV DIII provide close contacts with the antibody, including residues 302 to 308, 330 to 333, 366 to 368 and 389 to 391. Because the contact area of the four loops that E16 Fab binds is not appreciably altered from that of unbound dengue and tick-borne encephalitis virus DIII (see Modis et al., 2003, *Proc. Natl. Sci. USA* 100:6986-91; Rey et al., 1995, *Nature* 375:291-8), the Fab does not appears to induce significant conformational change in WNV DIII. The structure of E16 Fab was also modeled onto the structure of the virion. The face of DIII that binds to E16 Fab is exposed to solvent and not sterically blocked by other envelope proteins in the virion. The Fab binding face points at the outer ring of the five-fold axis, in addition to other sites in the virion.

The interaction between the Fab and DIII is dominated by hydrogen bonding, with only a limited number of hydrophobic contacts. Of the 7 total hydrophobic contacts, Trp50L accounts for all but one of these (Ser30L-Asn368A), as it interacts with Thr330A, Asn368A and Ala367A (see Table 2). In comparison, there are 16 hydrogen bonds directly connecting the antibody to the antigen (see Table 3). Despite the large number of hydrogen bonds, no salt bridges are formed between DIII and E16. The hydrogen bonds generate an elaborate network, with a number of critical residues coordinating multiple bonds between DIII and E16. Notably, six of the hydrogen bonds involve main-chain interactions on WNV DIII. Such interactions may be invariant with respect to sequence and side-chain and thus, could explain the broad reactivity of this antibody with divergent lineage I and II strains. For example, Tyr92L and Ser97H contact WNV DIII through main-chain to main-chain interactions. In contrast, Thr93L, Asp31H, Arg56H, and Asp100H use their side chains to bond to main chain atoms in WNV DIII.

TABLE 2

Hydrophobic Contacts Between E16 and domain III

| Atom 1 | | | Atom 2 | | | Distance |
|---|---|---|---|---|---|---|
| ASN | A368 | CB | SER | L30 | CB | 3.99 |
| THR | A330 | CA | TRP | L50 | CZ2 | 3.66 |
| THR | A330 | CB | TRP | L50 | CZ2 | 3.62 |
| THR | A330 | CG2 | TRP | L50 | CZ2 | 3.85 |
| ASN | A368 | CB | TRP | L50 | CZ3 | 3.85 |
| ASN | A368 | CG | TRP | L50 | CZ3 | 3.76 |
| ALA | A367 | CB | TRP | L50 | CH2 | 3.87 |

TABLE 3

Hydrogen Bond Contacts Between E16 and domain III

| Donor | | | Acceptor | | | Distance |
|---|---|---|---|---|---|---|
| SER | L30 | OG | ASN | A368 | OD1 | 2.59 |
| ALA | A367 | N | TYR | L92 | O | 2.82 |
| THR | L93 | OG1 | ALA | A365 | O | 2.98 |
| THR | H28 | N | GLU | A390 | OE2 | 2.61 |
| THR | H28 | OG1 | GLU | A390 | OE2 | 2.59 |
| GLU | A390 | N | ASP | H31 | OD2 | 3.01 |
| GLN | A391 | NE2 | ASP | H31 | O | 3.05 |
| TYR | H32 | OH | GLU | A390 | OE1 | 2.48 |
| TRP | H33 | NE1 | SER | A306 | OG | 2.62 |
| ARG | H56 | NH1 | ASP | A333 | O | 2.91 |
| ARG | H58 | NH1 | THR | A332 | OG1 | 2.78 |
| LYS | A307 | NZ | SER | H95 | OG | 2.50 |
| LYS | A307 | NZ | ALA | H96 | O | 2.87 |
| SER | H97 | OG | GLN | A391 | OE1 | 2.80 |
| ALA | A308 | N | SER | H97 | O | 2.79 |
| THR | A332 | N | ASP | H100 | OD1 | 3.27 |
| Wat | 24 | OH2 | SER | A306 | O | 2.74 |
| Wat | 24 | OH2 | Wat | 7 | OH2 | 2.63 |
| Wat | 24 | OH2 | ASP | H31 | O | 2.88 |
| LYS | A307 | NZ | Wat | 7 | OH2 | 2.92 |
| TRP | H33 | N | Wat | 7 | OH2 | 2.77 |
| Wat | 7 | OH2 | SER | H95 | O | 2.83 |
| TYR | H98 | OH | Wat | 243 | OH2 | 3.00 |
| Wat | 243 | OH2 | PHE | A309 | O | 2.71 |
| Wat | 14 | OH2 | THR | A330 | O | 2.80 |
| HIS | L91 | ND1 | Wat | 14 | OH2 | 2.90 |
| Wat | 14 | OH2 | HIS | L91 | O | 2.63 |
| ASP | H100 | N | Wat | 14 | OH2 | 2.81 |
| Wat | 160 | OH2 | THR | A332 | O | 2.96 |
| Wat | 160 | OH2 | ALA | A365 | O | 2.83 |
| THR | L93 | OG1 | Wat | 160 | OH2 | 2.96 |
| THR | L94 | N | Wat | 160 | OH2 | 3.08 |
| THR | L94 | OG1 | Wat | 160 | OH2 | 3.07 |

Ten of the hydrogen bonds interact with side chains on WNV DIII. Lys307A uses its amine hydrogen to form hydrogen bonds with Ala96H and Ser95H, in addition to water-7. Glu390A is coordinated by Thr28H and Asp31H, and Gln391A contacts Asp31H and Ser97H. WNV DIII residues that contact multiple residues in E16 are likely to be required for high affinity antibody binding.

In addition to direct interactions between E16 and WNV DIII, numerous hydrogen bond networks are formed through intervening water molecules present at the antibody-antigen interface. All but one of the water molecules involve main chain atoms in WNV DIII. Lys307A is the only side chain that connects to the antibody by hydrogen bonding to Ser95H and Trp33H through water-7. Waters-14, -24, -160, and -243 all hydrogen bond with the main chain of DIII in addition to contacting multiple residues in E16. Although most of the water molecules are peripheral, waters-7 and 14 are found within the binding pocket.

5.6 Structure Coordinates

The atomic structure coordinates can be used in molecular modeling and design, as described more fully below. The present invention encompasses the structure coordinates and other information, e.g., amino acid sequence, connectivity tables, vector-based representations, temperature factors, etc., used to generate the three-dimensional structure of the polypeptide for use in the software programs described below and other software programs.

The invention encompasses machine-readable media embedded with the three-dimensional structure of the model described herein, or with portions thereof. As used herein, "machine-readable medium" refers to any medium that can be read and accessed directly by a computer or scanner. Such media include, but are not limited to: magnetic storage media, such as floppy discs, hard disc storage medium and magnetic tape; optical storage media such as optical discs or CD-ROM; electrical storage media such as RAM or ROM; and hybrids of these categories such as magnetic/optical storage media. Such media further include paper on which is recorded a representation of the atomic structure coordinates, e.g., Cartesian coordinates, that can be read by a scanning device and converted into a three-dimensional structure with an OCR.

A variety of data storage structures are available to a skilled artisan for creating a computer readable medium having recorded thereon the atomic structure coordinates of the invention or portions thereof and/or X-ray diffraction data. The choice of the data storage structure will generally be based on the means chosen to access the stored information. In addition, a variety of data processor programs and formats can be used to store the sequence and X-ray data information on a computer readable medium. Such formats include, but are not limited to, Protein Data Bank ("PDB") format (Research Collaboratory for Structural Bioinformatics; Cambridge Crystallographic Data Centre format; Structure-data ("SD") file format (MDL Information Systems, Inc.; Dalby et al., 1992, *J. Chem. Inf. Comp. Sci.* 32:244-255), and line-notation, e.g., as used in SMILES (Weininger, 1988, *J. Chem. Inf. Comp. Sci.* 28:31-36). Methods of converting between various formats read by different computer software will be readily apparent to those of skill in the art, e.g., BABEL (v. 1.06, Walters & Stahl, ©1992, 1993, 1994). All format representations of the polypeptide coordinates described herein, or portions thereof, are contemplated by the present invention. By providing computer readable medium having stored thereon the atomic coordinates of the invention, one of skill in the art can routinely access the atomic coordinates of the invention, or portions thereof, and related information for use in modeling and design programs, described in detail below.

While Cartesian coordinates are important and convenient representations of the three-dimensional structure of a polypeptide, those of skill in the art will readily recognize that other representations of the structure are also useful. Therefore, the three-dimensional structure of a polypeptide, as discussed herein, includes not only the Cartesian coordinate representation, but also all alternative representations of the three-dimensional distribution of atoms. For example, atomic coordinates may be represented as a Z-matrix, wherein a first atom of the protein is chosen, a second atom is placed at a defined distance from the first atom, a third atom is placed at a defined distance from the second atom so that it makes a defined angle with the first atom. Each subsequent atom is placed at a defined distance from a previously placed atom with a specified angle with respect to the third atom, and at a specified torsion angle with respect to a fourth atom. Atomic coordinates may also be represented as a Patterson function, wherein all interatomic vectors are drawn and are then placed with their tails at the origin. This representation is particularly useful for locating heavy atoms in a unit cell. In addition, atomic coordinates may be represented as a series of vectors having magnitude and direction and drawn from a chosen origin to each atom in the polypeptide structure. Furthermore, the positions of atoms in a three-dimensional structure may be represented as fractions of the unit cell (fractional coordinates), or in spherical polar coordinates.

Additional information, such as thermal parameters, which measure the motion of each atom in the structure, chain identifiers, which identify the particular chain of a multi-chain protein in which an atom is located, and connectivity information, which indicates to which atoms a particular atom is bonded, is also useful for representing a three-dimensional molecular structure.

5.7 Uses of the Automic Structure Coordinates

Structure information, typically in the form of the atomic structure coordinates, can be used in a variety of computational or computer-based methods to, for example, design, screen for and/or identify compounds that bind the crystallized polypeptide or a portion or fragment thereof, to intelligently design mutants that have altered biological properties, to intelligently design and/or modify antibodies that have desirable binding characteristics, and the like.

In one embodiment, the crystals and structure coordinates obtained therefrom are useful for identifying and/or designing compounds that bind WNV DIII as an approach towards developing new therapeutic agents. For example, a high resolution X-ray structure will often show the locations of ordered solvent molecules around the protein, and in particular at or near putative binding sites on the protein. This information can then be used to design molecules that bind these sites, the compounds synthesized and tested for binding in biological assays. See Travis, 1993, *Science* 262:1374. Such compounds may be useful, for example, to inhibit binding of WNV E protein to its cognate receptor or to induce production of antibodies or other immune responses that can protect against WNV infection.

In another embodiment, the structure is probed with a plurality of molecules to determine their ability to bind to the WNV DIII alone or in complex with a monoclonal antibody such as E16 at various sites. Such compounds can be used as targets or leads in medicinal chemistry efforts to identify, for example, inhibitors of potential therapeutic importance or molecules that enhance antibody binding and/or neutralization of WNV DIII.

In yet another embodiment, the structure is probed with a plurality of molecules to determine their ability to bind to the WNV DIII binding site of E16. Such compounds can be used, for example, as targets or leads in medicinal chemistry efforts to identify, for example, compounds that can be used to induce an immune response that can provide prophylactic and/or therapeutic benefit against WNV infection.

In yet another embodiment, the structure can be used to computationally screen small molecule data bases for chemical entities or compounds that can bind in whole, or in part, to WNV DIII. In this screening, the quality of fit of such entities or compounds to the binding site may be judged either by shape complementarity or by estimated interaction energy. See Meng et al., 1992, *J. Comp. Chem.* 13:505-524.

The design of compounds that bind to WNV DIII, inhibit the interaction of WNV DIII with its cognate receptor, or inhibit WNV infection, according to this invention generally involves consideration of two factors. First, the compound should be capable of physically and structurally associating with WNV DIII. This association can be covalent or non-covalent. For example, covalent interactions may be important for designing irreversible inhibitors of WNV DIII. Non-covalent molecular interactions important in the association of WNV DIII with its substrate include hydrogen bonding, ionic interactions and van der Waals and hydrophobic interactions. Second, the compound should be able to assume a conformation that allows it to associate with WNV DIII. Although certain portions of the compound will not directly participate in this association with WNV DIII, those portions may still influence the overall conformation of the molecule. This, in turn, may impact potency. Such conformational requirements include the overall three-dimensional structure and orientation of the chemical group or compound in relation to all or a portion of the binding site, or the spacing between functional groups of a compound comprising several chemical groups that directly interact with WNV DIII.

The potential inhibitory or binding effect of a chemical compound on WNV DIII binding may be analyzed prior to its actual synthesis and testing by the use of computer modeling techniques. If the theoretical structure of the given compound suggests insufficient interaction and association between it and WNV DIII, synthesis and testing of the compound is unnecessary. However, if computer modeling indicates a strong interaction, the molecule may then be synthesized and tested for its ability to bind to WNV DIII and inhibit its binding activity. In this manner, synthesis of ineffective compounds may be avoided.

An inhibitory or other binding compound of WNV DIII may be computationally evaluated and designed by means of a series of steps in which chemical groups or fragments are screened and selected for their ability to associate with the individual binding pockets or other areas of WNV DIII. One skilled in the art may use one of several methods to screen chemical groups or fragments for their ability to associate with WNV DIII. This process may begin by visual inspection of, for example, the binding site on the computer screen based on the WNV DIII coordinates. Selected fragments or chemical groups may then be positioned in a variety of orientations, or docked, within an individual binding pocket of WNV DIII as described above. Docking may be accomplished using software such as QUANTA and SYBYL, followed by energy minimization and molecular dynamics with standard molecular mechanics force fields, such as CHARMM and AMBER.

These principles may also be used to design and evaluate compounds that can mimic WNV DIII. However, in designing and evaluating such compounds, the chemical groups or fragments are screened and selected for their ability to associate with the individual binding pockets of E16 that recognize WNV DIII. Preferably, the chemical groups or fragments together are able to associate with two, three, four, five, or six of the individual binding pockets that together recognize WNV DIII.

Specialized computer programs may also assist in the process of selecting fragments or chemical groups. These include:

1. GRID (Goodford, 1985, *J. Med. Chem.* 28:849-857). GRID is available from Oxford University, Oxford, UK;

2. MCSS (Miranker & Karplus, 1991, *Proteins: Structure, Function and Genetics* 11:29-34). MCSS is available from Molecular Simulations, Burlington, Mass.;

3. AUTODOCK (Goodsell & Olsen, 1990, *Proteins: Structure, Function, and Genetics* 8:195-202). AUTODOCK is available from Scripps Research Institute, La Jolla, Calif.; and 4. DOCK (Kuntz et al., 1982, *J. Mol. Biol.* 161:269-288). DOCK is available in several versions from University of California, San Francisco, Calif.

5. CombiDOCK (Sun et al., 1998, *J. Comput. Aided Mol. Des.* 12:597-604). CombiDOCK is available from Univeristy of California, San Francisco, Calif.).

6. FRED (available from OpenEye Scientific Software, Santa Fe, N. Mex.). Based on an original scientific perspective and efficient computational algorithms, FRED is an accurate and extremely fast docking program. With equivalent resolution settings, FRED will out-perform all known docking programs, typically examining about a dozen ligand conformers in a second. For each, FRED exhaustively examines all possible poses within the protein active site, filtering for shape complementarity and pharmacophoric features before scoring with more traditional functions.

7. ROCS (available from OpenEye Scientific Software, Santa Fe, N. Mex.). ROCS is a shape comparison program, based on the idea that molecules have similar shape if their volumes overlay well and any volume mismatch is a measure of dissimilarity. ROCS uses a smooth Gaussian function to represent the molecular volume, so it is possible to routinely minimize to the best global match. ROCS is capable of processing 600-800 comparisons each second, making it possible to search multi-conformer representations of corporate collections in a day on a single processor to find compounds with similar shape to a lead compound.

Once suitable chemical groups or fragments have been selected, they can be assembled into a single compound or inhibitor. Assembly may proceed by visual inspection of the relationship of the fragments to each other in the three-dimensional image displayed on a computer screen in relation to the structure coordinates of WNV DIII. This would be followed by manual model building using software such as QUANTA or SYBYL.

Useful programs to aid one of skill in the art in connecting the individual chemical groups or fragments include:

1. CAVEAT (Bartlett et al., 1989, "CAVEAT: A Program to Facilitate the Structure-Derived Design of Biologically Active Molecules," In Molecular Recognition in Chemical and Biological Problems', *Special Pub., Royal Chem. Soc.* 78:182-196). CAVEAT is available from the University of California, Berkeley, Calif.;

2. 3D Database systems such as MACCS-3D (MDL Information Systems, San Leandro, Calif). This area is reviewed in Martin, 1992, *J. Med. Chem.* 35:2145-2154); and 3. HOOK (available from Molecular Simulations, Burlington, Mass.).

4. FILTER (available from OpenEye Scientific Software, Santa Fe, N. Mex.). FILTER is a molecular screening and selection tool that uses a combination of physical-property calculations and functional-group knowledge to assess compound collections. In selection mode, FILTER can be used to choose reagents appropriate for specific syntheses. In filter mode, it quickly removes compounds with undesirable elements, functional groups, or physical properties. FILTER is a command line utility that reads and writes many file formats including SDF, Mol, Mol2, SMILES, and OEBinary. Filter is supported on Linux, Windows and ilux; other platforms are available upon request.

5. SMACK (available from OpenEye Scientific Software, Santa Fe, N. Mex.). SMACK converts and optimizes molecular database queries. SMACK can quickly convert from sub-structure and reaction queries expressed in MDL file format to SMARTS strings. Additionally, SMACK will automatically optimize each resulting query for pattern-matching performance. Typical transformations simplify redundant atom and bond expressions and reorder atoms for faster matching against medicinal/organic chemistry databases.

Instead of proceeding to build a WNV DIII binding inhibitor in a step-wise fashion one fragment or chemical group at a time, as described above, WNV DIII binding compounds may be designed as a whole or "de novo" using either an empty WNV DIII binding site or optionally including some portion(s) of a known inhibitor(s). These methods include:

1. LUDI (Bohm, 1992, *J. Comp. Aid. Molec. Design* 6:61-78). LUDI is available from Molecular Simulations, Inc., San Diego, Calif.;

2. LEGEND (Nishibata & Itai, 1991, *Tetrahedron* 47:8985). LEGEND is available from Molecular Simulations, Burlington, Mass.; and 3. LeapFrog (available from Tripos, Inc., St. Louis, Mo.).

4. WABE (available from OpenEye Scientific Software, Santa Fe, N. Mex.). WABE is a de similis design program, as opposed to de novo design. Using a graph-invariant replacement algorithm, it quickly generates large numbers of isosteres to a lead molecule. The method resembles the process of chemical substitution, e.g. carboxylate to amnide or amidine, used in medicinal chemistry to create molecules having the same physical shape but varying in electrostatics. The similarities between analogs eliminate computationally demanding terms, so WABE can also quickly rank them by electrostatic similarity to a known binder or by protein-ligand binding. WABE is useful for exploring the chemical space around a lead compound to elucidate candidates with improved drug profiles or novel scaffolds to avoid patent coverage.

Other modeling and simulation computer programs include, but are not restricted to the following:

1. AMBER (available from University of California, San Francisco). AMBER (Assisted Model Building with Energy Refinement) is a molecular dynamics and energy minimization program.

2. CHARMM (available from Harvard University). CHARMM (Chemistry at HARvard Macromolecular Mechanics) is a program for macromolecular simulations, including energy minimization, molecular dynamics and Monte Carlo simulations.

3 Disulfide by Design (available from Wayne State University). Disulfide by Design is an application for the rational design of disulfide bonds in proteins and for exporting mutant PDB files containing the modeled disulfides for visualization in other molecular modeling software. For a given protein structural model, all residue pairs are rapidly assessed for proximity and geometry consistent with disulfide formation assuming the residues were mutated to cysteines. The output displays residue pairs meeting the appropriate criteria. The input model will typically be a PDB structure for the protein of interest; however, structures developed through homology modeling may also be used. Engineered disulfides have proven useful for increasing the stability of proteins and to assist the investigation of protein dynamics and interactions.

4. FTDOCK (available from the Biomolecular Modelling Laboratory of Cancer Research UK). FTDOCK is a program for carrying out rigid-body docking between biomolecules.

5. GROMOS (available from Laboratory of Physical Chemistry; ETH Honggerberg, HC). GROMOS is a general purpose molecular dynamics computer simulation package for the study of biomolecular systems.

6. GROMACS (an open-source tool freely available on the internet). GROMACS is a complete modeling package for proteins, membrane systems and more, including fast molecular dynamics, normal mode analysis, essential dynamics analysis and many trajectory analysis utilities.

7. ICM (Molsoft LLC, San Diego, Calif.). ICM from Molsoft provides programs and modules for applications including for structure analysis, modeling, docking, homology modeling and virtual ligand screening.

8. JACKAL (available from Columbia University). JACKAL is a suite of tools for model building, structure prediction and refinement, reconstruction, and minimization; for SGI, Linux, and Sun Solaris 9. LOOPP (available from Cornell University). LOOP (Linear Optimization of Protein Potentials) is available form Cornell Theory Center program for potential optimization and alignments of sequences and structures.

10. MAMMOTH (available from New York University). MAMMOTH (MAtching Molecular Models Obtained from Theory) is a program for automated pairwise and multiple structural alignments; for SGI, Linux, and Sun Solaris.

11. MCCE (available from the City College of New York). The MCCE (Multi-Conformation Continuum Electrostatics) software calculates theoretical pKas of residues in proteins and provides the modulating factors of pKas based on the structure in PDB format.

12. MidasPlus (available from University of California, San Francisco) MidasPlus is a program for displaying, manipulating and analysing macromolecules.

13. MODELLER (available from University of California, San Francisco). MODELLER is a program for automated protein homology modeling.

14. MOIL (available from Cornell University). MOIL is another program from the Cornell Theory Center package for molecular dynamics simulation of biological molecules.

15. NAMD (available from the University of Illinois at Urbana-Champaign). NAMD is a parallel object-oriented molecular dynamics simulation program.

16. WAM (available from the University of Bath). WAM (Web Antibody Modeling) provides a server for automated structure modeling from antibody Fv sequences.

17. 123D (Ceres Inc., Malibu, Calif.). 123D is a program which threads a sequence through a set of structures using substitution matrix, secondary structure prediction and contact capacity potential.

Additional molecular modeling techniques may also be employed in accordance with this invention. See, e.g., Cohen et al., 1990, *J. Med. Chem.* 33:883-894. See also Navia & Murcko, 1992, *Cur. Op. Struct. Biol.* 2:202-210.

Once a compound has been designed or selected by the above methods, the efficiency with which that compound may bind to WNV DIII may be tested and optimized by computational evaluation. For example, a compound that has been designed or selected to function as a WNV DIII binding inhibitor should also preferably occupy a volume not overlapping the volume occupied by the binding site residues when the native receptor is bound. An effective WNV DIII inhibitor preferably demonstrates a relatively small difference in energy between its bound and free states (i.e., it should have a small deformation energy of binding). Thus, the most efficient WNV DIII binding inhibitors should preferably be designed with a deformation energy of binding of not greater than about 10 kcal/mol, preferably, not greater than 7 kcal/mol. WNV DIII binding inhibitors may interact with the protein in more than one conformation that is similar in overall binding energy. In those cases, the deformation energy of binding is taken to be the difference between the energy of the free compound and the average energy of the conformations observed when the inhibitor binds to the enzyme.

A compound selected or designed for binding to WNV DIII may be further computationally optimized so that in its bound state it would preferably lack repulsive electrostatic interaction with the target protein. Such non-complementary electrostatic interactions include repulsive charge-charge, dipole-dipole and charge-dipole interactions. Specifically, the sum of all electrostatic interactions between the inhibitor and the protein when the inhibitor is bound to it preferably make a neutral or favorable contribution to the enthalpy of binding.

Specific computer software is available in the art to evaluate compound deformation energy and electrostatic interaction. Examples of programs designed for such uses include: Gaussian 92, revision C (Frisch, Gaussian, Inc., Pittsburgh, Pa. (01992); AMBER, version 4.0 (Kollman, University of California at San Francisco, ©1994); QUANTA/CHARMM (Molecular Simulations, Inc., Burlington, Mass., ©1994); and Insight II/Discover (Biosym Technologies Inc., San Diego, Calif., (1994). These programs may be implemented, for instance, using a computer workstation, as are well-known in the art. Other hardware systems and software packages will be known to those skilled in the art.

Once a WNV DIII-binding compound has been optimally selected or designed, as described above, substitutions may then be made in some of its atoms or chemical groups in order to improve or modify its binding properties. Generally, initial substitutions are conservative, i.e., the replacement group will have approximately the same size, shape, hydrophobicity and charge as the original group. One of skill in the art will understand that substitutions known in the art to alter conformation should be avoided. Such altered chemical compounds may then be analyzed for efficiency of binding to WNV DIII by the same computer methods described in detail above.

Because WNV DIII-E16 Fab complex may crystallize in more than one form, the structure coordinates of WNV DIII-E16 Fab complex, or portions thereof, are particularly useful to solve the structure of those other crystal forms of WNV DIII-E16 Fab complex. They may also be used to solve the structure of WNV DIII-E16 Fab complex mutants, WNV DIII-E16 Fab poly-complex that is complexed with one or more additional molecules, or of the crystalline form of any other protein with significant amino acid sequence homology to any functional domain of WNV DIII and/or E16 Fab.

One method that may be employed for this purpose is molecular replacement. In this method, the unknown crystal structure, whether it is another crystal form of WNV DIII-E16 Fab complex, a mutant WNV DIII-E16 Fab complex, a WNV DIII-mutant E16 Fab complex, or a WNV DIII-E16 Fab poly-complex that is complexed with one or more additional molecules, or the crystal of some other protein with significant amino acid sequence homology to any functional domain of WNV DIII and/or E16 Fab, may be determined using phase information from the WNV DIII-E16 Fab complex structure coordinates. This method may provide an accurate three-dimensional structure for the unknown protein in the new crystal more quickly and efficiently than attempting to determine such information ab initio. In addition, in accordance with this invention, WNV DIII-E16 Fab complex mutants may be crystallized in complex with known WNV DIII binding inhibitors. The crystal structures of a series of such complexes may then be solved by molecular replacement and compared with that of wild-type WNV DIII. Potential sites for modification within the various binding sites of the protein may thus be identified. This information provides an additional tool for determining the most efficient binding interactions, for example, increased hydrophobic interactions, between WNV DIII and a chemical group, compound, or monoclonal antibody such as E16.

If an unknown crystal form has the same space group as and similar cell dimensions to the known orthorhombic crystal form, then the phases derived from the known crystal form can be directly applied to the unknown crystal form, and in turn, an electron density map for the unknown crystal form can be calculated. Difference electron density maps can then be used to examine the differences between the unknown crystal form and the known crystal form. A difference electron density map is a subtraction of one electron density map, e.g., that derived from the known crystal form, from another electron density map, e.g., that derived from the unknown crystal form. Therefore, all similar features of the two electron density maps are eliminated in the subtraction and only the differences between the two structures remain. For example, if the unknown crystal form is of a WNV DIII-E16 Fab complex in complex with one or more additional molecules, then a difference electron density map between this map and the map derived from the WNV DIII-E16 Fab complex crystal will ideally show only the electron density of the ligand. Similarly, if amino acid side chains have different conformations in the two crystal forms, then those differences will be highlighted by peaks (positive electron density) and valleys (negative electron density) in the difference electron density map, making the differences between the two crystal forms easy to detect. However, if the space groups and/or cell dimensions of the two crystal forms are different, then this approach will not work and molecular replacement can be used in order to derive phases for the unknown crystal form.

All of the complexes referred to above may be studied using well-known X-ray diffraction techniques and may be refined versus 50 Å to 1.5 Å or greater resolution X-ray data to an R value of about 0.20 or less using computer software, such as CNS (Yale University, (c) 1992, distributed by Molecular Simulations, Inc.). See, e.g., Blundel et al., 1976, *Protein Crystallography,* Academic Press.; Methods in Enzymology, vols. 114 & 115, Wyckoff et al., eds., Academic Press, 1985. This information may thus be used to optimize known classes of WNV DIII binding inhibitors, and more importantly, to design and synthesize novel classes of WNV DIII binding inhibitors.

The structure coordinates of mutant WNV DIII-E16 Fab complex and/or WNV DIII-mutant E16 Fab complex will also facilitate the identification of related proteins or enzymes analogous to WNV DIII and/or E16 Fab in function, structure or both, thereby further leading to novel therapeutic modes for treating or preventing WNV or other flavivirus-mediated diseases.

Subsets of the atomic structure coordinates can be used in any of the above methods. Particularly useful subsets of the coordinates include, but are not limited to, coordinates of single domains, coordinates of residues lining an active site, coordinates of residues that participate in important protein-protein contacts at an interface, and Ca coordinates. For example, the coordinates of one domain of a protein that contains the active site may be used to design inhibitors that bind to that site, even though the protein is fully described by a larger set of atomic coordinates. Therefore, a set of atomic coordinates that define the entire polypeptide chain, although useful for many applications, do not necessarily need to be used for the methods described herein.

5.8 Methods of Identifying Neutralizing Epitopes of Flaviviral Envelope Proteins In yet another aspect, the invention provides a method for identifying a neutralizing epitope of a domain III of a flaviviral envelope protein. In certain embodiments, the method comprises comparing an amino acid sequence of the domain III of the flaviviral envelope protein to an amino acid sequence of a domain III of a WNV E protein, and identifying the amino acids of the domain III of the flaviviral envelope protein corresponding to a neutralizing epitope of the domain III of the WNV E protein, thereby identifying the neutralizing epitope of the flaviviral envelope protein. The methods can be performed with any flaviviral envelope protein known to one of skill in the art without limitation. For example, the methods can be performed with flaviviral envelope protein from Japanese Encephalitus Virus, Dengue Virus, Yellow Fever Virus, St. Louis Encephalitus Virus, Murray Valley Encephalitus Virus, Rocio Virus, Tick-borne Encephalitis Virus, Kyasanur Forest Disease Virus, Omsk Hemorrhagic Fever Virus, Montana myotis leukoencephalitis virus, Modoc virus, Powssan Virus, and Kunjin Virus.

The amino acid sequences of these envelope proteins, and references describing the determination of these amino acid sequences are described in Table 4, below

TABLE 4

| Virus | Accession Number | For | Reference |
|---|---|---|---|
| Japanese Encephalitus Virus | NP_775666 | Envelope protein | Sumiyoshi et al., 1987, Virology 161(2), 497–510 |
| Dengue Virus | NP_739583 | E protein | Hahn et al., 1988, Virology 162(2), 167–180 |
| Yellow Fever Virus | NP_740305 | Envelope protein | Rice et al., 1985, Science 229(4715), 726–733 |
| St. Louis Encephalitus Virus | AAF22698 to AAF22719 | Envelope protein | Charrel et al., 1999, J. Clin. Microbiol. 37(6), 1936–1940 |
| Murray Valley Encephalitus Virus | NP_722531 | Envelope protein | Hurrelbrink et al., 1999, J. Gen. Virol. 80(pt 12), 3115–3125 |
| Rocio Virus | AAK91596 | Envelope protein | Gaunt et al., 2001, J. Gen. Virol. 82(pt 8), 1867–1876 |
| Tick-borne Encephalitus Virus | NP_775503 | Envelope protein | Wallner et al., 1995, Virology 213(1), 169–178 |
| Kyasanur Forest Disease Virus | X74111 | Virus DNA sequence for core, membrane & envelope proteins | Venugopal et al., 1994, J. Gen. Virol. 75 (pt1), 227–232 |
| Omsk Hemorrhagic Fever Virus | NP_932085 | Envelope protein | Lin et al., 2003, Virology 313(1), 81–90 |
| Montana myotis leukoencephalitis virus | NP_740277 | Envelope protein | Charlier et al., 2002, J. Gen. Virol. 80(pt 8), 1875–1885 |
| Modoc virus | NP_740260 | Envelope protein | Leyssen et al., 2002, Thesis, Department of Microbiology, Rega Institute for Medical Research, Leuven, Belguim |

TABLE 4-continued

| Virus | Accession Number | For | Reference |
|---|---|---|---|
| Powssan Virus | NP_775516 | Envelope protein | Mandl et al., 1993, Virology 194(1), 173–184 |
| Kunjin Virus | P14335 | Amino acid sequence of viral polyprotein; envelope protein defined by amino acids 291–791 | Coia et al., 1988, J. Gen. Virol. 69: 1–21 |

In certain embodiments, the neutralizing epitope of the domain III of the WNV E protein comprises an amino acid sequence corresponding to amino acids 300-309, 330-333, 365-368, or 389-391 of WNV E protein, using SEQ ID NO:4 for numbering. In certain embodiments, the neutralizing epitope of the domain III of the WNV E protein comprises an amino acid sequence corresponding to amino acids 300-309 of WNV E protein, using SEQ ID NO:4 for numbering. In certain embodiments, the neutralizing epitope of the domain III of the WNV E protein comprises an amino acid sequence corresponding to amino acids 330-333 of WNV E protein, using SEQ ID NO:4 for numbering. In certain embodiments, the neutralizing epitope of the domain III of the WNV E protein comprises an amino acid sequence corresponding to amino acids 365-368 of WNV E protein, using SEQ ID NO:4 for numbering. In certain embodiments, the neutralizing epitope of the domain III of the WNV E protein comprises an amino acid sequence corresponding to amino acids 389-391 of WNV E protein, using SEQ ID NO:4 for numbering. In certain embodiments, the neutralizing epitope of the domain III of the WNV E protein comprises an amino acid sequence corresponding to amino acids 300-309, 330-333, 365-368, and 389-391 of WNV E protein, using SEQ ID NO:4 for numbering. Exemplary regions corresponding to portions of the neutralizing epitope of WNV DIII are presented in FIG. 15.

Any suitable method known to one of skill in the art can be used to compare sequences of envelope proteins in the methods of the invention. Conveniently, such comparisons can be performed using one of many suitable computer-implemented algorithms known to the art. These algorithms generally identify regions of greatest homology and identity between two or more related amino acid and/or nucleotide sequences and thus can be used to identify sequences in flaviviral envelope proteins that correspond to sequences that make up, in whole or in part, a WNV neutralizing epitope as described herein.

Exemplary algorithms which can be used to determine identity and/or homology between two sequences include, but are not limited to, the suite of BLAST programs, e.g., BLASTN, BLASTX, and TBLASTX, BLASTP and TBLASTN, publicly available on the Internet at the NCBI website. See also Altschul et al., 1990, *J. Mol. Biol.* 215:403-10 (with special reference to the published default setting, i.e., parameters w=4, t=17) and Altschul et al., 1997, *Nucleic Acids Res.*, 25:3389-3402. Sequence searches are typically carried out using the BLASTP program when evaluating a given amino acid sequence relative to amino acid sequences in the GenBank Protein Sequences and other public databases. The BLASTX program is preferred for searching nucleic acid sequences that have been translated in all reading frames against amino acid sequences in the GenBank Protein Sequences and other public databases. Both BLASTP and BLASTX are run using default parameters of an open gap penalty of 11.0, and an extended gap penalty of 1.0, and utilize the BLOSUM-62 matrix. See id.

Alignments of selected sequences in order to determine homology and/or identity between two or more sequences, can also be performed using for example, the CLUSTAL-W program in MacVector version 6.5, operated with default parameters, including an open gap penalty of 10.0, an extended gap penalty of 0.1, and a BLOSUM 30 similarity matrix.

The present invention is also intended to encompass immunogens comprising neutralizing epitopes from the flaviviruses described above, antibodies that specifically bind such neutralizing epitopes, methods of inducing immune responses against such epitopes, methods of treating or preventing infection with the flaviviruses, and the like. One of skill in the art can, after identifying such neutralizing epitopes as described above, construct such immunogens, make such antibodies, and perform such methods by adapting the invention described herein to use the neutralizing epitope identified above.

5.9 Methods of Making High Affinity Antibodies to WNV DIII

In yet another aspect, the present invention provides methods of making antibodies that bind WNV DIII with high affinity. In general, the methods rely on use of the three-dimensional structure of WNV DIII-E16 Fab complex to identify one or more amino acid residues present in the Fab fragment that can be altered in order to increase the affinity of E16 for WNV DIII. Thus, in certain embodiments, the methods comprise mutating an amino acid of the antibody which when mutated is predicted to increase the affinity with which the antibody binds the domain III of WNV E protein.

In certain embodiments, the amino acid that is mutated contacts the domain III of WNV E protein more closely than the wild-type amino acid. In certain embodiments, the mutated amino acid excludes a water molecule from a hydrophobic region of the domain III that is not excluded by the wild-type amino acid. In certain embodiments, the mutated amino acid forms a hydrogen bond with the domain III that is not formed by the first amino acid. In certain embodiments, the mutated amino acid is an amino acid selected from Table 1. In certain embodiments, the mutated amino acid is an amino acid selected from Table 2. In certain embodiments, the mutated amino acid is an amino acid selected from Table 3.

In certain embodiments, more than one amino acid of the antibody can be mutated. Thus, in certain embodiments, one, two, three, four, five, six, seven, eight, nine, ten, eleven, twelve, thirteen, fourteen, fifteen, twenty, twenty-five, thirty, forty, fifty, or more amino acids can be mutated. In certain embodiments, two, three, four, five, six, seven, eight, nine, ten, eleven, twelve, thirteen, fourteen, fifteen, twenty, twenty-five, or twenty-nine amino acids selected from Table 1 are mutated. In certain embodiments, two, three, four, five, six, or seven amino acids selected from Table 2 are mutated. In certain embodiments, two, three, four, five, six, seven, eight, nine, ten, eleven, twelve, thirteen, fourteen, fifteen, twenty, twenty-five, or thirty amino acids selected from Table 3 are mutated.

In still another aspect, the invention provides methods of making antibodies that bind flaviviral envelope proteins with high affinity. Using the three-dimensional structural coordinates provided in the present application and structural information about flaviviral envelope proteins available to one skilled in the art, one or more amino acid residues that affect the affinity of an antibody, or fragment thereof, for a flaviviral envelope protein can be identified. Such amino acids can be mutated to increase or decrease the affinity of the antibody for the envelope protein. Thus, the methods of the invention can also be used to make antibodies that bind with high affinity an envelope protein from a flavivirus, including, but not limited to, WNV, Japanese encephalitis virus, Kunjin virus, Murray Valley encephalitis virus, Dengue virus, Montana myotis leukoencephalitis virus, Modoc virus, and Yellow Fever virus.

Exemplary sources available to one skilled in the art for structural information regarding envelope proteins from other flaviviruses may be found, for example, in Beasley et al., 2002, *J. Virol.* 76:13097-13100; Mukhopadhyay et al., 2003, *Science* 302:248; Rey et al., 1995, *Nature* 375:291-8; Roehrig et al., 2001, *Ann. N.Y. Acad. Sci.* 951:286-297; Zhang et al., 2003, *EMBO J* 22:2604-13; and Zhang et al., 2003, *Nat. Struct. Biol.* 10:907-912; Kuhn et al., 2002, *Cell* 108:717-25; Modis et al., 2003, *Proc. Natl. Acad. Sci. USA* 100:6986-91; Beasley and Aaskov, 2001, *Virology* 279:447-58; Cecilia and Gould, 1991, *Virology* 181:70-7; Crill and Roehrig, 2001, *J. Virol.* 75:7769-73; Lin et al., 1994, *Virology* 202:885-90; Roehrig et al., 1983, *Virology* 128:118-26; Schlesinger et al., 1996, *J. Gen. Virol.* 77:1277-85; Seifetal., 1995, *Vaccine* 13:1515-21; Volketal., 2004, *J. Biol. Chem.* 279:38755-38761; Wu et al., 1997, *Virus. Res.* 51:173-81; and Wu et al., 2003, *J. Biol. Chem.* 278:46007-46013.

Standard techniques known to those skilled in the art can be used to introduce mutations in the nucleotide sequence encoding an antibody, or fragment thereof, including, e.g., site-directed mutagenesis and PCR-mediated mutagenesis, which results in amino acid substitutions. In certain embodiments, the E16 derivatives include less than 15 amino acid substitutions, less than 10 amino acid substitutions, less than 5 amino acid substitutions, less than 4 amino acid substitutions, less than 3 amino acid substitutions, or less than 2 amino acid substitutions relative to the original antibody or fragment thereof. In a preferred embodiment, the derivatives have conservative amino acid substitutions made at one or more amino acid residues wherein the substitutions are predicted to increase the affinity of the antibody for WNV DIII. In an equally preferred embodiment, the derivatives have conservative amino acid substitutions made at one or more amino acid residues wherein the substitutions are predicted to increase the affinity of the antibody for WNV DIII The antibodies thus made may be characterized for specific binding to a WNV DIII, or any other flaviviral envelope protein, using any immunological or biochemical based method known in the art for characterizing including quantitating, the interaction of the antibody to a flaviviral envelope protein. Specific binding of an antibody to a flaviviral envelope protein may be determined, for example, using immunological or biochemical based methods including, but not limited to, an ELISA assay, surface plasmon resonance assays, immunoprecipitation assays, affinity chromatography, and equilibrium dialysis. Immunoassays which can be used to analyze immunospecific binding and cross-reactivity of the antibodies of the invention include, but are not limited to, competitive and non-competitive assay systems using techniques such as western blots, radioimmunoassays, ELISA assays, "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, and protein A immunoassays, to name but a few. Such assays are routine and well known in the art (see, e.g., Ausubel et al., eds, 2004, *Current Protocols in Molecular Biology*, Vol. 1, John Wiley & Sons, Inc., New York, which is incorporated by reference herein in its entirety).

Antibodies that bind to a flaviviral envelope protein may also be assayed using any surface plasmon resonance based assays known in the art for characterizing the kinetic parameters of the interaction of the antibody with a flaviviral. Any SPR instrument commercially available including, but not limited to, BIAcore Instruments, available from Biacore AB (Uppsala, Sweden); IAsys instruments available from Affinity Sensors (Franklin, Mass.); IBIS system available from Windsor Scientific Limited (Berks, UK), SPR-CELLIA systems available from Nippon Laser and Electronics Lab (Hokkaido, Japan), and SPR Detector Spreeta available from Texas Instruments (Dallas, Tex.) can be used in the instant invention. For a review of SPR-based technology see Mullet et al., 2000, *Methods* 22: 77-91; Dong et al., 2002, *Review in Mol. Biotech.*, 82: 303-23; Fivash et al., 1998, *Current Opinion in Biotechnology* 9: 97-101; Rich et al., 2000, *Current Opinion in Biotechnology* 11: 54-61; all of which are incorporated herein by reference in their entirety. Additionally, any of the SPR instruments and SPR based methods for measuring protein-protein interactions described in U.S. Pat. Nos. 6,373,577; 6,289,286; 5,322,798; 5,341,215; and 6,268,125 are contemplated in the methods of the invention, all of which are incorporated herein by reference in their entirety.

The invention also encompasses characterization of the antibodies produced by the methods of the invention using certain characterization assays for identifying the function of the antibodies of the invention, particularly the activity to inhibit a flaviviral infection using *in vitro* and *in vivo* based assays. Further, the invention encompasses cell based and cell free assays for characterization or use of the antibodies. Additional methods of characterizing antibodies made according to a method of the invention are described below.

5.10 Antibodies Binding a Neutralizing Epitope of WNV DIII

In yet another aspect, the invention provides antibodies, or fragments thereof, that specifically bind a neutralizing epitope of WNV DIII as described herein. In certain embodiments, the antibody, or fragment thereof, is a purified antibody, or fragment thereof. In certain embodiments, the antibody, or fragment thereof, is a monoclonal antibody, or fragment thereof. In certain embodiments, the antibody, or fragment thereof, is an antibody, or fragment thereof, purified from a polyclonal antibody preparation such that the antibody, or fragment thereof, is substantially isolated from antibodies, or fragments thereof, that bind WNV epitopes other than neutralizing epitopes. In certain embodiments, the antibody, or fragment thereof, is in the form of a composition that is purified to homogeneity. In certain embodiments, the antibody, or fragment thereof, is not 5H10, 3A3, 5C5, 7H2, 11C, 17C8, 10C5, 8B10, E1, E16, E24, E27, E33, E34, E40, E43, E47, E49, and/or E58, or any fragment thereof.

In certain embodiments, the antibody, or fragment thereof, binds the neutralizing epitope of domain III of WNV E protein with higher affinity than the antibody, or fragment thereof, binds an enhancing epitope of domain III of WNV E protein. In certain embodiments, the neutralizing epitope of the domain III of the WNV E protein comprises an amino acid sequence corresponding to amino acids 300-309, 330-333, 365-368, or 389-391 of WNV E protein, using SEQ ID NO:4 for numbering. In certain embodiments, the neutralizing epitope of the domain III of the WNV E protein comprises an amino acid sequence corresponding to amino acids 300-309 of WNV E protein, using SEQ ID NO:4 for numbering. In certain embodiments, the neutralizing epitope of the domain III of the WNV E protein comprises an amino acid sequence corresponding to amino acids 330-333 of WNV E protein, using SEQ ID NO:4 for numbering. In certain embodiments, the neutralizing epitope of the domain III of the WNV E protein comprises an amino acid sequence corresponding to amino acids 365-368 of WNV E protein, using SEQ ID NO:4 for numbering. In certain embodiments, the neutralizing epitope of the domain III of the WNV E protein comprises an amino acid sequence corresponding to amino acids 389-391 of WNV E protein, using SEQ ID NO:4 for numbering. In certain embodiments, the neutralizing epitope of the domain III of the WNV E protein comprises an amino acid sequence corresponding to amino acids 300-309, 330-333, 365-368, and 389-391 of WNV E protein, using SEQ ID NO:4 for numbering.

In another aspect, the invention provides a pharmaceutical composition comprising an antibody, or fragment thereof, of the invention, as described herein, and a pharmaceutically acceptable excipient, diluent, vehicle, or carrier. In certain embodiments, the pharmaceutical composition comprises a monoclonal antibody. In certain embodiments, the pharmaceutical composition is a single unit dosage form. In certain embodiments, the pharmaceutical composition further comprises a stabilizer. In certain embodiments, the pharmaceutical composition is formulated for storage for at least about 6 months without loss of more than about 20% activity.

In another aspect, the invention provides a kit comprising a pharmaceutical composition of the invention. In certain embodiments, the antibody of the pharmaceutical composition is a monoclonal antibody. In certain embodiments, the pharmaceutical composition is in a single unit dosage form. In certain embodiments, the kit further comprises instructions directing administration of the pharmaceutical composition to a subject.

The antibodies or fragments thereof may be characterized in a variety of ways in addition to those described above. In particular, antibodies of the invention or fragments thereof may be assayed for the ability to immunospecifically bind to a WNV antigen. Such an assay may be performed in solution (e.g., Houghten, 1992, *Bio/Techniques* 13:412-421), on beads (Lam, 1991, *Nature* 354:82-84), on chips (Fodor, 1993, *Nature* 364:555-556), on bacteria (U.S. Pat. No. 5,223,409), on spores (U.S. Pat. Nos. 5,571,698; 5,403,484; and 5,223, 409), on plasmids (Cull et al., 1992, *Proc. Natl. Acad. Sci. USA* 89:1865-1869) or on phage (Scott and Smith, 1990, *Science* 249:386-390; Devlin, 1990, *Science* 249:404-406; Cwirla et al., 1990, *Proc. Natl. Acad. Sci. USA* 87:6378-6382; and Felici, 1991, *J. Mol. Biol.* 222:301-310) (each of these references is incorporated herein in its entirety by reference). Antibodies or fragments thereof that have been identified to immunospecifically bind to a flaviviral antigen or a fragment thereof can then be assayed for their specificity and affinity for a flaviviral antigen.

The antibodies or fragments thereof may be assayed for immunospecific binding to a flaviviral antigen, particularly WNV antigen and cross-reactivity with other antigens by any method known in the art. Immunoassays which can be used to analyze immunospecific binding and cross-reactivity include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 2004, *Current Protocols in Molecular Biology*, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1 to 4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 2004, *Current Protocols in Molecular Biology*, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}P$ or $^{125}I$) diluted in blocking buffer, washing the membrane in wash buffer, and detecting the presence of the antigen. One of skill in the art would be knowledgeable as to the parameters that can be modified to increase the signal detected and to reduce the background noise. For fuirther discussion regarding western blot protocols see, e.g., Ausubel et al, eds, 2004, *Current Protocols in Molecular Biology*, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 2004, *Current Protocols in Molecular Biology*, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^3$H or $^{125}$I) with the antibody of interest in the presence of increasing amounts of unlabeled antigen, and the detection of the antibody bound to the labeled antigen. The affinity of the antibody of the present invention or a fragment thereof for a WNV antigen and the binding off-rates can be determined from the data by scatchard plot analysis. Competition with a second antibody can also be determined using radioimmunoassays. In this case, a WNV antigen is incubated with an antibody of the present invention or a fragment thereof conjugated to a labeled compound (e.g., $^3$H or $^{125}$I) in the presence of increasing amounts of an unlabeled second antibody.

In a preferred embodiment, BIAcore kinetic analysis is used to determine the binding on and off rates of antibodies or fragments thereof to a WNV antigen. BIAcore kinetic analysis comprises analyzing the binding and dissociation of a WNV antigen from chips with immobilized antibodies or fragments thereof on their surface.

The antibodies or fragments thereof can also be assayed for their ability to inhibit the binding of a flaviviral antigen to its host cell receptor using techniques known to those of skill in the art and exemplified herein. For example, cells expressing the receptor for WNV can be contacted with WNV in the presence or absence of an antibody or fragment thereof and the ability of the antibody or fragment thereof to inhibit WNV's binding can measured by, for example, flow cytometry or a scintillation assay. WNV (e.g., WNV antigen such as E protein) or the antibody or antibody fragment can be labeled with a detectable compound such as a radioactive label (e.g., 32P, 35S, and 125I) or a fluorescent label (e.g., fluorescein isothiocyanate, rhodamine, phycoerythrin, phycocyanin, allophycocyanin, o-phthaldehyde and fluorescamine) to enable detection of an interaction between WNV and its host cell receptor. Alternatively, the ability of antibodies or fragments thereof to inhibit WNV from binding to its receptor can be determined in cell-free assays. For example, WNV or a WNV antigen can be contacted with an antibody or fragment thereof and the ability of the antibody or antibody fragment to inhibit WNV or the WNV antigen from binding to its host cell receptor can be determined. Preferably, the antibody or the antibody fragment is immobilized on a solid support and WNV or a WNV antigen is labeled with a detectable compound. Alternatively, WNV or a WNv antigen is immobilized on a solid support and the antibody or fragment thereof is labeled with a detectable compound. WNV or a WNV antigen may be partially or completely purified (e.g., partially or completely free of other polypeptides) or part of a cell lysate. Further, a WNV antigen may be a fusion protein comprising the WNV antigen and a domain such as glutathionine-S-transferase. Alternatively, a WNV antigen can be biotinylated using techniques well known to those of skill in the art (e.g., biotinylation kit, Pierce Chemicals; Rockford, Ill.).

The antibodies or fragments thereof are preferably tested *in vitro*, and then *in vivo* for the desired therapeutic or prophylactic activity, prior to use in humans. For example, in vitro assays which can be used to determine whether administration of a specific antibody or composition of the present invention is indicated, include *in vitro* cell culture assays in which a subject tissue sample is grown in culture, and exposed to or otherwise administered an antibody or composition of the present invention, and the effect of such an antibody or composition of the present invention upon the tissue sample is observed. In various specific embodiments, in vitro assays can be carried out with representative cells of cell types involved in a WNV infection to determine if an antibody or composition of the present invention has a desired effect upon such cell types. Preferably, the antibodies or compositions of the invention are also tested in in vitro assays and animal model systems prior to administration to humans. In a specific embodiment, mice are administered an antibody the invention or fragment thereof, or a composition of the invention, challenged with 100 to 1000 pfu of WNV, and four or more days later the mice are sacrificed and WNV titer and anti-WNV antibody serum titer is determined. In another specific embodiment, mice are administered 100 or 1000 pfu of WNV at day 0. At a point following infection, e.g., day 1, 2, 3, 4, 5, or 6, antibody or antibody variants are administered as a single does or as multiple doses. The therapeutic effect of the antibody or antibody variant can be assessed by monitoring, for example, the WNV titer, anti-WNV antibody titer, and/or the health and/or survival of the mice administered the antibody or antibody variant.

In accordance with the invention, clinical trials with human subjects need not be performed in order to demonstrate the prophylactic and/or therapeutic efficacy of antibodies or fragments thereof. *In vitro* and animal model studies using the antibodies or fragments thereof can be extrapolated to humans and are sufficient for demonstrating the prophylactic and/or therapeutic utility of said antibodies or antibody fragments.

Antibodies or compositions of the present invention for use in therapy can be tested for their toxicity in suitable animal model systems, including but not limited to rats, mice, cows, monkeys, and rabbits. For *in vivo* testing of an antibody or composition's toxicity any animal model system known in the art may be used.

Efficacy in treating or preventing viral infection may be demonstrated by detecting the ability of an antibody or composition of the invention to inhibit the replication of the virus, to inhibit transmission or prevent the virus from establishing itself in its host, to reduce the incidence of WNV infection, or to prevent, ameliorate or alleviate one or more symptoms associated with WNV infection. The treatment is considered therapeutic if there is, for example, a reduction is viral load, amelioration of one or more symptoms, a reduction in the duration of a WNV infection, or a decrease in mortality and/or morbidity following administration of an antibody or composition of the invention. Further, the treatment is considered therapeutic if there is an increase in the immune response following the administration of one or more antibodies or fragments thereof which immunospecifically bind to one or more WNV antigens.

Antibodies or compositions of the invention can be tested in vitro and in vivo for the ability to induce the expression of cytokines such as IFN-α, IFN-β, IFN-γ, IL-2, IL-3, IL-4, IL-5, IL-6, IL-7, IL-8, IL-9, IL-10, IL-12 and IL-15. Techniques known to those of skill in the art can be used to measure the level of expression of cytokines. For example, the level of expression of cytokines can be measured by analyzing the level of RNA of cytokines by, for example, RT-PCR and Northern blot analysis, and by analyzing the level of cytokines by, for example, immunoprecipitation followed by western blot analysis and ELISA.

Antibodies or compositions of the invention can be tested in vitro and in vivo for their ability to modulate the biological activity of immune cells, preferably human immune cells (e.g., T-cells, B-cells, and Natural Killer cells). The ability of an antibody or composition of the invention to modulate the biological activity of immune cells can be assessed by detecting the expression of antigens, detecting the proliferation of immune cells, detecting the activation of signaling molecules, detecting the effector function of immune cells, or detecting the differentiation of immune cells. Techniques known to those of skill in the art can be used for measuring these activities. For example, cellular proliferation can be assayed by $^3$H-thymidine incorporation assays and trypan blue cell counts. Antigen expression can be assayed, for example, by immunoassays including, but are not limited to, competitive and non-competitive assay systems using techniques such as western blots, immunohistochemistry radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays and FACS analysis. The activation of signaling molecules can be assayed, for example, by kinase assays and electrophoretic shift assays (EMSAs).

Antibodies or compositions of the invention can also be tested for their ability to inhibit viral replication or reduce viral load in in vitro, ex vivo and in vivo assays. Antibodies or compositions of the invention can also be tested for their ability to decrease the time course of WNV infection. Antibodies or compositions of the invention can also be tested for their ability to increase the survival period of humans suffering from WNV infection by at least 25%, preferably at least 50%, at least 60%, at least 75%, at least 85%, at least 95%, or at least 99%. Further, antibodies or compositions of the invention can be tested for their ability reduce the hospitalization period of humans suffering from WNV infection by at least 60%, preferably at least 75%, at least 85%, at least 95%, or at least 99%. Techniques known to those of skill in the art can be used to analyze the function of the antibodies or compositions of the invention in vivo.

Compounds for use in therapy can be tested in suitable animal model systems prior to testing in humans, including, but not limited to, in rats, mice, chicken, cows, monkeys, pigs, dogs, rabbits, hamsters, etc., for example, the animal models described above. Any animal system well-known in the art may be used.

Combinations of prophylactic and/or therapeutic agents can be tested in suitable animal model systems prior to use in humans. In a specific embodiment of the invention, combinations of prophylactic and/or therapeutic agents are tested in a mouse model system. Such model systems are widely used and well-known to the skilled artisan. Prophylactic and/or therapeutic agents can be administered repeatedly. Several aspects of the procedure may vary such as the temporal regime of administering the prophylactic and/or therapeutic agents, and whether such agents are administered separately or as an admixture.

Once the prophylactic and/or therapeutic agents of the invention have been tested in an animal model they can be tested in clinical trials to establish their efficacy. Establishing clinical trials will be done in accordance with common methodologies known to one skilled in the art, and the optimal dosages and routes of administration as well as toxicity profiles of the compositions of the invention can be established using routine experimentation.

The data obtained from the cell culture assays and animal studies can be used in formulating a range of dosage of the prophylactic and/or therapeutic agents for use in humans. The dosage of such agents lies preferably within a range of circulating concentrations that include the $ED_{50}$ with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

Additional description of antibodies in general, as well as antibodies that bind WNV E protein, including the E16 monoclonal antibody, methods of making such antibodies, methods of using such antibodies, methods of characterizing such antibodies, and the like, may be found in U.S. Provisional Application No. 60/581,819 and U.S. application Ser. No. 11/159,046, filed Jun. 21, 2005, each of which is hereby incorporated by reference in its entirety for all purposes. In particular, all of the disclosure of these applications relating to antibodies, antibody derivatives, methods of making or characterizing, and all other disclosure relating to antibodies in general can be used to make, use, modify, manipulate, and otherwise engineer the antibodies of the invention as described herein.

5.11 Methods of Treating or Preventing WNV Infection

In yet another aspect, the invention provides a method of treating WNV infection. In certain embodiments, the methods comprising administering to a subject an effective amount of an antibody of the invention, as described herein. In certain embodiments, the antibody is a purified antibody. In certain embodiments, the antibody is not 5H10, 3A3, 5C5, 7H2, 11C, 17C8, 10C5, 8B10, E1, E16, E24, E27, E33, E34, E40, E43, E47, E49, and/or E58. In certain embodiments, the antibody is a monoclonal antibody.

In certain embodiments, the antibody binds the neutralizing epitope of domain III of WNV E protein with higher affinity than the antibody binds an enhancing epitope of domain III of WNV E protein. In certain embodiments, the neutralizing epitope of the domain III of the WNV E protein comprises an amino acid sequence corresponding to amino acids 300-309, 330-333, 365-368, or 389-391 of WNV E protein, using SEQ ID NO:4 for numbering. In certain embodiments, the neutralizing epitope of the domain III of the WNV E protein comprises an amino acid sequence corresponding to amino acids 300-309 of WNV E protein, using SEQ ID NO:4 for numbering. In certain embodiments, the neutralizing epitope of the domain III of the WNV E protein comprises an amino acid sequence corresponding to amino acids 330-333 of WNV E protein, using SEQ ID NO:4 for numbering. In certain embodiments, the neutralizing epitope of the domain III of the WNV E protein comprises an amino acid sequence corresponding to amino acids 365-368 of WNV E protein, using SEQ ID NO:4 for numbering. In certain embodiments, the neutralizing epitope of the domain III of the WNV E protein comprises an amino acid sequence corresponding to amino acids 389-391 of WNV E protein, using SEQ ID NO:4 for numbering. In certain embodiments, the neutralizing epitope of the domain III of the WNV E protein comprises an amino acid sequence corresponding to amino acids 300-309, 330-333, 365-368, and 389-391 of WNV E protein, using SEQ ID NO:4 for numbering.

In certain embodiments, the antibody is administered to the subject in the form of a pharmaceutical composition.

In another aspect, the invention provides a method of preventing WNV infection, comprising administering to a subject an effective amount of an antibody of the invention. In certain embodiments, the antibody binds a neutralizing epitope of domain III of WNV E protein with higher affinity than the antibody binds an enhancing epitope of domain III of WNV E protein. In certain embodiments, the antibody is not 5H10, 3A3, 5C5, 7H2, 11C, 17C8, 10C5, 8B10, E1, E16, E24, E27, E33, E34, E40, E43, E47, E49, and/or E58. In certain embodiments, the antibody is a monoclonal antibody. In certain embodiments, the antibody binds the neutralizing epitope of domain III of WNV E protein with higher affinity than the antibody binds an enhancing epitope of domain III of WNV E protein. In certain embodiments, the neutralizing epitope of the domain III of the WNV E protein comprises an amino acid sequence corresponding to amino acids 300-309, 330-333, 365-368, or 389-391 of WNV E protein, using SEQ ID NO:4 for numbering. In certain embodiments, the neutralizing epitope of the domain III of the WNV E protein comprises an amino acid sequence corresponding to amino acids 300-309 of WNV E protein, using SEQ ID NO:4 for numbering. In certain embodiments, the neutralizing epitope of the domain III of the WNV E protein comprises an amino acid sequence corresponding to amino acids 330-333 of WNV E protein, using SEQ ID NO:4 for numbering. In certain embodiments, the neutralizing epitope of the domain III of the WNV E protein comprises an amino acid sequence corresponding to amino acids 365-368 of WNV E protein, using SEQ ID NO:4 for numbering. In certain embodiments, the neutralizing epitope of the domain III of the WNV E protein comprises an amino acid sequence corresponding to amino acids 389-391 of WNV E protein, using SEQ ID NO:4 for numbering. In certain embodiments, the neutralizing epitope of the domain III of the WNV E protein comprises an amino acid sequence corresponding to amino acids 300-309, 330-333, 365-368, and 389-391 of WNV E protein, using SEQ ID NO:4 for numbering. In certain embodiments, the antibody is administered to the subject in the form of a pharmaceutical composition.

5.12 WNV Immunogens

In yet another aspect, the invention provides WNV immunogens. The WNV immunogens of the invention are useful, for example, for inducing an immune response in a subject against a WNV epitope and, for example, in pharmaceutical compositions as described below. Preferably, the WNV epitope is a neutralizing epitope. The immune response that is induced preferably is effective to reduce, more preferably prevent, WNV infection in the subject following induction of the immune response.

Accordingly, in certain embodiments, the invention provides a WNV immunogen that comprises a peptide corresponding to amino acids 300-309, 330-333, 365-368, or 389-391 of WNV E protein, using SEQ ID NO:4 for numbering, wherein the peptide is arranged in the three dimensional conformation of amino acids 300-309, 330-333, 365-368, or 389-391, respectively, of WNV E protein according to the structural coordinates shown in Table 7. In certain embodiments, the immunogen does not comprise the entire amino acid sequence of domain III of WNV E protein.

In certain embodiments, the WNV immunogen comprises a peptide corresponding to amino acids 300-309 of WNV E protein, using SEQ ID NO:4 for numbering. In certain embodiments, the WNV immunogen comprises a peptide corresponding to amino acids 330-333 of WNV E protein, using SEQ ID NO:4 for numbering. In certain embodiments, immunogen comprises a peptide corresponding to amino acids 365-368 of WNV E protein, using SEQ ID NO:4 for numbering. In certain embodiments, the immunogen comprises a peptide corresponding to amino acids 389-391 of WNV E protein, using SEQ ID NO:4 for numbering. In certain embodiments, the immunogen comprises peptides corresponding to amino acids 300-309 and 330-333 of WNV E protein, using SEQ ID NO:4 for numbering. In certain embodiments, the immunogen comprises peptides corresponding to amino acids 300-309 and 365-368 of WNV E protein, using SEQ ID NO:4 for numbering. In certain embodiments, the immunogen comprises peptides corresponding to amino acids 300-309 and 389-391 of WNV E protein, using SEQ ID NO:4 for numbering. In certain embodiments, the immunogen comprises peptides corresponding to amino acids 330-333 and 365-368 of WNV E protein, using SEQ ID NO:4 for numbering. In certain embodiments, the immunogen comprises peptides corresponding to amino acids 330-333 and 389-391 of WNV E protein, using SEQ ID NO:4 for numbering. In certain embodiments, the immunogen comprises peptides corresponding to amino acids 300-309, 330-333, and 365-368, of WNV E protein, using SEQ ID NO:4 for numbering. In certain embodiments, the immunogen comprises peptides corresponding to amino acids 300-309, 330-333, and 389-391 of WNV E protein, using SEQ ID NO:4 for numbering. In certain embodiments, the immunogen comprises peptides corresponding to amino acids 300-309, 365-368, and 389-391 of WNV E protein, using SEQ ID NO:4 for numbering. In certain embodiments, the immunogen comprises peptides corresponding to amino acids 330-333, 365-368, and 389-391 of WNV E protein, using SEQ ID NO:4 for numbering. In a preferred embodiment, the immunogen comprises peptides corresponding to amino acids 300-309, 330-333, 365-368, and 389-391 of WNV E protein, using SEQ ID NO:4 for numbering. In certain embodiments, the immunogen comprises an amino acid sequence corresponding to amino acids 300-391 of WNV E protein, using SEQ ID NO:4 for numbering.

In certain embodiments, the peptide linkers comprise one or more glycines. In certain embodiments, the peptides corresponding to amino acids 300-309, 330-333, 365-368, and/or 389-391 of WNV E protein, using SEQ ID NO:4 for numbering, are connected with each other with linkers. In general, the exact nature of the linker used in the WNV immunogens is unimportant, so long as the linker links the peptides of the WNV immunogen in a manner that permits the peptides to assume the proper molecular conformation, such as that presented in Table 7. In certain embodiments, the linker can form a covalent bond between the peptides of the WNV immunogen. In other embodiments, the linker can link peptides of the WNV immunogen with one or more non-covalent interactions of sufficient affinity. One of skill in the art can readily recognize linkers that interact with each other with sufficient affinity to be useful in the WNV immunogens of the invention. For example, biotin can be attached to a peptide of the WNV immunogen, and streptavidin can be attached to another peptide. In certain embodiments, the linker can directly link peptides of the WNV immunogen, e.g., via a covalent bond. In other embodiments, the linker itself comprises two or more molecules that associate in order to link the peptides of the WNV immunogen. Exemplary linkers include, but are not limited to, straight or branchedchain carbon linkers, heterocyclic carbon linkers, substituted carbon linkers, unsaturated carbon linkers, aromatic carbon linkers, peptide linkers, etc. In certain embodiments, the peptides corresponding to amino acids 300-309, 330-333, 365-368, and/or 389-391 of WNV E protein, using SEQ ID NO:4 for numbering, are connected with each other with peptide linkers. In certain embodiments, the peptide linkers comprise one or more amino acids selected from the group consisting of alanine (A), cysteine (C), aspartate (D), glutamate (E), glycine (G), isoleucine (I), lysine (K), leucine (L), methionine (M), asparagine (N), glutamine (Q), arginine (R), serine (S), threonine (T), and valine (V).

In embodiments where a linker is used to connect peptides of the WNV immunogen, the linkers can be attached to the peptides by any means or method known by one of skill in the art without limitation. For example, the linker can be attached to the peptides of the WNV immunogen with an ether, ester, thioether, thioester, amide, imide, disulfide or other suitable moieties. The skilled artisan can select the appropriate linker and means for attaching the linker based on the physical and chemical properties of the chosen linker. The linker can be attached to any suitable functional group on the molecule(s). For example, the linker can be attached to sulfhydryl (—S), carboxylic acid (COOH) or free amine (—NH2) groups, which are available for reaction with a suitable functional group on a linker. These groups can also be used to directly connect the peptides of the WNV immunogen in the absence of a linker.

Further, peptides of the WNV immunogen can be derivatized, for example, to facilitate attachment of a linker to these moieties. For example, such derivatization can be accomplished by attaching suitable derivatives such as those available from Pierce Chemical Company, Rockford, Ill. Alternatively, derivatization may involve chemical treatment of peptides of the WNV immunogen. For example, glycol cleavage of the sugar moiety of a carbohydrate attached to a WNV immunogen with periodate generates free aldehyde groups. These free aldehyde groups may be reacted with free amine or hydrazine groups on the remainder of the molecule in order to connect these portions of the molecule. See U.S. Pat. No. 4,671,958. Further, the skilled artisan can generate free sulfhydryl groups on proteins to provide a reactive moiety for making a disulfide, thioether, theioester, etc. linkage. See U.S. Pat. No. 4,659,839.

In certain embodiments, the peptides corresponding to amino acids 300-309, 330-333, 365-368, and 389-391 of WNV E protein, using SEQ ID NO:4 for numbering, are expressed as a single polypeptide. In certain embodiments, the peptides corresponding to amino acids 300-309, 330-333, 365-368, and 389-391 of WNV E protein, using SEQ ID NO:4 for numbering, are expressed as a plurality of peptides. In certain embodiments, the WNV immunogen comprises at least two cysteine residues that form a disulfide bond. In certain embodiments, the WNV immunogen comprises at least four cysteine residues that collectively form two disulfide bonds.

In certain embodiments, the WNV immunogen comprises an amino acid sequence corresponding to the variable domain of an immunoglobulin molecule, wherein the peptide corresponding to amino acids 330-333 of WNV E protein replaces one or more amino acids of the immunoglobulin molecule corresponding to CDR1; the peptide corresponding to amino acids 365-368 of WNV E protein replaces one or more amino acids of the immunoglobulin molecule corresponding to CDR2, and the peptide corresponding to amino acids 389-391 of WNV E protein replaces one or more amino acids of the immunoglobulin molecule corresponding to CDR3.

In certain embodiments, the WNV immunogen, when administered in to a subject, induces production of antibodies in the subject that bind domain III of WNV E protein. In certain embodiments, the WNV immunogen, when administered in to a subject, induces production of antibodies in the subject that neutralize infection by WNV.

The WNV immunogens can be prepared using any suitable method. In certain embodiments, the WNV immunogens can be prepared by chemical synthesis. In other embodiments, the WNV immunogens can be prepared biologically using suitable vectors in appropriate cell cultures as described below.

In certain embodiments, the WNV immunogens can be used in pharmaceutical compositions without further modification. In certain embodiments, the WNV immunogens can be modified, e.g., chemical conjugates, fusion proteins, pegylation, and the like. For example, chemical or nucleotidic or peptidic modifications can be made to allow the peptides to pass through certain biological barriers, to solubilize better, or to facilitate their incorporation into particular galenical forms, such as, e.g., liposomes or microparticles. Further, the WNV immunogens can be deglycosylated or glycosylated, as appropriate.

In certain embodiments, at least one portion of the WNV immunogens of the invention can be conjugated to a support onto which it is absorbed or bound in a covalent or non-covalent manner. The support can be, e.g., natural or synthetic carrier molecules. Such embodiments are useful, for example, in methods of purifying antibodies reactive with the antigens using WNV immunogens bountd to solid supports and in methods of inducing an immune response with the immunogens using immunogens bound to carrier molecules to increase the immunogenicity of the antigens. Preferably, the carrier molecules are physiologically acceptable and non toxic. The carrier molecules, in the context of an pharmaceutical composition, also preferably can increase the immunogenicity of the WNV immunogens. The WNV immunogens can be connected with the carrier molecules by, e.g., complementary reactive groups respectively present on the carrier molecule and the peptide known to those skilled in the art. Useful chemical compounds for coupling include, without limitation, dinitrophenol groups and arsonilic acid. Examples of carrier molecules include, but are not limited to, natural proteins such as, e.g., tetanus anatoxin, ovalbumin, serum albumin, hemocyamines, keyhole limpet hemocyanin (KLH), PPD (purified protein derivative) of tuberculin, red blood cells, tetanus toxoid, cholera toxoid, agarose beads, activated carbon, bentonite, etc.; synthetic macromolecular supports such as, e.g., polylysine or poly(D-L-alanine)-poly (L-lysine); hydrocarbon or lipid supports such as, e.g., saturated or unsaturated fatty acids. For a review of some general considerations in use of such compounds, see Harlow and Lane, eds., 1988, *Antibodies, A Laboratory Manual*, Cold Spring Harbor Laboratory Press, Cold Spring Harbor, N.Y. Further, liposomes, particles and microparticles, vesicles, latex bead microspheres, polyphosphoglycans (PGLA) or polystyrene can also be used as a support in the pharmaceutical compositions of the invention.

In yet another embodiment, the WNV immunogens may be in the form of a multiple antigenic peptide ("MAP", also referred to as an octameric lysine core peptide) construct. Such a construct may be designed employing the MAP system described by Tam, 1988, *Proc. Natl. Acad. Sci. USA* 85:5409. In this system, multiple copies of a WNV antigen are synthesized onto a core matrix of lysine residues as described in Posnett et al., 1988, *J. Biol. Chem.* 263:1719; and Tam, 1992, "Chemically Defined Synthetic Immunogens and Vaccines by the Multiple Antigen Peptide Approach", *Vac-* cine Research and Developments, Vol. 1, Koff and Six, eds., Marcel Deblau, Inc., New York, N.Y., pp. 51-87. Each MAP contains multiple copies of one antigen.

Still other modified WNV immunogens may be prepared by any number of conventional techniques to improve production thereof, to enhance protein stability or other characteristics, e.g., binding activity or bioavailability, or to confer some other desired property upon the protein. Further, useful fragments of these polypeptides may be readily prepared by one of skill in the art using known techniques, such as deletion mutagenesis and expression.

The WNV immunogens of the present invention may also be constructed, using conventional genetic engineering techniques as part of a larger and/or multimeric protein or protein compositions. Antigens of this invention may be in combination with outer surface proteins or other proteins or antigens of other pathogens, such as those described herein, or various fragments of the antigens described herein may be in combination with each other. In such combination, the antigen may be in the form of a fusion protein. The antigen of the invention may be optionally fused to a selected polypeptide or protein derived from other microorganisms. For example, an antigen or polypeptide of this invention may be fused at its N-terminus or C-terminus to a polypeptide from another pathogen or to more than one polypeptide in sequence. Any polypeptides, without limitation, known by those of skill in the art to be useful for this purpose may be used in such embodiments.

A WNV immunogen of the present invention may also be used in the form of a pharmaceutically acceptable salt. Suitable acids and bases which are capable of forming salts with the polypeptides of the present invention are well known to those of skill in the art, and include inorganic and organic acids and bases.

5.12.1 Pharamaceutical Compositions Comprising a WNV Immunogen

In another aspect, the invention provides a pharmaceutical composition comprising a WNV immunogen of the invention and a pharmaceutically acceptable excipient, diluent, vehicle, or carrier. Any such pharmaceutically acceptable excipient, diluent, carrier, or vehicle known to one of skill in the art without limitation can be used. Examples of a suitable excipient, diluent, carrier, or vehicle can be found in *Remington's Pharmaceutical Sciences,* 19th Ed. 1995, Mack Publishing Co., Easton. Preferably, the pharmaceutical compositions induce a protective immune response when administered to a subject. In certain embodiments, the pharmaceutical composition is in a single unit dosage form. In certain embodiments, the pharmaceutical composition comprises a stabilizer. In certain embodiments, the pharmaceutical composition is formulated for storage for at least about 6 months without loss of more than about 20% activity. In certain embodiments, the pharmaceutical composition is an immunogenic composition.

The pharmaceutical compositions can be administered to a human for the treatment or prevention of WNV infection. Thus, the pharmaceutical compositions are generally compatible with administration to a human. In certain embodiments, the pharmaceutical compositions can be in any suitable solid or liquid form for pharmaceutical administration, e.g., in liquid administration forms, as a gel, or any other support allowing controlled release, for example. For example, the pharmaceutical composition can be an injectable composition, e.g., a pharmaceutical composition formulated for injection into the blood in a human.

The pharmaceutical compositions of the invention can also comprise components that increase the immunogenicity of a WNV immunogen. For example, the pharmaceutical compositions can comprise immunogenic peptides other than WNV immunogens, specific or nonspecific immunogenic adjuvants such as, e.g., alum, aluminum hydroxide, aluminum phosphate, QS21, Freund's adjuvant, $SBA_2$ adjuvant, montanide, polysaccharides, lipopolysaccharides, lipopolysaccharide derivatives, lipid A, CpG-containing nucleic acids, non-CpG containing nucleic acids, oil-in-water emulsions, or equivalent compounds. Other suitable adjuvants are described in Sheikh et al., 2000, *Cur. Opin. Mol. Ther.* 2:37-54. The immunogen may also be modified by other techniques, such as denaturation with heat and/or SDS.

The pharmaceutical compositions of the invention may comprise one or a plurality of WNV immunogens. For example, a pharmaceutical composition can include WNV immunogens from several circulating strains of a pathogen, e.g., from more than one WNV strain or from more than one flavivirus. In certain embodiments, the pharmaceutical composition can comprise a combination of WNV immunogens from two, three, four, five, six, seven, eight, nine, ten, eleven, twelve, thirteen, fourteen, fifteen, sixteen, seventeen, or more strains of WNV. In certain embodiments, the pharmaceutical composition can comprise a combination of immunogens from two, three, four, five, six, seven, eight, nine, ten, eleven, twelve, thirteen, fourteen, fifteen, sixteen, seventeen, or more different flaviviruses. In certain embodiments, the pharmaceutical composition comprises a combination of WNV immunogens that, when administered to a subject, induces an immune response in the subject that recognizes an E protein from more than one WNV strain. In certain embodiments, the pharmaceutical composition comprises a combination of immunogens that, when administered to a subject, induces an immune response in the subject that recognizes an E protein from more than one flavivirus.

The pharmaceutical compositions are generally formulated appropriately for the immediate use intended for the composition. For example, if the composition is not to be administered immediately, it can be formulated suitably for storage. One such composition is a lyophilized preparation of the WNV immunogen(s) together with a suitable stabilizer. Alternatively, the pharmaceutical composition can be formulated for storage in a solution with one or more suitable stabilizers. Any such stabilizer known to one of skill in the art without limitation can be used. For example, stabilizers suitable for lyophilized preparations include, but are not limited to, sugars, salts, surfactants, proteins, chaotropic agents, lipids, and amino acids. Stabilizers suitable for liquid preparations include, but are not limited to, sugars, salts, surfactants, proteins, chaotropic agents, lipids, and amino acids. Specific stabilizers than can be used in the pharmaceutical compositions include, but are not limited to, trehalose, serum albumin, phosphatidylcholine, lecithin, and arginine. Other compounds, compositions, and methods for stabilizing a lyophilized or liquid preparation of the WNV immunogens may be found, for example, in U.S. Pat. Nos. 6,573,237; 6,525,102; 6,391,296; 6,255,284; 6,133,229; 6,007,791; 5,997,856; and 5,917,021.

In an alternate embodiment, the pharmaceutical compositions may also comprise nucleic acids that express one or more WNV immunogen(s) described herein. For example, when injecting naked DNA encoding a WNV immunogen as described herein, this injection can result in expression of the encoded immunogen and an immune response against the immunogen. It is also possible to use naked DNA systems that comprise expression system or expression vectors. The expression vectors can in some cases improve the activity of the expressed immunogens. Any suitable immunization system employing DNA known by one of skill in the art, whether as part of an expression system or not, can be used to administer DNA to a subject. Examples of such immunization systems can be found, for example, in International Patent Publication No. WO 95/111307 and in Bot et al., 1996, *Viral Immunol* 9:207. Additional exemplary vectors for in vivo gene delivery and include, e.g., adeno-associated virus (International patent application No. PCT/US91/03440), adenovirus vectors (Kay et al., 1994, *Proc. Natl. Acad. Sci. USA* 91:2353; Ishibashi et al., 1993, *J. Clin. Invest.* 92:883), or other viral vectors, e.g., various poxviruses, vaccinia, etc. Methods for insertion of a desired gene, e.g., a WNV immunogen and obtaining in vivo expression of the encoded protein are well known to those of skill in the art. In certain embodiments, vectors incorporating sequences that are capable of increasing the immunogenicity of the WNV immunogens of the present invention, such as CpG sequences, the GMCSF (granulocyte macrophage colony stimulating factor) gene, or cytokine genes can be employed. The specific constructions depend on the host, the epitope and on the vector selected.

5.12.2 Kits Comprising Pharmaceutical Compositions

In yet another aspect, the invention provides a kit comprising a pharmaceutical composition of the invention. In certain embodiments, the kit comprises a pharmaceutical composition is in a single unit dosage form. In certain embodiments, the kit further comprises instructions directing administration of the pharmaceutical composition to a subject. In certain embodiments, the kit further comprises instructions directing a medical professional to administer the pharmaceutical composition to a subject.

5.12.3 Dosage and Regimen of WNV Immunogens

Generally, a pharmaceutically effective amount of the WNV immunogens of the invention is administered to a subject. The skilled artisan can readily determine if the dosage of the WNV immunogen is sufficient to elicit an immune response by monitoring the immune response so elicited, as described below. In certain embodiments, an amount of pharmaceutical composition corresponding to between about 1 µg and about 1000 µg of WNV immunogen is administered. In other embodiments, an amount of pharmaceutical composition corresponding to between about 10 µg and about 500 µg of WNV immunogen is administered. In still other embodiments, an amount of pharmaceutical composition corresponding to between about 10 µg and about 250 µg of WNV immunogen is administered. In yet other embodiments, an amount of pharmaceutical composition corresponding to between about 10 µg and about 100 µg of WNV immunogen is administered. In certain embodiments, an amount of pharmaceutical composition corresponding to between about 10 µg and about 50 µg of WNV immunogen is administered. Further guidance on selecting an effective dose of the pharmaceutical compositions may be found, for example, in Rose and Friedman, 1980, *Manual of Clinical Immunology*, American Society for Microbiology, Washington, D.C.

The volume of pharmaceutical composition administered will generally depend on the concentration of WNV immunogen and the formulation of the composition. In certain embodiments, a unit dose of the pharmaceutical composition is between about 0.05 ml and about 1 ml, preferably about 0.5 ml. The pharmaceutical compositions can be prepared in dosage forms containing between 1 and 50 doses (e.g., 0.5 ml to 25 ml), more usually between 1 and 10 doses (e.g., 0.5 ml to 5 ml)

The pharmaceutical compositions of the invention can be administered in one dose or in multiple doses. A dose can be followed by one or more doses spaced by about 4 to about 8 weeks, by about 1 to about 3 months, or by about 1 to about 6 months. Additional booster doses can be administered as needed. In certain embodiments, booster doses are administered in about 1 to about 10 years.

5.12.4 Administration of WNV Immunogens

The WNV immunogens of the invention can be administered to a subject by any method known to one of skill in the art. In certain embodiments, the pharmaceutical compositions are injected into the subject. The pharmaceutical composition can be injected subcutaneously, intramuscularly, intravenously, intra-arterially, or parenterally. In such embodiments, the pharmaceutical composition preferably comprises an adjuvant, as described above.

5.12.5 Methods of Making WNV Immunogens

Any suitable expression system known by one of skill in the art for producing a peptide, polypeptide, or nucleic acid immunogen can be used to produce the WNV immunogens of the invention. Alternately, the WNV immunogens can be chemically synthesized, either in whole or in part. To produce recombinant WNV immunogens, the nucleic acid sequences encoding the immunogens can be inserted into a suitable expression system. Desirably, a recombinant molecule or vector can be constructed in which the polynucleotide sequence encoding the selected protein, e.g., a WNV immunogen, is operably linked to a heterologous expression control sequence permitting expression of the protein. Numerous types of appropriate expression vectors are known in the art for protein expression by standard molecular biology techniques. Such vectors can be selected from among conventional vector types including insects, e.g., baculovirus expression, or yeast, fungal, bacterial or viral expression systems. Other appropriate expression vectors, of which numerous types are known in the art, can also be used for this purpose. Methods for obtaining such expression vectors are well-known. See, e.g., Sambrook et al., 2001, *Molecular Cloning: A Laboratory Manual*, 3$^{rd}$ edition, Cold Spring Harbor Laboratory, Cold Spring Harbor, N.Y., and Ausubel et al., eds., Current Edition, *Current Protocols in Molecular Biology*, Greene Publishing Associates and Wiley Interscience, NY, and references cited therein.

Suitable host cells or cell lines for transfection by this method include bacterial cells, such as, for example, *E. coli* (e.g., HB101, MC 1061, etc.) *B. subtilis*, *Pseudomonas* ssp., *Streptomyces* ssp., and the like; and mammalian cells, such as, for example, human 293 cells, Chinese hamster ovary cells (CHO), monkey COS-1 cells, and murine 3T3 cells. Indeed, any suitable host cell, method for transfection, culture, amplification, screening, production, purification, etc. known to one of skill in the art without limitation can be used to produce a WNV immunogen. Further, strains of yeast cells or other fungal systems known to those skilled in the art are also available as host cells for expression of the WNV immunogens of the present invention. Alternatively, insect cells such as *Spodoptera frugipedera* (Sf9) cells may be used.

Thus, the present invention provides a method for producing a WNV immunogen that comprises transfecting, e.g., by conventional means such as electroporation, a host cell with at least one expression vector containing a polynucleotide encoding the WNV immunogen under the control of a transcriptional regulatory sequence. The transfected or transformed host cell can be then cultured under conditions that allow expression of the protein. The expressed protein can be recovered, isolated, and optionally purified from the cell (or from the culture medium, if expressed extracellularly) by appropriate means known to one of skill in the art. For example, an antibody that specifically binds a WNV immunogen, e.g., E16, can be conveniently used to affinity purify a WNV inmmunogens of the invention.

For example, the immunogens can be isolated in soluble form following cell lysis, or extracted using known techniques, e.g., in guanidine chloride. If desired, the proteins or fragments of the invention are produced as a fusion protein such as those described above. Alternatively, for example, it may be desirable to produce fusion proteins to enhance expression of the immunogen in a selected host cell, to improve purification, or for use in monitoring the presence of the immunogen in tissues, cells or cell extracts. Suitable fusion partners for the proteins of the invention are well known to those of skill in the art and include, among others, β-galactosidase, glutathione-S-transferase, poly-histidine and maltose binding protein.

Thus, the invention also provides a method for preparing a WNV immunogen of the invention by transforming a host cell using an expression vector (plasmid, cosmid, virus, etc.) comprising DNA sequences encoding the immunogens of the invention, and culturing the transformed host cell and recovering the peptide in the culture medium.

The invention further provides a vector (either cloning and/or expression) and a host cell (prokaryotic or eukaryotic) transformed by the vector and comprising regulating elements allowing expression of the nucleotide sequence coding for a immunogen of the invention.

5.12.6 Polynucleotides Encoding WNV Immunogens

In another aspect, the invention provides polynucleotides comprising a nucleotide sequence encoding a WNV immunogen of the invention as described herein. These polynucleotides are useful, for example, for making the WNV immunogens. In certain embodiments, the recombinant polynucleotides are based on polynucleotides encoding a WNV immunogen, as described herein. In other embodiments, the recombinant polynucleotides are based on polynucleotides that hybridize to a polynucleotide that encodes a WNV immunogen under stringent hybridization conditions.

In vitro methods that can be used to prepare a polynucleotide encoding WNV immunogens of the invention include, but are not limited to, reverse transcription, the polymerase chain reaction (PCR), the ligase chain reaction (LCR), the transcription-based amplification system (TAS), the self-sustained sequence replication system (3SR) and the QP replicase amplification system (QB). Any such technique known by one of skill in the art to be useful in construction of recombinant nucleic acids can be used. For example, a polynucleotide encoding the protein or a portion thereof can be isolated by polymerase chain reaction of cDNA using primers based on the DNA sequence of PE or another polynucleotide encoding a receptor binding domain.

Guidance for using these cloning and *in vitro* amplification methodologies are described in, for example, U.S. Pat. No. 4,683,195; Mullis et al., 1987, *Cold Spring Harbor Symp. Quant. Biol.* 51:263; and Erlich, ed., 1989, *PCR Technology*, Stockton Press, NY. Polynucleotides encoding a WNV immunogen or a portion thereof also can be isolated by screening genomic or cDNA libraries with probes selected from the sequences of the desired polynucleotide under stringent, moderately stringent, or highly stringent hybridization conditions.

Further, the polynucleotides can also encode a secretory sequence at the amino terminus of the encoded WNV immunogen. Such constructs are useful for producing the WNV immunogens in mammalian cells as they simplify isolation of the immunogen.

Furthermore, the polynucleotides of the invention also encompass derivative versions of polynucleotides encoding a WNV immunogen. Such derivatives can be made by any method known by one of skill in the art without limitation. For example, derivatives can be made by site-specific mutagenesis, including substitution, insertion, or deletion of one, two, three, five, ten or more nucleotides, of polynucleotides encoding the WNV immunogen. Alternatively, derivatives can be made by random mutagenesis. One method for randomly mutagenizing a nucleic acid comprises amplifying the nucleic acid in a PCR reaction in the presence of 0.1 mM $MnCl_2$ and unbalanced nucleotide concentrations. These conditions increase the misincorporation rate of the polymerase used in the PCR reaction and result in random mutagenesis of the amplified nucleic acid.

5.12.7 Expression Vectors

In still another aspect, the invention provides expression vectors for expressing the WNV immunogens. Generally, expression vectors are recombinant polynucleotide molecules comprising expression control sequences operatively linked to a nucleotide sequence encoding a polypeptide. Expression vectors can readily be adapted for function in prokaryotes or eukaryotes by inclusion of appropriate promoters, replication sequences, selectable markers, etc. to result in stable transcription and translation of mRNA. Techniques for construction of expression vectors and expression of genes in cells comprising the expression vectors are well known in the art. See, e.g., Sambrook et al., 2001, *Molecular Cloning: A Laboratory Manual*, $3^{rd}$ edition, Cold Spring Harbor Laboratory, Cold Spring Harbor, N.Y., and Ausubel et al., eds., Current Edition, *Current Protocols in Molecular Biology*, Greene Publishing Associates and Wiley Interscience, NY.

Useful promoters for use in expression vectors include, but are not limited to, a metallothionein promoter, a constitutive adenovirus major late promoter, a dexamethasone-inducible MMTV promoter, a SV40 promoter, a MRP pol III promoter, a constitutive MPSV promoter, a tetracycline-inducible CMV promoter (such as the human immediate-early CMV promoter), and a constitutive CMV promoter.

The expression vectors should contain expression and replication signals compatible with the cell in which the WNV immunogens are expressed. Expression vectors useful for expressing WNV immunogens include viral vectors such as retroviruses, adenoviruses and adenoassociated viruses, plasmid vectors, cosmids, and the like. Viral and plasmid vectors are preferred for transfecting the expression vectors into mammalian cells. For example, the expression vector pcDNA1 (Invitrogen, San Diego, Calif.), in which the expression control sequence comprises the CMV promoter, provides good rates of transfection and expression into such cells.

The expression vectors can be introduced into the cell for expression of the WNV immunogens by any method known to one of skill in the art without limitation. Such methods include, but are not limited to, e.g., direct uptake of the molecule by a cell from solution; facilitated uptake through lipofection using, e.g., liposomes or immunoliposomes; particle-mediated transfection; etc. See, e.g., U.S. Pat. No. 5,272,065; Goeddel et al., eds, 1990, *Methods in Enzymology*, vol. 185, Academic Press, Inc., CA; Krieger, 1990, *Gene Transfer and Expression: A Laboratory Manual*, Stockton Press, NY; Sambrook et al., 2001, *Molecular Cloning: A Laboratory Manual*, $3^{rd}$ edition, Cold Spring Harbor Laboratory, Cold Spring Harbor, N.Y., and Ausubel et al., eds., Current Edition, *Current Protocols in Molecular Biology*, Greene Publishing Associates and Wiley Interscience, NY.

The expression vectors can also contain a purification moiety that simplifies isolation of the protein. For example, a polyhistidine moiety of, e.g., six histidine residues, can be incorporated at the amino terminal end of the protein. The polyhistidine moiety allows convenient isolation of the protein in a single step by nickel-chelate chromatography. In certain embodiments, the purification moiety can be cleaved from the remainder of the WNV immunogen following purification. In other embodiments, the moiety does not interfere with the function of the functional domains of the WNV immunogen and thus need not be cleaved.

5.12.8 Cells for Expressing a WNV Immunogen

In yet another aspect, the invention provides a cell comprising an expression vector for expression of the WNV immunogens, or portions thereof. The cell is preferably selected for its ability to express high concentrations of the WNV immunogen to facilitate purification of the protein. In certain embodiments, the cell is a prokaryotic cell, for example, E. coli.

In other embodiments, the cell is a eukaryotic cell. Useful eukaryotic cells include yeast and mammalian cells. Any mammalian cell known by one of skill in the art to be useful for expressing a recombinant polypeptide, without limitation, can be used to express the WNV immunogens. For example, Chinese hamster ovary (CHO) cells can be used to express the WNV immunogens.

5.13 Methods of Inducing an Immune Response Against WNV DIII

In another aspect, the invention provides methods of inducing an immune response in a subject against domain III of WNV E protein. In general, the methods comprise administering a WNV immunogen of the invention to a subject in whom the immune response is to be induced. Typically, such WNV immunogens are administered in the form of a pharmaceutical composition, as described herein. In certain embodiments, the immune response that is induced is a prophylactic immune response, i.e., the subject is not already afflicted with WNV infection. In other embodiments, the immune response that is induced is therapeutic, i.e., the subject is already afflicted with WNV infection. The resultant immune responses can protect against infection by WNV or against cells that express WNV immunogens. For example, the immune response can be mounted against WNV, itself, or against cells containing intracellular WNV.

In certain embodiments, the methods comprise administering to a subject a WNV immunogen that comprises one or more peptides corresponding to amino acids 300-309, 330-333, 365-368, and 389-391 of WNV E protein, using SEQ ID NO:4 for numbering, wherein the peptide(s) is (are) arranged in the three dimensional conformation of amino acids 300-309, 330-333, 365-368, and 389-391, respectively, of WNV E protein according to the structural coordinates shown in Table 7. In certain embodiments, the immunogen does not comprise the entire amino acid sequence of domain III of WNV E protein.

In certain embodiments, the immune response induced in the subject is effective to prevent a WNV infection in the subject following exposure to WNV. In certain embodiments, the immune response that is induced is effective to prevent WNV from fusing with a cell that expresses a receptor ordinarily bound by a WNV. In certain embodiments, the immune response that is induced is effective to prevent infection of the cell expressing a receptor ordinarily bound by WNV but is not effective to prevent attachment of the WNV to the cell. In certain embodiments, an antibody produced by the immune response in the subject neutralizes WNV infection. In certain embodiments, the induced immune response is effective to reduce the severity of a WNV infection in the subject. In certain embodiments, the induced immune response is effective to treat a WNV infection in the subject. In certain embodiments, the induced immune response is effective to treat a disease, or a symptom thereof, mediated by WNV infection in the subject. In certain embodiments, the induced immune response is effective to treat or prevent one or more symptoms associated with WNV infection in a subject.

In certain embodiments, the subject is a mammal or bird. In certain embodiments, the subject is a goat, cow, rabbit, mouse, rat, horse, pig, ferret, weasel, or primate. In certain embodiments, the subject is a human.

In certain embodiments, the WNV immunogen is administered in a single dose. In certain embodiments, the WNV immunogen is administered in multiple doses. In certain embodiments, a WNV immunogen can be administered at a first time, then a WNV immunogen can be administered at a later second time. In certain embodiments, the administrations can be separated by one, two, three, four, five, six, nine, twelve, fifteen, or eighteen months or one, two, three, four, five, six, seven, eight, nine, ten, or more years. In certain embodiments, the subject's immune response against a WNV immunogen or a WNV can be assessed to determine whether the subject would benefit from a repeated (e.g., booster) administration of a WNV immunogen. In certain embodiments, the WNV immunogen administered at the first time is the same WNV immunogen as the immunogen administered at the later second time. In certain embodiments, the WNV immunogen administered at the first time is a different WNV immunogen from the immunogen administered at the later second time.

In certain embodiments, the methods comprise administering a WNV immunogen of the invention to a subject two, three, four, five, six, seven, eight, nine, ten, eleven, twelve, fifteen, twenty, or more times. In certain embodiments, the WNV immunogen can be administered at regular intervals until death of the subject. The administration can be by any method described herein. Further, the administrations can be separated by as little as, e.g., about 1 month or as much as e.g., about ten or more years. In certain embodiments, the administrations can be at regular periods, e.g., about every six months, about every year, about every 18 months, about every two years. In other embodiments, the administrations can be irregular, e.g., a second administration after about three months of the first administration, then a third administration at about 2 years after the first. In still other embodiments, the administration can be variously irregular and regular, e.g., a second administration after about three months of the first administration, then a third administration at about 2 years after the first and further administrations every two years thereafter. In certain embodiments, the administrations are separated by about 1, 2, 3, 4, 5, 6, 7, 8, 9, 10, 11, or 12 months. In certain embodiments, the administrations are separated by about 1, 2, 3, 4, 5, 6, 7, 8, 9, 10, 11, or 12 years.

6. EXAMPLES

The following examples are provided to illustrate aspects of the invention, and are not intended to limit the scope of the invention in any way.

6.1 Example 1

Preparation of Crystals of WNV DIII-E16 Fab Complex

The subsections below describe the production of WNV DIII polypeptide; E16 Fab fragments, and the preparation and characterization of diffraction quality WNV DIII-E16 Fab complex crystals.

6.1.1 Production and Purification of WNV DIII

This example describes the expression and purification of a polypeptide corresponding to domain III of WNV E protein. A plasmid for expressing WNV DIII, pWNV-DIII, was constructed in the following manner: PCR primers that correspond to nucleotides 1852-1866 as the forward primer and nucleotides 2201-2211 as the reverse primer with added 5' BamH I and 3' Xho I sites were used to PCR a 359 nucleotide fragment from an infectious cDNA clone of WNV generated from the NY1999 strain. After restriction digest, domain III of WNV was cloned into a modified PET21 vector (Novagen) that contains histidine and BirA tags at the amino terminus. After sequencing, a clone with complete identity to the parent domain III sequence was transformed into BL21 E. coli cells.

BL21 bacteria that contained the pWNV-DIII plasmid were grown overnight at 37° C. as a six-liter batch. After centrifugation (7,500×g for 30 minutes) and lysis of cells by sonication, inclusion bodies were isolated. Refolding of WNV-DIII was performed according to the protocol described in Carayannopoulos et al., 2002, *J. Immunol.* 169: 4079-83. BL21 cells containing the WNV-DIII plasmid were grown to an optical density of 0.8 at 595 nm in Luria broth medium at 37° C. Bacteria were then induced with 0.5 mM isopropyl thiogalactoside (IPTG). After 4 hours, the cell pellets were harvested and suspended in 50 mM Tris-HCl, pH 8.0, 0.2 M NaCl, 5 mM EDTA and 5 mM DTT. Bacteria were lysed after lysozyme addition (final concentration of 1 mg/ml), and the viscosity was reduced by sonication. The WNV-DIII protein was obtained as insoluble aggregates in inclusion bodies, which were washed once in 50 mM Tris-HCl, pH 8.0, 0.1 M NaCl, 1 mM EDTA, 1 mM DTT, and 0.5% (v/v) Triton X-100, and once in 50 mM Tris-HCl, pH 8.0, 2 M NaCl, 1 M urea, 1 mM EDTA and 1 mM DTT. 0.5 mls of an 80% slurry of inclusion body was solubilized in 5 ml of 20 mM Tris (pH 8.0), 6M Guanidine HCl and 1 mM DTT; insoluble material was removed by centrifugation.

The remaining soluble WNV-DIII was refolded by slowly diluting out the denaturing reagents according to the protocol of Miley et al., 2003, *J. Immunol.* 170:6090-8. Briefly, 1.6 ml of guanidine HCl-solubilized WNV-DIII was added dropwise to 0.5 liter of 0.1 M Tris-HCl, pH 8.5, 400 mM L-arginine, 2 mM EDTA, 5 mM reduced glutathione, 0.5 mM oxidized glutathione, 0.1 mM phenylmethylsulfonyl fluoride. Additional aliquots were added every 4 h. After 24 h, the refolding mixture was concentrated under nitrogen to a volume of 2 ml. Refolded WNV-DIII was separated from aggregates on a Superdex 75 16/60 size exclusion column (Amersham Biosciences), treated with thrombin to remove the N-terminal BirA biotinylation tag and re-purified by size excusion chromatography. WNV-DIII was concentrated using a centricon-10 spin column and buffer exchanged into 10 mM Hepes pH 7.3, 100 mM NaCl, and 0.02% NaN$_3$

6.1.2 Production and Purification of E16 Fab Fragments

Fab fragments of E16 (IgG2b) were generated from purified IgG after papain digestion, protein A affinity chromatography and gel filtration chromatography according to the protocol presented in Harlow and Lane, 1988, *Antibodies, A laboratory manual.* Cold Spring Harbor Laboratory, Cold Spring Harbor. E16 is expressed by a hybridoma assigned ATCC Accession No. PTA-6050 and can be obtained from this hybridoma according to standard techniques. The purity of Fab fragments was confirmed by non-reducing SDS-PAGE and silver staining.

6.1.3 Preparation of WNV DIII-E16 Fab Complex Crystals

Fab fragments of E16 were mixed with WNV-DIII in an equimolar ratio for 2 hours at 4° C., and then isolated after gel filtration (Superdex 75) chromatography. Fab-WNV-DIII complexes were concentrated using a centricon-10 spin column to 10-15 mg/ml and used for crystallization experiments.

The E16 Fab-DIII complex was crystallized by hanging drop vapor diffusion at 20° C. from a 1.5 µl drop containing a mixture of 0.5 µl protein in 20 mM HEPES (pH 7.5), 0.01% NaN$_3$, 0.5 µl of 0.1 M HEPES (pH 8.5), 19% PEG 4000, 0.1 M glycine and 0.5 µl of deionized water over wells containing precipitant solution. The E16-DIII crystals were dragged through a drop that contained well solution and 20% ethylene glycol and was rapidly cooled in a gaseous stream of liquid nitrogen at 100K. The crystals were annealed by blocking the cryostream twice for five seconds each.

6.2 Analysis and Characterization of WNV DIII-E16 Fab Complex Crystals

This example describes the methods used to generate and collect diffraction data from WNV DIII-E16 Fab complex crystals and determine the structure of the WNV DIII-E16 Fab complex from such data.

6.2.1 Diffraction Data Collection

A dataset was collected at ALS beamline 4.2.2 (Lawrence Berkeley Laboratories, Berkeley, Calif.) by the oscillation method at a wavelength of 1.5498 Å with a large-area CCD X-ray detector. Data was processed, scaled and merged with d*trek. See Pflugrath, 1999, *Acta Crystallogr. D. Biol. Crystallogr.* 55:1718-25. The crystals were in the space group P2$_1$2$_1$2$_1$ with unit cell dimensions of a=52.4 Å, b=83.3 Å and c=110.6 Å with one molecule of WNV-DIII, one light chain of E16 and one papain cleaved heavy chain of E16 in the asymmetric unit.

6.2.2 Structure Determination and Analyses

The structure of WNV DIII-E16 Fab complex was determined using molecular replacement in molrep of CCP4i (see Vagin & Teplyakov, 2000, *Acta Crystallogr D Biol Crystallogr.* 56:1622-4) using the variable domain of an IgG1 Fab' (PDB ID 2IGF) as a model for the variable domains, then the constant domains of and IgG1 Fab' (PDB ID 2IGF) as a model for the constant domains, and finally the averaged domain III of WNV (PDB ID 1S6N) for the DIII fragment. The initial R$_{cryst}$ and correlation coefficient were 43.3 and 56.3, respectively. The models were iteratively altered to the correct sequence using the program InsightII (Accelrys). The models were built in O (see Jones et al., 1991, *Acta Crystallogr.* 47:753-70) and refined in CNS (see Brunger et al., 1998, *Acta Crystallogr. D. Biol. Crystallogr.* 54:905-21) against all F>0. The final model contained 788 amino acids (residues 1-212 of chain L, 1-228 of chain H and residues 300-400 of chain A), 255 water molecules and one sodium ion. The final R$_{cryst}$ and R$_{free}$ were 20.5 and 28.1, respectively after restrained B factor and positional refinement. A summary of these data is shown in Table 5. The refinement statistics are shown in Table 6; the accuracy of the model is reflected by the Ramachandran plot (FIG. 8) which disallowed only a single amino acid residue (Ala 51L), belonging to the L2 hypervariable loop of the V$_L$.

TABLE 5

Summary of Data Collection
Data Collection for WNV DIII-E16 complex[a]

| | |
|---|---|
| Space Group | P2(1)2(1)2(1) |
| Unit Cell (Å$^3$) | a = 52.4 b = 83.3 c = 110.6 |
| Data Set | Native |
| Wavelength(Å) | 1.5498 |
| X-ray Source | ALS |
| Resolution(Å) (outer shell) | 50–2.50 (2.59–2.50)* |
| Observations/Unique | 59923/16985[d] |
| Completeness (%) | 97.6 (82.7)[c] |
| Redundancy | 3.53 (1.99) |
| R$_{sym}$[b] (%) | 8.3 (30.6)[c] |
| I/σ | 11.3 (2.7)[c] |

[a]Values as defined in d * trek (Pflugrath, JW)
[b]R$_{sym}$ = 100 × Σ$_h$Σ$_i$I$_i$(h) − <I(h)>|/Σ$_h$Σ$_i$I$_i$(h)
[c]Value in parentheses is for the highest resolution shell.
[d]I(+h) and I(−h) processed as independent reflections. Anomalous scattering contributions were included.

TABLE 6

Refinement Statistics

| | |
|---|---|
| Reflections R$_{work}$[a]/R$_{free}$ | 16752/817 |
| #Protein Atoms[b]/Solvent | 4044/255 |
| R$_{work}$ overall(outer shell) (%) | 20.8 (25.9)[c] |
| R$_{free}$ overall(outer shell) (%) | 28.2 (36.7)[c] |
| Rmsd Bond lengths (Å)/angles(°) | 0.007/1.5 |
| Rmsd Dihedral/Improper (°) | 27.3/0.83 |
| Ramachandran plot | |
| Most Favored/Additional (%) | 87.1/12.2 |
| Generous/Disallowed (%) | 0.4/0.2 |
| No. Protein Atoms | 4040 |
| No. Water Atoms | 256 |
| Average B-values (protein) | 32.7 |
| Average B-values (water) | 32.4 |
| Est. Coordinate Error (Å) | 0.44 |

[a]R-value = 100 × Σ$_h$||F$_{obs}$(h)| − |F$_{calc}$(h)||/Σ$_h$|F$_{obs}$(h)| for reflections with F$_{obs}$ > 2σ.
[b]For bonded protein atoms.
[c]Value in parentheses is the free R-value (Brunger, 1992, "Free R value: a novel statistical quantity for assessing the accuracy of crystal structures," Nature 355: 472–475) determined from 5% of the data Table 7, following below, provides the atomic structure coordinates of WNV DIII-E16 Fab complex. In the Table, coordinates for one WNV DIII polypeptide and one E16 Fab fragment, comprising one E16 light chain and one papain cleaved heavy chain of E16, comprising the asymmetric unit are provided. The amino acid residue numbers coincide with those used in FIGS. 1-3. In the first molecule of the WNV DIII-E16 Fab complex, the residue number is preceded by a 1, i.e., residue number 464 of the WNV DIII molecule of the dimer is denoted by "1464;" residue number 464 of the E16 light chain is denoted by "2464;" and residue number 464 of the E16 papain-cleaved heavy chain is denoted by "3464."

The following abbreviations are used in Table 7:

"Atom Type" refers to the element whose coordinates are provided. The first letter in the column defines the element.

"A.A." refers to amino acid.

"X, Y and Z" provide the Cartesian coordinates of the element.

"B" is a thermal factor that measures movement of the atom around its atomic center.

"OCC" refers to occupancy, and represents the percentage of time the atom type occupies the particular coordinate. OCC values range from 0 to 1, with 1 being 100%.

"PRT1" or "PRT2" relate to occupancy, with PRT1 designating the coordinates of the atom when in the first conformation and PRT2 designating the coordinates of the atom when in the second or alternate conformation.

Structures coordinates for WNV DIII-E16 Fab complex according to Table 7 may be modified by mathematical manipulation. Such manipulations include, but are not limited to, crystallographic permutations of the raw structure coordinates, fractionalization of the raw structure coordinates, integer additions or subtractions to sets of the raw structure coordinates, inversion of the raw structure coordinates and any combination of the above.

6.2.3 Summary of Conclusions Regarding the Structure of WNV DIII-E16 Fab Complex The structure determined above revealed that WNV DIII adopted an Ig-like β-sandwich topology similar to that found in other flavivirus E proteins, while the E16 Fab adopts a typical quaternary assembly (FIG. 9). The binding interface had a high degree of shape complementarily (S$_c$=0.763)$^9$ and occludes 1550 Å$^2$ of surface area, with VH accounting for 67% of the total antibody-combining site (FIG. 10). E16 contacted DIII with 18 residues spread along all 6 of its CDR loops in addition to three V$_H$ framework residues (Tables 1, 2, and 3). The interaction between E16 and DIII was dominated by hydrogen bonds, with 16 direct hydrogen bonds and numerous water mediated networks at the interface of the complex.

E16 engaged four discontinuous segments of DIII, including the N-terminal region (residues E302-E309) and three strand-connecting loops: BC (E330-E333), DE (E365-E368) and FG (E389-E391). E16 contacted a total of 16 DIII residues, which together formed a single convex surface patch. Strikingly, yeast surface display epitope mapping of DIII identified four residues at the core of this binding site that are critical for E16 recognition (FIG. 12). To perform these yeast display mapping studies, an error-prone PCR derived library of WNV E (residues 296-415) was on the surface of yeast as Aga2 fusion proteins. See Chao et al., 2004, *J Mol Biol* 342:539-50 and Oliphant et al., 2005, *Nat Med* 11:522-30 (2005). Yeasts were screened for selective loss of E16 binding relative to other DIII specific mAbs by multiple rounds of fluorescence-activated cell sorting. Isolated clones were recovered, sequenced and evaluated for binding to E16 and the non-neutralizing, WNV DIII-specific mAb E22.

Non-conservative substitution at Ser$^{E306}$, Lys$^{E307}$, Thr$^{E330}$ or Thr$^{E332}$ disrupted E16 binding but not that of a non-neutralizing DIII-specific mAb, E22. These four residues clustered at the center of the E16IDIII interface (FIG. 10). The decreased binding associated with mutation of Ser$^{E306}$, Lys$^{E307}$ and Thr$^{E332}$ was most likely attributable to loss of hydrogen bonding potential with E16, while Thr$^{E330}$ appeared to stabilize the DIII N-terminal strand conformation and provided numerous van der Waals contacts with the Fab (FIGS. 13 and 14). Collectively, these structural studies defined the E16 epitope as a large surface patch on DIII created by four distinct secondary-structure elements, and the previously-performed yeast mapping highlighted the critical contributions of four central residues.

Comparison of available WNV sequences revealed nearly complete conservation of the structurally defined E16 epitope (FIG. 15). Not surprisingly, E16 blocked infection of ten different lineage I and II WNV strains. See Oliphant et al., 2005, *Nat Med* 11:522-30 (2005). Notably, nine other neutralizing mAbs also lost the ability to recognize DIII after mutation of Ser$^{E306}$, Lys$^{E307}$, Ihr$^{E330}$ or Thr$^{E332}$. Importantly, this epitope is also key in the humoral immune response of humans, as E16 Fabs effectively competed WNV convalescent antibodies for DIII bindings. Sequence analysis of other flaviviruses reveals a high degree of diversity in the four segments of the E16 epitope, with notable variation even between dengue serotypes (FIG. 15). Not surprisingly, E16 did not cross-neutralize dengue, Japanese or St. Louis encephalitis viruses. Interestingly, other flavivirus-specific neutralizing antibodies localize to an analogous DIII binding region. See Wu et al., 2003, *J. Biol. Chem.* 278:46007-13; Volk et al., 2004, *J. Biol. Chem.* 279:38755-61; and Hiramatsu et al., 1996, *Virology* 224:437-45. Thus, the coincident mapping of mAbs that neutralize WNV and other flaviviruses suggested that the structural epitope recognized by E16 has a dominant role in flavivirus neutralization.

6.3 Superimposition of WNV D16-E16 Fab Structures onto Viral Structures

To gain additional insight into the structural basis of E16-mediated neutralization, the structure of the WNV DIII-E16 Fab complex was superimposed onto the structures of the pre-fusion dengue E dimer (see Modis et al., 2003, *Proc Natl Acad Sci USA* 100:6986-91 and post-fusion trimer (see Modis et al., 2004, *Nature* 427:313-9) (FIGS. 17 and 18, respectively). The E16 epitope was unencumbered in either configuration, although intact E16 IgG is unlikely to bivalently recognize these isolated oligomers due to extensive CHI domain splaying[15] (FIGS. 17 and 18). DIII undergoes an ~70° rotation towards DII in the dimer to trimer transition (see Bressanelli et al., 2004, *EMBO J.* 23:728-38 and Modis et al., 2004, *Nature* 427:313-9), and E16 ligation per se could serve to hinder this conformational change. Moreover, E16 bound part of the linker that connects DIII to DI, and the N-terminus of truncated WNV DIII fragment adopts a unique conformation that enables $Tyr^{E302}$ to make contact with the E16 VH domain (FIG. 19). In E trimers, the flavivirus invariant $Tyr^{E302}$ interacts with DI in a manner that would be disrupted if re-oriented as observed in the E16/DIII complex. Thus, without intending to be bound to any particular theory or mechanism of action, E16 binding could stabilize the mature state or alternatively, restrict transition to the post-fusion conformation.

To better understand how E16 recognizes DIII in the context of the mature virus, the structure of WNV DIII-E16 Fab was superimposed onto the cryo-electron microscopy derived pseudo-atomic model of the intact WNV virion. See Mukhopadhyay et al., 2003, *Science* 302:248 and Kuhn et al., 2002, *Cell* 108:717-25. With three E proteins in the asymmetric unit, there were three potential Fab binding environments (FIG. 20). Two binding modes were clearly allowed: one that closely circles the three-fold axis and a second disposed symmetrically about the icosahedral dyad that was permuted as an outer five-fold ring (FIGS. 21A and 21B). However, the DIII epitopes were too tightly clustered at the true five-fold axis to permit E16 engagement without steric overlap with adjacent DIII residues. Thus, without intending to be bound to any particular theory or mechanism of action, it is believed that at saturation no more than 120 Fabs can bind the 180 E proteins in the mature virion, with exclusion of Fab binding to DIII around the inner five-fold ring (FIG. 22). Additional exclusions may occur for intact antibody, although it is noted that E16 Fab alone neutralizes WNV.

6.4 Functional Characterization of E16

Next, the ability of E16 to block cellular attachment of WNV was assessed. Binding assays were performed with Vero cells, a cell line permissive for WNV infection. After a 4° C. incubation with WNV in the presence of control (anti-SARS ORF7a), non-neutralizing (E22), or neutralizing mAbs that map within (E16 or E24) or outside (E53 or E60) of DIII, cell-associated viral RNA was measured by fluorogenic RT-PCR as described in Diamond et al., 2003, *J. Virol.* 77: 2578-2586. Briefly, individual purified mAbs (50 µg/ml of anti-SARS ORF7a, E16, E22, E24, E53, or E60) or medium alone were incubated with $10^3$ PFU of WNV for one hour at 4° C. These virus-antibody mixtures were then added to Vero cells in 12-well plates for one hour on ice. Unbound virus was removed after six washes with PBS at 4° C. Cells were lysed with guanidinium isothiocyanate, RNA was purified, and viral RNA was quantified by fluorogenic RT-PCR[18].

Importantly, the non-binding and non-neutralizing mAbs did not inhibit virus binding. In contrast, E53 and E60 blocked virus attachment by 8 to 9 fold (P<0.001) whereas E16 and E24, which recognize the same dominant DIII epitope, only inhibited binding by 3.5-fold (P=0.003) (FIG. 23). The observation that E53 and E60 blocked virus binding more efficiently than E16 was not expected, as E53 and E60 were tenfold less potent in plaque reduction neutralization assays. See Oliphant et al., 2005, *Nat. Med.* 11:522-30.

Because E16 only partially blocked virus binding yet completely neutralized infection, whether E16 inhibits flavivirus infection by blocking a step after cellular attachment was next assessed. Using a previously described assay, E16 or E53 was incubated with WNV prior to, or after, mixing with a monolayer of Vero cells and infection was measured as described in Crill & Roehrig J, 2001, *J. Virol.* 75:7769-73 and Hung et al., 1999, *Virology* 257:156-67. Briefly, increasing concentrations of E16 or E53 were added prior to or after WNV (102 PFU) binding (one hour on ice) to Vero cells. In the post-adsorption assay, after washing away unbound virus, mAb was allowed to bind for an additional hour. All cells were washed and an agarose overlay was added. Three days later, plaques were scored after fixation and staining with crystal violet.

Pre-binding of WNV with either E16 or E53 significantly protected against infection (FIG. 24). In contrast, E16 but not E53 significantly inhibited infection when added after virus binding. Because E16-mediated protection was not appreciably affected by the time of addition, it is believed that it acts primarily after WNV cellular attachment.

To further define the mechanism of WNV neutralization, the ability of E16 or other mAbs to enhance infection in macrophages was evaluated. Antibody-dependent enhancement of infection occurs when antibody/virus complexes are preferentially internalized through Fcγ receptors on myeloid cells. Although the in vivo consequences remain uncertain, many mAbs efficiently enhance flavivirus infection of Fcγ receptor bearing cells even when inhibitory in fibroblast neutralization assays. See Halstead & O'Rourke, 1977, *Nature* 265:739-41. The ability of saturating concentrations of non-neutralizing (E5) or neutralizing (E16, E24, or E60) mAbs to enhance WNV infection was therefore assessed in macrophages. Briefly, WNV ($5 \times 10^2$ PFU) was pre-incubated with media, individual mAbs (50 µg/ml of E5, E16, E24 or E60) or combinations of mAbs (E16+E5, E60+E5, or E16+E60, E24+E5, E24+E60) and then added to a monolayer ($10^5$) of J774.2 murine macrophages. After 6 hours, cells were washed extensively with PBS to remove unbound virus and mAb. After an additional 24 hours, supernatants were harvested for a viral plaque assay on Vero cells.

While E5 and E60 augmented infection 270 and 3,000-fold respectively, E16 potently inhibited macrophage infection at the same concentration. Strikingly, when E16 is combined with E5 or E60, it completely blocks enhancement as judged by reduction of virus yield (FIG. 25) or viral RNA. E24, which maps to the E16 dominant epitope, also blocked E5 and E60-dependent enhancement. Finally, the blockade of enhancement was not due to epitope competition as E16 and E24 do not cross-compete E5 or E60 for WNV E binding (FIG. 26). To perform the competition experiments, yeast expressing the empty vector pY D 1 or the WNV E ectodomain (residues 1-415) were incubated with 2.5 μg unlabeled E16 or E60 antibody for one hour on ice. Unbound antibody was removed after three PBS washes containing 1 mg/ml BSA. E16 and E60 were conjugated using an Alexa Flour 647 Monoclonal Antibody Labeling Kit (Molecular Probes). Conjugated E16 or E60 (25 μg/ml) was then added to the cells for 30 minutes at 4° C. Yeasts were washed three times with PBS, fixed with 1% paraformaldehyde, and analyzed using flow cytometry.

Collectively, these virologic experiments strongly suggest E16 blocked WNV infection primarily after cellular attachment.

In summary, E16 binds a dominant neutralizing epitope on WNV E defined by four distinct secondary-structure elements that create a large surface patch on DIII, a region associated with pH-dependent conformational changes. Modeling studies suggest that E16 was excluded from five-fold clustered DIII epitopes on mature virions, potentially leaving them free to serve in receptor binding. Consistent with this, E16 inhibits WNV infection primarily at a step after virus attachment. Moreover, these data suggest a potential advantage for interfering with post-attachment events The present invention is not to be limited in scope by the exemplified embodiments, which are intended as illustrations of single aspects of the invention. Indeed, various modifications of the invention in addition to those described herein will become apparent to those having skill in the art from the foregoing description and accompanying drawings. Such modifications are intended to fall with in the scope of the appended claims.

All documents referenced in this application, whether patents, published or unpublished patent applications, either U.S. or foreign, literature references, nucleotide or amino acid sequences identified by Accession No. or otherwise, are hereby incorporated by reference in their entireties for any and all purposes.

TABLE 7

| ATOM | 1 | CB | ASP | L | 1 | −35.475 | 10.622 | 12.124 | 1 | 30.78 | L |
|---|---|---|---|---|---|---|---|---|---|---|---|
| ATOM | 2 | CG | ASP | L | 1 | −34.677 | 11.822 | 11.637 | 1 | 33.43 | L |
| ATOM | 3 | OD1 | ASP | L | 1 | −35.196 | 12.58 | 10.789 | 1 | 33.95 | L |
| ATOM | 4 | OD2 | ASP | L | 1 | −33.529 | 12.007 | 12.093 | 1 | 37.37 | L |
| ATOM | 5 | C | ASP | L | 1 | −37.648 | 9.792 | 13.041 | 1 | 30.81 | L |
| ATOM | 6 | O | ASP | L | 1 | −38.023 | 9.855 | 14.209 | 1 | 34.21 | L |
| ATOM | 7 | N | ASP | L | 1 | −37.02 | 12.125 | 13.334 | 1 | 28.93 | L |
| ATOM | 8 | CA | ASP | L | 1 | −36.938 | 10.97 | 12.402 | 1 | 30.33 | L |
| ATOM | 9 | N | ILE | L | 2 | −37.837 | 8.713 | 12.292 | 1 | 28.58 | L |
| ATOM | 10 | CA | ILE | L | 2 | −38.533 | 7.567 | 12.852 | 1 | 27.42 | L |
| ATOM | 11 | CB | ILE | L | 2 | −39.122 | 6.655 | 11.743 | 1 | 28.5 | L |
| ATOM | 12 | CG2 | ILE | L | 2 | −39.914 | 5.507 | 12.373 | 1 | 23.83 | L |
| ATOM | 13 | CG1 | ILE | L | 2 | −40.05 | 7.483 | 10.843 | 1 | 28.97 | L |
| ATOM | 14 | CD1 | ILE | L | 2 | −40.839 | 6.681 | 9.836 | 1 | 31.74 | L |
| ATOM | 15 | C | ILE | L | 2 | −37.625 | 6.764 | 13.769 | 1 | 26.09 | L |
| ATOM | 16 | O | ILE | L | 2 | −36.557 | 6.313 | 13.377 | 1 | 24.34 | L |
| ATOM | 17 | N | VAL | L | 3 | −38.073 | 6.603 | 15.007 | 1 | 26.39 | L |
| ATOM | 18 | CA | VAL | L | 3 | −37.324 | 5.878 | 16.017 | 1 | 24.96 | L |
| ATOM | 19 | CB | VAL | L | 3 | −37.489 | 6.563 | 17.393 | 1 | 24.46 | L |
| ATOM | 20 | CG1 | VAL | L | 3 | −36.764 | 5.776 | 18.476 | 1 | 26.77 | L |
| ATOM | 21 | CG2 | VAL | L | 3 | −36.933 | 7.966 | 17.321 | 1 | 22.59 | L |
| ATOM | 22 | C | VAL | L | 3 | −37.774 | 4.426 | 16.096 | 1 | 23.93 | L |
| ATOM | 23 | O | VAL | L | 3 | −38.955 | 4.139 | 16.27 | 1 | 24.37 | L |
| ATOM | 24 | N | MET | L | 4 | −36.818 | 3.517 | 15.959 | 1 | 23.88 | L |
| ATOM | 25 | CA | MET | L | 4 | −37.1 | 2.094 | 16.01 | 1 | 26.48 | L |
| ATOM | 26 | CB | MET | L | 4 | −36.377 | 1.361 | 14.875 | 1 | 26.68 | L |
| ATOM | 27 | CG | MET | L | 4 | −36.771 | 1.83 | 13.485 | 1 | 27.04 | L |
| ATOM | 28 | SD | MET | L | 4 | −38.549 | 1.793 | 13.233 | 1 | 29.49 | L |
| ATOM | 29 | CE | MET | L | 4 | −38.785 | 0.088 | 12.812 | 1 | 25.37 | L |
| ATOM | 30 | C | MET | L | 4 | −36.666 | 1.516 | 17.344 | 1 | 28.26 | L |
| ATOM | 31 | O | MET | L | 4 | −35.477 | 1.486 | 17.677 | 1 | 29.27 | L |
| ATOM | 32 | N | THR | L | 5 | −37.639 | 1.043 | 18.105 | 1 | 28.06 | L |
| ATOM | 33 | CA | THR | L | 5 | −37.343 | 0.47 | 19.4 | 1 | 30.04 | L |
| ATOM | 34 | CB | THR | L | 5 | −38.063 | 1.247 | 20.512 | 1 | 30.06 | L |
| ATOM | 35 | OG1 | THR | L | 5 | −38.025 | 0.488 | 21.726 | 1 | 30.53 | L |
| ATOM | 36 | CG2 | THR | L | 5 | −39.503 | 1.512 | 20.125 | 1 | 32.13 | L |
| ATOM | 37 | C | THR | L | 5 | −37.74 | −0.996 | 19.454 | 1 | 27.75 | L |
| ATOM | 38 | O | THR | L | 5 | −38.903 | −1.341 | 19.262 | 1 | 26.81 | L |
| ATOM | 39 | N | GLN | L | 6 | −36.755 | −1.85 | 19.717 | 1 | 27.96 | L |
| ATOM | 40 | CA | GLN | L | 6 | −36.967 | −3.293 | 19.802 | 1 | 28.11 | L |
| ATOM | 41 | CB | GLN | L | 6 | −35.754 | −4.025 | 19.233 | 1 | 24.74 | L |
| ATOM | 42 | CG | GLN | L | 6 | −35.445 | −3.659 | 17.8 | 1 | 26.48 | L |
| ATOM | 43 | CD | GLN | L | 6 | −34.369 | −4.54 | 17.203 | 1 | 29.46 | L |
| ATOM | 44 | OE1 | GLN | L | 6 | −33.968 | −5.54 | 17.802 | 1 | 30.77 | L |
| ATOM | 45 | NE2 | GLN | L | 6 | −33.902 | −4.184 | 16.012 | 1 | 30.91 | L |
| ATOM | 46 | C | GLN | L | 6 | −37.212 | −3.767 | 21.238 | 1 | 28.49 | L |
| ATOM | 47 | O | GLN | L | 6 | −36.892 | −3.061 | 22.201 | 1 | 24.09 | L |
| ATOM | 48 | N | SER | L | 7 | −37.785 | −4.961 | 21.374 | 1 | 28.74 | L |
| ATOM | 49 | CA | SER | L | 7 | −38.046 | −5.521 | 22.696 | 1 | 35.25 | L |
| ATOM | 50 | CB | SER | L | 7 | −38.811 | −6.853 | 22.581 | 1 | 34.58 | L |
| ATOM | 51 | OG | SER | L | 7 | −38.283 | −7.686 | 21.559 | 1 | 37.01 | L |
| ATOM | 52 | C | SER | L | 7 | −36.707 | −5.716 | 23.417 | 1 | 36.8 | L |

TABLE 7-continued

| ATOM | 53 | O | SER | L | 7 | −35.652 | −5.705 | 22.776 | 1 | 38.22 | L |
| ATOM | 54 | N | HIS | L | 8 | −36.753 | −5.892 | 24.735 | 1 | 37.65 | L |
| ATOM | 55 | CA | HIS | L | 8 | −35.539 | −6.051 | 25.539 | 1 | 41.93 | L |
| ATOM | 56 | CB | HIS | L | 8 | −35.853 | −6.806 | 26.843 | 1 | 47.76 | L |
| ATOM | 57 | CG | HIS | L | 8 | −36.614 | −8.082 | 26.651 | 1 | 53.99 | L |
| ATOM | 58 | CD2 | HIS | L | 8 | −37.855 | −8.317 | 26.163 | 1 | 56.53 | L |
| ATOM | 59 | ND1 | HIS | L | 8 | −36.111 | −9.311 | 27.028 | 1 | 56.37 | L |
| ATOM | 60 | CE1 | HIS | L | 8 | −37.01 | −10.247 | 26.781 | 1 | 56.96 | L |
| ATOM | 61 | NE2 | HIS | L | 8 | −38.077 | −9.67 | 26.256 | 1 | 59.42 | L |
| ATOM | 62 | C | HIS | L | 8 | −34.346 | −6.688 | 24.821 | 1 | 40.37 | L |
| ATOM | 63 | O | HIS | L | 8 | −34.409 | −7.835 | 24.373 | 1 | 41.01 | L |
| ATOM | 64 | N | LYS | L | 9 | −33.259 | −5.918 | 24.738 | 1 | 37.22 | L |
| ATOM | 65 | CA | LYS | L | 9 | −32.022 | −6.315 | 24.065 | 1 | 37.72 | L |
| ATOM | 66 | CB | LYS | L | 9 | −30.957 | −5.237 | 24.266 | 1 | 36.46 | L |
| ATOM | 67 | CG | LYS | L | 9 | −29.714 | −5.454 | 23.428 | 1 | 37.92 | L |
| ATOM | 68 | CD | LYS | L | 9 | −28.909 | −4.178 | 23.31 | 1 | 41.81 | L |
| ATOM | 69 | CE | LYS | L | 9 | −27.874 | −4.282 | 22.196 | 1 | 43.88 | L |
| ATOM | 70 | NZ | LYS | L | 9 | −27.162 | −2.987 | 21.979 | 1 | 45.07 | L |
| ATOM | 71 | C | LYS | L | 9 | −31.412 | −7.671 | 24.418 | 1 | 38.69 | L |
| ATOM | 72 | O | LYS | L | 9 | −30.833 | −8.335 | 23.559 | 1 | 40.24 | L |
| ATOM | 73 | N | PHE | L | 10 | −31.51 | −8.083 | 25.675 | 1 | 38.73 | L |
| ATOM | 74 | CA | PHE | L | 10 | −30.938 | −9.364 | 26.059 | 1 | 38.54 | L |
| ATOM | 75 | CB | PHE | L | 10 | −29.949 | −9.183 | 27.208 | 1 | 35.83 | L |
| ATOM | 76 | CG | PHE | L | 10 | −28.768 | −8.339 | 26.847 | 1 | 31.3 | L |
| ATOM | 77 | CD1 | PHE | L | 10 | −28.872 | −6.951 | 26.82 | 1 | 28.99 | L |
| ATOM | 78 | CD2 | PHE | L | 10 | −27.562 | −8.935 | 26.485 | 1 | 29.58 | L |
| ATOM | 79 | CE1 | PHE | L | 10 | −27.791 | −6.162 | 26.434 | 1 | 29.51 | L |
| ATOM | 80 | CE2 | PHE | L | 10 | −26.469 | −8.159 | 26.096 | 1 | 29.5 | L |
| ATOM | 81 | CZ | PHE | L | 10 | −26.584 | −6.765 | 26.071 | 1 | 28.97 | L |
| ATOM | 82 | C | PHE | L | 10 | −32.011 | −10.363 | 26.436 | 1 | 41.36 | L |
| ATOM | 83 | O | PHE | L | 10 | −32.318 | −10.563 | 27.616 | 1 | 41.31 | L |
| ATOM | 84 | N | MET | L | 11 | −32.582 | −10.989 | 25.414 | 1 | 42.37 | L |
| ATOM | 85 | CA | MET | L | 11 | −33.625 | −11.971 | 25.625 | 1 | 42.65 | L |
| ATOM | 86 | CB | MET | L | 11 | −34.709 | −11.815 | 24.558 | 1 | 45.16 | L |
| ATOM | 87 | CG | MET | L | 11 | −34.302 | −12.238 | 23.161 | 1 | 48.29 | L |
| ATOM | 88 | SD | MET | L | 11 | −34.879 | −13.901 | 22.774 | 1 | 52.68 | L |
| ATOM | 89 | CE | MET | L | 11 | −33.388 | −14.833 | 22.912 | 1 | 51.29 | L |
| ATOM | 90 | C | MET | L | 11 | −33.034 | −13.373 | 25.589 | 1 | 41.43 | L |
| ATOM | 91 | O | MET | L | 11 | −31.969 | −13.595 | 25.01 | 1 | 41.95 | L |
| ATOM | 92 | N | SER | L | 12 | −33.727 | −14.314 | 26.221 | 1 | 39.4 | L |
| ATOM | 93 | CA | SER | L | 12 | −33.272 | −15.696 | 26.268 | 1 | 36.95 | L |
| ATOM | 94 | CB | SER | L | 12 | −32.894 | −16.08 | 27.696 | 1 | 35.26 | L |
| ATOM | 95 | OG | SER | L | 12 | −31.886 | −15.223 | 28.192 | 1 | 43.53 | L |
| ATOM | 96 | C | SER | L | 12 | −34.344 | −16.648 | 25.772 | 1 | 34.68 | L |
| ATOM | 97 | O | SER | L | 12 | −35.517 | −16.301 | 25.715 | 1 | 33.89 | L |
| ATOM | 98 | N | THR | L | 13 | −33.927 | −17.854 | 25.414 | 1 | 33.57 | L |
| ATOM | 99 | CA | THR | L | 13 | −34.846 | −18.874 | 24.944 | 1 | 34.81 | L |
| ATOM | 100 | CB | THR | L | 13 | −35.316 | −18.6 | 23.506 | 1 | 36.65 | L |
| ATOM | 101 | OG1 | THR | L | 13 | −36.301 | −19.574 | 23.127 | 1 | 37.88 | L |
| ATOM | 102 | CG2 | THR | L | 13 | −34.139 | −18.668 | 22.54 | 1 | 34.9 | L |
| ATOM | 103 | C | THR | L | 13 | −34.104 | −20.193 | 24.969 | 1 | 35.21 | L |
| ATOM | 104 | O | THR | L | 13 | −32.891 | −20.224 | 25.135 | 1 | 35.62 | L |
| ATOM | 105 | N | SER | L | 14 | −34.835 | −21.282 | 24.807 | 1 | 34.54 | L |
| ATOM | 106 | CA | SER | L | 14 | −34.22 | −22.593 | 24.804 | 1 | 36.72 | L |
| ATOM | 107 | CB | SER | L | 14 | −34.931 | −23.488 | 25.81 | 1 | 38.64 | L |
| ATOM | 108 | OG | SER | L | 14 | −36.332 | −23.371 | 25.666 | 1 | 43.39 | L |
| ATOM | 109 | C | SER | L | 14 | −34.317 | −23.181 | 23.405 | 1 | 37.15 | L |
| ATOM | 110 | O | SER | L | 14 | −35.317 | −22.996 | 22.715 | 1 | 38.61 | L |
| ATOM | 111 | N | VAL | L | 15 | −33.272 | −23.88 | 22.982 | 1 | 35.82 | L |
| ATOM | 112 | CA | VAL | L | 15 | −33.264 | −24.482 | 21.658 | 1 | 36.21 | L |
| ATOM | 113 | CB | VAL | L | 15 | −32.116 | −25.511 | 21.524 | 1 | 36.7 | L |
| ATOM | 114 | CG1 | VAL | L | 15 | −32.292 | −26.344 | 20.259 | 1 | 34.02 | L |
| ATOM | 115 | CG2 | VAL | L | 15 | −30.778 | −24.784 | 21.493 | 1 | 37.6 | L |
| ATOM | 116 | C | VAL | L | 15 | −34.587 | −25.176 | 21.363 | 1 | 35.63 | L |
| ATOM | 117 | O | VAL | L | 15 | −35.11 | −25.902 | 22.199 | 1 | 33.85 | L |
| ATOM | 118 | N | GLY | L | 16 | −35.127 | −24.935 | 20.172 | 1 | 36.61 | L |
| ATOM | 119 | CA | GLY | L | 16 | −36.375 | −25.564 | 19.779 | 1 | 37.2 | L |
| ATOM | 120 | C | GLY | L | 16 | −37.617 | −24.763 | 20.097 | 1 | 37.26 | L |
| ATOM | 121 | O | GLY | L | 16 | −38.681 | −25.004 | 19.53 | 1 | 38.61 | L |
| ATOM | 122 | N | ASP | L | 17 | −37.495 | −23.809 | 21.006 | 1 | 38.32 | L |
| ATOM | 123 | CA | ASP | L | 17 | −38.638 | −22.987 | 21.364 | 1 | 39.24 | L |
| ATOM | 124 | CB | ASP | L | 17 | −38.421 | −22.332 | 22.727 | 1 | 41.91 | L |
| ATOM | 125 | CG | ASP | L | 17 | −39.453 | −22.766 | 23.736 | 1 | 45.3 | L |
| ATOM | 126 | OD1 | ASP | L | 17 | −40.656 | −22.541 | 23.485 | 1 | 46.3 | L |
| ATOM | 127 | OD2 | ASP | L | 17 | −39.068 | −23.341 | 24.773 | 1 | 48.62 | L |
| ATOM | 128 | C | ASP | L | 17 | −38.909 | −21.913 | 20.321 | 1 | 38.09 | L |
| ATOM | 129 | O | ASP | L | 17 | −38.175 | −21.774 | 19.342 | 1 | 34.63 | L |
| ATOM | 130 | N | ARG | L | 18 | −39.982 | −21.165 | 20.54 | 1 | 38.88 | L |
| ATOM | 131 | CA | ARG | L | 18 | −40.369 | −20.091 | 19.644 | 1 | 40.46 | L |

TABLE 7-continued

| ATOM | 132 | CB | ARG | L | 18 | −41.862 | −20.17 | 19.325 | 1 | 43.7 | L |
|---|---|---|---|---|---|---|---|---|---|---|---|
| ATOM | 133 | CG | ARG | L | 18 | −42.402 | −21.568 | 19.113 | 1 | 49.69 | L |
| ATOM | 134 | CD | ARG | L | 18 | −43.843 | −21.509 | 18.635 | 1 | 55.22 | L |
| ATOM | 135 | NE | ARG | L | 18 | −43.943 | −20.903 | 17.306 | 1 | 60.22 | L |
| ATOM | 136 | CZ | ARG | L | 18 | −45.075 | −20.78 | 16.617 | 1 | 61.55 | L |
| ATOM | 137 | NH1 | ARG | L | 18 | −46.22 | −21.217 | 17.128 | 1 | 62.33 | L |
| ATOM | 138 | NH2 | ARG | L | 18 | −45.061 | −20.234 | 15.406 | 1 | 60.76 | L |
| ATOM | 139 | C | ARG | L | 18 | −40.097 | −18.78 | 20.366 | 1 | 39.91 | L |
| ATOM | 140 | O | ARG | L | 18 | −40.417 | −18.643 | 21.542 | 1 | 41.43 | L |
| ATOM | 141 | N | VAL | L | 19 | −39.5 | −17.82 | 19.675 | 1 | 37.42 | L |
| ATOM | 142 | CA | VAL | L | 19 | −39.24 | −16.526 | 20.289 | 1 | 35.66 | L |
| ATOM | 143 | CB | VAL | L | 19 | −37.743 | −16.284 | 20.528 | 1 | 35.42 | L |
| ATOM | 144 | CG1 | VAL | L | 19 | −37.179 | −17.419 | 21.333 | 1 | 39.42 | L |
| ATOM | 145 | CG2 | VAL | L | 19 | −37.012 | −16.136 | 19.202 | 1 | 32.76 | L |
| ATOM | 146 | C | VAL | L | 19 | −39.751 | −15.438 | 19.375 | 1 | 33.44 | L |
| ATOM | 147 | O | VAL | L | 19 | −40.015 | −15.682 | 18.195 | 1 | 33.86 | L |
| ATOM | 148 | N | SER | L | 20 | −39.89 | −14.239 | 19.927 | 1 | 30.78 | L |
| ATOM | 149 | CA | SER | L | 20 | −40.351 | −13.095 | 19.151 | 1 | 29.79 | L |
| ATOM | 150 | CB | SER | L | 20 | −41.865 | −12.903 | 19.315 | 1 | 27 | L |
| ATOM | 151 | OG | SER | L | 20 | −42.587 | −14.032 | 18.867 | 1 | 22.54 | L |
| ATOM | 152 | C | SER | L | 20 | −39.637 | −11.81 | 19.563 | 1 | 28.33 | L |
| ATOM | 153 | O | SER | L | 20 | −39.775 | −11.339 | 20.696 | 1 | 27.37 | L |
| ATOM | 154 | N | ILE | L | 21 | −38.849 | −11.256 | 18.651 | 1 | 27.04 | L |
| ATOM | 155 | CA | ILE | L | 21 | −38.182 | −9.999 | 18.942 | 1 | 26.07 | L |
| ATOM | 156 | CB | ILE | L | 21 | −36.828 | −9.839 | 18.228 | 1 | 23.33 | L |
| ATOM | 157 | CG2 | ILE | L | 21 | −36.203 | −8.518 | 18.626 | 1 | 23.97 | L |
| ATOM | 158 | CG1 | ILE | L | 21 | −35.888 | −10.982 | 18.59 | 1 | 23.16 | L |
| ATOM | 159 | CD1 | ILE | L | 21 | −36.186 | −12.255 | 17.85 | 1 | 26.47 | L |
| ATOM | 160 | C | ILE | L | 21 | −39.141 | −9.012 | 18.325 | 1 | 25.95 | L |
| ATOM | 161 | O | ILE | L | 21 | −39.53 | −9.174 | 17.169 | 1 | 25.34 | L |
| ATOM | 162 | N | THR | L | 22 | −39.551 | −8.007 | 19.082 | 1 | 24.86 | L |
| ATOM | 163 | CA | THR | L | 22 | −40.472 | −7.043 | 18.52 | 1 | 25.78 | L |
| ATOM | 164 | CB | THR | L | 22 | −41.627 | −6.748 | 19.483 | 1 | 26.92 | L |
| ATOM | 165 | OG1 | THR | L | 22 | −41.108 | −6.381 | 20.766 | 1 | 30.07 | L |
| ATOM | 166 | CG2 | THR | L | 22 | −42.51 | −7.974 | 19.614 | 1 | 26.84 | L |
| ATOM | 167 | C | THR | L | 22 | −39.773 | −5.757 | 18.138 | 1 | 24.77 | L |
| ATOM | 168 | O | THR | L | 22 | −38.652 | −5.487 | 18.566 | 1 | 22.7 | L |
| ATOM | 169 | N | CYS | L | 23 | −40.453 | −4.969 | 17.321 | 1 | 25.79 | L |
| ATOM | 170 | CA | CYS | L | 23 | −39.917 | −3.713 | 16.843 | 1 | 28.58 | L |
| ATOM | 171 | C | CYS | L | 23 | −41.051 | −2.707 | 16.786 | 1 | 28.73 | L |
| ATOM | 172 | O | CYS | L | 23 | −42.083 | −2.962 | 16.17 | 1 | 28.61 | L |
| ATOM | 173 | CB | CYS | L | 23 | −39.332 | −3.933 | 15.448 | 1 | 31.5 | L |
| ATOM | 174 | SG | CYS | L | 23 | −38.547 | −2.535 | 14.577 | 1 | 35.43 | L |
| ATOM | 175 | N | LYS | L | 24 | −40.864 | −1.571 | 17.442 | 1 | 29.33 | L |
| ATOM | 176 | CA | LYS | L | 24 | −41.872 | −0.526 | 17.43 | 1 | 32.95 | L |
| ATOM | 177 | CB | LYS | L | 24 | −42.305 | −0.16 | 18.854 | 1 | 38.59 | L |
| ATOM | 178 | CG | LYS | L | 24 | −43.375 | 0.933 | 18.893 | 1 | 45.28 | L |
| ATOM | 179 | CD | LYS | L | 24 | −43.655 | 1.411 | 20.312 | 1 | 50.68 | L |
| ATOM | 180 | CE | LYS | L | 24 | −44.83 | 2.387 | 20.349 | 1 | 52.5 | L |
| ATOM | 181 | NZ | LYS | L | 24 | −46.127 | 1.738 | 19.996 | 1 | 52.23 | L |
| ATOM | 182 | C | LYS | L | 24 | −41.309 | 0.713 | 16.756 | 1 | 30.25 | L |
| ATOM | 183 | O | LYS | L | 24 | −40.172 | 1.099 | 17.011 | 1 | 32.95 | L |
| ATOM | 184 | N | ALA | L | 25 | −42.105 | 1.329 | 15.891 | 1 | 29.22 | L |
| ATOM | 185 | CA | ALA | L | 25 | −41.68 | 2.542 | 15.207 | 1 | 27.96 | L |
| ATOM | 186 | CB | ALA | L | 25 | −41.877 | 2.405 | 13.708 | 1 | 26.41 | L |
| ATOM | 187 | C | ALA | L | 25 | −42.524 | 3.683 | 15.753 | 1 | 26.47 | L |
| ATOM | 188 | O | ALA | L | 25 | −43.712 | 3.513 | 15.999 | 1 | 21.99 | L |
| ATOM | 189 | N | SER | L | 26 | −41.9 | 4.841 | 15.949 | 1 | 28.43 | L |
| ATOM | 190 | CA | SER | L | 26 | −42.589 | 6.016 | 16.479 | 1 | 29.22 | L |
| ATOM | 191 | CB | SER | L | 26 | −41.592 | 7.17 | 16.626 | 1 | 27.56 | L |
| ATOM | 192 | OG | SER | L | 26 | −40.8 | 7.32 | 15.46 | 1 | 28.74 | L |
| ATOM | 193 | C | SER | L | 26 | −43.819 | 6.452 | 15.657 | 1 | 29.46 | L |
| ATOM | 194 | O | SER | L | 26 | −44.611 | 7.282 | 16.106 | 1 | 26.09 | L |
| ATOM | 195 | N | GLN | L | 27 | −43.972 | 5.885 | 14.461 | 1 | 30.97 | L |
| ATOM | 196 | CA | GLN | L | 27 | −45.116 | 6.179 | 13.6 | 1 | 31.29 | L |
| ATOM | 197 | CB | GLN | L | 27 | −44.906 | 7.491 | 12.825 | 1 | 34.18 | L |
| ATOM | 198 | CG | GLN | L | 27 | −43.578 | 7.639 | 12.109 | 1 | 36.72 | L |
| ATOM | 199 | CD | GLN | L | 27 | −43.439 | 8.999 | 11.437 | 1 | 38.14 | L |
| ATOM | 200 | OE1 | GLN | L | 27 | −44.176 | 9.325 | 10.503 | 1 | 38.97 | L |
| ATOM | 201 | NE2 | GLN | L | 27 | −42.496 | 9.802 | 11.915 | 1 | 38.77 | L |
| ATOM | 202 | C | GLN | L | 27 | −45.379 | 5.023 | 12.639 | 1 | 30.09 | L |
| ATOM | 203 | O | GLN | L | 27 | −44.548 | 4.122 | 12.509 | 1 | 29.44 | L |
| ATOM | 204 | N | ASP | L | 28 | −46.543 | 5.043 | 11.991 | 1 | 27.3 | L |
| ATOM | 205 | CA | ASP | L | 28 | −46.932 | 3.994 | 11.05 | 1 | 25.1 | L |
| ATOM | 206 | CB | ASP | L | 28 | −48.333 | 4.283 | 10.501 | 1 | 24.08 | L |
| ATOM | 207 | CG | ASP | L | 28 | −48.934 | 3.099 | 9.75 | 1 | 29.29 | L |
| ATOM | 208 | OD1 | ASP | L | 28 | −48.175 | 2.208 | 9.312 | 1 | 32.01 | L |
| ATOM | 209 | OD2 | ASP | L | 28 | −50.176 | 3.062 | 9.583 | 1 | 28.91 | L |
| ATOM | 210 | C | ASP | L | 28 | −45.926 | 3.96 | 9.901 | 1 | 26.55 | L |

TABLE 7-continued

| ATOM | 211 | O | ASP | L | 28 | −45.831 | 4.912 | 9.128 | 1 | 27.44 | L |
| ATOM | 212 | N | VAL | L | 29 | −45.161 | 2.877 | 9.797 | 1 | 25.47 | L |
| ATOM | 213 | CA | VAL | L | 29 | −44.178 | 2.751 | 8.722 | 1 | 25.32 | L |
| ATOM | 214 | CB | VAL | L | 29 | −42.846 | 2.171 | 9.234 | 1 | 26.06 | L |
| ATOM | 215 | CG1 | VAL | L | 29 | −42.018 | 3.288 | 9.867 | 1 | 23.41 | L |
| ATOM | 216 | CG2 | VAL | L | 29 | −43.116 | 1.056 | 10.244 | 1 | 21.47 | L |
| ATOM | 217 | C | VAL | L | 29 | −44.726 | 1.866 | 7.612 | 1 | 24.8 | L |
| ATOM | 218 | O | VAL | L | 29 | −43.99 | 1.18 | 6.906 | 1 | 24.35 | L |
| ATOM | 219 | N | SER | L | 30 | −46.047 | 1.907 | 7.487 | 1 | 26.52 | L |
| ATOM | 220 | CA | SER | L | 30 | −46.809 | 1.172 | 6.492 | 1 | 26 | L |
| ATOM | 221 | CB | SER | L | 30 | −47.044 | 2.083 | 5.291 | 1 | 24.48 | L |
| ATOM | 222 | OG | SER | L | 30 | −48.007 | 1.526 | 4.421 | 1 | 31.89 | L |
| ATOM | 223 | C | SER | L | 30 | −46.255 | −0.184 | 6.023 | 1 | 26.66 | L |
| ATOM | 224 | O | SER | L | 30 | −46.06 | −0.401 | 4.821 | 1 | 23.27 | L |
| ATOM | 225 | N | THR | L | 31 | −46.003 | −1.095 | 6.964 | 1 | 25.31 | L |
| ATOM | 226 | CA | THR | L | 31 | −45.513 | −2.423 | 6.599 | 1 | 25.99 | L |
| ATOM | 227 | CB | THR | L | 31 | −46.478 | −3.045 | 5.539 | 1 | 25.05 | L |
| ATOM | 228 | OG1 | THR | L | 31 | −47.553 | −3.698 | 6.224 | 1 | 25.02 | L |
| ATOM | 229 | CG2 | THR | L | 31 | −45.775 | −4.02 | 4.618 | 1 | 21.63 | L |
| ATOM | 230 | C | THR | L | 31 | −44.068 | −2.463 | 6.092 | 1 | 25.19 | L |
| ATOM | 231 | O | THR | L | 31 | −43.49 | −3.537 | 5.919 | 1 | 24.76 | L |
| ATOM | 232 | N | ALA | L | 32 | −43.479 | −1.292 | 5.871 | 1 | 24.51 | L |
| ATOM | 233 | CA | ALA | L | 32 | −42.111 | −1.214 | 5.371 | 1 | 23.42 | L |
| ATOM | 234 | CB | ALA | L | 32 | −41.902 | 0.115 | 4.65 | 1 | 25.37 | L |
| ATOM | 235 | C | ALA | L | 32 | −41.052 | −1.392 | 6.459 | 1 | 20.82 | L |
| ATOM | 236 | O | ALA | L | 32 | −40.422 | −0.427 | 6.888 | 1 | 19.59 | L |
| ATOM | 237 | N | VAL | L | 33 | −40.852 | −2.631 | 6.897 | 1 | 20.92 | L |
| ATOM | 238 | CA | VAL | L | 33 | −39.861 | −2.927 | 7.927 | 1 | 19.82 | L |
| ATOM | 239 | CB | VAL | L | 33 | −40.521 | −3.096 | 9.336 | 1 | 20.11 | L |
| ATOM | 240 | CG1 | VAL | L | 33 | −39.538 | −3.724 | 10.325 | 1 | 19.01 | L |
| ATOM | 241 | CG2 | VAL | L | 33 | −40.951 | −1.755 | 9.865 | 1 | 18.53 | L |
| ATOM | 242 | C | VAL | L | 33 | −39.1 | −4.202 | 7.57 | 1 | 20.5 | L |
| ATOM | 243 | O | VAL | L | 33 | −39.678 | −5.186 | 7.091 | 1 | 17.51 | L |
| ATOM | 244 | N | ALA | L | 34 | −37.795 | −4.174 | 7.809 | 1 | 18.68 | L |
| ATOM | 245 | CA | ALA | L | 34 | −36.944 | −5.316 | 7.515 | 1 | 18.72 | L |
| ATOM | 246 | CB | ALA | L | 34 | −35.957 | −4.949 | 6.417 | 1 | 12.5 | L |
| ATOM | 247 | C | ALA | L | 34 | −36.188 | −5.795 | 8.757 | 1 | 20.05 | L |
| ATOM | 248 | O | ALA | L | 34 | −36.031 | −5.057 | 9.739 | 1 | 19.38 | L |
| ATOM | 249 | N | TRP | L | 35 | −35.729 | −7.039 | 8.712 | 1 | 17.67 | L |
| ATOM | 250 | CA | TRP | L | 35 | −34.968 | −7.586 | 9.815 | 1 | 17.47 | L |
| ATOM | 251 | CB | TRP | L | 35 | −35.759 | −8.67 | 10.533 | 1 | 17.5 | L |
| ATOM | 252 | CG | TRP | L | 35 | −36.962 | −8.18 | 11.266 | 1 | 21.69 | L |
| ATOM | 253 | CD2 | TRP | L | 35 | −37.034 | −7.833 | 12.653 | 1 | 21.78 | L |
| ATOM | 254 | CE2 | TRP | L | 35 | −38.374 | −7.476 | 12.924 | 1 | 22.24 | L |
| ATOM | 255 | CE3 | TRP | L | 35 | −36.094 | −7.788 | 13.695 | 1 | 22.95 | L |
| ATOM | 256 | CD1 | TRP | L | 35 | −38.225 | −8.018 | 10.763 | 1 | 20.24 | L |
| ATOM | 257 | NE1 | TRP | L | 35 | −39.076 | −7.601 | 11.754 | 1 | 21.01 | L |
| ATOM | 258 | CZ2 | TRP | L | 35 | −38.803 | −7.079 | 14.198 | 1 | 23.86 | L |
| ATOM | 259 | CZ3 | TRP | L | 35 | −36.517 | −7.391 | 14.964 | 1 | 25.12 | L |
| ATOM | 260 | CH2 | TRP | L | 35 | −37.863 | −7.041 | 15.203 | 1 | 25.78 | L |
| ATOM | 261 | C | TRP | L | 35 | −33.651 | −8.167 | 9.328 | 1 | 15.83 | L |
| ATOM | 262 | O | TRP | L | 35 | −33.603 | −8.86 | 8.323 | 1 | 15.93 | L |
| ATOM | 263 | N | TYR | L | 36 | −32.577 | −7.882 | 10.049 | 1 | 16.64 | L |
| ATOM | 264 | CA | TYR | L | 36 | −31.271 | −8.404 | 9.679 | 1 | 21.5 | L |
| ATOM | 265 | CB | TYR | L | 36 | −30.285 | −7.267 | 9.379 | 1 | 19.96 | L |
| ATOM | 266 | CG | TYR | L | 36 | −30.714 | −6.347 | 8.261 | 1 | 21.18 | L |
| ATOM | 267 | CD1 | TYR | L | 36 | −30.503 | −6.688 | 6.925 | 1 | 20.53 | L |
| ATOM | 268 | CE1 | TYR | L | 36 | −30.89 | −5.835 | 5.893 | 1 | 19.8 | L |
| ATOM | 269 | CD2 | TYR | L | 36 | −31.329 | −5.126 | 8.543 | 1 | 22.81 | L |
| ATOM | 270 | CE2 | TYR | L | 36 | −31.726 | −4.263 | 7.522 | 1 | 20.1 | L |
| ATOM | 271 | CZ | TYR | L | 36 | −31.504 | −4.621 | 6.201 | 1 | 21.52 | L |
| ATOM | 272 | OH | TYR | L | 36 | −31.9 | −3.764 | 5.198 | 1 | 18.17 | L |
| ATOM | 273 | C | TYR | L | 36 | −30.739 | −9.218 | 10.842 | 1 | 21.62 | L |
| ATOM | 274 | O | TYR | L | 36 | −31.117 | −8.993 | 11.992 | 1 | 21.98 | L |
| ATOM | 275 | N | GLN | L | 37 | −29.862 | −10.164 | 10.528 | 1 | 22.38 | L |
| ATOM | 276 | CA | GLN | L | 37 | −29.23 | −11.007 | 11.53 | 1 | 21.58 | L |
| ATOM | 277 | CB | GLN | L | 37 | −29.485 | −12.488 | 11.24 | 1 | 22.59 | L |
| ATOM | 278 | CG | GLN | L | 37 | −28.769 | −13.432 | 12.192 | 1 | 20.06 | L |
| ATOM | 279 | CD | GLN | L | 37 | −28.824 | −14.868 | 11.73 | 1 | 24.01 | L |
| ATOM | 280 | OE1 | GLN | L | 37 | −28.373 | −15.194 | 10.63 | 1 | 24.4 | L |
| ATOM | 281 | NE2 | GLN | L | 37 | −29.377 | −15.742 | 12.566 | 1 | 24.16 | L |
| ATOM | 282 | C | GLN | L | 37 | −27.736 | −10.739 | 11.453 | 1 | 22.35 | L |
| ATOM | 283 | O | GLN | L | 37 | −27.155 | −10.709 | 10.372 | 1 | 19.14 | L |
| ATOM | 284 | N | GLN | L | 38 | −27.107 | −10.52 | 12.597 | 1 | 26.93 | L |
| ATOM | 285 | CA | GLN | L | 38 | −25.678 | −10.286 | 12.582 | 1 | 28.65 | L |
| ATOM | 286 | CB | GLN | L | 38 | −25.362 | −8.817 | 12.815 | 1 | 28.44 | L |
| ATOM | 287 | CG | GLN | L | 38 | −23.879 | −8.555 | 12.826 | 1 | 30.45 | L |
| ATOM | 288 | CD | GLN | L | 38 | −23.55 | −7.093 | 12.869 | 1 | 31.99 | L |
| ATOM | 289 | OE1 | GLN | L | 38 | −24.099 | −6.336 | 13.681 | 1 | 33.27 | L |

TABLE 7-continued

| | | | | | | | | | | |
|---|---|---|---|---|---|---|---|---|---|---|
| ATOM | 290 | NE2 | GLN | L | 38 | −22.638 | −6.677 | 11.999 | 1 | 32.4 | L |
| ATOM | 291 | C | GLN | L | 38 | −24.953 | −11.141 | 13.6 | 1 | 29.69 | L |
| ATOM | 292 | O | GLN | L | 38 | −25.154 | −11.008 | 14.806 | 1 | 28.23 | L |
| ATOM | 293 | N | LYS | L | 39 | −24.116 | −12.034 | 13.084 | 1 | 33.97 | L |
| ATOM | 294 | CA | LYS | L | 39 | −23.324 | −12.935 | 13.907 | 1 | 36.3 | L |
| ATOM | 295 | CB | LYS | L | 39 | −23.229 | −14.306 | 13.231 | 1 | 33.95 | L |
| ATOM | 296 | CG | LYS | L | 39 | −24.566 | −15.002 | 13.168 | 1 | 32.64 | L |
| ATOM | 297 | CD | LYS | L | 39 | −24.509 | −16.344 | 12.469 | 1 | 32.98 | L |
| ATOM | 298 | CE | LYS | L | 39 | −25.863 | −17.034 | 12.602 | 1 | 31.48 | L |
| ATOM | 299 | NZ | LYS | L | 39 | −25.98 | −18.286 | 11.819 | 1 | 35.86 | L |
| ATOM | 300 | C | LYS | L | 39 | −21.938 | −12.334 | 14.107 | 1 | 38.02 | L |
| ATOM | 301 | O | LYS | L | 39 | −21.411 | −11.656 | 13.223 | 1 | 37.92 | L |
| ATOM | 302 | N | PRO | L | 40 | −21.336 | −12.572 | 15.281 | 1 | 38.79 | L |
| ATOM | 303 | CD | PRO | L | 40 | −21.857 | −13.483 | 16.315 | 1 | 39.44 | L |
| ATOM | 304 | CA | PRO | L | 40 | −20.009 | −12.075 | 15.652 | 1 | 39.28 | L |
| ATOM | 305 | CB | PRO | L | 40 | −19.593 | −13.033 | 16.756 | 1 | 40.48 | L |
| ATOM | 306 | CG | PRO | L | 40 | −20.881 | −13.269 | 17.46 | 1 | 41.08 | L |
| ATOM | 307 | C | PRO | L | 40 | −19.005 | −12.036 | 14.502 | 1 | 38.95 | L |
| ATOM | 308 | O | PRO | L | 40 | −18.731 | −13.057 | 13.865 | 1 | 36.36 | L |
| ATOM | 309 | N | GLY | L | 41 | −18.468 | −10.844 | 14.247 | 1 | 38.48 | L |
| ATOM | 310 | CA | GLY | L | 41 | −17.497 | −10.67 | 13.182 | 1 | 38.13 | L |
| ATOM | 311 | C | GLY | L | 41 | −18.038 | −11.086 | 11.831 | 1 | 38.14 | L |
| ATOM | 312 | O | GLY | L | 41 | −17.392 | −11.831 | 11.098 | 1 | 39.38 | L |
| ATOM | 313 | N | GLN | L | 42 | −19.235 | −10.608 | 11.508 | 1 | 37.31 | L |
| ATOM | 314 | CA | GLN | L | 42 | −19.876 | −10.917 | 10.238 | 1 | 34.17 | L |
| ATOM | 315 | CB | GLN | L | 42 | −20.751 | −12.16 | 10.364 | 1 | 34.42 | L |
| ATOM | 316 | CG | GLN | L | 42 | −19.988 | −13.453 | 10.31 | 1 | 36.12 | L |
| ATOM | 317 | CD | GLN | L | 42 | −20.896 | −14.647 | 10.086 | 1 | 39.96 | L |
| ATOM | 318 | OE1 | GLN | L | 42 | −21.833 | −14.594 | 9.275 | 1 | 37.78 | L |
| ATOM | 319 | NE2 | GLN | L | 42 | −20.617 | −15.74 | 10.791 | 1 | 40.29 | L |
| ATOM | 320 | C | GLN | L | 42 | −20.73 | −9.751 | 9.781 | 1 | 34.27 | L |
| ATOM | 321 | O | GLN | L | 42 | −21.189 | −8.942 | 10.589 | 1 | 35.05 | L |
| ATOM | 322 | N | SER | L | 43 | −20.94 | −9.661 | 8.477 | 1 | 32.51 | L |
| ATOM | 323 | CA | SER | L | 43 | −21.756 | −8.59 | 7.938 | 1 | 30.71 | L |
| ATOM | 324 | CB | SER | L | 43 | −21.585 | −8.512 | 6.421 | 1 | 33.35 | L |
| ATOM | 325 | OG | SER | L | 43 | −20.217 | −8.381 | 6.074 | 1 | 40.08 | L |
| ATOM | 326 | C | SER | L | 43 | −23.202 | −8.923 | 8.265 | 1 | 28.28 | L |
| ATOM | 327 | O | SER | L | 43 | −23.544 | −10.085 | 8.471 | 1 | 28.57 | L |
| ATOM | 328 | N | PRO | L | 44 | −24.068 | −7.906 | 8.345 | 1 | 24.68 | L |
| ATOM | 329 | CD | PRO | L | 44 | −23.796 | −6.46 | 8.39 | 1 | 21.7 | L |
| ATOM | 330 | CA | PRO | L | 44 | −25.47 | −8.181 | 8.643 | 1 | 20.8 | L |
| ATOM | 331 | CB | PRO | L | 44 | −26.089 | −6.799 | 8.66 | 1 | 19.34 | L |
| ATOM | 332 | CG | PRO | L | 44 | −24.985 | −5.946 | 9.149 | 1 | 19.68 | L |
| ATOM | 333 | C | PRO | L | 44 | −26.017 | −9.025 | 7.503 | 1 | 24.4 | L |
| ATOM | 334 | O | PRO | L | 44 | −25.49 | −8.977 | 6.388 | 1 | 25.24 | L |
| ATOM | 335 | N | LYS | L | 45 | −27.057 | −9.808 | 7.78 | 1 | 27.66 | L |
| ATOM | 336 | CA | LYS | L | 45 | −27.681 | −10.644 | 6.752 | 1 | 27.45 | L |
| ATOM | 337 | CB | LYS | L | 45 | −27.445 | −12.132 | 7.025 | 1 | 28.38 | L |
| ATOM | 338 | CG | LYS | L | 45 | −25.973 | −12.507 | 7.118 | 1 | 35.81 | L |
| ATOM | 339 | CD | LYS | L | 45 | −25.189 | −11.936 | 5.939 | 1 | 40.78 | L |
| ATOM | 340 | CE | LYS | L | 45 | −23.697 | −12.201 | 6.061 | 1 | 41.63 | L |
| ATOM | 341 | NZ | LYS | L | 45 | −23.408 | −13.66 | 6.047 | 1 | 46.51 | L |
| ATOM | 342 | C | LYS | L | 45 | −29.169 | −10.354 | 6.731 | 1 | 26.01 | L |
| ATOM | 343 | O | LYS | L | 45 | −29.827 | −10.358 | 7.774 | 1 | 25.82 | L |
| ATOM | 344 | N | LEU | L | 46 | −29.696 | −10.09 | 5.543 | 1 | 22.57 | L |
| ATOM | 345 | CA | LEU | L | 46 | −31.113 | −9.788 | 5.404 | 1 | 24.84 | L |
| ATOM | 346 | CB | LEU | L | 46 | −31.396 | −9.282 | 3.992 | 1 | 24.51 | L |
| ATOM | 347 | CG | LEU | L | 46 | −32.851 | −8.956 | 3.692 | 1 | 23.39 | L |
| ATOM | 348 | CD1 | LEU | L | 46 | −33.306 | −7.822 | 4.583 | 1 | 25.7 | L |
| ATOM | 349 | CD2 | LEU | L | 46 | −32.993 | −8.581 | 2.228 | 1 | 25.19 | L |
| ATOM | 350 | C | LEU | L | 46 | −31.984 | −11.007 | 5.703 | 1 | 22.66 | L |
| ATOM | 351 | O | LEU | L | 46 | −31.747 | −12.088 | 5.179 | 1 | 26.72 | L |
| ATOM | 352 | N | LEU | L | 47 | −32.994 | −10.833 | 6.542 | 1 | 20.56 | L |
| ATOM | 353 | CA | LEU | L | 47 | −33.885 | −11.94 | 6.882 | 1 | 19.62 | L |
| ATOM | 354 | CB | LEU | L | 47 | −33.985 | −12.107 | 8.402 | 1 | 15.41 | L |
| ATOM | 355 | CG | LEU | L | 47 | −32.715 | −12.505 | 9.152 | 1 | 16.42 | L |
| ATOM | 356 | CD1 | LEU | L | 47 | −33.008 | −12.532 | 10.644 | 1 | 14.57 | L |
| ATOM | 357 | CD2 | LEU | L | 47 | −32.208 | −13.86 | 8.657 | 1 | 8.77 | L |
| ATOM | 358 | C | LEU | L | 47 | −35.291 | −11.747 | 6.339 | 1 | 19.36 | L |
| ATOM | 359 | O | LEU | L | 47 | −35.845 | −12.617 | 5.67 | 1 | 20.87 | L |
| ATOM | 360 | N | ILE | L | 48 | −35.854 | −10.588 | 6.641 | 1 | 20.51 | L |
| ATOM | 361 | CA | ILE | L | 48 | −37.208 | −10.25 | 6.25 | 1 | 22.66 | L |
| ATOM | 362 | CB | ILE | L | 48 | −38.155 | −10.304 | 7.475 | 1 | 23.74 | L |
| ATOM | 363 | CG2 | ILE | L | 48 | −39.56 | −9.871 | 7.068 | 1 | 25.37 | L |
| ATOM | 364 | CG1 | ILE | L | 48 | −38.165 | −11.711 | 8.076 | 1 | 23.46 | L |
| ATOM | 365 | CD1 | ILE | L | 48 | −38.789 | −12.751 | 7.182 | 1 | 21.29 | L |
| ATOM | 366 | C | ILE | L | 48 | −37.28 | −8.835 | 5.706 | 1 | 22.85 | L |
| ATOM | 367 | O | ILE | L | 48 | −36.61 | −7.936 | 6.213 | 1 | 23.92 | L |
| ATOM | 368 | N | SER | L | 49 | −38.095 | −8.644 | 4.676 | 1 | 22.66 | L |

TABLE 7-continued

| | | | | | | | | | | |
|---|---|---|---|---|---|---|---|---|---|---|
| ATOM | 369 | CA | SER | L | 49 | −38.308 | −7.32 | 4.104 | 1 | 23.07 | L |
| ATOM | 370 | CB | SER | L | 49 | −37.718 | −7.212 | 2.687 | 1 | 24.44 | L |
| ATOM | 371 | OG | SER | L | 49 | −38.398 | −8.042 | 1.763 | 1 | 24.39 | L |
| ATOM | 372 | C | SER | L | 49 | −39.825 | −7.128 | 4.069 | 1 | 21.99 | L |
| ATOM | 373 | O | SER | L | 49 | −40.581 | −8.092 | 3.93 | 1 | 20.34 | L |
| ATOM | 374 | N | TRP | L | 50 | −40.27 | −5.89 | 4.218 | 1 | 22.89 | L |
| ATOM | 375 | CA | TRP | L | 50 | −41.699 | −5.597 | 4.203 | 1 | 23.76 | L |
| ATOM | 376 | CB | TRP | L | 50 | −42.278 | −5.815 | 2.805 | 1 | 22.11 | L |
| ATOM | 377 | CG | TRP | L | 50 | −41.931 | −4.711 | 1.859 | 1 | 21.52 | L |
| ATOM | 378 | CD2 | TRP | L | 50 | −42.594 | −3.441 | 1.746 | 1 | 18.16 | L |
| ATOM | 379 | CE2 | TRP | L | 50 | −41.928 | −2.712 | 0.732 | 1 | 15.73 | L |
| ATOM | 380 | CE3 | TRP | L | 50 | −43.685 | −2.851 | 2.403 | 1 | 13.3 | L |
| ATOM | 381 | CD1 | TRP | L | 50 | −40.922 | −4.7 | 0.942 | 1 | 19.62 | L |
| ATOM | 382 | NE1 | TRP | L | 50 | −40.914 | −3.503 | 0.262 | 1 | 19.88 | L |
| ATOM | 383 | CZ2 | TRP | L | 50 | −42.317 | −1.418 | 0.354 | 1 | 13.28 | L |
| ATOM | 384 | CZ3 | TRP | L | 50 | −44.073 | −1.56 | 2.028 | 1 | 13.71 | L |
| ATOM | 385 | CH2 | TRP | L | 50 | −43.387 | −0.861 | 1.011 | 1 | 12.41 | L |
| ATOM | 386 | C | TRP | L | 50 | −42.486 | −6.416 | 5.213 | 1 | 20.91 | L |
| ATOM | 387 | O | TRP | L | 50 | −43.497 | −7.02 | 4.887 | 1 | 22.48 | L |
| ATOM | 388 | N | ALA | L | 51 | −41.992 | −6.433 | 6.441 | 1 | 21.79 | L |
| ATOM | 389 | CA | ALA | L | 51 | −42.635 | −7.129 | 7.543 | 1 | 24.98 | L |
| ATOM | 390 | CB | ALA | L | 51 | −44.048 | −6.565 | 7.751 | 1 | 23.42 | L |
| ATOM | 391 | C | ALA | L | 51 | −42.704 | −8.648 | 7.471 | 1 | 26.66 | L |
| ATOM | 392 | O | ALA | L | 51 | −42.403 | −9.317 | 8.456 | 1 | 24.85 | L |
| ATOM | 393 | N | SER | L | 52 | −43.085 | −9.197 | 6.321 | 1 | 26.55 | L |
| ATOM | 394 | CA | SER | L | 52 | −43.24 | −10.64 | 6.223 | 1 | 29.15 | L |
| ATOM | 395 | CB | SER | L | 52 | −44.735 | −10.979 | 6.17 | 1 | 27.5 | L |
| ATOM | 396 | OG | SER | L | 52 | −45.347 | −10.433 | 5.008 | 1 | 27.5 | L |
| ATOM | 397 | C | SER | L | 52 | −42.536 | −11.381 | 5.096 | 1 | 32.33 | L |
| ATOM | 398 | O | SER | L | 52 | −42.484 | −12.613 | 5.11 | 1 | 34.93 | L |
| ATOM | 399 | N | THR | L | 53 | −41.999 | −10.661 | 4.119 | 1 | 33.9 | L |
| ATOM | 400 | CA | THR | L | 53 | −41.336 | −11.333 | 3.008 | 1 | 33.22 | L |
| ATOM | 401 | CB | THR | L | 53 | −41.073 | −10.366 | 1.853 | 1 | 33.67 | L |
| ATOM | 402 | OG1 | THR | L | 53 | −42.295 | −9.703 | 1.499 | 1 | 33.66 | L |
| ATOM | 403 | CG2 | THR | L | 53 | −40.548 | −11.126 | 0.644 | 1 | 33.16 | L |
| ATOM | 404 | C | THR | L | 53 | −40.018 | −11.965 | 3.43 | 1 | 32.99 | L |
| ATOM | 405 | O | THR | L | 53 | −39.082 | −11.271 | 3.811 | 1 | 33.34 | L |
| ATOM | 406 | N | ARG | L | 54 | −39.951 | −13.291 | 3.364 | 1 | 33.79 | L |
| ATOM | 407 | CA | ARG | L | 54 | −38.735 | −13.999 | 3.746 | 1 | 35.92 | L |
| ATOM | 408 | CB | ARG | L | 54 | −39.038 | −15.424 | 4.197 | 1 | 32.75 | L |
| ATOM | 409 | CG | ARG | L | 54 | −37.793 | −16.192 | 4.587 | 1 | 31.53 | L |
| ATOM | 410 | CD | ARG | L | 54 | −38.148 | −17.568 | 5.079 | 1 | 33.63 | L |
| ATOM | 411 | NE | ARG | L | 54 | −39.309 | −17.503 | 5.953 | 1 | 37.86 | L |
| ATOM | 412 | CZ | ARG | L | 54 | −40.467 | −18.095 | 5.687 | 1 | 40.65 | L |
| ATOM | 413 | NH1 | ARG | L | 54 | −40.607 | −18.8 | 4.574 | 1 | 42.43 | L |
| ATOM | 414 | NH2 | ARG | L | 54 | −41.49 | −17.969 | 6.523 | 1 | 43.56 | L |
| ATOM | 415 | C | ARG | L | 54 | −37.737 | −14.059 | 2.608 | 1 | 37.11 | L |
| ATOM | 416 | O | ARG | L | 54 | −38.039 | −14.559 | 1.528 | 1 | 38.23 | L |
| ATOM | 417 | N | HIS | L | 55 | −36.539 | −13.558 | 2.867 | 1 | 38.89 | L |
| ATOM | 418 | CA | HIS | L | 55 | −35.491 | −13.554 | 1.87 | 1 | 39.76 | L |
| ATOM | 419 | CB | HIS | L | 55 | −34.322 | −12.715 | 2.366 | 1 | 44.09 | L |
| ATOM | 420 | CG | HIS | L | 55 | −33.465 | −12.176 | 1.27 | 1 | 49.71 | L |
| ATOM | 421 | CD2 | HIS | L | 55 | −33.733 | −11.95 | −0.039 | 1 | 52.46 | L |
| ATOM | 422 | ND1 | HIS | L | 55 | −32.158 | −11.788 | 1.469 | 1 | 52.09 | L |
| ATOM | 423 | CE1 | HIS | L | 55 | −31.655 | −11.346 | 0.329 | 1 | 54.31 | L |
| ATOM | 424 | NE2 | HIS | L | 55 | −32.59 | −11.434 | −0.601 | 1 | 54.67 | L |
| ATOM | 425 | C | HIS | L | 55 | −35.033 | −14.988 | 1.61 | 1 | 39.61 | L |
| ATOM | 426 | O | HIS | L | 55 | −35.236 | −15.871 | 2.442 | 1 | 39.28 | L |
| ATOM | 427 | N | THR | L | 56 | −34.423 | −15.219 | 0.451 | 1 | 41.6 | L |
| ATOM | 428 | CA | THR | L | 56 | −33.934 | −16.55 | 0.098 | 1 | 42.65 | L |
| ATOM | 429 | CB | THR | L | 56 | −33.583 | −16.654 | −1.401 | 1 | 43.79 | L |
| ATOM | 430 | OG1 | THR | L | 56 | −32.671 | −15.607 | −1.752 | 1 | 45.15 | L |
| ATOM | 431 | CG2 | THR | L | 56 | −34.836 | −16.548 | −2.257 | 1 | 43.55 | L |
| ATOM | 432 | C | THR | L | 56 | −32.684 | −16.867 | 0.905 | 1 | 42.41 | L |
| ATOM | 433 | O | THR | L | 56 | −31.952 | −15.964 | 1.308 | 1 | 43.65 | L |
| ATOM | 434 | N | GLY | L | 57 | −32.434 | −18.151 | 1.133 | 1 | 41.88 | L |
| ATOM | 435 | CA | GLY | L | 57 | −31.274 | −18.53 | 1.912 | 1 | 40.66 | L |
| ATOM | 436 | C | GLY | L | 57 | −31.583 | −18.259 | 3.369 | 1 | 40.72 | L |
| ATOM | 437 | O | GLY | L | 57 | −30.679 | −18.096 | 4.196 | 1 | 43.22 | L |
| ATOM | 438 | N | VAL | L | 58 | −32.879 | −18.195 | 3.668 | 1 | 37.17 | L |
| ATOM | 439 | CA | VAL | L | 58 | −33.373 | −17.956 | 5.019 | 1 | 34.34 | L |
| ATOM | 440 | CB | VAL | L | 58 | −34.042 | −16.562 | 5.132 | 1 | 32.13 | L |
| ATOM | 441 | CG1 | VAL | L | 58 | −34.629 | −16.363 | 6.519 | 1 | 30.74 | L |
| ATOM | 442 | CG2 | VAL | L | 58 | −33.025 | −15.481 | 4.853 | 1 | 28.46 | L |
| ATOM | 443 | C | VAL | L | 58 | −34.408 | −19.039 | 5.315 | 1 | 34.51 | L |
| ATOM | 444 | O | VAL | L | 58 | −35.437 | −19.121 | 4.643 | 1 | 33.67 | L |
| ATOM | 445 | N | PRO | L | 59 | −34.142 | −19.891 | 6.319 | 1 | 34.54 | L |
| ATOM | 446 | CD | PRO | L | 59 | −32.978 | −19.84 | 7.221 | 1 | 35.91 | L |
| ATOM | 447 | CA | PRO | L | 59 | −35.051 | −20.979 | 6.703 | 1 | 35.62 | L |

TABLE 7-continued

| | | | | | | | | | | |
|---|---|---|---|---|---|---|---|---|---|---|
| ATOM | 448 | CB | PRO | L | 59 | −34.287 | −21.693 | 7.819 | 1 | 35.06 | L |
| ATOM | 449 | CG | PRO | L | 59 | −33.474 | −20.611 | 8.423 | 1 | 35.87 | L |
| ATOM | 450 | C | PRO | L | 59 | −36.434 | −20.503 | 7.146 | 1 | 37.99 | L |
| ATOM | 451 | O | PRO | L | 59 | −36.563 | −19.528 | 7.89 | 1 | 38.44 | L |
| ATOM | 452 | N | ASP | L | 60 | −37.467 | −21.209 | 6.695 | 1 | 38.64 | L |
| ATOM | 453 | CA | ASP | L | 60 | −38.835 | −20.841 | 7.029 | 1 | 40.72 | L |
| ATOM | 454 | CB | ASP | L | 60 | −39.833 | −21.755 | 6.313 | 1 | 46.03 | L |
| ATOM | 455 | CG | ASP | L | 60 | −39.453 | −23.218 | 6.391 | 1 | 50.98 | L |
| ATOM | 456 | OD1 | ASP | L | 60 | −39.135 | −23.703 | 7.507 | 1 | 53.57 | L |
| ATOM | 457 | OD2 | ASP | L | 60 | −39.484 | −23.88 | 5.326 | 1 | 53.05 | L |
| ATOM | 458 | C | ASP | L | 60 | −39.165 | −20.805 | 8.509 | 1 | 38.96 | L |
| ATOM | 459 | O | ASP | L | 60 | −40.285 | −20.443 | 8.876 | 1 | 39.35 | L |
| ATOM | 460 | N | ARG | L | 61 | −38.22 | −21.179 | 9.366 | 1 | 36.43 | L |
| ATOM | 461 | CA | ARG | L | 61 | −38.495 | −21.126 | 10.797 | 1 | 34.89 | L |
| ATOM | 462 | CB | ARG | L | 61 | −37.461 | −21.917 | 11.606 | 1 | 32.74 | L |
| ATOM | 463 | CG | ARG | L | 61 | −36.073 | −21.325 | 11.651 | 1 | 31.93 | L |
| ATOM | 464 | CD | ARG | L | 61 | −35.364 | −21.796 | 12.909 | 1 | 33.12 | L |
| ATOM | 465 | NE | ARG | L | 61 | −33.928 | −21.579 | 12.843 | 1 | 32.95 | L |
| ATOM | 466 | CZ | ARG | L | 61 | −33.155 | −22.096 | 11.896 | 1 | 36.68 | L |
| ATOM | 467 | NH1 | ARG | L | 61 | −33.696 | −22.852 | 10.949 | 1 | 40.54 | L |
| ATOM | 468 | NH2 | ARG | L | 61 | −31.848 | −21.863 | 11.891 | 1 | 38.42 | L |
| ATOM | 469 | C | ARG | L | 61 | −38.476 | −19.655 | 11.195 | 1 | 34.36 | L |
| ATOM | 470 | O | ARG | L | 61 | −38.859 | −19.291 | 12.312 | 1 | 35.8 | L |
| ATOM | 471 | N | PHE | L | 62 | −38.023 | −18.817 | 10.264 | 1 | 32.14 | L |
| ATOM | 472 | CA | PHE | L | 62 | −37.975 | −17.374 | 10.475 | 1 | 32.9 | L |
| ATOM | 473 | CB | PHE | L | 62 | −36.7 | −16.745 | 9.888 | 1 | 32.92 | L |
| ATOM | 474 | CG | PHE | L | 62 | −35.444 | −17.057 | 10.648 | 1 | 36.82 | L |
| ATOM | 475 | CD1 | PHE | L | 62 | −34.86 | −18.317 | 10.575 | 1 | 37.85 | L |
| ATOM | 476 | CD2 | PHE | L | 62 | −34.833 | −16.081 | 11.428 | 1 | 37.67 | L |
| ATOM | 477 | CE1 | PHE | L | 62 | −33.685 | −18.597 | 11.27 | 1 | 38.25 | L |
| ATOM | 478 | CE2 | PHE | L | 62 | −33.66 | −16.351 | 12.126 | 1 | 36.8 | L |
| ATOM | 479 | CZ | PHE | L | 62 | −33.085 | −17.611 | 12.046 | 1 | 38.55 | L |
| ATOM | 480 | C | PHE | L | 62 | −39.177 | −16.723 | 9.781 | 1 | 32.54 | L |
| ATOM | 481 | O | PHE | L | 62 | −39.28 | −16.723 | 8.55 | 1 | 29.09 | L |
| ATOM | 482 | N | THR | L | 63 | −40.09 | −16.178 | 10.57 | 1 | 30.13 | L |
| ATOM | 483 | CA | THR | L | 63 | −41.233 | −15.503 | 9.993 | 1 | 32.36 | L |
| ATOM | 484 | CB | THR | L | 63 | −42.554 | −16.272 | 10.202 | 1 | 32.47 | L |
| ATOM | 485 | OG1 | THR | L | 63 | −42.751 | −16.513 | 11.6 | 1 | 30.8 | L |
| ATOM | 486 | CG2 | THR | L | 63 | −42.536 | −17.584 | 9.425 | 1 | 30.63 | L |
| ATOM | 487 | C | THR | L | 63 | −41.368 | −14.151 | 10.652 | 1 | 34.24 | L |
| ATOM | 488 | O | THR | L | 63 | −41.119 | −13.993 | 11.853 | 1 | 35.43 | L |
| ATOM | 489 | N | GLY | L | 64 | −41.744 | −13.17 | 9.848 | 1 | 33.55 | L |
| ATOM | 490 | CA | GLY | L | 64 | −41.937 | −11.835 | 10.364 | 1 | 31.62 | L |
| ATOM | 491 | C | GLY | L | 64 | −43.395 | −11.51 | 10.15 | 1 | 27.73 | L |
| ATOM | 492 | O | GLY | L | 64 | −44.073 | −12.167 | 9.364 | 1 | 26.61 | L |
| ATOM | 493 | N | SER | L | 65 | −43.889 | −10.515 | 10.865 | 1 | 25.86 | L |
| ATOM | 494 | CA | SER | L | 65 | −45.275 | −10.118 | 10.719 | 1 | 26.08 | L |
| ATOM | 495 | CB | SER | L | 65 | −46.197 | −11.079 | 11.474 | 1 | 24.82 | L |
| ATOM | 496 | OG | SER | L | 65 | −46.05 | −10.925 | 12.877 | 1 | 28.94 | L |
| ATOM | 497 | C | SER | L | 65 | −45.362 | −8.736 | 11.318 | 1 | 25.33 | L |
| ATOM | 498 | O | SER | L | 65 | −44.575 | −8.391 | 12.198 | 1 | 26.68 | L |
| ATOM | 499 | N | GLY | L | 66 | −46.299 | −7.934 | 10.834 | 1 | 23.56 | L |
| ATOM | 500 | CA | GLY | L | 66 | −46.425 | −6.601 | 11.377 | 1 | 22.21 | L |
| ATOM | 501 | C | GLY | L | 66 | −47.062 | −5.619 | 10.431 | 1 | 20.55 | L |
| ATOM | 502 | O | GLY | L | 66 | −47.261 | −5.902 | 9.251 | 1 | 22.08 | L |
| ATOM | 503 | N | SER | L | 67 | −47.376 | −4.448 | 10.961 | 1 | 20.16 | L |
| ATOM | 504 | CA | SER | L | 67 | −48.007 | −3.411 | 10.176 | 1 | 22.22 | L |
| ATOM | 505 | CB | SER | L | 67 | −49.395 | −3.866 | 9.727 | 1 | 21.86 | L |
| ATOM | 506 | OG | SER | L | 67 | −49.981 | −2.938 | 8.834 | 1 | 24 | L |
| ATOM | 507 | C | SER | L | 67 | −48.132 | −2.178 | 11.042 | 1 | 23.38 | L |
| ATOM | 508 | O | SER | L | 67 | −47.716 | −2.171 | 12.198 | 1 | 24.48 | L |
| ATOM | 509 | N | GLY | L | 68 | −48.717 | −1.134 | 10.475 | 1 | 25.95 | L |
| ATOM | 510 | CA | GLY | L | 68 | −48.883 | 0.091 | 11.217 | 1 | 24.39 | L |
| ATOM | 511 | C | GLY | L | 68 | −47.614 | 0.492 | 11.931 | 1 | 23.89 | L |
| ATOM | 512 | O | GLY | L | 68 | −46.69 | 1.013 | 11.313 | 1 | 25.46 | L |
| ATOM | 513 | N | THR | L | 69 | −47.558 | 0.208 | 13.227 | 1 | 23.66 | L |
| ATOM | 514 | CA | THR | L | 69 | −46.426 | 0.591 | 14.051 | 1 | 24.04 | L |
| ATOM | 515 | CB | THR | L | 69 | −46.909 | 1.585 | 15.112 | 1 | 26.03 | L |
| ATOM | 516 | OG1 | THR | L | 69 | −45.794 | 2.302 | 15.651 | 1 | 34.3 | L |
| ATOM | 517 | CG2 | THR | L | 69 | −47.629 | 0.843 | 16.238 | 1 | 24.28 | L |
| ATOM | 518 | C | THR | L | 69 | −45.695 | −0.565 | 14.754 | 1 | 25.45 | L |
| ATOM | 519 | O | THR | L | 69 | −44.611 | −0.372 | 15.309 | 1 | 23.36 | L |
| ATOM | 520 | N | ASP | L | 70 | −46.281 | −1.76 | 14.729 | 1 | 25.24 | L |
| ATOM | 521 | CA | ASP | L | 70 | −45.686 | −2.915 | 15.396 | 1 | 26.45 | L |
| ATOM | 522 | CB | ASP | L | 70 | −46.654 | −3.473 | 16.439 | 1 | 29.94 | L |
| ATOM | 523 | CG | ASP | L | 70 | −46.812 | −2.565 | 17.634 | 1 | 32.11 | L |
| ATOM | 524 | OD1 | ASP | L | 70 | −46.437 | −1.377 | 17.535 | 1 | 33.82 | L |
| ATOM | 525 | OD2 | ASP | L | 70 | −47.323 | −3.042 | 18.673 | 1 | 34.38 | L |
| ATOM | 526 | C | ASP | L | 70 | −45.295 | −4.034 | 14.447 | 1 | 27.14 | L |

TABLE 7-continued

| | | | | | | | | | | |
|---|---|---|---|---|---|---|---|---|---|---|
| ATOM | 527 | O | ASP | L | 70 | −46.069 | −4.424 | 13.574 | 1 | 27.48 | L |
| ATOM | 528 | N | TYR | L | 71 | −44.091 | −4.562 | 14.648 | 1 | 27.09 | L |
| ATOM | 529 | CA | TYR | L | 71 | −43.56 | −5.636 | 13.82 | 1 | 25.67 | L |
| ATOM | 530 | CB | TYR | L | 71 | −42.584 | −5.041 | 12.789 | 1 | 22.93 | L |
| ATOM | 531 | CG | TYR | L | 71 | −43.252 | −3.965 | 11.963 | 1 | 19.63 | L |
| ATOM | 532 | CD1 | TYR | L | 71 | −43.514 | −2.701 | 12.505 | 1 | 16.75 | L |
| ATOM | 533 | CE1 | TYR | L | 71 | −44.28 | −1.758 | 11.812 | 1 | 16.18 | L |
| ATOM | 534 | CD2 | TYR | L | 71 | −43.758 | −4.253 | 10.696 | 1 | 19.84 | L |
| ATOM | 535 | CE2 | TYR | L | 71 | −44.521 | −3.319 | 9.994 | 1 | 22.27 | L |
| ATOM | 536 | CZ | TYR | L | 71 | −44.783 | −2.075 | 10.562 | 1 | 20.24 | L |
| ATOM | 537 | OH | TYR | L | 71 | −45.583 | −1.18 | 9.884 | 1 | 22.36 | L |
| ATOM | 538 | C | TYR | L | 71 | −42.882 | −6.704 | 14.68 | 1 | 26.55 | L |
| ATOM | 539 | O | TYR | L | 71 | −42.192 | −6.398 | 15.661 | 1 | 26.09 | L |
| ATOM | 540 | N | THR | L | 72 | −43.094 | −7.961 | 14.313 | 1 | 26.01 | L |
| ATOM | 541 | CA | THR | L | 72 | −42.518 | −9.067 | 15.056 | 1 | 27.48 | L |
| ATOM | 542 | CB | THR | L | 72 | −43.602 | −9.87 | 15.804 | 1 | 27.52 | L |
| ATOM | 543 | OG1 | THR | L | 72 | −44.351 | −8.992 | 16.648 | 1 | 30.44 | L |
| ATOM | 544 | CG2 | THR | L | 72 | −42.962 | −10.957 | 16.666 | 1 | 28.87 | L |
| ATOM | 545 | C | THR | L | 72 | −41.752 | −10.035 | 14.169 | 1 | 28.75 | L |
| ATOM | 546 | O | THR | L | 72 | −42.17 | −10.358 | 13.052 | 1 | 29.88 | L |
| ATOM | 547 | N | LEU | L | 73 | −40.616 | −10.483 | 14.685 | 1 | 28.5 | L |
| ATOM | 548 | CA | LEU | L | 73 | −39.772 | −11.443 | 13.999 | 1 | 30.08 | L |
| ATOM | 549 | CB | LEU | L | 73 | −38.326 | −10.93 | 13.925 | 1 | 30.95 | L |
| ATOM | 550 | CG | LEU | L | 73 | −37.209 | −11.719 | 13.22 | 1 | 32.74 | L |
| ATOM | 551 | CD1 | LEU | L | 73 | −36.737 | −12.849 | 14.102 | 1 | 38.04 | L |
| ATOM | 552 | CD2 | LEU | L | 73 | −37.697 | −12.254 | 11.886 | 1 | 32.53 | L |
| ATOM | 553 | C | LEU | L | 73 | −39.871 | −12.675 | 14.884 | 1 | 30.34 | L |
| ATOM | 554 | O | LEU | L | 73 | −39.398 | −12.672 | 16.019 | 1 | 31.95 | L |
| ATOM | 555 | N | THR | L | 74 | −40.532 | −13.711 | 14.384 | 1 | 28.68 | L |
| ATOM | 556 | CA | THR | L | 74 | −40.669 | −14.931 | 15.155 | 1 | 26.67 | L |
| ATOM | 557 | CB | THR | L | 74 | −42.118 | −15.483 | 15.124 | 1 | 27.43 | L |
| ATOM | 558 | OG1 | THR | L | 74 | −43.005 | −14.586 | 15.81 | 1 | 24.66 | L |
| ATOM | 559 | CG2 | THR | L | 74 | −42.17 | −16.854 | 15.793 | 1 | 26 | L |
| ATOM | 560 | C | THR | L | 74 | −39.731 | −15.999 | 14.608 | 1 | 25.39 | L |
| ATOM | 561 | O | THR | L | 74 | −39.604 | −16.177 | 13.396 | 1 | 21.17 | L |
| ATOM | 562 | N | ILE | L | 75 | −39.051 | −16.684 | 15.518 | 1 | 26.91 | L |
| ATOM | 563 | CA | ILE | L | 75 | −38.154 | −17.761 | 15.137 | 1 | 27.42 | L |
| ATOM | 564 | CB | ILE | L | 75 | −36.715 | −17.538 | 15.667 | 1 | 23.84 | L |
| ATOM | 565 | CG2 | ILE | L | 75 | −35.8 | −18.7 | 15.225 | 1 | 24.53 | L |
| ATOM | 566 | CG1 | ILE | L | 75 | −36.164 | −16.209 | 15.145 | 1 | 19.54 | L |
| ATOM | 567 | CD1 | ILE | L | 75 | −34.723 | −15.917 | 15.577 | 1 | 18.05 | L |
| ATOM | 568 | C | ILE | L | 75 | −38.731 | −19.025 | 15.759 | 1 | 29.37 | L |
| ATOM | 569 | O | ILE | L | 75 | −38.614 | −19.244 | 16.963 | 1 | 27.99 | L |
| ATOM | 570 | N | SER | L | 76 | −39.39 | −19.837 | 14.94 | 1 | 32.4 | L |
| ATOM | 571 | CA | SER | L | 76 | −39.972 | −21.085 | 15.422 | 1 | 35.69 | L |
| ATOM | 572 | CB | SER | L | 76 | −40.994 | −21.619 | 14.425 | 1 | 34.27 | L |
| ATOM | 573 | OG | SER | L | 76 | −42.058 | −20.705 | 14.251 | 1 | 41.41 | L |
| ATOM | 574 | C | SER | L | 76 | −38.854 | −22.102 | 15.58 | 1 | 37.52 | L |
| ATOM | 575 | O | SER | L | 76 | −37.901 | −22.108 | 14.795 | 1 | 39.37 | L |
| ATOM | 576 | N | SER | L | 77 | −38.963 | −22.956 | 16.59 | 1 | 37.95 | L |
| ATOM | 577 | CA | SER | L | 77 | −37.944 | −23.971 | 16.817 | 1 | 39.62 | L |
| ATOM | 578 | CB | SER | L | 77 | −38.088 | −25.087 | 15.778 | 1 | 39.48 | L |
| ATOM | 579 | OG | SER | L | 77 | −36.932 | −25.903 | 15.738 | 1 | 43.84 | L |
| ATOM | 580 | C | SER | L | 77 | −36.547 | −23.36 | 16.732 | 1 | 38.3 | L |
| ATOM | 581 | O | SER | L | 77 | −35.786 | −23.654 | 15.814 | 1 | 41.65 | L |
| ATOM | 582 | N | VAL | L | 78 | −36.217 | −22.504 | 17.69 | 1 | 37.08 | L |
| ATOM | 583 | CA | VAL | L | 78 | −34.914 | −21.854 | 17.714 | 1 | 33.69 | L |
| ATOM | 584 | CB | VAL | L | 78 | −34.782 | −20.971 | 18.955 | 1 | 32.5 | L |
| ATOM | 585 | CG1 | VAL | L | 78 | −33.444 | −20.258 | 18.951 | 1 | 32.68 | L |
| ATOM | 586 | CG2 | VAL | L | 78 | −35.917 | −19.967 | 18.984 | 1 | 34.67 | L |
| ATOM | 587 | C | VAL | L | 78 | −33.771 | −22.865 | 17.7 | 1 | 34.31 | L |
| ATOM | 588 | O | VAL | L | 78 | −33.877 | −23.947 | 18.277 | 1 | 35.13 | L |
| ATOM | 589 | N | GLN | L | 79 | −32.681 | −22.506 | 17.027 | 1 | 34.75 | L |
| ATOM | 590 | CA | GLN | L | 79 | −31.503 | −23.361 | 16.933 | 1 | 33.83 | L |
| ATOM | 591 | CB | GLN | L | 79 | −31.245 | −23.758 | 15.48 | 1 | 35.05 | L |
| ATOM | 592 | CG | GLN | L | 79 | −31.467 | −25.229 | 15.195 | 1 | 40.46 | L |
| ATOM | 593 | CD | GLN | L | 79 | −32.895 | −25.669 | 15.454 | 1 | 44.87 | L |
| ATOM | 594 | OE1 | GLN | L | 79 | −33.814 | −25.307 | 14.717 | 1 | 44.9 | L |
| ATOM | 595 | NE2 | GLN | L | 79 | −33.091 | −26.456 | 16.513 | 1 | 46.97 | L |
| ATOM | 596 | C | GLN | L | 79 | −30.283 | −22.64 | 17.486 | 1 | 33.42 | L |
| ATOM | 597 | O | GLN | L | 79 | −30.297 | −21.424 | 17.68 | 1 | 32.99 | L |
| ATOM | 598 | N | ALA | L | 80 | −29.221 | −23.393 | 17.739 | 1 | 33.27 | L |
| ATOM | 599 | CA | ALA | L | 80 | −28.003 | −22.807 | 18.272 | 1 | 31.75 | L |
| ATOM | 600 | CB | ALA | L | 80 | −27.053 | −23.904 | 18.703 | 1 | 32.15 | L |
| ATOM | 601 | C | ALA | L | 80 | −27.336 | −21.896 | 17.243 | 1 | 32.69 | L |
| ATOM | 602 | O | ALA | L | 80 | −26.637 | −20.947 | 17.604 | 1 | 31.8 | L |
| ATOM | 603 | N | GLU | L | 81 | −27.558 | −22.182 | 15.963 | 1 | 32.33 | L |
| ATOM | 604 | CA | GLU | L | 81 | −26.974 | −21.382 | 14.892 | 1 | 32.85 | L |
| ATOM | 605 | CB | GLU | L | 81 | −27.006 | −22.153 | 13.566 | 1 | 36.21 | L |

TABLE 7-continued

| | | | | | | | | | | |
|---|---|---|---|---|---|---|---|---|---|---|
| ATOM | 606 | CG | GLU | L | 81 | −28.411 | −22.437 | 13.046 | 1 | 44.3 | L |
| ATOM | 607 | CD | GLU | L | 81 | −28.438 | −23.334 | 11.81 | 1 | 48.2 | L |
| ATOM | 608 | OE1 | GLU | L | 81 | −27.753 | −23.01 | 10.81 | 1 | 50.13 | L |
| ATOM | 609 | OE2 | GLU | L | 81 | −29.158 | −24.36 | 11.839 | 1 | 49.51 | L |
| ATOM | 610 | C | GLU | L | 81 | −27.73 | −20.069 | 14.741 | 1 | 31.6 | L |
| ATOM | 611 | O | GLU | L | 81 | −27.373 | −19.233 | 13.914 | 1 | 32.12 | L |
| ATOM | 612 | N | ASP | L | 82 | −28.78 | −19.889 | 15.536 | 1 | 29.09 | L |
| ATOM | 613 | CA | ASP | L | 82 | −29.555 | −18.659 | 15.47 | 1 | 29.13 | L |
| ATOM | 614 | CB | ASP | L | 82 | −31.044 | −18.942 | 15.688 | 1 | 28.38 | L |
| ATOM | 615 | CG | ASP | L | 82 | −31.611 | −19.894 | 14.648 | 1 | 31.59 | L |
| ATOM | 616 | OD1 | ASP | L | 82 | −31.344 | −19.691 | 13.439 | 1 | 30.2 | L |
| ATOM | 617 | OD2 | ASP | L | 82 | −32.329 | −20.843 | 15.034 | 1 | 30.04 | L |
| ATOM | 618 | C | ASP | L | 82 | −29.054 | −17.636 | 16.481 | 1 | 28.07 | L |
| ATOM | 619 | O | ASP | L | 82 | −29.578 | −16.525 | 16.562 | 1 | 26.56 | L |
| ATOM | 620 | N | LEU | L | 83 | −28.044 | −18.014 | 17.26 | 1 | 27.17 | L |
| ATOM | 621 | CA | LEU | L | 83 | −27.465 | −17.086 | 18.226 | 1 | 26.08 | L |
| ATOM | 622 | CB | LEU | L | 83 | −26.355 | −17.755 | 19.053 | 1 | 25.04 | L |
| ATOM | 623 | CG | LEU | L | 83 | −26.718 | −18.882 | 20.031 | 1 | 24.92 | L |
| ATOM | 624 | CD1 | LEU | L | 83 | −25.444 | −19.443 | 20.667 | 1 | 20.63 | L |
| ATOM | 625 | CD2 | LEU | L | 83 | −27.666 | −18.361 | 21.094 | 1 | 20.79 | L |
| ATOM | 626 | C | LEU | L | 83 | −26.87 | −15.954 | 17.393 | 1 | 25.94 | L |
| ATOM | 627 | O | LEU | L | 83 | −26.023 | −16.184 | 16.526 | 1 | 24.91 | L |
| ATOM | 628 | N | ALA | L | 84 | −27.325 | −14.735 | 17.648 | 1 | 25.72 | L |
| ATOM | 629 | CA | ALA | L | 84 | −26.845 | −13.586 | 16.903 | 1 | 25.28 | L |
| ATOM | 630 | CB | ALA | L | 84 | −27.113 | −13.796 | 15.417 | 1 | 24.65 | L |
| ATOM | 631 | C | ALA | L | 84 | −27.52 | −12.3 | 17.374 | 1 | 26.49 | L |
| ATOM | 632 | O | ALA | L | 84 | −28.344 | −12.303 | 18.297 | 1 | 23.91 | L |
| ATOM | 633 | N | LEU | L | 85 | −27.149 | −11.198 | 16.733 | 1 | 24.66 | L |
| ATOM | 634 | CA | LEU | L | 85 | −27.718 | −9.902 | 17.042 | 1 | 23 | L |
| ATOM | 635 | CB | LEU | L | 85 | −26.618 | −8.846 | 17.01 | 1 | 22.46 | L |
| ATOM | 636 | CG | LEU | L | 85 | −26.858 | −7.554 | 17.791 | 1 | 26.05 | L |
| ATOM | 637 | CD1 | LEU | L | 85 | −27.387 | −7.838 | 19.199 | 1 | 23.12 | L |
| ATOM | 638 | CD2 | LEU | L | 85 | −25.543 | −6.8 | 17.854 | 1 | 26.91 | L |
| ATOM | 639 | C | LEU | L | 85 | −28.761 | −9.657 | 15.948 | 1 | 23.66 | L |
| ATOM | 640 | O | LEU | L | 85 | −28.496 | −9.895 | 14.769 | 1 | 22.22 | L |
| ATOM | 641 | N | TYR | L | 86 | −29.954 | −9.217 | 16.341 | 1 | 23.7 | L |
| ATOM | 642 | CA | TYR | L | 86 | −31.028 | −8.977 | 15.385 | 1 | 22.23 | L |
| ATOM | 643 | CB | TYR | L | 86 | −32.208 | −9.912 | 15.669 | 1 | 20.35 | L |
| ATOM | 644 | CG | TYR | L | 86 | −31.893 | −11.382 | 15.457 | 1 | 21.38 | L |
| ATOM | 645 | CD1 | TYR | L | 86 | −31.326 | −12.154 | 16.471 | 1 | 20.46 | L |
| ATOM | 646 | CE1 | TYR | L | 86 | −30.983 | −13.49 | 16.259 | 1 | 16.21 | L |
| ATOM | 647 | CD2 | TYR | L | 86 | −32.114 | −11.987 | 14.22 | 1 | 21.25 | L |
| ATOM | 648 | CE2 | TYR | L | 86 | −31.772 | −13.317 | 13.995 | 1 | 21.34 | L |
| ATOM | 649 | CZ | TYR | L | 86 | −31.205 | −14.061 | 15.019 | 1 | 19.18 | L |
| ATOM | 650 | OH | TYR | L | 86 | −30.839 | −15.365 | 14.781 | 1 | 20.03 | L |
| ATOM | 651 | C | TYR | L | 86 | −31.511 | −7.532 | 15.385 | 1 | 24.29 | L |
| ATOM | 652 | O | TYR | L | 86 | −31.887 | −6.983 | 16.428 | 1 | 24.91 | L |
| ATOM | 653 | N | TYR | L | 87 | −31.489 | −6.911 | 14.21 | 1 | 21.91 | L |
| ATOM | 654 | CA | TYR | L | 87 | −31.937 | −5.537 | 14.093 | 1 | 22.37 | L |
| ATOM | 655 | CB | TYR | L | 87 | −30.843 | −4.616 | 13.553 | 1 | 23.27 | L |
| ATOM | 656 | CG | TYR | L | 87 | −29.551 | −4.574 | 14.319 | 1 | 28.68 | L |
| ATOM | 657 | CD1 | TYR | L | 87 | −28.578 | −5.553 | 14.129 | 1 | 28.71 | L |
| ATOM | 658 | CE1 | TYR | L | 87 | −27.352 | −5.479 | 14.779 | 1 | 33.56 | L |
| ATOM | 659 | CD2 | TYR | L | 87 | −29.269 | −3.518 | 15.188 | 1 | 29.31 | L |
| ATOM | 660 | CE2 | TYR | L | 87 | −28.043 | −3.432 | 15.843 | 1 | 31.52 | L |
| ATOM | 661 | CZ | TYR | L | 87 | −27.086 | −4.415 | 15.634 | 1 | 33.34 | L |
| ATOM | 662 | OH | TYR | L | 87 | −25.855 | −4.336 | 16.26 | 1 | 35.51 | L |
| ATOM | 663 | C | TYR | L | 87 | −33.096 | −5.434 | 13.126 | 1 | 24 | L |
| ATOM | 664 | O | TYR | L | 87 | −33.215 | −6.214 | 12.178 | 1 | 20.82 | L |
| ATOM | 665 | N | CYS | L | 88 | −33.954 | −4.458 | 13.379 | 1 | 23.57 | L |
| ATOM | 666 | CA | CYS | L | 88 | −35.062 | −4.194 | 12.496 | 1 | 25.15 | L |
| ATOM | 667 | C | CYS | L | 88 | −34.712 | −2.841 | 11.912 | 1 | 23.75 | L |
| ATOM | 668 | O | CYS | L | 88 | −33.978 | −2.062 | 12.521 | 1 | 23.73 | L |
| ATOM | 669 | CB | CYS | L | 88 | −36.389 | −4.149 | 13.258 | 1 | 26.56 | L |
| ATOM | 670 | SG | CYS | L | 88 | −36.559 | −2.976 | 14.646 | 1 | 31.43 | L |
| ATOM | 671 | N | GLN | L | 89 | −35.219 | −2.565 | 10.724 | 1 | 24.24 | L |
| ATOM | 672 | CA | GLN | L | 89 | −34.931 | −1.307 | 10.062 | 1 | 22.23 | L |
| ATOM | 673 | CB | GLN | L | 89 | −33.747 | −1.492 | 9.111 | 1 | 19.89 | L |
| ATOM | 674 | CG | GLN | L | 89 | −33.406 | −0.283 | 8.27 | 1 | 21.51 | L |
| ATOM | 675 | CD | GLN | L | 89 | −33.483 | −0.584 | 6.782 | 1 | 21.16 | L |
| ATOM | 676 | OE1 | GLN | L | 89 | −32.872 | −1.539 | 6.3 | 1 | 22.19 | L |
| ATOM | 677 | NE2 | GLN | L | 89 | −34.231 | 0.231 | 6.049 | 1 | 17.88 | L |
| ATOM | 678 | C | GLN | L | 89 | −36.161 | −0.907 | 9.287 | 1 | 21.86 | L |
| ATOM | 679 | O | GLN | L | 89 | −36.757 | −1.741 | 8.604 | 1 | 23.52 | L |
| ATOM | 680 | N | GLN | L | 90 | −36.566 | 0.352 | 9.396 | 1 | 19.94 | L |
| ATOM | 681 | CA | GLN | L | 90 | −37.732 | 0.773 | 8.641 | 1 | 20.67 | L |
| ATOM | 682 | CB | GLN | L | 90 | −38.545 | 1.836 | 9.406 | 1 | 19.9 | L |
| ATOM | 683 | CG | GLN | L | 90 | −37.805 | 3.097 | 9.807 | 1 | 20.58 | L |
| ATOM | 684 | CD | GLN | L | 90 | −37.73 | 4.137 | 8.698 | 1 | 24.36 | L |

TABLE 7-continued

| ATOM | 685 | OE1 | GLN | L | 90 | −38.593 | 4.189 | 7.808 | 1 | 19.07 | L |
| ATOM | 686 | NE2 | GLN | L | 90 | −36.702 | 4.994 | 8.762 | 1 | 20.34 | L |
| ATOM | 687 | C | GLN | L | 90 | −37.268 | 1.305 | 7.304 | 1 | 19.46 | L |
| ATOM | 688 | O | GLN | L | 90 | −36.249 | 1.991 | 7.223 | 1 | 16.88 | L |
| ATOM | 689 | N | HIS | L | 91 | −37.984 | 0.939 | 6.248 | 1 | 18.39 | L |
| ATOM | 690 | CA | HIS | L | 91 | −37.648 | 1.428 | 4.921 | 1 | 22.42 | L |
| ATOM | 691 | CB | HIS | L | 91 | −37.153 | 0.285 | 3.993 | 1 | 23.41 | L |
| ATOM | 692 | CG | HIS | L | 91 | −37.957 | −0.985 | 4.048 | 1 | 24.78 | L |
| ATOM | 693 | CD2 | HIS | L | 91 | −37.791 | −2.111 | 4.788 | 1 | 20.04 | L |
| ATOM | 694 | ND1 | HIS | L | 91 | −39.017 | −1.24 | 3.2 | 1 | 23.86 | L |
| ATOM | 695 | CE1 | HIS | L | 91 | −39.463 | −2.468 | 3.411 | 1 | 21.59 | L |
| ATOM | 696 | NE2 | HIS | L | 91 | −38.736 | −3.017 | 4.369 | 1 | 17.36 | L |
| ATOM | 697 | C | HIS | L | 91 | −38.842 | 2.186 | 4.341 | 1 | 21.15 | L |
| ATOM | 698 | O | HIS | L | 91 | −39.143 | 2.117 | 3.151 | 1 | 21.21 | L |
| ATOM | 699 | N | TYR | L | 92 | −39.489 | 2.944 | 5.225 | 1 | 19.56 | L |
| ATOM | 700 | CA | TYR | L | 92 | −40.666 | 3.748 | 4.908 | 1 | 19.53 | L |
| ATOM | 701 | CB | TYR | L | 92 | −41.53 | 3.905 | 6.168 | 1 | 21.02 | L |
| ATOM | 702 | CG | TYR | L | 92 | −42.787 | 4.731 | 6.001 | 1 | 18.63 | L |
| ATOM | 703 | CD1 | TYR | L | 92 | −43.81 | 4.316 | 5.138 | 1 | 21.58 | L |
| ATOM | 704 | CE1 | TYR | L | 92 | −44.983 | 5.062 | 4.989 | 1 | 21.19 | L |
| ATOM | 705 | CD2 | TYR | L | 92 | −42.965 | 5.92 | 6.714 | 1 | 18.34 | L |
| ATOM | 706 | CE2 | TYR | L | 92 | −44.137 | 6.681 | 6.575 | 1 | 19.57 | L |
| ATOM | 707 | CZ | TYR | L | 92 | −45.136 | 6.242 | 5.708 | 1 | 23.05 | L |
| ATOM | 708 | OH | TYR | L | 92 | −46.273 | 6.985 | 5.531 | 1 | 24.67 | L |
| ATOM | 709 | C | TYR | L | 92 | −40.27 | 5.124 | 4.396 | 1 | 19.03 | L |
| ATOM | 710 | O | TYR | L | 92 | −40.909 | 5.681 | 3.503 | 1 | 18.47 | L |
| ATOM | 711 | N | THR | L | 93 | −39.214 | 5.68 | 4.967 | 1 | 19.88 | L |
| ATOM | 712 | CA | THR | L | 93 | −38.775 | 6.996 | 4.541 | 1 | 20.71 | L |
| ATOM | 713 | CB | THR | L | 93 | −39.764 | 8.069 | 5.016 | 1 | 20.02 | L |
| ATOM | 714 | OG1 | THR | L | 93 | −39.56 | 9.272 | 4.262 | 1 | 22.94 | L |
| ATOM | 715 | CG2 | THR | L | 93 | −39.574 | 8.344 | 6.507 | 1 | 12.63 | L |
| ATOM | 716 | C | THR | L | 93 | −37.389 | 7.331 | 5.074 | 1 | 22.15 | L |
| ATOM | 717 | O | THR | L | 93 | −36.919 | 6.727 | 6.038 | 1 | 25 | L |
| ATOM | 718 | N | THR | L | 94 | −36.73 | 8.291 | 4.44 | 1 | 21.44 | L |
| ATOM | 719 | CA | THR | L | 94 | −35.408 | 8.68 | 4.889 | 1 | 23.37 | L |
| ATOM | 720 | CB | THR | L | 94 | −34.56 | 9.259 | 3.731 | 1 | 21.39 | L |
| ATOM | 721 | OG1 | THR | L | 94 | −35.141 | 10.479 | 3.267 | 1 | 21.96 | L |
| ATOM | 722 | CG2 | THR | L | 94 | −34.492 | 8.267 | 2.584 | 1 | 21.61 | L |
| ATOM | 723 | C | THR | L | 94 | −35.566 | 9.724 | 5.99 | 1 | 22.48 | L |
| ATOM | 724 | O | THR | L | 94 | −36.519 | 10.5 | 5.988 | 1 | 24.55 | L |
| ATOM | 725 | N | PRO | L | 95 | −34.64 | 9.741 | 6.953 | 1 | 20.82 | L |
| ATOM | 726 | CD | PRO | L | 95 | −34.57 | 10.684 | 8.084 | 1 | 19.76 | L |
| ATOM | 727 | CA | PRO | L | 95 | −33.509 | 8.813 | 6.98 | 1 | 22.19 | L |
| ATOM | 728 | CB | PRO | L | 95 | −32.566 | 9.466 | 7.984 | 1 | 20.89 | L |
| ATOM | 729 | CG | PRO | L | 95 | −33.531 | 10.035 | 8.981 | 1 | 22.02 | L |
| ATOM | 730 | C | PRO | L | 95 | −33.91 | 7.405 | 7.412 | 1 | 21.88 | L |
| ATOM | 731 | O | PRO | L | 95 | −34.825 | 7.23 | 8.215 | 1 | 25.53 | L |
| ATOM | 732 | N | LEU | L | 96 | −33.223 | 6.406 | 6.874 | 1 | 19.75 | L |
| ATOM | 733 | CA | LEU | L | 96 | −33.485 | 5.025 | 7.242 | 1 | 19.84 | L |
| ATOM | 734 | CB | LEU | L | 96 | −32.757 | 4.074 | 6.291 | 1 | 17.28 | L |
| ATOM | 735 | CG | LEU | L | 96 | −33.179 | 4.145 | 4.826 | 1 | 15.85 | L |
| ATOM | 736 | CD1 | LEU | L | 96 | −32.438 | 3.078 | 4.015 | 1 | 11.63 | L |
| ATOM | 737 | CD2 | LEU | L | 96 | −34.688 | 3.951 | 4.739 | 1 | 15.01 | L |
| ATOM | 738 | C | LEU | L | 96 | −32.969 | 4.821 | 8.665 | 1 | 21.55 | L |
| ATOM | 739 | O | LEU | L | 96 | −31.857 | 5.244 | 8.992 | 1 | 22.96 | L |
| ATOM | 740 | N | THR | L | 97 | −33.764 | 4.164 | 9.504 | 1 | 22.43 | L |
| ATOM | 741 | CA | THR | L | 97 | −33.372 | 3.94 | 10.895 | 1 | 21.97 | L |
| ATOM | 742 | CB | THR | L | 97 | −34.191 | 4.836 | 11.815 | 1 | 18.78 | L |
| ATOM | 743 | OG1 | THR | L | 97 | −35.572 | 4.781 | 11.43 | 1 | 17.77 | L |
| ATOM | 744 | CG2 | THR | L | 97 | −33.695 | 6.262 | 11.718 | 1 | 16.65 | L |
| ATOM | 745 | C | THR | L | 97 | −33.47 | 2.496 | 11.39 | 1 | 22.79 | L |
| ATOM | 746 | O | THR | L | 97 | −34.374 | 1.754 | 11.016 | 1 | 25.6 | L |
| ATOM | 747 | N | PHE | L | 98 | −32.528 | 2.109 | 12.243 | 1 | 24.33 | L |
| ATOM | 748 | CA | PHE | L | 98 | −32.492 | 0.754 | 12.786 | 1 | 25.34 | L |
| ATOM | 749 | CB | PHE | L | 98 | −31.098 | 0.136 | 12.614 | 1 | 24.41 | L |
| ATOM | 750 | CG | PHE | L | 98 | −30.609 | 0.111 | 11.207 | 1 | 24.08 | L |
| ATOM | 751 | CD1 | PHE | L | 98 | −30.178 | 1.276 | 10.585 | 1 | 23.59 | L |
| ATOM | 752 | CD2 | PHE | L | 98 | −30.58 | −1.084 | 10.493 | 1 | 24.56 | L |
| ATOM | 753 | CE1 | PHE | L | 98 | −29.726 | 1.248 | 9.27 | 1 | 23.14 | L |
| ATOM | 754 | CE2 | PHE | L | 98 | −30.129 | −1.119 | 9.175 | 1 | 23.11 | L |
| ATOM | 755 | CZ | PHE | L | 98 | −29.703 | 0.046 | 8.565 | 1 | 19.74 | L |
| ATOM | 756 | C | PHE | L | 98 | −32.819 | 0.701 | 14.267 | 1 | 27.37 | L |
| ATOM | 757 | O | PHE | L | 98 | −32.667 | 1.689 | 14.988 | 1 | 26.55 | L |
| ATOM | 758 | N | GLY | L | 99 | −33.262 | −0.467 | 14.718 | 1 | 28.26 | L |
| ATOM | 759 | CA | GLY | L | 99 | −33.537 | −0.643 | 16.128 | 1 | 29.27 | L |
| ATOM | 760 | C | GLY | L | 99 | −32.179 | −0.92 | 16.76 | 1 | 29.59 | L |
| ATOM | 761 | O | GLY | L | 99 | −31.223 | −1.247 | 16.051 | 1 | 29.47 | L |
| ATOM | 762 | N | ALA | L | 100 | −32.084 | −0.801 | 18.08 | 1 | 29.37 | L |
| ATOM | 763 | CA | ALA | L | 100 | −30.824 | −1.029 | 18.778 | 1 | 29.08 | L |

TABLE 7-continued

| | | | | | | | | | | |
|---|---|---|---|---|---|---|---|---|---|---|
| ATOM | 764 | CB | ALA | L | 100 | −30.967 | −0.623 | 20.241 | 1 | 29.66 | L |
| ATOM | 765 | C | ALA | L | 100 | −30.347 | −2.475 | 18.677 | 1 | 29.38 | L |
| ATOM | 766 | O | ALA | L | 100 | −29.187 | −2.779 | 18.954 | 1 | 30.49 | L |
| ATOM | 767 | N | GLY | L | 101 | −31.244 | −3.367 | 18.284 | 1 | 29.12 | L |
| ATOM | 768 | CA | GLY | L | 101 | −30.871 | −4.762 | 18.154 | 1 | 29.81 | L |
| ATOM | 769 | C | GLY | L | 101 | −31.219 | −5.594 | 19.375 | 1 | 29.76 | L |
| ATOM | 770 | O | GLY | L | 101 | −31.258 | −5.091 | 20.497 | 1 | 29.97 | L |
| ATOM | 771 | N | THR | L | 102 | −31.491 | −6.872 | 19.144 | 1 | 29.24 | L |
| ATOM | 772 | CA | THR | L | 102 | −31.817 | −7.8 | 20.215 | 1 | 29.33 | L |
| ATOM | 773 | CB | THR | L | 102 | −33.287 | −8.287 | 20.116 | 1 | 28.76 | L |
| ATOM | 774 | OG1 | THR | L | 102 | −34.174 | −7.194 | 20.398 | 1 | 29.56 | L |
| ATOM | 775 | CG2 | THR | L | 102 | −33.554 | −9.403 | 21.112 | 1 | 29.19 | L |
| ATOM | 776 | C | THR | L | 102 | −30.86 | −8.99 | 20.117 | 1 | 29.39 | L |
| ATOM | 777 | O | THR | L | 102 | −30.742 | −9.627 | 19.068 | 1 | 27.17 | L |
| ATOM | 778 | N | LYS | L | 103 | −30.16 | −9.266 | 21.21 | 1 | 29.91 | L |
| ATOM | 779 | CA | LYS | L | 103 | −29.212 | −10.365 | 21.243 | 1 | 33.61 | L |
| ATOM | 780 | CB | LYS | L | 103 | −28.046 | −10.015 | 22.172 | 1 | 33.62 | L |
| ATOM | 781 | CG | LYS | L | 103 | −26.929 | −11.053 | 22.205 | 1 | 36.67 | L |
| ATOM | 782 | CD | LYS | L | 103 | −25.893 | −10.716 | 23.282 | 1 | 38.03 | L |
| ATOM | 783 | CE | LYS | L | 103 | −24.961 | −11.895 | 23.533 | 1 | 41.32 | L |
| ATOM | 784 | NZ | LYS | L | 103 | −24.031 | −11.696 | 24.697 | 1 | 44.17 | L |
| ATOM | 785 | C | LYS | L | 103 | −29.904 | −11.651 | 21.709 | 1 | 34.54 | L |
| ATOM | 786 | O | LYS | L | 103 | −30.346 | −11.754 | 22.854 | 1 | 36.77 | L |
| ATOM | 787 | N | LEU | L | 104 | −30.011 | −12.62 | 20.805 | 1 | 34 | L |
| ATOM | 788 | CA | LEU | L | 104 | −30.639 | −13.888 | 21.129 | 1 | 32.56 | L |
| ATOM | 789 | CB | LEU | L | 104 | −31.074 | −14.624 | 19.861 | 1 | 33.44 | L |
| ATOM | 790 | CG | LEU | L | 104 | −31.886 | −15.91 | 20.066 | 1 | 32.97 | L |
| ATOM | 791 | CD1 | LEU | L | 104 | −32.632 | −16.262 | 18.783 | 1 | 36.14 | L |
| ATOM | 792 | CD2 | LEU | L | 104 | −30.975 | −17.047 | 20.484 | 1 | 32.63 | L |
| ATOM | 793 | C | LEU | L | 104 | −29.655 | −14.742 | 21.902 | 1 | 32.52 | L |
| ATOM | 794 | O | LEU | L | 104 | −28.535 | −14.985 | 21.456 | 1 | 27.38 | L |
| ATOM | 795 | N | GLU | L | 105 | −30.095 | −15.187 | 23.071 | 1 | 33.48 | L |
| ATOM | 796 | CA | GLU | L | 105 | −29.289 | −16.012 | 23.946 | 1 | 31.91 | L |
| ATOM | 797 | CB | GLU | L | 105 | −28.951 | −15.226 | 25.194 | 1 | 33.27 | L |
| ATOM | 798 | CG | GLU | L | 105 | −28.427 | −13.85 | 24.876 | 1 | 35.49 | L |
| ATOM | 799 | CD | GLU | L | 105 | −28.069 | −13.085 | 26.118 | 1 | 37.33 | L |
| ATOM | 800 | OE1 | GLU | L | 105 | −28.985 | −12.763 | 26.907 | 1 | 36.87 | L |
| ATOM | 801 | OE2 | GLU | L | 105 | −26.865 | −12.818 | 26.306 | 1 | 39.96 | L |
| ATOM | 802 | C | GLU | L | 105 | −30.112 | −17.231 | 24.298 | 1 | 30.52 | L |
| ATOM | 803 | O | GLU | L | 105 | −31.333 | −17.19 | 24.253 | 1 | 31.61 | L |
| ATOM | 804 | N | LEU | L | 106 | −29.443 | −18.316 | 24.654 | 1 | 30.57 | L |
| ATOM | 805 | CA | LEU | L | 106 | −30.134 | −19.546 | 24.984 | 1 | 29.34 | L |
| ATOM | 806 | CB | LEU | L | 106 | −29.666 | −20.666 | 24.057 | 1 | 28.9 | L |
| ATOM | 807 | CG | LEU | L | 106 | −29.949 | −20.475 | 22.567 | 1 | 28.82 | L |
| ATOM | 808 | CD1 | LEU | L | 106 | −29.112 | −21.461 | 21.758 | 1 | 26.11 | L |
| ATOM | 809 | CD2 | LEU | L | 106 | −31.437 | −20.66 | 22.303 | 1 | 26.85 | L |
| ATOM | 810 | C | LEU | L | 106 | −29.979 | −20.004 | 26.418 | 1 | 30.22 | L |
| ATOM | 811 | O | LEU | L | 106 | −28.968 | −19.761 | 27.073 | 1 | 29.39 | L |
| ATOM | 812 | N | LYS | L | 107 | −31.018 | −20.672 | 26.894 | 1 | 33.45 | L |
| ATOM | 813 | CA | LYS | L | 107 | −31.042 | −21.234 | 28.226 | 1 | 33.81 | L |
| ATOM | 814 | CB | LYS | L | 107 | −32.449 | −21.141 | 28.814 | 1 | 33.84 | L |
| ATOM | 815 | CG | LYS | L | 107 | −32.842 | −19.75 | 29.232 | 1 | 37.64 | L |
| ATOM | 816 | CD | LYS | L | 107 | −31.984 | −19.28 | 30.4 | 1 | 45.3 | L |
| ATOM | 817 | CE | LYS | L | 107 | −32.175 | −20.179 | 31.63 | 1 | 49.65 | L |
| ATOM | 818 | NZ | LYS | L | 107 | −31.369 | −19.742 | 32.81 | 1 | 51.56 | L |
| ATOM | 819 | C | LYS | L | 107 | −30.672 | −22.694 | 28.031 | 1 | 35.03 | L |
| ATOM | 820 | O | LYS | L | 107 | −31.213 | −23.357 | 27.143 | 1 | 35.03 | L |
| ATOM | 821 | N | ARG | L | 108 | −29.737 | −23.185 | 28.838 | 1 | 33.52 | L |
| ATOM | 822 | CA | ARG | L | 108 | −29.327 | −24.579 | 28.76 | 1 | 31.49 | L |
| ATOM | 823 | CB | ARG | L | 108 | −28.151 | −24.741 | 27.791 | 1 | 31.04 | L |
| ATOM | 824 | CG | ARG | L | 108 | −26.917 | −23.91 | 28.111 | 1 | 32.01 | L |
| ATOM | 825 | CD | ARG | L | 108 | −25.676 | −24.664 | 27.669 | 1 | 30.51 | L |
| ATOM | 826 | NE | ARG | L | 108 | −25.535 | −25.897 | 28.441 | 1 | 34.19 | L |
| ATOM | 827 | CZ | ARG | L | 108 | −24.851 | −26.966 | 28.046 | 1 | 34.38 | L |
| ATOM | 828 | NH1 | ARG | L | 108 | −24.233 | −26.97 | 26.872 | 1 | 36.37 | L |
| ATOM | 829 | NH2 | ARG | L | 108 | −24.781 | −28.032 | 28.834 | 1 | 35.47 | L |
| ATOM | 830 | C | ARG | L | 108 | −28.959 | −25.113 | 30.146 | 1 | 31.09 | L |
| ATOM | 831 | O | ARG | L | 108 | −29.008 | −24.384 | 31.139 | 1 | 32.47 | L |
| ATOM | 832 | N | ALA | L | 109 | −28.613 | −26.391 | 30.219 | 1 | 29.57 | L |
| ATOM | 833 | CA | ALA | L | 109 | −28.247 | −26.992 | 31.495 | 1 | 28.76 | L |
| ATOM | 834 | CB | ALA | L | 109 | −28.254 | −28.516 | 31.384 | 1 | 28.18 | L |
| ATOM | 835 | C | ALA | L | 109 | −26.866 | −26.506 | 31.902 | 1 | 28.65 | L |
| ATOM | 836 | O | ALA | L | 109 | −26.028 | −26.21 | 31.048 | 1 | 28.71 | L |
| ATOM | 837 | N | ASP | L | 110 | −26.631 | −26.418 | 33.207 | 1 | 27.68 | L |
| ATOM | 838 | CA | ASP | L | 110 | −25.337 | −25.98 | 33.697 | 1 | 26.42 | L |
| ATOM | 839 | CB | ASP | L | 110 | −25.295 | −26.021 | 35.219 | 1 | 26.12 | L |
| ATOM | 840 | CG | ASP | L | 110 | −26.256 | −25.055 | 35.843 | 1 | 26.37 | L |
| ATOM | 841 | OD1 | ASP | L | 110 | −26.691 | −24.127 | 35.129 | 1 | 22.25 | L |
| ATOM | 842 | OD2 | ASP | L | 110 | −26.568 | −25.216 | 37.044 | 1 | 29.32 | L |

TABLE 7-continued

| | | | | | | | | | | |
|---|---|---|---|---|---|---|---|---|---|---|
| ATOM | 843 | C | ASP | L | 110 | −24.265 | −26.893 | 33.144 | 1 | 25.99 | L |
| ATOM | 844 | O | ASP | L | 110 | −24.548 | −28.024 | 32.758 | 1 | 25.07 | L |
| ATOM | 845 | N | ALA | L | 111 | −23.036 | −26.395 | 33.106 | 1 | 24.91 | L |
| ATOM | 846 | CA | ALA | L | 111 | −21.914 | −27.175 | 32.609 | 1 | 24.41 | L |
| ATOM | 847 | CB | ALA | L | 111 | −21.857 | −27.115 | 31.093 | 1 | 21.51 | L |
| ATOM | 848 | C | ALA | L | 111 | −20.644 | −26.605 | 33.206 | 1 | 24.54 | L |
| ATOM | 849 | O | ALA | L | 111 | −20.408 | −25.398 | 33.146 | 1 | 24.68 | L |
| ATOM | 850 | N | ALA | L | 112 | −19.833 | −27.482 | 33.788 | 1 | 26.58 | L |
| ATOM | 851 | CA | ALA | L | 112 | −18.574 | −27.085 | 34.415 | 1 | 28.57 | L |
| ATOM | 852 | CB | ALA | L | 112 | −18.067 | −28.207 | 35.325 | 1 | 27.25 | L |
| ATOM | 853 | C | ALA | L | 112 | −17.51 | −26.737 | 33.379 | 1 | 27.17 | L |
| ATOM | 854 | O | ALA | L | 112 | −17.285 | −27.485 | 32.43 | 1 | 28.07 | L |
| ATOM | 855 | N | PRO | L | 113 | −16.83 | −25.599 | 33.561 | 1 | 24.92 | L |
| ATOM | 856 | CD | PRO | L | 113 | −16.9 | −24.689 | 34.719 | 1 | 26.19 | L |
| ATOM | 857 | CA | PRO | L | 113 | −15.788 | −25.168 | 32.63 | 1 | 24.99 | L |
| ATOM | 858 | CB | PRO | L | 113 | −15.409 | −23.789 | 33.155 | 1 | 23.49 | L |
| ATOM | 859 | CG | PRO | L | 113 | −15.571 | −23.953 | 34.625 | 1 | 22.47 | L |
| ATOM | 860 | C | PRO | L | 113 | −14.588 | −26.092 | 32.59 | 1 | 24.43 | L |
| ATOM | 861 | O | PRO | L | 113 | −14.271 | −26.761 | 33.564 | 1 | 26.16 | L |
| ATOM | 862 | N | THR | L | 114 | −13.932 | −26.138 | 31.443 | 1 | 24.86 | L |
| ATOM | 863 | CA | THR | L | 114 | −12.733 | −26.934 | 31.301 | 1 | 25.05 | L |
| ATOM | 864 | CB | THR | L | 114 | −12.706 | −27.712 | 29.972 | 1 | 27.63 | L |
| ATOM | 865 | OG1 | THR | L | 114 | −13.745 | −28.702 | 29.976 | 1 | 32.5 | L |
| ATOM | 866 | CG2 | THR | L | 114 | −11.363 | −28.411 | 29.792 | 1 | 28.26 | L |
| ATOM | 867 | C | THR | L | 114 | −11.648 | −25.869 | 31.322 | 1 | 23.47 | L |
| ATOM | 868 | O | THR | L | 114 | −11.55 | −25.048 | 30.411 | 1 | 27.13 | L |
| ATOM | 869 | N | VAL | L | 115 | −10.86 | −25.876 | 32.387 | 1 | 19.01 | L |
| ATOM | 870 | CA | VAL | L | 115 | −9.805 | −24.905 | 32.586 | 1 | 16.43 | L |
| ATOM | 871 | CB | VAL | L | 115 | −9.637 | −24.628 | 34.085 | 1 | 15.97 | L |
| ATOM | 872 | CG1 | VAL | L | 115 | −8.551 | −23.585 | 34.311 | 1 | 10.09 | L |
| ATOM | 873 | CG2 | VAL | L | 115 | −10.983 | −24.208 | 34.681 | 1 | 10.52 | L |
| ATOM | 874 | C | VAL | L | 115 | −8.458 | −25.322 | 32.014 | 1 | 19.89 | L |
| ATOM | 875 | O | VAL | L | 115 | −7.977 | −26.423 | 32.265 | 1 | 21.12 | L |
| ATOM | 876 | N | SER | L | 116 | −7.849 | −24.423 | 31.251 | 1 | 21.56 | L |
| ATOM | 877 | CA | SER | L | 116 | −6.55 | −24.674 | 30.653 | 1 | 23.75 | L |
| ATOM | 878 | CB | SER | L | 116 | −6.656 | −24.72 | 29.126 | 1 | 24.69 | L |
| ATOM | 879 | OG | SER | L | 116 | −7.572 | −25.708 | 28.697 | 1 | 27.61 | L |
| ATOM | 880 | C | SER | L | 116 | −5.647 | −23.519 | 31.05 | 1 | 24.78 | L |
| ATOM | 881 | O | SER | L | 116 | −6.069 | −22.365 | 31.026 | 1 | 25.92 | L |
| ATOM | 882 | N | ILE | L | 117 | −4.406 | −23.819 | 31.413 | 1 | 25.28 | L |
| ATOM | 883 | CA | ILE | L | 117 | −3.482 | −22.759 | 31.797 | 1 | 23.6 | L |
| ATOM | 884 | CB | ILE | L | 117 | −3.084 | −22.875 | 33.284 | 1 | 23.08 | L |
| ATOM | 885 | CG2 | ILE | L | 117 | −2.101 | −24.022 | 33.479 | 1 | 17.48 | L |
| ATOM | 886 | CG1 | ILE | L | 117 | −2.522 | −21.532 | 33.762 | 1 | 23.72 | L |
| ATOM | 887 | CD1 | ILE | L | 117 | −2.149 | −21.5 | 35.228 | 1 | 22.35 | L |
| ATOM | 888 | C | ILE | L | 117 | −2.252 | −22.825 | 30.904 | 1 | 20.29 | L |
| ATOM | 889 | O | ILE | L | 117 | −1.785 | −23.899 | 30.56 | 1 | 20.43 | L |
| ATOM | 890 | N | PHE | L | 118 | −1.737 | −21.664 | 30.53 | 1 | 20.61 | L |
| ATOM | 891 | CA | PHE | L | 118 | −0.598 | −21.589 | 29.633 | 1 | 21.15 | L |
| ATOM | 892 | CB | PHE | L | 118 | −1.065 | −21.101 | 28.268 | 1 | 18.27 | L |
| ATOM | 893 | CG | PHE | L | 118 | −2.134 | −21.947 | 27.671 | 1 | 19.43 | L |
| ATOM | 894 | CD1 | PHE | L | 118 | −1.809 | −23.074 | 26.93 | 1 | 17.8 | L |
| ATOM | 895 | CD2 | PHE | L | 118 | −3.472 | −21.642 | 27.884 | 1 | 19.5 | L |
| ATOM | 896 | CE1 | PHE | L | 118 | −2.791 | −23.883 | 26.411 | 1 | 18.23 | L |
| ATOM | 897 | CE2 | PHE | L | 118 | −4.465 | −22.444 | 27.371 | 1 | 21.64 | L |
| ATOM | 898 | CZ | PHE | L | 118 | −4.128 | −23.571 | 26.628 | 1 | 21.36 | L |
| ATOM | 899 | C | PHE | L | 118 | 0.499 | −20.669 | 30.106 | 1 | 21.75 | L |
| ATOM | 900 | O | PHE | L | 118 | 0.237 | −19.567 | 30.584 | 1 | 23.16 | L |
| ATOM | 901 | N | PRO | L | 119 | 1.753 | −21.112 | 29.975 | 1 | 22.12 | L |
| ATOM | 902 | CD | PRO | L | 119 | 2.198 | −22.482 | 29.669 | 1 | 21.31 | L |
| ATOM | 903 | CA | PRO | L | 119 | 2.885 | −20.288 | 30.391 | 1 | 23.47 | L |
| ATOM | 904 | CB | PRO | L | 119 | 3.998 | −21.313 | 30.587 | 1 | 24.07 | L |
| ATOM | 905 | CG | PRO | L | 119 | 3.701 | −22.301 | 29.525 | 1 | 22.51 | L |
| ATOM | 906 | C | PRO | L | 119 | 3.214 | −19.314 | 29.27 | 1 | 23.79 | L |
| ATOM | 907 | O | PRO | L | 119 | 2.684 | −19.421 | 28.156 | 1 | 20.05 | L |
| ATOM | 908 | N | PRO | L | 120 | 4.087 | −18.34 | 29.553 | 1 | 26.14 | L |
| ATOM | 909 | CD | PRO | L | 120 | 4.635 | −17.97 | 30.869 | 1 | 25.53 | L |
| ATOM | 910 | CA | PRO | L | 120 | 4.473 | −17.362 | 28.532 | 1 | 25.8 | L |
| ATOM | 911 | CB | PRO | L | 120 | 5.414 | −16.428 | 29.287 | 1 | 25.5 | L |
| ATOM | 912 | CG | PRO | L | 120 | 4.899 | −16.495 | 30.691 | 1 | 27.71 | L |
| ATOM | 913 | C | PRO | L | 120 | 5.189 | −18.077 | 27.384 | 1 | 25.45 | L |
| ATOM | 914 | O | PRO | L | 120 | 5.877 | −19.085 | 27.586 | 1 | 26.64 | L |
| ATOM | 915 | N | SER | L | 121 | 5.024 | −17.566 | 26.177 | 1 | 24.25 | L |
| ATOM | 916 | CA | SER | L | 121 | 5.686 | −18.17 | 25.038 | 1 | 23.53 | L |
| ATOM | 917 | CB | SER | L | 121 | 5.119 | −17.606 | 23.735 | 1 | 21.46 | L |
| ATOM | 918 | OG | SER | L | 121 | 5.214 | −16.19 | 23.711 | 1 | 24.99 | L |
| ATOM | 919 | C | SER | L | 121 | 7.185 | −17.886 | 25.098 | 1 | 23.69 | L |
| ATOM | 920 | O | SER | L | 121 | 7.625 | −16.888 | 25.665 | 1 | 21.3 | L |
| ATOM | 921 | N | SER | L | 122 | 7.964 | −18.789 | 24.524 | 1 | 26 | L |

TABLE 7-continued

| ATOM | 922 | CA | SER | L | 122 | 9.399 | −18.622 | 24.456 | 1 | 25.49 | L |
| --- | --- | --- | --- | --- | --- | --- | --- | --- | --- | --- | --- |
| ATOM | 923 | CB | SER | L | 122 | 9.995 | −19.783 | 23.644 | 1 | 27.93 | L |
| ATOM | 924 | OG | SER | L | 122 | 11.416 | −19.771 | 23.635 | 1 | 34.44 | L |
| ATOM | 925 | C | SER | L | 122 | 9.593 | −17.281 | 23.727 | 1 | 24.57 | L |
| ATOM | 926 | O | SER | L | 122 | 10.448 | −16.472 | 24.091 | 1 | 23.46 | L |
| ATOM | 927 | N | GLU | L | 123 | 8.758 | −17.052 | 22.715 | 1 | 24.73 | L |
| ATOM | 928 | CA | GLU | L | 123 | 8.8 | −15.839 | 21.903 | 1 | 26.2 | L |
| ATOM | 929 | CB | GLU | L | 123 | 7.687 | −15.849 | 20.849 | 1 | 26.46 | L |
| ATOM | 930 | CG | GLU | L | 123 | 7.91 | −16.791 | 19.692 | 1 | 26.81 | L |
| ATOM | 931 | CD | GLU | L | 123 | 7.329 | −18.158 | 19.941 | 1 | 29.3 | L |
| ATOM | 932 | OE1 | GLU | L | 123 | 7.65 | −18.768 | 20.985 | 1 | 32.39 | L |
| ATOM | 933 | OE2 | GLU | L | 123 | 6.549 | −18.627 | 19.088 | 1 | 31.33 | L |
| ATOM | 934 | C | GLU | L | 123 | 8.69 | −14.538 | 22.683 | 1 | 27.76 | L |
| ATOM | 935 | O | GLU | L | 123 | 9.424 | −13.579 | 22.414 | 1 | 30 | L |
| ATOM | 936 | N | GLN | L | 124 | 7.765 | −14.495 | 23.637 | 1 | 27.59 | L |
| ATOM | 937 | CA | GLN | L | 124 | 7.551 | −13.287 | 24.426 | 1 | 26.21 | L |
| ATOM | 938 | CB | GLN | L | 124 | 6.161 | −13.325 | 25.061 | 1 | 25.73 | L |
| ATOM | 939 | CG | GLN | L | 124 | 5.878 | −12.157 | 25.978 | 1 | 25.41 | L |
| ATOM | 940 | CD | GLN | L | 124 | 4.564 | −12.31 | 26.7 | 1 | 28.18 | L |
| ATOM | 941 | OE1 | GLN | L | 124 | 4.194 | −13.414 | 27.104 | 1 | 30.55 | L |
| ATOM | 942 | NE2 | GLN | L | 124 | 3.853 | −11.202 | 26.883 | 1 | 29.49 | L |
| ATOM | 943 | C | GLN | L | 124 | 8.612 | −13.057 | 25.498 | 1 | 24.05 | L |
| ATOM | 944 | O | GLN | L | 124 | 9.081 | −11.937 | 25.68 | 1 | 20.76 | L |
| ATOM | 945 | N | LEU | L | 125 | 8.975 | −14.117 | 26.21 | 1 | 25.83 | L |
| ATOM | 946 | CA | LEU | L | 125 | 9.985 | −14.039 | 27.259 | 1 | 27.51 | L |
| ATOM | 947 | CB | LEU | L | 125 | 10.244 | −15.429 | 27.829 | 1 | 26.43 | L |
| ATOM | 948 | CG | LEU | L | 125 | 9.11 | −15.942 | 28.714 | 1 | 27.18 | L |
| ATOM | 949 | CD1 | LEU | L | 125 | 9.232 | −17.439 | 28.926 | 1 | 24.94 | L |
| ATOM | 950 | CD2 | LEU | L | 125 | 9.144 | −15.179 | 30.037 | 1 | 28.78 | L |
| ATOM | 951 | C | LEU | L | 125 | 11.265 | −13.471 | 26.684 | 1 | 29.33 | L |
| ATOM | 952 | O | LEU | L | 125 | 11.957 | −12.69 | 27.32 | 1 | 27.27 | L |
| ATOM | 953 | N | THR | L | 126 | 11.565 | −13.883 | 25.462 | 1 | 34.71 | L |
| ATOM | 954 | CA | THR | L | 126 | 12.744 | −13.422 | 24.747 | 1 | 38.58 | L |
| ATOM | 955 | CB | THR | L | 126 | 12.898 | −14.217 | 23.418 | 1 | 38.73 | L |
| ATOM | 956 | OG1 | THR | L | 126 | 13.508 | −15.485 | 23.694 | 1 | 41.44 | L |
| ATOM | 957 | CG2 | THR | L | 126 | 13.747 | −13.456 | 22.415 | 1 | 42.63 | L |
| ATOM | 958 | C | THR | L | 126 | 12.649 | −11.918 | 24.454 | 1 | 37.67 | L |
| ATOM | 959 | O | THR | L | 126 | 13.661 | −11.244 | 24.277 | 1 | 38.38 | L |
| ATOM | 960 | N | SER | L | 127 | 11.424 | −11.404 | 24.424 | 1 | 38.31 | L |
| ATOM | 961 | CA | SER | L | 127 | 11.174 | −9.999 | 24.126 | 1 | 38.16 | L |
| ATOM | 962 | CB | SER | L | 127 | 9.895 | −9.873 | 23.287 | 1 | 39.09 | L |
| ATOM | 963 | OG | SER | L | 127 | 9.902 | −10.772 | 22.184 | 1 | 37.74 | L |
| ATOM | 964 | C | SER | L | 127 | 11.053 | −9.124 | 25.373 | 1 | 38.2 | L |
| ATOM | 965 | O | SER | L | 127 | 10.884 | −7.912 | 25.267 | 1 | 39.47 | L |
| ATOM | 966 | N | GLY | L | 128 | 11.131 | −9.736 | 26.55 | 1 | 38.8 | L |
| ATOM | 967 | CA | GLY | L | 128 | 11.028 | −8.974 | 27.784 | 1 | 36.79 | L |
| ATOM | 968 | C | GLY | L | 128 | 9.684 | −9.089 | 28.483 | 1 | 36.17 | L |
| ATOM | 969 | O | GLY | L | 128 | 9.528 | −8.655 | 29.628 | 1 | 37.33 | L |
| ATOM | 970 | N | GLY | L | 129 | 8.704 | −9.676 | 27.807 | 1 | 33.66 | L |
| ATOM | 971 | CA | GLY | L | 129 | 7.396 | −9.811 | 28.415 | 1 | 32.96 | L |
| ATOM | 972 | C | GLY | L | 129 | 7.086 | −11.202 | 28.933 | 1 | 33.4 | L |
| ATOM | 973 | O | GLY | L | 129 | 7.796 | −12.165 | 28.639 | 1 | 35.68 | L |
| ATOM | 974 | N | ALA | L | 130 | 6.021 | −11.305 | 29.72 | 1 | 32.57 | L |
| ATOM | 975 | CA | ALA | L | 130 | 5.59 | −12.585 | 30.271 | 1 | 29.83 | L |
| ATOM | 976 | CB | ALA | L | 130 | 6.379 | −12.917 | 31.528 | 1 | 25.9 | L |
| ATOM | 977 | C | ALA | L | 130 | 4.095 | −12.524 | 30.579 | 1 | 30.21 | L |
| ATOM | 978 | O | ALA | L | 130 | 3.649 | −11.822 | 31.491 | 1 | 29.97 | L |
| ATOM | 979 | N | SER | L | 131 | 3.319 | −13.253 | 29.794 | 1 | 28.89 | L |
| ATOM | 980 | CA | SER | L | 131 | 1.885 | −13.283 | 29.991 | 1 | 28.16 | L |
| ATOM | 981 | CB | SER | L | 131 | 1.16 | −12.762 | 28.748 | 1 | 27.57 | L |
| ATOM | 982 | OG | SER | L | 131 | 1.43 | −11.384 | 28.549 | 1 | 28.65 | L |
| ATOM | 983 | C | SER | L | 131 | 1.462 | −14.7 | 30.259 | 1 | 26.48 | L |
| ATOM | 984 | O | SER | L | 131 | 1.884 | −15.622 | 29.571 | 1 | 29.19 | L |
| ATOM | 985 | N | VAL | L | 132 | 0.651 | −14.886 | 31.284 | 1 | 25.94 | L |
| ATOM | 986 | CA | VAL | L | 132 | 0.159 | −16.217 | 31.579 | 1 | 26.65 | L |
| ATOM | 987 | CB | VAL | L | 132 | 0.316 | −16.551 | 33.066 | 1 | 26.59 | L |
| ATOM | 988 | CG1 | VAL | L | 132 | −0.139 | −17.966 | 33.322 | 1 | 28.59 | L |
| ATOM | 989 | CG2 | VAL | L | 132 | 1.771 | −16.413 | 33.46 | 1 | 28.88 | L |
| ATOM | 990 | C | VAL | L | 132 | −1.312 | −16.234 | 31.159 | 1 | 25.12 | L |
| ATOM | 991 | O | VAL | L | 132 | −2.047 | −15.268 | 31.38 | 1 | 22.4 | L |
| ATOM | 992 | N | VAL | L | 133 | −1.737 | −17.324 | 30.534 | 1 | 23.9 | L |
| ATOM | 993 | CA | VAL | L | 133 | −3.106 | −17.4 | 30.058 | 1 | 23.63 | L |
| ATOM | 994 | CB | VAL | L | 133 | −3.149 | −17.498 | 28.531 | 1 | 18.35 | L |
| ATOM | 995 | CG1 | VAL | L | 133 | −4.592 | −17.507 | 28.056 | 1 | 16.02 | L |
| ATOM | 996 | CG2 | VAL | L | 133 | −2.379 | −16.339 | 27.922 | 1 | 16.76 | L |
| ATOM | 997 | C | VAL | L | 133 | −3.952 | −18.528 | 30.609 | 1 | 26.12 | L |
| ATOM | 998 | O | VAL | L | 133 | −3.487 | −19.65 | 30.816 | 1 | 27.97 | L |
| ATOM | 999 | N | CYS | L | 134 | −5.223 | −18.216 | 30.823 | 1 | 27.09 | L |
| ATOM | 1000 | CA | CYS | L | 134 | −6.155 | −19.197 | 31.326 | 1 | 24.04 | L |

TABLE 7-continued

| | | | | | | | | | | | |
|---|---|---|---|---|---|---|---|---|---|---|---|
| ATOM | 1001 | C | CYS | L | 134 | −7.442 | −19.179 | 30.513 | 1 | 20.92 | L |
| ATOM | 1002 | O | CYS | L | 134 | −8.063 | −18.133 | 30.339 | 1 | 17.8 | L |
| ATOM | 1003 | CB | CYS | L | 134 | −6.463 | −18.91 | 32.786 | 1 | 27.07 | L |
| ATOM | 1004 | SG | CYS | L | 134 | −7.308 | −20.273 | 33.647 | 1 | 32.1 | L |
| ATOM | 1005 | N | PHE | L | 135 | −7.809 | −20.334 | 29.977 | 1 | 18.32 | L |
| ATOM | 1006 | CA | PHE | L | 135 | −9.05 | −20.447 | 29.238 | 1 | 22.12 | L |
| ATOM | 1007 | CB | PHE | L | 135 | −8.859 | −21.182 | 27.905 | 1 | 23.68 | L |
| ATOM | 1008 | CG | PHE | L | 135 | −8.09 | −20.412 | 26.875 | 1 | 24.88 | L |
| ATOM | 1009 | CD1 | PHE | L | 135 | −8.396 | −19.085 | 26.598 | 1 | 24.99 | L |
| ATOM | 1010 | CD2 | PHE | L | 135 | −7.055 | −21.023 | 26.168 | 1 | 25.75 | L |
| ATOM | 1011 | CE1 | PHE | L | 135 | −7.675 | −18.376 | 25.632 | 1 | 26.43 | L |
| ATOM | 1012 | CE2 | PHE | L | 135 | −6.328 | −20.326 | 25.201 | 1 | 23.36 | L |
| ATOM | 1013 | CZ | PHE | L | 135 | −6.636 | −19.003 | 24.932 | 1 | 24.32 | L |
| ATOM | 1014 | C | PHE | L | 135 | −10.025 | −21.259 | 30.093 | 1 | 24.84 | L |
| ATOM | 1015 | O | PHE | L | 135 | −9.694 | −22.349 | 30.569 | 1 | 23.35 | L |
| ATOM | 1016 | N | LEU | L | 136 | −11.211 | −20.707 | 30.319 | 1 | 25.26 | L |
| ATOM | 1017 | CA | LEU | L | 136 | −12.259 | −21.407 | 31.056 | 1 | 27.46 | L |
| ATOM | 1018 | CB | LEU | L | 136 | −12.831 | −20.515 | 32.156 | 1 | 28.39 | L |
| ATOM | 1019 | CG | LEU | L | 136 | −11.758 | −19.815 | 32.994 | 1 | 27.24 | L |
| ATOM | 1020 | CD1 | LEU | L | 136 | −12.352 | −19.383 | 34.319 | 1 | 29.28 | L |
| ATOM | 1021 | CD2 | LEU | L | 136 | −10.598 | −20.749 | 33.234 | 1 | 30.57 | L |
| ATOM | 1022 | C | LEU | L | 136 | −13.255 | −21.606 | 29.926 | 1 | 28.23 | L |
| ATOM | 1023 | O | LEU | L | 136 | −13.909 | −20.657 | 29.487 | 1 | 28.24 | L |
| ATOM | 1024 | N | ASN | L | 137 | −13.356 | −22.836 | 29.436 | 1 | 28.97 | L |
| ATOM | 1025 | CA | ASN | L | 137 | −14.207 | −23.09 | 28.285 | 1 | 29.74 | L |
| ATOM | 1026 | CB | ASN | L | 137 | −13.336 | −23.608 | 27.155 | 1 | 28.72 | L |
| ATOM | 1027 | CG | ASN | L | 137 | −12.318 | −22.595 | 26.72 | 1 | 28.86 | L |
| ATOM | 1028 | OD1 | ASN | L | 137 | −12.602 | −21.716 | 25.909 | 1 | 26.84 | L |
| ATOM | 1029 | ND2 | ASN | L | 137 | −11.125 | −22.69 | 27.281 | 1 | 31.61 | L |
| ATOM | 1030 | C | ASN | L | 137 | −15.425 | −23.972 | 28.406 | 1 | 30.68 | L |
| ATOM | 1031 | O | ASN | L | 137 | −15.478 | −24.895 | 29.219 | 1 | 34.35 | L |
| ATOM | 1032 | N | ASN | L | 138 | −16.396 | −23.672 | 27.551 | 1 | 27.83 | L |
| ATOM | 1033 | CA | ASN | L | 138 | −17.651 | −24.399 | 27.48 | 1 | 27.16 | L |
| ATOM | 1034 | CB | ASN | L | 138 | −17.44 | −25.751 | 26.788 | 1 | 26.26 | L |
| ATOM | 1035 | CG | ASN | L | 138 | −16.718 | −25.615 | 25.455 | 1 | 25.93 | L |
| ATOM | 1036 | OD1 | ASN | L | 138 | −15.494 | −25.5 | 25.41 | 1 | 26.96 | L |
| ATOM | 1037 | ND2 | ASN | L | 138 | −17.476 | −25.609 | 24.365 | 1 | 24.51 | L |
| ATOM | 1038 | C | ASN | L | 138 | −18.297 | −24.602 | 28.839 | 1 | 26.32 | L |
| ATOM | 1039 | O | ASN | L | 138 | −18.376 | −25.717 | 29.348 | 1 | 26.78 | L |
| ATOM | 1040 | N | PHE | L | 139 | −18.759 | −23.509 | 29.43 | 1 | 25.31 | L |
| ATOM | 1041 | CA | PHE | L | 139 | −19.416 | −23.585 | 30.722 | 1 | 24.07 | L |
| ATOM | 1042 | CB | PHE | L | 139 | −18.509 | −23.036 | 31.818 | 1 | 19.54 | L |
| ATOM | 1043 | CG | PHE | L | 139 | −18.23 | −21.566 | 31.7 | 1 | 20.07 | L |
| ATOM | 1044 | CD1 | PHE | L | 139 | −19.147 | −20.627 | 32.162 | 1 | 18.64 | L |
| ATOM | 1045 | CD2 | PHE | L | 139 | −17.039 | −21.118 | 31.137 | 1 | 20.02 | L |
| ATOM | 1046 | CE1 | PHE | L | 139 | −18.879 | −19.267 | 32.071 | 1 | 17.09 | L |
| ATOM | 1047 | CE2 | PHE | L | 139 | −16.764 | −19.763 | 31.042 | 1 | 19.25 | L |
| ATOM | 1048 | CZ | PHE | L | 139 | −17.687 | −18.834 | 31.512 | 1 | 19.5 | L |
| ATOM | 1049 | C | PHE | L | 139 | −20.705 | −22.787 | 30.676 | 1 | 23.85 | L |
| ATOM | 1050 | O | PHE | L | 139 | −20.896 | −21.94 | 29.804 | 1 | 21.84 | L |
| ATOM | 1051 | N | TYR | L | 140 | −21.592 | −23.076 | 31.615 | 1 | 23.69 | L |
| ATOM | 1052 | CA | TYR | L | 140 | −22.854 | −22.37 | 31.699 | 1 | 25.1 | L |
| ATOM | 1053 | CB | TYR | L | 140 | −23.862 | −22.977 | 30.724 | 1 | 23.87 | L |
| ATOM | 1054 | CG | TYR | L | 140 | −25.156 | −22.205 | 30.639 | 1 | 26.42 | L |
| ATOM | 1055 | CD1 | TYR | L | 140 | −26.198 | −22.452 | 31.534 | 1 | 25.3 | L |
| ATOM | 1056 | CE1 | TYR | L | 140 | −27.381 | −21.728 | 31.477 | 1 | 24.72 | L |
| ATOM | 1057 | CD2 | TYR | L | 140 | −25.334 | −21.206 | 29.68 | 1 | 26.48 | L |
| ATOM | 1058 | CE2 | TYR | L | 140 | −26.516 | −20.474 | 29.615 | 1 | 25.77 | L |
| ATOM | 1059 | CZ | TYR | L | 140 | −27.535 | −20.743 | 30.517 | 1 | 27.81 | L |
| ATOM | 1060 | OH | TYR | L | 140 | −28.715 | −20.036 | 30.457 | 1 | 33.77 | L |
| ATOM | 1061 | C | TYR | L | 140 | −23.343 | −22.482 | 33.137 | 1 | 26.07 | L |
| ATOM | 1062 | O | TYR | L | 140 | −23.196 | −23.538 | 33.77 | 1 | 25.34 | L |
| ATOM | 1063 | N | PRO | L | 141 | −23.918 | −21.393 | 33.681 | 1 | 25.3 | L |
| ATOM | 1064 | CD | PRO | L | 141 | −24.375 | −21.396 | 35.085 | 1 | 25.57 | L |
| ATOM | 1065 | CA | PRO | L | 141 | −24.154 | −20.076 | 33.07 | 1 | 25.39 | L |
| ATOM | 1066 | CB | PRO | L | 141 | −25.164 | −19.447 | 34.018 | 1 | 24.54 | L |
| ATOM | 1067 | CG | PRO | L | 141 | −24.663 | −19.922 | 35.344 | 1 | 24.38 | L |
| ATOM | 1068 | C | PRO | L | 141 | −22.908 | −19.199 | 32.897 | 1 | 26.25 | L |
| ATOM | 1069 | O | PRO | L | 141 | −21.828 | −19.53 | 33.387 | 1 | 26.01 | L |
| ATOM | 1070 | N | LYS | L | 142 | −23.087 | −18.072 | 32.206 | 1 | 27.27 | L |
| ATOM | 1071 | CA | LYS | L | 142 | −22.017 | −17.117 | 31.914 | 1 | 27.69 | L |
| ATOM | 1072 | CB | LYS | L | 142 | −22.593 | −15.898 | 31.191 | 1 | 30.96 | L |
| ATOM | 1073 | CG | LYS | L | 142 | −21.564 | −14.897 | 30.677 | 1 | 33.13 | L |
| ATOM | 1074 | CD | LYS | L | 142 | −22.264 | −13.639 | 30.169 | 1 | 38.48 | L |
| ATOM | 1075 | CE | LYS | L | 142 | −21.328 | −12.707 | 29.408 | 1 | 41.44 | L |
| ATOM | 1076 | NZ | LYS | L | 142 | −21.046 | −13.194 | 28.018 | 1 | 45.59 | L |
| ATOM | 1077 | C | LYS | L | 142 | −21.293 | −16.647 | 33.161 | 1 | 28.47 | L |
| ATOM | 1078 | O | LYS | L | 142 | −20.081 | −16.423 | 33.15 | 1 | 31.54 | L |
| ATOM | 1079 | N | ASP | L | 143 | −22.038 | −16.485 | 34.24 | 1 | 28.45 | L |

TABLE 7-continued

| | | | | | | | | | | |
|---|---|---|---|---|---|---|---|---|---|---|
| ATOM | 1080 | CA | ASP | L | 143 | −21.446 | −16.029 | 35.482 | 1 | 29.7 | L |
| ATOM | 1081 | CB | ASP | L | 143 | −22.511 | −15.959 | 36.569 | 1 | 33.15 | L |
| ATOM | 1082 | CG | ASP | L | 143 | −21.982 | −15.368 | 37.852 | 1 | 40.2 | L |
| ATOM | 1083 | OD1 | ASP | L | 143 | −21.041 | −15.944 | 38.444 | 1 | 46.49 | L |
| ATOM | 1084 | OD2 | ASP | L | 143 | −22.505 | −14.319 | 38.271 | 1 | 46.81 | L |
| ATOM | 1085 | C | ASP | L | 143 | −20.304 | −16.935 | 35.936 | 1 | 28.58 | L |
| ATOM | 1086 | O | ASP | L | 143 | −20.479 | −18.139 | 36.116 | 1 | 28.93 | L |
| ATOM | 1087 | N | ILE | L | 144 | −19.129 | −16.349 | 36.12 | 1 | 27.19 | L |
| ATOM | 1088 | CA | ILE | L | 144 | −17.973 | −17.107 | 36.571 | 1 | 25.59 | L |
| ATOM | 1089 | CB | ILE | L | 144 | −17.359 | −17.946 | 35.426 | 1 | 24.34 | L |
| ATOM | 1090 | CG2 | ILE | L | 144 | −16.577 | −17.053 | 34.467 | 1 | 20.3 | L |
| ATOM | 1091 | CG1 | ILE | L | 144 | −16.447 | −19.02 | 36.016 | 1 | 22.26 | L |
| ATOM | 1092 | CD1 | ILE | L | 144 | −15.87 | −19.955 | 34.987 | 1 | 20.56 | L |
| ATOM | 1093 | C | ILE | L | 144 | −16.944 | −16.125 | 37.098 | 1 | 26.4 | L |
| ATOM | 1094 | O | ILE | L | 144 | −16.891 | −14.976 | 36.668 | 1 | 25.51 | L |
| ATOM | 1095 | N | ASN | L | 145 | −16.13 | −16.571 | 38.037 | 1 | 26.05 | L |
| ATOM | 1096 | CA | ASN | L | 145 | −15.144 | −15.69 | 38.612 | 1 | 30 | L |
| ATOM | 1097 | CB | ASN | L | 145 | −15.607 | −15.247 | 39.996 | 1 | 34.32 | L |
| ATOM | 1098 | CG | ASN | L | 145 | −14.724 | −14.174 | 40.582 | 1 | 43.24 | L |
| ATOM | 1099 | OD1 | ASN | L | 145 | −13.553 | −14.421 | 40.894 | 1 | 48.53 | L |
| ATOM | 1100 | ND2 | ASN | L | 145 | −15.271 | −12.965 | 40.728 | 1 | 41.97 | L |
| ATOM | 1101 | C | ASN | L | 145 | −13.82 | −16.411 | 38.693 | 1 | 30.84 | L |
| ATOM | 1102 | O | ASN | L | 145 | −13.729 | −17.499 | 39.249 | 1 | 34.14 | L |
| ATOM | 1103 | N | VAL | L | 146 | −12.785 | −15.807 | 38.133 | 1 | 30.13 | L |
| ATOM | 1104 | CA | VAL | L | 146 | −11.481 | −16.443 | 38.15 | 1 | 30.11 | L |
| ATOM | 1105 | CB | VAL | L | 146 | −10.989 | −16.699 | 36.716 | 1 | 29.97 | L |
| ATOM | 1106 | CG1 | VAL | L | 146 | −10.938 | −15.4 | 35.956 | 1 | 29.52 | L |
| ATOM | 1107 | CG2 | VAL | L | 146 | −9.623 | −17.351 | 36.743 | 1 | 27.67 | L |
| ATOM | 1108 | C | VAL | L | 146 | −10.429 | −15.624 | 38.882 | 1 | 29.94 | L |
| ATOM | 1109 | O | VAL | L | 146 | −10.411 | −14.398 | 38.793 | 1 | 29.16 | L |
| ATOM | 1110 | N | LYS | L | 147 | −9.562 | −16.302 | 39.624 | 1 | 28.51 | L |
| ATOM | 1111 | CA | LYS | L | 147 | −8.498 | −15.604 | 40.318 | 1 | 29.5 | L |
| ATOM | 1112 | CB | LYS | L | 147 | −8.765 | −15.514 | 41.824 | 1 | 31.78 | L |
| ATOM | 1113 | CG | LYS | L | 147 | −8.653 | −16.816 | 42.597 | 1 | 37.8 | L |
| ATOM | 1114 | CD | LYS | L | 147 | −8.961 | −16.584 | 44.078 | 1 | 42.9 | L |
| ATOM | 1115 | CE | LYS | L | 147 | −10.364 | −15.973 | 44.267 | 1 | 45.51 | L |
| ATOM | 1116 | NZ | LYS | L | 147 | −10.704 | −15.665 | 45.69 | 1 | 44.32 | L |
| ATOM | 1117 | C | LYS | L | 147 | −7.191 | −16.323 | 40.056 | 1 | 29.15 | L |
| ATOM | 1118 | O | LYS | L | 147 | −7.163 | −17.54 | 39.845 | 1 | 29.01 | L |
| ATOM | 1119 | N | TRP | L | 148 | −6.111 | −15.555 | 40.034 | 1 | 27.93 | L |
| ATOM | 1120 | CA | TRP | L | 148 | −4.791 | −16.11 | 39.798 | 1 | 25.36 | L |
| ATOM | 1121 | CB | TRP | L | 148 | −3.979 | −15.218 | 38.855 | 1 | 23.96 | L |
| ATOM | 1122 | CG | TRP | L | 148 | −4.46 | −15.205 | 37.44 | 1 | 25.11 | L |
| ATOM | 1123 | CD2 | TRP | L | 148 | −3.937 | −15.979 | 36.357 | 1 | 24.69 | L |
| ATOM | 1124 | CE2 | TRP | L | 148 | −4.7 | −15.665 | 35.209 | 1 | 25.65 | L |
| ATOM | 1125 | CE3 | TRP | L | 148 | −2.898 | −16.908 | 36.244 | 1 | 20.89 | L |
| ATOM | 1126 | CD1 | TRP | L | 148 | −5.489 | −14.472 | 36.924 | 1 | 25.85 | L |
| ATOM | 1127 | NE1 | TRP | L | 148 | −5.64 | −14.743 | 35.583 | 1 | 27.1 | L |
| ATOM | 1128 | CZ2 | TRP | L | 148 | −4.455 | −16.249 | 33.961 | 1 | 27.55 | L |
| ATOM | 1129 | CZ3 | TRP | L | 148 | −2.654 | −17.487 | 35.008 | 1 | 24.29 | L |
| ATOM | 1130 | CH2 | TRP | L | 148 | −3.43 | −17.156 | 33.879 | 1 | 23.39 | L |
| ATOM | 1131 | C | TRP | L | 148 | −4.062 | −16.198 | 41.119 | 1 | 25.07 | L |
| ATOM | 1132 | O | TRP | L | 148 | −4.217 | −15.337 | 41.982 | 1 | 27.06 | L |
| ATOM | 1133 | N | LYS | L | 149 | −3.28 | −17.248 | 41.289 | 1 | 21.62 | L |
| ATOM | 1134 | CA | LYS | L | 149 | −2.512 | −17.386 | 42.5 | 1 | 23.23 | L |
| ATOM | 1135 | CB | LYS | L | 149 | −3.093 | −18.473 | 43.398 | 1 | 25.26 | L |
| ATOM | 1136 | CG | LYS | L | 149 | −4.325 | −18.05 | 44.176 | 1 | 29.81 | L |
| ATOM | 1137 | CD | LYS | L | 149 | −4.696 | −19.134 | 45.173 | 1 | 33.68 | L |
| ATOM | 1138 | CE | LYS | L | 149 | −5.822 | −18.71 | 46.084 | 1 | 32.5 | L |
| ATOM | 1139 | NZ | LYS | L | 149 | −6.016 | −19.734 | 47.149 | 1 | 37.48 | L |
| ATOM | 1140 | C | LYS | L | 149 | −1.102 | −17.74 | 42.09 | 1 | 22.55 | L |
| ATOM | 1141 | O | LYS | L | 149 | −0.89 | −18.682 | 41.331 | 1 | 24.56 | L |
| ATOM | 1142 | N | ILE | L | 150 | −0.141 | −16.96 | 42.564 | 1 | 21.76 | L |
| ATOM | 1143 | CA | ILE | L | 150 | 1.257 | −17.214 | 42.256 | 1 | 21.17 | L |
| ATOM | 1144 | CB | ILE | L | 150 | 1.943 | −15.949 | 41.716 | 1 | 19.92 | L |
| ATOM | 1145 | CG2 | ILE | L | 150 | 3.425 | −16.201 | 41.534 | 1 | 23.07 | L |
| ATOM | 1146 | CG1 | ILE | L | 150 | 1.287 | −15.548 | 40.388 | 1 | 17.1 | L |
| ATOM | 1147 | CD1 | ILE | L | 150 | 1.818 | −14.283 | 39.765 | 1 | 15.75 | L |
| ATOM | 1148 | C | ILE | L | 150 | 1.89 | −17.659 | 43.555 | 1 | 22.72 | L |
| ATOM | 1149 | O | ILE | L | 150 | 1.857 | −16.94 | 44.55 | 1 | 22.25 | L |
| ATOM | 1150 | N | ASP | L | 151 | 2.449 | −18.863 | 43.547 | 1 | 26.06 | L |
| ATOM | 1151 | CA | ASP | L | 151 | 3.046 | −19.426 | 44.745 | 1 | 27.39 | L |
| ATOM | 1152 | CB | ASP | L | 151 | 4.395 | −18.778 | 45.042 | 1 | 28.35 | L |
| ATOM | 1153 | CG | ASP | L | 151 | 5.475 | −19.246 | 44.09 | 1 | 30.41 | L |
| ATOM | 1154 | OD1 | ASP | L | 151 | 5.454 | −20.438 | 43.718 | 1 | 31.21 | L |
| ATOM | 1155 | OD2 | ASP | L | 151 | 6.349 | −18.438 | 43.717 | 1 | 34.1 | L |
| ATOM | 1156 | C | ASP | L | 151 | 2.096 | −19.236 | 45.907 | 1 | 29.88 | L |
| ATOM | 1157 | O | ASP | L | 151 | 2.453 | −18.65 | 46.928 | 1 | 31.68 | L |
| ATOM | 1158 | N | GLY | L | 152 | 0.867 | −19.714 | 45.713 | 1 | 34 | L |

TABLE 7-continued

| | | | | | | | | | | |
|---|---|---|---|---|---|---|---|---|---|---|
| ATOM | 1159 | CA | GLY | L | 152 | −0.163 | −19.644 | 46.737 | 1 | 37.59 | L |
| ATOM | 1160 | C | GLY | L | 152 | −0.932 | −18.353 | 46.977 | 1 | 39.86 | L |
| ATOM | 1161 | O | GLY | L | 152 | −2.115 | −18.402 | 47.347 | 1 | 41.89 | L |
| ATOM | 1162 | N | SER | L | 153 | −0.284 | −17.206 | 46.779 | 1 | 38.11 | L |
| ATOM | 1163 | CA | SER | L | 153 | −0.93 | −15.92 | 47.019 | 1 | 37.57 | L |
| ATOM | 1164 | CB | SER | L | 153 | 0.083 | −14.952 | 47.64 | 1 | 41.4 | L |
| ATOM | 1165 | OG | SER | L | 153 | 1.233 | −14.8 | 46.821 | 1 | 47.97 | L |
| ATOM | 1166 | C | SER | L | 153 | −1.602 | −15.283 | 45.795 | 1 | 36.54 | L |
| ATOM | 1167 | O | SER | L | 153 | −1.01 | −15.166 | 44.719 | 1 | 33.76 | L |
| ATOM | 1168 | N | GLU | L | 154 | −2.847 | −14.857 | 45.986 | 1 | 36.02 | L |
| ATOM | 1169 | CA | GLU | L | 154 | −3.638 | −14.249 | 44.922 | 1 | 36.77 | L |
| ATOM | 1170 | CB | GLU | L | 154 | −5.065 | −13.974 | 45.405 | 1 | 37.67 | L |
| ATOM | 1171 | CG | GLU | L | 154 | −5.894 | −13.178 | 44.399 | 1 | 43.6 | L |
| ATOM | 1172 | CD | GLU | L | 154 | −7.238 | −12.738 | 44.944 | 1 | 47.14 | L |
| ATOM | 1173 | OE1 | GLU | L | 154 | −7.272 | −12.138 | 46.04 | 1 | 52.56 | L |
| ATOM | 1174 | OE2 | GLU | L | 154 | −8.262 | −12.979 | 44.273 | 1 | 50.9 | L |
| ATOM | 1175 | C | GLU | L | 154 | −3.072 | −12.96 | 44.353 | 1 | 34.65 | L |
| ATOM | 1176 | O | GLU | L | 154 | −2.561 | −12.121 | 45.084 | 1 | 36.38 | L |
| ATOM | 1177 | N | ARG | L | 155 | −3.189 | −12.811 | 43.038 | 1 | 33.44 | L |
| ATOM | 1178 | CA | ARG | L | 155 | −2.733 | −11.618 | 42.343 | 1 | 32.29 | L |
| ATOM | 1179 | CB | ARG | L | 155 | −1.44 | −11.88 | 41.583 | 1 | 29.56 | L |
| ATOM | 1180 | CG | ARG | L | 155 | −1.085 | −10.751 | 40.643 | 1 | 27.75 | L |
| ATOM | 1181 | CD | ARG | L | 155 | 0.387 | −10.718 | 40.331 | 1 | 28.16 | L |
| ATOM | 1182 | NE | ARG | L | 155 | 0.7 | −9.6 | 39.452 | 1 | 29.97 | L |
| ATOM | 1183 | CZ | ARG | L | 155 | 1.915 | −9.085 | 39.307 | 1 | 32.61 | L |
| ATOM | 1184 | NH1 | ARG | L | 155 | 2.942 | −9.59 | 39.99 | 1 | 28.73 | L |
| ATOM | 1185 | NH2 | ARG | L | 155 | 2.101 | −8.06 | 38.483 | 1 | 32.32 | L |
| ATOM | 1186 | C | ARG | L | 155 | −3.798 | −11.163 | 41.361 | 1 | 33.97 | L |
| ATOM | 1187 | O | ARG | L | 155 | −4.191 | −11.914 | 40.464 | 1 | 34.48 | L |
| ATOM | 1188 | N | GLN | L | 156 | −4.262 | −9.93 | 41.527 | 1 | 35.27 | L |
| ATOM | 1189 | CA | GLN | L | 156 | −5.289 | −9.388 | 40.648 | 1 | 35.74 | L |
| ATOM | 1190 | CB | GLN | L | 156 | −6.416 | −8.752 | 41.469 | 1 | 34.74 | L |
| ATOM | 1191 | CG | GLN | L | 156 | −6.968 | −9.643 | 42.56 | 1 | 35.69 | L |
| ATOM | 1192 | CD | GLN | L | 156 | −8.263 | −9.112 | 43.152 | 1 | 39.08 | L |
| ATOM | 1193 | OE1 | GLN | L | 156 | −8.803 | −9.684 | 44.105 | 1 | 38.61 | L |
| ATOM | 1194 | NE2 | GLN | L | 156 | −8.773 | −8.018 | 42.586 | 1 | 37.2 | L |
| ATOM | 1195 | C | GLN | L | 156 | −4.689 | −8.343 | 39.722 | 1 | 36.18 | L |
| ATOM | 1196 | O | GLN | L | 156 | −5.228 | −8.067 | 38.65 | 1 | 37.15 | L |
| ATOM | 1197 | N | ASN | L | 157 | −3.568 | −7.767 | 40.14 | 1 | 35.69 | L |
| ATOM | 1198 | CA | ASN | L | 157 | −2.904 | −6.737 | 39.354 | 1 | 36.05 | L |
| ATOM | 1199 | CB | ASN | L | 157 | −1.721 | −6.159 | 40.138 | 1 | 35.1 | L |
| ATOM | 1200 | CG | ASN | L | 157 | −1.028 | −5.022 | 39.4 | 1 | 35.71 | L |
| ATOM | 1201 | OD1 | ASN | L | 157 | −1.67 | −4.069 | 38.954 | 1 | 36.03 | L |
| ATOM | 1202 | ND2 | ASN | L | 157 | 0.289 | −5.114 | 39.279 | 1 | 35.37 | L |
| ATOM | 1203 | C | ASN | L | 157 | −2.422 | −7.265 | 38.016 | 1 | 35.99 | L |
| ATOM | 1204 | O | ASN | L | 157 | −1.729 | −8.277 | 37.956 | 1 | 39.57 | L |
| ATOM | 1205 | N | GLY | L | 158 | −2.801 | −6.579 | 36.942 | 1 | 36.3 | L |
| ATOM | 1206 | CA | GLY | L | 158 | −2.381 | −6.983 | 35.612 | 1 | 35.15 | L |
| ATOM | 1207 | C | GLY | L | 158 | −3.187 | −8.1 | 34.965 | 1 | 35.9 | L |
| ATOM | 1208 | O | GLY | L | 158 | −2.68 | −8.797 | 34.082 | 1 | 37.31 | L |
| ATOM | 1209 | N | VAL | L | 159 | −4.44 | −8.269 | 35.388 | 1 | 34.93 | L |
| ATOM | 1210 | CA | VAL | L | 159 | −5.307 | −9.302 | 34.834 | 1 | 31.19 | L |
| ATOM | 1211 | CB | VAL | L | 159 | −6.04 | −10.096 | 35.949 | 1 | 29.22 | L |
| ATOM | 1212 | CG1 | VAL | L | 159 | −6.974 | −11.124 | 35.331 | 1 | 30.23 | L |
| ATOM | 1213 | CG2 | VAL | L | 159 | −5.04 | −10.796 | 36.846 | 1 | 30.04 | L |
| ATOM | 1214 | C | VAL | L | 159 | −6.358 | −8.705 | 33.902 | 1 | 31.34 | L |
| ATOM | 1215 | O | VAL | L | 159 | −6.862 | −7.606 | 34.136 | 1 | 30.61 | L |
| ATOM | 1216 | N | LEU | L | 160 | −6.67 | −9.442 | 32.84 | 1 | 29.96 | L |
| ATOM | 1217 | CA | LEU | L | 160 | −7.671 | −9.036 | 31.863 | 1 | 31.26 | L |
| ATOM | 1218 | CB | LEU | L | 160 | −7.01 | −8.526 | 30.581 | 1 | 33.29 | L |
| ATOM | 1219 | CG | LEU | L | 160 | −7.101 | −7.018 | 30.349 | 1 | 36.88 | L |
| ATOM | 1220 | CD1 | LEU | L | 160 | −6.227 | −6.301 | 31.361 | 1 | 37.95 | L |
| ATOM | 1221 | CD2 | LEU | L | 160 | −6.662 | −6.678 | 28.933 | 1 | 41.51 | L |
| ATOM | 1222 | C | LEU | L | 160 | −8.548 | −10.237 | 31.543 | 1 | 29.31 | L |
| ATOM | 1223 | O | LEU | L | 160 | −8.056 | −11.312 | 31.202 | 1 | 31.42 | L |
| ATOM | 1224 | N | ASN | L | 161 | −9.853 | −10.049 | 31.645 | 1 | 27.25 | L |
| ATOM | 1225 | CA | ASN | L | 161 | −10.783 | −11.138 | 31.397 | 1 | 25.18 | L |
| ATOM | 1226 | CB | ASN | L | 161 | −11.621 | −11.375 | 32.648 | 1 | 23.62 | L |
| ATOM | 1227 | CG | ASN | L | 161 | −10.765 | −11.708 | 33.86 | 1 | 21.66 | L |
| ATOM | 1228 | OD1 | ASN | L | 161 | −11.118 | −11.391 | 34.987 | 1 | 22.63 | L |
| ATOM | 1229 | ND2 | ASN | L | 161 | −9.642 | −12.366 | 33.625 | 1 | 20.25 | L |
| ATOM | 1230 | C | ASN | L | 161 | −11.672 | −10.794 | 30.23 | 1 | 26.21 | L |
| ATOM | 1231 | O | ASN | L | 161 | −12.17 | −9.676 | 30.131 | 1 | 27.59 | L |
| ATOM | 1232 | N | SER | L | 162 | −11.868 | −11.761 | 29.344 | 1 | 25.37 | L |
| ATOM | 1233 | CA | SER | L | 162 | −12.701 | −11.555 | 28.177 | 1 | 25.42 | L |
| ATOM | 1234 | CB | SER | L | 162 | −11.835 | −11.356 | 26.932 | 1 | 23.65 | L |
| ATOM | 1235 | OG | SER | L | 162 | −12.626 | −10.895 | 25.852 | 1 | 25.84 | L |
| ATOM | 1236 | C | SER | L | 162 | −13.628 | −12.741 | 27.969 | 1 | 25.48 | L |
| ATOM | 1237 | O | SER | L | 162 | −13.174 | −13.884 | 27.879 | 1 | 25.86 | L |

TABLE 7-continued

| ATOM | 1238 | N | TRP | L | 163 | −14.925 | −12.458 | 27.9 | 1 | 25.51 | L |
|---|---|---|---|---|---|---|---|---|---|---|---|
| ATOM | 1239 | CA | TRP | L | 163 | −15.942 | −13.481 | 27.695 | 1 | 25.99 | L |
| ATOM | 1240 | CB | TRP | L | 163 | −17.227 | −13.107 | 28.43 | 1 | 27.7 | L |
| ATOM | 1241 | CG | TRP | L | 163 | −17.326 | −13.609 | 29.825 | 1 | 29.4 | L |
| ATOM | 1242 | CD2 | TRP | L | 163 | −16.764 | −13.006 | 30.995 | 1 | 29.19 | L |
| ATOM | 1243 | CE2 | TRP | L | 163 | −17.132 | −13.814 | 32.1 | 1 | 28.6 | L |
| ATOM | 1244 | CE3 | TRP | L | 163 | −15.985 | −11.862 | 31.218 | 1 | 28.24 | L |
| ATOM | 1245 | CD1 | TRP | L | 163 | −17.991 | −14.728 | 30.251 | 1 | 29.98 | L |
| ATOM | 1246 | NE1 | TRP | L | 163 | −17.88 | −14.855 | 31.616 | 1 | 29.35 | L |
| ATOM | 1247 | CZ2 | TRP | L | 163 | −16.749 | −13.515 | 33.407 | 1 | 26.04 | L |
| ATOM | 1248 | CZ3 | TRP | L | 163 | −15.602 | −11.562 | 32.519 | 1 | 31.38 | L |
| ATOM | 1249 | CH2 | TRP | L | 163 | −15.987 | −12.39 | 33.601 | 1 | 31.7 | L |
| ATOM | 1250 | C | TRP | L | 163 | −16.272 | −13.594 | 26.221 | 1 | 28.83 | L |
| ATOM | 1251 | O | TRP | L | 163 | −16.162 | −12.623 | 25.476 | 1 | 32.11 | L |
| ATOM | 1252 | N | THR | L | 164 | −16.681 | −14.782 | 25.806 | 1 | 27.08 | L |
| ATOM | 1253 | CA | THR | L | 164 | −17.078 | −15.006 | 24.434 | 1 | 27.43 | L |
| ATOM | 1254 | CB | THR | L | 164 | −16.682 | −16.405 | 23.983 | 1 | 28.7 | L |
| ATOM | 1255 | OG1 | THR | L | 164 | −17.458 | −17.372 | 24.705 | 1 | 28.81 | L |
| ATOM | 1256 | CG2 | THR | L | 164 | −15.222 | −16.654 | 24.269 | 1 | 31.49 | L |
| ATOM | 1257 | C | THR | L | 164 | −18.602 | −14.94 | 24.459 | 1 | 29.01 | L |
| ATOM | 1258 | O | THR | L | 164 | −19.203 | −14.85 | 25.526 | 1 | 28.21 | L |
| ATOM | 1259 | N | ASP | L | 165 | −19.226 | −14.965 | 23.289 | 1 | 31.53 | L |
| ATOM | 1260 | CA | ASP | L | 165 | −20.681 | −14.982 | 23.207 | 1 | 33.5 | L |
| ATOM | 1261 | CB | ASP | L | 165 | −21.163 | −14.457 | 21.85 | 1 | 41.28 | L |
| ATOM | 1262 | CG | ASP | L | 165 | −21.484 | −12.973 | 21.872 | 1 | 46.64 | L |
| ATOM | 1263 | OD1 | ASP | L | 165 | −22.521 | −12.597 | 22.455 | 1 | 45.9 | L |
| ATOM | 1264 | OD2 | ASP | L | 165 | −20.698 | −12.182 | 21.305 | 1 | 51.89 | L |
| ATOM | 1265 | C | ASP | L | 165 | −21.006 | −16.464 | 23.309 | 1 | 33.28 | L |
| ATOM | 1266 | O | ASP | L | 165 | −20.099 | −17.306 | 23.336 | 1 | 28.73 | L |
| ATOM | 1267 | N | GLN | L | 166 | −22.285 | −16.804 | 23.348 | 1 | 32.73 | L |
| ATOM | 1268 | CA | GLN | L | 166 | −22.624 | −18.211 | 23.435 | 1 | 35.31 | L |
| ATOM | 1269 | CB | GLN | L | 166 | −24.115 | −18.393 | 23.67 | 1 | 36.18 | L |
| ATOM | 1270 | CG | GLN | L | 166 | −24.44 | −18.734 | 25.094 | 1 | 37.34 | L |
| ATOM | 1271 | CD | GLN | L | 166 | −25.92 | −18.774 | 25.338 | 1 | 38.66 | L |
| ATOM | 1272 | OE1 | GLN | L | 166 | −26.635 | −17.825 | 25.012 | 1 | 39.76 | L |
| ATOM | 1273 | NE2 | GLN | L | 166 | −26.397 | −19.87 | 25.919 | 1 | 37.06 | L |
| ATOM | 1274 | C | GLN | L | 166 | −22.194 | −18.962 | 22.186 | 1 | 36.1 | L |
| ATOM | 1275 | O | GLN | L | 166 | −22.494 | −18.554 | 21.065 | 1 | 37.39 | L |
| ATOM | 1276 | N | ASP | L | 167 | −21.486 | −20.066 | 22.392 | 1 | 37.21 | L |
| ATOM | 1277 | CA | ASP | L | 167 | −21.003 | −20.877 | 21.29 | 1 | 37.98 | L |
| ATOM | 1278 | CB | ASP | L | 167 | −19.97 | −21.88 | 21.803 | 1 | 35.08 | L |
| ATOM | 1279 | CG | ASP | L | 167 | −19.118 | −22.442 | 20.692 | 1 | 32.96 | L |
| ATOM | 1280 | OD1 | ASP | L | 167 | −19.565 | −23.384 | 20.013 | 1 | 32.35 | L |
| ATOM | 1281 | OD2 | ASP | L | 167 | −18.004 | −21.921 | 20.487 | 1 | 33.42 | L |
| ATOM | 1282 | C | ASP | L | 167 | −22.147 | −21.6 | 20.572 | 1 | 39.75 | L |
| ATOM | 1283 | O | ASP | L | 167 | −23.015 | −22.209 | 21.198 | 1 | 37.53 | L |
| ATOM | 1284 | N | SER | L | 168 | −22.128 | −21.532 | 19.248 | 1 | 41 | L |
| ATOM | 1285 | CA | SER | L | 168 | −23.165 | −22.144 | 18.429 | 1 | 42.55 | L |
| ATOM | 1286 | CB | SER | L | 168 | −23.013 | −21.678 | 16.982 | 1 | 42.6 | L |
| ATOM | 1287 | OG | SER | L | 168 | −23.892 | −22.39 | 16.133 | 1 | 44.47 | L |
| ATOM | 1288 | C | SER | L | 168 | −23.235 | −23.669 | 18.445 | 1 | 43.61 | L |
| ATOM | 1289 | O | SER | L | 168 | −24.193 | −24.244 | 17.928 | 1 | 43.79 | L |
| ATOM | 1290 | N | LYS | L | 169 | −22.238 | −24.333 | 19.023 | 1 | 43.24 | L |
| ATOM | 1291 | CA | LYS | L | 169 | −22.25 | −25.792 | 19.04 | 1 | 42.34 | L |
| ATOM | 1292 | CB | LYS | L | 169 | −20.822 | −26.342 | 18.94 | 1 | 44.46 | L |
| ATOM | 1293 | CG | LYS | L | 169 | −20.758 | −27.822 | 18.57 | 1 | 47.38 | L |
| ATOM | 1294 | CD | LYS | L | 169 | −19.368 | −28.244 | 18.088 | 1 | 48.53 | L |
| ATOM | 1295 | CE | LYS | L | 169 | −19.399 | −29.643 | 17.459 | 1 | 50.07 | L |
| ATOM | 1296 | NZ | LYS | L | 169 | −18.129 | −30.007 | 16.751 | 1 | 47.84 | L |
| ATOM | 1297 | C | LYS | L | 169 | −22.947 | −26.372 | 20.265 | 1 | 41.98 | L |
| ATOM | 1298 | O | LYS | L | 169 | −23.792 | −27.256 | 20.132 | 1 | 45.03 | L |
| ATOM | 1299 | N | ASP | L | 170 | −22.601 | −25.879 | 21.451 | 1 | 38.81 | L |
| ATOM | 1300 | CA | ASP | L | 170 | −23.208 | −26.369 | 22.684 | 1 | 34.26 | L |
| ATOM | 1301 | CB | ASP | L | 170 | −22.166 | −27.092 | 23.532 | 1 | 34.62 | L |
| ATOM | 1302 | CG | ASP | L | 170 | −20.945 | −26.238 | 23.806 | 1 | 33.54 | L |
| ATOM | 1303 | OD1 | ASP | L | 170 | −21.023 | −25.004 | 23.622 | 1 | 33.09 | L |
| ATOM | 1304 | OD2 | ASP | L | 170 | −19.911 | −26.803 | 24.218 | 1 | 31.32 | L |
| ATOM | 1305 | C | ASP | L | 170 | −23.829 | −25.244 | 23.505 | 1 | 32.56 | L |
| ATOM | 1306 | O | ASP | L | 170 | −24.205 | −25.438 | 24.66 | 1 | 29.27 | L |
| ATOM | 1307 | N | SER | L | 171 | −23.939 | −24.072 | 22.895 | 1 | 30.66 | L |
| ATOM | 1308 | CA | SER | L | 171 | −24.504 | −22.898 | 23.551 | 1 | 32.6 | L |
| ATOM | 1309 | CB | SER | L | 171 | −26.047 | −22.996 | 23.596 | 1 | 34.23 | L |
| ATOM | 1310 | OG | SER | L | 171 | −26.513 | −24.277 | 23.983 | 1 | 38.27 | L |
| ATOM | 1311 | C | SER | L | 171 | −23.929 | −22.596 | 24.945 | 1 | 30.66 | L |
| ATOM | 1312 | O | SER | L | 171 | −24.647 | −22.188 | 25.861 | 1 | 28.18 | L |
| ATOM | 1313 | N | THR | L | 172 | −22.619 | −22.778 | 25.089 | 1 | 29.01 | L |
| ATOM | 1314 | CA | THR | L | 172 | −21.947 | −22.5 | 26.353 | 1 | 25.48 | L |
| ATOM | 1315 | CB | THR | L | 172 | −20.963 | −23.606 | 26.751 | 1 | 26.78 | L |
| ATOM | 1316 | OG1 | THR | L | 172 | −19.894 | −23.643 | 25.799 | 1 | 27.48 | L |

TABLE 7-continued

| | | | | | | | | | | |
|---|---|---|---|---|---|---|---|---|---|---|
| ATOM | 1317 | CG2 | THR | L | 172 | −21.653 | −24.957 | 26.804 | 1 | 27.4 | L |
| ATOM | 1318 | C | THR | L | 172 | −21.117 | −21.248 | 26.183 | 1 | 23.04 | L |
| ATOM | 1319 | O | THR | L | 172 | −20.908 | −20.778 | 25.072 | 1 | 20.92 | L |
| ATOM | 1320 | N | TYR | L | 173 | −20.636 | −20.715 | 27.296 | 1 | 20.97 | L |
| ATOM | 1321 | CA | TYR | L | 173 | −19.803 | −19.541 | 27.25 | 1 | 22.45 | L |
| ATOM | 1322 | CB | TYR | L | 173 | −20.231 | −18.537 | 28.316 | 1 | 22.19 | L |
| ATOM | 1323 | CG | TYR | L | 173 | −21.587 | −17.901 | 28.079 | 1 | 26.18 | L |
| ATOM | 1324 | CD1 | TYR | L | 173 | −21.743 | −16.838 | 27.186 | 1 | 21.86 | L |
| ATOM | 1325 | CE1 | TYR | L | 173 | −22.993 | −16.256 | 26.971 | 1 | 22.12 | L |
| ATOM | 1326 | CD2 | TYR | L | 173 | −22.717 | −18.368 | 28.752 | 1 | 24.39 | L |
| ATOM | 1327 | CE2 | TYR | L | 173 | −23.962 | −17.799 | 28.546 | 1 | 24.98 | L |
| ATOM | 1328 | CZ | TYR | L | 173 | −24.1 | −16.744 | 27.659 | 1 | 25.53 | L |
| ATOM | 1329 | OH | TYR | L | 173 | −25.351 | −16.187 | 27.484 | 1 | 27.31 | L |
| ATOM | 1330 | C | TYR | L | 173 | −18.385 | −19.996 | 27.536 | 1 | 25.87 | L |
| ATOM | 1331 | O | TYR | L | 173 | −18.164 | −21.097 | 28.046 | 1 | 28.06 | L |
| ATOM | 1332 | N | SER | L | 174 | −17.429 | −19.145 | 27.191 | 1 | 24.94 | L |
| ATOM | 1333 | CA | SER | L | 174 | −16.021 | −19.402 | 27.441 | 1 | 23.7 | L |
| ATOM | 1334 | CB | SER | L | 174 | −15.339 | −19.973 | 26.194 | 1 | 24.79 | L |
| ATOM | 1335 | OG | SER | L | 174 | −15.497 | −21.378 | 26.126 | 1 | 22.74 | L |
| ATOM | 1336 | C | SER | L | 174 | −15.401 | −18.062 | 27.809 | 1 | 23.62 | L |
| ATOM | 1337 | O | SER | L | 174 | −15.907 | −17.005 | 27.429 | 1 | 21.15 | L |
| ATOM | 1338 | N | MET | L | 175 | −14.324 | −18.088 | 28.579 | 1 | 26.28 | L |
| ATOM | 1339 | CA | MET | L | 175 | −13.676 | −16.844 | 28.947 | 1 | 28.1 | L |
| ATOM | 1340 | CB | MET | L | 175 | −14.152 | −16.37 | 30.325 | 1 | 28.69 | L |
| ATOM | 1341 | CG | MET | L | 175 | −13.07 | −16.359 | 31.386 | 1 | 36.54 | L |
| ATOM | 1342 | SD | MET | L | 175 | −13.289 | −15.026 | 32.567 | 1 | 40.45 | L |
| ATOM | 1343 | CE | MET | L | 175 | −11.621 | −14.589 | 32.87 | 1 | 41.95 | L |
| ATOM | 1344 | C | MET | L | 175 | −12.158 | −16.974 | 28.915 | 1 | 27.05 | L |
| ATOM | 1345 | O | MET | L | 175 | −11.599 | −18.048 | 29.131 | 1 | 25.75 | L |
| ATOM | 1346 | N | SER | L | 176 | −11.501 | −15.862 | 28.63 | 1 | 27.02 | L |
| ATOM | 1347 | CA | SER | L | 176 | −10.053 | −15.826 | 28.556 | 1 | 27.71 | L |
| ATOM | 1348 | CB | SER | L | 176 | −9.612 | −15.335 | 27.175 | 1 | 25.91 | L |
| ATOM | 1349 | OG | SER | L | 176 | −8.207 | −15.348 | 27.048 | 1 | 28.02 | L |
| ATOM | 1350 | C | SER | L | 176 | −9.542 | −14.88 | 29.619 | 1 | 28.26 | L |
| ATOM | 1351 | O | SER | L | 176 | −9.999 | −13.746 | 29.72 | 1 | 28.42 | L |
| ATOM | 1352 | N | SER | L | 177 | −8.594 | −15.352 | 30.418 | 1 | 30.11 | L |
| ATOM | 1353 | CA | SER | L | 177 | −8.012 | −14.534 | 31.471 | 1 | 29.35 | L |
| ATOM | 1354 | CB | SER | L | 177 | −8.288 | −15.167 | 32.838 | 1 | 27.49 | L |
| ATOM | 1355 | OG | SER | L | 177 | −7.717 | −14.4 | 33.878 | 1 | 28.99 | L |
| ATOM | 1356 | C | SER | L | 177 | −6.507 | −14.432 | 31.231 | 1 | 31.17 | L |
| ATOM | 1357 | O | SER | L | 177 | −5.808 | −15.45 | 31.17 | 1 | 31.02 | L |
| ATOM | 1358 | N | THR | L | 178 | −6.01 | −13.208 | 31.079 | 1 | 31.47 | L |
| ATOM | 1359 | CA | THR | L | 178 | −4.585 | −12.998 | 30.845 | 1 | 31.49 | L |
| ATOM | 1360 | CB | THR | L | 178 | −4.312 | −12.274 | 29.518 | 1 | 29.61 | L |
| ATOM | 1361 | OG1 | THR | L | 178 | −4.819 | −13.049 | 28.434 | 1 | 30.85 | L |
| ATOM | 1362 | CG2 | THR | L | 178 | −2.822 | −12.1 | 29.316 | 1 | 30.54 | L |
| ATOM | 1363 | C | THR | L | 178 | −3.949 | −12.17 | 31.941 | 1 | 32 | L |
| ATOM | 1364 | O | THR | L | 178 | −4.424 | −11.086 | 32.263 | 1 | 32.95 | L |
| ATOM | 1365 | N | LEU | L | 179 | −2.867 | −12.7 | 32.503 | 1 | 33.31 | L |
| ATOM | 1366 | CA | LEU | L | 179 | −2.111 | −12.034 | 33.554 | 1 | 32.35 | L |
| ATOM | 1367 | CB | LEU | L | 179 | −1.936 | −12.973 | 34.739 | 1 | 30.55 | L |
| ATOM | 1368 | CG | LEU | L | 179 | −0.966 | −12.495 | 35.812 | 1 | 31.83 | L |
| ATOM | 1369 | CD1 | LEU | L | 179 | −1.346 | −11.11 | 36.283 | 1 | 33.11 | L |
| ATOM | 1370 | CD2 | LEU | L | 179 | −0.987 | −13.476 | 36.958 | 1 | 33.87 | L |
| ATOM | 1371 | C | LEU | L | 179 | −0.744 | −11.654 | 32.985 | 1 | 34.38 | L |
| ATOM | 1372 | O | LEU | L | 179 | 0.067 | −12.523 | 32.649 | 1 | 33.53 | L |
| ATOM | 1373 | N | THR | L | 180 | −0.49 | −10.354 | 32.872 | 1 | 35.39 | L |
| ATOM | 1374 | CA | THR | L | 180 | 0.77 | −9.881 | 32.319 | 1 | 36.62 | L |
| ATOM | 1375 | CB | THR | L | 180 | 0.533 | −8.674 | 31.397 | 1 | 39.73 | L |
| ATOM | 1376 | OG1 | THR | L | 180 | −0.598 | −8.937 | 30.555 | 1 | 43.88 | L |
| ATOM | 1377 | CG2 | THR | L | 180 | 1.757 | −8.423 | 30.519 | 1 | 38.15 | L |
| ATOM | 1378 | C | THR | L | 180 | 1.769 | −9.495 | 33.403 | 1 | 36.52 | L |
| ATOM | 1379 | O | THR | L | 180 | 1.461 | −8.72 | 34.306 | 1 | 35.29 | L |
| ATOM | 1380 | N | LEU | L | 181 | 2.972 | −10.045 | 33.307 | 1 | 37.48 | L |
| ATOM | 1381 | CA | LEU | L | 181 | 4.013 | −9.756 | 34.28 | 1 | 38.06 | L |
| ATOM | 1382 | CB | LEU | L | 181 | 4.33 | −11.002 | 35.103 | 1 | 41.2 | L |
| ATOM | 1383 | CG | LEU | L | 181 | 3.182 | −11.9 | 35.56 | 1 | 43.89 | L |
| ATOM | 1384 | CD1 | LEU | L | 181 | 3.772 | −13.128 | 36.213 | 1 | 45.68 | L |
| ATOM | 1385 | CD2 | LEU | L | 181 | 2.265 | −11.163 | 36.526 | 1 | 46.83 | L |
| ATOM | 1386 | C | LEU | L | 181 | 5.269 | −9.343 | 33.536 | 1 | 38.17 | L |
| ATOM | 1387 | O | LEU | L | 181 | 5.323 | −9.397 | 32.306 | 1 | 39.52 | L |
| ATOM | 1388 | N | THR | L | 182 | 6.279 | −8.92 | 34.285 | 1 | 37.35 | L |
| ATOM | 1389 | CA | THR | L | 182 | 7.548 | −8.552 | 33.681 | 1 | 35.94 | L |
| ATOM | 1390 | CB | THR | L | 182 | 8.337 | −7.573 | 34.553 | 1 | 34.46 | L |
| ATOM | 1391 | OG1 | THR | L | 182 | 8.89 | −8.283 | 35.665 | 1 | 32.62 | L |
| ATOM | 1392 | CG2 | THR | L | 182 | 7.43 | −6.458 | 35.062 | 1 | 31.83 | L |
| ATOM | 1393 | C | THR | L | 182 | 8.314 | −9.866 | 33.655 | 1 | 36.08 | L |
| ATOM | 1394 | O | THR | L | 182 | 8.057 | −10.746 | 34.481 | 1 | 34.23 | L |
| ATOM | 1395 | N | LYS | L | 183 | 9.246 | −10.004 | 32.716 | 1 | 35.5 | L |

TABLE 7-continued

| | | | | | | | | | | |
|---|---|---|---|---|---|---|---|---|---|---|
| ATOM | 1396 | CA | LYS | L | 183 | 10.034 | −11.225 | 32.623 | 1 | 34.49 | L |
| ATOM | 1397 | CB | LYS | L | 183 | 11.15 | −11.055 | 31.595 | 1 | 33.98 | L |
| ATOM | 1398 | CG | LYS | L | 183 | 11.953 | −12.317 | 31.341 | 1 | 31.95 | L |
| ATOM | 1399 | CD | LYS | L | 183 | 12.894 | −12.128 | 30.166 | 1 | 32.27 | L |
| ATOM | 1400 | CE | LYS | L | 183 | 13.615 | −13.415 | 29.817 | 1 | 33.24 | L |
| ATOM | 1401 | NZ | LYS | L | 183 | 14.518 | −13.856 | 30.91 | 1 | 34.93 | L |
| ATOM | 1402 | C | LYS | L | 183 | 10.637 | −11.575 | 33.982 | 1 | 35.2 | L |
| ATOM | 1403 | O | LYS | L | 183 | 10.611 | −12.733 | 34.403 | 1 | 35.19 | L |
| ATOM | 1404 | N | ASP | L | 184 | 11.166 | −10.568 | 34.669 | 1 | 33.82 | L |
| ATOM | 1405 | CA | ASP | L | 184 | 11.777 | −10.778 | 35.972 | 1 | 34.87 | L |
| ATOM | 1406 | CB | ASP | L | 184 | 12.337 | −9.467 | 36.512 | 1 | 39.39 | L |
| ATOM | 1407 | CG | ASP | L | 184 | 13.617 | −9.066 | 35.828 | 1 | 44.5 | L |
| ATOM | 1408 | OD1 | ASP | L | 184 | 14.481 | −9.953 | 35.637 | 1 | 46.62 | L |
| ATOM | 1409 | OD2 | ASP | L | 184 | 13.76 | −7.871 | 35.492 | 1 | 47.09 | L |
| ATOM | 1410 | C | ASP | L | 184 | 10.842 | −11.382 | 37.004 | 1 | 35.74 | L |
| ATOM | 1411 | O | ASP | L | 184 | 11.188 | −12.381 | 37.644 | 1 | 35.61 | L |
| ATOM | 1412 | N | GLU | L | 185 | 9.672 | −10.766 | 37.178 | 1 | 34.16 | L |
| ATOM | 1413 | CA | GLU | L | 185 | 8.682 | −11.244 | 38.137 | 1 | 34.81 | L |
| ATOM | 1414 | CB | GLU | L | 185 | 7.383 | −10.453 | 38.027 | 1 | 37.64 | L |
| ATOM | 1415 | CG | GLU | L | 185 | 7.409 | −9.078 | 38.631 | 1 | 40.47 | L |
| ATOM | 1416 | CD | GLU | L | 185 | 6.124 | −8.331 | 38.355 | 1 | 46.02 | L |
| ATOM | 1417 | OE1 | GLU | L | 185 | 5.865 | −8.011 | 37.168 | 1 | 46.14 | L |
| ATOM | 1418 | OE2 | GLU | L | 185 | 5.367 | −8.076 | 39.319 | 1 | 48.58 | L |
| ATOM | 1419 | C | GLU | L | 185 | 8.358 | −12.698 | 37.881 | 1 | 34.43 | L |
| ATOM | 1420 | O | GLU | L | 185 | 8.452 | −13.539 | 38.777 | 1 | 34.75 | L |
| ATOM | 1421 | N | TYR | L | 186 | 7.96 | −12.981 | 36.647 | 1 | 32.69 | L |
| ATOM | 1422 | CA | TYR | L | 186 | 7.601 | −14.332 | 36.254 | 1 | 30.01 | L |
| ATOM | 1423 | CB | TYR | L | 186 | 7.285 | −14.375 | 34.757 | 1 | 28.03 | L |
| ATOM | 1424 | CG | TYR | L | 186 | 7.114 | −15.773 | 34.206 | 1 | 23.69 | L |
| ATOM | 1425 | CD1 | TYR | L | 186 | 6.049 | −16.577 | 34.604 | 1 | 20.38 | L |
| ATOM | 1426 | CE1 | TYR | L | 186 | 5.902 | −17.866 | 34.115 | 1 | 21.84 | L |
| ATOM | 1427 | CD2 | TYR | L | 186 | 8.031 | −16.295 | 33.299 | 1 | 21.65 | L |
| ATOM | 1428 | CE2 | TYR | L | 186 | 7.893 | −17.577 | 32.801 | 1 | 23.26 | L |
| ATOM | 1429 | CZ | TYR | L | 186 | 6.826 | −18.361 | 33.21 | 1 | 23.63 | L |
| ATOM | 1430 | OH | TYR | L | 186 | 6.685 | −19.629 | 32.693 | 1 | 25.99 | L |
| ATOM | 1431 | C | TYR | L | 186 | 8.69 | −15.347 | 36.578 | 1 | 29.28 | L |
| ATOM | 1432 | O | TYR | L | 186 | 8.389 | −16.464 | 36.983 | 1 | 28.24 | L |
| ATOM | 1433 | N | GLU | L | 187 | 9.951 | −14.962 | 36.421 | 1 | 29.32 | L |
| ATOM | 1434 | CA | GLU | L | 187 | 11.042 | −15.889 | 36.687 | 1 | 31.9 | L |
| ATOM | 1435 | CB | GLU | L | 187 | 12.259 | −15.514 | 35.843 | 1 | 35.89 | L |
| ATOM | 1436 | CG | GLU | L | 187 | 11.983 | −15.468 | 34.352 | 1 | 41.42 | L |
| ATOM | 1437 | CD | GLU | L | 187 | 13.249 | −15.31 | 33.531 | 1 | 46.71 | L |
| ATOM | 1438 | OE1 | GLU | L | 187 | 14.167 | −14.586 | 33.985 | 1 | 49.02 | L |
| ATOM | 1439 | OE2 | GLU | L | 187 | 13.322 | −15.896 | 32.426 | 1 | 47.81 | L |
| ATOM | 1440 | C | GLU | L | 187 | 11.466 | −16.045 | 38.146 | 1 | 30.53 | L |
| ATOM | 1441 | O | GLU | L | 187 | 12.341 | −16.844 | 38.448 | 1 | 30.22 | L |
| ATOM | 1442 | N | ARG | L | 188 | 10.858 | −15.291 | 39.051 | 1 | 30.76 | L |
| ATOM | 1443 | CA | ARG | L | 188 | 11.216 | −15.385 | 40.459 | 1 | 32.11 | L |
| ATOM | 1444 | CB | ARG | L | 188 | 11.141 | −14.004 | 41.118 | 1 | 34.69 | L |
| ATOM | 1445 | CG | ARG | L | 188 | 12.121 | −12.992 | 40.546 | 1 | 40.37 | L |
| ATOM | 1446 | CD | ARG | L | 188 | 13.537 | −13.11 | 41.129 | 1 | 43.37 | L |
| ATOM | 1447 | NE | ARG | L | 188 | 14.184 | −14.411 | 40.938 | 1 | 47.83 | L |
| ATOM | 1448 | CZ | ARG | L | 188 | 14.139 | −15.416 | 41.815 | 1 | 47.96 | L |
| ATOM | 1449 | NH1 | ARG | L | 188 | 13.473 | −15.286 | 42.956 | 1 | 45.99 | L |
| ATOM | 1450 | NH2 | ARG | L | 188 | 14.774 | −16.551 | 41.557 | 1 | 47.26 | L |
| ATOM | 1451 | C | ARG | L | 188 | 10.289 | −16.34 | 41.189 | 1 | 32.53 | L |
| ATOM | 1452 | O | ARG | L | 188 | 10.504 | −16.664 | 42.356 | 1 | 33.78 | L |
| ATOM | 1453 | N | HIS | L | 189 | 9.266 | −16.807 | 40.486 | 1 | 33.05 | L |
| ATOM | 1454 | CA | HIS | L | 189 | 8.282 | −17.69 | 41.086 | 1 | 31.8 | L |
| ATOM | 1455 | CB | HIS | L | 189 | 6.939 | −16.973 | 41.069 | 1 | 30.04 | L |
| ATOM | 1456 | CG | HIS | L | 189 | 6.96 | −15.68 | 41.821 | 1 | 28.38 | L |
| ATOM | 1457 | CD2 | HIS | L | 189 | 7.114 | −14.403 | 41.395 | 1 | 27.92 | L |
| ATOM | 1458 | ND1 | HIS | L | 189 | 6.897 | −15.621 | 43.198 | 1 | 25.92 | L |
| ATOM | 1459 | CE1 | HIS | L | 189 | 7.012 | −14.363 | 43.586 | 1 | 29.08 | L |
| ATOM | 1460 | NE2 | HIS | L | 189 | 7.146 | −13.604 | 42.512 | 1 | 27.83 | L |
| ATOM | 1461 | C | HIS | L | 189 | 8.183 | −19.083 | 40.467 | 1 | 33.49 | L |
| ATOM | 1462 | O | HIS | L | 189 | 8.781 | −19.368 | 39.434 | 1 | 33.11 | L |
| ATOM | 1463 | N | ASN | L | 190 | 7.418 | −19.951 | 41.113 | 1 | 33.72 | L |
| ATOM | 1464 | CA | ASN | L | 190 | 7.292 | −21.312 | 40.647 | 1 | 34.37 | L |
| ATOM | 1465 | CB | ASN | L | 190 | 7.859 | −22.254 | 41.707 | 1 | 39.62 | L |
| ATOM | 1466 | CG | ASN | L | 190 | 7.431 | −23.686 | 41.488 | 1 | 45.15 | L |
| ATOM | 1467 | OD1 | ASN | L | 190 | 7.872 | −24.336 | 40.537 | 1 | 47.16 | L |
| ATOM | 1468 | ND2 | ASN | L | 190 | 6.561 | −24.188 | 42.364 | 1 | 44.99 | L |
| ATOM | 1469 | C | ASN | L | 190 | 5.886 | −21.779 | 40.261 | 1 | 32.92 | L |
| ATOM | 1470 | O | ASN | L | 190 | 5.669 | −22.211 | 39.126 | 1 | 32.41 | L |
| ATOM | 1471 | N | SER | L | 191 | 4.942 | −21.726 | 41.2 | 1 | 29.03 | L |
| ATOM | 1472 | CA | SER | L | 191 | 3.583 | −22.178 | 40.91 | 1 | 26.27 | L |
| ATOM | 1473 | CB | SER | L | 191 | 2.982 | −22.937 | 42.091 | 1 | 27.46 | L |
| ATOM | 1474 | OG | SER | L | 191 | 1.622 | −23.25 | 41.826 | 1 | 27.07 | L |

TABLE 7-continued

| | | | | | | | | | | |
|---|---|---|---|---|---|---|---|---|---|---|
| ATOM | 1475 | C | SER | L | 191 | 2.601 | −21.101 | 40.495 | 1 | 24.38 | L |
| ATOM | 1476 | O | SER | L | 191 | 2.327 | −20.154 | 41.237 | 1 | 23.92 | L |
| ATOM | 1477 | N | TYR | L | 192 | 2.08 | −21.268 | 39.287 | 1 | 20.25 | L |
| ATOM | 1478 | CA | TYR | L | 192 | 1.096 | −20.367 | 38.734 | 1 | 20.14 | L |
| ATOM | 1479 | CB | TYR | L | 192 | 1.518 | −19.919 | 37.342 | 1 | 19.68 | L |
| ATOM | 1480 | CG | TYR | L | 192 | 2.707 | −19.005 | 37.396 | 1 | 19.45 | L |
| ATOM | 1481 | CD1 | TYR | L | 192 | 3.999 | −19.511 | 37.535 | 1 | 17.45 | L |
| ATOM | 1482 | CE1 | TYR | L | 192 | 5.096 | −18.654 | 37.658 | 1 | 21.02 | L |
| ATOM | 1483 | CD2 | TYR | L | 192 | 2.536 | −17.623 | 37.377 | 1 | 19.72 | L |
| ATOM | 1484 | CE2 | TYR | L | 192 | 3.617 | −16.761 | 37.497 | 1 | 21.17 | L |
| ATOM | 1485 | CZ | TYR | L | 192 | 4.892 | −17.278 | 37.636 | 1 | 21.38 | L |
| ATOM | 1486 | OH | TYR | L | 192 | 5.951 | −16.405 | 37.735 | 1 | 24.43 | L |
| ATOM | 1487 | C | TYR | L | 192 | −0.23 | −21.114 | 38.693 | 1 | 21.58 | L |
| ATOM | 1488 | O | TYR | L | 192 | −0.367 | −22.145 | 38.032 | 1 | 21.82 | L |
| ATOM | 1489 | N | THR | L | 193 | −1.209 | −20.588 | 39.409 | 1 | 20.4 | L |
| ATOM | 1490 | CA | THR | L | 193 | −2.491 | −21.243 | 39.485 | 1 | 24.31 | L |
| ATOM | 1491 | CB | THR | L | 193 | −2.757 | −21.705 | 40.925 | 1 | 26.79 | L |
| ATOM | 1492 | OG1 | THR | L | 193 | −1.554 | −22.253 | 41.48 | 1 | 31.26 | L |
| ATOM | 1493 | CG2 | THR | L | 193 | −3.828 | −22.76 | 40.954 | 1 | 25.88 | L |
| ATOM | 1494 | C | THR | L | 193 | −3.628 | −20.347 | 39.048 | 1 | 25.3 | L |
| ATOM | 1495 | O | THR | L | 193 | −3.688 | −19.173 | 39.397 | 1 | 26.69 | L |
| ATOM | 1496 | N | CYS | L | 194 | −4.535 | −20.923 | 38.279 | 1 | 25.93 | L |
| ATOM | 1497 | CA | CYS | L | 194 | −5.703 | −20.209 | 37.8 | 1 | 28.68 | L |
| ATOM | 1498 | C | CYS | L | 194 | −6.9 | −20.9 | 38.446 | 1 | 26.29 | L |
| ATOM | 1499 | O | CYS | L | 194 | −7.132 | −22.088 | 38.219 | 1 | 23.6 | L |
| ATOM | 1500 | CB | CYS | L | 194 | −5.776 | −20.302 | 36.275 | 1 | 30.58 | L |
| ATOM | 1501 | SG | CYS | L | 194 | −7.316 | −19.641 | 35.58 | 1 | 37.8 | L |
| ATOM | 1502 | N | GLU | L | 195 | −7.645 | −20.167 | 39.267 | 1 | 25.68 | L |
| ATOM | 1503 | CA | GLU | L | 195 | −8.787 | −20.757 | 39.951 | 1 | 24.58 | L |
| ATOM | 1504 | CB | GLU | L | 195 | −8.678 | −20.557 | 41.46 | 1 | 30.25 | L |
| ATOM | 1505 | CG | GLU | L | 195 | −7.31 | −20.86 | 42.031 | 1 | 33.55 | L |
| ATOM | 1506 | CD | GLU | L | 195 | −7.349 | −21.025 | 43.526 | 1 | 38.55 | L |
| ATOM | 1507 | OE1 | GLU | L | 195 | −8.034 | −20.212 | 44.191 | 1 | 41.68 | L |
| ATOM | 1508 | OE2 | GLU | L | 195 | −6.695 | −21.961 | 44.035 | 1 | 40.72 | L |
| ATOM | 1509 | C | GLU | L | 195 | −10.101 | −20.19 | 39.468 | 1 | 23.83 | L |
| ATOM | 1510 | O | GLU | L | 195 | −10.289 | −18.972 | 39.395 | 1 | 19.93 | L |
| ATOM | 1511 | N | ALA | L | 196 | −11.012 | −21.101 | 39.15 | 1 | 23.99 | L |
| ATOM | 1512 | CA | ALA | L | 196 | −12.324 | −20.738 | 38.654 | 1 | 23.37 | L |
| ATOM | 1513 | CB | ALA | L | 196 | −12.597 | −21.475 | 37.353 | 1 | 20.82 | L |
| ATOM | 1514 | C | ALA | L | 196 | −13.408 | −21.064 | 39.662 | 1 | 23.23 | L |
| ATOM | 1515 | O | ALA | L | 196 | −13.475 | −22.174 | 40.185 | 1 | 25.37 | L |
| ATOM | 1516 | N | THR | L | 197 | −14.25 | −20.084 | 39.946 | 1 | 24.13 | L |
| ATOM | 1517 | CA | THR | L | 197 | −15.367 | −20.288 | 40.851 | 1 | 22.79 | L |
| ATOM | 1518 | CB | THR | L | 197 | −15.396 | −19.231 | 41.964 | 1 | 23.35 | L |
| ATOM | 1519 | OG1 | THR | L | 197 | −14.312 | −19.483 | 42.862 | 1 | 28.46 | L |
| ATOM | 1520 | CG2 | THR | L | 197 | −16.705 | −19.293 | 42.746 | 1 | 24.14 | L |
| ATOM | 1521 | C | THR | L | 197 | −16.599 | −20.187 | 39.968 | 1 | 23.18 | L |
| ATOM | 1522 | O | THR | L | 197 | −16.814 | −19.182 | 39.288 | 1 | 20.44 | L |
| ATOM | 1523 | N | HIS | L | 198 | −17.385 | −21.256 | 39.962 | 1 | 24.07 | L |
| ATOM | 1524 | CA | HIS | L | 198 | −18.579 | −21.34 | 39.143 | 1 | 24.32 | L |
| ATOM | 1525 | CB | HIS | L | 198 | −18.202 | −21.968 | 37.803 | 1 | 25.38 | L |
| ATOM | 1526 | CG | HIS | L | 198 | −19.321 | −22.008 | 36.815 | 1 | 29.02 | L |
| ATOM | 1527 | CD2 | HIS | L | 198 | −19.631 | −21.182 | 35.788 | 1 | 28.67 | L |
| ATOM | 1528 | ND1 | HIS | L | 198 | −20.294 | −22.983 | 36.833 | 1 | 29.44 | L |
| ATOM | 1529 | CE1 | HIS | L | 198 | −21.157 | −22.756 | 35.858 | 1 | 31.04 | L |
| ATOM | 1530 | NE2 | HIS | L | 198 | −20.778 | −21.669 | 35.21 | 1 | 30.62 | L |
| ATOM | 1531 | C | HIS | L | 198 | −19.603 | −22.189 | 39.895 | 1 | 26.72 | L |
| ATOM | 1532 | O | HIS | L | 198 | −19.236 | −23.036 | 40.711 | 1 | 25.66 | L |
| ATOM | 1533 | N | LYS | L | 199 | −20.884 | −21.97 | 39.622 | 1 | 25.17 | L |
| ATOM | 1534 | CA | LYS | L | 199 | −21.927 | −22.696 | 40.332 | 1 | 25.25 | L |
| ATOM | 1535 | CB | LYS | L | 199 | −23.293 | −22.121 | 39.98 | 1 | 25.87 | L |
| ATOM | 1536 | CG | LYS | L | 199 | −23.775 | −22.463 | 38.59 | 1 | 25.86 | L |
| ATOM | 1537 | CD | LYS | L | 199 | −25.151 | −21.89 | 38.392 | 1 | 28.54 | L |
| ATOM | 1538 | CE | LYS | L | 199 | −26.118 | −22.43 | 39.436 | 1 | 30.74 | L |
| ATOM | 1539 | NZ | LYS | L | 199 | −27.463 | −21.792 | 39.348 | 1 | 33.3 | L |
| ATOM | 1540 | C | LYS | L | 199 | −21.956 | −24.204 | 40.127 | 1 | 26.62 | L |
| ATOM | 1541 | O | LYS | L | 199 | −22.658 | −24.907 | 40.85 | 1 | 28.56 | L |
| ATOM | 1542 | N | THR | L | 200 | −21.205 | −24.704 | 39.151 | 1 | 27.16 | L |
| ATOM | 1543 | CA | THR | L | 200 | −21.176 | −26.138 | 38.876 | 1 | 26.19 | L |
| ATOM | 1544 | CB | THR | L | 200 | −20.77 | −26.402 | 37.422 | 1 | 25.98 | L |
| ATOM | 1545 | OG1 | THR | L | 200 | −19.635 | −25.595 | 37.094 | 1 | 26.58 | L |
| ATOM | 1546 | CG2 | THR | L | 200 | −21.919 | −26.069 | 36.477 | 1 | 26.9 | L |
| ATOM | 1547 | C | THR | L | 200 | −20.221 | −26.893 | 39.8 | 1 | 27.16 | L |
| ATOM | 1548 | O | THR | L | 200 | −20.068 | −28.119 | 39.711 | 1 | 27.77 | L |
| ATOM | 1549 | N | SER | L | 201 | −19.577 | −26.153 | 40.691 | 1 | 25.31 | L |
| ATOM | 1550 | CA | SER | L | 201 | −18.645 | −26.747 | 41.63 | 1 | 24.1 | L |
| ATOM | 1551 | CB | SER | L | 201 | −17.229 | −26.682 | 41.078 | 1 | 20.07 | L |
| ATOM | 1552 | OG | SER | L | 201 | −16.317 | −27.119 | 42.061 | 1 | 18.73 | L |
| ATOM | 1553 | C | SER | L | 201 | −18.689 | −26.041 | 42.978 | 1 | 25.8 | L |

TABLE 7-continued

| | | | | | | | | | | |
|---|---|---|---|---|---|---|---|---|---|---|
| ATOM | 1554 | O | SER | L | 201 | −18.703 | −24.813 | 43.053 | 1 | 23.37 | L |
| ATOM | 1555 | N | THR | L | 202 | −18.717 | −26.826 | 44.046 | 1 | 28.38 | L |
| ATOM | 1556 | CA | THR | L | 202 | −18.74 | −26.261 | 45.385 | 1 | 29.58 | L |
| ATOM | 1557 | CB | THR | L | 202 | −19.066 | −27.341 | 46.424 | 1 | 30.37 | L |
| ATOM | 1558 | OG1 | THR | L | 202 | −20.407 | −27.803 | 46.217 | 1 | 33.81 | L |
| ATOM | 1559 | CG2 | THR | L | 202 | −18.931 | −26.788 | 47.826 | 1 | 30.43 | L |
| ATOM | 1560 | C | THR | L | 202 | −17.375 | −25.647 | 45.685 | 1 | 28.79 | L |
| ATOM | 1561 | O | THR | L | 202 | −17.274 | −24.594 | 46.316 | 1 | 26.39 | L |
| ATOM | 1562 | N | SER | L | 203 | −16.326 | −26.303 | 45.209 | 1 | 28.25 | L |
| ATOM | 1563 | CA | SER | L | 203 | −14.973 | −25.823 | 45.426 | 1 | 31.48 | L |
| ATOM | 1564 | CB | SER | L | 203 | −14.04 | −26.985 | 45.75 | 1 | 30.8 | L |
| ATOM | 1565 | OG | SER | L | 203 | −13.848 | −27.801 | 44.603 | 1 | 35.58 | L |
| ATOM | 1566 | C | SER | L | 203 | −14.467 | −25.138 | 44.173 | 1 | 32.55 | L |
| ATOM | 1567 | O | SER | L | 203 | −15.096 | −25.197 | 43.121 | 1 | 34.09 | L |
| ATOM | 1568 | N | PRO | L | 204 | −13.311 | −24.476 | 44.271 | 1 | 32.91 | L |
| ATOM | 1569 | CD | PRO | L | 204 | −12.652 | −24.015 | 45.503 | 1 | 34.19 | L |
| ATOM | 1570 | CA | PRO | L | 204 | −12.757 | −23.796 | 43.103 | 1 | 29.91 | L |
| ATOM | 1571 | CB | PRO | L | 204 | −11.681 | −22.896 | 43.705 | 1 | 32.01 | L |
| ATOM | 1572 | CG | PRO | L | 204 | −12.184 | −22.64 | 45.097 | 1 | 33.94 | L |
| ATOM | 1573 | C | PRO | L | 204 | −12.163 | −24.812 | 42.144 | 1 | 29.65 | L |
| ATOM | 1574 | O | PRO | L | 204 | −11.408 | −25.7 | 42.558 | 1 | 28.69 | L |
| ATOM | 1575 | N | ILE | L | 205 | −12.526 | −24.688 | 40.872 | 1 | 27.52 | L |
| ATOM | 1576 | CA | ILE | L | 205 | −12.014 | −25.561 | 39.823 | 1 | 25.93 | L |
| ATOM | 1577 | CB | ILE | L | 205 | −12.931 | −25.553 | 38.608 | 1 | 24.84 | L |
| ATOM | 1578 | CG2 | ILE | L | 205 | −12.352 | −26.442 | 37.528 | 1 | 22.4 | L |
| ATOM | 1579 | CG1 | ILE | L | 205 | −14.333 | −25.996 | 39.027 | 1 | 22.64 | L |
| ATOM | 1580 | CD1 | ILE | L | 205 | −15.31 | −26.084 | 37.893 | 1 | 27.42 | L |
| ATOM | 1581 | C | ILE | L | 205 | −10.689 | −24.931 | 39.442 | 1 | 27.85 | L |
| ATOM | 1582 | O | ILE | L | 205 | −10.663 | −23.817 | 38.908 | 1 | 27.35 | L |
| ATOM | 1583 | N | VAL | L | 206 | −9.592 | −25.641 | 39.693 | 1 | 29.18 | L |
| ATOM | 1584 | CA | VAL | L | 206 | −8.279 | −25.071 | 39.438 | 1 | 29.6 | L |
| ATOM | 1585 | CB | VAL | L | 206 | −7.581 | −24.788 | 40.783 | 1 | 31.17 | L |
| ATOM | 1586 | CG1 | VAL | L | 206 | −6.77 | −26.007 | 41.228 | 1 | 28.47 | L |
| ATOM | 1587 | CG2 | VAL | L | 206 | −6.725 | −23.558 | 40.663 | 1 | 32.18 | L |
| ATOM | 1588 | C | VAL | L | 206 | −7.317 | −25.858 | 38.556 | 1 | 29.44 | L |
| ATOM | 1589 | O | VAL | L | 206 | −7.346 | −27.087 | 38.523 | 1 | 33.05 | L |
| ATOM | 1590 | N | LYS | L | 207 | −6.443 | −25.135 | 37.862 | 1 | 26.67 | L |
| ATOM | 1591 | CA | LYS | L | 207 | −5.449 | −25.747 | 36.989 | 1 | 26.89 | L |
| ATOM | 1592 | CB | LYS | L | 207 | −5.934 | −25.682 | 35.546 | 1 | 30.37 | L |
| ATOM | 1593 | CG | LYS | L | 207 | −5.217 | −26.621 | 34.596 | 1 | 33.58 | L |
| ATOM | 1594 | CD | LYS | L | 207 | −5.748 | −28.03 | 34.722 | 1 | 35.21 | L |
| ATOM | 1595 | CE | LYS | L | 207 | −5.121 | −28.948 | 33.679 | 1 | 40.24 | L |
| ATOM | 1596 | NZ | LYS | L | 207 | −3.641 | −29.062 | 33.831 | 1 | 44.1 | L |
| ATOM | 1597 | C | LYS | L | 207 | −4.124 | −24.986 | 37.131 | 1 | 26.74 | L |
| ATOM | 1598 | O | LYS | L | 207 | −4.121 | −23.767 | 37.258 | 1 | 26.03 | L |
| ATOM | 1599 | N | SER | L | 208 | −3 | −25.694 | 37.096 | 1 | 28.03 | L |
| ATOM | 1600 | CA | SER | L | 208 | −1.705 | −25.034 | 37.239 | 1 | 30.63 | L |
| ATOM | 1601 | CB | SER | L | 208 | −1.218 | −25.113 | 38.701 | 1 | 32.54 | L |
| ATOM | 1602 | OG | SER | L | 208 | −2.183 | −24.625 | 39.623 | 1 | 35.32 | L |
| ATOM | 1603 | C | SER | L | 208 | −0.611 | −25.616 | 36.347 | 1 | 29.96 | L |
| ATOM | 1604 | O | SER | L | 208 | −0.747 | −26.708 | 35.793 | 1 | 29.65 | L |
| ATOM | 1605 | N | PHE | L | 209 | 0.461 | −24.848 | 36.185 | 1 | 31.99 | L |
| ATOM | 1606 | CA | PHE | L | 209 | 1.641 | −25.286 | 35.441 | 1 | 33.23 | L |
| ATOM | 1607 | CB | PHE | L | 209 | 1.782 | −24.561 | 34.087 | 1 | 28.82 | L |
| ATOM | 1608 | CG | PHE | L | 209 | 2.181 | −23.123 | 34.169 | 1 | 27.52 | L |
| ATOM | 1609 | CD1 | PHE | L | 209 | 3.47 | −22.758 | 34.552 | 1 | 26.04 | L |
| ATOM | 1610 | CD2 | PHE | L | 209 | 1.297 | −22.13 | 33.752 | 1 | 27.83 | L |
| ATOM | 1611 | CE1 | PHE | L | 209 | 3.876 | −21.42 | 34.509 | 1 | 25.58 | L |
| ATOM | 1612 | CE2 | PHE | L | 209 | 1.692 | −20.791 | 33.704 | 1 | 26.94 | L |
| ATOM | 1613 | CZ | PHE | L | 209 | 2.985 | −20.436 | 34.081 | 1 | 25.94 | L |
| ATOM | 1614 | C | PHE | L | 209 | 2.699 | −24.947 | 36.477 | 1 | 35.23 | L |
| ATOM | 1615 | O | PHE | L | 209 | 2.397 | −24.216 | 37.418 | 1 | 33.97 | L |
| ATOM | 1616 | N | ASN | L | 210 | 3.928 | −25.414 | 36.339 | 1 | 40.46 | L |
| ATOM | 1617 | CA | ASN | L | 210 | 4.809 | −25.173 | 37.461 | 1 | 45.08 | L |
| ATOM | 1618 | CB | ASN | L | 210 | 4.696 | −26.398 | 38.364 | 1 | 46.07 | L |
| ATOM | 1619 | CG | ASN | L | 210 | 4.953 | −26.079 | 39.798 | 1 | 47.59 | L |
| ATOM | 1620 | OD1 | ASN | L | 210 | 6.076 | −26.213 | 40.281 | 1 | 52.21 | L |
| ATOM | 1621 | ND2 | ASN | L | 210 | 3.912 | −25.655 | 40.503 | 1 | 48.79 | L |
| ATOM | 1622 | C | ASN | L | 210 | 6.264 | −24.76 | 37.397 | 1 | 48.6 | L |
| ATOM | 1623 | O | ASN | L | 210 | 7.071 | −25.309 | 38.136 | 1 | 52.51 | L |
| ATOM | 1624 | N | ARG | L | 211 | 6.63 | −23.81 | 36.553 | 1 | 50.38 | L |
| ATOM | 1625 | CA | ARG | L | 211 | 8.027 | −23.381 | 36.531 | 1 | 55.12 | L |
| ATOM | 1626 | CB | ARG | L | 211 | 8.854 | −24.314 | 35.647 | 1 | 56.21 | L |
| ATOM | 1627 | CG | ARG | L | 211 | 10.013 | −25.016 | 36.385 | 1 | 54.65 | L |
| ATOM | 1628 | CD | ARG | L | 211 | 9.524 | −26.033 | 37.398 | 1 | 56.33 | L |
| ATOM | 1629 | NE | ARG | L | 211 | 9.655 | −27.429 | 36.963 | 1 | 58.85 | L |
| ATOM | 1630 | CZ | ARG | L | 211 | 9.003 | −27.997 | 35.945 | 1 | 59.6 | L |
| ATOM | 1631 | NH1 | ARG | L | 211 | 8.138 | −27.309 | 35.206 | 1 | 60.35 | L |
| ATOM | 1632 | NH2 | ARG | L | 211 | 9.228 | −29.273 | 35.659 | 1 | 59.17 | L |

TABLE 7-continued

| | | | | | | | | | | |
|---|---|---|---|---|---|---|---|---|---|---|
| ATOM | 1633 | C | ARG | L | 211 | 8.086 | −21.948 | 36.016 | 1 | 59.17 | L |
| ATOM | 1634 | O | ARG | L | 211 | 7.1 | −21.448 | 35.472 | 1 | 63.18 | L |
| ATOM | 1635 | N | ASN | L | 212 | 9.206 | −21.263 | 36.227 | 1 | 62.81 | L |
| ATOM | 1636 | CA | ASN | L | 212 | 9.343 | −19.884 | 35.751 | 1 | 64.64 | L |
| ATOM | 1637 | CB | ASN | L | 212 | 9.893 | −18.979 | 36.856 | 1 | 64.51 | L |
| ATOM | 1638 | CG | ASN | L | 212 | 11.232 | −19.443 | 37.385 | 1 | 65.7 | L |
| ATOM | 1639 | OD1 | ASN | L | 212 | 11.303 | −20.364 | 38.197 | 1 | 69.15 | L |
| ATOM | 1640 | ND2 | ASN | L | 212 | 12.305 | −18.809 | 36.927 | 1 | 66.81 | L |
| ATOM | 1641 | C | ASN | L | 212 | 10.256 | −19.809 | 34.527 | 1 | 68.47 | L |
| ATOM | 1642 | O | ASN | L | 212 | 11.336 | −19.187 | 34.621 | 1 | 70.6 | L |
| ATOM | 1643 | OXT | ASN | L | 212 | 9.884 | −20.387 | 33.481 | 1 | 70.56 | L |
| ATOM | 1644 | CB | GLN | H | 1 | −22.086 | −14.508 | −7.075 | 1 | 26.29 | H |
| ATOM | 1645 | CG | GLN | H | 1 | −20.652 | −14.421 | −7.602 | 1 | 32.57 | H |
| ATOM | 1646 | CD | GLN | H | 1 | −20.557 | −14.579 | −9.118 | 1 | 34.89 | H |
| ATOM | 1647 | OE1 | GLN | H | 1 | −21.038 | −15.562 | −9.679 | 1 | 37.29 | H |
| ATOM | 1648 | NE2 | GLN | H | 1 | −19.934 | −13.606 | −9.784 | 1 | 36.04 | H |
| ATOM | 1649 | C | GLN | H | 1 | −22.835 | −12.119 | −7.279 | 1 | 21.84 | H |
| ATOM | 1650 | O | GLN | H | 1 | −21.754 | −11.559 | −7.446 | 1 | 22.55 | H |
| ATOM | 1651 | N | GLN | H | 1 | −22.88 | −13.61 | −9.234 | 1 | 25.61 | H |
| ATOM | 1652 | CA | GLN | H | 1 | −23.062 | −13.544 | −7.756 | 1 | 24.49 | H |
| ATOM | 1653 | N | VAL | H | 2 | −23.868 | −11.52 | −6.71 | 1 | 21.4 | H |
| ATOM | 1654 | CA | VAL | H | 2 | −23.753 | −10.155 | −6.218 | 1 | 25.31 | H |
| ATOM | 1655 | CB | VAL | H | 2 | −25.111 | −9.613 | −5.698 | 1 | 24.56 | H |
| ATOM | 1656 | CG1 | VAL | H | 2 | −24.905 | −8.286 | −4.997 | 1 | 22.03 | H |
| ATOM | 1657 | CG2 | VAL | H | 2 | −26.08 | −9.436 | −6.85 | 1 | 25.35 | H |
| ATOM | 1658 | C | VAL | H | 2 | −22.765 | −10.104 | −5.065 | 1 | 27.12 | H |
| ATOM | 1659 | O | VAL | H | 2 | −22.928 | −10.809 | −4.076 | 1 | 26.63 | H |
| ATOM | 1660 | N | GLN | H | 3 | −21.735 | −9.28 | −5.198 | 1 | 31.38 | H |
| ATOM | 1661 | CA | GLN | H | 3 | −20.761 | −9.13 | −4.13 | 1 | 35.8 | H |
| ATOM | 1662 | CB | GLN | H | 3 | −19.685 | −10.216 | −4.223 | 1 | 37.26 | H |
| ATOM | 1663 | CG | GLN | H | 3 | −19.196 | −10.531 | −5.609 | 1 | 42.81 | H |
| ATOM | 1664 | CD | GLN | H | 3 | −18.323 | −11.772 | −5.617 | 1 | 46.01 | H |
| ATOM | 1665 | OE1 | GLN | H | 3 | −18.748 | −12.846 | −5.186 | 1 | 45.7 | H |
| ATOM | 1666 | NE2 | GLN | H | 3 | −17.096 | −11.631 | −6.101 | 1 | 47.01 | H |
| ATOM | 1667 | C | GLN | H | 3 | −20.134 | −7.736 | −4.069 | 1 | 36.25 | H |
| ATOM | 1668 | O | GLN | H | 3 | −19.987 | −7.053 | −5.086 | 1 | 34.29 | H |
| ATOM | 1669 | N | LEU | H | 4 | −19.777 | −7.328 | −2.855 | 1 | 36.84 | H |
| ATOM | 1670 | CA | LEU | H | 4 | −19.192 | −6.016 | −2.615 | 1 | 38.19 | H |
| ATOM | 1671 | CB | LEU | H | 4 | −20.171 | −5.176 | −1.792 | 1 | 37.01 | H |
| ATOM | 1672 | CG | LEU | H | 4 | −21.599 | −5.129 | −2.335 | 1 | 35.4 | H |
| ATOM | 1673 | CD1 | LEU | H | 4 | −22.525 | −4.511 | −1.302 | 1 | 32.9 | H |
| ATOM | 1674 | CD2 | LEU | H | 4 | −21.615 | −4.341 | −3.639 | 1 | 35.39 | H |
| ATOM | 1675 | C | LEU | H | 4 | −17.846 | −6.096 | −1.887 | 1 | 38.77 | H |
| ATOM | 1676 | O | LEU | H | 4 | −17.777 | −6.489 | −0.718 | 1 | 39.1 | H |
| ATOM | 1677 | N | GLN | H | 5 | −16.78 | −5.708 | −2.579 | 1 | 37.65 | H |
| ATOM | 1678 | CA | GLN | H | 5 | −15.457 | −5.74 | −1.986 | 1 | 38.61 | H |
| ATOM | 1679 | CB | GLN | H | 5 | −14.459 | −6.348 | −2.975 | 1 | 41.32 | H |
| ATOM | 1680 | CG | GLN | H | 5 | −13.209 | −6.874 | −2.299 | 1 | 51.07 | H |
| ATOM | 1681 | CD | GLN | H | 5 | −13.536 | −7.799 | −1.128 | 1 | 56.81 | H |
| ATOM | 1682 | OE1 | GLN | H | 5 | −13.909 | −8.962 | −1.316 | 1 | 59.1 | H |
| ATOM | 1683 | NE2 | GLN | H | 5 | −13.413 | −7.275 | 0.089 | 1 | 59.64 | H |
| ATOM | 1684 | C | GLN | H | 5 | −15.035 | −4.326 | −1.574 | 1 | 36.03 | H |
| ATOM | 1685 | O | GLN | H | 5 | −14.778 | −3.474 | −2.42 | 1 | 36.13 | H |
| ATOM | 1686 | N | GLN | H | 6 | −14.974 | −4.086 | −0.267 | 1 | 33.5 | H |
| ATOM | 1687 | CA | GLN | H | 6 | −14.607 | −2.776 | 0.273 | 1 | 33.36 | H |
| ATOM | 1688 | CB | GLN | H | 6 | −15.299 | −2.551 | 1.619 | 1 | 30.65 | H |
| ATOM | 1689 | CG | GLN | H | 6 | −16.799 | −2.751 | 1.588 | 1 | 30.36 | H |
| ATOM | 1690 | CD | GLN | H | 6 | −17.459 | −2.383 | 2.905 | 1 | 30.69 | H |
| ATOM | 1691 | OE1 | GLN | H | 6 | −18.563 | −2.844 | 3.211 | 1 | 29.76 | H |
| ATOM | 1692 | NE2 | GLN | H | 6 | −16.794 | −1.539 | 3.685 | 1 | 26.25 | H |
| ATOM | 1693 | C | GLN | H | 6 | −13.106 | −2.609 | 0.471 | 1 | 33.62 | H |
| ATOM | 1694 | O | GLN | H | 6 | −12.36 | −3.589 | 0.46 | 1 | 35 | H |
| ATOM | 1695 | N | SER | H | 7 | −12.663 | −1.367 | 0.66 | 1 | 32.15 | H |
| ATOM | 1696 | CA | SER | H | 7 | −11.247 | −1.104 | 0.885 | 1 | 31.54 | H |
| ATOM | 1697 | CB | SER | H | 7 | −10.939 | 0.39 | 0.754 | 1 | 33.62 | H |
| ATOM | 1698 | OG | SER | H | 7 | −11.584 | 1.152 | 1.76 | 1 | 36.36 | H |
| ATOM | 1699 | C | SER | H | 7 | −10.908 | −1.593 | 2.288 | 1 | 31.21 | H |
| ATOM | 1700 | O | SER | H | 7 | −11.802 | −1.786 | 3.112 | 1 | 31.96 | H |
| ATOM | 1701 | N | GLY | H | 8 | −9.625 | −1.801 | 2.561 | 1 | 30.61 | H |
| ATOM | 1702 | CA | GLY | H | 8 | −9.23 | −2.289 | 3.872 | 1 | 29.48 | H |
| ATOM | 1703 | C | GLY | H | 8 | −9.337 | −1.294 | 5.017 | 1 | 30.07 | H |
| ATOM | 1704 | O | GLY | H | 8 | −9.365 | −0.08 | 4.799 | 1 | 26.82 | H |
| ATOM | 1705 | N | SER | H | 9 | −9.398 | −1.817 | 6.242 | 1 | 30.18 | H |
| ATOM | 1706 | CA | SER | H | 9 | −9.484 | −0.983 | 7.435 | 1 | 31.66 | H |
| ATOM | 1707 | CB | SER | H | 9 | −9.394 | −1.837 | 8.699 | 1 | 29.38 | H |
| ATOM | 1708 | OG | SER | H | 9 | −10.459 | −2.766 | 8.763 | 1 | 32.73 | H |
| ATOM | 1709 | C | SER | H | 9 | −8.336 | 0.015 | 7.417 | 1 | 33.59 | H |
| ATOM | 1710 | O | SER | H | 9 | −7.322 | −0.209 | 6.753 | 1 | 32.55 | H |
| ATOM | 1711 | N | GLU | H | 10 | −8.492 | 1.115 | 8.145 | 1 | 35.94 | H |

TABLE 7-continued

| | | | | | | | | | | |
|---|---|---|---|---|---|---|---|---|---|---|
| ATOM | 1712 | CA | GLU | H | 10 | −7.454 | 2.135 | 8.181 | 1 | 37.9 | H |
| ATOM | 1713 | CB | GLU | H | 10 | −7.563 | 3.046 | 6.955 | 1 | 39.79 | H |
| ATOM | 1714 | CG | GLU | H | 10 | −6.331 | 3.024 | 6.061 | 1 | 45.36 | H |
| ATOM | 1715 | CD | GLU | H | 10 | −6.374 | 4.079 | 4.967 | 1 | 49.51 | H |
| ATOM | 1716 | OE1 | GLU | H | 10 | −7.365 | 4.12 | 4.197 | 1 | 51.22 | H |
| ATOM | 1717 | OE2 | GLU | H | 10 | −5.407 | 4.868 | 4.876 | 1 | 50.77 | H |
| ATOM | 1718 | C | GLU | H | 10 | −7.483 | 2.995 | 9.433 | 1 | 37.37 | H |
| ATOM | 1719 | O | GLU | H | 10 | −8.529 | 3.202 | 10.038 | 1 | 37.12 | H |
| ATOM | 1720 | N | LEU | H | 11 | −6.31 | 3.488 | 9.812 | 1 | 38.36 | H |
| ATOM | 1721 | CA | LEU | H | 11 | −6.162 | 4.358 | 10.969 | 1 | 38.49 | H |
| ATOM | 1722 | CB | LEU | H | 11 | −4.981 | 3.899 | 11.828 | 1 | 39.9 | H |
| ATOM | 1723 | CG | LEU | H | 11 | −4.625 | 4.687 | 13.093 | 1 | 42.26 | H |
| ATOM | 1724 | CD1 | LEU | H | 11 | −5.844 | 4.869 | 13.986 | 1 | 41.04 | H |
| ATOM | 1725 | CD2 | LEU | H | 11 | −3.533 | 3.937 | 13.837 | 1 | 42.34 | H |
| ATOM | 1726 | C | LEU | H | 11 | −5.884 | 5.725 | 10.367 | 1 | 38.46 | H |
| ATOM | 1727 | O | LEU | H | 11 | −4.973 | 5.866 | 9.554 | 1 | 37.95 | H |
| ATOM | 1728 | N | MET | H | 12 | −6.681 | 6.72 | 10.742 | 1 | 39.26 | H |
| ATOM | 1729 | CA | MET | H | 12 | −6.517 | 8.067 | 10.208 | 1 | 40.3 | H |
| ATOM | 1730 | CB | MET | H | 12 | −7.723 | 8.439 | 9.338 | 1 | 42.96 | H |
| ATOM | 1731 | CG | MET | H | 12 | −7.926 | 7.559 | 8.111 | 1 | 46.74 | H |
| ATOM | 1732 | SD | MET | H | 12 | −6.952 | 8.06 | 6.679 | 1 | 50.76 | H |
| ATOM | 1733 | CE | MET | H | 12 | −5.458 | 7.117 | 6.92 | 1 | 52.67 | H |
| ATOM | 1734 | C | MET | H | 12 | −6.373 | 9.09 | 11.324 | 1 | 40.83 | H |
| ATOM | 1735 | O | MET | H | 12 | −6.936 | 8.922 | 12.409 | 1 | 38.81 | H |
| ATOM | 1736 | N | LYS | H | 13 | −5.609 | 10.146 | 11.054 | 1 | 41.42 | H |
| ATOM | 1737 | CA | LYS | H | 13 | −5.409 | 11.205 | 12.031 | 1 | 41.93 | H |
| ATOM | 1738 | CB | LYS | H | 13 | −4.309 | 12.173 | 11.576 | 1 | 45.64 | H |
| ATOM | 1739 | CG | LYS | H | 13 | −2.934 | 11.546 | 11.363 | 1 | 50.85 | H |
| ATOM | 1740 | CD | LYS | H | 13 | −2.304 | 11.066 | 12.671 | 1 | 53.64 | H |
| ATOM | 1741 | CE | LYS | H | 13 | −0.976 | 10.356 | 12.411 | 1 | 55.04 | H |
| ATOM | 1742 | NZ | LYS | H | 13 | −0.323 | 9.871 | 13.663 | 1 | 57 | H |
| ATOM | 1743 | C | LYS | H | 13 | −6.717 | 11.961 | 12.1 | 1 | 40.27 | H |
| ATOM | 1744 | O | LYS | H | 13 | −7.425 | 12.07 | 11.102 | 1 | 38.48 | H |
| ATOM | 1745 | N | PRO | H | 14 | −7.078 | 12.469 | 13.282 | 1 | 40.78 | H |
| ATOM | 1746 | CD | PRO | H | 14 | −6.492 | 12.295 | 14.621 | 1 | 40.41 | H |
| ATOM | 1747 | CA | PRO | H | 14 | −8.337 | 13.212 | 13.343 | 1 | 41.09 | H |
| ATOM | 1748 | CB | PRO | H | 14 | −8.432 | 13.608 | 14.814 | 1 | 40.82 | H |
| ATOM | 1749 | CG | PRO | H | 14 | −7.688 | 12.5 | 15.51 | 1 | 41.75 | H |
| ATOM | 1750 | C | PRO | H | 14 | −8.174 | 14.428 | 12.425 | 1 | 41.45 | H |
| ATOM | 1751 | O | PRO | H | 14 | −7.063 | 14.948 | 12.276 | 1 | 40.34 | H |
| ATOM | 1752 | N | GLY | H | 15 | −9.262 | 14.866 | 11.798 | 1 | 40.4 | H |
| ATOM | 1753 | CA | GLY | H | 15 | −9.181 | 16.017 | 10.914 | 1 | 38.46 | H |
| ATOM | 1754 | C | GLY | H | 15 | −8.88 | 15.635 | 9.479 | 1 | 38.1 | H |
| ATOM | 1755 | O | GLY | H | 15 | −9.232 | 16.36 | 8.543 | 1 | 39.47 | H |
| ATOM | 1756 | N | ALA | H | 16 | −8.226 | 14.49 | 9.306 | 1 | 36.33 | H |
| ATOM | 1757 | CA | ALA | H | 16 | −7.87 | 13.988 | 7.984 | 1 | 33.38 | H |
| ATOM | 1758 | CB | ALA | H | 16 | −6.938 | 12.79 | 8.114 | 1 | 31.78 | H |
| ATOM | 1759 | C | ALA | H | 16 | −9.113 | 13.593 | 7.202 | 1 | 33.67 | H |
| ATOM | 1760 | O | ALA | H | 16 | −10.23 | 13.612 | 7.724 | 1 | 31.81 | H |
| ATOM | 1761 | N | SER | H | 17 | −8.902 | 13.222 | 5.945 | 1 | 33.93 | H |
| ATOM | 1762 | CA | SER | H | 17 | −9.987 | 12.828 | 5.062 | 1 | 32.25 | H |
| ATOM | 1763 | CB | SER | H | 17 | −10.14 | 13.876 | 3.96 | 1 | 33.54 | H |
| ATOM | 1764 | OG | SER | H | 17 | −11.336 | 13.698 | 3.228 | 1 | 40.78 | H |
| ATOM | 1765 | C | SER | H | 17 | −9.651 | 11.464 | 4.466 | 1 | 31.37 | H |
| ATOM | 1766 | O | SER | H | 17 | −8.5 | 11.196 | 4.128 | 1 | 31.74 | H |
| ATOM | 1767 | N | VAL | H | 18 | −10.648 | 10.597 | 4.345 | 1 | 31.07 | H |
| ATOM | 1768 | CA | VAL | H | 18 | −10.413 | 9.263 | 3.798 | 1 | 29.32 | H |
| ATOM | 1769 | CB | VAL | H | 18 | −10.425 | 8.194 | 4.902 | 1 | 29.78 | H |
| ATOM | 1770 | CG1 | VAL | H | 18 | −11.861 | 7.978 | 5.403 | 1 | 24.72 | H |
| ATOM | 1771 | CG2 | VAL | H | 18 | −9.826 | 6.903 | 4.375 | 1 | 26.97 | H |
| ATOM | 1772 | C | VAL | H | 18 | −11.452 | 8.857 | 2.766 | 1 | 29.69 | H |
| ATOM | 1773 | O | VAL | H | 18 | −12.55 | 9.409 | 2.71 | 1 | 29.79 | H |
| ATOM | 1774 | N | GLN | H | 19 | −11.105 | 7.867 | 1.96 | 1 | 30.13 | H |
| ATOM | 1775 | CA | GLN | H | 19 | −12.021 | 7.396 | 0.946 | 1 | 31.78 | H |
| ATOM | 1776 | CB | GLN | H | 19 | −11.49 | 7.752 | −0.441 | 1 | 35.28 | H |
| ATOM | 1777 | CG | GLN | H | 19 | −12.442 | 7.443 | −1.573 | 1 | 41.49 | H |
| ATOM | 1778 | CD | GLN | H | 19 | −11.772 | 7.499 | −2.934 | 1 | 45.43 | H |
| ATOM | 1779 | OE1 | GLN | H | 19 | −10.8 | 6.78 | −3.189 | 1 | 48.52 | H |
| ATOM | 1780 | NE2 | GLN | H | 19 | −12.291 | 8.347 | −3.82 | 1 | 44.84 | H |
| ATOM | 1781 | C | GLN | H | 19 | −12.18 | 5.892 | 1.047 | 1 | 31.93 | H |
| ATOM | 1782 | O | GLN | H | 19 | −11.205 | 5.162 | 0.901 | 1 | 33.61 | H |
| ATOM | 1783 | N | ILE | H | 20 | −13.398 | 5.43 | 1.326 | 1 | 29.39 | H |
| ATOM | 1784 | CA | ILE | H | 20 | −13.659 | 3.994 | 1.368 | 1 | 26.84 | H |
| ATOM | 1785 | CB | ILE | H | 20 | −14.719 | 3.591 | 2.42 | 1 | 26.42 | H |
| ATOM | 1786 | CG2 | ILE | H | 20 | −15.287 | 2.215 | 2.079 | 1 | 24.44 | H |
| ATOM | 1787 | CG1 | ILE | H | 20 | −14.098 | 3.52 | 3.815 | 1 | 29.02 | H |
| ATOM | 1788 | CD1 | ILE | H | 20 | −13.655 | 4.838 | 4.367 | 1 | 32.54 | H |
| ATOM | 1789 | C | ILE | H | 20 | −14.205 | 3.62 | −0.01 | 1 | 24.86 | H |
| ATOM | 1790 | O | ILE | H | 20 | −15.044 | 4.322 | −0.569 | 1 | 19.67 | H |

TABLE 7-continued

| ATOM | 1791 | N | SER | H | 21 | −13.718 | 2.519 | −0.562 | 1 | 25 | H |
| ATOM | 1792 | CA | SER | H | 21 | −14.185 | 2.086 | −1.866 | 1 | 27.35 | H |
| ATOM | 1793 | CB | SER | H | 21 | −13.008 | 1.709 | −2.766 | 1 | 24.52 | H |
| ATOM | 1794 | OG | SER | H | 21 | −12.455 | 0.475 | −2.353 | 1 | 30.13 | H |
| ATOM | 1795 | C | SER | H | 21 | −15.099 | 0.883 | −1.708 | 1 | 26.54 | H |
| ATOM | 1796 | O | SER | H | 21 | −15.047 | 0.165 | −0.703 | 1 | 25.88 | H |
| ATOM | 1797 | N | CYS | H | 22 | −15.948 | 0.685 | −2.705 | 1 | 25.26 | H |
| ATOM | 1798 | CA | CYS | H | 22 | −16.865 | −0.435 | −2.713 | 1 | 26.51 | H |
| ATOM | 1799 | C | CYS | H | 22 | −17.05 | −0.897 | −4.15 | 1 | 26.06 | H |
| ATOM | 1800 | O | CYS | H | 22 | −17.814 | −0.297 | −4.916 | 1 | 24.2 | H |
| ATOM | 1801 | CB | CYS | H | 22 | −18.213 | −0.041 | −2.125 | 1 | 30.22 | H |
| ATOM | 1802 | SG | CYS | H | 22 | −19.285 | −1.495 | −1.9 | 1 | 33.16 | H |
| ATOM | 1803 | N | LYS | H | 23 | −16.336 | −1.961 | −4.507 | 1 | 25.29 | H |
| ATOM | 1804 | CA | LYS | H | 23 | −16.4 | −2.519 | −5.851 | 1 | 27.21 | H |
| ATOM | 1805 | CB | LYS | H | 23 | −15.073 | −3.193 | −6.222 | 1 | 30.38 | H |
| ATOM | 1806 | CG | LYS | H | 23 | −15.027 | −3.666 | −7.671 | 1 | 35.19 | H |
| ATOM | 1807 | CD | LYS | H | 23 | −13.64 | −4.122 | −8.083 | 1 | 37.69 | H |
| ATOM | 1808 | CE | LYS | H | 23 | −13.617 | −4.582 | −9.54 | 1 | 36.88 | H |
| ATOM | 1809 | NZ | LYS | H | 23 | −14.043 | −3.5 | −10.468 | 1 | 35.83 | H |
| ATOM | 1810 | C | LYS | H | 23 | −17.531 | −3.527 | −5.983 | 1 | 24.02 | H |
| ATOM | 1811 | O | LYS | H | 23 | −17.544 | −4.552 | −5.313 | 1 | 22.08 | H |
| ATOM | 1812 | N | ALA | H | 24 | −18.476 | −3.221 | −6.862 | 1 | 25.47 | H |
| ATOM | 1813 | CA | ALA | H | 24 | −19.627 | −4.084 | −7.095 | 1 | 24.88 | H |
| ATOM | 1814 | CB | ALA | H | 24 | −20.881 | −3.235 | −7.253 | 1 | 20.38 | H |
| ATOM | 1815 | C | ALA | H | 24 | −19.446 | −4.965 | −8.328 | 1 | 26.09 | H |
| ATOM | 1816 | O | ALA | H | 24 | −18.975 | −4.515 | −9.378 | 1 | 26.88 | H |
| ATOM | 1817 | N | THR | H | 25 | −19.81 | −6.231 | −8.191 | 1 | 24.75 | H |
| ATOM | 1818 | CA | THR | H | 25 | −19.73 | −7.156 | −9.304 | 1 | 23.77 | H |
| ATOM | 1819 | CB | THR | H | 25 | −18.397 | −7.921 | −9.315 | 1 | 22.97 | H |
| ATOM | 1820 | OG1 | THR | H | 25 | −18.238 | −8.626 | −8.081 | 1 | 23.52 | H |
| ATOM | 1821 | CG2 | THR | H | 25 | −17.239 | −6.962 | −9.505 | 1 | 21.95 | H |
| ATOM | 1822 | C | THR | H | 25 | −20.877 | −8.138 | −9.154 | 1 | 23.54 | H |
| ATOM | 1823 | O | THR | H | 25 | −21.458 | −8.263 | −8.076 | 1 | 21.65 | H |
| ATOM | 1824 | N | GLY | H | 26 | −21.218 | −8.819 | −10.24 | 1 | 23.86 | H |
| ATOM | 1825 | CA | GLY | H | 26 | −22.294 | −9.792 | −10.181 | 1 | 24.4 | H |
| ATOM | 1826 | C | GLY | H | 26 | −23.692 | −9.253 | −10.44 | 1 | 24.22 | H |
| ATOM | 1827 | O | GLY | H | 26 | −24.669 | −9.997 | −10.324 | 1 | 23.31 | H |
| ATOM | 1828 | N | TYR | H | 27 | −23.797 | −7.971 | −10.786 | 1 | 21.92 | H |
| ATOM | 1829 | CA | TYR | H | 27 | −25.097 | −7.369 | −11.064 | 1 | 21.3 | H |
| ATOM | 1830 | CB | TYR | H | 27 | −25.862 | −7.149 | −9.753 | 1 | 22.54 | H |
| ATOM | 1831 | CG | TYR | H | 27 | −25.364 | −5.986 | −8.929 | 1 | 20.9 | H |
| ATOM | 1832 | CD1 | TYR | H | 27 | −25.857 | −4.696 | −9.138 | 1 | 18.51 | H |
| ATOM | 1833 | CE1 | TYR | H | 27 | −25.414 | −3.621 | −8.375 | 1 | 16.6 | H |
| ATOM | 1834 | CD2 | TYR | H | 27 | −24.405 | −6.173 | −7.935 | 1 | 22.7 | H |
| ATOM | 1835 | CE2 | TYR | H | 27 | −23.95 | −5.101 | −7.165 | 1 | 21.37 | H |
| ATOM | 1836 | CZ | TYR | H | 27 | −24.464 | −3.831 | −7.388 | 1 | 19.5 | H |
| ATOM | 1837 | OH | TYR | H | 27 | −24.047 | −2.785 | −6.599 | 1 | 18.29 | H |
| ATOM | 1838 | C | TYR | H | 27 | −24.948 | −6.044 | −11.8 | 1 | 19.83 | H |
| ATOM | 1839 | O | TYR | H | 27 | −23.852 | −5.491 | −11.883 | 1 | 19.39 | H |
| ATOM | 1840 | N | THR | H | 28 | −26.057 | −5.536 | −12.329 | 1 | 19.67 | H |
| ATOM | 1841 | CA | THR | H | 28 | −26.049 | −4.266 | −13.047 | 1 | 17.55 | H |
| ATOM | 1842 | CB | THR | H | 28 | −27.348 | −4.073 | −13.82 | 1 | 17.4 | H |
| ATOM | 1843 | OG1 | THR | H | 28 | −27.634 | −5.271 | −14.56 | 1 | 20.26 | H |
| ATOM | 1844 | CG2 | THR | H | 28 | −27.222 | −2.898 | −14.787 | 1 | 14.93 | H |
| ATOM | 1845 | C | THR | H | 28 | −25.86 | −3.117 | −12.061 | 1 | 19.8 | H |
| ATOM | 1846 | O | THR | H | 28 | −26.816 | −2.619 | −11.45 | 1 | 19.37 | H |
| ATOM | 1847 | N | PHE | H | 29 | −24.6 | −2.719 | −11.914 | 1 | 21.18 | H |
| ATOM | 1848 | CA | PHE | H | 29 | −24.18 | −1.657 | −11.009 | 1 | 22.53 | H |
| ATOM | 1849 | CB | PHE | H | 29 | −22.772 | −1.18 | −11.396 | 1 | 21.17 | H |
| ATOM | 1850 | CG | PHE | H | 29 | −22.197 | −0.141 | −10.469 | 1 | 18.49 | H |
| ATOM | 1851 | CD1 | PHE | H | 29 | −21.855 | −0.466 | −9.161 | 1 | 19.16 | H |
| ATOM | 1852 | CD2 | PHE | H | 29 | −21.993 | 1.162 | −10.907 | 1 | 19.6 | H |
| ATOM | 1853 | CE1 | PHE | H | 29 | −21.316 | 0.493 | −8.3 | 1 | 18.58 | H |
| ATOM | 1854 | CE2 | PHE | H | 29 | −21.452 | 2.132 | −10.051 | 1 | 21.63 | H |
| ATOM | 1855 | CZ | PHE | H | 29 | −21.115 | 1.792 | −8.743 | 1 | 19.01 | H |
| ATOM | 1856 | C | PHE | H | 29 | −25.121 | −0.462 | −10.98 | 1 | 24.39 | H |
| ATOM | 1857 | O | PHE | H | 29 | −25.622 | −0.085 | −9.925 | 1 | 24.92 | H |
| ATOM | 1858 | N | SER | H | 30 | −25.361 | 0.121 | −12.149 | 1 | 24.35 | H |
| ATOM | 1859 | CA | SER | H | 30 | −26.197 | 1.307 | −12.265 | 1 | 24.36 | H |
| ATOM | 1860 | CB | SER | H | 30 | −26.094 | 1.864 | −13.685 | 1 | 22.4 | H |
| ATOM | 1861 | OG | SER | H | 30 | −26.714 | 0.985 | −14.607 | 1 | 24.52 | H |
| ATOM | 1862 | C | SER | H | 30 | −27.678 | 1.194 | −11.887 | 1 | 25.6 | H |
| ATOM | 1863 | O | SER | H | 30 | −28.312 | 2.216 | −11.62 | 1 | 26.55 | H |
| ATOM | 1864 | N | ASP | H | 31 | −28.246 | −0.009 | −11.85 | 1 | 24.12 | H |
| ATOM | 1865 | CA | ASP | H | 31 | −29.672 | −0.104 | −11.518 | 1 | 23.11 | H |
| ATOM | 1866 | CB | ASP | H | 31 | −30.311 | −1.354 | −12.126 | 1 | 20.9 | H |
| ATOM | 1867 | CG | ASP | H | 31 | −30.311 | −1.343 | −13.64 | 1 | 21.07 | H |
| ATOM | 1868 | OD1 | ASP | H | 31 | −30.177 | −0.26 | −14.251 | 1 | 21.33 | H |
| ATOM | 1869 | OD2 | ASP | H | 31 | −30.464 | −2.432 | −14.221 | 1 | 21.23 | H |

TABLE 7-continued

| | | | | | | | | | | |
|---|---|---|---|---|---|---|---|---|---|---|
| ATOM | 1870 | C | ASP | H | 31 | −29.985 | −0.102 | −10.034 | 1 | 24.52 | H |
| ATOM | 1871 | O | ASP | H | 31 | −31.148 | −0.233 | −9.648 | 1 | 26.44 | H |
| ATOM | 1872 | N | TYR | H | 32 | −28.97 | 0.057 | −9.195 | 1 | 23.91 | H |
| ATOM | 1873 | CA | TYR | H | 32 | −29.218 | 0.024 | −7.766 | 1 | 21.89 | H |
| ATOM | 1874 | CB | TYR | H | 32 | −28.696 | −1.283 | −7.17 | 1 | 22.5 | H |
| ATOM | 1875 | CG | TYR | H | 32 | −29.387 | −2.527 | −7.674 | 1 | 22.19 | H |
| ATOM | 1876 | CD1 | TYR | H | 32 | −29.099 | −3.046 | −8.933 | 1 | 23.07 | H |
| ATOM | 1877 | CE1 | TYR | H | 32 | −29.722 | −4.205 | −9.396 | 1 | 23.2 | H |
| ATOM | 1878 | CD2 | TYR | H | 32 | −30.323 | −3.193 | −6.885 | 1 | 21.22 | H |
| ATOM | 1879 | CE2 | TYR | H | 32 | −30.952 | −4.347 | −7.337 | 1 | 20.23 | H |
| ATOM | 1880 | CZ | TYR | H | 32 | −30.644 | −4.849 | −8.594 | 1 | 22.35 | H |
| ATOM | 1881 | OH | TYR | H | 32 | −31.255 | −5.997 | −9.048 | 1 | 22.85 | H |
| ATOM | 1882 | C | TYR | H | 32 | −28.655 | 1.166 | −6.955 | 1 | 23.86 | H |
| ATOM | 1883 | O | TYR | H | 32 | −27.876 | 1.99 | −7.436 | 1 | 23.76 | H |
| ATOM | 1884 | N | TRP | H | 33 | −29.077 | 1.195 | −5.698 | 1 | 22.85 | H |
| ATOM | 1885 | CA | TRP | H | 33 | −28.623 | 2.19 | −4.753 | 1 | 22.55 | H |
| ATOM | 1886 | CB | TRP | H | 33 | −29.77 | 2.686 | −3.869 | 1 | 21.08 | H |
| ATOM | 1887 | CG | TRP | H | 33 | −30.734 | 3.631 | −4.506 | 1 | 20.86 | H |
| ATOM | 1888 | CD2 | TRP | H | 33 | −30.787 | 5.045 | −4.307 | 1 | 20.3 | H |
| ATOM | 1889 | CE2 | TRP | H | 33 | −31.902 | 5.529 | −5.035 | 1 | 19.41 | H |
| ATOM | 1890 | CE3 | TRP | H | 33 | −30.003 | 5.953 | −3.581 | 1 | 20.24 | H |
| ATOM | 1891 | CD1 | TRP | H | 33 | −31.782 | 3.319 | −5.332 | 1 | 19.75 | H |
| ATOM | 1892 | NE1 | TRP | H | 33 | −32.49 | 4.455 | −5.649 | 1 | 16.56 | H |
| ATOM | 1893 | CZ2 | TRP | H | 33 | −32.254 | 6.885 | −5.056 | 1 | 20.07 | H |
| ATOM | 1894 | CZ3 | TRP | H | 33 | −30.354 | 7.307 | −3.601 | 1 | 23.51 | H |
| ATOM | 1895 | CH2 | TRP | H | 33 | −31.472 | 7.757 | −4.335 | 1 | 20.45 | H |
| ATOM | 1896 | C | TRP | H | 33 | −27.635 | 1.478 | −3.854 | 1 | 23.23 | H |
| ATOM | 1897 | O | TRP | H | 33 | −27.898 | 0.361 | −3.406 | 1 | 23.43 | H |
| ATOM | 1898 | N | ILE | H | 34 | −26.497 | 2.11 | −3.601 | 1 | 21.7 | H |
| ATOM | 1899 | CA | ILE | H | 34 | −25.519 | 1.541 | −2.687 | 1 | 19.36 | H |
| ATOM | 1900 | CB | ILE | H | 34 | −24.066 | 1.743 | −3.187 | 1 | 19.9 | H |
| ATOM | 1901 | CG2 | ILE | H | 34 | −23.086 | 1.483 | −2.056 | 1 | 19.58 | H |
| ATOM | 1902 | CG1 | ILE | H | 34 | −23.774 | 0.797 | −4.357 | 1 | 18.89 | H |
| ATOM | 1903 | CD1 | ILE | H | 34 | −23.809 | −0.669 | −3.979 | 1 | 21.63 | H |
| ATOM | 1904 | C | ILE | H | 34 | −25.736 | 2.309 | −1.384 | 1 | 18.33 | H |
| ATOM | 1905 | O | ILE | H | 34 | −25.782 | 3.542 | −1.379 | 1 | 16.4 | H |
| ATOM | 1906 | N | GLU | H | 35 | −25.905 | 1.58 | −0.287 | 1 | 18.42 | H |
| ATOM | 1907 | CA | GLU | H | 35 | −26.121 | 2.205 | 1.01 | 1 | 18.46 | H |
| ATOM | 1908 | CB | GLU | H | 35 | −27.126 | 1.412 | 1.851 | 1 | 18.97 | H |
| ATOM | 1909 | CG | GLU | H | 35 | −28.435 | 1.135 | 1.17 | 1 | 21.62 | H |
| ATOM | 1910 | CD | GLU | H | 35 | −29.15 | 2.396 | 0.78 | 1 | 19.89 | H |
| ATOM | 1911 | OE1 | GLU | H | 35 | −29.586 | 3.135 | 1.684 | 1 | 20.57 | H |
| ATOM | 1912 | OE2 | GLU | H | 35 | −29.269 | 2.648 | −0.435 | 1 | 26.49 | H |
| ATOM | 1913 | C | GLU | H | 35 | −24.817 | 2.23 | 1.766 | 1 | 19.64 | H |
| ATOM | 1914 | O | GLU | H | 35 | −23.964 | 1.365 | 1.575 | 1 | 20.3 | H |
| ATOM | 1915 | N | TRP | H | 36 | −24.669 | 3.227 | 2.626 | 1 | 18.16 | H |
| ATOM | 1916 | CA | TRP | H | 36 | −23.495 | 3.333 | 3.454 | 1 | 18.95 | H |
| ATOM | 1917 | CB | TRP | H | 36 | −22.718 | 4.608 | 3.13 | 1 | 18.6 | H |
| ATOM | 1918 | CG | TRP | H | 36 | −22.005 | 4.51 | 1.814 | 1 | 21.47 | H |
| ATOM | 1919 | CD2 | TRP | H | 36 | −20.77 | 3.832 | 1.563 | 1 | 18.88 | H |
| ATOM | 1920 | CE2 | TRP | H | 36 | −20.5 | 3.953 | 0.185 | 1 | 21.86 | H |
| ATOM | 1921 | CE3 | TRP | H | 36 | −19.866 | 3.131 | 2.371 | 1 | 20.92 | H |
| ATOM | 1922 | CD1 | TRP | H | 36 | −22.426 | 5.001 | 0.606 | 1 | 21.64 | H |
| ATOM | 1923 | NE1 | TRP | H | 36 | −21.526 | 4.67 | −0.377 | 1 | 22.42 | H |
| ATOM | 1924 | CZ2 | TRP | H | 36 | −19.354 | 3.398 | −0.407 | 1 | 24.84 | H |
| ATOM | 1925 | CZ3 | TRP | H | 36 | −18.729 | 2.578 | 1.785 | 1 | 22.34 | H |
| ATOM | 1926 | CH2 | TRP | H | 36 | −18.484 | 2.716 | 0.408 | 1 | 22.84 | H |
| ATOM | 1927 | C | TRP | H | 36 | −24.001 | 3.329 | 4.888 | 1 | 22.08 | H |
| ATOM | 1928 | O | TRP | H | 36 | −24.678 | 4.261 | 5.331 | 1 | 22.48 | H |
| ATOM | 1929 | N | VAL | H | 37 | −23.695 | 2.255 | 5.605 | 1 | 23.94 | H |
| ATOM | 1930 | CA | VAL | H | 37 | −24.143 | 2.127 | 6.979 | 1 | 26.78 | H |
| ATOM | 1931 | CB | VAL | H | 37 | −24.917 | 0.814 | 7.204 | 1 | 27.47 | H |
| ATOM | 1932 | CG1 | VAL | H | 37 | −25.416 | 0.746 | 8.65 | 1 | 24.44 | H |
| ATOM | 1933 | CG2 | VAL | H | 37 | −26.084 | 0.729 | 6.235 | 1 | 26.91 | H |
| ATOM | 1934 | C | VAL | H | 37 | −22.99 | 2.172 | 7.956 | 1 | 28.44 | H |
| ATOM | 1935 | O | VAL | H | 37 | −21.958 | 1.52 | 7.764 | 1 | 26.59 | H |
| ATOM | 1936 | N | LYS | H | 38 | −23.186 | 2.939 | 9.018 | 1 | 28.56 | H |
| ATOM | 1937 | CA | LYS | H | 38 | −22.167 | 3.087 | 10.034 | 1 | 30.4 | H |
| ATOM | 1938 | CB | LYS | H | 38 | −22.016 | 4.572 | 10.376 | 1 | 32.38 | H |
| ATOM | 1939 | CG | LYS | H | 38 | −21.131 | 4.892 | 11.563 | 1 | 31.19 | H |
| ATOM | 1940 | CD | LYS | H | 38 | −21.092 | 6.39 | 11.783 | 1 | 33.36 | H |
| ATOM | 1941 | CE | LYS | H | 38 | −20.284 | 6.748 | 13.015 | 1 | 39.61 | H |
| ATOM | 1942 | NZ | LYS | H | 38 | −20.029 | 8.21 | 13.122 | 1 | 38.99 | H |
| ATOM | 1943 | C | LYS | H | 38 | −22.535 | 2.297 | 11.28 | 1 | 31.25 | H |
| ATOM | 1944 | O | LYS | H | 38 | −23.713 | 2.107 | 11.581 | 1 | 27.61 | H |
| ATOM | 1945 | N | GLN | H | 39 | −21.515 | 1.818 | 11.983 | 1 | 32.31 | H |
| ATOM | 1946 | CA | GLN | H | 39 | −21.714 | 1.092 | 13.227 | 1 | 34.45 | H |
| ATOM | 1947 | CB | GLN | H | 39 | −21.982 | −0.396 | 12.99 | 1 | 35.26 | H |
| ATOM | 1948 | CG | GLN | H | 39 | −22.102 | −1.191 | 14.304 | 1 | 37.54 | H |

TABLE 7-continued

| | | | | | | | | | | |
|---|---|---|---|---|---|---|---|---|---|---|
| ATOM | 1949 | CD | GLN | H | 39 | −22.299 | −2.685 | 14.096 | 1 | 37.74 | H |
| ATOM | 1950 | OE1 | GLN | H | 39 | −21.676 | −3.292 | 13.219 | 1 | 39.37 | H |
| ATOM | 1951 | NE2 | GLN | H | 39 | −23.152 | −3.288 | 14.918 | 1 | 36.99 | H |
| ATOM | 1952 | C | GLN | H | 39 | −20.497 | 1.247 | 14.126 | 1 | 35.83 | H |
| ATOM | 1953 | O | GLN | H | 39 | −19.479 | 0.577 | 13.938 | 1 | 31.33 | H |
| ATOM | 1954 | N | ARG | H | 40 | −20.602 | 2.161 | 15.085 | 1 | 40.48 | H |
| ATOM | 1955 | CA | ARG | H | 40 | −19.531 | 2.384 | 16.044 | 1 | 44.61 | H |
| ATOM | 1956 | CB | ARG | H | 40 | −19.805 | 3.64 | 16.867 | 1 | 46 | |
| ATOM | 1957 | CG | ARG | H | 40 | −19.921 | 4.929 | 16.054 | 1 | 47.23 | H |
| ATOM | 1958 | CD | ARG | H | 40 | −20.17 | 6.121 | 16.971 | 1 | 51.07 | H |
| ATOM | 1959 | NE | ARG | H | 40 | −19.057 | 6.348 | 17.895 | 1 | 53.99 | H |
| ATOM | 1960 | CZ | ARG | H | 40 | −19.109 | 7.17 | 18.941 | 1 | 56.17 | H |
| ATOM | 1961 | NH1 | ARG | H | 40 | −20.223 | 7.844 | 19.205 | 1 | 56.52 | H |
| ATOM | 1962 | NH2 | ARG | H | 40 | −18.044 | 7.33 | 19.718 | 1 | 55.66 | H |
| ATOM | 1963 | C | ARG | H | 40 | −19.544 | 1.142 | 16.934 | 1 | 47.66 | H |
| ATOM | 1964 | O | ARG | H | 40 | −20.608 | 0.699 | 17.376 | 1 | 47.1 | H |
| ATOM | 1965 | N | PRO | H | 41 | −18.36 | 0.566 | 17.203 | 1 | 50.56 | H |
| ATOM | 1966 | CD | PRO | H | 41 | −17.081 | 1.273 | 16.999 | 1 | 51.94 | H |
| ATOM | 1967 | CA | PRO | H | 41 | −18.15 | −0.637 | 18.019 | 1 | 52.23 | H |
| ATOM | 1968 | CB | PRO | H | 41 | −16.798 | −0.37 | 18.663 | 1 | 53.82 | H |
| ATOM | 1969 | CG | PRO | H | 41 | −16.058 | 0.271 | 17.53 | 1 | 54.36 | H |
| ATOM | 1970 | C | PRO | H | 41 | −19.225 | −1.034 | 19.032 | 1 | 52.28 | H |
| ATOM | 1971 | O | PRO | H | 41 | −19.808 | −2.115 | 18.935 | 1 | 52.75 | H |
| ATOM | 1972 | N | GLY | H | 42 | −19.489 | −0.179 | 20.009 | 1 | 51.81 | H |
| ATOM | 1973 | CA | GLY | H | 42 | −20.491 | −0.537 | 20.992 | 1 | 55.15 | H |
| ATOM | 1974 | C | GLY | H | 42 | −21.912 | −0.169 | 20.61 | 1 | 56.46 | H |
| ATOM | 1975 | O | GLY | H | 42 | −22.864 | −0.548 | 21.296 | 1 | 55.69 | H |
| ATOM | 1976 | N | HIS | H | 43 | −22.059 | 0.546 | 19.5 | 1 | 57.72 | H |
| ATOM | 1977 | CA | HIS | H | 43 | −23.369 | 0.999 | 19.046 | 1 | 57.08 | H |
| ATOM | 1978 | CB | HIS | H | 43 | −23.218 | 2.386 | 18.426 | 1 | 58.6 | H |
| ATOM | 1979 | CG | HIS | H | 43 | −22.676 | 3.404 | 19.38 | 1 | 62.89 | H |
| ATOM | 1980 | CD2 | HIS | H | 43 | −21.414 | 3.85 | 19.587 | 1 | 64.88 | H |
| ATOM | 1981 | ND1 | HIS | H | 43 | −23.47 | 4.063 | 20.294 | 1 | 66.25 | H |
| ATOM | 1982 | CE1 | HIS | H | 43 | −22.721 | 4.875 | 21.02 | 1 | 67.36 | H |
| ATOM | 1983 | NE2 | HIS | H | 43 | −21.469 | 4.764 | 20.612 | 1 | 67.26 | H |
| ATOM | 1984 | C | HIS | H | 43 | −24.093 | 0.069 | 18.078 | 1 | 55.71 | H |
| ATOM | 1985 | O | HIS | H | 43 | −23.619 | −1.029 | 17.766 | 1 | 54.99 | H |
| ATOM | 1986 | N | GLY | H | 44 | −25.26 | 0.52 | 17.622 | 1 | 52.16 | H |
| ATOM | 1987 | CA | GLY | H | 44 | −26.044 | −0.255 | 16.68 | 1 | 48.21 | H |
| ATOM | 1988 | C | GLY | H | 44 | −25.774 | 0.217 | 15.262 | 1 | 45.07 | H |
| ATOM | 1989 | O | GLY | H | 44 | −24.668 | 0.659 | 14.941 | 1 | 44.58 | H |
| ATOM | 1990 | N | LEU | H | 45 | −26.788 | 0.128 | 14.41 | 1 | 41.56 | H |
| ATOM | 1991 | CA | LEU | H | 45 | −26.661 | 0.538 | 13.018 | 1 | 37.28 | H |
| ATOM | 1992 | CB | LEU | H | 45 | −27.291 | −0.515 | 12.108 | 1 | 36.2 | H |
| ATOM | 1993 | CG | LEU | H | 45 | −26.493 | −1.752 | 11.694 | 1 | 35.94 | H |
| ATOM | 1994 | CD1 | LEU | H | 45 | −25.679 | −2.29 | 12.856 | 1 | 36.28 | H |
| ATOM | 1995 | CD2 | LEU | H | 45 | −27.468 | −2.797 | 11.172 | 1 | 31.97 | H |
| ATOM | 1996 | C | LEU | H | 45 | −27.304 | 1.884 | 12.707 | 1 | 36.54 | H |
| ATOM | 1997 | O | LEU | H | 45 | −28.451 | 2.139 | 13.073 | 1 | 38.5 | H |
| ATOM | 1998 | N | GLU | H | 46 | −26.561 | 2.743 | 12.021 | 1 | 35.04 | H |
| ATOM | 1999 | CA | GLU | H | 46 | −27.093 | 4.033 | 11.618 | 1 | 35.12 | H |
| ATOM | 2000 | CB | GLU | H | 46 | −26.563 | 5.158 | 12.517 | 1 | 38.57 | H |
| ATOM | 2001 | CG | GLU | H | 46 | −25.077 | 5.211 | 12.695 | 1 | 46.18 | H |
| ATOM | 2002 | CD | GLU | H | 46 | −24.669 | 6.258 | 13.72 | 1 | 51.8 | H |
| ATOM | 2003 | OE1 | GLU | H | 46 | −25.111 | 7.424 | 13.595 | 1 | 54.76 | H |
| ATOM | 2004 | OE2 | GLU | H | 46 | −23.903 | 5.914 | 14.647 | 1 | 54.83 | H |
| ATOM | 2005 | C | GLU | H | 46 | −26.812 | 4.318 | 10.14 | 1 | 30.78 | H |
| ATOM | 2006 | O | GLU | H | 46 | −25.707 | 4.11 | 9.635 | 1 | 30.57 | H |
| ATOM | 2007 | N | TRP | H | 47 | −27.849 | 4.776 | 9.456 | 1 | 26.63 | H |
| ATOM | 2008 | CA | TRP | H | 47 | −27.796 | 5.086 | 8.034 | 1 | 26.33 | H |
| ATOM | 2009 | CB | TRP | H | 47 | −29.224 | 5.227 | 7.508 | 1 | 24.4 | H |
| ATOM | 2010 | CG | TRP | H | 47 | −29.334 | 5.42 | 6.027 | 1 | 25.57 | H |
| ATOM | 2011 | CD2 | TRP | H | 47 | −29.812 | 6.59 | 5.354 | 1 | 22.44 | H |
| ATOM | 2012 | CE2 | TRP | H | 47 | −29.844 | 6.295 | 3.974 | 1 | 22.06 | H |
| ATOM | 2013 | CE3 | TRP | H | 47 | −30.221 | 7.858 | 5.786 | 1 | 23.3 | H |
| ATOM | 2014 | CD1 | TRP | H | 47 | −29.09 | 4.49 | 5.053 | 1 | 24.8 | H |
| ATOM | 2015 | NE1 | TRP | H | 47 | −29.398 | 5.008 | 3.817 | 1 | 22.98 | H |
| ATOM | 2016 | CZ2 | TRP | H | 47 | −30.274 | 7.223 | 3.019 | 1 | 23.86 | H |
| ATOM | 2017 | CZ3 | TRP | H | 47 | −30.649 | 8.783 | 4.84 | 1 | 25.22 | H |
| ATOM | 2018 | CH2 | TRP | H | 47 | −30.672 | 8.459 | 3.469 | 1 | 25.87 | H |
| ATOM | 2019 | C | TRP | H | 47 | −27.011 | 6.355 | 7.716 | 1 | 23.65 | H |
| ATOM | 2020 | O | TRP | H | 47 | −27.354 | 7.438 | 8.18 | 1 | 24.01 | H |
| ATOM | 2021 | N | ILE | H | 48 | −25.965 | 6.232 | 6.912 | 1 | 20.54 | H |
| ATOM | 2022 | CA | ILE | H | 48 | −25.18 | 7.407 | 6.558 | 1 | 19.71 | H |
| ATOM | 2023 | CB | ILE | H | 48 | −23.723 | 7.028 | 6.279 | 1 | 17.95 | H |
| ATOM | 2024 | CG2 | ILE | H | 48 | −22.931 | 8.27 | 5.884 | 1 | 18.96 | H |
| ATOM | 2025 | CG1 | ILE | H | 48 | −23.122 | 6.369 | 7.524 | 1 | 17.37 | H |
| ATOM | 2026 | CD1 | ILE | H | 48 | −21.716 | 5.859 | 7.332 | 1 | 16.67 | H |
| ATOM | 2027 | C | ILE | H | 48 | −25.762 | 8.099 | 5.323 | 1 | 20.71 | H |

TABLE 7-continued

| ATOM | 2028 | O | ILE | H | 48 | −25.717 | 9.323 | 5.191 | 1 | 19.38 | H |
|------|------|-----|-----|---|----|---------|-------|-------|---|-------|---|
| ATOM | 2029 | N | GLY | H | 49 | −26.317 | 7.294 | 4.425 | 1 | 22.82 | H |
| ATOM | 2030 | CA | GLY | H | 49 | −26.898 | 7.813 | 3.204 | 1 | 19.83 | H |
| ATOM | 2031 | C | GLY | H | 49 | −26.678 | 6.803 | 2.101 | 1 | 19.96 | H |
| ATOM | 2032 | O | GLY | H | 49 | −26.064 | 5.76 | 2.323 | 1 | 20.94 | H |
| ATOM | 2033 | N | ASP | H | 50 | −27.185 | 7.099 | 0.912 | 1 | 18.66 | H |
| ATOM | 2034 | CA | ASP | H | 50 | −27.017 | 6.199 | −0.214 | 1 | 17.79 | H |
| ATOM | 2035 | CB | ASP | H | 50 | −28.218 | 5.255 | −0.352 | 1 | 16.18 | H |
| ATOM | 2036 | CG | ASP | H | 50 | −29.564 | 5.982 | −0.299 | 1 | 22.26 | H |
| ATOM | 2037 | OD1 | ASP | H | 50 | −29.644 | 7.197 | −0.605 | 1 | 21.47 | H |
| ATOM | 2038 | OD2 | ASP | H | 50 | −30.562 | 5.319 | 0.045 | 1 | 23.16 | H |
| ATOM | 2039 | C | ASP | H | 50 | −26.828 | 6.991 | −1.494 | 1 | 18.09 | H |
| ATOM | 2040 | O | ASP | H | 50 | −26.895 | 8.219 | −1.492 | 1 | 19.7 | H |
| ATOM | 2041 | N | ILE | H | 51 | −26.588 | 6.278 | −2.586 | 1 | 19.3 | H |
| ATOM | 2042 | CA | ILE | H | 51 | −26.387 | 6.909 | −3.878 | 1 | 19.6 | H |
| ATOM | 2043 | CB | ILE | H | 51 | −24.899 | 7.23 | −4.092 | 1 | 20.23 | H |
| ATOM | 2044 | CG2 | ILE | H | 51 | −24.057 | 5.97 | −3.888 | 1 | 17.18 | H |
| ATOM | 2045 | CG1 | ILE | H | 51 | −24.692 | 7.86 | −5.47 | 1 | 19.45 | H |
| ATOM | 2046 | CD1 | ILE | H | 51 | −23.294 | 8.421 | −5.669 | 1 | 18.02 | H |
| ATOM | 2047 | C | ILE | H | 51 | −26.878 | 6.002 | −4.997 | 1 | 21.67 | H |
| ATOM | 2048 | O | ILE | H | 51 | −26.547 | 4.816 | −5.042 | 1 | 23.17 | H |
| ATOM | 2049 | N | LEU | H | 52 | −27.689 | 6.559 | −5.889 | 1 | 23.52 | H |
| ATOM | 2050 | CA | LEU | H | 52 | −28.214 | 5.796 | −7.015 | 1 | 22.8 | H |
| ATOM | 2051 | CB | LEU | H | 52 | −29.472 | 6.463 | −7.572 | 1 | 19.93 | H |
| ATOM | 2052 | CG | LEU | H | 52 | −30.56 | 5.528 | −8.11 | 1 | 19.45 | H |
| ATOM | 2053 | CD1 | LEU | H | 52 | −31.483 | 6.341 | −9.01 | 1 | 17 | H |
| ATOM | 2054 | CD2 | LEU | H | 52 | −29.952 | 4.354 | −8.868 | 1 | 10.59 | H |
| ATOM | 2055 | C | LEU | H | 52 | −27.113 | 5.762 | −8.079 | 1 | 22.63 | H |
| ATOM | 2056 | O | LEU | H | 52 | −27.002 | 6.659 | −8.912 | 1 | 22.12 | H |
| ATOM | 2057 | N | CYS | H | 52A | −26.304 | 4.712 | −8.03 | 1 | 22.25 | H |
| ATOM | 2058 | CA | CYS | H | 52A | −25.186 | 4.544 | −8.939 | 1 | 24.62 | H |
| ATOM | 2059 | CB | CYS | H | 52A | −24.647 | 3.12 | −8.804 | 1 | 24.23 | H |
| ATOM | 2060 | SG | CYS | H | 52A | −24.071 | 2.736 | −7.113 | 1 | 22.95 | H |
| ATOM | 2061 | C | CYS | H | 52A | −25.479 | 4.874 | −10.4 | 1 | 26.06 | H |
| ATOM | 2062 | O | CYS | H | 52A | −24.602 | 5.342 | −11.128 | 1 | 28.55 | H |
| ATOM | 2063 | N | GLY | H | 53 | −26.714 | 4.652 | −10.828 | 1 | 24.42 | H |
| ATOM | 2064 | CA | GLY | H | 53 | −27.061 | 4.927 | −12.207 | 1 | 23.12 | H |
| ATOM | 2065 | C | GLY | H | 53 | −27.24 | 6.389 | −12.567 | 1 | 24.51 | H |
| ATOM | 2066 | O | GLY | H | 53 | −27.046 | 6.763 | −13.724 | 1 | 27.27 | H |
| ATOM | 2067 | N | THR | H | 54 | −27.611 | 7.224 | −11.602 | 1 | 22.58 | H |
| ATOM | 2068 | CA | THR | H | 54 | −27.815 | 8.636 | −11.9 | 1 | 23.15 | H |
| ATOM | 2069 | CB | THR | H | 54 | −29.263 | 9.064 | −11.636 | 1 | 24.4 | H |
| ATOM | 2070 | OG1 | THR | H | 54 | −29.489 | 9.128 | −10.223 | 1 | 21.63 | H |
| ATOM | 2071 | CG2 | THR | H | 54 | −30.228 | 8.074 | −12.261 | 1 | 22.77 | H |
| ATOM | 2072 | C | THR | H | 54 | −26.921 | 9.548 | −11.083 | 1 | 23.15 | H |
| ATOM | 2073 | O | THR | H | 54 | −26.739 | 10.716 | −11.422 | 1 | 26.47 | H |
| ATOM | 2074 | N | GLY | H | 55 | −26.381 | 9.02 | −9.995 | 1 | 21.87 | H |
| ATOM | 2075 | CA | GLY | H | 55 | −25.522 | 9.82 | −9.154 | 1 | 18.75 | H |
| ATOM | 2076 | C | GLY | H | 55 | −26.298 | 10.539 | −8.074 | 1 | 20.96 | H |
| ATOM | 2077 | O | GLY | H | 55 | −25.712 | 11.277 | −7.284 | 1 | 23.14 | H |
| ATOM | 2078 | N | ARG | H | 56 | −27.613 | 10.331 | −8.02 | 1 | 21.63 | H |
| ATOM | 2079 | CA | ARG | H | 56 | −28.415 | 10.996 | −6.999 | 1 | 21.59 | H |
| ATOM | 2080 | CB | ARG | H | 56 | −29.904 | 10.683 | −7.165 | 1 | 21.22 | H |
| ATOM | 2081 | CG | ARG | H | 56 | −30.764 | 11.464 | −6.181 | 1 | 20.85 | H |
| ATOM | 2082 | CD | ARG | H | 56 | −32.199 | 10.971 | −6.117 | 1 | 18.23 | H |
| ATOM | 2083 | NE | ARG | H | 56 | −32.89 | 11.535 | −4.956 | 1 | 15.79 | H |
| ATOM | 2084 | CZ | ARG | H | 56 | −34.129 | 11.223 | −4.594 | 1 | 16.38 | H |
| ATOM | 2085 | NH1 | ARG | H | 56 | −34.824 | 10.351 | −5.307 | 1 | 14.78 | H |
| ATOM | 2086 | NH2 | ARG | H | 56 | −34.67 | 11.774 | −3.511 | 1 | 17.33 | H |
| ATOM | 2087 | C | ARG | H | 56 | −27.959 | 10.556 | −5.612 | 1 | 21.59 | H |
| ATOM | 2088 | O | ARG | H | 56 | −27.71 | 9.378 | −5.371 | 1 | 22.43 | H |
| ATOM | 2089 | N | THR | H | 57 | −27.852 | 11.508 | −4.697 | 1 | 22.54 | H |
| ATOM | 2090 | CA | THR | H | 57 | −27.417 | 11.19 | −3.345 | 1 | 23.23 | H |
| ATOM | 2091 | CB | THR | H | 57 | −26.048 | 11.839 | −3.009 | 1 | 21.89 | H |
| ATOM | 2092 | OG1 | THR | H | 57 | −26.145 | 13.255 | −3.161 | 1 | 20.5 | H |
| ATOM | 2093 | CG2 | THR | H | 57 | −24.949 | 11.31 | −3.921 | 1 | 20.02 | H |
| ATOM | 2094 | C | THR | H | 57 | −28.407 | 11.657 | −2.299 | 1 | 23.21 | H |
| ATOM | 2095 | O | THR | H | 57 | −29.097 | 12.66 | −2.476 | 1 | 25.08 | H |
| ATOM | 2096 | N | ARG | H | 58 | −28.477 | 10.902 | −1.212 | 1 | 22.91 | H |
| ATOM | 2097 | CA | ARG | H | 58 | −29.338 | 11.225 | −0.091 | 1 | 21.69 | H |
| ATOM | 2098 | CB | ARG | H | 58 | −30.564 | 10.307 | −0.049 | 1 | 21.46 | H |
| ATOM | 2099 | CG | ARG | H | 58 | −31.557 | 10.528 | −1.174 | 1 | 18.91 | H |
| ATOM | 2100 | CD | ARG | H | 58 | −32.816 | 9.708 | −0.973 | 1 | 16.44 | H |
| ATOM | 2101 | NE | ARG | H | 58 | −32.529 | 8.277 | −0.945 | 1 | 18.57 | H |
| ATOM | 2102 | CZ | ARG | H | 58 | −33.441 | 7.331 | −0.73 | 1 | 20.56 | H |
| ATOM | 2103 | NH1 | ARG | H | 58 | −34.716 | 7.661 | −0.52 | 1 | 17.73 | H |
| ATOM | 2104 | NH2 | ARG | H | 58 | −33.078 | 6.051 | −0.725 | 1 | 16.01 | H |
| ATOM | 2105 | C | ARG | H | 58 | −28.478 | 11.016 | 1.146 | 1 | 23.65 | H |
| ATOM | 2106 | O | ARG | H | 58 | −27.971 | 9.92 | 1.389 | 1 | 24.01 | H |

TABLE 7-continued

| | | | | | | | | | | |
|---|---|---|---|---|---|---|---|---|---|---|
| ATOM | 2107 | N | TYR | H | 59 | −28.304 | 12.081 | 1.917 | 1 | 26.46 | H |
| ATOM | 2108 | CA | TYR | H | 59 | −27.485 | 12.03 | 3.119 | 1 | 28.75 | H |
| ATOM | 2109 | CB | TYR | H | 59 | −26.444 | 13.147 | 3.082 | 1 | 24.76 | H |
| ATOM | 2110 | CG | TYR | H | 59 | −25.493 | 13.067 | 1.923 | 1 | 23.56 | H |
| ATOM | 2111 | CD1 | TYR | H | 59 | −24.463 | 12.141 | 1.917 | 1 | 21.53 | H |
| ATOM | 2112 | CE1 | TYR | H | 59 | −23.586 | 12.049 | 0.849 | 1 | 22.58 | H |
| ATOM | 2113 | CD2 | TYR | H | 59 | −25.631 | 13.911 | 0.823 | 1 | 22.39 | H |
| ATOM | 2114 | CE2 | TYR | H | 59 | −24.759 | 13.828 | −0.257 | 1 | 23.74 | H |
| ATOM | 2115 | CZ | TYR | H | 59 | −23.735 | 12.891 | −0.234 | 1 | 23.29 | H |
| ATOM | 2116 | OH | TYR | H | 59 | −22.85 | 12.789 | −1.288 | 1 | 26.35 | H |
| ATOM | 2117 | C | TYR | H | 59 | −28.286 | 12.177 | 4.405 | 1 | 31.04 | H |
| ATOM | 2118 | O | TYR | H | 59 | −29.295 | 12.887 | 4.445 | 1 | 30.15 | H |
| ATOM | 2119 | N | ASN | H | 60 | −27.83 | 11.495 | 5.453 | 1 | 31.95 | H |
| ATOM | 2120 | CA | ASN | H | 60 | −28.465 | 11.614 | 6.751 | 1 | 34.28 | H |
| ATOM | 2121 | CB | ASN | H | 60 | −28.025 | 10.484 | 7.686 | 1 | 32.08 | H |
| ATOM | 2122 | CG | ASN | H | 60 | −28.923 | 10.353 | 8.907 | 1 | 32.62 | H |
| ATOM | 2123 | OD1 | ASN | H | 60 | −29.277 | 11.347 | 9.546 | 1 | 32.55 | H |
| ATOM | 2124 | ND2 | ASN | H | 60 | −29.289 | 9.119 | 9.242 | 1 | 32.09 | H |
| ATOM | 2125 | C | ASN | H | 60 | −27.898 | 12.953 | 7.227 | 1 | 36.98 | H |
| ATOM | 2126 | O | ASN | H | 60 | −26.914 | 13.008 | 7.971 | 1 | 35.09 | H |
| ATOM | 2127 | N | GLU | H | 61 | −28.519 | 14.026 | 6.748 | 1 | 41.41 | H |
| ATOM | 2128 | CA | GLU | H | 61 | −28.129 | 15.402 | 7.056 | 1 | 46.47 | H |
| ATOM | 2129 | CB | GLU | H | 61 | −29.296 | 16.344 | 6.72 | 1 | 50.66 | H |
| ATOM | 2130 | CG | GLU | H | 61 | −29.788 | 16.276 | 5.27 | 1 | 57.21 | H |
| ATOM | 2131 | CD | GLU | H | 61 | −28.826 | 16.927 | 4.28 | 1 | 60.6 | H |
| ATOM | 2132 | OE1 | GLU | H | 61 | −28.482 | 18.112 | 4.481 | 1 | 63.78 | H |
| ATOM | 2133 | OE2 | GLU | H | 61 | −28.419 | 16.262 | 3.3 | 1 | 61.22 | H |
| ATOM | 2134 | C | GLU | H | 61 | −27.684 | 15.664 | 8.5 | 1 | 46.04 | H |
| ATOM | 2135 | O | GLU | H | 61 | −26.693 | 16.36 | 8.736 | 1 | 44.28 | H |
| ATOM | 2136 | N | LYS | H | 62 | −28.418 | 15.095 | 9.452 | 1 | 46.41 | H |
| ATOM | 2137 | CA | LYS | H | 62 | −28.154 | 15.289 | 10.873 | 1 | 47.28 | H |
| ATOM | 2138 | CB | LYS | H | 62 | −29.355 | 14.798 | 11.686 | 1 | 46.97 | H |
| ATOM | 2139 | CG | LYS | H | 62 | −29.31 | 13.325 | 12.055 | 1 | 49.13 | H |
| ATOM | 2140 | CD | LYS | H | 62 | −30.493 | 12.959 | 12.935 | 1 | 50.46 | H |
| ATOM | 2141 | CE | LYS | H | 62 | −30.232 | 11.681 | 13.707 | 1 | 53.67 | H |
| ATOM | 2142 | NZ | LYS | H | 62 | −29.048 | 11.82 | 14.603 | 1 | 55.56 | H |
| ATOM | 2143 | C | LYS | H | 62 | −26.883 | 14.681 | 11.466 | 1 | 46.68 | H |
| ATOM | 2144 | O | LYS | H | 62 | −26.538 | 14.97 | 12.61 | 1 | 47.76 | H |
| ATOM | 2145 | N | LEU | H | 63 | −26.179 | 13.846 | 10.719 | 1 | 46.97 | H |
| ATOM | 2146 | CA | LEU | H | 63 | −24.98 | 13.245 | 11.283 | 1 | 47.83 | H |
| ATOM | 2147 | CB | LEU | H | 63 | −24.631 | 11.952 | 10.546 | 1 | 45.64 | H |
| ATOM | 2148 | CG | LEU | H | 63 | −25.234 | 10.7 | 11.194 | 1 | 44.86 | H |
| ATOM | 2149 | CD1 | LEU | H | 63 | −26.643 | 10.991 | 11.677 | 1 | 45.16 | H |
| ATOM | 2150 | CD2 | LEU | H | 63 | −25.217 | 9.545 | 10.202 | 1 | 44.38 | H |
| ATOM | 2151 | C | LEU | H | 63 | −23.778 | 14.163 | 11.334 | 1 | 49.14 | H |
| ATOM | 2152 | O | LEU | H | 63 | −23.44 | 14.836 | 10.357 | 1 | 46.89 | H |
| ATOM | 2153 | N | LYS | H | 64 | −23.15 | 14.188 | 12.507 | 1 | 52.76 | H |
| ATOM | 2154 | CA | LYS | H | 64 | −21.966 | 14.998 | 12.747 | 1 | 55.38 | H |
| ATOM | 2155 | CB | LYS | H | 64 | −21.658 | 15.067 | 14.244 | 1 | 57.52 | H |
| ATOM | 2156 | CG | LYS | H | 64 | −22.678 | 15.827 | 15.075 | 1 | 60.99 | H |
| ATOM | 2157 | CD | LYS | H | 64 | −22.216 | 15.908 | 16.523 | 1 | 63.36 | H |
| ATOM | 2158 | CE | LYS | H | 64 | −23.105 | 16.811 | 17.356 | 1 | 63.31 | H |
| ATOM | 2159 | NZ | LYS | H | 64 | −22.64 | 16.848 | 18.771 | 1 | 65.48 | H |
| ATOM | 2160 | C | LYS | H | 64 | −20.794 | 14.362 | 12.018 | 1 | 55.7 | H |
| ATOM | 2161 | O | LYS | H | 64 | −19.9 | 13.782 | 12.638 | 1 | 57.16 | H |
| ATOM | 2162 | N | ALA | H | 65 | −20.82 | 14.465 | 10.693 | 1 | 55.2 | H |
| ATOM | 2163 | CA | ALA | H | 65 | −19.777 | 13.914 | 9.836 | 1 | 53.24 | H |
| ATOM | 2164 | CB | ALA | H | 65 | −19.797 | 12.384 | 9.875 | 1 | 53.25 | H |
| ATOM | 2165 | C | ALA | H | 65 | −20.033 | 14.406 | 8.423 | 1 | 51.43 | H |
| ATOM | 2166 | O | ALA | H | 65 | −21.184 | 14.549 | 7.998 | 1 | 50.07 | H |
| ATOM | 2167 | N | MET | H | 66 | −18.956 | 14.665 | 7.699 | 1 | 47.89 | H |
| ATOM | 2168 | CA | MET | H | 66 | −19.076 | 15.159 | 6.346 | 1 | 46.16 | H |
| ATOM | 2169 | CB | MET | H | 66 | −18.089 | 16.3 | 6.156 | 1 | 49.61 | H |
| ATOM | 2170 | CG | MET | H | 66 | −18.035 | 17.199 | 7.381 | 1 | 54.5 | H |
| ATOM | 2171 | SD | MET | H | 66 | −17.455 | 18.875 | 7.071 | 1 | 63.85 | H |
| ATOM | 2172 | CE | MET | H | 66 | −19.064 | 19.742 | 6.86 | 1 | 59.59 | H |
| ATOM | 2173 | C | MET | H | 66 | −18.832 | 14.03 | 5.354 | 1 | 43.02 | H |
| ATOM | 2174 | O | MET | H | 66 | −17.696 | 13.62 | 5.13 | 1 | 41.87 | H |
| ATOM | 2175 | N | ALA | H | 67 | −19.921 | 13.529 | 4.773 | 1 | 39.48 | H |
| ATOM | 2176 | CA | ALA | H | 67 | −19.868 | 12.434 | 3.814 | 1 | 36.35 | H |
| ATOM | 2177 | CB | ALA | H | 67 | −20.869 | 11.371 | 4.199 | 1 | 33.12 | H |
| ATOM | 2178 | C | ALA | H | 67 | −20.122 | 12.87 | 2.378 | 1 | 36.2 | H |
| ATOM | 2179 | O | ALA | H | 67 | −20.839 | 13.837 | 2.111 | 1 | 35.86 | H |
| ATOM | 2180 | N | THR | H | 68 | −19.534 | 12.126 | 1.453 | 1 | 35.87 | H |
| ATOM | 2181 | CA | THR | H | 68 | −19.674 | 12.398 | 0.033 | 1 | 35.01 | H |
| ATOM | 2182 | CB | THR | H | 68 | −18.513 | 13.274 | −0.483 | 1 | 35.44 | H |
| ATOM | 2183 | OG1 | THR | H | 68 | −18.578 | 14.564 | 0.132 | 1 | 35.02 | H |
| ATOM | 2184 | CG2 | THR | H | 68 | −18.589 | 13.43 | −1.993 | 1 | 37.2 | H |
| ATOM | 2185 | C | THR | H | 68 | −19.665 | 11.071 | −0.716 | 1 | 34.17 | H |

TABLE 7-continued

| | | | | | | | | | | |
|---|---|---|---|---|---|---|---|---|---|---|
| ATOM | 2186 | O | THR | H | 68 | −18.734 | 10.273 | −0.575 | 1 | 33.07 | H |
| ATOM | 2187 | N | PHE | H | 69 | −20.707 | 10.834 | −1.503 | 1 | 31.6 | H |
| ATOM | 2188 | CA | PHE | H | 69 | −20.798 | 9.603 | −2.265 | 1 | 28.86 | H |
| ATOM | 2189 | CB | PHE | H | 69 | −22.185 | 8.964 | −2.112 | 1 | 26.83 | H |
| ATOM | 2190 | CG | PHE | H | 69 | −22.622 | 8.78 | −0.687 | 1 | 27.85 | H |
| ATOM | 2191 | CD1 | PHE | H | 69 | −21.726 | 8.334 | 0.283 | 1 | 27.07 | H |
| ATOM | 2192 | CD2 | PHE | H | 69 | −23.939 | 9.036 | −0.315 | 1 | 27.53 | H |
| ATOM | 2193 | CE1 | PHE | H | 69 | −22.135 | 8.146 | 1.603 | 1 | 27.42 | H |
| ATOM | 2194 | CE2 | PHE | H | 69 | −24.364 | 8.853 | 1.002 | 1 | 26.6 | H |
| ATOM | 2195 | CZ | PHE | H | 69 | −23.46 | 8.407 | 1.965 | 1 | 28.96 | H |
| ATOM | 2196 | C | PHE | H | 69 | −20.555 | 9.882 | −3.736 | 1 | 28.68 | H |
| ATOM | 2197 | O | PHE | H | 69 | −20.999 | 10.895 | −4.264 | 1 | 28.94 | H |
| ATOM | 2198 | N | THR | H | 70 | −19.834 | 8.98 | −4.387 | 1 | 26.97 | H |
| ATOM | 2199 | CA | THR | H | 70 | −19.573 | 9.079 | −5.811 | 1 | 27.96 | H |
| ATOM | 2200 | CB | THR | H | 70 | −18.175 | 9.67 | −6.134 | 1 | 29.86 | H |
| ATOM | 2201 | OG1 | THR | H | 70 | −17.202 | 9.186 | −5.199 | 1 | 33.81 | H |
| ATOM | 2202 | CG2 | THR | H | 70 | −18.223 | 11.177 | −6.085 | 1 | 30.79 | H |
| ATOM | 2203 | C | THR | H | 70 | −19.659 | 7.668 | −6.345 | 1 | 27.47 | H |
| ATOM | 2204 | O | THR | H | 70 | −19.368 | 6.715 | −5.632 | 1 | 27.45 | H |
| ATOM | 2205 | N | ALA | H | 71 | −20.09 | 7.529 | −7.589 | 1 | 30.73 | H |
| ATOM | 2206 | CA | ALA | H | 71 | −20.198 | 6.211 | −8.195 | 1 | 32.03 | H |
| ATOM | 2207 | CB | ALA | H | 71 | −21.665 | 5.835 | −8.408 | 1 | 32.14 | H |
| ATOM | 2208 | C | ALA | H | 71 | −19.458 | 6.219 | −9.52 | 1 | 32.58 | H |
| ATOM | 2209 | O | ALA | H | 71 | −19.775 | 7 | −10.425 | 1 | 32.18 | H |
| ATOM | 2210 | N | ASP | H | 72 | −18.455 | 5.357 | −9.616 | 1 | 33.49 | H |
| ATOM | 2211 | CA | ASP | H | 72 | −17.664 | 5.24 | −10.826 | 1 | 34.6 | H |
| ATOM | 2212 | CB | ASP | H | 72 | −16.204 | 4.983 | −10.472 | 1 | 34.52 | H |
| ATOM | 2213 | CG | ASP | H | 72 | −15.298 | 5.046 | −11.674 | 1 | 32.73 | H |
| ATOM | 2214 | OD1 | ASP | H | 72 | −15.522 | 4.283 | −12.632 | 1 | 33.2 | H |
| ATOM | 2215 | OD2 | ASP | H | 72 | −14.357 | 5.863 | −11.661 | 1 | 36.91 | H |
| ATOM | 2216 | C | ASP | H | 72 | −18.232 | 4.065 | −11.605 | 1 | 36.6 | H |
| ATOM | 2217 | O | ASP | H | 72 | −17.828 | 2.916 | −11.411 | 1 | 36.75 | H |
| ATOM | 2218 | N | THR | H | 73 | −19.185 | 4.364 | −12.478 | 1 | 37.82 | H |
| ATOM | 2219 | CA | THR | H | 73 | −19.841 | 3.347 | −13.284 | 1 | 39.48 | H |
| ATOM | 2220 | CB | THR | H | 73 | −21.023 | 3.964 | −14.058 | 1 | 40.05 | H |
| ATOM | 2221 | OG1 | THR | H | 73 | −20.617 | 5.211 | −14.635 | 1 | 38.17 | H |
| ATOM | 2222 | CG2 | THR | H | 73 | −22.2 | 4.204 | −13.126 | 1 | 38.01 | H |
| ATOM | 2223 | C | THR | H | 73 | −18.881 | 2.658 | −14.256 | 1 | 40.22 | H |
| ATOM | 2224 | O | THR | H | 73 | −19.212 | 1.626 | −14.848 | 1 | 42.22 | H |
| ATOM | 2225 | N | SER | H | 74 | −17.693 | 3.229 | −14.416 | 1 | 38.54 | H |
| ATOM | 2226 | CA | SER | H | 74 | −16.698 | 2.651 | −15.305 | 1 | 36.16 | H |
| ATOM | 2227 | CB | SER | H | 74 | −15.635 | 3.679 | −15.65 | 1 | 37.12 | H |
| ATOM | 2228 | OG | SER | H | 74 | −16.167 | 4.648 | −16.531 | 1 | 46.87 | H |
| ATOM | 2229 | C | SER | H | 74 | −16.049 | 1.454 | −14.645 | 1 | 35.12 | H |
| ATOM | 2230 | O | SER | H | 74 | −15.804 | 0.435 | −15.291 | 1 | 38.02 | H |
| ATOM | 2231 | N | SER | H | 75 | −15.775 | 1.581 | −13.351 | 1 | 30.84 | H |
| ATOM | 2232 | CA | SER | H | 75 | −15.156 | 0.509 | −12.591 | 1 | 26.56 | H |
| ATOM | 2233 | CB | SER | H | 75 | −14.069 | 1.074 | −11.686 | 1 | 24.36 | H |
| ATOM | 2234 | OG | SER | H | 75 | −14.639 | 1.708 | −10.557 | 1 | 23.71 | H |
| ATOM | 2235 | C | SER | H | 75 | −16.197 | −0.206 | −11.729 | 1 | 26.8 | H |
| ATOM | 2236 | O | SER | H | 75 | −15.883 | −1.188 | −11.061 | 1 | 24.01 | H |
| ATOM | 2237 | N | ASN | H | 76 | −17.437 | 0.282 | −11.758 | 1 | 27.22 | H |
| ATOM | 2238 | CA | ASN | H | 76 | −18.507 | −0.301 | −10.949 | 1 | 27.68 | H |
| ATOM | 2239 | CB | ASN | H | 76 | −18.804 | −1.736 | −11.393 | 1 | 27.7 | H |
| ATOM | 2240 | CG | ASN | H | 76 | −19.486 | −1.803 | −12.751 | 1 | 31.28 | H |
| ATOM | 2241 | OD1 | ASN | H | 76 | −19.611 | −2.877 | −13.334 | 1 | 35.89 | H |
| ATOM | 2242 | ND2 | ASN | H | 76 | −19.94 | −0.658 | −13.255 | 1 | 30.38 | H |
| ATOM | 2243 | C | ASN | H | 76 | −18.048 | −0.276 | −9.494 | 1 | 26.29 | H |
| ATOM | 2244 | O | ASN | H | 76 | −17.971 | −1.303 | −8.818 | 1 | 24.22 | H |
| ATOM | 2245 | N | THR | H | 77 | −17.728 | 0.921 | −9.024 | 1 | 25.91 | H |
| ATOM | 2246 | CA | THR | H | 77 | −17.263 | 1.097 | −7.662 | 1 | 26.59 | H |
| ATOM | 2247 | CB | THR | H | 77 | −15.713 | 1.275 | −7.616 | 1 | 28 | H |
| ATOM | 2248 | OG1 | THR | H | 77 | −15.083 | 0.176 | −8.291 | 1 | 27.85 | H |
| ATOM | 2249 | CG2 | THR | H | 77 | −15.213 | 1.321 | −6.174 | 1 | 24.58 | H |
| ATOM | 2250 | C | THR | H | 77 | −17.933 | 2.322 | −7.066 | 1 | 24.64 | H |
| ATOM | 2251 | O | THR | H | 77 | −18.065 | 3.357 | −7.721 | 1 | 24.74 | H |
| ATOM | 2252 | N | ALA | H | 78 | −18.383 | 2.182 | −5.827 | 1 | 23.55 | H |
| ATOM | 2253 | CA | ALA | H | 78 | −19.027 | 3.275 | −5.122 | 1 | 21.51 | H |
| ATOM | 2254 | CB | ALA | H | 78 | −20.329 | 2.797 | −4.465 | 1 | 15.25 | H |
| ATOM | 2255 | C | ALA | H | 78 | −18.029 | 3.719 | −4.067 | 1 | 21.89 | H |
| ATOM | 2256 | O | ALA | H | 78 | −17.408 | 2.895 | −3.398 | 1 | 23.36 | H |
| ATOM | 2257 | N | PHE | H | 79 | −17.858 | 5.02 | −3.925 | 1 | 23.17 | H |
| ATOM | 2258 | CA | PHE | H | 79 | −16.932 | 5.517 | −2.935 | 1 | 24.04 | H |
| ATOM | 2259 | CB | PHE | H | 79 | −15.829 | 6.338 | −3.588 | 1 | 28.12 | H |
| ATOM | 2260 | CG | PHE | H | 79 | −15.072 | 5.607 | −4.654 | 1 | 28.58 | H |
| ATOM | 2261 | CD1 | PHE | H | 79 | −15.557 | 5.556 | −5.957 | 1 | 28.92 | H |
| ATOM | 2262 | CD2 | PHE | H | 79 | −13.87 | 4.973 | −4.356 | 1 | 28.25 | H |
| ATOM | 2263 | CE1 | PHE | H | 79 | −14.853 | 4.883 | −6.955 | 1 | 32.13 | H |
| ATOM | 2264 | CE2 | PHE | H | 79 | −13.159 | 4.297 | −5.343 | 1 | 31.64 | H |

TABLE 7-continued

| ATOM | 2265 | CZ | PHE | H | 79 | −13.652 | 4.252 | −6.648 | 1 | 29.74 | H |
| --- | --- | --- | --- | --- | --- | --- | --- | --- | --- | --- | --- |
| ATOM | 2266 | C | PHE | H | 79 | −17.636 | 6.396 | −1.939 | 1 | 25.52 | H |
| ATOM | 2267 | O | PHE | H | 79 | −18.729 | 6.903 | −2.189 | 1 | 27.79 | H |
| ATOM | 2268 | N | MET | H | 80 | −17 | 6.553 | −0.789 | 1 | 28.16 | H |
| ATOM | 2269 | CA | MET | H | 80 | −17.506 | 7.425 | 0.249 | 1 | 27.74 | H |
| ATOM | 2270 | CB | MET | H | 80 | −18.14 | 6.662 | 1.404 | 1 | 26.83 | H |
| ATOM | 2271 | CG | MET | H | 80 | −18.645 | 7.625 | 2.487 | 1 | 26.82 | H |
| ATOM | 2272 | SD | MET | H | 80 | −19.346 | 6.844 | 3.937 | 1 | 28.75 | H |
| ATOM | 2273 | CE | MET | H | 80 | −17.861 | 5.956 | 4.567 | 1 | 25.98 | H |
| ATOM | 2274 | C | MET | H | 80 | −16.321 | 8.209 | 0.772 | 1 | 28.71 | H |
| ATOM | 2275 | O | MET | H | 80 | −15.344 | 7.634 | 1.246 | 1 | 27.48 | H |
| ATOM | 2276 | N | GLN | H | 81 | −16.411 | 9.527 | 0.659 | 1 | 32.15 | H |
| ATOM | 2277 | CA | GLN | H | 81 | −15.358 | 10.405 | 1.133 | 1 | 36.24 | H |
| ATOM | 2278 | CB | GLN | H | 81 | −15.163 | 11.564 | 0.153 | 1 | 40.78 | H |
| ATOM | 2279 | CG | GLN | H | 81 | −14.004 | 12.488 | 0.503 | 1 | 47.71 | H |
| ATOM | 2280 | CD | GLN | H | 81 | −12.667 | 11.782 | 0.431 | 1 | 51.74 | H |
| ATOM | 2281 | OE1 | GLN | H | 81 | −12.281 | 11.268 | −0.62 | 1 | 55.57 | H |
| ATOM | 2282 | NE2 | GLN | H | 81 | −11.951 | 11.747 | 1.551 | 1 | 54.75 | H |
| ATOM | 2283 | C | GLN | H | 81 | −15.764 | 10.944 | 2.497 | 1 | 35.32 | H |
| ATOM | 2284 | O | GLN | H | 81 | −16.841 | 11.519 | 2.639 | 1 | 35.15 | H |
| ATOM | 2285 | N | LEU | H | 82 | −14.913 | 10.741 | 3.498 | 1 | 35.8 | H |
| ATOM | 2286 | CA | LEU | H | 82 | −15.19 | 11.229 | 4.847 | 1 | 35.77 | H |
| ATOM | 2287 | CB | LEU | H | 82 | −15.26 | 10.064 | 5.833 | 1 | 32.43 | H |
| ATOM | 2288 | CG | LEU | H | 82 | −16.522 | 9.208 | 5.733 | 1 | 33.01 | H |
| ATOM | 2289 | CD1 | LEU | H | 82 | −16.386 | 7.982 | 6.624 | 1 | 31.81 | H |
| ATOM | 2290 | CD2 | LEU | H | 82 | −17.732 | 10.038 | 6.138 | 1 | 30.13 | H |
| ATOM | 2291 | C | LEU | H | 82 | −14.116 | 12.215 | 5.289 | 1 | 37.04 | H |
| ATOM | 2292 | O | LEU | H | 82 | −12.984 | 11.823 | 5.571 | 1 | 36.26 | H |
| ATOM | 2293 | N | SER | H | 82A | −14.474 | 13.494 | 5.35 | 1 | 38.53 | H |
| ATOM | 2294 | CA | SER | H | 82A | −13.529 | 14.526 | 5.753 | 1 | 41.94 | H |
| ATOM | 2295 | CB | SER | H | 82A | −13.593 | 15.703 | 4.777 | 1 | 43.28 | H |
| ATOM | 2296 | OG | SER | H | 82A | −14.832 | 16.381 | 4.881 | 1 | 50.55 | H |
| ATOM | 2297 | C | SER | H | 82A | −13.764 | 15.018 | 7.185 | 1 | 42.59 | H |
| ATOM | 2298 | O | SER | H | 82A | −14.8 | 14.733 | 7.793 | 1 | 37.55 | H |
| ATOM | 2299 | N | SER | H | 82B | −12.784 | 15.761 | 7.704 | 1 | 45.27 | H |
| ATOM | 2300 | CA | SER | H | 82B | −12.815 | 16.305 | 9.062 | 1 | 47.02 | H |
| ATOM | 2301 | CB | SER | H | 82B | −13.83 | 17.45 | 9.154 | 1 | 49.74 | H |
| ATOM | 2302 | OG | SER | H | 82B | −15.162 | 16.976 | 9.048 | 1 | 55.67 | H |
| ATOM | 2303 | C | SER | H | 82B | −13.158 | 15.21 | 10.077 | 1 | 45.72 | H |
| ATOM | 2304 | O | SER | H | 82B | −14.092 | 15.342 | 10.87 | 1 | 44.1 | H |
| ATOM | 2305 | N | LEU | H | 82C | −12.38 | 14.132 | 10.044 | 1 | 45.48 | H |
| ATOM | 2306 | CA | LEU | H | 82C | −12.582 | 12.989 | 10.93 | 1 | 45.09 | H |
| ATOM | 2307 | CB | LEU | H | 82C | −11.623 | 11.86 | 10.548 | 1 | 45.44 | H |
| ATOM | 2308 | CG | LEU | H | 82C | −12.191 | 10.823 | 9.573 | 1 | 44.73 | H |
| ATOM | 2309 | CD1 | LEU | H | 82C | −13.207 | 11.462 | 8.643 | 1 | 43.75 | H |
| ATOM | 2310 | CD2 | LEU | H | 82C | −11.044 | 10.196 | 8.79 | 1 | 46.77 | H |
| ATOM | 2311 | C | LEU | H | 82C | −12.456 | 13.283 | 12.413 | 1 | 43.98 | H |
| ATOM | 2312 | O | LEU | H | 82C | −11.649 | 14.108 | 12.829 | 1 | 44.39 | H |
| ATOM | 2313 | N | THR | H | 83 | −13.26 | 12.569 | 13.195 | 1 | 43.97 | H |
| ATOM | 2314 | CA | THR | H | 83 | −13.313 | 12.707 | 14.643 | 1 | 44.91 | H |
| ATOM | 2315 | CB | THR | H | 83 | −14.572 | 13.475 | 15.042 | 1 | 46.59 | H |
| ATOM | 2316 | OG1 | THR | H | 83 | −14.476 | 14.816 | 14.548 | 1 | 46.18 | H |
| ATOM | 2317 | CG2 | THR | H | 83 | −14.751 | 13.485 | 16.558 | 1 | 49.35 | H |
| ATOM | 2318 | C | THR | H | 83 | −13.348 | 11.337 | 15.315 | 1 | 46.38 | H |
| ATOM | 2319 | O | THR | H | 83 | −13.652 | 10.333 | 14.674 | 1 | 48.88 | H |
| ATOM | 2320 | N | SER | H | 84 | −13.042 | 11.292 | 16.607 | 1 | 46.34 | H |
| ATOM | 2321 | CA | SER | H | 84 | −13.065 | 10.029 | 17.323 | 1 | 45.35 | H |
| ATOM | 2322 | CB | SER | H | 84 | −12.639 | 10.231 | 18.779 | 1 | 45.13 | H |
| ATOM | 2323 | OG | SER | H | 84 | −13.582 | 11.007 | 19.494 | 1 | 45.06 | H |
| ATOM | 2324 | C | SER | H | 84 | −14.493 | 9.5 | 17.258 | 1 | 46.01 | H |
| ATOM | 2325 | O | SER | H | 84 | −14.739 | 8.311 | 17.463 | 1 | 46.32 | H |
| ATOM | 2326 | N | GLU | H | 85 | −15.428 | 10.398 | 16.959 | 1 | 45.5 | H |
| ATOM | 2327 | CA | GLU | H | 85 | −16.842 | 10.051 | 16.858 | 1 | 45.98 | H |
| ATOM | 2328 | CB | GLU | H | 85 | −17.688 | 11.331 | 16.825 | 1 | 50.25 | H |
| ATOM | 2329 | CG | GLU | H | 85 | −19.179 | 11.117 | 16.555 | 1 | 54.41 | H |
| ATOM | 2330 | CD | GLU | H | 85 | −20.058 | 11.461 | 17.751 | 1 | 58.62 | H |
| ATOM | 2331 | OE1 | GLU | H | 85 | −19.977 | 10.756 | 18.784 | 1 | 60.55 | H |
| ATOM | 2332 | OE2 | GLU | H | 85 | −20.831 | 12.44 | 17.657 | 1 | 59.71 | H |
| ATOM | 2333 | C | GLU | H | 85 | −17.117 | 9.218 | 15.608 | 1 | 43.77 | H |
| ATOM | 2334 | O | GLU | H | 85 | −18.03 | 8.391 | 15.589 | 1 | 44.09 | H |
| ATOM | 2335 | N | ASP | H | 86 | −16.322 | 9.441 | 14.567 | 1 | 41.14 | H |
| ATOM | 2336 | CA | ASP | H | 86 | −16.479 | 8.721 | 13.304 | 1 | 37.01 | H |
| ATOM | 2337 | CB | ASP | H | 86 | −15.949 | 9.564 | 12.14 | 1 | 39.51 | H |
| ATOM | 2338 | CG | ASP | H | 86 | −16.466 | 10.986 | 12.167 | 1 | 42.15 | H |
| ATOM | 2339 | OD1 | ASP | H | 86 | −17.64 | 11.187 | 12.54 | 1 | 43.42 | H |
| ATOM | 2340 | OD2 | ASP | H | 86 | −15.701 | 11.904 | 11.807 | 1 | 42.9 | H |
| ATOM | 2341 | C | ASP | H | 86 | −15.769 | 7.369 | 13.299 | 1 | 33.42 | H |
| ATOM | 2342 | O | ASP | H | 86 | −15.824 | 6.639 | 12.313 | 1 | 30.78 | H |
| ATOM | 2343 | N | SER | H | 87 | −15.086 | 7.035 | 14.387 | 1 | 29.56 | H |

TABLE 7-continued

| | | | | | | | | | | |
|---|---|---|---|---|---|---|---|---|---|---|
| ATOM | 2344 | CA | SER | H | 87 | −14.409 | 5.748 | 14.441 | 1 | 28.75 | H |
| ATOM | 2345 | CB | SER | H | 87 | −13.499 | 5.653 | 15.667 | 1 | 27.53 | H |
| ATOM | 2346 | OG | SER | H | 87 | −12.347 | 6.458 | 15.496 | 1 | 31.1 | H |
| ATOM | 2347 | C | SER | H | 87 | −15.469 | 4.668 | 14.499 | 1 | 25.65 | H |
| ATOM | 2348 | O | SER | H | 87 | −16.296 | 4.655 | 15.412 | 1 | 23.46 | H |
| ATOM | 2349 | N | ALA | H | 88 | −15.451 | 3.776 | 13.514 | 1 | 24 | H |
| ATOM | 2350 | CA | ALA | H | 88 | −16.426 | 2.692 | 13.467 | 1 | 24.79 | H |
| ATOM | 2351 | CB | ALA | H | 88 | −17.845 | 3.268 | 13.44 | 1 | 24.51 | H |
| ATOM | 2352 | C | ALA | H | 88 | −16.239 | 1.756 | 12.279 | 1 | 23.07 | H |
| ATOM | 2353 | O | ALA | H | 88 | −15.384 | 1.966 | 11.417 | 1 | 21.27 | H |
| ATOM | 2354 | N | VAL | H | 89 | −17.042 | 0.701 | 12.255 | 1 | 22.59 | H |
| ATOM | 2355 | CA | VAL | H | 89 | −16.996 | −0.229 | 11.145 | 1 | 24.19 | H |
| ATOM | 2356 | CB | VAL | H | 89 | −17.445 | −1.654 | 11.572 | 1 | 24.22 | H |
| ATOM | 2357 | CG1 | VAL | H | 89 | −18.787 | −1.585 | 12.283 | 1 | 31.12 | H |
| ATOM | 2358 | CG2 | VAL | H | 89 | −17.549 | −2.559 | 10.354 | 1 | 20.23 | H |
| ATOM | 2359 | C | VAL | H | 89 | −17.968 | 0.359 | 10.12 | 1 | 23.16 | H |
| ATOM | 2360 | O | VAL | H | 89 | −19.111 | 0.696 | 10.443 | 1 | 18.77 | H |
| ATOM | 2361 | N | TYR | H | 90 | −17.498 | 0.539 | 8.896 | 1 | 22.89 | H |
| ATOM | 2362 | CA | TYR | H | 90 | −18.368 | 1.086 | 7.875 | 1 | 23.13 | H |
| ATOM | 2363 | CB | TYR | H | 90 | −17.703 | 2.253 | 7.164 | 1 | 22.49 | H |
| ATOM | 2364 | CG | TYR | H | 90 | −17.6 | 3.455 | 8.044 | 1 | 23.74 | H |
| ATOM | 2365 | CD1 | TYR | H | 90 | −16.574 | 3.571 | 8.98 | 1 | 21.39 | H |
| ATOM | 2366 | CE1 | TYR | H | 90 | −16.523 | 4.656 | 9.845 | 1 | 24.6 | H |
| ATOM | 2367 | CD2 | TYR | H | 90 | −18.572 | 4.452 | 7.99 | 1 | 22.12 | H |
| ATOM | 2368 | CE2 | TYR | H | 90 | −18.533 | 5.531 | 8.846 | 1 | 23.11 | H |
| ATOM | 2369 | CZ | TYR | H | 90 | −17.511 | 5.632 | 9.771 | 1 | 23.88 | H |
| ATOM | 2370 | OH | TYR | H | 90 | −17.49 | 6.709 | 10.623 | 1 | 26.15 | H |
| ATOM | 2371 | C | TYR | H | 90 | −18.734 | 0.023 | 6.878 | 1 | 23.35 | H |
| ATOM | 2372 | O | TYR | H | 90 | −17.863 | −0.643 | 6.318 | 1 | 23.56 | H |
| ATOM | 2373 | N | TYR | H | 91 | −20.031 | −0.139 | 6.667 | 1 | 23.24 | H |
| ATOM | 2374 | CA | TYR | H | 91 | −20.512 | −1.133 | 5.731 | 1 | 25.43 | H |
| ATOM | 2375 | CB | TYR | H | 91 | −21.67 | −1.931 | 6.329 | 1 | 24.11 | H |
| ATOM | 2376 | CG | TYR | H | 91 | −21.256 | −2.896 | 7.407 | 1 | 22.57 | H |
| ATOM | 2377 | CD1 | TYR | H | 91 | −20.497 | −4.017 | 7.103 | 1 | 21.38 | H |
| ATOM | 2378 | CE1 | TYR | H | 91 | −20.132 | −4.916 | 8.089 | 1 | 25.79 | H |
| ATOM | 2379 | CD2 | TYR | H | 91 | −21.638 | −2.694 | 8.729 | 1 | 21.45 | H |
| ATOM | 2380 | CE2 | TYR | H | 91 | −21.278 | −3.585 | 9.725 | 1 | 23.8 | H |
| ATOM | 2381 | CZ | TYR | H | 91 | −20.527 | −4.695 | 9.401 | 1 | 25.11 | H |
| ATOM | 2382 | OH | TYR | H | 91 | −20.162 | −5.583 | 10.389 | 1 | 30.55 | H |
| ATOM | 2383 | C | TYR | H | 91 | −20.972 | −0.544 | 4.422 | 1 | 26.48 | H |
| ATOM | 2384 | O | TYR | H | 91 | −21.47 | 0.582 | 4.355 | 1 | 27.26 | H |
| ATOM | 2385 | N | CYS | H | 92 | −20.789 | −1.338 | 3.381 | 1 | 27.58 | H |
| ATOM | 2386 | CA | CYS | H | 92 | −21.213 | −0.985 | 2.051 | 1 | 27.08 | H |
| ATOM | 2387 | C | CYS | H | 92 | −22.366 | −1.949 | 1.819 | 1 | 24.59 | H |
| ATOM | 2388 | O | CYS | H | 92 | −22.194 | −3.161 | 1.958 | 1 | 25.45 | H |
| ATOM | 2389 | CB | CYS | H | 92 | −20.099 | −1.255 | 1.039 | 1 | 29.34 | H |
| ATOM | 2390 | SG | CYS | H | 92 | −20.701 | −0.853 | −0.617 | 1 | 40.33 | H |
| ATOM | 2391 | N | ALA | H | 93 | −23.54 | −1.435 | 1.485 | 1 | 20.72 | H |
| ATOM | 2392 | CA | ALA | H | 93 | −24.677 | −2.325 | 1.259 | 1 | 20.15 | H |
| ATOM | 2393 | CB | ALA | H | 93 | −25.653 | −2.239 | 2.431 | 1 | 21.64 | H |
| ATOM | 2394 | C | ALA | H | 93 | −25.4 | −2.01 | −0.03 | 1 | 16.99 | H |
| ATOM | 2395 | O | ALA | H | 93 | −25.338 | −0.891 | −0.525 | 1 | 19.38 | H |
| ATOM | 2396 | N | ARG | H | 94 | −26.09 | −2.995 | −0.582 | 1 | 14.06 | H |
| ATOM | 2397 | CA | ARG | H | 94 | −26.826 | −2.755 | −1.809 | 1 | 14.37 | H |
| ATOM | 2398 | CB | ARG | H | 94 | −26.552 | −3.861 | −2.813 | 1 | 15.99 | H |
| ATOM | 2399 | CG | ARG | H | 94 | −27.17 | −3.601 | −4.169 | 1 | 14.05 | H |
| ATOM | 2400 | CD | ARG | H | 94 | −28.155 | −4.682 | −4.468 | 1 | 17.49 | H |
| ATOM | 2401 | NE | ARG | H | 94 | −27.842 | −5.38 | −5.699 | 1 | 19.37 | H |
| ATOM | 2402 | CZ | ARG | H | 94 | −28.383 | −6.545 | −6.036 | 1 | 21.79 | H |
| ATOM | 2403 | NH1 | ARG | H | 94 | −29.248 | −7.129 | −5.216 | 1 | 16.63 | H |
| ATOM | 2404 | NH2 | ARG | H | 94 | −28.088 | −7.107 | −7.205 | 1 | 24.27 | H |
| ATOM | 2405 | C | ARG | H | 94 | −28.312 | −2.687 | −1.511 | 1 | 14.69 | H |
| ATOM | 2406 | O | ARG | H | 94 | −28.87 | −3.613 | −0.927 | 1 | 13.41 | H |
| ATOM | 2407 | N | SER | H | 95 | −28.946 | −1.586 | −1.906 | 1 | 15.09 | H |
| ATOM | 2408 | CA | SER | H | 95 | −30.377 | −1.404 | −1.676 | 1 | 16.18 | H |
| ATOM | 2409 | CB | SER | H | 95 | −30.761 | 0.066 | −1.812 | 1 | 16.17 | H |
| ATOM | 2410 | OG | SER | H | 95 | −32.091 | 0.272 | −1.38 | 1 | 17.85 | H |
| ATOM | 2411 | C | SER | H | 95 | −31.17 | −2.235 | −2.674 | 1 | 17.05 | H |
| ATOM | 2412 | O | SER | H | 95 | −30.996 | −2.101 | −3.884 | 1 | 18.33 | H |
| ATOM | 2413 | N | ALA | H | 96 | −32.047 | −3.085 | −2.15 | 1 | 16.69 | H |
| ATOM | 2414 | CA | ALA | H | 96 | −32.86 | −3.979 | −2.962 | 1 | 16.13 | H |
| ATOM | 2415 | CB | ALA | H | 96 | −33.622 | −4.935 | −2.053 | 1 | 15.97 | H |
| ATOM | 2416 | C | ALA | H | 96 | −33.829 | −3.303 | −3.922 | 1 | 15.41 | H |
| ATOM | 2417 | O | ALA | H | 96 | −34.273 | −2.177 | −3.707 | 1 | 16.59 | H |
| ATOM | 2418 | N | SER | H | 97 | −34.164 | −4.013 | −4.988 | 1 | 15.94 | H |
| ATOM | 2419 | CA | SER | H | 97 | −35.086 | −3.48 | −5.972 | 1 | 21.08 | H |
| ATOM | 2420 | CB | SER | H | 97 | −35.283 | −4.47 | −7.123 | 1 | 19.36 | H |
| ATOM | 2421 | OG | SER | H | 97 | −34.133 | −4.546 | −7.936 | 1 | 19.33 | H |
| ATOM | 2422 | C | SER | H | 97 | −36.438 | −3.18 | −5.347 | 1 | 22.46 | H |

TABLE 7-continued

| ATOM | 2423 | O | SER | H | 97 | −37.103 | −2.233 | −5.748 | 1 | 23.48 | H |
|---|---|---|---|---|---|---|---|---|---|---|---|
| ATOM | 2424 | N | TYR | H | 98 | −36.828 | −3.987 | −4.361 | 1 | 23.91 | H |
| ATOM | 2425 | CA | TYR | H | 98 | −38.121 | −3.839 | −3.706 | 1 | 24.89 | H |
| ATOM | 2426 | CB | TYR | H | 98 | −38.683 | −5.215 | −3.359 | 1 | 25.72 | H |
| ATOM | 2427 | CG | TYR | H | 98 | −39.358 | −5.903 | −4.519 | 1 | 29.65 | H |
| ATOM | 2428 | CD1 | TYR | H | 98 | −40.44 | −5.312 | −5.171 | 1 | 31.3 | H |
| ATOM | 2429 | CE1 | TYR | H | 98 | −41.077 | −5.95 | −6.237 | 1 | 31.57 | H |
| ATOM | 2430 | CD2 | TYR | H | 98 | −38.927 | −7.15 | −4.962 | 1 | 29.26 | H |
| ATOM | 2431 | CE2 | TYR | H | 98 | −39.555 | −7.795 | −6.025 | 1 | 29.82 | H |
| ATOM | 2432 | CZ | TYR | H | 98 | −40.627 | −7.192 | −6.658 | 1 | 31.67 | H |
| ATOM | 2433 | OH | TYR | H | 98 | −41.246 | −7.837 | −7.711 | 1 | 32.36 | H |
| ATOM | 2434 | C | TYR | H | 98 | −38.203 | −2.952 | −2.474 | 1 | 25.8 | H |
| ATOM | 2435 | O | TYR | H | 98 | −39.141 | −3.081 | −1.684 | 1 | 22.28 | H |
| ATOM | 2436 | N | GLY | H | 99 | −37.243 | −2.049 | −2.301 | 1 | 26.59 | H |
| ATOM | 2437 | CA | GLY | H | 99 | −37.304 | −1.168 | −1.149 | 1 | 26.74 | H |
| ATOM | 2438 | C | GLY | H | 99 | −35.972 | −0.741 | −0.574 | 1 | 28.24 | H |
| ATOM | 2439 | O | GLY | H | 99 | −34.922 | −1.275 | −0.933 | 1 | 27.76 | H |
| ATOM | 2440 | N | ASP | H | 100 | −36.021 | 0.22 | 0.342 | 1 | 27.68 | H |
| ATOM | 2441 | CA | ASP | H | 100 | −34.808 | 0.724 | 0.959 | 1 | 27.85 | H |
| ATOM | 2442 | CB | ASP | H | 100 | −35.036 | 2.139 | 1.488 | 1 | 27.83 | H |
| ATOM | 2443 | CG | ASP | H | 100 | −35.313 | 3.13 | 0.376 | 1 | 28.79 | H |
| ATOM | 2444 | OD1 | ASP | H | 100 | −36.389 | 3.037 | −0.246 | 1 | 33.65 | H |
| ATOM | 2445 | OD2 | ASP | H | 100 | −34.457 | 3.997 | 0.114 | 1 | 28.79 | H |
| ATOM | 2446 | C | ASP | H | 100 | −34.216 | −0.173 | 2.045 | 1 | 26.78 | H |
| ATOM | 2447 | O | ASP | H | 100 | −33.776 | 0.289 | 3.096 | 1 | 27.25 | H |
| ATOM | 2448 | N | TYR | H | 100A | −34.22 | −1.471 | 1.785 | 1 | 25.66 | H |
| ATOM | 2449 | CA | TYR | H | 100A | −33.607 | −2.421 | 2.7 | 1 | 22.34 | H |
| ATOM | 2450 | CB | TYR | H | 100A | −34.597 | −3.507 | 3.134 | 1 | 19.31 | H |
| ATOM | 2451 | CG | TYR | H | 100A | −35.24 | −4.243 | 1.997 | 1 | 22.22 | H |
| ATOM | 2452 | CD1 | TYR | H | 100A | −36.344 | −3.713 | 1.342 | 1 | 22.59 | H |
| ATOM | 2453 | CE1 | TYR | H | 100A | −36.938 | −4.379 | 0.29 | 1 | 22.5 | H |
| ATOM | 2454 | CD2 | TYR | H | 100A | −34.74 | −5.47 | 1.564 | 1 | 23.36 | H |
| ATOM | 2455 | CE2 | TYR | H | 100A | −35.329 | −6.147 | 0.509 | 1 | 23.22 | H |
| ATOM | 2456 | CZ | TYR | H | 100A | −36.432 | −5.592 | −0.124 | 1 | 24.18 | H |
| ATOM | 2457 | OH | TYR | H | 100A | −37.034 | −6.249 | −1.175 | 1 | 24.68 | H |
| ATOM | 2458 | C | TYR | H | 100A | −32.449 | −3.02 | 1.899 | 1 | 18.6 | H |
| ATOM | 2459 | O | TYR | H | 100A | −32.502 | −3.078 | 0.664 | 1 | 13.67 | H |
| ATOM | 2460 | N | ALA | H | 100B | −31.394 | −3.435 | 2.588 | 1 | 19.07 | H |
| ATOM | 2461 | CA | ALA | H | 100B | −30.236 | −3.994 | 1.904 | 1 | 18.47 | H |
| ATOM | 2462 | CB | ALA | H | 100B | −28.956 | −3.5 | 2.564 | 1 | 16.36 | H |
| ATOM | 2463 | C | ALA | H | 100B | −30.262 | −5.512 | 1.875 | 1 | 17.86 | H |
| ATOM | 2464 | O | ALA | H | 100B | −30.508 | −6.16 | 2.89 | 1 | 20.82 | H |
| ATOM | 2465 | N | ASP | H | 101 | −30.014 | −6.07 | 0.696 | 1 | 19.66 | H |
| ATOM | 2466 | CA | ASP | H | 101 | −29.993 | −7.515 | 0.516 | 1 | 23.51 | H |
| ATOM | 2467 | CB | ASP | H | 101 | −30.811 | −7.897 | −0.715 | 1 | 23.84 | H |
| ATOM | 2468 | CG | ASP | H | 101 | −30.437 | −7.085 | −1.935 | 1 | 25.73 | H |
| ATOM | 2469 | OD1 | ASP | H | 101 | −29.455 | −6.311 | −1.857 | 1 | 23.8 | H |
| ATOM | 2470 | OD2 | ASP | H | 101 | −31.126 | −7.228 | −2.971 | 1 | 23.43 | H |
| ATOM | 2471 | C | ASP | H | 101 | −28.566 | −8.072 | 0.392 | 1 | 24.71 | H |
| ATOM | 2472 | O | ASP | H | 101 | −28.355 | −9.288 | 0.423 | 1 | 26.02 | H |
| ATOM | 2473 | N | TYR | H | 102 | −27.591 | −7.181 | 0.253 | 1 | 24.58 | H |
| ATOM | 2474 | CA | TYR | H | 102 | −26.193 | −7.587 | 0.15 | 1 | 25.52 | H |
| ATOM | 2475 | CB | TYR | H | 102 | −25.793 | −7.757 | −1.318 | 1 | 28.06 | H |
| ATOM | 2476 | CG | TYR | H | 102 | −26.451 | −8.936 | −2.007 | 1 | 30.4 | H |
| ATOM | 2477 | CD1 | TYR | H | 102 | −25.934 | −10.229 | −1.877 | 1 | 28.54 | H |
| ATOM | 2478 | CE1 | TYR | H | 102 | −26.533 | −11.317 | −2.524 | 1 | 28.74 | H |
| ATOM | 2479 | CD2 | TYR | H | 102 | −27.592 | −8.758 | −2.799 | 1 | 30.81 | H |
| ATOM | 2480 | CE2 | TYR | H | 102 | −28.202 | −9.84 | −3.446 | 1 | 30.98 | H |
| ATOM | 2481 | CZ | TYR | H | 102 | −27.666 | −11.113 | −3.306 | 1 | 30.96 | H |
| ATOM | 2482 | OH | TYR | H | 102 | −28.267 | −12.17 | −3.956 | 1 | 29.64 | H |
| ATOM | 2483 | C | TYR | H | 102 | −25.312 | −6.54 | 0.818 | 1 | 23.98 | H |
| ATOM | 2484 | O | TYR | H | 102 | −25.402 | −5.348 | 0.521 | 1 | 25.69 | H |
| ATOM | 2485 | N | TRP | H | 103 | −24.462 | −7 | 1.728 | 1 | 23.67 | H |
| ATOM | 2486 | CA | TRP | H | 103 | −23.566 | −6.127 | 2.474 | 1 | 18.64 | H |
| ATOM | 2487 | CB | TRP | H | 103 | −23.812 | −6.265 | 3.974 | 1 | 18.93 | H |
| ATOM | 2488 | CG | TRP | H | 103 | −25.21 | −5.98 | 4.403 | 1 | 18.53 | H |
| ATOM | 2489 | CD2 | TRP | H | 103 | −25.632 | −4.934 | 5.273 | 1 | 15.85 | H |
| ATOM | 2490 | CE2 | TRP | H | 103 | −27.032 | −5.023 | 5.383 | 1 | 16.74 | H |
| ATOM | 2491 | CE3 | TRP | H | 103 | −24.96 | −3.924 | 5.97 | 1 | 20.28 | H |
| ATOM | 2492 | CD1 | TRP | H | 103 | −26.342 | −6.651 | 4.031 | 1 | 17.82 | H |
| ATOM | 2493 | NE1 | TRP | H | 103 | −27.44 | −6.083 | 4.615 | 1 | 17.13 | H |
| ATOM | 2494 | CZ2 | TRP | H | 103 | −27.778 | −4.138 | 6.16 | 1 | 16.77 | H |
| ATOM | 2495 | CZ3 | TRP | H | 103 | −25.701 | −3.04 | 6.746 | 1 | 19.94 | H |
| ATOM | 2496 | CH2 | TRP | H | 103 | −27.095 | −3.154 | 6.831 | 1 | 19.4 | H |
| ATOM | 2497 | C | TRP | H | 103 | −22.129 | −6.505 | 2.217 | 1 | 20.41 | H |
| ATOM | 2498 | O | TRP | H | 103 | −21.822 | −7.672 | 1.95 | 1 | 20.83 | H |
| ATOM | 2499 | N | GLY | H | 104 | −21.246 | −5.514 | 2.287 | 1 | 21.1 | H |
| ATOM | 2500 | CA | GLY | H | 104 | −19.833 | −5.786 | 2.12 | 1 | 23.14 | H |
| ATOM | 2501 | C | GLY | H | 104 | −19.396 | −6.261 | 3.494 | 1 | 24.35 | H |

TABLE 7-continued

| ATOM | 2502 | O | GLY | H | 104 | −20.184 | −6.201 | 4.444 | 1 | 22.07 | H |
|---|---|---|---|---|---|---|---|---|---|---|---|
| ATOM | 2503 | N | HIS | H | 105 | −18.162 | −6.723 | 3.63 | 1 | 27.31 | H |
| ATOM | 2504 | CA | HIS | H | 105 | −17.715 | −7.197 | 4.933 | 1 | 31.34 | H |
| ATOM | 2505 | CB | HIS | H | 105 | −16.574 | −8.196 | 4.761 | 1 | 36.95 | H |
| ATOM | 2506 | CG | HIS | H | 105 | −16.958 | −9.371 | 3.922 | 1 | 45.33 | H |
| ATOM | 2507 | CD2 | HIS | H | 105 | −16.395 | −9.899 | 2.81 | 1 | 47.96 | H |
| ATOM | 2508 | ND1 | HIS | H | 105 | −18.115 | −10.087 | 4.146 | 1 | 47.69 | H |
| ATOM | 2509 | CE1 | HIS | H | 105 | −18.251 | −11.003 | 3.203 | 1 | 51.12 | H |
| ATOM | 2510 | NE2 | HIS | H | 105 | −17.221 | −10.91 | 2.379 | 1 | 50.5 | H |
| ATOM | 2511 | C | HIS | H | 105 | −17.322 | −6.069 | 5.865 | 1 | 28.34 | H |
| ATOM | 2512 | O | HIS | H | 105 | −16.789 | −6.299 | 6.942 | 1 | 29.33 | H |
| ATOM | 2513 | N | GLY | H | 106 | −17.607 | −4.846 | 5.447 | 1 | 27.15 | H |
| ATOM | 2514 | CA | GLY | H | 106 | −17.289 | −3.704 | 6.273 | 1 | 28.86 | H |
| ATOM | 2515 | C | GLY | H | 106 | −15.811 | −3.387 | 6.36 | 1 | 28.45 | H |
| ATOM | 2516 | O | GLY | H | 106 | −14.959 | −4.274 | 6.39 | 1 | 30.58 | H |
| ATOM | 2517 | N | THR | H | 107 | −15.508 | −2.098 | 6.376 | 1 | 28.87 | H |
| ATOM | 2518 | CA | THR | H | 107 | −14.137 | −1.637 | 6.497 | 1 | 28.05 | H |
| ATOM | 2519 | CB | THR | H | 107 | −13.746 | −0.72 | 5.32 | 1 | 26.06 | H |
| ATOM | 2520 | OG1 | THR | H | 107 | −12.69 | 0.147 | 5.731 | 1 | 31.24 | H |
| ATOM | 2521 | CG2 | THR | H | 107 | −14.918 | 0.102 | 4.862 | 1 | 28.02 | H |
| ATOM | 2522 | C | THR | H | 107 | −14.072 | −0.878 | 7.82 | 1 | 26.61 | H |
| ATOM | 2523 | O | THR | H | 107 | −14.914 | −0.022 | 8.09 | 1 | 25.66 | H |
| ATOM | 2524 | N | THR | H | 108 | −13.1 | −1.223 | 8.661 | 1 | 25.86 | H |
| ATOM | 2525 | CA | THR | H | 108 | −12.962 | −0.572 | 9.961 | 1 | 23.72 | H |
| ATOM | 2526 | CB | THR | H | 108 | −12.349 | −1.526 | 11.023 | 1 | 23.76 | H |
| ATOM | 2527 | OG1 | THR | H | 108 | −13.217 | −2.653 | 11.232 | 1 | 22.42 | H |
| ATOM | 2528 | CG2 | THR | H | 108 | −12.164 | −0.797 | 12.342 | 1 | 19.8 | H |
| ATOM | 2529 | C | THR | H | 108 | −12.111 | 0.693 | 9.888 | 1 | 24.39 | H |
| ATOM | 2530 | O | THR | H | 108 | −10.968 | 0.679 | 9.428 | 1 | 24.52 | H |
| ATOM | 2531 | N | LEU | H | 109 | −12.691 | 1.793 | 10.345 | 1 | 23.92 | H |
| ATOM | 2532 | CA | LEU | H | 109 | −12.013 | 3.071 | 10.352 | 1 | 23.67 | H |
| ATOM | 2533 | CB | LEU | H | 109 | −12.832 | 4.098 | 9.575 | 1 | 23.95 | H |
| ATOM | 2534 | CG | LEU | H | 109 | −12.365 | 5.549 | 9.684 | 1 | 23.82 | H |
| ATOM | 2535 | CD1 | LEU | H | 109 | −10.918 | 5.672 | 9.22 | 1 | 25.23 | H |
| ATOM | 2536 | CD2 | LEU | H | 109 | −13.274 | 6.423 | 8.847 | 1 | 22.33 | H |
| ATOM | 2537 | C | LEU | H | 109 | −11.814 | 3.544 | 11.789 | 1 | 25.63 | H |
| ATOM | 2538 | O | LEU | H | 109 | −12.765 | 3.647 | 12.568 | 1 | 25.05 | H |
| ATOM | 2539 | N | THR | H | 110 | −10.565 | 3.826 | 12.135 | 1 | 26.28 | H |
| ATOM | 2540 | CA | THR | H | 110 | −10.237 | 4.287 | 13.472 | 1 | 27.28 | H |
| ATOM | 2541 | CB | THR | H | 110 | −9.26 | 3.317 | 14.176 | 1 | 29.45 | H |
| ATOM | 2542 | OG1 | THR | H | 110 | −9.753 | 1.97 | 14.081 | 1 | 30.69 | H |
| ATOM | 2543 | CG2 | THR | H | 110 | −9.11 | 3.706 | 15.648 | 1 | 27.31 | H |
| ATOM | 2544 | C | THR | H | 110 | −9.596 | 5.669 | 13.375 | 1 | 26.95 | H |
| ATOM | 2545 | O | THR | H | 110 | −8.536 | 5.838 | 12.778 | 1 | 25.4 | H |
| ATOM | 2546 | N | VAL | H | 111 | −10.263 | 6.66 | 13.953 | 1 | 27.85 | H |
| ATOM | 2547 | CA | VAL | H | 111 | −9.764 | 8.022 | 13.937 | 1 | 26.78 | H |
| ATOM | 2548 | CB | VAL | H | 111 | −10.923 | 9.033 | 13.872 | 1 | 28.9 | H |
| ATOM | 2549 | CG1 | VAL | H | 111 | −10.371 | 10.45 | 13.829 | 1 | 24.78 | H |
| ATOM | 2550 | CG2 | VAL | H | 111 | −11.798 | 8.749 | 12.646 | 1 | 23.25 | H |
| ATOM | 2551 | C | VAL | H | 111 | −8.991 | 8.215 | 15.227 | 1 | 30.11 | H |
| ATOM | 2552 | O | VAL | H | 111 | −9.579 | 8.284 | 16.31 | 1 | 31.03 | H |
| ATOM | 2553 | N | SER | H | 112 | −7.67 | 8.296 | 15.107 | 1 | 31.29 | H |
| ATOM | 2554 | CA | SER | H | 112 | −6.802 | 8.458 | 16.265 | 1 | 32.03 | H |
| ATOM | 2555 | CB | SER | H | 112 | −6.668 | 7.117 | 16.999 | 1 | 33.27 | H |
| ATOM | 2556 | OG | SER | H | 112 | −5.6 | 7.124 | 17.933 | 1 | 35.37 | H |
| ATOM | 2557 | C | SER | H | 112 | −5.425 | 8.947 | 15.848 | 1 | 32.3 | H |
| ATOM | 2558 | O | SER | H | 112 | −4.954 | 8.643 | 14.748 | 1 | 31.76 | H |
| ATOM | 2559 | N | SER | H | 113 | −4.787 | 9.703 | 16.736 | 1 | 31.76 | H |
| ATOM | 2560 | CA | SER | H | 113 | −3.45 | 10.23 | 16.489 | 1 | 31.47 | H |
| ATOM | 2561 | CB | SER | H | 113 | −3.233 | 11.512 | 17.308 | 1 | 33.88 | H |
| ATOM | 2562 | OG | SER | H | 113 | −4.25 | 11.685 | 18.29 | 1 | 38.4 | H |
| ATOM | 2563 | C | SER | H | 113 | −2.39 | 9.179 | 16.843 | 1 | 30.34 | H |
| ATOM | 2564 | O | SER | H | 113 | −1.197 | 9.4 | 16.676 | 1 | 28.95 | H |
| ATOM | 2565 | N | ALA | H | 114 | −2.843 | 8.023 | 17.316 | 1 | 29.4 | H |
| ATOM | 2566 | CA | ALA | H | 114 | −1.938 | 6.945 | 17.684 | 1 | 28.43 | H |
| ATOM | 2567 | CB | ALA | H | 114 | −2.665 | 5.93 | 18.565 | 1 | 25.6 | H |
| ATOM | 2568 | C | ALA | H | 114 | −1.399 | 6.262 | 16.439 | 1 | 28.8 | H |
| ATOM | 2569 | O | ALA | H | 114 | −2.036 | 6.276 | 15.392 | 1 | 32.36 | H |
| ATOM | 2570 | N | LYS | H | 115 | −0.226 | 5.656 | 16.561 | 1 | 30.91 | H |
| ATOM | 2571 | CA | LYS | H | 115 | 0.387 | 4.952 | 15.445 | 1 | 32.2 | H |
| ATOM | 2572 | CB | LYS | H | 115 | 1.913 | 5.098 | 15.517 | 1 | 36.6 | H |
| ATOM | 2573 | CG | LYS | H | 115 | 2.399 | 6.456 | 15.013 | 1 | 41.36 | H |
| ATOM | 2574 | CD | LYS | H | 115 | 3.852 | 6.753 | 15.357 | 1 | 43.53 | H |
| ATOM | 2575 | CE | LYS | H | 115 | 4.287 | 8.076 | 14.725 | 1 | 45.01 | H |
| ATOM | 2576 | NZ | LYS | H | 115 | 3.399 | 9.23 | 15.08 | 1 | 47.73 | H |
| ATOM | 2577 | C | LYS | H | 115 | −0.011 | 3.472 | 15.336 | 1 | 31.8 | H |
| ATOM | 2578 | O | LYS | H | 115 | −0.237 | 2.776 | 16.334 | 1 | 29.54 | H |
| ATOM | 2579 | N | THR | H | 116 | −0.1 | 3.009 | 14.094 | 1 | 32.32 | H |
| ATOM | 2580 | CA | THR | H | 116 | −0.472 | 1.636 | 13.791 | 1 | 31.75 | H |

TABLE 7-continued

| | | | | | | | | | | |
|---|---|---|---|---|---|---|---|---|---|---|
| ATOM | 2581 | CB | THR | H | 116 | −0.538 | 1.424 | 12.278 | 1 | 30.67 | H |
| ATOM | 2582 | OG1 | THR | H | 116 | −1.555 | 2.269 | 11.732 | 1 | 33.19 | H |
| ATOM | 2583 | CG2 | THR | H | 116 | −0.836 | −0.035 | 11.951 | 1 | 29.22 | H |
| ATOM | 2584 | C | THR | H | 116 | 0.525 | 0.644 | 14.366 | 1 | 32.75 | H |
| ATOM | 2585 | O | THR | H | 116 | 1.715 | 0.705 | 14.064 | 1 | 32.95 | H |
| ATOM | 2586 | N | THR | H | 117 | 0.035 | −0.273 | 15.188 | 1 | 32.66 | H |
| ATOM | 2587 | CA | THR | H | 117 | 0.903 | −1.276 | 15.783 | 1 | 32.97 | H |
| ATOM | 2588 | CB | THR | H | 117 | 0.99 | −1.149 | 17.328 | 1 | 34.5 | H |
| ATOM | 2589 | OG1 | THR | H | 117 | 1.269 | 0.205 | 17.7 | 1 | 37.69 | H |
| ATOM | 2590 | CG2 | THR | H | 117 | 2.098 | −2.04 | 17.86 | 1 | 35.92 | H |
| ATOM | 2591 | C | THR | H | 117 | 0.353 | −2.657 | 15.495 | 1 | 30.42 | H |
| ATOM | 2592 | O | THR | H | 117 | −0.766 | −2.977 | 15.89 | 1 | 28.68 | H |
| ATOM | 2593 | N | PRO | H | 118 | 1.118 | −3.488 | 14.777 | 1 | 29.41 | H |
| ATOM | 2594 | CD | PRO | H | 118 | 2.425 | −3.275 | 14.131 | 1 | 28.81 | H |
| ATOM | 2595 | CA | PRO | H | 118 | 0.606 | −4.832 | 14.507 | 1 | 27.06 | H |
| ATOM | 2596 | CB | PRO | H | 118 | 1.582 | −5.365 | 13.462 | 1 | 28.68 | H |
| ATOM | 2597 | CG | PRO | H | 118 | 2.877 | −4.689 | 13.835 | 1 | 27.03 | H |
| ATOM | 2598 | C | PRO | H | 118 | 0.694 | −5.56 | 15.853 | 1 | 26.72 | H |
| ATOM | 2599 | O | PRO | H | 118 | 1.337 | −5.067 | 16.784 | 1 | 27.22 | H |
| ATOM | 2600 | N | PRO | H | 119 | 0.049 | −6.728 | 15.986 | 1 | 24.12 | H |
| ATOM | 2601 | CD | PRO | H | 119 | −0.998 | −7.346 | 15.148 | 1 | 21.57 | H |
| ATOM | 2602 | CA | PRO | H | 119 | 0.138 | −7.404 | 17.278 | 1 | 22.05 | H |
| ATOM | 2603 | CB | PRO | H | 119 | −1.245 | −8.007 | 17.417 | 1 | 21.54 | H |
| ATOM | 2604 | CG | PRO | H | 119 | −1.469 | −8.515 | 16.01 | 1 | 20.32 | H |
| ATOM | 2605 | C | PRO | H | 119 | 1.209 | −8.484 | 17.334 | 1 | 23.34 | H |
| ATOM | 2606 | O | PRO | H | 119 | 1.642 | −9.011 | 16.31 | 1 | 23.27 | H |
| ATOM | 2607 | N | SER | H | 120 | 1.643 | −8.81 | 18.541 | 1 | 23.35 | H |
| ATOM | 2608 | CA | SER | H | 120 | 2.604 | −9.885 | 18.697 | 1 | 24.56 | H |
| ATOM | 2609 | CB | SER | H | 120 | 3.441 | −9.714 | 19.965 | 1 | 20.54 | H |
| ATOM | 2610 | OG | SER | H | 120 | 4.305 | −8.602 | 19.855 | 1 | 23.2 | H |
| ATOM | 2611 | C | SER | H | 120 | 1.694 | −11.09 | 18.84 | 1 | 23.57 | H |
| ATOM | 2612 | O | SER | H | 120 | 0.739 | −11.061 | 19.613 | 1 | 25.37 | H |
| ATOM | 2613 | N | VAL | H | 121 | 1.956 | −12.131 | 18.071 | 1 | 22.62 | H |
| ATOM | 2614 | CA | VAL | H | 121 | 1.138 | −13.314 | 18.165 | 1 | 22.29 | H |
| ATOM | 2615 | CB | VAL | H | 121 | 0.782 | −13.868 | 16.779 | 1 | 23.47 | H |
| ATOM | 2616 | CG1 | VAL | H | 121 | −0.172 | −15.053 | 16.922 | 1 | 19.89 | H |
| ATOM | 2617 | CG2 | VAL | H | 121 | 0.153 | −12.763 | 15.934 | 1 | 22.32 | H |
| ATOM | 2618 | C | VAL | H | 121 | 1.959 | −14.319 | 18.929 | 1 | 23.79 | H |
| ATOM | 2619 | O | VAL | H | 121 | 2.981 | −14.802 | 18.437 | 1 | 23 | H |
| ATOM | 2620 | N | TYR | H | 122 | 1.521 | −14.609 | 20.148 | 1 | 24.01 | H |
| ATOM | 2621 | CA | TYR | H | 122 | 2.226 | −15.552 | 20.99 | 1 | 25.51 | H |
| ATOM | 2622 | CB | TYR | H | 122 | 2.376 | −14.988 | 22.404 | 1 | 24.61 | H |
| ATOM | 2623 | CG | TYR | H | 122 | 3.214 | −13.731 | 22.451 | 1 | 30.94 | H |
| ATOM | 2624 | CD1 | TYR | H | 122 | 4.501 | −13.706 | 21.903 | 1 | 33.19 | H |
| ATOM | 2625 | CE1 | TYR | H | 122 | 5.28 | −12.544 | 21.93 | 1 | 30.97 | H |
| ATOM | 2626 | CD2 | TYR | H | 122 | 2.727 | −12.56 | 23.029 | 1 | 31.97 | H |
| ATOM | 2627 | CE2 | TYR | H | 122 | 3.5 | −11.393 | 23.06 | 1 | 31.89 | H |
| ATOM | 2628 | CZ | TYR | H | 122 | 4.774 | −11.397 | 22.51 | 1 | 31.43 | H |
| ATOM | 2629 | OH | TYR | H | 122 | 5.545 | −10.259 | 22.552 | 1 | 31.29 | H |
| ATOM | 2630 | C | TYR | H | 122 | 1.496 | −16.877 | 21.025 | 1 | 24.8 | H |
| ATOM | 2631 | O | TYR | H | 122 | 0.276 | −16.917 | 21.149 | 1 | 27.73 | H |
| ATOM | 2632 | N | PRO | H | 123 | 2.235 | −17.985 | 20.879 | 1 | 23.29 | H |
| ATOM | 2633 | CD | PRO | H | 123 | 3.653 | −18.086 | 20.478 | 1 | 20.29 | H |
| ATOM | 2634 | CA | PRO | H | 123 | 1.602 | −19.301 | 20.909 | 1 | 21.41 | H |
| ATOM | 2635 | CB | PRO | H | 123 | 2.67 | −20.204 | 20.297 | 1 | 22.22 | H |
| ATOM | 2636 | CG | PRO | H | 123 | 3.961 | −19.541 | 20.731 | 1 | 17.63 | H |
| ATOM | 2637 | C | PRO | H | 123 | 1.236 | −19.708 | 22.339 | 1 | 24.48 | H |
| ATOM | 2638 | O | PRO | H | 123 | 1.918 | −19.34 | 23.302 | 1 | 25.06 | H |
| ATOM | 2639 | N | LEU | H | 124 | 0.148 | −20.456 | 22.472 | 1 | 25.43 | H |
| ATOM | 2640 | CA | LEU | H | 124 | −0.304 | −20.923 | 23.769 | 1 | 26.22 | H |
| ATOM | 2641 | CB | LEU | H | 124 | −1.696 | −20.366 | 24.072 | 1 | 26.87 | H |
| ATOM | 2642 | CG | LEU | H | 124 | −1.768 | −19.04 | 24.844 | 1 | 28.04 | H |
| ATOM | 2643 | CD1 | LEU | H | 124 | −0.634 | −18.111 | 24.435 | 1 | 25.09 | H |
| ATOM | 2644 | CD2 | LEU | H | 124 | −3.131 | −18.392 | 24.589 | 1 | 27.98 | H |
| ATOM | 2645 | C | LEU | H | 124 | −0.32 | −22.442 | 23.785 | 1 | 28.92 | H |
| ATOM | 2646 | O | LEU | H | 124 | −1.197 | −23.083 | 23.186 | 1 | 28.5 | H |
| ATOM | 2647 | N | ALA | H | 125 | 0.67 | −23.011 | 24.469 | 1 | 30.55 | H |
| ATOM | 2648 | CA | ALA | H | 125 | 0.806 | −24.456 | 24.586 | 1 | 29.96 | H |
| ATOM | 2649 | CB | ALA | H | 125 | 1.972 | −24.932 | 23.755 | 1 | 29.46 | H |
| ATOM | 2650 | C | ALA | H | 125 | 1.013 | −24.848 | 26.038 | 1 | 32.47 | H |
| ATOM | 2651 | O | ALA | H | 125 | 1.637 | −24.115 | 26.807 | 1 | 31.17 | H |
| ATOM | 2652 | N | PRO | H | 126 | 0.497 | −26.021 | 26.428 | 1 | 35.22 | H |
| ATOM | 2653 | CD | PRO | H | 126 | −0.212 | −26.945 | 25.527 | 1 | 34.56 | H |
| ATOM | 2654 | CA | PRO | H | 126 | 0.584 | −26.579 | 27.783 | 1 | 37.74 | H |
| ATOM | 2655 | CB | PRO | H | 126 | −0.065 | −27.952 | 27.63 | 1 | 36.57 | H |
| ATOM | 2656 | CG | PRO | H | 126 | −1.025 | −27.75 | 26.494 | 1 | 38.9 | H |
| ATOM | 2657 | C | PRO | H | 126 | 2.017 | −26.683 | 28.324 | 1 | 41.77 | H |
| ATOM | 2658 | O | PRO | H | 126 | 2.971 | −26.794 | 27.553 | 1 | 40.49 | H |
| ATOM | 2659 | N | GLY | H | 127 | 2.146 | −26.662 | 29.652 | 1 | 46.28 | H |

TABLE 7-continued

| | | | | | | | | | | |
|---|---|---|---|---|---|---|---|---|---|---|
| ATOM | 2660 | CA | GLY | H | 127 | 3.446 | −26.755 | 30.3 | 1 | 50.84 | H |
| ATOM | 2661 | C | GLY | H | 127 | 4.123 | −28.108 | 30.168 | 1 | 55.49 | H |
| ATOM | 2662 | O | GLY | H | 127 | 4.44 | −28.526 | 29.061 | 1 | 56.73 | H |
| ATOM | 2663 | N | CYS | H | 128 | 4.349 | −28.795 | 31.288 | 1 | 60.96 | H |
| ATOM | 2664 | CA | CYS | H | 128 | 5.01 | −30.104 | 31.266 | 1 | 65.66 | H |
| ATOM | 2665 | CB | CYS | H | 128 | 6.336 | −30.046 | 32.036 | 1 | 64.76 | H |
| ATOM | 2666 | SG | CYS | H | 128 | 7.689 | −29.222 | 31.164 | 1 | 65.85 | H |
| ATOM | 2667 | C | CYS | H | 128 | 4.175 | −31.268 | 31.806 | 1 | 68.44 | H |
| ATOM | 2668 | O | CYS | H | 128 | 3.593 | −32.031 | 31.034 | 1 | 69.11 | H |
| ATOM | 2669 | N | GLY | H | 129 | 4.131 | −31.406 | 33.13 | 1 | 71.63 | H |
| ATOM | 2670 | CA | GLY | H | 129 | 3.383 | −32.491 | 33.75 | 1 | 76.46 | H |
| ATOM | 2671 | C | GLY | H | 129 | 1.88 | −32.281 | 33.867 | 1 | 80.03 | H |
| ATOM | 2672 | O | GLY | H | 129 | 1.387 | −31.785 | 34.885 | 1 | 79.58 | H |
| ATOM | 2673 | N | ASP | H | 130 | 1.149 | −32.678 | 32.827 | 1 | 82.64 | H |
| ATOM | 2674 | CA | ASP | H | 130 | −0.303 | −32.529 | 32.803 | 1 | 84.12 | H |
| ATOM | 2675 | CB | ASP | H | 130 | −0.686 | −31.181 | 32.172 | 1 | 84.72 | H |
| ATOM | 2676 | CG | ASP | H | 130 | 0.001 | −30.939 | 30.834 | 1 | 84.6 | H |
| ATOM | 2677 | OD1 | ASP | H | 130 | 1.245 | −30.81 | 30.815 | 1 | 82.66 | H |
| ATOM | 2678 | OD2 | ASP | H | 130 | −0.704 | −30.877 | 29.802 | 1 | 85.79 | H |
| ATOM | 2679 | C | ASP | H | 130 | −1.021 | −33.657 | 32.062 | 1 | 84.81 | H |
| ATOM | 2680 | O | ASP | H | 130 | −2.122 | −34.055 | 32.453 | 1 | 85.5 | H |
| ATOM | 2681 | N | THR | H | 133 | −0.394 | −34.168 | 31.001 | 1 | 84.51 | H |
| ATOM | 2682 | CA | THR | H | 133 | −0.971 | −35.239 | 30.182 | 1 | 83.51 | H |
| ATOM | 2683 | CB | THR | H | 133 | −0.541 | −36.646 | 30.688 | 1 | 84.81 | H |
| ATOM | 2684 | OG1 | THR | H | 133 | −0.887 | −36.796 | 32.072 | 1 | 87.07 | H |
| ATOM | 2685 | CG2 | THR | H | 133 | 0.959 | −36.833 | 30.52 | 1 | 84.91 | H |
| ATOM | 2686 | C | THR | H | 133 | −2.498 | −35.151 | 30.149 | 1 | 81.09 | H |
| ATOM | 2687 | O | THR | H | 133 | −3.201 | −36.091 | 30.529 | 1 | 82.19 | H |
| ATOM | 2688 | N | THR | H | 134 | −2.99 | −34.002 | 29.694 | 1 | 76.75 | H |
| ATOM | 2689 | CA | THR | H | 134 | −4.418 | −33.72 | 29.592 | 1 | 72.89 | H |
| ATOM | 2690 | CB | THR | H | 134 | −4.664 | −32.554 | 28.62 | 1 | 73.75 | H |
| ATOM | 2691 | OG1 | THR | H | 134 | −4.232 | −32.931 | 27.307 | 1 | 74.08 | H |
| ATOM | 2692 | CG2 | THR | H | 134 | −3.879 | −31.321 | 29.064 | 1 | 73.63 | H |
| ATOM | 2693 | C | THR | H | 134 | −5.243 | −34.924 | 29.137 | 1 | 69.33 | H |
| ATOM | 2694 | O | THR | H | 134 | −4.703 | −35.889 | 28.596 | 1 | 70.8 | H |
| ATOM | 2695 | N | GLY | H | 135 | −6.556 | −34.845 | 29.344 | 1 | 64.05 | H |
| ATOM | 2696 | CA | GLY | H | 135 | −7.453 | −35.933 | 28.982 | 1 | 55.58 | H |
| ATOM | 2697 | C | GLY | H | 135 | −7.546 | −36.338 | 27.521 | 1 | 50.06 | H |
| ATOM | 2698 | O | GLY | H | 135 | −6.538 | −36.564 | 26.854 | 1 | 47.47 | H |
| ATOM | 2699 | N | SER | H | 136 | −8.774 | −36.448 | 27.027 | 1 | 46.15 | H |
| ATOM | 2700 | CA | SER | H | 136 | −9.015 | −36.841 | 25.646 | 1 | 43.05 | H |
| ATOM | 2701 | CB | SER | H | 136 | −10.43 | −37.4 | 25.491 | 1 | 42.17 | H |
| ATOM | 2702 | OG | SER | H | 136 | −10.499 | −38.762 | 25.868 | 1 | 41.16 | H |
| ATOM | 2703 | C | SER | H | 136 | −8.818 | −35.697 | 24.659 | 1 | 41.99 | H |
| ATOM | 2704 | O | SER | H | 136 | −8.761 | −35.919 | 23.449 | 1 | 43.69 | H |
| ATOM | 2705 | N | SER | H | 137 | −8.72 | −34.474 | 25.164 | 1 | 37.32 | H |
| ATOM | 2706 | CA | SER | H | 137 | −8.53 | −33.34 | 24.279 | 1 | 34.59 | H |
| ATOM | 2707 | CB | SER | H | 137 | −9.869 | −32.663 | 23.999 | 1 | 33.93 | H |
| ATOM | 2708 | OG | SER | H | 137 | −10.296 | −31.9 | 25.112 | 1 | 35.89 | H |
| ATOM | 2709 | C | SER | H | 137 | −7.562 | −32.32 | 24.856 | 1 | 32.47 | H |
| ATOM | 2710 | O | SER | H | 137 | −7.541 | −32.082 | 26.063 | 1 | 33.35 | H |
| ATOM | 2711 | N | VAL | H | 138 | −6.748 | −31.725 | 23.991 | 1 | 29.19 | H |
| ATOM | 2712 | CA | VAL | H | 138 | −5.811 | −30.705 | 24.438 | 1 | 26.57 | H |
| ATOM | 2713 | CB | VAL | H | 138 | −4.345 | −31.029 | 24.023 | 1 | 25.65 | H |
| ATOM | 2714 | CG1 | VAL | H | 138 | −4.18 | −30.917 | 22.523 | 1 | 26.61 | H |
| ATOM | 2715 | CG2 | VAL | H | 138 | −3.384 | −30.086 | 24.728 | 1 | 25.78 | H |
| ATOM | 2716 | C | VAL | H | 138 | −6.248 | −29.374 | 23.825 | 1 | 23.93 | H |
| ATOM | 2717 | O | VAL | H | 138 | −6.633 | −29.31 | 22.662 | 1 | 22.96 | H |
| ATOM | 2718 | N | THR | H | 139 | −6.222 | −28.32 | 24.63 | 1 | 22.44 | H |
| ATOM | 2719 | CA | THR | H | 139 | −6.605 | −27 | 24.163 | 1 | 21.65 | H |
| ATOM | 2720 | CB | THR | H | 139 | −7.536 | −26.295 | 25.163 | 1 | 20.78 | H |
| ATOM | 2721 | OG1 | THR | H | 139 | −8.721 | −27.081 | 25.352 | 1 | 21.51 | H |
| ATOM | 2722 | CG2 | THR | H | 139 | −7.911 | −24.913 | 24.638 | 1 | 15.29 | H |
| ATOM | 2723 | C | THR | H | 139 | −5.366 | −26.139 | 23.978 | 1 | 21.78 | H |
| ATOM | 2724 | O | THR | H | 139 | −4.546 | −26.008 | 24.89 | 1 | 22.31 | H |
| ATOM | 2725 | N | LEU | H | 140 | −5.231 | −25.557 | 22.795 | 1 | 20.44 | H |
| ATOM | 2726 | CA | LEU | H | 140 | −4.091 | −24.703 | 22.501 | 1 | 21.47 | H |
| ATOM | 2727 | CB | LEU | H | 140 | −3.319 | −25.233 | 21.297 | 1 | 21.98 | H |
| ATOM | 2728 | CG | LEU | H | 140 | −2.908 | −26.703 | 21.275 | 1 | 22.97 | H |
| ATOM | 2729 | CD1 | LEU | H | 140 | −2.369 | −27.067 | 19.885 | 1 | 19.48 | H |
| ATOM | 2730 | CD2 | LEU | H | 140 | −1.879 | −26.955 | 22.353 | 1 | 21.81 | H |
| ATOM | 2731 | C | LEU | H | 140 | −4.66 | −23.344 | 22.157 | 1 | 21.57 | H |
| ATOM | 2732 | O | LEU | H | 140 | −5.878 | −23.143 | 22.219 | 1 | 18.79 | H |
| ATOM | 2733 | N | GLY | H | 141 | −3.784 | −22.42 | 21.774 | 1 | 20.53 | H |
| ATOM | 2734 | CA | GLY | H | 141 | −4.253 | −21.099 | 21.415 | 1 | 21.99 | H |
| ATOM | 2735 | C | GLY | H | 141 | −3.185 | −20.104 | 21.005 | 1 | 22.57 | H |
| ATOM | 2736 | O | GLY | H | 141 | −2.008 | −20.435 | 20.886 | 1 | 20.97 | H |
| ATOM | 2737 | N | CYS | H | 142 | −3.624 | −18.869 | 20.786 | 1 | 23.01 | H |
| ATOM | 2738 | CA | CYS | H | 142 | −2.754 | −17.775 | 20.399 | 1 | 22.78 | H |

TABLE 7-continued

| ATOM | 2739 | C | CYS | H | 142 | −3.174 | −16.516 | 21.129 | 1 | 23.48 | H |
| ATOM | 2740 | O | CYS | H | 142 | −4.364 | −16.221 | 21.259 | 1 | 24.59 | H |
| ATOM | 2741 | CB | CYS | H | 142 | −2.826 | −17.53 | 18.891 | 1 | 23.52 | H |
| ATOM | 2742 | SG | CYS | H | 142 | −1.882 | −18.718 | 17.881 | 1 | 28.33 | H |
| ATOM | 2743 | N | LEU | H | 143 | −2.186 | −15.786 | 21.624 | 1 | 24.17 | H |
| ATOM | 2744 | CA | LEU | H | 143 | −2.432 | −14.54 | 22.32 | 1 | 23.71 | H |
| ATOM | 2745 | CB | LEU | H | 143 | −1.616 | −14.482 | 23.607 | 1 | 21.28 | H |
| ATOM | 2746 | CG | LEU | H | 143 | −1.7 | −13.152 | 24.345 | 1 | 23.06 | H |
| ATOM | 2747 | CD1 | LEU | H | 143 | −3.089 | −12.963 | 24.909 | 1 | 25.91 | H |
| ATOM | 2748 | CD2 | LEU | H | 143 | −0.677 | −13.121 | 25.445 | 1 | 22.79 | H |
| ATOM | 2749 | C | LEU | H | 143 | −1.984 | −13.443 | 21.361 | 1 | 27.23 | H |
| ATOM | 2750 | O | LEU | H | 143 | −0.808 | −13.373 | 20.99 | 1 | 29.27 | H |
| ATOM | 2751 | N | VAL | H | 144 | −2.936 | −12.619 | 20.935 | 1 | 26.57 | H |
| ATOM | 2752 | CA | VAL | H | 144 | −2.678 | −11.515 | 20.015 | 1 | 24.48 | H |
| ATOM | 2753 | CB | VAL | H | 144 | −3.864 | −11.356 | 19.032 | 1 | 24.79 | H |
| ATOM | 2754 | CG1 | VAL | H | 144 | −3.539 | −10.348 | 17.95 | 1 | 23.2 | H |
| ATOM | 2755 | CG2 | VAL | H | 144 | −4.189 | −12.698 | 18.413 | 1 | 23.76 | H |
| ATOM | 2756 | C | VAL | H | 144 | −2.553 | −10.294 | 20.921 | 1 | 26.92 | H |
| ATOM | 2757 | O | VAL | H | 144 | −3.554 | −9.72 | 21.354 | 1 | 26.36 | H |
| ATOM | 2758 | N | LYS | H | 145 | −1.316 | −9.892 | 21.198 | 1 | 27.8 | H |
| ATOM | 2759 | CA | LYS | H | 145 | −1.078 | −8.792 | 22.12 | 1 | 29.63 | H |
| ATOM | 2760 | CB | LYS | H | 145 | −0.23 | −9.326 | 23.281 | 1 | 27.41 | H |
| ATOM | 2761 | CG | LYS | H | 145 | 0.097 | −8.312 | 24.345 | 1 | 31.17 | H |
| ATOM | 2762 | CD | LYS | H | 145 | 0.872 | −8.934 | 25.495 | 1 | 32.78 | H |
| ATOM | 2763 | CE | LYS | H | 145 | 1.2 | −7.877 | 26.538 | 1 | 33.51 | H |
| ATOM | 2764 | NZ | LYS | H | 145 | −0.031 | −7.126 | 26.946 | 1 | 36.05 | H |
| ATOM | 2765 | C | LYS | H | 145 | −0.475 | −7.479 | 21.606 | 1 | 30.6 | H |
| ATOM | 2766 | O | LYS | H | 145 | 0.355 | −7.464 | 20.7 | 1 | 31.17 | H |
| ATOM | 2767 | N | GLY | H | 146 | −0.929 | −6.384 | 22.215 | 1 | 30.75 | H |
| ATOM | 2768 | CA | GLY | H | 146 | −0.443 | −5.049 | 21.914 | 1 | 32.51 | H |
| ATOM | 2769 | C | GLY | H | 146 | −0.56 | −4.519 | 20.503 | 1 | 33.52 | H |
| ATOM | 2770 | O | GLY | H | 146 | 0.455 | −4.241 | 19.865 | 1 | 34.32 | H |
| ATOM | 2771 | N | TYR | H | 147 | −1.785 | −4.341 | 20.02 | 1 | 31.35 | H |
| ATOM | 2772 | CA | TYR | H | 147 | −1.978 | −3.841 | 18.67 | 1 | 30.36 | H |
| ATOM | 2773 | CB | TYR | H | 147 | −2.427 | −4.984 | 17.753 | 1 | 28.17 | H |
| ATOM | 2774 | CG | TYR | H | 147 | −3.806 | −5.52 | 18.06 | 1 | 29.92 | H |
| ATOM | 2775 | CD1 | TYR | H | 147 | −4.94 | −4.926 | 17.507 | 1 | 29.62 | H |
| ATOM | 2776 | CE1 | TYR | H | 147 | −6.212 | −5.4 | 17.795 | 1 | 29.64 | H |
| ATOM | 2777 | CD2 | TYR | H | 147 | −3.984 | −6.611 | 18.919 | 1 | 28.56 | H |
| ATOM | 2778 | CE2 | TYR | H | 147 | −5.255 | −7.092 | 19.216 | 1 | 26.84 | H |
| ATOM | 2779 | CZ | TYR | H | 147 | −6.362 | −6.48 | 18.646 | 1 | 27.77 | H |
| ATOM | 2780 | OH | TYR | H | 147 | −7.625 | −6.943 | 18.909 | 1 | 29.25 | H |
| ATOM | 2781 | C | TYR | H | 147 | −2.96 | −2.672 | 18.596 | 1 | 30.43 | H |
| ATOM | 2782 | O | TYR | H | 147 | −3.71 | −2.405 | 19.543 | 1 | 29.48 | H |
| ATOM | 2783 | N | PHE | H | 148 | −2.945 | −1.977 | 17.461 | 1 | 29.2 | H |
| ATOM | 2784 | CA | PHE | H | 148 | −3.818 | −0.827 | 17.253 | 1 | 29.41 | H |
| ATOM | 2785 | CB | PHE | H | 148 | −3.339 | 0.346 | 18.107 | 1 | 30.71 | H |
| ATOM | 2786 | CG | PHE | H | 148 | −4.307 | 1.494 | 18.151 | 1 | 31.27 | H |
| ATOM | 2787 | CD1 | PHE | H | 148 | −5.406 | 1.459 | 19.005 | 1 | 30.32 | H |
| ATOM | 2788 | CD2 | PHE | H | 148 | −4.153 | 2.585 | 17.305 | 1 | 30.76 | H |
| ATOM | 2789 | CE1 | PHE | H | 148 | −6.328 | 2.489 | 19.019 | 1 | 28.57 | H |
| ATOM | 2790 | CE2 | PHE | H | 148 | −5.075 | 3.623 | 17.312 | 1 | 29.76 | H |
| ATOM | 2791 | CZ | PHE | H | 148 | −6.166 | 3.573 | 18.169 | 1 | 28.87 | H |
| ATOM | 2792 | C | PHE | H | 148 | −3.775 | −0.428 | 15.787 | 1 | 29.92 | H |
| ATOM | 2793 | O | PHE | H | 148 | −2.712 | −0.497 | 15.162 | 1 | 30.58 | H |
| ATOM | 2794 | N | PRO | H | 149 | −4.923 | −0.034 | 15.211 | 1 | 30.8 | H |
| ATOM | 2795 | CD | PRO | H | 149 | −4.966 | 0.398 | 13.804 | 1 | 31.07 | H |
| ATOM | 2796 | CA | PRO | H | 149 | −6.25 | 0.059 | 15.824 | 1 | 31.64 | H |
| ATOM | 2797 | CB | PRO | H | 149 | −7.014 | 0.904 | 14.828 | 1 | 30.75 | H |
| ATOM | 2798 | CG | PRO | H | 149 | −6.451 | 0.416 | 13.522 | 1 | 31.45 | H |
| ATOM | 2799 | C | PRO | H | 149 | −6.833 | −1.338 | 15.96 | 1 | 35.7 | H |
| ATOM | 2800 | O | PRO | H | 149 | −6.136 | −2.324 | 15.721 | 1 | 37.22 | H |
| ATOM | 2801 | N | GLU | H | 150 | −8.107 | −1.447 | 16.319 | 1 | 38.82 | H |
| ATOM | 2802 | CA | GLU | H | 150 | −8.674 | −2.775 | 16.463 | 1 | 42.16 | H |
| ATOM | 2803 | CB | GLU | H | 150 | −9.751 | −2.82 | 17.547 | 1 | 43.28 | H |
| ATOM | 2804 | CG | GLU | H | 150 | −9.651 | −4.096 | 18.362 | 1 | 49.59 | H |
| ATOM | 2805 | CD | GLU | H | 150 | −10.953 | −4.471 | 18.99 | 1 | 52.69 | H |
| ATOM | 2806 | OE1 | GLU | H | 150 | −11.574 | −3.578 | 19.603 | 1 | 58.52 | H |
| ATOM | 2807 | OE2 | GLU | H | 150 | −11.346 | −5.656 | 18.883 | 1 | 53.82 | H |
| ATOM | 2808 | C | GLU | H | 150 | −9.203 | −3.446 | 15.2 | 1 | 42.64 | H |
| ATOM | 2809 | O | GLU | H | 150 | −9.114 | −2.903 | 14.088 | 1 | 38.81 | H |
| ATOM | 2810 | N | SER | H | 151 | −9.756 | −4.636 | 15.436 | 1 | 44.26 | H |
| ATOM | 2811 | CA | SER | H | 151 | −10.273 | −5.542 | 14.442 | 1 | 44.02 | H |
| ATOM | 2812 | CB | SER | H | 151 | −10.998 | −4.814 | 13.308 | 1 | 47.18 | H |
| ATOM | 2813 | OG | SER | H | 151 | −11.139 | −5.69 | 12.176 | 1 | 50.49 | H |
| ATOM | 2814 | C | SER | H | 151 | −9.103 | −6.356 | 13.874 | 1 | 42.18 | H |
| ATOM | 2815 | O | SER | H | 151 | −8.257 | −5.854 | 13.128 | 1 | 38.7 | H |
| ATOM | 2816 | N | VAL | H | 152 | −9.038 | −7.613 | 14.282 | 1 | 39.36 | H |
| ATOM | 2817 | CA | VAL | H | 152 | −8.035 | −8.526 | 13.775 | 1 | 36.34 | H |

TABLE 7-continued

| | | | | | | | | | | |
|---|---|---|---|---|---|---|---|---|---|---|
| ATOM | 2818 | CB | VAL | H | 152 | −6.922 | −8.814 | 14.791 | 1 | 37.24 | H |
| ATOM | 2819 | CG1 | VAL | H | 152 | −6.175 | −7.546 | 15.129 | 1 | 39.5 | H |
| ATOM | 2820 | CG2 | VAL | H | 152 | −7.497 | −9.444 | 16.025 | 1 | 35.37 | H |
| ATOM | 2821 | C | VAL | H | 152 | −8.816 | −9.8 | 13.533 | 1 | 36.17 | H |
| ATOM | 2822 | O | VAL | H | 152 | −9.867 | −10.017 | 14.137 | 1 | 31.54 | H |
| ATOM | 2823 | N | THR | H | 153 | −8.331 | −10.634 | 12.631 | 1 | 35.21 | H |
| ATOM | 2824 | CA | THR | H | 153 | −9.038 | −11.865 | 12.361 | 1 | 36.21 | H |
| ATOM | 2825 | CB | THR | H | 153 | −9.552 | −11.904 | 10.919 | 1 | 38.68 | H |
| ATOM | 2826 | OG1 | THR | H | 153 | −10.67 | −11.018 | 10.806 | 1 | 41.43 | H |
| ATOM | 2827 | CG2 | THR | H | 153 | −9.977 | −13.317 | 10.527 | 1 | 39.83 | H |
| ATOM | 2828 | C | THR | H | 153 | −8.118 | −13.031 | 12.609 | 1 | 34.92 | H |
| ATOM | 2829 | O | THR | H | 153 | −7.016 | −13.088 | 12.071 | 1 | 33.33 | H |
| ATOM | 2830 | N | VAL | H | 154 | −8.576 | −13.947 | 13.451 | 1 | 31.5 | H |
| ATOM | 2831 | CA | VAL | H | 154 | −7.809 | −15.12 | 13.792 | 1 | 31.22 | H |
| ATOM | 2832 | CB | VAL | H | 154 | −7.737 | −15.309 | 15.303 | 1 | 30.78 | H |
| ATOM | 2833 | CG1 | VAL | H | 154 | −7.012 | −16.601 | 15.62 | 1 | 27.95 | H |
| ATOM | 2834 | CG2 | VAL | H | 154 | −7.045 | −14.121 | 15.938 | 1 | 29.29 | H |
| ATOM | 2835 | C | VAL | H | 154 | −8.459 | −16.346 | 13.193 | 1 | 32.63 | H |
| ATOM | 2836 | O | VAL | H | 154 | −9.475 | −16.839 | 13.69 | 1 | 33.63 | H |
| ATOM | 2837 | N | THR | H | 156 | −7.872 | −16.828 | 12.11 | 1 | 31.88 | H |
| ATOM | 2838 | CA | THR | H | 156 | −8.369 | −18.018 | 11.459 | 1 | 30.95 | H |
| ATOM | 2839 | CB | THR | H | 156 | −8.482 | −17.807 | 9.942 | 1 | 31.53 | H |
| ATOM | 2840 | OG1 | THR | H | 156 | −7.19 | −17.529 | 9.396 | 1 | 36.55 | H |
| ATOM | 2841 | CG2 | THR | H | 156 | −9.389 | −16.631 | 9.651 | 1 | 34.65 | H |
| ATOM | 2842 | C | THR | H | 156 | −7.363 | −19.12 | 11.786 | 1 | 29.23 | H |
| ATOM | 2843 | O | THR | H | 156 | −6.154 | −18.955 | 11.601 | 1 | 27.96 | H |
| ATOM | 2844 | N | TRP | H | 157 | −7.872 | −20.227 | 12.31 | 1 | 26.51 | H |
| ATOM | 2845 | CA | TRP | H | 157 | −7.035 | −21.349 | 12.68 | 1 | 24.63 | H |
| ATOM | 2846 | CB | TRP | H | 157 | −7.557 | −22.029 | 13.937 | 1 | 23.99 | H |
| ATOM | 2847 | CG | TRP | H | 157 | −7.307 | −21.306 | 15.21 | 1 | 22.27 | H |
| ATOM | 2848 | CD2 | TRP | H | 157 | −6.163 | −21.45 | 16.058 | 1 | 24.4 | H |
| ATOM | 2849 | CE2 | TRP | H | 157 | −6.385 | −20.644 | 17.196 | 1 | 23.46 | H |
| ATOM | 2850 | CE3 | TRP | H | 157 | −4.971 | −22.187 | 15.967 | 1 | 22.9 | H |
| ATOM | 2851 | CD1 | TRP | H | 157 | −8.146 | −20.44 | 15.84 | 1 | 21.83 | H |
| ATOM | 2852 | NE1 | TRP | H | 157 | −7.602 | −20.04 | 17.037 | 1 | 25.72 | H |
| ATOM | 2853 | CZ2 | TRP | H | 157 | −5.462 | −20.551 | 18.239 | 1 | 23.3 | H |
| ATOM | 2854 | CZ3 | TRP | H | 157 | −4.052 | −22.094 | 17.004 | 1 | 24.96 | H |
| ATOM | 2855 | CH2 | TRP | H | 157 | −4.306 | −21.279 | 18.128 | 1 | 24.38 | H |
| ATOM | 2856 | C | TRP | H | 157 | −6.996 | −22.387 | 11.583 | 1 | 27.71 | H |
| ATOM | 2857 | O | TRP | H | 157 | −8.001 | −22.652 | 10.919 | 1 | 26.57 | H |
| ATOM | 2858 | N | ASN | H | 162 | −5.825 | −22.984 | 11.405 | 1 | 30 | H |
| ATOM | 2859 | CA | ASN | H | 162 | −5.647 | −24.022 | 10.411 | 1 | 31.28 | H |
| ATOM | 2860 | CB | ASN | H | 162 | −4.63 | −23.565 | 9.367 | 1 | 38.76 | H |
| ATOM | 2861 | CG | ASN | H | 162 | −4.665 | −24.413 | 8.114 | 1 | 44.91 | H |
| ATOM | 2862 | OD1 | ASN | H | 162 | −5.676 | −24.456 | 7.411 | 1 | 49.41 | H |
| ATOM | 2863 | ND2 | ASN | H | 162 | −3.56 | −25.101 | 7.828 | 1 | 50.92 | H |
| ATOM | 2864 | C | ASN | H | 162 | −5.144 | −25.255 | 11.164 | 1 | 29.56 | H |
| ATOM | 2865 | O | ASN | H | 162 | −4.057 | −25.24 | 11.743 | 1 | 29.02 | H |
| ATOM | 2866 | N | SER | H | 163 | −5.944 | −26.315 | 11.182 | 1 | 28.36 | H |
| ATOM | 2867 | CA | SER | H | 163 | −5.549 | −27.535 | 11.884 | 1 | 27.36 | H |
| ATOM | 2868 | CB | SER | H | 163 | −6.497 | −27.805 | 13.059 | 1 | 28.61 | H |
| ATOM | 2869 | OG | SER | H | 163 | −7.826 | −28.039 | 12.615 | 1 | 30.36 | H |
| ATOM | 2870 | C | SER | H | 163 | −5.524 | −28.75 | 10.958 | 1 | 26.27 | H |
| ATOM | 2871 | O | SER | H | 163 | −6.063 | −28.714 | 9.851 | 1 | 23.64 | H |
| ATOM | 2872 | N | GLY | H | 164 | −4.884 | −29.82 | 11.422 | 1 | 26.21 | H |
| ATOM | 2873 | CA | GLY | H | 164 | −4.797 | −31.037 | 10.642 | 1 | 23.94 | H |
| ATOM | 2874 | C | GLY | H | 164 | −5.895 | −31.992 | 11.06 | 1 | 24.52 | H |
| ATOM | 2875 | O | GLY | H | 164 | −6.263 | −32.895 | 10.313 | 1 | 26.76 | H |
| ATOM | 2876 | N | SER | H | 165 | −6.419 | −31.787 | 12.262 | 1 | 23.72 | H |
| ATOM | 2877 | CA | SER | H | 165 | −7.489 | −32.624 | 12.796 | 1 | 24.33 | H |
| ATOM | 2878 | CB | SER | H | 165 | −7.412 | −32.669 | 14.325 | 1 | 22.62 | H |
| ATOM | 2879 | OG | SER | H | 165 | −7.511 | −31.362 | 14.873 | 1 | 24.65 | H |
| ATOM | 2880 | C | SER | H | 165 | −8.84 | −32.062 | 12.38 | 1 | 24.08 | H |
| ATOM | 2881 | O | SER | H | 165 | −9.039 | −30.845 | 12.388 | 1 | 25.83 | H |
| ATOM | 2882 | N | LEU | H | 166 | −9.766 | −32.944 | 12.017 | 1 | 24.1 | H |
| ATOM | 2883 | CA | LEU | H | 166 | −11.101 | −32.519 | 11.616 | 1 | 24.5 | H |
| ATOM | 2884 | CB | LEU | H | 166 | −11.905 | −33.705 | 11.085 | 1 | 24.2 | H |
| ATOM | 2885 | CG | LEU | H | 166 | −11.383 | −34.429 | 9.843 | 1 | 24.41 | H |
| ATOM | 2886 | CD1 | LEU | H | 166 | −12.384 | −35.495 | 9.452 | 1 | 20.24 | H |
| ATOM | 2887 | CD2 | LEU | H | 166 | −11.178 | −33.449 | 8.695 | 1 | 26.17 | H |
| ATOM | 2888 | C | LEU | H | 166 | −11.821 | −31.899 | 12.81 | 1 | 25.68 | H |
| ATOM | 2889 | O | LEU | H | 166 | −12.782 | −31.156 | 12.653 | 1 | 28.87 | H |
| ATOM | 2890 | N | SER | H | 167 | −11.363 | −32.223 | 14.011 | 1 | 27.47 | H |
| ATOM | 2891 | CA | SER | H | 167 | −11.956 | −31.656 | 15.214 | 1 | 30.09 | H |
| ATOM | 2892 | CB | SER | H | 167 | −12.045 | −32.696 | 16.338 | 1 | 28.81 | H |
| ATOM | 2893 | OG | SER | H | 167 | −13.107 | −33.609 | 16.121 | 1 | 28.47 | H |
| ATOM | 2894 | C | SER | H | 167 | −11.088 | −30.495 | 15.669 | 1 | 30.95 | H |
| ATOM | 2895 | O | SER | H | 167 | −9.891 | −30.66 | 15.913 | 1 | 30.82 | H |
| ATOM | 2896 | N | SER | H | 168 | −11.698 | −29.321 | 15.758 | 1 | 31.76 | H |

TABLE 7-continued

| | | | | | | | | | | |
|---|---|---|---|---|---|---|---|---|---|---|
| ATOM | 2897 | CA | SER | H | 168 | −11.011 | −28.11 | 16.2 | 1 | 34.66 | H |
| ATOM | 2898 | CB | SER | H | 168 | −10.246 | −27.449 | 15.053 | 1 | 32.7 | H |
| ATOM | 2899 | OG | SER | H | 168 | −9.8 | −28.396 | 14.106 | 1 | 38.8 | H |
| ATOM | 2900 | C | SER | H | 168 | −12.101 | −27.156 | 16.639 | 1 | 36.62 | H |
| ATOM | 2901 | O | SER | H | 168 | −12.705 | −26.483 | 15.804 | 1 | 42.63 | H |
| ATOM | 2902 | N | SER | H | 169 | −12.392 | −27.108 | 17.928 | 1 | 35.82 | H |
| ATOM | 2903 | CA | SER | H | 169 | −13.41 | −26.18 | 18.386 | 1 | 33.04 | H |
| ATOM | 2904 | CB | SER | H | 169 | −14.198 | −26.779 | 19.558 | 1 | 35.47 | H |
| ATOM | 2905 | OG | SER | H | 169 | −13.365 | −27.141 | 20.646 | 1 | 40.34 | H |
| ATOM | 2906 | C | SER | H | 169 | −12.674 | −24.903 | 18.79 | 1 | 29.06 | H |
| ATOM | 2907 | O | SER | H | 169 | −11.85 | −24.913 | 19.703 | 1 | 28.2 | H |
| ATOM | 2908 | N | VAL | H | 171 | −12.942 | −23.812 | 18.081 | 1 | 25.62 | H |
| ATOM | 2909 | CA | VAL | H | 171 | −12.27 | −22.564 | 18.391 | 1 | 26.6 | H |
| ATOM | 2910 | CB | VAL | H | 171 | −11.68 | −21.886 | 17.117 | 1 | 25.15 | H |
| ATOM | 2911 | CG1 | VAL | H | 171 | −11.072 | −22.931 | 16.189 | 1 | 19.83 | H |
| ATOM | 2912 | CG2 | VAL | H | 171 | −12.742 | −21.082 | 16.418 | 1 | 25.61 | H |
| ATOM | 2913 | C | VAL | H | 171 | −13.162 | −21.552 | 19.103 | 1 | 26.99 | H |
| ATOM | 2914 | O | VAL | H | 171 | −14.359 | −21.458 | 18.848 | 1 | 26.41 | H |
| ATOM | 2915 | N | HIS | H | 172 | −12.552 | −20.809 | 20.018 | 1 | 28.53 | H |
| ATOM | 2916 | CA | HIS | H | 172 | −13.241 | −19.774 | 20.766 | 1 | 28.37 | H |
| ATOM | 2917 | CB | HIS | H | 172 | −13.294 | −20.102 | 22.263 | 1 | 27.07 | H |
| ATOM | 2918 | CG | HIS | H | 172 | −14.108 | −21.313 | 22.588 | 1 | 26.96 | H |
| ATOM | 2919 | CD2 | HIS | H | 172 | −13.774 | −22.471 | 23.204 | 1 | 27.44 | H |
| ATOM | 2920 | ND1 | HIS | H | 172 | −15.438 | −21.425 | 22.252 | 1 | 27.1 | H |
| ATOM | 2921 | CE1 | HIS | H | 172 | −15.89 | −22.603 | 22.646 | 1 | 27.32 | H |
| ATOM | 2922 | NE2 | HIS | H | 172 | −14.901 | −23.256 | 23.225 | 1 | 28.19 | H |
| ATOM | 2923 | C | HIS | H | 172 | −12.418 | −18.523 | 20.57 | 1 | 28.96 | H |
| ATOM | 2924 | O | HIS | H | 172 | −11.214 | −18.513 | 20.828 | 1 | 30.62 | H |
| ATOM | 2925 | N | THR | H | 173 | −13.057 | −17.474 | 20.084 | 1 | 28.64 | H |
| ATOM | 2926 | CA | THR | H | 173 | −12.364 | −16.222 | 19.891 | 1 | 29.04 | H |
| ATOM | 2927 | CB | THR | H | 173 | −12.64 | −15.666 | 18.498 | 1 | 29.22 | H |
| ATOM | 2928 | OG1 | THR | H | 173 | −12.194 | −16.619 | 17.527 | 1 | 29.59 | H |
| ATOM | 2929 | CG2 | THR | H | 173 | −11.893 | −14.358 | 18.289 | 1 | 29.24 | H |
| ATOM | 2930 | C | THR | H | 173 | −12.858 | −15.263 | 20.969 | 1 | 28.6 | H |
| ATOM | 2931 | O | THR | H | 173 | −14.058 | −15.037 | 21.114 | 1 | 28.8 | H |
| ATOM | 2932 | N | PHE | H | 174 | −11.925 | −14.717 | 21.736 | 1 | 27.18 | H |
| ATOM | 2933 | CA | PHE | H | 174 | −12.274 | −13.813 | 22.814 | 1 | 29.8 | H |
| ATOM | 2934 | CB | PHE | H | 174 | −11.43 | −14.145 | 24.043 | 1 | 31.04 | H |
| ATOM | 2935 | CG | PHE | H | 174 | −11.466 | −15.599 | 24.417 | 1 | 33.26 | H |
| ATOM | 2936 | CD1 | PHE | H | 174 | −10.714 | −16.533 | 23.707 | 1 | 34.51 | H |
| ATOM | 2937 | CD2 | PHE | H | 174 | −12.283 | −16.044 | 25.451 | 1 | 33.41 | H |
| ATOM | 2938 | CE1 | PHE | H | 174 | −10.774 | −17.889 | 24.018 | 1 | 33.07 | H |
| ATOM | 2939 | CE2 | PHE | H | 174 | −12.35 | −17.401 | 25.771 | 1 | 34.61 | H |
| ATOM | 2940 | CZ | PHE | H | 174 | −11.594 | −18.323 | 25.053 | 1 | 34.29 | H |
| ATOM | 2941 | C | PHE | H | 174 | −12.099 | −12.354 | 22.426 | 1 | 30.35 | H |
| ATOM | 2942 | O | PHE | H | 174 | −11.035 | −11.943 | 21.984 | 1 | 30.72 | H |
| ATOM | 2943 | N | PRO | H | 175 | −13.155 | −11.549 | 22.592 | 1 | 31.64 | H |
| ATOM | 2944 | CD | PRO | H | 175 | −14.404 | −11.865 | 23.303 | 1 | 34.54 | H |
| ATOM | 2945 | CA | PRO | H | 175 | −13.101 | −10.128 | 22.25 | 1 | 33.1 | H |
| ATOM | 2946 | CB | PRO | H | 175 | −14.421 | −9.585 | 22.808 | 1 | 32.79 | H |
| ATOM | 2947 | CG | PRO | H | 175 | −14.757 | −10.531 | 23.914 | 1 | 34.31 | H |
| ATOM | 2948 | C | PRO | H | 175 | −11.876 | −9.41 | 22.81 | 1 | 35.29 | H |
| ATOM | 2949 | O | PRO | H | 175 | −11.34 | −9.78 | 23.855 | 1 | 35.64 | H |
| ATOM | 2950 | N | ALA | H | 176 | −11.435 | −8.38 | 22.1 | 1 | 36.8 | H |
| ATOM | 2951 | CA | ALA | H | 176 | −10.27 | −7.617 | 22.513 | 1 | 39.38 | H |
| ATOM | 2952 | CB | ALA | H | 176 | −9.719 | −6.834 | 21.327 | 1 | 39.49 | H |
| ATOM | 2953 | C | ALA | H | 176 | −10.599 | −6.67 | 23.656 | 1 | 41.44 | H |
| ATOM | 2954 | O | ALA | H | 176 | −11.761 | −6.319 | 23.876 | 1 | 42.26 | H |
| ATOM | 2955 | N | LEU | H | 177 | −9.567 | −6.264 | 24.388 | 1 | 42.6 | H |
| ATOM | 2956 | CA | LEU | H | 177 | −9.734 | −5.341 | 25.501 | 1 | 42.99 | H |
| ATOM | 2957 | CB | LEU | H | 177 | −9.694 | −6.085 | 26.833 | 1 | 41.78 | H |
| ATOM | 2958 | CG | LEU | H | 177 | −10.642 | −7.268 | 26.989 | 1 | 41.02 | H |
| ATOM | 2959 | CD1 | LEU | H | 177 | −10.095 | −8.463 | 26.214 | 1 | 44.32 | H |
| ATOM | 2960 | CD2 | LEU | H | 177 | −10.772 | −7.618 | 28.456 | 1 | 40.99 | H |
| ATOM | 2961 | C | LEU | H | 177 | −8.594 | −4.342 | 25.449 | 1 | 44.35 | H |
| ATOM | 2962 | O | LEU | H | 177 | −7.456 | −4.713 | 25.149 | 1 | 46.44 | H |
| ATOM | 2963 | N | LEU | H | 178 | −8.896 | −3.076 | 25.724 | 1 | 43.97 | H |
| ATOM | 2964 | CA | LEU | H | 178 | −7.867 | −2.046 | 25.71 | 1 | 42.55 | H |
| ATOM | 2965 | CB | LEU | H | 178 | −8.473 | −0.658 | 25.521 | 1 | 39.68 | H |
| ATOM | 2966 | CG | LEU | H | 178 | −8.545 | −0.099 | 24.098 | 1 | 39.33 | H |
| ATOM | 2967 | CD1 | LEU | H | 178 | −8.813 | 1.405 | 24.17 | 1 | 34.97 | H |
| ATOM | 2968 | CD2 | LEU | H | 178 | −7.234 | −0.36 | 23.359 | 1 | 36.38 | H |
| ATOM | 2969 | C | LEU | H | 178 | −7.072 | −2.057 | 26.996 | 1 | 43.27 | H |
| ATOM | 2970 | O | LEU | H | 178 | −7.583 | −2.414 | 28.056 | 1 | 43.59 | H |
| ATOM | 2971 | N | GLN | H | 179 | −5.808 | −1.673 | 26.891 | 1 | 45.59 | H |
| ATOM | 2972 | CA | GLN | H | 179 | −4.927 | −1.609 | 28.047 | 1 | 49.17 | H |
| ATOM | 2973 | CB | GLN | H | 179 | −4.589 | −3.013 | 28.561 | 1 | 52.14 | H |
| ATOM | 2974 | CG | GLN | H | 179 | −3.741 | −3.016 | 29.829 | 1 | 55.63 | H |
| ATOM | 2975 | CD | GLN | H | 179 | −3.319 | −4.418 | 30.251 | 1 | 60.07 | H |

TABLE 7-continued

| | | | | | | | | | | |
|---|---|---|---|---|---|---|---|---|---|---|
| ATOM | 2976 | OE1 | GLN | H | 179 | −2.758 | −5.176 | 29.457 | 1 | 62.32 | H |
| ATOM | 2977 | NE2 | GLN | H | 179 | −3.58 | −4.765 | 31.508 | 1 | 61.27 | H |
| ATOM | 2978 | C | GLN | H | 179 | −3.659 | −0.887 | 27.624 | 1 | 48.5 | H |
| ATOM | 2979 | O | GLN | H | 179 | −2.888 | −1.396 | 26.807 | 1 | 48.4 | H |
| ATOM | 2980 | N | SER | H | 180 | −3.468 | 0.31 | 28.174 | 1 | 46.95 | H |
| ATOM | 2981 | CA | SER | H | 180 | −2.304 | 1.131 | 27.87 | 1 | 43.33 | H |
| ATOM | 2982 | CB | SER | H | 180 | −1.022 | 0.353 | 28.152 | 1 | 43.86 | H |
| ATOM | 2983 | OG | SER | H | 180 | −1.014 | −0.124 | 29.484 | 1 | 45.65 | H |
| ATOM | 2984 | C | SER | H | 180 | −2.322 | 1.582 | 26.417 | 1 | 41.61 | H |
| ATOM | 2985 | O | SER | H | 180 | −1.272 | 1.737 | 25.791 | 1 | 41.93 | H |
| ATOM | 2986 | N | GLY | H | 183 | −3.522 | 1.783 | 25.882 | 1 | 38.23 | H |
| ATOM | 2987 | CA | GLY | H | 183 | −3.646 | 2.232 | 24.508 | 1 | 36.69 | H |
| ATOM | 2988 | C | GLY | H | 183 | −3.568 | 1.119 | 23.483 | 1 | 36.11 | H |
| ATOM | 2989 | O | GLY | H | 183 | −3.763 | 1.35 | 22.284 | 1 | 36.5 | H |
| ATOM | 2990 | N | LEU | H | 184 | −3.29 | −0.093 | 23.947 | 1 | 32.43 | H |
| ATOM | 2991 | CA | LEU | H | 184 | −3.194 | −1.221 | 23.049 | 1 | 29.54 | H |
| ATOM | 2992 | CB | LEU | H | 184 | −1.813 | −1.867 | 23.157 | 1 | 28.68 | H |
| ATOM | 2993 | CG | LEU | H | 184 | −0.633 | −0.982 | 22.757 | 1 | 26.45 | H |
| ATOM | 2994 | CD1 | LEU | H | 184 | 0.644 | −1.792 | 22.835 | 1 | 26.83 | H |
| ATOM | 2995 | CD2 | LEU | H | 184 | −0.835 | −0.447 | 21.345 | 1 | 26.29 | H |
| ATOM | 2996 | C | LEU | H | 184 | −4.267 | −2.265 | 23.298 | 1 | 31.02 | H |
| ATOM | 2997 | O | LEU | H | 184 | −4.671 | −2.507 | 24.441 | 1 | 31.73 | H |
| ATOM | 2998 | N | TYR | H | 185 | −4.718 | −2.873 | 22.204 | 1 | 31.2 | H |
| ATOM | 2999 | CA | TYR | H | 185 | −5.731 | −3.919 | 22.228 | 1 | 32.06 | H |
| ATOM | 3000 | CB | TYR | H | 185 | −6.533 | −3.92 | 20.925 | 1 | 33.17 | H |
| ATOM | 3001 | CG | TYR | H | 185 | −7.589 | −2.858 | 20.843 | 1 | 35.48 | H |
| ATOM | 3002 | CD1 | TYR | H | 185 | −8.747 | −2.944 | 21.613 | 1 | 37.25 | H |
| ATOM | 3003 | CE1 | TYR | H | 185 | −9.727 | −1.958 | 21.552 | 1 | 39.1 | H |
| ATOM | 3004 | CD2 | TYR | H | 185 | −7.432 | −1.759 | 20.005 | 1 | 38.27 | H |
| ATOM | 3005 | CE2 | TYR | H | 185 | −8.405 | −0.765 | 19.936 | 1 | 41.84 | H |
| ATOM | 3006 | CZ | TYR | H | 185 | −9.549 | −0.872 | 20.714 | 1 | 41.51 | H |
| ATOM | 3007 | OH | TYR | H | 185 | −10.507 | 0.113 | 20.661 | 1 | 46.97 | H |
| ATOM | 3008 | C | TYR | H | 185 | −5.081 | −5.286 | 22.376 | 1 | 32.82 | H |
| ATOM | 3009 | O | TYR | H | 185 | −4.076 | −5.591 | 21.725 | 1 | 32.31 | H |
| ATOM | 3010 | N | THR | H | 186 | −5.644 | −6.11 | 23.246 | 1 | 32.05 | H |
| ATOM | 3011 | CA | THR | H | 186 | −5.126 | −7.45 | 23.406 | 1 | 30.58 | H |
| ATOM | 3012 | CB | THR | H | 186 | −4.459 | −7.662 | 24.761 | 1 | 31.9 | H |
| ATOM | 3013 | OG1 | THR | H | 186 | −3.274 | −6.857 | 24.833 | 1 | 35.66 | H |
| ATOM | 3014 | CG2 | THR | H | 186 | −4.074 | −9.118 | 24.928 | 1 | 29.99 | H |
| ATOM | 3015 | C | THR | H | 186 | −6.303 | −8.378 | 23.24 | 1 | 29.64 | H |
| ATOM | 3016 | O | THR | H | 186 | −7.43 | −8.059 | 23.633 | 1 | 30.02 | H |
| ATOM | 3017 | N | MET | H | 187 | −6.038 | −9.526 | 22.639 | 1 | 27.85 | H |
| ATOM | 3018 | CA | MET | H | 187 | −7.084 | −10.484 | 22.37 | 1 | 26.53 | H |
| ATOM | 3019 | CB | MET | H | 187 | −7.82 | −10.03 | 21.103 | 1 | 26.47 | H |
| ATOM | 3020 | CG | MET | H | 187 | −8.619 | −11.082 | 20.394 | 1 | 31.53 | H |
| ATOM | 3021 | SD | MET | H | 187 | −7.652 | −11.96 | 19.158 | 1 | 33.24 | H |
| ATOM | 3022 | CE | MET | H | 187 | −8.895 | −13.055 | 18.545 | 1 | 29.37 | H |
| ATOM | 3023 | C | MET | H | 187 | −6.481 | −11.866 | 22.209 | 1 | 24.8 | H |
| ATOM | 3024 | O | MET | H | 187 | −5.274 | −12.007 | 22.067 | 1 | 27.57 | H |
| ATOM | 3025 | N | SER | H | 188 | −7.319 | −12.889 | 22.245 | 1 | 22.52 | H |
| ATOM | 3026 | CA | SER | H | 188 | −6.837 | −14.25 | 22.094 | 1 | 22.83 | H |
| ATOM | 3027 | CB | SER | H | 188 | −6.438 | −14.82 | 23.465 | 1 | 22.1 | H |
| ATOM | 3028 | OG | SER | H | 188 | −7.537 | −14.84 | 24.366 | 1 | 22.78 | H |
| ATOM | 3029 | C | SER | H | 188 | −7.879 | −15.159 | 21.439 | 1 | 22.3 | H |
| ATOM | 3030 | O | SER | H | 188 | −9.04 | −14.794 | 21.274 | 1 | 21.25 | H |
| ATOM | 3031 | N | SER | H | 189 | −7.439 | −16.348 | 21.057 | 1 | 22.45 | H |
| ATOM | 3032 | CA | SER | H | 189 | −8.316 | −17.333 | 20.459 | 1 | 20 | H |
| ATOM | 3033 | CB | SER | H | 189 | −8.218 | −17.278 | 18.934 | 1 | 20.62 | H |
| ATOM | 3034 | OG | SER | H | 189 | −9.092 | −18.218 | 18.328 | 1 | 25.43 | H |
| ATOM | 3035 | C | SER | H | 189 | −7.834 | −18.685 | 20.971 | 1 | 19.5 | H |
| ATOM | 3036 | O | SER | H | 189 | −6.637 | −18.891 | 21.163 | 1 | 15.41 | H |
| ATOM | 3037 | N | SER | H | 190 | −8.764 | −19.592 | 21.234 | 1 | 17.6 | H |
| ATOM | 3038 | CA | SER | H | 190 | −8.38 | −20.916 | 21.688 | 1 | 18.83 | H |
| ATOM | 3039 | CB | SER | H | 190 | −8.93 | −21.228 | 23.086 | 1 | 16.76 | H |
| ATOM | 3040 | OG | SER | H | 190 | −10.303 | −21.563 | 23.051 | 1 | 17.98 | H |
| ATOM | 3041 | C | SER | H | 190 | −8.934 | −21.909 | 20.692 | 1 | 20.96 | H |
| ATOM | 3042 | O | SER | H | 190 | −9.926 | −21.646 | 20.005 | 1 | 22.66 | H |
| ATOM | 3043 | N | VAL | H | 191 | −8.269 | −23.046 | 20.599 | 1 | 20.07 | H |
| ATOM | 3044 | CA | VAL | H | 191 | −8.689 | −24.09 | 19.696 | 1 | 18.23 | H |
| ATOM | 3045 | CB | VAL | H | 191 | −7.883 | −24.029 | 18.369 | 1 | 19.67 | H |
| ATOM | 3046 | CG1 | VAL | H | 191 | −6.392 | −24.086 | 18.656 | 1 | 14.01 | H |
| ATOM | 3047 | CG2 | VAL | H | 191 | −8.307 | −25.152 | 17.448 | 1 | 17.22 | H |
| ATOM | 3048 | C | VAL | H | 191 | −8.427 | −25.373 | 20.459 | 1 | 18.73 | H |
| ATOM | 3049 | O | VAL | H | 191 | −7.378 | −25.534 | 21.086 | 1 | 17.82 | H |
| ATOM | 3050 | N | THR | H | 192 | −9.409 | −26.263 | 20.449 | 1 | 19.74 | H |
| ATOM | 3051 | CA | THR | H | 192 | −9.283 | −27.526 | 21.155 | 1 | 18.94 | H |
| ATOM | 3052 | CB | THR | H | 192 | −10.449 | −27.697 | 22.148 | 1 | 17.25 | H |
| ATOM | 3053 | OG1 | THR | H | 192 | −10.294 | −26.744 | 23.211 | 1 | 20.87 | H |
| ATOM | 3054 | CG2 | THR | H | 192 | −10.483 | −29.096 | 22.727 | 1 | 12.72 | H |

TABLE 7-continued

| ATOM | 3055 | C | THR | H | 192 | −9.273 | −28.641 | 20.129 | 1 | 20.2 | H |
|------|------|------|-----|---|-----|--------|---------|--------|---|-------|---|
| ATOM | 3056 | O | THR | H | 192 | −10.036 | −28.601 | 19.155 | 1 | 23.51 | H |
| ATOM | 3057 | N | VAL | H | 193 | −8.397 | −29.622 | 20.335 | 1 | 16.09 | H |
| ATOM | 3058 | CA | VAL | H | 193 | −8.285 | −30.747 | 19.413 | 1 | 16.6 | H |
| ATOM | 3059 | CB | VAL | H | 193 | −7.123 | −30.529 | 18.427 | 1 | 15.63 | H |
| ATOM | 3060 | CG1 | VAL | H | 193 | −7.171 | −29.118 | 17.879 | 1 | 16.41 | H |
| ATOM | 3061 | CG2 | VAL | H | 193 | −5.794 | −30.806 | 19.113 | 1 | 15.42 | H |
| ATOM | 3062 | C | VAL | H | 193 | −8.043 | −32.065 | 20.148 | 1 | 18.34 | H |
| ATOM | 3063 | O | VAL | H | 193 | −7.796 | −32.077 | 21.357 | 1 | 19.21 | H |
| ATOM | 3064 | N | PRO | H | 194 | −8.109 | −33.197 | 19.426 | 1 | 19.37 | H |
| ATOM | 3065 | CD | PRO | H | 194 | −8.563 | −33.396 | 18.038 | 1 | 19.18 | H |
| ATOM | 3066 | CA | PRO | H | 194 | −7.877 | −34.486 | 20.084 | 1 | 22.24 | H |
| ATOM | 3067 | CB | PRO | H | 194 | −8.116 | −35.493 | 18.957 | 1 | 21.44 | H |
| ATOM | 3068 | CG | PRO | H | 194 | −9.105 | −34.8 | 18.077 | 1 | 18 | H |
| ATOM | 3069 | C | PRO | H | 194 | −6.446 | −34.565 | 20.644 | 1 | 24.6 | H |
| ATOM | 3070 | O | PRO | H | 194 | −5.485 | −34.253 | 19.943 | 1 | 24.2 | H |
| ATOM | 3071 | N | SER | H | 195 | −6.318 | −34.973 | 21.905 | 1 | 26.72 | H |
| ATOM | 3072 | CA | SER | H | 195 | −5.014 | −35.1 | 22.563 | 1 | 29.45 | H |
| ATOM | 3073 | CB | SER | H | 195 | −5.193 | −35.721 | 23.944 | 1 | 28.57 | H |
| ATOM | 3074 | OG | SER | H | 195 | −6.008 | −34.894 | 24.752 | 1 | 38.46 | H |
| ATOM | 3075 | C | SER | H | 195 | −4.021 | −35.943 | 21.765 | 1 | 29.09 | H |
| ATOM | 3076 | O | SER | H | 195 | −2.827 | −35.646 | 21.723 | 1 | 29.64 | H |
| ATOM | 3077 | N | SER | H | 196 | −4.534 | −37.001 | 21.151 | 1 | 29.83 | H |
| ATOM | 3078 | CA | SER | H | 196 | −3.748 | −37.916 | 20.336 | 1 | 31.64 | H |
| ATOM | 3079 | CB | SER | H | 196 | −4.66 | −39.007 | 19.786 | 1 | 31.29 | H |
| ATOM | 3080 | OG | SER | H | 196 | −5.7 | −38.419 | 19.014 | 1 | 31.39 | H |
| ATOM | 3081 | C | SER | H | 196 | −3.084 | −37.215 | 19.154 | 1 | 31.76 | H |
| ATOM | 3082 | O | SER | H | 196 | −2.088 | −37.693 | 18.618 | 1 | 33.34 | H |
| ATOM | 3083 | N | THR | H | 198 | −3.64 | −36.081 | 18.751 | 1 | 30.54 | H |
| ATOM | 3084 | CA | THR | H | 198 | −3.12 | −35.356 | 17.606 | 1 | 29.91 | H |
| ATOM | 3085 | CB | THR | H | 198 | −4.267 | −34.692 | 16.837 | 1 | 29.73 | H |
| ATOM | 3086 | OG1 | THR | H | 198 | −4.786 | −33.597 | 17.603 | 1 | 27.57 | H |
| ATOM | 3087 | CG2 | THR | H | 198 | −5.376 | −35.712 | 16.58 | 1 | 25.77 | H |
| ATOM | 3088 | C | THR | H | 198 | −2.06 | −34.305 | 17.906 | 1 | 29.71 | H |
| ATOM | 3089 | O | THR | H | 198 | −1.444 | −33.76 | 16.982 | 1 | 27.43 | H |
| ATOM | 3090 | N | TRP | H | 199 | −1.84 | −34.008 | 19.182 | 1 | 29.35 | H |
| ATOM | 3091 | CA | TRP | H | 199 | −0.822 | −33.021 | 19.524 | 1 | 28.32 | H |
| ATOM | 3092 | CB | TRP | H | 199 | −1.438 | −31.832 | 20.252 | 1 | 28.31 | H |
| ATOM | 3093 | CG | TRP | H | 199 | −0.739 | −30.566 | 19.9 | 1 | 29.39 | H |
| ATOM | 3094 | CD2 | TRP | H | 199 | 0.129 | −29.807 | 20.742 | 1 | 30.09 | H |
| ATOM | 3095 | CE2 | TRP | H | 199 | 0.648 | −28.746 | 19.96 | 1 | 30.58 | H |
| ATOM | 3096 | CE3 | TRP | H | 199 | 0.526 | −29.919 | 22.08 | 1 | 29.79 | H |
| ATOM | 3097 | CD1 | TRP | H | 199 | −0.722 | −29.953 | 18.678 | 1 | 31.51 | H |
| ATOM | 3098 | NE1 | TRP | H | 199 | 0.112 | −28.858 | 18.705 | 1 | 30.06 | H |
| ATOM | 3099 | CZ2 | TRP | H | 199 | 1.542 | −27.804 | 20.474 | 1 | 29.69 | H |
| ATOM | 3100 | CZ3 | TRP | H | 199 | 1.416 | −28.984 | 22.591 | 1 | 31.66 | H |
| ATOM | 3101 | CH2 | TRP | H | 199 | 1.914 | −27.938 | 21.786 | 1 | 30.85 | H |
| ATOM | 3102 | C | TRP | H | 199 | 0.296 | −33.622 | 20.368 | 1 | 26.48 | H |
| ATOM | 3103 | O | TRP | H | 199 | 0.057 | −34.481 | 21.208 | 1 | 27.32 | H |
| ATOM | 3104 | N | PRO | H | 200 | 1.539 | −33.157 | 20.166 | 1 | 26.79 | H |
| ATOM | 3105 | CD | PRO | H | 200 | 2.675 | −33.526 | 21.03 | 1 | 23.84 | H |
| ATOM | 3106 | CA | PRO | H | 200 | 1.947 | −32.117 | 19.215 | 1 | 25.58 | H |
| ATOM | 3107 | CB | PRO | H | 200 | 3.113 | −31.471 | 19.924 | 1 | 25.21 | H |
| ATOM | 3108 | CG | PRO | H | 200 | 3.823 | −32.689 | 20.449 | 1 | 23.8 | H |
| ATOM | 3109 | C | PRO | H | 200 | 2.372 | −32.635 | 17.848 | 1 | 25.26 | H |
| ATOM | 3110 | O | PRO | H | 200 | 3.189 | −32.005 | 17.186 | 1 | 27.47 | H |
| ATOM | 3111 | N | SER | H | 202 | 1.84 | −33.775 | 17.427 | 1 | 25.77 | H |
| ATOM | 3112 | CA | SER | H | 202 | 2.216 | −34.328 | 16.132 | 1 | 25.92 | H |
| ATOM | 3113 | CB | SER | H | 202 | 1.859 | −35.813 | 16.058 | 1 | 25.33 | H |
| ATOM | 3114 | OG | SER | H | 202 | 0.458 | −36.001 | 16.15 | 1 | 35.16 | H |
| ATOM | 3115 | C | SER | H | 202 | 1.585 | −33.581 | 14.956 | 1 | 25.44 | H |
| ATOM | 3116 | O | SER | H | 202 | 2.186 | −33.498 | 13.89 | 1 | 25.63 | H |
| ATOM | 3117 | N | GLN | H | 203 | 0.389 | −33.027 | 15.134 | 1 | 26.68 | H |
| ATOM | 3118 | CA | GLN | H | 203 | −0.239 | −32.307 | 14.027 | 1 | 29.32 | H |
| ATOM | 3119 | CB | GLN | H | 203 | −1.771 | −32.341 | 14.113 | 1 | 27.47 | H |
| ATOM | 3120 | CG | GLN | H | 203 | −2.373 | −31.332 | 15.077 | 1 | 31.13 | H |
| ATOM | 3121 | CD | GLN | H | 203 | −3.861 | −31.132 | 14.852 | 1 | 33.58 | H |
| ATOM | 3122 | OE1 | GLN | H | 203 | −4.276 | −30.566 | 13.84 | 1 | 34.02 | H |
| ATOM | 3123 | NE2 | GLN | H | 203 | −4.672 | −31.603 | 15.794 | 1 | 33.5 | H |
| ATOM | 3124 | C | GLN | H | 203 | 0.211 | −30.859 | 13.974 | 1 | 29.93 | H |
| ATOM | 3125 | O | GLN | H | 203 | 0.769 | −30.321 | 14.934 | 1 | 33.44 | H |
| ATOM | 3126 | N | THR | H | 204 | −0.045 | −30.227 | 12.837 | 1 | 29.05 | H |
| ATOM | 3127 | CA | THR | H | 204 | 0.319 | −28.84 | 12.647 | 1 | 25.77 | H |
| ATOM | 3128 | CB | THR | H | 204 | 0.916 | −28.636 | 11.266 | 1 | 24.61 | H |
| ATOM | 3129 | OG1 | THR | H | 204 | 2.154 | −29.353 | 11.192 | 1 | 21.97 | H |
| ATOM | 3130 | CG2 | THR | H | 204 | 1.149 | −27.163 | 11.001 | 1 | 22.09 | H |
| ATOM | 3131 | C | THR | H | 204 | −0.898 | −27.952 | 12.825 | 1 | 26.63 | H |
| ATOM | 3132 | O | THR | H | 204 | −1.833 | −27.98 | 12.028 | 1 | 27.24 | H |
| ATOM | 3133 | N | VAL | H | 205 | −0.878 | −27.173 | 13.896 | 1 | 28.23 | H |

TABLE 7-continued

| | | | | | | | | | | |
|---|---|---|---|---|---|---|---|---|---|---|
| ATOM | 3134 | CA | VAL | H | 205 | −1.966 | −26.266 | 14.216 | 1 | 26.73 | H |
| ATOM | 3135 | CB | VAL | H | 205 | −2.541 | −26.565 | 15.603 | 1 | 26.06 | H |
| ATOM | 3136 | CG1 | VAL | H | 205 | −3.438 | −25.432 | 16.049 | 1 | 26.94 | H |
| ATOM | 3137 | CG2 | VAL | H | 205 | −3.309 | −27.876 | 15.568 | 1 | 26.49 | H |
| ATOM | 3138 | C | VAL | H | 205 | −1.421 | −24.858 | 14.222 | 1 | 28.23 | H |
| ATOM | 3139 | O | VAL | H | 205 | −0.537 | −24.531 | 15.016 | 1 | 27.35 | H |
| ATOM | 3140 | N | THR | H | 206 | −1.938 | −24.02 | 13.333 | 1 | 27.87 | H |
| ATOM | 3141 | CA | THR | H | 206 | −1.467 | −22.651 | 13.278 | 1 | 29.33 | H |
| ATOM | 3142 | CB | THR | H | 206 | −0.547 | −22.419 | 12.057 | 1 | 30.95 | H |
| ATOM | 3143 | OG1 | THR | H | 206 | −1.345 | −22.243 | 10.883 | 1 | 33.35 | H |
| ATOM | 3144 | CG2 | THR | H | 206 | 0.373 | −23.613 | 11.853 | 1 | 30.47 | H |
| ATOM | 3145 | C | THR | H | 206 | −2.606 | −21.647 | 13.225 | 1 | 28.51 | H |
| ATOM | 3146 | O | THR | H | 206 | −3.655 | −21.9 | 12.629 | 1 | 28.96 | H |
| ATOM | 3147 | N | CYS | H | 208 | −2.384 | −20.511 | 13.876 | 1 | 27.16 | H |
| ATOM | 3148 | CA | CYS | H | 208 | −3.348 | −19.43 | 13.897 | 1 | 26.06 | H |
| ATOM | 3149 | C | CYS | H | 208 | −2.754 | −18.323 | 13.031 | 1 | 24.84 | H |
| ATOM | 3150 | O | CYS | H | 208 | −1.66 | −17.827 | 13.296 | 1 | 24.56 | H |
| ATOM | 3151 | CB | CYS | H | 208 | −3.545 | −18.906 | 15.327 | 1 | 28.28 | H |
| ATOM | 3152 | SG | CYS | H | 208 | −2.094 | −18.015 | 15.991 | 1 | 30.17 | H |
| ATOM | 3153 | N | SER | H | 209 | −3.452 | −17.963 | 11.969 | 1 | 23.05 | H |
| ATOM | 3154 | CA | SER | H | 209 | −2.973 | −16.892 | 11.117 | 1 | 22.76 | H |
| ATOM | 3155 | CB | SER | H | 209 | −3.253 | −17.21 | 9.649 | 1 | 21.71 | H |
| ATOM | 3156 | OG | SER | H | 209 | −4.486 | −17.892 | 9.51 | 1 | 30.48 | H |
| ATOM | 3157 | C | SER | H | 209 | −3.736 | −15.669 | 11.597 | 1 | 21.89 | H |
| ATOM | 3158 | O | SER | H | 209 | −4.966 | −15.658 | 11.618 | 1 | 25.21 | H |
| ATOM | 3159 | N | VAL | H | 210 | −2.993 | −14.658 | 12.02 | 1 | 18.09 | H |
| ATOM | 3160 | CA | VAL | H | 210 | −3.577 | −13.448 | 12.558 | 1 | 16.35 | H |
| ATOM | 3161 | CB | VAL | H | 210 | −2.85 | −13.025 | 13.859 | 1 | 14.54 | H |
| ATOM | 3162 | CG1 | VAL | H | 210 | −3.513 | −11.811 | 14.466 | 1 | 16.17 | H |
| ATOM | 3163 | CG2 | VAL | H | 210 | −2.858 | −14.167 | 14.85 | 1 | 12.31 | H |
| ATOM | 3164 | C | VAL | H | 210 | −3.516 | −12.302 | 11.568 | 1 | 21.67 | H |
| ATOM | 3165 | O | VAL | H | 210 | −2.441 | −11.779 | 11.266 | 1 | 20.4 | H |
| ATOM | 3166 | N | ALA | H | 211 | −4.686 | −11.91 | 11.076 | 1 | 25.15 | H |
| ATOM | 3167 | CA | ALA | H | 211 | −4.793 | −10.819 | 10.12 | 1 | 28.64 | H |
| ATOM | 3168 | CB | ALA | H | 211 | −5.837 | −11.159 | 9.06 | 1 | 27.27 | H |
| ATOM | 3169 | C | ALA | H | 211 | −5.151 | −9.494 | 10.799 | 1 | 30.29 | H |
| ATOM | 3170 | O | ALA | H | 211 | −6.108 | −9.408 | 11.579 | 1 | 31.11 | H |
| ATOM | 3171 | N | HIS | H | 212 | −4.367 | −8.465 | 10.496 | 1 | 30.86 | H |
| ATOM | 3172 | CA | HIS | H | 212 | −4.589 | −7.131 | 11.034 | 1 | 31.54 | H |
| ATOM | 3173 | CB | HIS | H | 212 | −3.385 | −6.699 | 11.87 | 1 | 32.43 | H |
| ATOM | 3174 | CG | HIS | H | 212 | −3.613 | −5.451 | 12.667 | 1 | 32.79 | H |
| ATOM | 3175 | CD2 | HIS | H | 212 | −4.58 | −5.126 | 13.556 | 1 | 33.22 | H |
| ATOM | 3176 | ND1 | HIS | H | 212 | −2.766 | −4.366 | 12.608 | 1 | 32.09 | H |
| ATOM | 3177 | CE1 | HIS | H | 212 | −3.2 | −3.425 | 13.426 | 1 | 32.9 | H |
| ATOM | 3178 | NE2 | HIS | H | 212 | −4.3 | −3.861 | 14.014 | 1 | 33.97 | H |
| ATOM | 3179 | C | HIS | H | 212 | −4.73 | −6.234 | 9.8 | 1 | 33.24 | H |
| ATOM | 3180 | O | HIS | H | 212 | −3.747 | −5.663 | 9.322 | 1 | 32.73 | H |
| ATOM | 3181 | N | PRO | H | 213 | −5.956 | −6.115 | 9.256 | 1 | 32.76 | H |
| ATOM | 3182 | CD | PRO | H | 213 | −7.228 | −6.729 | 9.681 | 1 | 30 | H |
| ATOM | 3183 | CA | PRO | H | 213 | −6.157 | −5.279 | 8.069 | 1 | 32.17 | H |
| ATOM | 3184 | CB | PRO | H | 213 | −7.681 | −5.213 | 7.952 | 1 | 31.98 | H |
| ATOM | 3185 | CG | PRO | H | 213 | −8.096 | −6.573 | 8.438 | 1 | 29.41 | H |
| ATOM | 3186 | C | PRO | H | 213 | −5.505 | −3.904 | 8.157 | 1 | 31.23 | H |
| ATOM | 3187 | O | PRO | H | 213 | −4.78 | −3.495 | 7.246 | 1 | 30.71 | H |
| ATOM | 3188 | N | ALA | H | 214 | −5.749 | −3.203 | 9.259 | 1 | 30.34 | H |
| ATOM | 3189 | CA | ALA | H | 214 | −5.189 | −1.869 | 9.451 | 1 | 31.28 | H |
| ATOM | 3190 | CB | ALA | H | 214 | −5.462 | −1.394 | 10.867 | 1 | 33.75 | H |
| ATOM | 3191 | C | ALA | H | 214 | −3.687 | −1.771 | 9.148 | 1 | 32.3 | H |
| ATOM | 3192 | O | ALA | H | 214 | −3.22 | −0.736 | 8.673 | 1 | 33.96 | H |
| ATOM | 3193 | N | SER | H | 215 | −2.926 | −2.829 | 9.417 | 1 | 31.08 | H |
| ATOM | 3194 | CA | SER | H | 215 | −1.491 | −2.783 | 9.153 | 1 | 30.2 | H |
| ATOM | 3195 | CB | SER | H | 215 | −0.699 | −3.272 | 10.375 | 1 | 33.35 | H |
| ATOM | 3196 | OG | SER | H | 215 | −0.753 | −4.679 | 10.516 | 1 | 34.86 | H |
| ATOM | 3197 | C | SER | H | 215 | −1.105 | −3.596 | 7.922 | 1 | 30.55 | H |
| ATOM | 3198 | O | SER | H | 215 | 0.078 | −3.775 | 7.627 | 1 | 30.68 | H |
| ATOM | 3199 | N | SER | H | 216 | −2.111 | −4.087 | 7.204 | 1 | 30.46 | H |
| ATOM | 3200 | CA | SER | H | 216 | −1.88 | −4.871 | 5.994 | 1 | 30.3 | H |
| ATOM | 3201 | CB | SER | H | 216 | −1.207 | −3.986 | 4.943 | 1 | 28.9 | H |
| ATOM | 3202 | OG | SER | H | 216 | −1.949 | −2.791 | 4.763 | 1 | 31.14 | H |
| ATOM | 3203 | C | SER | H | 216 | −1.026 | −6.113 | 6.266 | 1 | 29.8 | H |
| ATOM | 3204 | O | SER | H | 216 | −0.324 | −6.602 | 5.382 | 1 | 28.07 | H |
| ATOM | 3205 | N | THR | H | 217 | −1.106 | −6.629 | 7.489 | 1 | 30.23 | H |
| ATOM | 3206 | CA | THR | H | 217 | −0.325 | −7.793 | 7.87 | 1 | 30.99 | H |
| ATOM | 3207 | CB | THR | H | 217 | 0.596 | −7.479 | 9.05 | 1 | 32.81 | H |
| ATOM | 3208 | OG1 | THR | H | 217 | −0.189 | −7.044 | 10.169 | 1 | 31.41 | H |
| ATOM | 3209 | CG2 | THR | H | 217 | 1.585 | −6.411 | 8.666 | 1 | 34.03 | H |
| ATOM | 3210 | C | THR | H | 217 | −1.117 | −9.03 | 8.251 | 1 | 30.77 | H |
| ATOM | 3211 | O | THR | H | 217 | −2.311 | −8.98 | 8.555 | 1 | 29.94 | H |
| ATOM | 3212 | N | THR | H | 218 | −0.409 | −10.146 | 8.241 | 1 | 29.71 | H |

TABLE 7-continued

| | | | | | | | | | | |
|---|---|---|---|---|---|---|---|---|---|---|
| ATOM | 3213 | CA | THR | H | 218 | −0.981 | −11.42 | 8.592 | 1 | 31.98 | H |
| ATOM | 3214 | CB | THR | H | 218 | −1.667 | −12.072 | 7.376 | 1 | 33.33 | H |
| ATOM | 3215 | OG1 | THR | H | 218 | −2.872 | −11.354 | 7.078 | 1 | 35.24 | H |
| ATOM | 3216 | CG2 | THR | H | 218 | −2.006 | −13.533 | 7.657 | 1 | 33.67 | H |
| ATOM | 3217 | C | THR | H | 218 | 0.164 | −12.276 | 9.085 | 1 | 31.47 | H |
| ATOM | 3218 | O | THR | H | 218 | 1.096 | −12.571 | 8.339 | 1 | 31.87 | H |
| ATOM | 3219 | N | VAL | H | 219 | 0.095 | −12.656 | 10.357 | 1 | 32.84 | H |
| ATOM | 3220 | CA | VAL | H | 219 | 1.128 | −13.477 | 10.964 | 1 | 34.38 | H |
| ATOM | 3221 | CB | VAL | H | 219 | 1.57 | −12.918 | 12.312 | 1 | 34.49 | H |
| ATOM | 3222 | CG1 | VAL | H | 219 | 2.7 | −13.776 | 12.861 | 1 | 37.59 | H |
| ATOM | 3223 | CG2 | VAL | H | 219 | 2.022 | −11.469 | 12.157 | 1 | 34.89 | H |
| ATOM | 3224 | C | VAL | H | 219 | 0.679 | −14.909 | 11.188 | 1 | 35.93 | H |
| ATOM | 3225 | O | VAL | H | 219 | −0.377 | −15.166 | 11.768 | 1 | 34.39 | H |
| ATOM | 3226 | N | ASP | H | 220 | 1.501 | −15.842 | 10.73 | 1 | 36.44 | H |
| ATOM | 3227 | CA | ASP | H | 220 | 1.2 | −17.25 | 10.881 | 1 | 37.22 | H |
| ATOM | 3228 | CB | ASP | H | 220 | 1.545 | −17.988 | 9.595 | 1 | 41.17 | H |
| ATOM | 3229 | CG | ASP | H | 220 | 0.624 | −17.619 | 8.461 | 1 | 45.72 | H |
| ATOM | 3230 | OD1 | ASP | H | 220 | −0.594 | −17.841 | 8.61 | 1 | 50.06 | H |
| ATOM | 3231 | OD2 | ASP | H | 220 | 1.106 | −17.105 | 7.428 | 1 | 50.88 | H |
| ATOM | 3232 | C | ASP | H | 220 | 1.968 | −17.847 | 12.047 | 1 | 35.86 | H |
| ATOM | 3233 | O | ASP | H | 220 | 3.196 | −17.83 | 12.066 | 1 | 38.85 | H |
| ATOM | 3234 | N | LYS | H | 221 | 1.242 | −18.369 | 13.027 | 1 | 32.81 | H |
| ATOM | 3235 | CA | LYS | H | 221 | 1.885 | −18.972 | 14.18 | 1 | 30.93 | H |
| ATOM | 3236 | CB | LYS | H | 221 | 1.395 | −18.329 | 15.479 | 1 | 31.24 | H |
| ATOM | 3237 | CG | LYS | H | 221 | 2.43 | −17.481 | 16.167 | 1 | 31.26 | H |
| ATOM | 3238 | CD | LYS | H | 221 | 3.737 | −18.231 | 16.361 | 1 | 28.08 | H |
| ATOM | 3239 | CE | LYS | H | 221 | 4.831 | −17.249 | 16.725 | 1 | 26.73 | H |
| ATOM | 3240 | NZ | LYS | H | 221 | 6.184 | −17.853 | 16.668 | 1 | 32.05 | H |
| ATOM | 3241 | C | LYS | H | 221 | 1.65 | −20.467 | 14.264 | 1 | 29.05 | H |
| ATOM | 3242 | O | LYS | H | 221 | 0.533 | −20.919 | 14.507 | 1 | 22.27 | H |
| ATOM | 3243 | N | LYS | H | 222 | 2.709 | −21.235 | 14.053 | 1 | 29.9 | H |
| ATOM | 3244 | CA | LYS | H | 222 | 2.599 | −22.675 | 14.166 | 1 | 34.28 | H |
| ATOM | 3245 | CB | LYS | H | 222 | 3.69 | −23.376 | 13.35 | 1 | 34.48 | H |
| ATOM | 3246 | CG | LYS | H | 222 | 3.831 | −24.868 | 13.64 | 1 | 34.6 | H |
| ATOM | 3247 | CD | LYS | H | 222 | 4.998 | −25.452 | 12.85 | 1 | 40.57 | H |
| ATOM | 3248 | CE | LYS | H | 222 | 5.329 | −26.886 | 13.264 | 1 | 43.98 | H |
| ATOM | 3249 | NZ | LYS | H | 222 | 4.198 | −27.839 | 13.083 | 1 | 44.62 | H |
| ATOM | 3250 | C | LYS | H | 222 | 2.809 | −22.927 | 15.647 | 1 | 35.44 | H |
| ATOM | 3251 | O | LYS | H | 222 | 3.762 | −22.42 | 16.238 | 1 | 36.24 | H |
| ATOM | 3252 | N | LEU | H | 223 | 1.911 | −23.682 | 16.261 | 1 | 37.71 | H |
| ATOM | 3253 | CA | LEU | H | 223 | 2.06 | −23.959 | 17.676 | 1 | 41.2 | H |
| ATOM | 3254 | CB | LEU | H | 223 | 0.733 | −24.436 | 18.266 | 1 | 40.43 | H |
| ATOM | 3255 | CG | LEU | H | 223 | −0.44 | −23.472 | 18.046 | 1 | 43.19 | H |
| ATOM | 3256 | CD1 | LEU | H | 223 | −1.594 | −23.885 | 18.938 | 1 | 44.63 | H |
| ATOM | 3257 | CD2 | LEU | H | 223 | −0.034 | −22.042 | 18.358 | 1 | 40.69 | H |
| ATOM | 3258 | C | LEU | H | 223 | 3.158 | −24.994 | 17.9 | 1 | 44.39 | H |
| ATOM | 3259 | O | LEU | H | 223 | 3.28 | −25.975 | 17.155 | 1 | 44.48 | H |
| ATOM | 3260 | N | GLU | H | 226 | 3.97 | −24.758 | 18.923 | 1 | 47.06 | H |
| ATOM | 3261 | CA | GLU | H | 226 | 5.063 | −25.659 | 19.25 | 1 | 50.27 | H |
| ATOM | 3262 | CB | GLU | H | 226 | 6.405 | −24.953 | 19.033 | 1 | 50.04 | H |
| ATOM | 3263 | CG | GLU | H | 226 | 6.605 | −24.412 | 17.621 | 1 | 50.6 | H |
| ATOM | 3264 | CD | GLU | H | 226 | 6.919 | −25.495 | 16.604 | 1 | 48.9 | H |
| ATOM | 3265 | OE1 | GLU | H | 226 | 6.256 | −26.556 | 16.624 | 1 | 47.3 | H |
| ATOM | 3266 | OE2 | GLU | H | 226 | 7.826 | −25.273 | 15.775 | 1 | 47.59 | H |
| ATOM | 3267 | C | GLU | H | 226 | 4.933 | −26.08 | 20.704 | 1 | 52.54 | H |
| ATOM | 3268 | O | GLU | H | 226 | 4.414 | −25.326 | 21.524 | 1 | 53.07 | H |
| ATOM | 3269 | N | PRO | H | 227 | 5.384 | −27.301 | 21.04 | 1 | 55.66 | H |
| ATOM | 3270 | CD | PRO | H | 227 | 5.853 | −28.358 | 20.126 | 1 | 55.34 | H |
| ATOM | 3271 | CA | PRO | H | 227 | 5.311 | −27.797 | 22.421 | 1 | 57.84 | H |
| ATOM | 3272 | CB | PRO | H | 227 | 5.907 | −29.198 | 22.314 | 1 | 56.01 | H |
| ATOM | 3273 | CG | PRO | H | 227 | 5.565 | −29.603 | 20.913 | 1 | 55.76 | H |
| ATOM | 3274 | C | PRO | H | 227 | 6.133 | −26.892 | 23.343 | 1 | 60.3 | H |
| ATOM | 3275 | O | PRO | H | 227 | 7.332 | −26.713 | 23.13 | 1 | 61.08 | H |
| ATOM | 3276 | N | SER | H | 228 | 5.492 | −26.322 | 24.361 | 1 | 63.5 | H |
| ATOM | 3277 | CA | SER | H | 228 | 6.189 | −25.428 | 25.285 | 1 | 66.55 | H |
| ATOM | 3278 | CB | SER | H | 228 | 5.224 | −24.356 | 25.818 | 1 | 67.37 | H |
| ATOM | 3279 | OG | SER | H | 228 | 4.06 | −24.926 | 26.387 | 1 | 68.18 | H |
| ATOM | 3280 | C | SER | H | 228 | 6.867 | −26.147 | 26.449 | 1 | 67.17 | H |
| ATOM | 3281 | O | SER | H | 228 | 8.102 | −25.991 | 26.592 | 1 | 68.28 | H |
| ATOM | 3282 | OXT | SER | H | 228 | 6.165 | −26.852 | 27.204 | 1 | 68.18 | H |
| ATOM | 3283 | CB | THR | A | 300 | −39.993 | 20.06 | −5.025 | 1 | 63.64 | A |
| ATOM | 3284 | OG1 | THR | A | 300 | −38.637 | 19.597 | −5.063 | 1 | 64.49 | A |
| ATOM | 3285 | CG2 | THR | A | 300 | −40.076 | 21.348 | −4.208 | 1 | 63.52 | A |
| ATOM | 3286 | C | THR | A | 300 | −41.057 | 17.834 | −5.415 | 1 | 60.23 | A |
| ATOM | 3287 | O | THR | A | 300 | −42.138 | 17.255 | −5.509 | 1 | 62.42 | A |
| ATOM | 3288 | N | THR | A | 300 | −40.313 | 18.493 | −3.114 | 1 | 60.6 | A |
| ATOM | 3289 | CA | THR | A | 300 | −40.883 | 18.971 | −4.405 | 1 | 61.67 | A |
| ATOM | 3290 | N | THR | A | 301 | −40.004 | 17.514 | −6.166 | 1 | 57.02 | A |
| ATOM | 3291 | CA | THR | A | 301 | −40.074 | 16.445 | −7.171 | 1 | 53.86 | A |

TABLE 7-continued

| | | | | | | | | | | |
|---|---|---|---|---|---|---|---|---|---|---|
| ATOM | 3292 | CB | THR | A | 301 | −40.912 | 16.886 | −8.388 | 1 | 54.85 | A |
| ATOM | 3293 | OG1 | THR | A | 301 | −42.277 | 17.061 | −7.988 | 1 | 55.11 | A |
| ATOM | 3294 | CG2 | THR | A | 301 | −40.839 | 15.846 | −9.496 | 1 | 54.22 | A |
| ATOM | 3295 | C | THR | A | 301 | −38.699 | 15.997 | −7.668 | 1 | 50.39 | A |
| ATOM | 3296 | O | THR | A | 301 | −37.799 | 16.816 | −7.854 | 1 | 52.5 | A |
| ATOM | 3297 | N | TYR | A | 302 | −38.548 | 14.696 | −7.903 | 1 | 44.26 | A |
| ATOM | 3298 | CA | TYR | A | 302 | −37.273 | 14.149 | −8.355 | 1 | 38.64 | A |
| ATOM | 3299 | CB | TYR | A | 302 | −36.757 | 13.132 | −7.334 | 1 | 38.4 | A |
| ATOM | 3300 | CG | TYR | A | 302 | −36.54 | 13.739 | −5.965 | 1 | 37.35 | A |
| ATOM | 3301 | CD1 | TYR | A | 302 | −35.445 | 14.56 | −5.714 | 1 | 36.62 | A |
| ATOM | 3302 | CE1 | TYR | A | 302 | −35.276 | 15.173 | −4.478 | 1 | 38.19 | A |
| ATOM | 3303 | CD2 | TYR | A | 302 | −37.465 | 13.541 | −4.941 | 1 | 36.87 | A |
| ATOM | 3304 | CE2 | TYR | A | 302 | −37.31 | 14.146 | −3.705 | 1 | 37.5 | A |
| ATOM | 3305 | CZ | TYR | A | 302 | −36.213 | 14.965 | −3.474 | 1 | 40.16 | A |
| ATOM | 3306 | OH | TYR | A | 302 | −36.055 | 15.577 | −2.244 | 1 | 39.05 | A |
| ATOM | 3307 | C | TYR | A | 302 | −37.337 | 13.516 | −9.734 | 1 | 35.23 | A |
| ATOM | 3308 | O | TYR | A | 302 | −38.221 | 13.83 | −10.527 | 1 | 36.08 | A |
| ATOM | 3309 | N | GLY | A | 303 | −36.389 | 12.628 | −10.014 | 1 | 31.15 | A |
| ATOM | 3310 | CA | GLY | A | 303 | −36.338 | 11.974 | −11.306 | 1 | 29 | A |
| ATOM | 3311 | C | GLY | A | 303 | −37.35 | 10.864 | −11.496 | 1 | 27.36 | A |
| ATOM | 3312 | O | GLY | A | 303 | −38.487 | 10.96 | −11.054 | 1 | 27.78 | A |
| ATOM | 3313 | N | VAL | A | 304 | −36.928 | 9.805 | −12.176 | 1 | 28.37 | A |
| ATOM | 3314 | CA | VAL | A | 304 | −37.783 | 8.653 | −12.439 | 1 | 25.45 | A |
| ATOM | 3315 | CB | VAL | A | 304 | −37.355 | 7.941 | −13.743 | 1 | 23.02 | A |
| ATOM | 3316 | CG1 | VAL | A | 304 | −38.345 | 6.841 | −14.08 | 1 | 22.44 | A |
| ATOM | 3317 | CG2 | VAL | A | 304 | −37.266 | 8.937 | −14.88 | 1 | 19.78 | A |
| ATOM | 3318 | C | VAL | A | 304 | −37.644 | 7.674 | −11.275 | 1 | 25.59 | A |
| ATOM | 3319 | O | VAL | A | 304 | −36.532 | 7.412 | −10.818 | 1 | 27.5 | A |
| ATOM | 3320 | N | CYS | A | 305 | −38.761 | 7.143 | −10.786 | 1 | 24.55 | A |
| ATOM | 3321 | CA | CYS | A | 305 | −38.714 | 6.192 | −9.675 | 1 | 23.42 | A |
| ATOM | 3322 | C | CYS | A | 305 | −37.698 | 5.08 | −9.971 | 1 | 24.43 | A |
| ATOM | 3323 | O | CYS | A | 305 | −37.74 | 4.453 | −11.031 | 1 | 23.32 | A |
| ATOM | 3324 | CB | CYS | A | 305 | −40.096 | 5.591 | −9.433 | 1 | 23.21 | A |
| ATOM | 3325 | SG | CYS | A | 305 | −41.409 | 6.808 | −9.079 | 1 | 22.86 | A |
| ATOM | 3326 | N | SER | A | 306 | −36.791 | 4.848 | −9.022 | 1 | 25.15 | A |
| ATOM | 3327 | CA | SER | A | 306 | −35.723 | 3.853 | −9.15 | 1 | 22.43 | A |
| ATOM | 3328 | CB | SER | A | 306 | −34.448 | 4.401 | −8.509 | 1 | 22.2 | A |
| ATOM | 3329 | OG | SER | A | 306 | −34.647 | 4.636 | −7.124 | 1 | 17.99 | A |
| ATOM | 3330 | C | SER | A | 306 | −36.032 | 2.483 | −8.541 | 1 | 21.94 | A |
| ATOM | 3331 | O | SER | A | 306 | −35.336 | 1.506 | −8.814 | 1 | 20.23 | A |
| ATOM | 3332 | N | LYS | A | 307 | −37.061 | 2.405 | −7.708 | 1 | 20.25 | A |
| ATOM | 3333 | CA | LYS | A | 307 | −37.415 | 1.128 | −7.1 | 1 | 20.29 | A |
| ATOM | 3334 | CB | LYS | A | 307 | −37.89 | 1.336 | −5.661 | 1 | 17.83 | A |
| ATOM | 3335 | CG | LYS | A | 307 | −36.843 | 1.928 | −4.742 | 1 | 18.48 | A |
| ATOM | 3336 | CD | LYS | A | 307 | −35.585 | 1.08 | −4.7 | 1 | 20.11 | A |
| ATOM | 3337 | CE | LYS | A | 307 | −34.685 | 1.512 | −3.562 | 1 | 23.13 | A |
| ATOM | 3338 | NZ | LYS | A | 307 | −33.554 | 0.58 | −3.379 | 1 | 22.66 | A |
| ATOM | 3339 | C | LYS | A | 307 | −38.496 | 0.398 | −7.903 | 1 | 19.89 | A |
| ATOM | 3340 | O | LYS | A | 307 | −39.182 | 0.984 | −8.734 | 1 | 19.77 | A |
| ATOM | 3341 | N | ALA | A | 308 | −38.637 | −0.893 | −7.655 | 1 | 19.8 | A |
| ATOM | 3342 | CA | ALA | A | 308 | −39.633 | −1.683 | −8.349 | 1 | 22.06 | A |
| ATOM | 3343 | CB | ALA | A | 308 | −39.309 | −3.16 | −8.199 | 1 | 17.28 | A |
| ATOM | 3344 | C | ALA | A | 308 | −41.046 | −1.395 | −7.827 | 1 | 23.71 | A |
| ATOM | 3345 | O | ALA | A | 308 | −41.231 | −0.934 | −6.697 | 1 | 22.91 | A |
| ATOM | 3346 | N | PHE | A | 309 | −42.035 | −1.658 | −8.673 | 1 | 25.12 | A |
| ATOM | 3347 | CA | PHE | A | 309 | −43.428 | −1.468 | −8.317 | 1 | 26.85 | A |
| ATOM | 3348 | CB | PHE | A | 309 | −44.183 | −0.705 | −9.407 | 1 | 26.25 | A |
| ATOM | 3349 | CG | PHE | A | 309 | −43.804 | 0.741 | −9.52 | 1 | 29.27 | A |
| ATOM | 3350 | CD1 | PHE | A | 309 | −42.56 | 1.116 | −10.019 | 1 | 28.25 | A |
| ATOM | 3351 | CD2 | PHE | A | 309 | −44.701 | 1.736 | −9.13 | 1 | 28.22 | A |
| ATOM | 3352 | CE1 | PHE | A | 309 | −42.212 | 2.463 | −10.13 | 1 | 27.47 | A |
| ATOM | 3353 | CE2 | PHE | A | 309 | −44.365 | 3.084 | −9.236 | 1 | 27.52 | A |
| ATOM | 3354 | CZ | PHE | A | 309 | −43.118 | 3.449 | −9.738 | 1 | 28.7 | A |
| ATOM | 3355 | C | PHE | A | 309 | −44.051 | −2.845 | −8.193 | 1 | 29.88 | A |
| ATOM | 3356 | O | PHE | A | 309 | −43.408 | −3.864 | −8.472 | 1 | 26.84 | A |
| ATOM | 3357 | N | LYS | A | 310 | −45.312 | −2.869 | −7.779 | 1 | 30.73 | A |
| ATOM | 3358 | CA | LYS | A | 310 | −46.035 | −4.116 | −7.651 | 1 | 31.75 | A |
| ATOM | 3359 | CB | LYS | A | 310 | −45.987 | −4.617 | −6.202 | 1 | 35.18 | A |
| ATOM | 3360 | CG | LYS | A | 310 | −46.277 | −6.11 | −6.067 | 1 | 40.9 | A |
| ATOM | 3361 | CD | LYS | A | 310 | −46.153 | −6.619 | −4.63 | 1 | 44.59 | A |
| ATOM | 3362 | CE | LYS | A | 310 | −46.262 | −8.154 | −4.58 | 1 | 46.43 | A |
| ATOM | 3363 | NZ | LYS | A | 310 | −46.255 | −8.719 | −3.193 | 1 | 49.07 | A |
| ATOM | 3364 | C | LYS | A | 310 | −47.478 | −3.881 | −8.095 | 1 | 32.4 | A |
| ATOM | 3365 | O | LYS | A | 310 | −48.092 | −2.864 | −7.755 | 1 | 29.67 | A |
| ATOM | 3366 | N | PHE | A | 311 | −48 | −4.811 | −8.886 | 1 | 33.4 | A |
| ATOM | 3367 | CA | PHE | A | 311 | −49.372 | −4.725 | −9.367 | 1 | 37.04 | A |
| ATOM | 3368 | CB | PHE | A | 311 | −49.557 | −5.616 | −10.601 | 1 | 36.39 | A |
| ATOM | 3369 | CG | PHE | A | 311 | −49.018 | −5.023 | −11.877 | 1 | 35.69 | A |
| ATOM | 3370 | CD1 | PHE | A | 311 | −49.786 | −4.137 | −12.627 | 1 | 37.17 | A |

TABLE 7-continued

| | | | | | | | | | | |
|---|---|---|---|---|---|---|---|---|---|---|
| ATOM | 3371 | CD2 | PHE | A | 311 | −47.75 | −5.356 | −12.333 | 1 | 35.82 | A |
| ATOM | 3372 | CE1 | PHE | A | 311 | −49.298 | −3.594 | −13.817 | 1 | 37.02 | A |
| ATOM | 3373 | CE2 | PHE | A | 311 | −47.251 | −4.817 | −13.519 | 1 | 36.63 | A |
| ATOM | 3374 | CZ | PHE | A | 311 | −48.027 | −3.936 | −14.262 | 1 | 35.98 | A |
| ATOM | 3375 | C | PHE | A | 311 | −50.335 | −5.174 | −8.268 | 1 | 38.96 | A |
| ATOM | 3376 | O | PHE | A | 311 | −50.138 | −6.215 | −7.649 | 1 | 40.29 | A |
| ATOM | 3377 | N | LEU | A | 312 | −51.37 | −4.38 | −8.024 | 1 | 41.96 | A |
| ATOM | 3378 | CA | LEU | A | 312 | −52.374 | −4.713 | −7.017 | 1 | 45.5 | A |
| ATOM | 3379 | CB | LEU | A | 312 | −52.713 | −3.473 | −6.19 | 1 | 44.96 | A |
| ATOM | 3380 | CG | LEU | A | 312 | −51.477 | −2.789 | −5.61 | 1 | 44.34 | A |
| ATOM | 3381 | CD1 | LEU | A | 312 | −51.845 | −1.424 | −5.073 | 1 | 44.91 | A |
| ATOM | 3382 | CD2 | LEU | A | 312 | −50.873 | −3.67 | −4.529 | 1 | 44.77 | A |
| ATOM | 3383 | C | LEU | A | 312 | −53.624 | −5.225 | −7.737 | 1 | 47.79 | A |
| ATOM | 3384 | O | LEU | A | 312 | −54.346 | −4.463 | −8.391 | 1 | 50.15 | A |
| ATOM | 3385 | N | GLY | A | 313 | −53.875 | −6.52 | −7.618 | 1 | 49.8 | A |
| ATOM | 3386 | CA | GLY | A | 313 | −55.024 | −7.105 | −8.283 | 1 | 51.57 | A |
| ATOM | 3387 | C | GLY | A | 313 | −54.628 | −7.535 | −9.681 | 1 | 52.43 | A |
| ATOM | 3388 | O | GLY | A | 313 | −53.66 | −8.277 | −9.869 | 1 | 54.68 | A |
| ATOM | 3389 | N | THR | A | 314 | −55.374 | −7.059 | −10.669 | 1 | 53.04 | A |
| ATOM | 3390 | CA | THR | A | 314 | −55.105 | −7.385 | −12.064 | 1 | 51.49 | A |
| ATOM | 3391 | CB | THR | A | 314 | −55.682 | −8.762 | −12.432 | 1 | 52.44 | A |
| ATOM | 3392 | OG1 | THR | A | 314 | −54.968 | −9.78 | −11.719 | 1 | 54.54 | A |
| ATOM | 3393 | CG2 | THR | A | 314 | −55.571 | −9.009 | −13.932 | 1 | 53.08 | A |
| ATOM | 3394 | C | THR | A | 314 | −55.742 | −6.33 | −12.948 | 1 | 48.79 | A |
| ATOM | 3395 | O | THR | A | 314 | −56.896 | −5.956 | −12.741 | 1 | 48.63 | A |
| ATOM | 3396 | N | PRO | A | 315 | −54.998 | −5.831 | −13.946 | 1 | 47.38 | A |
| ATOM | 3397 | CD | PRO | A | 315 | −53.645 | −6.226 | −14.377 | 1 | 47.03 | A |
| ATOM | 3398 | CA | PRO | A | 315 | −55.551 | −4.81 | −14.834 | 1 | 46.88 | A |
| ATOM | 3399 | CB | PRO | A | 315 | −54.616 | −4.863 | −16.032 | 1 | 46.34 | A |
| ATOM | 3400 | CG | PRO | A | 315 | −53.296 | −5.143 | −15.381 | 1 | 47.58 | A |
| ATOM | 3401 | C | PRO | A | 315 | −57.007 | −5.095 | −15.189 | 1 | 47.46 | A |
| ATOM | 3402 | O | PRO | A | 315 | −57.383 | −6.225 | −15.525 | 1 | 44.71 | A |
| ATOM | 3403 | N | ALA | A | 316 | −57.824 | −4.055 | −15.091 | 1 | 47.6 | A |
| ATOM | 3404 | CA | ALA | A | 316 | −59.239 | −4.173 | −15.372 | 1 | 46.94 | A |
| ATOM | 3405 | CB | ALA | A | 316 | −60.039 | −3.598 | −14.206 | 1 | 47.42 | A |
| ATOM | 3406 | C | ALA | A | 316 | −59.636 | −3.482 | −16.669 | 1 | 46.66 | A |
| ATOM | 3407 | O | ALA | A | 316 | −59.104 | −2.431 | −17.023 | 1 | 43.77 | A |
| ATOM | 3408 | N | ASP | A | 317 | −60.582 | −4.095 | −17.371 | 1 | 48.84 | A |
| ATOM | 3409 | CA | ASP | A | 317 | −61.097 | −3.555 | −18.618 | 1 | 49.79 | A |
| ATOM | 3410 | CB | ASP | A | 317 | −61.752 | −4.674 | −19.426 | 1 | 51.92 | A |
| ATOM | 3411 | CG | ASP | A | 317 | −61.941 | −4.306 | −20.885 | 1 | 55.75 | A |
| ATOM | 3412 | OD1 | ASP | A | 317 | −62.581 | −3.266 | −21.163 | 1 | 55.59 | A |
| ATOM | 3413 | OD2 | ASP | A | 317 | −61.444 | −5.06 | −21.753 | 1 | 56.72 | A |
| ATOM | 3414 | C | ASP | A | 317 | −62.139 | −2.5 | −18.241 | 1 | 49.14 | A |
| ATOM | 3415 | O | ASP | A | 317 | −63.011 | −2.765 | −17.419 | 1 | 48.28 | A |
| ATOM | 3416 | N | THR | A | 318 | −62.046 | −1.308 | −18.828 | 1 | 49.13 | A |
| ATOM | 3417 | CA | THR | A | 318 | −62.994 | −0.23 | −18.522 | 1 | 48.54 | A |
| ATOM | 3418 | CB | THR | A | 318 | −62.342 | 1.172 | −18.637 | 1 | 45.08 | A |
| ATOM | 3419 | OG1 | THR | A | 318 | −61.91 | 1.391 | −19.983 | 1 | 42.12 | A |
| ATOM | 3420 | CG2 | THR | A | 318 | −61.163 | 1.292 | −17.712 | 1 | 42.82 | A |
| ATOM | 3421 | C | THR | A | 318 | −64.196 | −0.234 | −19.456 | 1 | 50.01 | A |
| ATOM | 3422 | O | THR | A | 318 | −65.061 | 0.64 | −19.367 | 1 | 49.96 | A |
| ATOM | 3423 | N | GLY | A | 319 | −64.247 | −1.21 | −20.355 | 1 | 50.29 | A |
| ATOM | 3424 | CA | GLY | A | 319 | −65.35 | −1.269 | −21.293 | 1 | 50.96 | A |
| ATOM | 3425 | C | GLY | A | 319 | −65.344 | −0.036 | −22.174 | 1 | 51.2 | A |
| ATOM | 3426 | O | GLY | A | 319 | −66.272 | 0.187 | −22.95 | 1 | 53.64 | A |
| ATOM | 3427 | N | HIS | A | 320 | −64.291 | 0.767 | −22.05 | 1 | 51.62 | A |
| ATOM | 3428 | CA | HIS | A | 320 | −64.149 | 1.985 | −22.837 | 1 | 51.32 | A |
| ATOM | 3429 | CB | HIS | A | 320 | −64.009 | 3.204 | −21.921 | 1 | 54.93 | A |
| ATOM | 3430 | CG | HIS | A | 320 | −65.103 | 3.331 | −20.906 | 1 | 59.78 | A |
| ATOM | 3431 | CD2 | HIS | A | 320 | −65.057 | 3.473 | −19.559 | 1 | 61.42 | A |
| ATOM | 3432 | ND1 | HIS | A | 320 | −66.439 | 3.326 | −21.244 | 1 | 61.23 | A |
| ATOM | 3433 | CE1 | HIS | A | 320 | −67.169 | 3.457 | −20.15 | 1 | 62.96 | A |
| ATOM | 3434 | NE2 | HIS | A | 320 | −66.355 | 3.548 | −19.114 | 1 | 63.22 | A |
| ATOM | 3435 | C | HIS | A | 320 | −62.923 | 1.898 | −23.735 | 1 | 49.8 | A |
| ATOM | 3436 | O | HIS | A | 320 | −62.558 | 2.87 | −24.387 | 1 | 50.31 | A |
| ATOM | 3437 | N | GLY | A | 321 | −62.284 | 0.733 | −23.763 | 1 | 48.67 | A |
| ATOM | 3438 | CA | GLY | A | 321 | −61.103 | 0.563 | −24.593 | 1 | 46.45 | A |
| ATOM | 3439 | C | GLY | A | 321 | −59.819 | 0.795 | −23.816 | 1 | 46.22 | A |
| ATOM | 3440 | O | GLY | A | 321 | −58.713 | 0.692 | −24.355 | 1 | 46.09 | A |
| ATOM | 3441 | N | THR | A | 322 | −59.967 | 1.113 | −22.536 | 1 | 43.6 | A |
| ATOM | 3442 | CA | THR | A | 322 | −58.816 | 1.353 | −21.681 | 1 | 39.55 | A |
| ATOM | 3443 | CB | THR | A | 322 | −58.844 | 2.763 | −21.092 | 1 | 38.16 | A |
| ATOM | 3444 | OG1 | THR | A | 322 | −59.945 | 2.875 | −20.182 | 1 | 37.52 | A |
| ATOM | 3445 | CG2 | THR | A | 322 | −58.991 | 3.792 | −22.19 | 1 | 37.16 | A |
| ATOM | 3446 | C | THR | A | 322 | −58.813 | 0.373 | −20.521 | 1 | 37.54 | A |
| ATOM | 3447 | O | THR | A | 322 | −59.836 | −0.245 | −20.21 | 1 | 35.62 | A |
| ATOM | 3448 | N | VAL | A | 323 | −57.656 | 0.226 | −19.889 | 1 | 35.39 | A |
| ATOM | 3449 | CA | VAL | A | 323 | −57.534 | −0.655 | −18.738 | 1 | 34.7 | A |

TABLE 7-continued

| | | | | | | | | | | |
|---|---|---|---|---|---|---|---|---|---|---|
| ATOM | 3450 | CB | VAL | A | 323 | −56.494 | −1.772 | −18.978 | 1 | 32.69 | A |
| ATOM | 3451 | CG1 | VAL | A | 323 | −56.696 | −2.357 | −20.357 | 1 | 31.9 | A |
| ATOM | 3452 | CG2 | VAL | A | 323 | −55.082 | −1.231 | −18.827 | 1 | 31.65 | A |
| ATOM | 3453 | C | VAL | A | 323 | −57.101 | 0.189 | −17.548 | 1 | 34.44 | A |
| ATOM | 3454 | O | VAL | A | 323 | −56.333 | 1.144 | −17.7 | 1 | 32.87 | A |
| ATOM | 3455 | N | VAL | A | 324 | −57.626 | −0.146 | −16.375 | 1 | 34.69 | A |
| ATOM | 3456 | CA | VAL | A | 324 | −57.281 | 0.558 | −15.147 | 1 | 33.85 | A |
| ATOM | 3457 | CB | VAL | A | 324 | −58.528 | 1.102 | −14.421 | 1 | 32.65 | A |
| ATOM | 3458 | CG1 | VAL | A | 324 | −58.13 | 1.74 | −13.111 | 1 | 32.02 | A |
| ATOM | 3459 | CG2 | VAL | A | 324 | −59.208 | 2.133 | −15.279 | 1 | 33.74 | A |
| ATOM | 3460 | C | VAL | A | 324 | −56.554 | −0.406 | −14.223 | 1 | 34.46 | A |
| ATOM | 3461 | O | VAL | A | 324 | −57.039 | −1.506 | −13.93 | 1 | 34.21 | A |
| ATOM | 3462 | N | LEU | A | 325 | −55.375 | 0.007 | −13.78 | 1 | 34.48 | A |
| ATOM | 3463 | CA | LEU | A | 325 | −54.578 | −0.813 | −12.891 | 1 | 34.12 | A |
| ATOM | 3464 | CB | LEU | A | 325 | −53.423 | −1.469 | −13.66 | 1 | 34.48 | A |
| ATOM | 3465 | CG | LEU | A | 325 | −52.495 | −0.601 | −14.513 | 1 | 36.04 | A |
| ATOM | 3466 | CD1 | LEU | A | 325 | −51.692 | 0.345 | −13.641 | 1 | 35.91 | A |
| ATOM | 3467 | CD2 | LEU | A | 325 | −51.554 | −1.508 | −15.285 | 1 | 38.71 | A |
| ATOM | 3468 | C | LEU | A | 325 | −54.051 | 0.011 | −11.729 | 1 | 33.25 | A |
| ATOM | 3469 | O | LEU | A | 325 | −53.828 | 1.217 | −11.848 | 1 | 28.42 | A |
| ATOM | 3470 | N | GLU | A | 326 | −53.874 | −0.66 | −10.598 | 1 | 34.45 | A |
| ATOM | 3471 | CA | GLU | A | 326 | −53.377 | −0.029 | −9.388 | 1 | 34.48 | A |
| ATOM | 3472 | CB | GLU | A | 326 | −54.304 | −0.347 | −8.222 | 1 | 36.25 | A |
| ATOM | 3473 | CG | GLU | A | 326 | −54.743 | 0.859 | −7.423 | 1 | 40.98 | A |
| ATOM | 3474 | CD | GLU | A | 326 | −55.57 | 0.461 | −6.218 | 1 | 44.97 | A |
| ATOM | 3475 | OE1 | GLU | A | 326 | −56.491 | −0.374 | −6.38 | 1 | 45.89 | A |
| ATOM | 3476 | OE2 | GLU | A | 326 | −55.303 | 0.984 | −5.115 | 1 | 46.67 | A |
| ATOM | 3477 | C | GLU | A | 326 | −51.991 | −0.579 | −9.099 | 1 | 33.25 | A |
| ATOM | 3478 | O | GLU | A | 326 | −51.768 | −1.792 | −9.141 | 1 | 32.92 | A |
| ATOM | 3479 | N | LEU | A | 327 | −51.058 | 0.313 | −8.805 | 1 | 31.12 | A |
| ATOM | 3480 | CA | LEU | A | 327 | −49.696 | −0.101 | −8.514 | 1 | 31.14 | A |
| ATOM | 3481 | CB | LEU | A | 327 | −48.723 | 0.566 | −9.483 | 1 | 29.38 | A |
| ATOM | 3482 | CG | LEU | A | 327 | −48.791 | 0.226 | −10.962 | 1 | 29.29 | A |
| ATOM | 3483 | CD1 | LEU | A | 327 | −47.794 | 1.088 | −11.725 | 1 | 27.59 | A |
| ATOM | 3484 | CD2 | LEU | A | 327 | −48.494 | −1.25 | −11.147 | 1 | 27.01 | A |
| ATOM | 3485 | C | LEU | A | 327 | −49.285 | 0.285 | −7.109 | 1 | 32.57 | A |
| ATOM | 3486 | O | LEU | A | 327 | −49.769 | 1.283 | −6.566 | 1 | 32.67 | A |
| ATOM | 3487 | N | GLN | A | 328 | −48.4 | −0.515 | −6.517 | 1 | 32.21 | A |
| ATOM | 3488 | CA | GLN | A | 328 | −47.864 | −0.195 | −5.201 | 1 | 33.66 | A |
| ATOM | 3489 | CB | GLN | A | 328 | −48.014 | −1.352 | −4.206 | 1 | 38.45 | A |
| ATOM | 3490 | CG | GLN | A | 328 | −47.182 | −1.125 | −2.922 | 1 | 47.56 | A |
| ATOM | 3491 | CD | GLN | A | 328 | −47.265 | −2.265 | −1.904 | 1 | 53.01 | A |
| ATOM | 3492 | OE1 | GLN | A | 328 | −48.321 | −2.505 | −1.299 | 1 | 54.64 | A |
| ATOM | 3493 | NE2 | GLN | A | 328 | −46.144 | −2.968 | −1.705 | 1 | 50.24 | A |
| ATOM | 3494 | C | GLN | A | 328 | −46.381 | 0.084 | −5.418 | 1 | 30.77 | A |
| ATOM | 3495 | O | GLN | A | 328 | −45.664 | −0.758 | −5.97 | 1 | 31.78 | A |
| ATOM | 3496 | N | TYR | A | 329 | −45.924 | 1.266 | −5.01 | 1 | 27.23 | A |
| ATOM | 3497 | CA | TYR | A | 329 | −44.516 | 1.607 | −5.163 | 1 | 24.05 | A |
| ATOM | 3498 | CB | TYR | A | 329 | −44.339 | 3.08 | −5.545 | 1 | 23.61 | A |
| ATOM | 3499 | CG | TYR | A | 329 | −42.899 | 3.428 | −5.839 | 1 | 22.91 | A |
| ATOM | 3500 | CD1 | TYR | A | 329 | −42.14 | 2.637 | −6.702 | 1 | 24.27 | A |
| ATOM | 3501 | CE1 | TYR | A | 329 | −40.792 | 2.904 | −6.929 | 1 | 25.43 | A |
| ATOM | 3502 | CD2 | TYR | A | 329 | −42.278 | 4.505 | −5.214 | 1 | 21.99 | A |
| ATOM | 3503 | CE2 | TYR | A | 329 | −40.926 | 4.784 | −5.431 | 1 | 23.92 | A |
| ATOM | 3504 | CZ | TYR | A | 329 | −40.188 | 3.975 | −6.285 | 1 | 26.19 | A |
| ATOM | 3505 | OH | TYR | A | 329 | −38.842 | 4.197 | −6.455 | 1 | 25.17 | A |
| ATOM | 3506 | C | TYR | A | 329 | −43.782 | 1.307 | −3.863 | 1 | 21.92 | A |
| ATOM | 3507 | O | TYR | A | 329 | −44.272 | 1.634 | −2.781 | 1 | 17.52 | A |
| ATOM | 3508 | N | THR | A | 330 | −42.602 | 0.696 | −3.988 | 1 | 21.05 | A |
| ATOM | 3509 | CA | THR | A | 330 | −41.788 | 0.304 | −2.836 | 1 | 19.46 | A |
| ATOM | 3510 | CB | THR | A | 330 | −41.143 | −1.082 | −3.053 | 1 | 17.68 | A |
| ATOM | 3511 | OG1 | THR | A | 330 | −40.181 | −0.99 | −4.107 | 1 | 17.7 | A |
| ATOM | 3512 | CG2 | THR | A | 330 | −42.19 | −2.129 | −3.424 | 1 | 14.63 | A |
| ATOM | 3513 | C | THR | A | 330 | −40.65 | 1.247 | −2.449 | 1 | 21.28 | A |
| ATOM | 3514 | O | THR | A | 330 | −39.937 | 0.981 | −1.483 | 1 | 26.52 | A |
| ATOM | 3515 | N | GLY | A | 331 | −40.464 | 2.341 | −3.175 | 1 | 20.45 | A |
| ATOM | 3516 | CA | GLY | A | 331 | −39.366 | 3.23 | −2.836 | 1 | 19.42 | A |
| ATOM | 3517 | C | GLY | A | 331 | −39.674 | 4.419 | −1.95 | 1 | 19.59 | A |
| ATOM | 3518 | O | GLY | A | 331 | −40.833 | 4.74 | −1.692 | 1 | 20.07 | A |
| ATOM | 3519 | N | THR | A | 332 | −38.615 | 5.079 | −1.488 | 1 | 21.73 | A |
| ATOM | 3520 | CA | THR | A | 332 | −38.734 | 6.265 | −0.638 | 1 | 22.76 | A |
| ATOM | 3521 | CB | THR | A | 332 | −38.004 | 6.068 | 0.741 | 1 | 25.09 | A |
| ATOM | 3522 | OG1 | THR | A | 332 | −36.59 | 5.902 | 0.537 | 1 | 20.9 | A |
| ATOM | 3523 | CG2 | THR | A | 332 | −38.55 | 4.843 | 1.462 | 1 | 23.58 | A |
| ATOM | 3524 | C | THR | A | 332 | −38.098 | 7.453 | −1.359 | 1 | 19.89 | A |
| ATOM | 3525 | O | THR | A | 332 | −37.855 | 8.497 | −0.766 | 1 | 22.26 | A |
| ATOM | 3526 | N | ASP | A | 333 | −37.835 | 7.288 | −2.646 | 1 | 20.94 | A |
| ATOM | 3527 | CA | ASP | A | 333 | −37.186 | 8.333 | −3.426 | 1 | 24.06 | A |
| ATOM | 3528 | CB | ASP | A | 333 | −36.22 | 7.695 | −4.433 | 1 | 21.03 | A |

TABLE 7-continued

| ATOM | 3529 | CG  | ASP | A | 333 | −36.907 | 6.705  | −5.368  | 1 | 24.26 | A |
|------|------|-----|-----|---|-----|---------|--------|---------|---|-------|---|
| ATOM | 3530 | OD1 | ASP | A | 333 | −37.961 | 6.145  | −4.995  | 1 | 24.81 | A |
| ATOM | 3531 | OD2 | ASP | A | 333 | −36.382 | 6.469  | −6.478  | 1 | 21.88 | A |
| ATOM | 3532 | C   | ASP | A | 333 | −38.131 | 9.295  | −4.132  | 1 | 27.03 | A |
| ATOM | 3533 | O   | ASP | A | 333 | −37.694 | 10.157 | −4.897  | 1 | 29.68 | A |
| ATOM | 3534 | N   | GLY | A | 334 | −39.426 | 9.157  | −3.87   | 1 | 27.13 | A |
| ATOM | 3535 | CA  | GLY | A | 334 | −40.389 | 10.044 | −4.492  | 1 | 25.95 | A |
| ATOM | 3536 | C   | GLY | A | 334 | −40.328 | 11.411 | −3.844  | 1 | 24.5  | A |
| ATOM | 3537 | O   | GLY | A | 334 | −39.581 | 11.607 | −2.891  | 1 | 25.17 | A |
| ATOM | 3538 | N   | PRO | A | 335 | −41.086 | 12.388 | −4.35   | 1 | 26.13 | A |
| ATOM | 3539 | CD  | PRO | A | 335 | −41.244 | 13.713 | −3.725  | 1 | 26.69 | A |
| ATOM | 3540 | CA  | PRO | A | 335 | −41.985 | 12.244 | −5.501  | 1 | 26.01 | A |
| ATOM | 3541 | CB  | PRO | A | 335 | −42.662 | 13.614 | −5.586  | 1 | 23.99 | A |
| ATOM | 3542 | CG  | PRO | A | 335 | −42.638 | 14.105 | −4.171  | 1 | 25.33 | A |
| ATOM | 3543 | C   | PRO | A | 335 | −41.182 | 11.933 | −6.759  | 1 | 24.96 | A |
| ATOM | 3544 | O   | PRO | A | 335 | −40.204 | 12.617 | −7.047  | 1 | 25.01 | A |
| ATOM | 3545 | N   | CYS | A | 336 | −41.588 | 10.903 | −7.496  | 1 | 24.38 | A |
| ATOM | 3546 | CA  | CYS | A | 336 | −40.894 | 10.525 | −8.728  | 1 | 25.58 | A |
| ATOM | 3547 | C   | CYS | A | 336 | −41.875 | 10.098 | −9.818  | 1 | 26.25 | A |
| ATOM | 3548 | O   | CYS | A | 336 | −43.023 | 9.721  | −9.54   | 1 | 26.06 | A |
| ATOM | 3549 | CB  | CYS | A | 336 | −39.895 | 9.389  | −8.464  | 1 | 22.02 | A |
| ATOM | 3550 | SG  | CYS | A | 336 | −40.646 | 7.981  | −7.599  | 1 | 25.18 | A |
| ATOM | 3551 | N   | LYS | A | 337 | −41.412 | 10.157 | −11.061 | 1 | 25.38 | A |
| ATOM | 3552 | CA  | LYS | A | 337 | −42.242 | 9.789  | −12.201 | 1 | 27.71 | A |
| ATOM | 3553 | CB  | LYS | A | 337 | −41.713 | 10.464 | −13.483 | 1 | 29.76 | A |
| ATOM | 3554 | CG  | LYS | A | 337 | −42.609 | 10.297 | −14.699 | 1 | 29.43 | A |
| ATOM | 3555 | CD  | LYS | A | 337 | −42.066 | 11.04  | −15.899 | 1 | 33.81 | A |
| ATOM | 3556 | CE  | LYS | A | 337 | −43.023 | 10.958 | −17.089 | 1 | 35.15 | A |
| ATOM | 3557 | NZ  | LYS | A | 337 | −43.267 | 9.565  | −17.559 | 1 | 37.12 | A |
| ATOM | 3558 | C   | LYS | A | 337 | −42.267 | 8.278  | −12.386 | 1 | 26.22 | A |
| ATOM | 3559 | O   | LYS | A | 337 | −41.23  | 7.616  | −12.326 | 1 | 26.98 | A |
| ATOM | 3560 | N   | VAL | A | 338 | −43.455 | 7.736  | −12.615 | 1 | 24.74 | A |
| ATOM | 3561 | CA  | VAL | A | 338 | −43.6   | 6.305  | −12.811 | 1 | 25.92 | A |
| ATOM | 3562 | CB  | VAL | A | 338 | −45.054 | 5.853  | −12.61  | 1 | 23.67 | A |
| ATOM | 3563 | CG1 | VAL | A | 338 | −45.15  | 4.35   | −12.809 | 1 | 21.73 | A |
| ATOM | 3564 | CG2 | VAL | A | 338 | −45.538 | 6.245  | −11.224 | 1 | 22.91 | A |
| ATOM | 3565 | C   | VAL | A | 338 | −43.175 | 5.883  | −14.211 | 1 | 28.97 | A |
| ATOM | 3566 | O   | VAL | A | 338 | −43.677 | 6.402  | −15.207 | 1 | 31.92 | A |
| ATOM | 3567 | N   | PRO | A | 339 | −42.239 | 4.934  | −14.308 | 1 | 29.43 | A |
| ATOM | 3568 | CD  | PRO | A | 339 | −41.476 | 4.266  | −13.247 | 1 | 28.71 | A |
| ATOM | 3569 | CA  | PRO | A | 339 | −41.798 | 4.485  | −15.629 | 1 | 28.09 | A |
| ATOM | 3570 | CB  | PRO | A | 339 | −40.401 | 3.914  | −15.37  | 1 | 29.28 | A |
| ATOM | 3571 | CG  | PRO | A | 339 | −40.132 | 4.154  | −13.877 | 1 | 30.81 | A |
| ATOM | 3572 | C   | PRO | A | 339 | −42.765 | 3.405  | −16.099 | 1 | 28.41 | A |
| ATOM | 3573 | O   | PRO | A | 339 | −42.564 | 2.224  | −15.851 | 1 | 31.68 | A |
| ATOM | 3574 | N   | ILE | A | 340 | −43.834 | 3.802  | −16.759 | 1 | 31.06 | A |
| ATOM | 3575 | CA  | ILE | A | 340 | −44.787 | 2.814  | −17.232 | 1 | 29.83 | A |
| ATOM | 3576 | CB  | ILE | A | 340 | −46.109 | 2.909  | −16.451 | 1 | 29.64 | A |
| ATOM | 3577 | CG2 | ILE | A | 340 | −46.702 | 4.303  | −16.599 | 1 | 25.21 | A |
| ATOM | 3578 | CG1 | ILE | A | 340 | −47.076 | 1.834  | −16.942 | 1 | 29.06 | A |
| ATOM | 3579 | CD1 | ILE | A | 340 | −48.242 | 1.61   | −16.014 | 1 | 31.37 | A |
| ATOM | 3580 | C   | ILE | A | 340 | −45.047 | 3.012  | −18.712 | 1 | 29.28 | A |
| ATOM | 3581 | O   | ILE | A | 340 | −44.963 | 4.124  | −19.224 | 1 | 28.22 | A |
| ATOM | 3582 | N   | SER | A | 341 | −45.348 | 1.928  | −19.408 | 1 | 31.18 | A |
| ATOM | 3583 | CA  | SER | A | 341 | −45.613 | 2.037  | −20.831 | 1 | 33.15 | A |
| ATOM | 3584 | CB  | SER | A | 341 | −44.308 | 2.294  | −21.59  | 1 | 31.89 | A |
| ATOM | 3585 | OG  | SER | A | 341 | −43.348 | 1.306  | −21.28  | 1 | 35.88 | A |
| ATOM | 3586 | C   | SER | A | 341 | −46.302 | 0.815  | −21.397 | 1 | 31.64 | A |
| ATOM | 3587 | O   | SER | A | 341 | −46.187 | −0.287 | −20.862 | 1 | 32.31 | A |
| ATOM | 3588 | N   | SER | A | 342 | −47.044 | 1.035  | −22.475 | 1 | 33.03 | A |
| ATOM | 3589 | CA  | SER | A | 342 | −47.753 | −0.032 | −23.161 | 1 | 33.02 | A |
| ATOM | 3590 | CB  | SER | A | 342 | −49.163 | 0.42   | −23.541 | 1 | 31.92 | A |
| ATOM | 3591 | OG  | SER | A | 342 | −49.852 | −0.621 | −24.209 | 1 | 35.86 | A |
| ATOM | 3592 | C   | SER | A | 342 | −46.949 | −0.326 | −24.415 | 1 | 30.7  | A |
| ATOM | 3593 | O   | SER | A | 342 | −46.897 | 0.495  | −25.327 | 1 | 30.77 | A |
| ATOM | 3594 | N   | VAL | A | 343 | −46.303 | −1.484 | −24.443 | 1 | 29.8  | A |
| ATOM | 3595 | CA  | VAL | A | 343 | −45.489 | −1.874 | −25.586 | 1 | 30.71 | A |
| ATOM | 3596 | CB  | VAL | A | 343 | −44.032 | −2.174 | −25.171 | 1 | 30.39 | A |
| ATOM | 3597 | CG1 | VAL | A | 343 | −43.351 | −0.896 | −24.721 | 1 | 29.77 | A |
| ATOM | 3598 | CG2 | VAL | A | 343 | −44.011 | −3.207 | −24.049 | 1 | 27.81 | A |
| ATOM | 3599 | C   | VAL | A | 343 | −46.069 | −3.113 | −26.242 | 1 | 32.98 | A |
| ATOM | 3600 | O   | VAL | A | 343 | −46.802 | −3.876 | −25.604 | 1 | 31.51 | A |
| ATOM | 3601 | N   | ALA | A | 344 | −45.728 | −3.302 | −27.516 | 1 | 34.7  | A |
| ATOM | 3602 | CA  | ALA | A | 344 | −46.205 | −4.433 | −28.309 | 1 | 34.73 | A |
| ATOM | 3603 | CB  | ALA | A | 344 | −45.917 | −4.185 | −29.78  | 1 | 35.9  | A |
| ATOM | 3604 | C   | ALA | A | 344 | −45.577 | −5.75  | −27.874 | 1 | 35.91 | A |
| ATOM | 3605 | O   | ALA | A | 344 | −46.278 | −6.74  | −27.647 | 1 | 36.55 | A |
| ATOM | 3606 | N   | SER | A | 345 | −44.253 | −5.766 | −27.773 | 1 | 36.97 | A |
| ATOM | 3607 | CA  | SER | A | 345 | −43.546 | −6.968 | −27.353 | 1 | 39.5  | A |

TABLE 7-continued

| ATOM | 3608 | CB | SER | A | 345 | −42.877 | −7.666 | −28.542 | 1 | 39.64 | A |
| ATOM | 3609 | OG | SER | A | 345 | −41.551 | −7.196 | −28.723 | 1 | 38.31 | A |
| ATOM | 3610 | C | SER | A | 345 | −42.474 | −6.586 | −26.355 | 1 | 40.17 | A |
| ATOM | 3611 | O | SER | A | 345 | −42.085 | −5.42 | −26.265 | 1 | 38.89 | A |
| ATOM | 3612 | N | LEU | A | 346 | −41.996 | −7.579 | −25.612 | 1 | 41.76 | A |
| ATOM | 3613 | CA | LEU | A | 346 | −40.953 | −7.354 | −24.626 | 1 | 41.78 | A |
| ATOM | 3614 | CB | LEU | A | 346 | −40.908 | −8.521 | −23.635 | 1 | 39.71 | A |
| ATOM | 3615 | CG | LEU | A | 346 | −42.213 | −8.708 | −22.846 | 1 | 38.48 | A |
| ATOM | 3616 | CD1 | LEU | A | 346 | −42.133 | −9.934 | −21.952 | 1 | 34.83 | A |
| ATOM | 3617 | CD2 | LEU | A | 346 | −42.476 | −7.456 | −22.013 | 1 | 39.33 | A |
| ATOM | 3618 | C | LEU | A | 346 | −39.627 | −7.207 | −25.367 | 1 | 43.43 | A |
| ATOM | 3619 | O | LEU | A | 346 | −38.633 | −6.752 | −24.797 | 1 | 43.91 | A |
| ATOM | 3620 | N | ASN | A | 347 | −39.632 | −7.578 | −26.648 | 1 | 44.47 | A |
| ATOM | 3621 | CA | ASN | A | 347 | −38.441 | −7.48 | −27.49 | 1 | 45.37 | A |
| ATOM | 3622 | CB | ASN | A | 347 | −38.566 | −8.39 | −28.712 | 1 | 47.28 | A |
| ATOM | 3623 | CG | ASN | A | 347 | −38.732 | −9.85 | −28.335 | 1 | 49.37 | A |
| ATOM | 3624 | OD1 | ASN | A | 347 | −37.948 | −10.39 | −27.547 | 1 | 49.47 | A |
| ATOM | 3625 | ND2 | ASN | A | 347 | −39.752 | −10.5 | −28.9 | 1 | 46.9 | A |
| ATOM | 3626 | C | ASN | A | 347 | −38.234 | −6.04 | −27.942 | 1 | 44.98 | A |
| ATOM | 3627 | O | ASN | A | 347 | −37.175 | −5.685 | −28.455 | 1 | 43.46 | A |
| ATOM | 3628 | N | ASP | A | 348 | −39.26 | −5.218 | −27.755 | 1 | 45.11 | A |
| ATOM | 3629 | CA | ASP | A | 348 | −39.178 | −3.808 | −28.106 | 1 | 45.32 | A |
| ATOM | 3630 | CB | ASP | A | 348 | −39.664 | −3.56 | −29.535 | 1 | 47.04 | A |
| ATOM | 3631 | CG | ASP | A | 348 | −39.317 | −2.162 | −30.031 | 1 | 48.74 | A |
| ATOM | 3632 | OD1 | ASP | A | 348 | −39.557 | −1.187 | −29.29 | 1 | 48.07 | A |
| ATOM | 3633 | OD2 | ASP | A | 348 | −38.805 | −2.036 | −31.163 | 1 | 50 | A |
| ATOM | 3634 | C | ASP | A | 348 | −40.033 | −3.011 | −27.131 | 1 | 43.92 | A |
| ATOM | 3635 | O | ASP | A | 348 | −41.255 | −3.157 | −27.097 | 1 | 44.23 | A |
| ATOM | 3636 | N | LEU | A | 349 | −39.382 | −2.17 | −26.337 | 1 | 42.36 | A |
| ATOM | 3637 | CA | LEU | A | 349 | −40.081 | −1.358 | −25.351 | 1 | 41.12 | A |
| ATOM | 3638 | CB | LEU | A | 349 | −39.19 | −1.157 | −24.125 | 1 | 40.88 | A |
| ATOM | 3639 | CG | LEU | A | 349 | −39.106 | −2.307 | −23.114 | 1 | 39.94 | A |
| ATOM | 3640 | CD1 | LEU | A | 349 | −39.349 | −3.64 | −23.787 | 1 | 39.93 | A |
| ATOM | 3641 | CD2 | LEU | A | 349 | −37.749 | −2.271 | −22.439 | 1 | 37.85 | A |
| ATOM | 3642 | C | LEU | A | 349 | −40.541 | −0.007 | −25.888 | 1 | 40.26 | A |
| ATOM | 3643 | O | LEU | A | 349 | −40.815 | 0.911 | −25.114 | 1 | 42.06 | A |
| ATOM | 3644 | N | THR | A | 350 | −40.62 | 0.118 | −27.21 | 1 | 37.42 | A |
| ATOM | 3645 | CA | THR | A | 350 | −41.077 | 1.358 | −27.817 | 1 | 34.7 | A |
| ATOM | 3646 | CB | THR | A | 350 | −40.907 | 1.344 | −29.345 | 1 | 35.8 | A |
| ATOM | 3647 | OG1 | THR | A | 350 | −39.513 | 1.307 | −29.662 | 1 | 36.6 | A |
| ATOM | 3648 | CG2 | THR | A | 350 | −41.539 | 2.588 | −29.976 | 1 | 33.32 | A |
| ATOM | 3649 | C | THR | A | 350 | −42.557 | 1.505 | −27.485 | 1 | 34.44 | A |
| ATOM | 3650 | O | THR | A | 350 | −43.393 | 0.69 | −27.892 | 1 | 34.12 | A |
| ATOM | 3651 | N | PRO | A | 351 | −42.898 | 2.551 | −26.73 | 1 | 31.71 | A |
| ATOM | 3652 | CD | PRO | A | 351 | −42.005 | 3.605 | −26.226 | 1 | 28.37 | A |
| ATOM | 3653 | CA | PRO | A | 351 | −44.284 | 2.8 | −26.339 | 1 | 32.32 | A |
| ATOM | 3654 | CB | PRO | A | 351 | −44.195 | 4.133 | −25.606 | 1 | 33.14 | A |
| ATOM | 3655 | CG | PRO | A | 351 | −42.786 | 4.129 | −25.064 | 1 | 32.98 | A |
| ATOM | 3656 | C | PRO | A | 351 | −45.195 | 2.87 | −27.555 | 1 | 31.96 | A |
| ATOM | 3657 | O | PRO | A | 351 | −45.024 | 3.732 | −28.41 | 1 | 33.24 | A |
| ATOM | 3658 | N | VAL | A | 352 | −46.156 | 1.957 | −27.63 | 1 | 33.11 | A |
| ATOM | 3659 | CA | VAL | A | 352 | −47.096 | 1.923 | −28.744 | 1 | 34.44 | A |
| ATOM | 3660 | CB | VAL | A | 352 | −47.109 | 0.551 | −29.416 | 1 | 33.1 | A |
| ATOM | 3661 | CG1 | VAL | A | 352 | −45.734 | 0.244 | −29.97 | 1 | 35.53 | A |
| ATOM | 3662 | CG2 | VAL | A | 352 | −47.539 | −0.514 | −28.418 | 1 | 31.6 | A |
| ATOM | 3663 | C | VAL | A | 352 | −48.512 | 2.254 | −28.28 | 1 | 38.04 | A |
| ATOM | 3664 | O | VAL | A | 352 | −49.339 | 2.726 | −29.068 | 1 | 38.22 | A |
| ATOM | 3665 | N | GLY | A | 353 | −48.783 | 1.992 | −27.001 | 1 | 38.58 | A |
| ATOM | 3666 | CA | GLY | A | 353 | −50.085 | 2.287 | −26.435 | 1 | 37.9 | A |
| ATOM | 3667 | C | GLY | A | 353 | −49.988 | 3.677 | −25.847 | 1 | 39.58 | A |
| ATOM | 3668 | O | GLY | A | 353 | −48.937 | 4.31 | −25.951 | 1 | 39.86 | A |
| ATOM | 3669 | N | ARG | A | 354 | −51.055 | 4.168 | −25.228 | 1 | 40.79 | A |
| ATOM | 3670 | CA | ARG | A | 354 | −50.993 | 5.507 | −24.654 | 1 | 41.01 | A |
| ATOM | 3671 | CB | ARG | A | 354 | −51.695 | 6.527 | −25.563 | 1 | 42.06 | A |
| ATOM | 3672 | CG | ARG | A | 354 | −53.174 | 6.744 | −25.258 | 1 | 42.39 | A |
| ATOM | 3673 | CD | ARG | A | 354 | −53.632 | 8.126 | −25.718 | 1 | 44.11 | A |
| ATOM | 3674 | NE | ARG | A | 354 | −54.889 | 8.54 | −25.093 | 1 | 45.39 | A |
| ATOM | 3675 | CZ | ARG | A | 354 | −56.06 | 7.939 | −25.284 | 1 | 44.49 | A |
| ATOM | 3676 | NH1 | ARG | A | 354 | −56.139 | 6.892 | −26.091 | 1 | 42.28 | A |
| ATOM | 3677 | NH2 | ARG | A | 354 | −57.149 | 8.38 | −24.663 | 1 | 42.53 | A |
| ATOM | 3678 | C | ARG | A | 354 | −51.589 | 5.594 | −23.261 | 1 | 39.67 | A |
| ATOM | 3679 | O | ARG | A | 354 | −52.609 | 4.971 | −22.957 | 1 | 41.21 | A |
| ATOM | 3680 | N | LEU | A | 355 | −50.94 | 6.375 | −22.412 | 1 | 37.85 | A |
| ATOM | 3681 | CA | LEU | A | 355 | −51.418 | 6.563 | −21.059 | 1 | 37.76 | A |
| ATOM | 3682 | CB | LEU | A | 355 | −50.31 | 7.14 | −20.182 | 1 | 38.27 | A |
| ATOM | 3683 | CG | LEU | A | 355 | −49.547 | 6.159 | −19.3 | 1 | 39.1 | A |
| ATOM | 3684 | CD1 | LEU | A | 355 | −48.999 | 5.004 | −20.119 | 1 | 38.6 | A |
| ATOM | 3685 | CD2 | LEU | A | 355 | −48.434 | 6.92 | −18.613 | 1 | 41.05 | A |
| ATOM | 3686 | C | LEU | A | 355 | −52.596 | 7.517 | −21.064 | 1 | 36.81 | A |

TABLE 7-continued

| ATOM | 3687 | O | LEU | A | 355 | −52.565 | 8.556 | −21.726 | 1 | 36.66 | A |
| --- | --- | --- | --- | --- | --- | --- | --- | --- | --- | --- | --- |
| ATOM | 3688 | N | VAL | A | 356 | −53.644 | 7.158 | −20.334 | 1 | 35.43 | A |
| ATOM | 3689 | CA | VAL | A | 356 | −54.808 | 8.022 | −20.241 | 1 | 34.17 | A |
| ATOM | 3690 | CB | VAL | A | 356 | −56.114 | 7.218 | −20.067 | 1 | 33.95 | A |
| ATOM | 3691 | CG1 | VAL | A | 356 | −57.289 | 8.162 | −19.919 | 1 | 31.08 | A |
| ATOM | 3692 | CG2 | VAL | A | 356 | −56.326 | 6.324 | −21.265 | 1 | 30.39 | A |
| ATOM | 3693 | C | VAL | A | 356 | −54.586 | 8.897 | −19.021 | 1 | 34.44 | A |
| ATOM | 3694 | O | VAL | A | 356 | −54.969 | 10.062 | −19.004 | 1 | 33.61 | A |
| ATOM | 3695 | N | THR | A | 357 | −53.954 | 8.327 | −17.998 | 1 | 37.29 | A |
| ATOM | 3696 | CA | THR | A | 357 | −53.673 | 9.073 | −16.782 | 1 | 38.92 | A |
| ATOM | 3697 | CB | THR | A | 357 | −53.289 | 8.154 | −15.62 | 1 | 38.58 | A |
| ATOM | 3698 | OG1 | THR | A | 357 | −54.405 | 7.327 | −15.274 | 1 | 41.65 | A |
| ATOM | 3699 | CG2 | THR | A | 357 | −52.885 | 8.979 | −14.423 | 1 | 38.85 | A |
| ATOM | 3700 | C | THR | A | 357 | −52.51 | 10.005 | −17.065 | 1 | 40.94 | A |
| ATOM | 3701 | O | THR | A | 357 | −51.476 | 9.582 | −17.586 | 1 | 41.19 | A |
| ATOM | 3702 | N | VAL | A | 358 | −52.683 | 11.274 | −16.717 | 1 | 42.51 | A |
| ATOM | 3703 | CA | VAL | A | 358 | −51.656 | 12.275 | −16.951 | 1 | 44.51 | A |
| ATOM | 3704 | CB | VAL | A | 358 | −52.221 | 13.695 | −16.749 | 1 | 45.68 | A |
| ATOM | 3705 | CG1 | VAL | A | 358 | −51.084 | 14.698 | −16.685 | 1 | 44.38 | A |
| ATOM | 3706 | CG2 | VAL | A | 358 | −53.157 | 14.044 | −17.888 | 1 | 44.87 | A |
| ATOM | 3707 | C | VAL | A | 358 | −50.42 | 12.116 | −16.083 | 1 | 45.45 | A |
| ATOM | 3708 | O | VAL | A | 358 | −50.516 | 12.061 | −14.857 | 1 | 44.9 | A |
| ATOM | 3709 | N | ASN | A | 359 | −49.27 | 12.037 | −16.75 | 1 | 46.22 | A |
| ATOM | 3710 | CA | ASN | A | 359 | −47.964 | 11.908 | −16.111 | 1 | 44.58 | A |
| ATOM | 3711 | CB | ASN | A | 359 | −47.361 | 13.3 | −15.901 | 1 | 47.65 | A |
| ATOM | 3712 | CG | ASN | A | 359 | −45.855 | 13.278 | −15.824 | 1 | 49.05 | A |
| ATOM | 3713 | OD1 | ASN | A | 359 | −45.249 | 12.245 | −15.534 | 1 | 51.83 | A |
| ATOM | 3714 | ND2 | ASN | A | 359 | −45.236 | 14.423 | −16.091 | 1 | 49.2 | A |
| ATOM | 3715 | C | ASN | A | 359 | −48.017 | 11.183 | −14.767 | 1 | 40.66 | A |
| ATOM | 3716 | O | ASN | A | 359 | −47.926 | 11.8 | −13.711 | 1 | 40.16 | A |
| ATOM | 3717 | N | PRO | A | 360 | −48.182 | 9.863 | −14.791 | 1 | 38.08 | A |
| ATOM | 3718 | CD | PRO | A | 360 | −48.403 | 9.047 | −15.996 | 1 | 38.73 | A |
| ATOM | 3719 | CA | PRO | A | 360 | −48.246 | 9.047 | −13.57 | 1 | 37 | A |
| ATOM | 3720 | CB | PRO | A | 360 | −48.152 | 7.628 | −14.116 | 1 | 38.4 | A |
| ATOM | 3721 | CG | PRO | A | 360 | −48.919 | 7.738 | −15.401 | 1 | 40.41 | A |
| ATOM | 3722 | C | PRO | A | 360 | −47.1 | 9.38 | −12.611 | 1 | 34.63 | A |
| ATOM | 3723 | O | PRO | A | 360 | −45.943 | 9.41 | −13.032 | 1 | 33.21 | A |
| ATOM | 3724 | N | PHE | A | 361 | −47.425 | 9.615 | −11.338 | 1 | 30.6 | A |
| ATOM | 3725 | CA | PHE | A | 361 | −46.427 | 9.97 | −10.328 | 1 | 27.99 | A |
| ATOM | 3726 | CB | PHE | A | 361 | −46.363 | 11.483 | −10.142 | 1 | 27.19 | A |
| ATOM | 3727 | CG | PHE | A | 361 | −45.181 | 12.128 | −10.78 | 1 | 29.31 | A |
| ATOM | 3728 | CD1 | PHE | A | 361 | −45.116 | 12.272 | −12.161 | 1 | 28.76 | A |
| ATOM | 3729 | CD2 | PHE | A | 361 | −44.138 | 12.624 | −9.996 | 1 | 27.22 | A |
| ATOM | 3730 | CE1 | PHE | A | 361 | −44.03 | 12.905 | −12.761 | 1 | 28.47 | A |
| ATOM | 3731 | CE2 | PHE | A | 361 | −43.053 | 13.255 | −10.58 | 1 | 28.43 | A |
| ATOM | 3732 | CZ | PHE | A | 361 | −42.998 | 13.399 | −11.975 | 1 | 30.74 | A |
| ATOM | 3733 | C | PHE | A | 361 | −46.675 | 9.41 | −8.945 | 1 | 26.82 | A |
| ATOM | 3734 | O | PHE | A | 361 | −47.815 | 9.177 | −8.554 | 1 | 29.07 | A |
| ATOM | 3735 | N | VAL | A | 362 | −45.59 | 9.219 | −8.204 | 1 | 25.53 | A |
| ATOM | 3736 | CA | VAL | A | 362 | −45.68 | 8.802 | −6.819 | 1 | 23.92 | A |
| ATOM | 3737 | CB | VAL | A | 362 | −44.505 | 7.917 | −6.396 | 1 | 23.48 | A |
| ATOM | 3738 | CG1 | VAL | A | 362 | −44.552 | 7.687 | −4.908 | 1 | 20.87 | A |
| ATOM | 3739 | CG2 | VAL | A | 362 | −44.561 | 6.593 | −7.122 | 1 | 22.04 | A |
| ATOM | 3740 | C | VAL | A | 362 | −45.506 | 10.173 | −6.181 | 1 | 27.55 | A |
| ATOM | 3741 | O | VAL | A | 362 | −44.428 | 10.762 | −6.276 | 1 | 30.15 | A |
| ATOM | 3742 | N | SER | A | 363 | −46.556 | 10.692 | −5.553 | 1 | 28.86 | A |
| ATOM | 3743 | CA | SER | A | 363 | −46.483 | 12.016 | −4.944 | 1 | 29.59 | A |
| ATOM | 3744 | CB | SER | A | 363 | −47.87 | 12.636 | −4.828 | 1 | 28.72 | A |
| ATOM | 3745 | OG | SER | A | 363 | −48.283 | 13.163 | −6.077 | 1 | 36.53 | A |
| ATOM | 3746 | C | SER | A | 363 | −45.817 | 12.11 | −3.589 | 1 | 28.95 | A |
| ATOM | 3747 | O | SER | A | 363 | −45.652 | 13.21 | −3.055 | 1 | 29.26 | A |
| ATOM | 3748 | N | VAL | A | 364 | −45.419 | 10.976 | −3.032 | 1 | 26.75 | A |
| ATOM | 3749 | CA | VAL | A | 364 | −44.802 | 10.989 | −1.716 | 1 | 25.13 | A |
| ATOM | 3750 | CB | VAL | A | 364 | −45.66 | 10.186 | −0.704 | 1 | 25.5 | A |
| ATOM | 3751 | CG1 | VAL | A | 364 | −47.02 | 10.858 | −0.53 | 1 | 19.64 | A |
| ATOM | 3752 | CG2 | VAL | A | 364 | −45.827 | 8.743 | −1.194 | 1 | 21.22 | A |
| ATOM | 3753 | C | VAL | A | 364 | −43.386 | 10.441 | −1.69 | 1 | 23.92 | A |
| ATOM | 3754 | O | VAL | A | 364 | −42.919 | 9.839 | −2.651 | 1 | 22.44 | A |
| ATOM | 3755 | N | ALA | A | 365 | −42.711 | 10.672 | −0.57 | 1 | 23.86 | A |
| ATOM | 3756 | CA | ALA | A | 365 | −41.354 | 10.196 | −0.356 | 1 | 23.99 | A |
| ATOM | 3757 | CB | ALA | A | 365 | −40.453 | 11.342 | 0.073 | 1 | 22.69 | A |
| ATOM | 3758 | C | ALA | A | 365 | −41.419 | 9.122 | 0.734 | 1 | 24.52 | A |
| ATOM | 3759 | O | ALA | A | 365 | −40.444 | 8.866 | 1.443 | 1 | 26.51 | A |
| ATOM | 3760 | N | THR | A | 366 | −42.596 | 8.517 | 0.869 | 1 | 22.35 | A |
| ATOM | 3761 | CA | THR | A | 366 | −42.816 | 7.445 | 1.832 | 1 | 22.12 | A |
| ATOM | 3762 | CB | THR | A | 366 | −43.972 | 7.768 | 2.807 | 1 | 19.47 | A |
| ATOM | 3763 | OG1 | THR | A | 366 | −45.131 | 8.168 | 2.064 | 1 | 20.17 | A |
| ATOM | 3764 | CG2 | THR | A | 366 | −43.563 | 8.888 | 3.758 | 1 | 16.23 | A |
| ATOM | 3765 | C | THR | A | 366 | −43.171 | 6.225 | 1.003 | 1 | 21.03 | A |

TABLE 7-continued

| | | | | | | | | | | |
|---|---|---|---|---|---|---|---|---|---|---|
| ATOM | 3766 | O | THR | A | 366 | −43.815 | 6.345 | −0.034 | 1 | 23.24 | A |
| ATOM | 3767 | N | ALA | A | 367 | −42.747 | 5.054 | 1.453 | 1 | 21.27 | A |
| ATOM | 3768 | CA | ALA | A | 367 | −42.997 | 3.819 | 0.723 | 1 | 18.86 | A |
| ATOM | 3769 | CB | ALA | A | 367 | −42.026 | 2.753 | 1.195 | 1 | 16.21 | A |
| ATOM | 3770 | C | ALA | A | 367 | −44.432 | 3.309 | 0.836 | 1 | 19.31 | A |
| ATOM | 3771 | O | ALA | A | 367 | −45.23 | 3.793 | 1.642 | 1 | 20.14 | A |
| ATOM | 3772 | N | ASN | A | 368 | −44.75 | 2.323 | 0.009 | 1 | 19.42 | A |
| ATOM | 3773 | CA | ASN | A | 368 | −46.074 | 1.717 | −0.01 | 1 | 20.52 | A |
| ATOM | 3774 | CB | ASN | A | 368 | −46.516 | 1.354 | 1.408 | 1 | 19.96 | A |
| ATOM | 3775 | CG | ASN | A | 368 | −47.391 | 0.121 | 1.449 | 1 | 21.32 | A |
| ATOM | 3776 | OD1 | ASN | A | 368 | −48.13 | −0.1 | 2.408 | 1 | 23.07 | A |
| ATOM | 3777 | ND2 | ASN | A | 368 | −47.296 | −0.704 | 0.42 | 1 | 23.7 | A |
| ATOM | 3778 | C | ASN | A | 368 | −47.1 | 2.656 | −0.633 | 1 | 21.13 | A |
| ATOM | 3779 | O | ASN | A | 368 | −48.298 | 2.507 | −0.407 | 1 | 20.51 | A |
| ATOM | 3780 | N | ALA | A | 369 | −46.633 | 3.637 | −1.397 | 1 | 20.86 | A |
| ATOM | 3781 | CA | ALA | A | 369 | −47.558 | 4.562 | −2.038 | 1 | 26 | A |
| ATOM | 3782 | CB | ALA | A | 369 | −46.814 | 5.781 | −2.554 | 1 | 22.33 | A |
| ATOM | 3783 | C | ALA | A | 369 | −48.238 | 3.824 | −3.19 | 1 | 29.49 | A |
| ATOM | 3784 | O | ALA | A | 369 | −47.588 | 3.079 | −3.929 | 1 | 26.52 | A |
| ATOM | 3785 | N | LYS | A | 370 | −49.547 | 4.002 | −3.33 | 1 | 32.68 | A |
| ATOM | 3786 | CA | LYS | A | 370 | −50.252 | 3.332 | −4.413 | 1 | 37.07 | A |
| ATOM | 3787 | CB | LYS | A | 370 | −51.459 | 2.542 | −3.887 | 1 | 41.85 | A |
| ATOM | 3788 | CG | LYS | A | 370 | −52.639 | 3.387 | −3.43 | 1 | 48.33 | A |
| ATOM | 3789 | CD | LYS | A | 370 | −53.853 | 2.508 | −3.138 | 1 | 49.69 | A |
| ATOM | 3790 | CE | LYS | A | 370 | −55.111 | 3.341 | −2.869 | 1 | 51.84 | A |
| ATOM | 3791 | NZ | LYS | A | 370 | −56.333 | 2.481 | −2.777 | 1 | 50.27 | A |
| ATOM | 3792 | C | LYS | A | 370 | −50.692 | 4.353 | −5.452 | 1 | 36.03 | A |
| ATOM | 3793 | O | LYS | A | 370 | −51.118 | 5.457 | −5.116 | 1 | 33.89 | A |
| ATOM | 3794 | N | VAL | A | 371 | −50.567 | 3.973 | −6.718 | 1 | 36.96 | A |
| ATOM | 3795 | CA | VAL | A | 371 | −50.928 | 4.85 | −7.821 | 1 | 37.16 | A |
| ATOM | 3796 | CB | VAL | A | 371 | −49.671 | 5.308 | −8.586 | 1 | 37.16 | A |
| ATOM | 3797 | CG1 | VAL | A | 371 | −48.714 | 6.004 | −7.637 | 1 | 38.71 | A |
| ATOM | 3798 | CG2 | VAL | A | 371 | −48.985 | 4.116 | −9.211 | 1 | 39.91 | A |
| ATOM | 3799 | C | VAL | A | 371 | −51.887 | 4.166 | −8.792 | 1 | 36.22 | A |
| ATOM | 3800 | O | VAL | A | 371 | −51.748 | 2.981 | −9.107 | 1 | 35.25 | A |
| ATOM | 3801 | N | LEU | A | 372 | −52.857 | 4.934 | −9.266 | 1 | 36.24 | A |
| ATOM | 3802 | CA | LEU | A | 372 | −53.864 | 4.44 | −10.191 | 1 | 35.38 | A |
| ATOM | 3803 | CB | LEU | A | 372 | −55.228 | 4.988 | −9.77 | 1 | 36.5 | A |
| ATOM | 3804 | CG | LEU | A | 372 | −56.509 | 4.437 | −10.394 | 1 | 38.49 | A |
| ATOM | 3805 | CD1 | LEU | A | 372 | −56.58 | 2.931 | −10.204 | 1 | 39.04 | A |
| ATOM | 3806 | CD2 | LEU | A | 372 | −57.707 | 5.116 | −9.733 | 1 | 39.15 | A |
| ATOM | 3807 | C | LEU | A | 372 | −53.505 | 4.907 | −11.599 | 1 | 35.09 | A |
| ATOM | 3808 | O | LEU | A | 372 | −53.188 | 6.076 | −11.804 | 1 | 34.83 | A |
| ATOM | 3809 | N | ILE | A | 373 | −53.559 | 3.993 | −12.564 | 1 | 36.15 | A |
| ATOM | 3810 | CA | ILE | A | 373 | −53.225 | 4.31 | −13.951 | 1 | 34.51 | A |
| ATOM | 3811 | CB | ILE | A | 373 | −51.825 | 3.75 | −14.333 | 1 | 36.37 | A |
| ATOM | 3812 | CG2 | ILE | A | 373 | −51.406 | 4.284 | −15.696 | 1 | 35.11 | A |
| ATOM | 3813 | CG1 | ILE | A | 373 | −50.777 | 4.116 | −13.276 | 1 | 35.27 | A |
| ATOM | 3814 | CD1 | ILE | A | 373 | −50.495 | 5.582 | −13.173 | 1 | 34.41 | A |
| ATOM | 3815 | C | ILE | A | 373 | −54.222 | 3.73 | −14.957 | 1 | 34.65 | A |
| ATOM | 3816 | O | ILE | A | 373 | −54.636 | 2.582 | −14.849 | 1 | 33.98 | A |
| ATOM | 3817 | N | GLU | A | 374 | −54.597 | 4.54 | −15.938 | 1 | 37.03 | A |
| ATOM | 3818 | CA | GLU | A | 374 | −55.502 | 4.106 | −16.996 | 1 | 37.04 | A |
| ATOM | 3819 | CB | GLU | A | 374 | −56.758 | 4.998 | −17.026 | 1 | 37.83 | A |
| ATOM | 3820 | CG | GLU | A | 374 | −57.735 | 4.689 | −18.156 | 1 | 39.7 | A |
| ATOM | 3821 | CD | GLU | A | 374 | −59.08 | 5.397 | −18.006 | 1 | 41.38 | A |
| ATOM | 3822 | OE1 | GLU | A | 374 | −59.111 | 6.524 | −17.47 | 1 | 44.84 | A |
| ATOM | 3823 | OE2 | GLU | A | 374 | −60.11 | 4.832 | −18.437 | 1 | 40.46 | A |
| ATOM | 3824 | C | GLU | A | 374 | −54.71 | 4.202 | −18.308 | 1 | 35.72 | A |
| ATOM | 3825 | O | GLU | A | 374 | −54.08 | 5.222 | −18.583 | 1 | 31.75 | A |
| ATOM | 3826 | N | LEU | A | 375 | −54.719 | 3.123 | −19.089 | 1 | 37.32 | A |
| ATOM | 3827 | CA | LEU | A | 375 | −53.996 | 3.072 | −20.366 | 1 | 38.65 | A |
| ATOM | 3828 | CB | LEU | A | 375 | −52.814 | 2.091 | −20.322 | 1 | 37.96 | A |
| ATOM | 3829 | CG | LEU | A | 375 | −51.592 | 2.178 | −19.427 | 1 | 38.6 | A |
| ATOM | 3830 | CD1 | LEU | A | 375 | −51.971 | 1.97 | −17.971 | 1 | 40.96 | A |
| ATOM | 3831 | CD2 | LEU | A | 375 | −50.624 | 1.09 | −19.87 | 1 | 36.52 | A |
| ATOM | 3832 | C | LEU | A | 375 | −54.847 | 2.608 | −21.541 | 1 | 38.38 | A |
| ATOM | 3833 | O | LEU | A | 375 | −55.836 | 1.88 | −21.384 | 1 | 37 | A |
| ATOM | 3834 | N | GLU | A | 376 | −54.425 | 3.02 | −22.729 | 1 | 39.47 | A |
| ATOM | 3835 | CA | GLU | A | 376 | −55.077 | 2.594 | −23.958 | 1 | 43.74 | A |
| ATOM | 3836 | CB | GLU | A | 376 | −55.513 | 3.786 | −24.817 | 1 | 46.07 | A |
| ATOM | 3837 | CG | GLU | A | 376 | −56.041 | 3.366 | −26.195 | 1 | 51.12 | A |
| ATOM | 3838 | CD | GLU | A | 376 | −56.707 | 4.503 | −26.941 | 1 | 53.35 | A |
| ATOM | 3839 | OE1 | GLU | A | 376 | −57.76 | 4.97 | −26.459 | 1 | 55.13 | A |
| ATOM | 3840 | OE2 | GLU | A | 376 | −56.184 | 4.938 | −27.994 | 1 | 53.92 | A |
| ATOM | 3841 | C | GLU | A | 376 | −54.034 | 1.761 | −24.706 | 1 | 43.78 | A |
| ATOM | 3842 | O | GLU | A | 376 | −53.295 | 2.281 | −25.559 | 1 | 43.14 | A |
| ATOM | 3843 | N | PRO | A | 377 | −53.945 | 0.457 | −24.374 | 1 | 41.78 | A |
| ATOM | 3844 | CD | PRO | A | 377 | −54.792 | −0.297 | −23.43 | 1 | 40.55 | A |

TABLE 7-continued

| | | | | | | | | | | |
|---|---|---|---|---|---|---|---|---|---|---|
| ATOM | 3845 | CA | PRO | A | 377 | −52.983 | −0.435 | −25.022 | 1 | 40.61 | A |
| ATOM | 3846 | CB | PRO | A | 377 | −53.082 | −1.704 | −24.189 | 1 | 39.5 | A |
| ATOM | 3847 | CG | PRO | A | 377 | −54.523 | −1.742 | −23.833 | 1 | 40.14 | A |
| ATOM | 3848 | C | PRO | A | 377 | −53.403 | −0.673 | −26.463 | 1 | 40.85 | A |
| ATOM | 3849 | O | PRO | A | 377 | −54.575 | −0.496 | −26.811 | 1 | 40.53 | A |
| ATOM | 3850 | N | PRO | A | 378 | −52.454 | −1.055 | −27.33 | 1 | 40.26 | A |
| ATOM | 3851 | CD | PRO | A | 378 | −51.013 | −1.287 | −27.127 | 1 | 38.43 | A |
| ATOM | 3852 | CA | PRO | A | 378 | −52.833 | −1.299 | −28.723 | 1 | 39.63 | A |
| ATOM | 3853 | CB | PRO | A | 378 | −51.489 | −1.55 | −29.399 | 1 | 38.71 | A |
| ATOM | 3854 | CG | PRO | A | 378 | −50.67 | −2.161 | −28.302 | 1 | 37.56 | A |
| ATOM | 3855 | C | PRO | A | 378 | −53.78 | −2.5 | −28.823 | 1 | 39.1 | A |
| ATOM | 3856 | O | PRO | A | 378 | −54.044 | −3.178 | −27.829 | 1 | 40.34 | A |
| ATOM | 3857 | N | PHE | A | 379 | −54.307 | −2.754 | −30.012 | 1 | 38.56 | A |
| ATOM | 3858 | CA | PHE | A | 379 | −55.195 | −3.892 | −30.196 | 1 | 38.41 | A |
| ATOM | 3859 | CB | PHE | A | 379 | −56.082 | −3.676 | −31.42 | 1 | 37.4 | A |
| ATOM | 3860 | CG | PHE | A | 379 | −57.349 | −2.94 | −31.117 | 1 | 37.23 | A |
| ATOM | 3861 | CD1 | PHE | A | 379 | −58.406 | −3.585 | −30.477 | 1 | 36.17 | A |
| ATOM | 3862 | CD2 | PHE | A | 379 | −57.483 | −1.593 | −31.443 | 1 | 36.88 | A |
| ATOM | 3863 | CE1 | PHE | A | 379 | −59.577 | −2.9 | −30.166 | 1 | 33.86 | A |
| ATOM | 3864 | CE2 | PHE | A | 379 | −58.653 | −0.898 | −31.134 | 1 | 35.77 | A |
| ATOM | 3865 | CZ | PHE | A | 379 | −59.701 | −1.557 | −30.494 | 1 | 33.66 | A |
| ATOM | 3866 | C | PHE | A | 379 | −54.339 | −5.14 | −30.37 | 1 | 39.24 | A |
| ATOM | 3867 | O | PHE | A | 379 | −53.237 | −5.071 | −30.914 | 1 | 39.2 | A |
| ATOM | 3868 | N | GLY | A | 380 | −54.844 | −6.279 | −29.909 | 1 | 38.42 | A |
| ATOM | 3869 | CA | GLY | A | 380 | −54.078 | −7.501 | −30.017 | 1 | 37.47 | A |
| ATOM | 3870 | C | GLY | A | 380 | −53.242 | −7.674 | −28.765 | 1 | 38.09 | A |
| ATOM | 3871 | O | GLY | A | 380 | −53.705 | −7.375 | −27.666 | 1 | 39.96 | A |
| ATOM | 3872 | N | ASP | A | 381 | −52.009 | −8.141 | −28.921 | 1 | 37.08 | A |
| ATOM | 3873 | CA | ASP | A | 381 | −51.127 | −8.354 | −27.78 | 1 | 36.79 | A |
| ATOM | 3874 | CB | ASP | A | 381 | −50.24 | −9.573 | −28.028 | 1 | 38.65 | A |
| ATOM | 3875 | CG | ASP | A | 381 | −50.833 | −10.85 | −27.465 | 1 | 42.76 | A |
| ATOM | 3876 | OD1 | ASP | A | 381 | −52.079 | −10.967 | −27.421 | 1 | 43.71 | A |
| ATOM | 3877 | OD2 | ASP | A | 381 | −50.048 | −11.742 | −27.075 | 1 | 44.65 | A |
| ATOM | 3878 | C | ASP | A | 381 | −50.256 | −7.147 | −27.448 | 1 | 35.55 | A |
| ATOM | 3879 | O | ASP | A | 381 | −49.868 | −6.378 | −28.323 | 1 | 36.19 | A |
| ATOM | 3880 | N | SER | A | 382 | −49.959 | −6.992 | −26.166 | 1 | 31.97 | A |
| ATOM | 3881 | CA | SER | A | 382 | −49.138 | −5.898 | −25.689 | 1 | 29.45 | A |
| ATOM | 3882 | CB | SER | A | 382 | −49.901 | −4.572 | −25.776 | 1 | 28.32 | A |
| ATOM | 3883 | OG | SER | A | 382 | −50.866 | −4.465 | −24.739 | 1 | 25.09 | A |
| ATOM | 3884 | C | SER | A | 382 | −48.784 | −6.19 | −24.237 | 1 | 30.2 | A |
| ATOM | 3885 | O | SER | A | 382 | −49.327 | −7.109 | −23.623 | 1 | 28.41 | A |
| ATOM | 3886 | N | TYR | A | 383 | −47.873 | −5.403 | −23.686 | 1 | 30.32 | A |
| ATOM | 3887 | CA | TYR | A | 383 | −47.47 | −5.598 | −22.308 | 1 | 32.14 | A |
| ATOM | 3888 | CB | TYR | A | 383 | −46.064 | −6.203 | −22.237 | 1 | 33.07 | A |
| ATOM | 3889 | CG | TYR | A | 383 | −45.92 | −7.574 | −22.862 | 1 | 37.36 | A |
| ATOM | 3890 | CD1 | TYR | A | 383 | −46.291 | −8.731 | −22.17 | 1 | 38.95 | A |
| ATOM | 3891 | CE1 | TYR | A | 383 | −46.125 | −10.002 | −22.744 | 1 | 41.13 | A |
| ATOM | 3892 | CD2 | TYR | A | 383 | −45.389 | −7.716 | −24.14 | 1 | 39.47 | A |
| ATOM | 3893 | CE2 | TYR | A | 383 | −45.224 | −8.977 | −24.722 | 1 | 44.33 | A |
| ATOM | 3894 | CZ | TYR | A | 383 | −45.59 | −10.114 | −24.023 | 1 | 42.11 | A |
| ATOM | 3895 | OH | TYR | A | 383 | −45.415 | −11.347 | −24.619 | 1 | 42.76 | A |
| ATOM | 3896 | C | TYR | A | 383 | −47.464 | −4.262 | −21.596 | 1 | 31.89 | A |
| ATOM | 3897 | O | TYR | A | 383 | −47.199 | −3.22 | −22.207 | 1 | 31.24 | A |
| ATOM | 3898 | N | ILE | A | 384 | −47.785 | −4.301 | −20.307 | 1 | 30.93 | A |
| ATOM | 3899 | CA | ILE | A | 384 | −47.764 | −3.111 | −19.476 | 1 | 29.23 | A |
| ATOM | 3900 | CB | ILE | A | 384 | −48.92 | −3.088 | −18.465 | 1 | 28.41 | A |
| ATOM | 3901 | CG2 | ILE | A | 384 | −48.857 | −1.809 | −17.64 | 1 | 25.49 | A |
| ATOM | 3902 | CG1 | ILE | A | 384 | −50.256 | −3.181 | −19.199 | 1 | 27.33 | A |
| ATOM | 3903 | CD1 | ILE | A | 384 | −51.453 | −3.191 | −18.273 | 1 | 30.87 | A |
| ATOM | 3904 | C | ILE | A | 384 | −46.453 | −3.271 | −18.726 | 1 | 29.99 | A |
| ATOM | 3905 | O | ILE | A | 384 | −46.301 | −4.191 | −17.914 | 1 | 30.14 | A |
| ATOM | 3906 | N | VAL | A | 385 | −45.494 | −2.403 | −19.022 | 1 | 27.27 | A |
| ATOM | 3907 | CA | VAL | A | 385 | −44.204 | −2.491 | −18.374 | 1 | 25.77 | A |
| ATOM | 3908 | CB | VAL | A | 385 | −43.071 | −2.535 | −19.409 | 1 | 26.78 | A |
| ATOM | 3909 | CG1 | VAL | A | 385 | −41.71 | −2.513 | −18.701 | 1 | 24.17 | A |
| ATOM | 3910 | CG2 | VAL | A | 385 | −43.212 | −3.787 | −20.257 | 1 | 25.13 | A |
| ATOM | 3911 | C | VAL | A | 385 | −43.96 | −1.341 | −17.415 | 1 | 26.53 | A |
| ATOM | 3912 | O | VAL | A | 385 | −44.205 | −0.175 | −17.731 | 1 | 25.21 | A |
| ATOM | 3913 | N | VAL | A | 386 | −43.47 | −1.692 | −16.234 | 1 | 23.93 | A |
| ATOM | 3914 | CA | VAL | A | 386 | −43.18 | −0.71 | −15.214 | 1 | 22.01 | A |
| ATOM | 3915 | CB | VAL | A | 386 | −44.14 | −0.867 | −14.037 | 1 | 22.1 | A |
| ATOM | 3916 | CG1 | VAL | A | 386 | −43.914 | 0.242 | −13.026 | 1 | 14.98 | A |
| ATOM | 3917 | CG2 | VAL | A | 386 | −45.571 | −0.874 | −14.56 | 1 | 22.7 | A |
| ATOM | 3918 | C | VAL | A | 386 | −41.749 | −0.907 | −14.747 | 1 | 20.25 | A |
| ATOM | 3919 | O | VAL | A | 386 | −41.335 | −2.028 | −14.466 | 1 | 17.33 | A |
| ATOM | 3920 | N | GLY | A | 387 | −41 | 0.189 | −14.69 | 1 | 19.86 | A |
| ATOM | 3921 | CA | GLY | A | 387 | −39.617 | 0.131 | −14.264 | 1 | 24.46 | A |
| ATOM | 3922 | C | GLY | A | 387 | −38.686 | −0.273 | −15.388 | 1 | 27.99 | A |
| ATOM | 3923 | O | GLY | A | 387 | −39.112 | −0.476 | −16.526 | 1 | 28.8 | A |

TABLE 7-continued

| ATOM | 3924 | N | ARG | A | 388 | −37.403 | −0.385 | −15.074 | 1 | 30.3 | A |
| ATOM | 3925 | CA | ARG | A | 388 | −36.43 | −0.78 | −16.076 | 1 | 33.92 | A |
| ATOM | 3926 | CB | ARG | A | 388 | −35.942 | 0.453 | −16.855 | 1 | 39.24 | A |
| ATOM | 3927 | CG | ARG | A | 388 | −34.92 | 0.152 | −17.972 | 1 | 47.47 | A |
| ATOM | 3928 | CD | ARG | A | 388 | −35.308 | −1.085 | −18.811 | 1 | 52.19 | A |
| ATOM | 3929 | NE | ARG | A | 388 | −34.349 | −1.376 | −19.881 | 1 | 54.83 | A |
| ATOM | 3930 | CZ | ARG | A | 388 | −34.369 | −2.48 | −20.626 | 1 | 55.84 | A |
| ATOM | 3931 | NH1 | ARG | A | 388 | −35.298 | −3.401 | −20.415 | 1 | 57.41 | A |
| ATOM | 3932 | NH2 | ARG | A | 388 | −33.467 | −2.664 | −21.586 | 1 | 55.45 | A |
| ATOM | 3933 | C | ARG | A | 388 | −35.264 | −1.495 | −15.416 | 1 | 32.89 | A |
| ATOM | 3934 | O | ARG | A | 388 | −35.234 | −1.657 | −14.195 | 1 | 33.14 | A |
| ATOM | 3935 | N | GLY | A | 389 | −34.31 | −1.932 | −16.231 | 1 | 31.69 | A |
| ATOM | 3936 | CA | GLY | A | 389 | −33.151 | −2.619 | −15.706 | 1 | 29.14 | A |
| ATOM | 3937 | C | GLY | A | 389 | −33.562 | −3.881 | −14.995 | 1 | 27.89 | A |
| ATOM | 3938 | O | GLY | A | 389 | −34.457 | −4.596 | −15.44 | 1 | 27.07 | A |
| ATOM | 3939 | N | GLU | A | 390 | −32.912 | −4.15 | −13.875 | 1 | 29.38 | A |
| ATOM | 3940 | CA | GLU | A | 390 | −33.207 | −5.341 | −13.1 | 1 | 27.7 | A |
| ATOM | 3941 | CB | GLU | A | 390 | −32.043 | −5.64 | −12.162 | 1 | 27.62 | A |
| ATOM | 3942 | CG | GLU | A | 390 | −30.828 | −6.151 | −12.9 | 1 | 31.45 | A |
| ATOM | 3943 | CD | GLU | A | 390 | −29.698 | −6.554 | −11.985 | 1 | 31.31 | A |
| ATOM | 3944 | OE1 | GLU | A | 390 | −29.968 | −7.069 | −10.874 | 1 | 30.56 | A |
| ATOM | 3945 | OE2 | GLU | A | 390 | −28.533 | −6.373 | −12.394 | 1 | 31.78 | A |
| ATOM | 3946 | C | GLU | A | 390 | −34.511 | −5.262 | −12.313 | 1 | 27.76 | A |
| ATOM | 3947 | O | GLU | A | 390 | −34.99 | −6.28 | −11.816 | 1 | 27.45 | A |
| ATOM | 3948 | N | GLN | A | 391 | −35.091 | −4.069 | −12.19 | 1 | 26.73 | A |
| ATOM | 3949 | CA | GLN | A | 391 | −36.347 | −3.952 | −11.453 | 1 | 28.35 | A |
| ATOM | 3950 | CB | GLN | A | 391 | −36.249 | −2.897 | −10.336 | 1 | 26 | A |
| ATOM | 3951 | CG | GLN | A | 391 | −35.451 | −1.656 | −10.647 | 1 | 24.34 | A |
| ATOM | 3952 | CD | GLN | A | 391 | −33.956 | −1.915 | −10.696 | 1 | 25.55 | A |
| ATOM | 3953 | OE1 | GLN | A | 391 | −33.421 | −2.706 | −9.919 | 1 | 23.68 | A |
| ATOM | 3954 | NE2 | GLN | A | 391 | −33.271 | −1.23 | −11.6 | 1 | 27.54 | A |
| ATOM | 3955 | C | GLN | A | 391 | −37.553 | −3.678 | −12.353 | 1 | 29.91 | A |
| ATOM | 3956 | O | GLN | A | 391 | −38.581 | −3.153 | −11.917 | 1 | 30.87 | A |
| ATOM | 3957 | N | GLN | A | 392 | −37.423 | −4.055 | −13.618 | 1 | 28.06 | A |
| ATOM | 3958 | CA | GLN | A | 392 | −38.503 | −3.873 | −14.562 | 1 | 24.73 | A |
| ATOM | 3959 | CB | GLN | A | 392 | −37.952 | −3.802 | −15.98 | 1 | 25 | A |
| ATOM | 3960 | CG | GLN | A | 392 | −39.006 | −3.982 | −17.057 | 1 | 24.39 | A |
| ATOM | 3961 | CD | GLN | A | 392 | −38.419 | −3.895 | −18.448 | 1 | 26.15 | A |
| ATOM | 3962 | OE1 | GLN | A | 392 | −37.832 | −2.873 | −18.822 | 1 | 24.56 | A |
| ATOM | 3963 | NE2 | GLN | A | 392 | −38.567 | −4.968 | −19.225 | 1 | 24.99 | A |
| ATOM | 3964 | C | GLN | A | 392 | −39.442 | −5.058 | −14.443 | 1 | 24.52 | A |
| ATOM | 3965 | O | GLN | A | 392 | −38.996 | −6.2 | −14.347 | 1 | 23.24 | A |
| ATOM | 3966 | N | ILE | A | 393 | −40.74 | −4.78 | −14.433 | 1 | 23.15 | A |
| ATOM | 3967 | CA | ILE | A | 393 | −41.751 | −5.828 | −14.356 | 1 | 23.89 | A |
| ATOM | 3968 | CB | ILE | A | 393 | −42.533 | −5.792 | −13.034 | 1 | 20.25 | A |
| ATOM | 3969 | CG2 | ILE | A | 393 | −41.573 | −5.868 | −11.862 | 1 | 22.08 | A |
| ATOM | 3970 | CG1 | ILE | A | 393 | −43.366 | −4.513 | −12.962 | 1 | 16.82 | A |
| ATOM | 3971 | CD1 | ILE | A | 393 | −44.293 | −4.463 | −11.794 | 1 | 13.69 | A |
| ATOM | 3972 | C | ILE | A | 393 | −42.736 | −5.577 | −15.482 | 1 | 26.36 | A |
| ATOM | 3973 | O | ILE | A | 393 | −42.853 | −4.456 | −15.977 | 1 | 28.56 | A |
| ATOM | 3974 | N | ASN | A | 394 | −43.445 | −6.616 | −15.891 | 1 | 29.16 | A |
| ATOM | 3975 | CA | ASN | A | 394 | −44.416 | −6.453 | −16.958 | 1 | 33.73 | A |
| ATOM | 3976 | CB | ASN | A | 394 | −43.8 | −6.821 | −18.311 | 1 | 33.54 | A |
| ATOM | 3977 | CG | ASN | A | 394 | −43.282 | −8.24 | −18.345 | 1 | 37.25 | A |
| ATOM | 3978 | OD1 | ASN | A | 394 | −44.056 | −9.201 | −18.284 | 1 | 35.83 | A |
| ATOM | 3979 | ND2 | ASN | A | 394 | −41.96 | −8.383 | −18.439 | 1 | 36.25 | A |
| ATOM | 3980 | C | ASN | A | 394 | −45.639 | −7.304 | −16.705 | 1 | 33.07 | A |
| ATOM | 3981 | O | ASN | A | 394 | −45.628 | −8.202 | −15.866 | 1 | 33.86 | A |
| ATOM | 3982 | N | HIS | A | 395 | −46.704 | −6.99 | −17.424 | 1 | 32.43 | A |
| ATOM | 3983 | CA | HIS | A | 395 | −47.938 | −7.732 | −17.304 | 1 | 31.53 | A |
| ATOM | 3984 | CB | HIS | A | 395 | −48.936 | −7.009 | −16.4 | 1 | 30.12 | A |
| ATOM | 3985 | CG | HIS | A | 395 | −50.17 | −7.808 | −16.108 | 1 | 32.43 | A |
| ATOM | 3986 | CD2 | HIS | A | 395 | −50.724 | −8.196 | −14.933 | 1 | 31.12 | A |
| ATOM | 3987 | ND1 | HIS | A | 395 | −50.995 | −8.296 | −17.101 | 1 | 30.44 | A |
| ATOM | 3988 | CE1 | HIS | A | 395 | −52.003 | −8.949 | −16.551 | 1 | 29.5 | A |
| ATOM | 3989 | NE2 | HIS | A | 395 | −51.863 | −8.903 | −15.238 | 1 | 34.58 | A |
| ATOM | 3990 | C | HIS | A | 395 | −48.471 | −7.81 | −18.714 | 1 | 32.74 | A |
| ATOM | 3991 | O | HIS | A | 395 | −48.61 | −6.786 | −19.389 | 1 | 30.82 | A |
| ATOM | 3992 | N | HIS | A | 396 | −48.736 | −9.034 | −19.162 | 1 | 34.05 | A |
| ATOM | 3993 | CA | HIS | A | 396 | −49.249 | −9.258 | −20.502 | 1 | 30.98 | A |
| ATOM | 3994 | CB | HIS | A | 396 | −49.193 | −10.751 | −20.851 | 1 | 30.51 | A |
| ATOM | 3995 | CG | HIS | A | 396 | −49.803 | −11.08 | −22.176 | 1 | 29.82 | A |
| ATOM | 3996 | CD2 | HIS | A | 396 | −49.321 | −10.952 | −23.435 | 1 | 29.9 | A |
| ATOM | 3997 | ND1 | HIS | A | 396 | −51.098 | −11.534 | −22.306 | 1 | 29.99 | A |
| ATOM | 3998 | CE1 | HIS | A | 396 | −51.388 | −11.67 | −23.588 | 1 | 29.56 | A |
| ATOM | 3999 | NE2 | HIS | A | 396 | −50.328 | −11.322 | −24.294 | 1 | 31.1 | A |
| ATOM | 4000 | C | HIS | A | 396 | −50.673 | −8.739 | −20.615 | 1 | 28.74 | A |
| ATOM | 4001 | O | HIS | A | 396 | −51.353 | −8.525 | −19.61 | 1 | 24.91 | A |
| ATOM | 4002 | N | TRP | A | 397 | −51.112 | −8.523 | −21.846 | 1 | 28.3 | A |

TABLE 7-continued

| | | | | | | | | | | |
|---|---|---|---|---|---|---|---|---|---|---|
| ATOM | 4003 | CA | TRP | A | 397 | −52.454 | −8.036 | −22.089 | 1 | 31.79 | A |
| ATOM | 4004 | CB | TRP | A | 397 | −52.543 | −6.552 | −21.725 | 1 | 34.26 | A |
| ATOM | 4005 | CG | TRP | A | 397 | −53.931 | −6.04 | −21.737 | 1 | 37.71 | A |
| ATOM | 4006 | CD2 | TRP | A | 397 | −54.898 | −6.191 | −20.695 | 1 | 39.81 | A |
| ATOM | 4007 | CE2 | TRP | A | 397 | −56.107 | −5.634 | −21.165 | 1 | 41.46 | A |
| ATOM | 4008 | CE3 | TRP | A | 397 | −54.861 | −6.748 | −19.408 | 1 | 40.17 | A |
| ATOM | 4009 | CD1 | TRP | A | 397 | −54.567 | −5.411 | −22.766 | 1 | 39.17 | A |
| ATOM | 4010 | NE1 | TRP | A | 397 | −55.876 | −5.164 | −22.432 | 1 | 41.69 | A |
| ATOM | 4011 | CZ2 | TRP | A | 397 | −57.275 | −5.617 | −20.393 | 1 | 42.7 | A |
| ATOM | 4012 | CZ3 | TRP | A | 397 | −56.021 | −6.733 | −18.639 | 1 | 41.83 | A |
| ATOM | 4013 | CH2 | TRP | A | 397 | −57.212 | −6.169 | −19.136 | 1 | 44.03 | A |
| ATOM | 4014 | C | TRP | A | 397 | −52.831 | −8.239 | −23.551 | 1 | 32.49 | A |
| ATOM | 4015 | O | TRP | A | 397 | −51.973 | −8.22 | −24.434 | 1 | 32.14 | A |
| ATOM | 4016 | N | HIS | A | 398 | −54.117 | −8.457 | −23.798 | 1 | 33.24 | A |
| ATOM | 4017 | CA | HIS | A | 398 | −54.608 | −8.645 | −25.153 | 1 | 34.78 | A |
| ATOM | 4018 | CB | HIS | A | 398 | −54.824 | −10.12 | −25.471 | 1 | 39.72 | A |
| ATOM | 4019 | CG | HIS | A | 398 | −55.384 | −10.347 | −26.841 | 1 | 44.25 | A |
| ATOM | 4020 | CD2 | HIS | A | 398 | −56.658 | −10.527 | −27.263 | 1 | 45.49 | A |
| ATOM | 4021 | ND1 | HIS | A | 398 | −54.607 | −10.302 | −27.979 | 1 | 46.12 | A |
| ATOM | 4022 | CE1 | HIS | A | 398 | −55.379 | −10.441 | −29.043 | 1 | 46.48 | A |
| ATOM | 4023 | NE2 | HIS | A | 398 | −56.628 | −10.578 | −28.635 | 1 | 46.09 | A |
| ATOM | 4024 | C | HIS | A | 398 | −55.927 | −7.92 | −25.317 | 1 | 32.79 | A |
| ATOM | 4025 | O | HIS | A | 398 | −56.874 | −8.181 | −24.584 | 1 | 30.08 | A |
| ATOM | 4026 | N | LYS | A | 399 | −55.982 | −7.012 | −26.285 | 1 | 33.29 | A |
| ATOM | 4027 | CA | LYS | A | 399 | −57.186 | −6.238 | −26.542 | 1 | 33.44 | A |
| ATOM | 4028 | CB | LYS | A | 399 | −56.826 | −4.766 | −26.718 | 1 | 32.16 | A |
| ATOM | 4029 | CG | LYS | A | 399 | −58.005 | −3.838 | −26.977 | 1 | 31.71 | A |
| ATOM | 4030 | CD | LYS | A | 399 | −57.54 | −2.384 | −27.007 | 1 | 32.16 | A |
| ATOM | 4031 | CE | LYS | A | 399 | −58.701 | −1.416 | −27.187 | 1 | 34.69 | A |
| ATOM | 4032 | NZ | LYS | A | 399 | −58.237 | −0.001 | −27.321 | 1 | 33.07 | A |
| ATOM | 4033 | C | LYS | A | 399 | −57.896 | −6.74 | −27.785 | 1 | 35.18 | A |
| ATOM | 4034 | O | LYS | A | 399 | −57.387 | −6.588 | −28.894 | 1 | 36.94 | A |
| ATOM | 4035 | N | LYS | A | 400 | −59.066 | −7.346 | −27.592 | 1 | 36.95 | A |
| ATOM | 4036 | CA | LYS | A | 400 | −59.87 | −7.857 | −28.698 | 1 | 39.25 | A |
| ATOM | 4037 | CB | LYS | A | 400 | −61.003 | −8.732 | −28.148 | 1 | 41.37 | A |
| ATOM | 4038 | CG | LYS | A | 400 | −61.741 | −8.099 | −26.965 | 1 | 46.59 | A |
| ATOM | 4039 | CD | LYS | A | 400 | −62.899 | −8.965 | −26.468 | 1 | 52.09 | A |
| ATOM | 4040 | CE | LYS | A | 400 | −63.505 | −8.403 | −25.174 | 1 | 54.62 | A |
| ATOM | 4041 | NZ | LYS | A | 400 | −64.016 | −7 | −25.315 | 1 | 56.17 | A |
| ATOM | 4042 | C | LYS | A | 400 | −60.462 | −6.701 | −29.522 | 1 | 39.94 | A |
| ATOM | 4043 | O | LYS | A | 400 | −60.759 | −5.634 | −28.93 | 1 | 34.44 | A |
| ATOM | 4044 | OXT | LYS | A | 400 | −60.638 | −6.886 | −30.753 | 1 | 41.62 | A |
| ATOM | 4045 | NA | NA | | 1 | −50.542 | 0.414 | 8.067 | 1 | 29.56 | |
| ATOM | 4046 | OH2 | WAT | W | 3 | −43.941 | 4.79 | −2.357 | 1 | 18.34 | W |
| ATOM | 4047 | OH2 | WAT | W | 4 | −19.646 | −17.689 | 40.827 | 1 | 19.49 | W |
| ATOM | 4048 | OH2 | WAT | W | 5 | 1.086 | −6.228 | 36.071 | 1 | 34.43 | W |
| ATOM | 4049 | OH2 | WAT | W | 6 | −9.954 | −24.698 | 28.495 | 1 | 10.6 | W |
| ATOM | 4050 | OH2 | WAT | W | 7 | −31.62 | 0.121 | −5.52 | 1 | 5.87 | W |
| ATOM | 4051 | OH2 | WAT | W | 8 | −10.669 | 16.435 | 6.361 | 1 | 30.99 | W |
| ATOM | 4052 | OH2 | WAT | W | 9 | −11.045 | −8.113 | 17.167 | 1 | 20.54 | W |
| ATOM | 4053 | OH2 | WAT | W | 10 | −24.036 | −12.754 | 10.102 | 1 | 8.53 | W |
| ATOM | 4054 | OH2 | WAT | W | 11 | −57.533 | −2.732 | −11.116 | 1 | 38.68 | W |
| ATOM | 4055 | OH2 | WAT | W | 12 | −46.647 | −12.435 | −27.215 | 1 | 32.63 | W |
| ATOM | 4056 | OH2 | WAT | W | 13 | −19.137 | −11.152 | −8.672 | 1 | 20.57 | W |
| ATOM | 4057 | OH2 | WAT | W | 14 | −38.72 | 0.64 | 1.016 | 1 | 21.59 | W |
| ATOM | 4058 | OH2 | WAT | W | 15 | −34.334 | 9.295 | −12.941 | 1 | 40.13 | W |
| ATOM | 4059 | OH2 | WAT | W | 16 | −35.475 | 12.109 | 15.787 | 1 | 17.9 | W |
| ATOM | 4060 | OH2 | WAT | W | 17 | −27.27 | −10.354 | −10.034 | 1 | 26.77 | W |
| ATOM | 4061 | OH2 | WAT | W | 18 | −50.153 | 9.273 | −6.596 | 1 | 21.61 | W |
| ATOM | 4062 | OH2 | WAT | W | 19 | −54.458 | 7.632 | −7.685 | 1 | 35.4 | W |
| ATOM | 4063 | OH2 | WAT | W | 20 | −42.711 | −10.749 | −26.432 | 1 | 39.16 | W |
| ATOM | 4064 | OH2 | WAT | W | 21 | −16.864 | −7.007 | −6.017 | 1 | 21.82 | W |
| ATOM | 4065 | OH2 | WAT | W | 22 | −7.613 | −12.554 | 28.423 | 1 | 22 | W |
| ATOM | 4066 | OH2 | WAT | W | 23 | −4.625 | −8.443 | 6.447 | 1 | 27.94 | W |
| ATOM | 4067 | OH2 | WAT | W | 24 | −33.146 | 0.338 | −7.652 | 1 | 15.92 | W |
| ATOM | 4068 | OH2 | WAT | W | 25 | −42.132 | 9.317 | 14.521 | 1 | 36.69 | W |
| ATOM | 4069 | OH2 | WAT | W | 26 | −10.584 | −4.63 | 6.868 | 1 | 34.03 | W |
| ATOM | 4070 | OH2 | WAT | W | 27 | −40.841 | −2.544 | −11.395 | 1 | 26.86 | W |
| ATOM | 4071 | OH2 | WAT | W | 28 | 4.096 | −30.579 | 13.731 | 1 | 29.83 | W |
| ATOM | 4072 | OH2 | WAT | W | 29 | −9.395 | 0.621 | 17.188 | 1 | 22.04 | W |
| ATOM | 4073 | OH2 | WAT | W | 30 | −22.711 | −3.107 | −14.633 | 1 | 15.28 | W |
| ATOM | 4074 | OH2 | WAT | W | 31 | −20.21 | −8.921 | −0.257 | 1 | 28.57 | W |
| ATOM | 4075 | OH2 | WAT | W | 32 | −42.448 | −9.379 | −14.425 | 1 | 17.41 | W |
| ATOM | 4076 | OH2 | WAT | W | 33 | 1.681 | −10.01 | 5.93 | 1 | 25.24 | W |
| ATOM | 4077 | OH2 | WAT | W | 34 | −3.312 | −26.223 | 30.059 | 1 | 21.14 | W |
| ATOM | 4078 | OH2 | WAT | W | 36 | −25.451 | −0.275 | −7.377 | 1 | 28.12 | W |
| ATOM | 4079 | OH2 | WAT | W | 37 | −29.078 | 0.682 | 15.655 | 1 | 26.86 | W |
| ATOM | 4080 | OH2 | WAT | W | 38 | −7.919 | −26.525 | 9.384 | 1 | 40.51 | W |
| ATOM | 4081 | OH2 | WAT | W | 39 | −45.092 | −5.436 | −1.04 | 1 | 16.01 | W |

TABLE 7-continued

| | | | | | | | | | | |
|---|---|---|---|---|---|---|---|---|---|---|
| ATOM | 4082 | OH2 | WAT | W | 40 | −16.396 | −27.635 | 29.589 | 1 | 11.74 | W |
| ATOM | 4083 | OH2 | WAT | W | 41 | −21.452 | −7.414 | −13.818 | 1 | 20.73 | W |
| ATOM | 4084 | OH2 | WAT | W | 42 | −14.403 | 7.628 | −9.634 | 1 | 25.09 | W |
| ATOM | 4085 | OH2 | WAT | W | 43 | −23.999 | −0.875 | −14.736 | 1 | 16.91 | W |
| ATOM | 4086 | OH2 | WAT | W | 44 | −24.561 | 9.919 | 18.966 | 1 | 35.63 | W |
| ATOM | 4087 | OH2 | WAT | W | 45 | −16.117 | −17.767 | 19.742 | 1 | 18.5 | W |
| ATOM | 4088 | OH2 | WAT | W | 46 | −11.106 | −19.809 | 12.775 | 1 | 25.09 | W |
| ATOM | 4089 | OH2 | WAT | W | 47 | 2.761 | −21.103 | 26.079 | 1 | 26.92 | W |
| ATOM | 4090 | OH2 | WAT | W | 48 | −35.733 | −6.866 | −4.106 | 1 | 12.52 | W |
| ATOM | 4091 | OH2 | WAT | W | 50 | −49.069 | −8.508 | 11.032 | 1 | 24.85 | W |
| ATOM | 4092 | OH2 | WAT | W | 51 | −11.59 | −13.529 | 14.232 | 1 | 29.89 | W |
| ATOM | 4093 | OH2 | WAT | W | 52 | −61.671 | 7.809 | −18.787 | 1 | 42.95 | W |
| ATOM | 4094 | OH2 | WAT | W | 53 | −41.977 | −8.045 | 10.834 | 1 | 11.86 | W |
| ATOM | 4095 | OH2 | WAT | W | 54 | −15.503 | −9.76 | 26.774 | 1 | 28.9 | W |
| ATOM | 4096 | OH2 | WAT | W | 55 | −5.798 | −0.618 | 4.361 | 1 | 22.56 | W |
| ATOM | 4097 | OH2 | WAT | W | 56 | −25.556 | −3.307 | 19.778 | 1 | 27.17 | W |
| ATOM | 4098 | OH2 | WAT | W | 58 | −1.854 | −29.093 | 8.502 | 1 | 15.68 | W |
| ATOM | 4099 | OH2 | WAT | W | 59 | −43.778 | 6.888 | −18.587 | 1 | 31.84 | W |
| ATOM | 4100 | OH2 | WAT | W | 60 | −12.379 | −28.435 | 41.824 | 1 | 32.9 | W |
| ATOM | 4101 | OH2 | WAT | W | 61 | −35.591 | −8.493 | −2.033 | 1 | 20.68 | W |
| ATOM | 4102 | OH2 | WAT | W | 63 | −22.684 | −3.858 | 18.067 | 1 | 39.8 | W |
| ATOM | 4103 | OH2 | WAT | W | 64 | −59.578 | −7.443 | −11.929 | 1 | 37.29 | W |
| ATOM | 4104 | OH2 | WAT | W | 65 | −2.537 | −8.06 | 42.609 | 1 | 38.58 | W |
| ATOM | 4105 | OH2 | WAT | W | 67 | −30.333 | 8.228 | 12.443 | 1 | 34.69 | W |
| ATOM | 4106 | OH2 | WAT | W | 71 | −27.769 | 15.504 | −2.627 | 1 | 45.02 | W |
| ATOM | 4107 | OH2 | WAT | W | 72 | −44.297 | 12.041 | 8.685 | 1 | 40.86 | W |
| ATOM | 4108 | OH2 | WAT | W | 73 | −13.211 | −8.423 | 34.777 | 1 | 31.99 | W |
| ATOM | 4109 | OH2 | WAT | W | 75 | −19.2 | −12.653 | 36.524 | 1 | 36.24 | W |
| ATOM | 4110 | OH2 | WAT | W | 79 | −27.954 | −10.377 | 3.053 | 1 | 18.8 | W |
| ATOM | 4111 | OH2 | WAT | W | 80 | −34.448 | 10.284 | −8.574 | 1 | 21.89 | W |
| ATOM | 4112 | OH2 | WAT | W | 81 | −33.81 | 13.106 | −1.454 | 1 | 38.55 | W |
| ATOM | 4113 | OH2 | WAT | W | 82 | −16.27 | 10.2 | 20.687 | 1 | 49.84 | W |
| ATOM | 4114 | OH2 | WAT | W | 83 | −38.181 | 0.526 | −20.016 | 1 | 39.28 | W |
| ATOM | 4115 | OH2 | WAT | W | 84 | 1.364 | −36.226 | 19.122 | 1 | 29.53 | W |
| ATOM | 4116 | OH2 | WAT | W | 85 | −3.268 | −38.021 | 27.054 | 1 | 29.55 | W |
| ATOM | 4117 | OH2 | WAT | W | 86 | −48.693 | 8.433 | −23.867 | 1 | 33.43 | W |
| ATOM | 4118 | OH2 | WAT | W | 87 | −11.887 | −2.729 | 25.847 | 1 | 29.25 | W |
| ATOM | 4119 | OH2 | WAT | W | 89 | −42.718 | −14.193 | 7.358 | 1 | 26.37 | W |
| ATOM | 4120 | OH2 | WAT | W | 90 | 14.268 | −13.259 | 37.789 | 1 | 27.13 | W |
| ATOM | 4121 | OH2 | WAT | W | 91 | −51.051 | −9.194 | −31.598 | 1 | 24.62 | W |
| ATOM | 4122 | OH2 | WAT | W | 92 | 6.827 | −25.669 | 30.531 | 1 | 45.3 | W |
| ATOM | 4123 | OH2 | WAT | W | 93 | −7.182 | −14.475 | 9.866 | 1 | 29.24 | W |
| ATOM | 4124 | OH2 | WAT | W | 94 | 4.95 | −12.092 | 16.655 | 1 | 17.37 | W |
| ATOM | 4125 | OH2 | WAT | W | 95 | 5.197 | −8.421 | 26.118 | 1 | 33.31 | W |
| ATOM | 4126 | OH2 | WAT | W | 96 | −28.026 | −17.054 | 28.443 | 1 | 41.37 | W |
| ATOM | 4127 | OH2 | WAT | W | 98 | −7.529 | 7.352 | 1.881 | 1 | 36.14 | W |
| ATOM | 4128 | OH2 | WAT | W | 99 | −47.018 | 6.863 | 17.868 | 1 | 32.12 | W |
| ATOM | 4129 | OH2 | WAT | W | 100 | −12.153 | 3.851 | −9.904 | 1 | 37.54 | W |
| ATOM | 4130 | OH2 | WAT | W | 101 | −28.015 | −28.318 | 27.269 | 1 | 39.42 | W |
| ATOM | 4131 | OH2 | WAT | W | 102 | −44.13 | −23.562 | 13.784 | 1 | 31.09 | W |
| ATOM | 4132 | OH2 | WAT | W | 103 | −12.032 | −0.104 | −8.589 | 1 | 31.48 | W |
| ATOM | 4133 | OH2 | WAT | W | 104 | −3.184 | −28.525 | 37.438 | 1 | 34.01 | W |
| ATOM | 4134 | OH2 | WAT | W | 105 | −45 | −18.165 | 13.362 | 1 | 24.92 | W |
| ATOM | 4135 | OH2 | WAT | W | 106 | 3.14 | −4.373 | 20.948 | 1 | 31.28 | W |
| ATOM | 4136 | OH2 | WAT | W | 107 | 5.214 | −35.144 | 16.679 | 1 | 28.3 | W |
| ATOM | 4137 | OH2 | WAT | W | 108 | −14.904 | −29.092 | 15.767 | 1 | 29.14 | W |
| ATOM | 4138 | OH2 | WAT | W | 109 | −10.871 | 7.385 | −7.231 | 1 | 38.83 | W |
| ATOM | 4139 | OH2 | WAT | W | 111 | 3.837 | −13.403 | 44.67 | 1 | 17.58 | W |
| ATOM | 4140 | OH2 | WAT | W | 113 | 1.416 | −9.092 | 13.586 | 1 | 34.93 | W |
| ATOM | 4141 | OH2 | WAT | W | 115 | −34.024 | 3.785 | 15.713 | 1 | 21.73 | W |
| ATOM | 4142 | OH2 | WAT | W | 117 | −5.926 | 13.178 | 4.491 | 1 | 34.28 | W |
| ATOM | 4143 | OH2 | WAT | W | 118 | −9.712 | 10.888 | −2.079 | 1 | 28.67 | W |
| ATOM | 4144 | OH2 | WAT | W | 120 | −23.559 | 14.629 | −3.288 | 1 | 28.54 | W |
| ATOM | 4145 | OH2 | WAT | W | 122 | −46.401 | 7.792 | 9.601 | 1 | 29.9 | W |
| ATOM | 4146 | OH2 | WAT | W | 123 | 4.489 | −27.789 | 33.795 | 1 | 35.5 | W |
| ATOM | 4147 | OH2 | WAT | W | 124 | −41.971 | −14.555 | 2.195 | 1 | 23.34 | W |
| ATOM | 4148 | OH2 | WAT | W | 125 | 1.529 | −26.419 | 41.363 | 1 | 42.16 | W |
| ATOM | 4149 | OH2 | WAT | W | 126 | −54.535 | 5.369 | −5.331 | 1 | 41.52 | W |
| ATOM | 4150 | OH2 | WAT | W | 127 | −29.834 | 5.694 | 10.742 | 1 | 22.15 | W |
| ATOM | 4151 | OH2 | WAT | W | 131 | −25.016 | −9.801 | 3.443 | 1 | 27.15 | W |
| ATOM | 4152 | OH2 | WAT | W | 132 | −45.158 | −13.521 | 2.512 | 1 | 34.24 | W |
| ATOM | 4153 | OH2 | WAT | W | 134 | −53.605 | −1.141 | −32.217 | 1 | 30.09 | W |
| ATOM | 4154 | OH2 | WAT | W | 135 | −33.135 | 8.277 | 14.41 | 1 | 33.83 | W |
| ATOM | 4155 | OH2 | WAT | W | 141 | −27.743 | −25.418 | 15.495 | 1 | 34.83 | W |
| ATOM | 4156 | OH2 | WAT | W | 142 | −47.496 | −7.98 | 7.06 | 1 | 28.52 | W |
| ATOM | 4157 | OH2 | WAT | W | 143 | −41.532 | −24.816 | 17.896 | 1 | 44.67 | W |
| ATOM | 4158 | OH2 | WAT | W | 144 | −30.197 | −17.354 | 9.222 | 1 | 25.92 | W |
| ATOM | 4159 | OH2 | WAT | W | 146 | −18.969 | −15.665 | 13.523 | 1 | 44.99 | W |
| ATOM | 4160 | OH2 | WAT | W | 147 | 4.084 | −29.484 | 16.201 | 1 | 26.71 | W |

TABLE 7-continued

| | | | | | | | | | | |
|---|---|---|---|---|---|---|---|---|---|---|
| ATOM | 4161 | OH2 | WAT | W | 148 | −51.76 | −9.627 | −11.405 | 1 | 25.63 | W |
| ATOM | 4162 | OH2 | WAT | W | 149 | −9.797 | 2.005 | 3.417 | 1 | 30 | W |
| ATOM | 4163 | OH2 | WAT | W | 150 | −50.367 | −4.998 | −30.382 | 1 | 18.32 | W |
| ATOM | 4164 | OH2 | WAT | W | 151 | −48.037 | 5.738 | 3.02 | 1 | 31.66 | W |
| ATOM | 4165 | OH2 | WAT | W | 152 | −32.887 | −9.693 | −3.002 | 1 | 17.39 | W |
| ATOM | 4166 | OH2 | WAT | W | 153 | −2.606 | −7.463 | 27.853 | 1 | 37.76 | W |
| ATOM | 4167 | OH2 | WAT | W | 154 | 4.065 | 7.213 | 12.04 | 1 | 32.93 | W |
| ATOM | 4168 | OH2 | WAT | W | 155 | 2.121 | −14.399 | 49.961 | 1 | 27.98 | W |
| ATOM | 4169 | OH2 | WAT | W | 156 | −31.712 | 13.49 | −3.435 | 1 | 40.65 | W |
| ATOM | 4170 | OH2 | WAT | W | 157 | −59.365 | 9.966 | −23.221 | 1 | 31.27 | W |
| ATOM | 4171 | OH2 | WAT | W | 158 | −60.818 | −3.919 | −32.872 | 1 | 34.34 | W |
| ATOM | 4172 | OH2 | WAT | W | 159 | −8.748 | −29.386 | 26.436 | 1 | 24.58 | W |
| ATOM | 4173 | OH2 | WAT | W | 160 | −37.794 | 9.719 | 1.924 | 1 | 22.76 | W |
| ATOM | 4174 | OH2 | WAT | W | 161 | −3.91 | −39.855 | 17.062 | 1 | 29 | W |
| ATOM | 4175 | OH2 | WAT | W | 162 | −38.139 | 11.909 | 3.82 | 1 | 29.1 | W |
| ATOM | 4176 | OH2 | WAT | W | 163 | −36.45 | −6.944 | −14.523 | 1 | 18.56 | W |
| ATOM | 4177 | OH2 | WAT | W | 164 | −57.197 | 11.874 | −22.271 | 1 | 31.07 | W |
| ATOM | 4178 | OH2 | WAT | W | 165 | −26.891 | −0.921 | 20.238 | 1 | 25.62 | W |
| ATOM | 4179 | OH2 | WAT | W | 166 | 3.165 | −5.109 | 18.495 | 1 | 37.61 | W |
| ATOM | 4180 | OH2 | WAT | W | 167 | −10.745 | −12.212 | 45.915 | 1 | 24.8 | W |
| ATOM | 4181 | OH2 | WAT | W | 168 | −29.697 | −18.832 | 11.574 | 1 | 19.28 | W |
| ATOM | 4182 | OH2 | WAT | W | 169 | −23.691 | 13.603 | 20.492 | 1 | 19.08 | W |
| ATOM | 4183 | OH2 | WAT | W | 170 | −3.3 | −9.136 | 31.092 | 1 | 22.93 | W |
| ATOM | 4184 | OH2 | WAT | W | 171 | −20.25 | −29.811 | 32.651 | 1 | 33.97 | W |
| ATOM | 4185 | OH2 | WAT | W | 173 | −19.085 | −23.806 | 48.19 | 1 | 36.49 | W |
| ATOM | 4186 | OH2 | WAT | W | 174 | −40.994 | 1.49 | −18.977 | 1 | 32.56 | W |
| ATOM | 4187 | OH2 | WAT | W | 176 | −17.418 | −10.858 | 40.95 | 1 | 40.39 | W |
| ATOM | 4188 | OH2 | WAT | W | 177 | −21.842 | −19.888 | 37.57 | 1 | 26.47 | W |
| ATOM | 4189 | OH2 | WAT | W | 178 | −22.506 | −30.222 | 16.792 | 1 | 30.65 | W |
| ATOM | 4190 | OH2 | WAT | W | 179 | −19.863 | −11.605 | 6.897 | 1 | 39.38 | W |
| ATOM | 4191 | OH2 | WAT | W | 180 | −13.012 | −4.544 | 9.327 | 1 | 33.85 | W |
| ATOM | 4192 | OH2 | WAT | W | 181 | −25.176 | −27.068 | 38.91 | 1 | 37.85 | W |
| ATOM | 4193 | OH2 | WAT | W | 183 | −65.352 | 1.208 | −16.929 | 1 | 29.26 | W |
| ATOM | 4194 | OH2 | WAT | W | 184 | −19.994 | −15.102 | −3.378 | 1 | 31.19 | W |
| ATOM | 4195 | OH2 | WAT | W | 185 | −27.082 | 2.523 | 18.781 | 1 | 43.55 | W |
| ATOM | 4196 | OH2 | WAT | W | 186 | −5.039 | −16.797 | 48.678 | 1 | 35.97 | W |
| ATOM | 4197 | OH2 | WAT | W | 187 | −12.301 | −7.42 | 32.528 | 1 | 37.6 | W |
| ATOM | 4198 | OH2 | WAT | W | 188 | −16.588 | −22.993 | 42.555 | 1 | 34.44 | W |
| ATOM | 4199 | OH2 | WAT | W | 189 | −39.41 | −7.322 | −0.594 | 1 | 34.16 | W |
| ATOM | 4200 | OH2 | WAT | W | 190 | −33.056 | −6.953 | −5.163 | 1 | 23.53 | W |
| ATOM | 4201 | OH2 | WAT | W | 192 | −18.924 | −10.295 | 23.752 | 1 | 33.86 | W |
| ATOM | 4202 | OH2 | WAT | W | 193 | −53.265 | −4.866 | −26.022 | 1 | 27.56 | W |
| ATOM | 4203 | OH2 | WAT | W | 194 | −10.634 | −28.427 | 10.439 | 1 | 21.41 | W |
| ATOM | 4204 | OH2 | WAT | W | 195 | −26.216 | 19.288 | 9.166 | 1 | 29.18 | W |
| ATOM | 4205 | OH2 | WAT | W | 196 | −51.259 | 0.081 | 4.271 | 1 | 34.01 | W |
| ATOM | 4206 | OH2 | WAT | W | 198 | −54.493 | 9.814 | −11.966 | 1 | 35.64 | W |
| ATOM | 4207 | OH2 | WAT | W | 199 | −51.515 | 4.818 | 11.811 | 1 | 32.77 | W |
| ATOM | 4208 | OH2 | WAT | W | 201 | −19.904 | −0.946 | −16.34 | 1 | 46.53 | W |
| ATOM | 4209 | OH2 | WAT | W | 202 | −13.94 | −4.66 | 13.551 | 1 | 41.06 | W |
| ATOM | 4210 | OH2 | WAT | W | 203 | −41.991 | −9.96 | −11.181 | 1 | 39.22 | W |
| ATOM | 4211 | OH2 | WAT | W | 205 | −14.216 | −6.746 | −6.843 | 1 | 53.44 | W |
| ATOM | 4212 | OH2 | WAT | W | 206 | 0.066 | −36.97 | 22.173 | 1 | 42.85 | W |
| ATOM | 4213 | OH2 | WAT | W | 207 | −50.148 | 10.546 | −10.094 | 1 | 38.75 | W |
| ATOM | 4214 | OH2 | WAT | W | 209 | −2.26 | −22.521 | 7.468 | 1 | 35.58 | W |
| ATOM | 4215 | OH2 | WAT | W | 210 | −17.752 | −9.352 | 7.984 | 1 | 44.75 | W |
| ATOM | 4216 | OH2 | WAT | W | 211 | −40.052 | 19.82 | −8.619 | 1 | 36.84 | W |
| ATOM | 4217 | OH2 | WAT | W | 212 | −22.696 | 14.056 | 5.646 | 1 | 39.6 | W |
| ATOM | 4218 | OH2 | WAT | W | 215 | −11.847 | −4.126 | 4.173 | 1 | 34.71 | W |
| ATOM | 4219 | OH2 | WAT | W | 216 | −23.564 | −14.667 | 19.777 | 1 | 33.88 | W |
| ATOM | 4220 | OH2 | WAT | W | 217 | −39.052 | 1.855 | −11.372 | 1 | 28.38 | W |
| ATOM | 4221 | OH2 | WAT | W | 220 | −46.305 | −5.781 | 1.333 | 1 | 32.23 | W |
| ATOM | 4222 | OH2 | WAT | W | 221 | −2.553 | 2.228 | 8.94 | 1 | 32.35 | W |
| ATOM | 4223 | OH2 | WAT | W | 225 | −12.457 | −16.81 | 11.936 | 1 | 47.68 | W |
| ATOM | 4224 | OH2 | WAT | W | 226 | −33.784 | 10.504 | 15.992 | 1 | 28.25 | W |
| ATOM | 4225 | OH2 | WAT | W | 231 | −12.916 | 12.654 | 22.606 | 1 | 25.49 | W |
| ATOM | 4226 | OH2 | WAT | W | 232 | −1.305 | −3.793 | 26.802 | 1 | 41.27 | W |
| ATOM | 4227 | OH2 | WAT | W | 233 | 0.581 | −5.162 | 29.339 | 1 | 36.96 | W |
| ATOM | 4228 | OH2 | WAT | W | 234 | −40.776 | 21.479 | −0.151 | 1 | 45.9 | W |
| ATOM | 4229 | OH2 | WAT | W | 235 | −20.017 | −5.77 | −11.939 | 1 | 38.79 | W |
| ATOM | 4230 | OH2 | WAT | W | 237 | 11.881 | −19.428 | 41.503 | 1 | 33.47 | W |
| ATOM | 4231 | OH2 | WAT | W | 238 | −54.6 | 8.984 | −5.06 | 1 | 37.3 | W |
| ATOM | 4232 | OH2 | WAT | W | 241 | −52.322 | 8.463 | −9.917 | 1 | 35.79 | W |
| ATOM | 4233 | OH2 | WAT | W | 242 | −4.864 | −13.095 | 5.55 | 1 | 30.23 | W |
| ATOM | 4234 | OH2 | WAT | W | 243 | −43.731 | −6.541 | −8.789 | 1 | 37.23 | W |
| ATOM | 4235 | OH2 | WAT | W | 244 | −36.38 | −10.499 | 2.089 | 1 | 29.07 | W |
| ATOM | 4236 | OH2 | WAT | W | 245 | 1.749 | −27.24 | 15.175 | 1 | 29.12 | W |
| ATOM | 4237 | OH2 | WAT | W | 246 | −27.579 | −22.293 | 36.811 | 1 | 29.06 | W |
| ATOM | 4238 | OH2 | WAT | W | 247 | −59.057 | −3.569 | −23.512 | 1 | 25.71 | W |
| ATOM | 4239 | OH2 | WAT | W | 248 | −10.112 | −28.44 | 40.611 | 1 | 33.55 | W |

TABLE 7-continued

| | | | | | | | | | | |
|---|---|---|---|---|---|---|---|---|---|---|
| ATOM | 4240 | OH2 | WAT | W | 249 | −43.565 | −12.688 | 13.94 | 1 | 28.84 | W |
| ATOM | 4241 | OH2 | WAT | W | 250 | −40.113 | 3.976 | 19.024 | 1 | 31.05 | W |
| ATOM | 4242 | OH2 | WAT | W | 251 | −12.317 | −18.241 | 41.84 | 1 | 24.2 | W |
| ATOM | 4243 | OH2 | WAT | W | 252 | −47.3 | −8.272 | 14.822 | 1 | 42.45 | W |
| ATOM | 4244 | OH2 | WAT | W | 253 | −46.818 | 3.216 | 22.497 | 1 | 34.66 | W |
| ATOM | 4245 | OH2 | WAT | W | 254 | −48.175 | −3.685 | 1.054 | 1 | 44.8 | W |
| ATOM | 4246 | OH2 | WAT | W | 255 | −26.115 | 11.713 | 15.208 | 1 | 40.98 | W |
| ATOM | 4247 | OH2 | WAT | W | 256 | 0.124 | −26.024 | 31.564 | 1 | 20.75 | W |
| ATOM | 4248 | OH2 | WAT | W | 257 | −4.796 | 4.473 | 21.893 | 1 | 28.78 | W |
| ATOM | 4249 | OH2 | WAT | W | 259 | 4.803 | −14.905 | 46.635 | 1 | 24.03 | W |
| ATOM | 4250 | OH2 | WAT | W | 260 | −42.149 | −20.138 | 10.772 | 1 | 43.71 | W |
| ATOM | 4251 | OH2 | WAT | W | 261 | −18.067 | −21.798 | 24.685 | 1 | 37.58 | W |
| ATOM | 4252 | OH2 | WAT | W | 262 | −32.052 | 0.596 | −17.14 | 1 | 42.21 | W |
| ATOM | 4253 | OH2 | WAT | W | 263 | −37.602 | −6.314 | −21.983 | 1 | 23.91 | W |
| ATOM | 4254 | OH2 | WAT | W | 264 | −25.681 | 17.449 | −3.446 | 1 | 36.89 | W |
| ATOM | 4255 | OH2 | WAT | W | 265 | 7.708 | −21.023 | 28.678 | 1 | 35.8 | W |
| ATOM | 4256 | OH2 | WAT | W | 266 | −47.298 | 3.593 | −23.244 | 1 | 31.13 | W |
| ATOM | 4257 | OH2 | WAT | W | 267 | −32.028 | 11.145 | −13.252 | 1 | 29.35 | W |
| ATOM | 4258 | OH2 | WAT | W | 268 | −20.602 | −8.421 | 15.21 | 1 | 38.28 | W |
| ATOM | 4259 | OH2 | WAT | W | 269 | −23.157 | 3.393 | 15.329 | 1 | 42.06 | W |
| ATOM | 4260 | OH2 | WAT | W | 270 | −17.256 | −30.56 | 30.887 | 1 | 44.11 | W |
| ATOM | 4261 | OH2 | WAT | W | 271 | −54.012 | 4.538 | 10.175 | 1 | 33.57 | W |
| ATOM | 4262 | OH2 | WAT | W | 272 | −51.255 | −0.807 | −33.214 | 1 | 35.29 | W |
| ATOM | 4263 | OH2 | WAT | W | 273 | −53.7 | 3.991 | −28.662 | 1 | 38.54 | W |
| ATOM | 4264 | OH2 | WAT | W | 274 | −49.205 | −11.226 | −31.783 | 1 | 26.88 | W |
| ATOM | 4265 | OH2 | WAT | W | 275 | −3.226 | −31.205 | 6.922 | 1 | 28.58 | W |
| ATOM | 4266 | OH2 | WAT | W | 276 | −9.21 | 0.335 | 11.738 | 1 | 35.26 | W |
| ATOM | 4267 | OH2 | WAT | W | 277 | −56.373 | −3.491 | −6.947 | 1 | 47.25 | W |
| ATOM | 4268 | OH2 | WAT | W | 278 | −63.906 | −6.002 | −29.092 | 1 | 38.3 | W |
| ATOM | 4269 | OH2 | WAT | W | 279 | −6.353 | −16.779 | 6.373 | 1 | 35.03 | W |
| ATOM | 4270 | OH2 | WAT | W | 280 | −42.524 | −7.674 | −1.884 | 1 | 40.79 | W |
| ATOM | 4271 | OH2 | WAT | W | 281 | −50.135 | −2.304 | 3.398 | 1 | 43.58 | W |
| ATOM | 4272 | OH2 | WAT | W | 282 | −16.141 | 10.089 | −2.56 | 1 | 33.87 | W |
| ATOM | 4273 | OH2 | WAT | W | 284 | −21.282 | 9.545 | −9.077 | 1 | 31.69 | W |
| ATOM | 4274 | OH2 | WAT | W | 285 | −50.552 | 0.916 | −1.554 | 1 | 39.26 | W |
| ATOM | 4275 | OH2 | WAT | W | 286 | −54.679 | 10.607 | −23.413 | 1 | 40.45 | W |
| ATOM | 4276 | OH2 | WAT | W | 287 | 11.478 | −7.558 | 33.467 | 1 | 26.36 | W |
| ATOM | 4277 | OH2 | WAT | W | 288 | −16.509 | −20.371 | 17.394 | 1 | 32.57 | W |
| ATOM | 4278 | OH2 | WAT | W | 289 | −63.008 | −1.711 | −32.729 | 1 | 36.94 | W |
| ATOM | 4279 | OH2 | WAT | W | 291 | 3.093 | −5.855 | 28.07 | 1 | 38.84 | W |
| ATOM | 4280 | OH2 | WAT | W | 292 | −3.959 | 9.799 | 8.543 | 1 | 40.85 | W |
| ATOM | 4281 | OH2 | WAT | W | 293 | −9.428 | −2.653 | 30.598 | 1 | 31 | W |
| ATOM | 4282 | OH2 | WAT | W | 294 | −48.06 | −6.47 | −2.302 | 1 | 37.85 | W |
| ATOM | 4283 | OH2 | WAT | W | 295 | −36.722 | 8.58 | 9.827 | 1 | 35.28 | W |
| ATOM | 4284 | OH2 | WAT | W | 296 | 2.714 | 2.572 | 18.405 | 1 | 34.9 | W |
| ATOM | 4285 | OH2 | WAT | W | 297 | −25.826 | 6.21 | 20.872 | 1 | 37.94 | W |
| ATOM | 4286 | OH2 | WAT | W | 298 | −15.5 | −21.562 | 44.837 | 1 | 35.67 | W |
| ATOM | 4287 | OH2 | WAT | W | 301 | −57.718 | −5.868 | −9.553 | 1 | 48.56 | W |
| ATOM | 4288 | OH2 | WAT | W | 302 | −5.575 | −30.053 | 39.098 | 1 | 35.33 | W |
| ATOM | 4289 | OH2 | WAT | W | 303 | −14.494 | −3.265 | 16.496 | 1 | 31.26 | W |
| ATOM | 4290 | OH2 | WAT | W | 304 | −42.319 | −24.997 | 3.576 | 1 | 38.82 | W |
| ATOM | 4291 | OH2 | WAT | W | 305 | −3.526 | −28.656 | 40.417 | 1 | 38.42 | W |
| ATOM | 4292 | OH2 | WAT | W | 306 | −8.2 | −39.856 | 24.829 | 1 | 31.6 | W |
| ATOM | 4293 | OH2 | WAT | W | 307 | −45.478 | −15.91 | 4.085 | 1 | 30.64 | W |
| ATOM | 4294 | OH2 | WAT | W | 308 | −14.914 | 6.149 | 19.737 | 1 | 44.58 | W |
| ATOM | 4295 | OH2 | WAT | W | 309 | −7.269 | −5.334 | 36.669 | 1 | 33.28 | W |
| ATOM | 4296 | OH2 | WAT | W | 311 | −26.621 | −26.002 | 21.739 | 1 | 28.54 | W |
| ATOM | 4297 | OH2 | WAT | W | 312 | −36.374 | 3.519 | −13.879 | 1 | 41.18 | W |
| ATOM | 4298 | OH2 | WAT | W | 313 | −24.688 | −24.74 | 15.049 | 1 | 39.88 | W |
| ATOM | 4299 | OH2 | WAT | W | 314 | −40.996 | 11.854 | 4.511 | 1 | 31.76 | W |
| ATOM | 4300 | OH2 | WAT | W | 315 | −24.136 | −18.054 | 39.092 | 1 | 41.4 | W |

Coordinates from minimization and B-factor refinement
Refinement resolution: 50-2.50 A
Starting r=0.2080 free_r=0.2831
Final r=0.2046 free_r=0.2817
Rmsd bonds=0.006567 rmsd angles=1.44990
B rmsd for bonded mainchain atoms=1.833 target=2.0
B rmsd for bonded sidechain atoms=2.568 target=2.5
B rmsd for angle mainchain atoms=2.972 target=2.5
B rmsd for angle sidechain atoms=3.689 target=3.0
Target=mlf final wa=4.28786
Final rweight=0.0733 (with wa=4.28786)
Cycles=1 coordinate steps=50 B-factor steps=25

Sg=P2(1)2(1)2(1) a=52.4 b=83.3 c=110.6 alpha=90 beta=90 gamma=90
Topology file 1: CNS_TOPPAR:protein.top
Topology file 2: CNS_TOPPAR:dna-ma.top
Topology file 3: CNS_TOPPAR:water.top
Topology file 4: CNS_TOPPAR:ion.top
Parameter file 1: CNS_TOPPAR:protein—rep.param
Parameter file 2: CNS_TOPPAR:dna-ma—rep.param
Parameter file 3: CNS_TOPPAR:water_rep.param
Parameter file 4: CNS_TOPPAR:ion.param
Molecular structure file: gen.d.mtf
Input coordinates: gen.d.pdb
Reflection file=del_cv.hkl ncs=none
B-correction resolution: 6.0-2.50
Initial B-factor correction applied to fobs:
B11=−5.213 B22=2.248 B33=2.965
B12=0.000 B13=0.000 B23=0.000
B-factor correction applied to coordinate array B: 0.640
Bulk solvent: density level=0.356424 e/A^3, B-factor=44.9161 A^2
Reflections with |Fobs|/sigma_F<0.0 rejected
Reflections with |Fobs|>10000*rms(Fobs) rejected Theoretical total number of refl. in resol. range: 17370 (100.0%)
Number of unobserved reflections (no entry or |F|=0): 618 (3.6%)
Number of reflections rejected: 0 (0.0%)
Total number of reflections used: 16752 (96.4%)
Number of reflections in working set: 15935 (91.7%)
Number of reflections in test set: 817 (4.7%)
CRYST1 52.400 83.300 110.600 90.00 90.00 90.00 P21 21 21

---

What is claimed is:

1. A crystal comprising domain III of West Nile Virus (WNV) Envelope protein (E protein) in association with an E16 Fab fragment in crystalline form, wherein the domain III of WNV E protein consists of SEQ ID NO: 1, wherein the E16 Fab fragment consists of SEQ ID NOS: 2 and 3, wherein said crystal forms in space group $P2_1 2_1 2_1$ with unit cell dimensions a =52.4 ±0.2 Å, b =83.3 ±0.2 Å, and c =110.6 ±0.2 Å, and wherein $\alpha=\beta=\gamma=90°$.

* * * * *